US011969466B2

(12) United States Patent
Mascola et al.

(10) Patent No.: US 11,969,466 B2
(45) Date of Patent: Apr. 30, 2024

(54) STABILIZED INFLUENZA HEMAGGLUTININ STEM REGION TRIMERS AND USES THEREOF

(71) Applicant: The United States of America, as represented by the Secretary, Department of Health and Human Services, Bethesda, MD (US)

(72) Inventors: John R. Mascola, Rockville, MD (US); Jeffrey C. Boyington, Clarksburg, MD (US); Hadi M. Yassine, Doha (QA); Peter D. Kwong, Washington, DC (US); Barney S. Graham, Smyrna, GA (US); Masaru Kanekiyo, North Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 18/314,052

(22) Filed: May 8, 2023

(65) Prior Publication Data

US 2023/0330210 A1 Oct. 19, 2023

Related U.S. Application Data

(62) Division of application No. 17/504,002, filed on Oct. 18, 2021, now Pat. No. 11,679,151, which is a division of application No. 16/455,242, filed on Jun. 27, 2019, now Pat. No. 11,147,867, which is a division of application No. 15/313,265, filed as application No. PCT/US2015/032695 on May 27, 2015, now Pat. No. 10,363,301.

(60) Provisional application No. 62/003,471, filed on May 27, 2014.

(51) Int. Cl.

| | |
|---|---|
| ***A61K 39/145*** | (2006.01) |
| ***A61K 39/12*** | (2006.01) |
| ***C07K 14/005*** | (2006.01) |
| ***C07K 14/47*** | (2006.01) |
| ***C12N 7/00*** | (2006.01) |
| *A61K 39/00* | (2006.01) |

(52) U.S. Cl.

CPC ............ *A61K 39/145* (2013.01); *A61K 39/12* (2013.01); *C07K 14/005* (2013.01); *C07K 14/47* (2013.01); *C12N 7/00* (2013.01); *A61K 2039/55555* (2013.01); *A61K 2039/55566* (2013.01); *A61K 2039/6031* (2013.01); *C07K 2319/00* (2013.01); *C12N 2760/16122* (2013.01); *C12N 2760/16134* (2013.01)

(58) Field of Classification Search

None

See application file for complete search history.

(56) References Cited

U.S. PATENT DOCUMENTS

| | | | |
|---|---|---|---|
| 9,441,019 | B2 | 9/2016 | Nabel et al. |
| 10,363,301 | B2 | 7/2019 | Mascola et al. |
| 2011/0177122 | A1 | 7/2011 | Nabel et al. |

FOREIGN PATENT DOCUMENTS

| | | |
|---|---|---|
| WO | WO 2013/044203 | 3/2013 |

OTHER PUBLICATIONS

Cotter et al., "A Single Amino Acid in the Stalk Region of the H1N1pdm Influenza Virus HA Protein Affects Viral Fusion, Stability and Infectivity," *PLOS Pathogens* 10.1: e1003831, Jan. 2014 (9 pages).

Kenekiyo et al., "Self-assembling influenza nanoparticle vaccines elicit broadly neutralizing HINI antibodies", *Nature* 499.456: 102-106, Jul. 2013.

Khanna et al., "Protective Immunity Based on the Conserved Hemagglutinin Stalk Domain and Its Prospects for Universal Influenza Vaccine Development", *Biomed Res Internatl.* 284.13: 1655-1657, Jan. 1, 2014.

Krammer et al., "Influenza virus hemagglutinin stalk-based antibodies and vaccines", *Curr Opin Virol.* 3.51: 521-530, Oct. 1, 2013.

Robertson, "Sequence Analysis of the Haemagglutinin of A/Taiwan/1/86, a New Variant of Human Influenza A(HINI) Virus", *J Gen Virol.* 68.4: 1205-1208, Apr. 1, 1987.

Sagawa et al., "The immunological activity of a deletion mutant of influenza virus haemagglutinin lacking the globular region 11", *J Gen Virol.* 77.7: 1483-1487, Jan. 1, 1996.

Steel et al., "Influenza virus vaccine based on the conserved hemagglutinin stalk Domain", *MBIO* 1.1: e00018-10, May 18, 2010.

Sunil et al., "Vaccines based on structure-based design provide protection against infectious diseases", *Expert Reviews of Vaccines* 12.11: 1301-1311, Nov. 1, 2013.

Yang et al., "Structures of Receptor Complexes of a North American H7N2 Influenza Hemagglutinin with a Loop Deletion in the Receptor Binding Site", PLoS Pathog 6.9: e1001081, 2010 (11 pages).

(Continued)

*Primary Examiner* — Agnieszka Boesen

(74) *Attorney, Agent, or Firm* — Klarquist Sparkman, LLP

(57) ABSTRACT

Vaccines that elicit broadly protective anti-influenza antibodies. Some vaccines comprise nanoparticles that display HA trimers from influenza virus on their surface. The nanoparticles are fusion proteins comprising a monomeric subunit (e.g., ferritin) joined to the stem region of an influenza HA protein. The fusion proteins self-assemble to form the HA-displaying nanoparticles. The vaccines comprise only the stem region of an influenza HA protein joined to a trimerization domain. Also provided are fusion proteins, and nucleic acid molecules encoding such proteins, and assays using nanoparticles of the invention to detect anti-influenza antibodies.

20 Claims, 42 Drawing Sheets

Specification includes a Sequence Listing.

(56) References Cited

OTHER PUBLICATIONS

International Search Report and Written Opinion prepared by the European Patent Office dated Aug. 25, 2015, for International Application No. PCT/US2015/032695.

International Preliminary Report on Patentability for International (PCT) Patent Application No. PCT/US2015/032695, dated Dec. 8, 2016, 9 pages.

Official Action for Canada Patent Application No. 2,950,085, dated Oct. 30, 2017, 6 pages.

Official Action for European Patent Application No. 15727824.3, dated Dec. 11, 2017, 5 pages.

Official Action for European Patent Application No. 15727824.3, dated Jun. 22, 2018, 8 pages.

Official Action for U.S. Appl. No. 15/313,265, dated Feb. 8, 2018, 9 pages, Restriction Requirement.

Official Action for U.S. Appl. No. 15/313,265, dated May 29, 2018, 12 pages.

Official Action for U.S. Appl. No. 15/313,265, dated Dec. 11, 2018, 7 pages.

Notice of Allowance for U.S. Appl. No. 15/313,265, dated Mar. 11, 2019, 5 pages.

Official Action for Canada Patent Application No. 2,950,085, dated Dec. 17, 2018, 6 pages.

English Translation of Official Action for China Patent Application No. 201580041202.3, dated Oct. 22, 2019, 15 pages.

Official Action for European Patent Application No. 15727824.3, dated May 16, 2019, 6 pages.

Official Action for European Patent Application No. 15727824.3, dated Nov. 6, 2019, 4 pages.

Stabilized HA stem designs

| Trimer (%) Ab (Kd M) | 82 | 29 | 77 | 83 | 70 | 81 |
|---|---|---|---|---|---|---|
| CR6261 | 3.9E-10 | -- | 4.3E-09 | 7.7E-09 | 1.5E-08 | ND |
| CR9114 | <1.0E-12 | ND | <1.0E-12 | <1.0E-12 | <1.0E-12 | ND |
| F10 | 6.3E-11 | ND | 3.2E-10 | 9.9E-11 | 7.0E-10 | ND |
| 70-5B03 | 6.7E-11 | ND | 1.4E-09 | 1.7E-09 | 9.3E-9 | ND |

| Trimer (%) Ab (Kd M) | NA | NA | NA |
|---|---|---|---|
| CR6261 | 5.9E-09 | NA | 6.6E-09 |
| CR9114 | 1.1E-10 | NA | <1.0E-12 |
| F10 | 1.3E-10 | NA | 5.0E-10 |
| 70-5B03 | 1.4E-09 | NA | 4.3E-09 |

| HA stem percentage of immunogen surface | | |
|---|---|---|
| | Gen 4 | Gen6 |
| HA | HS-SS | HS-SS |
| 37% | 71% | 94% |

H1-SS-np cryo-EM

2D radial density profile

Gen6_H1NC99_K394M/E446L/E448Q/R449W/D452L/Y437D/N438L_N19Q

Nucleotide of sequence insert SEQ ID NO: 263

Nucleotide sequence of entire plasmid SEQ ID NO: 266

Gen6_H1CA09_K394M/E446L/E448Q/R449W/D452L/Y437D/N438L_N19Q

Nucleotide of sequence insert SEQ ID NO: 270

Nucleotide sequence of entire plasmid SEQ ID NO:273

Gen6_H2Sing57_K394M/M445L/E446L/E448Q/R449W/D452L/Y437D/N438L_N19Q

Nucleotide of sequence insert SEQ ID NO: 277

Nucleotide sequence of entire plasmid SEQ ID NO: 280

Gen6_H5Ind05_K394M/M445L/E446L/E448Q/R449W/D452L/Y437D/N438L/S49bW_N19Q

Nucleotide of sequence insert SEQ ID NO: 284

Nucleotide sequence of entire plasmid SEQ ID NO: 287

Gen6_H1NC99_K394M/E446L_N19Q

Nucleotide of sequence insert SEQ ID NO: 291

Nucleotide sequence of entire plasmid SEQ ID NO: 294

Gen6_H1NC99_K394M/E446L/Y437D/N438L_N19Q

Nucleotide of sequence insert SEQ ID NO: 298

Nucleotide sequence of entire plasmid SEQ ID NO: 301

Gen6_H1NC99_K394I/E446I/Y437D/N438L_N19Q

Nucleotide of sequence insert SEQ ID NO: 305

Nucleotide sequence of entire plasmid SEQ ID NO: 308

Gen6_H1NC99_K394L/E446I/Y437D/N438L_N19Q

Nucleotide of sequence insert SEQ ID NO: 312

Nucleotide sequence of entire plasmid SEQ ID NO: 315

Gen6_H1NC99_K394L/E446L/Y437D/N438L_N19Q

Nucleotide of sequence insert SEQ ID NO: 319

Nucleotide sequence of entire plasmid SEQ ID NO: 322

Gen6_H1NC99_K394M/E446M/Y437D/N438L_N19Q

Nucleotide of sequence insert SEQ ID NO: 326

Nucleotide sequence of entire plasmid SEQ ID NO: 329

Gen6_H1NC99_K394Q/E446Q/Y437D/N438L_N19Q

Nucleotide of sequence insert SEQ ID NO: 333

Nucleotide sequence of entire plasmid SEQ ID NO: 336

Gen6_H1NC99_K394M/E446L/Y437D/N438L/H45N/V47T_N19Q

Nucleotide of sequence insert SEQ ID NO: 340

Nucleotide sequence of entire plasmid SEQ ID NO: 343

Gen6_H1NC99_V36I/K394M/L445M/E446L/E448Q/R449F/D452L/Y437D/N438L_N19Q

Nucleotide of sequence insert SEQ ID NO: 347

Nucleotide sequence of entire plasmid SEQ ID NO: 350

Gen6_H1NC99_K394M/E446L/E448Q/R449W/D452L/S402aN/G402cT/S402dG/T402fA/Y437D/N438L_N19Q

Nucleotide of sequence insert SEQ ID NO: 354

Nucleotide sequence of entire plasmid SEQ ID NO: 357

Gen6_H1NC99_K394M/E446L/E448Q/R449W/D452L/S402bG/G402cN/S402eT/T402fA/Y437D/N438L_N19Q

Nucleotide of sequence insert SEQ ID NO: 361

Nucleotide sequence of entire plasmid SEQ ID NO: 364

Gen6_H1NC99_K394M/E446L/E448Q/R449W/D452L/S402eN/Y437D/N438L_N19Q

Nucleotide of sequence insert SEQ ID NO: 368

Nucleotide sequence of entire plasmid SEQ ID NO: 371

Gen6_H1NC99_K394M/E446L/E448Q/R449W/D452L/G402cN/G402eT/T402fA/Q370N/E372T/Y437D/N438L_S21T

Nucleotide of sequence insert SEQ ID NO: 375

Nucleotide sequence of entire plasmid SEQ ID NO: 378

Gen6_H1NC99_K394M/E446L/E448Q/R449W/D452L/G402cN/G402eT/T402fA/Q370N/E372T/Y437D/N438L_S21T/Q69N

Nucleotide of sequence insert SEQ ID NO: 382

Nucleotide sequence of entire plasmid SEQ ID NO: 385

Gen6_H1NC99_K394M/E446L/Y437D/N438L/Δ172-174

Nucleotide of sequence insert SEQ ID NO: 389

Nucleotide sequence of entire plasmid SEQ ID NO: 392

Gen6_H1NC99_rpk3_Dloop2

Nucleotide sequence of insert SEQ ID NO: 396

Nucleotide sequence of entire plasmid SEQ ID NO: 399

STABILIZED INFLUENZA HEMAGGLUTININ STEM REGION TRIMERS AND USES THEREOF

CROSS REFERENCE TO RELATED APPLICATIONS

This application is a divisional of U.S. patent application Ser. No. 17/504,002, filed Oct. 18, 2021, which is a divisional of U.S. patent application Ser. No. 16/455,242, filed Jun. 27, 2019, issued as U.S. Pat. No. 11,147,867, which is a divisional of U.S. application Ser. No. 15/313,265, filed Nov. 22, 2016, issued as U.S. Pat. No. 10,363,301, which is the U.S. National Stage of International Application No. PCT/US2015/032695, filed May 27, 2015, which designates the United States and was published in English under PCT Article 21(2), which in turn claims the benefit of U.S. Provisional Application Ser. No. 62/003,471 filed May 27, 2014. Each of these disclosures are incorporated herein by reference in their entirety.

SUMMARY OF THE INVENTION

The present invention provides novel hemagglutinin (HA) protein-based influenza vaccines that are easily manufactured, potent, and which elicit broadly neutralizing influenza antibodies against the stem region of the influenza HA protein. In particular, the present invention provides modified influenza HA stem-region proteins in the pre-fusion conformation, and portions thereof, that are useful for inducing the production of neutralizing antibodies. The present invention also provides novel nanoparticle (np)-based vaccines that express the influenza HA protein on their surface. Such nanoparticles comprise fusion proteins, each of which comprises a monomeric subunit of ferritin joined to an antigenic or immunogenic portion of the stem region from an influenza HA protein. Because such nanoparticles display influenza HA protein stem regions on their surface, they can be used to vaccinate an individual against influenza virus.

BACKGROUND

Protective immune responses induced by vaccination against influenza viruses are primarily directed to the viral HA protein, which is a glycoprotein on the surface of the virus responsible for interaction of the virus with host cell receptors. HA proteins on the virus surface are trimers of HA protein monomers that are enzymatically cleaved to yield amino-terminal HA1 and carboxy-terminal HA2 polypeptides. The globular head consists exclusively of the major portion of the HA1 polypeptide, whereas the stem that anchors the HA protein into the viral lipid envelope is comprised of HA2 and part of HAL The globular head of a HA protein includes two domains: the receptor binding domain (RBD), an ~148-amino acid residue domain that includes the sialic acid-binding site, and the vestigial esterase domain, a smaller ~75-amino acid residue region just below the RBD. The globular head includes several antigenic sites that include immunodominant epitopes. Examples include the Sa, Sb, $Ca_1$, $Ca_2$ and Cb antigenic sites (see, for example, Caton A J et al, 1982, Cell 31, 417-427). The RBD-A region includes the Sa antigenic site and part of the Sb antigenic site.

Antibodies against influenza often target variable antigenic sites in the globular head of HA, which surround a conserved sialic acid binding site, and thus, neutralize only antigenically closely related viruses. The variability of the HA head is due to the constant antigenic drift of influenza viruses and is responsible for seasonal endemics of influenza. In contrast, the HA stem is highly conserved and experiences little antigenic drift. Unfortunately, unlike the immunodominant head, the conserved HA stem is not very immunogenic. Furthermore, gene segments of the viral genome can undergo reassortment (antigenic shift) in host species, creating new viruses with altered antigenicity that are capable of becoming pandemics [Salomon, R. et al. Cell 136, 402-410 (2009)]. Until now, each year, influenza vaccine is updated to reflect the predicted HA and neuraminidase (NA) for upcoming circulating viruses.

Recently, an entirely new class of broadly neutralizing antibodies against influenza viruses was isolated that recognize the highly conserved HA stem [Corti, D. et al. *J Clin Invest* 120, 1663-1673 (2010); Ekiert, D. C. et al. *Science* 324, 246-251 (2009); Kashyap, A. K. et al. *Proc Natl Acad Sci USA* 105, 5986-5991 (2008); Okuno, Y. et al. J Virol 67, 2552-2558 (1993); Sui, J. et al. *Nat Struct Mol Biol* 16, 265-273 (2009); Ekiert, D. C. et al. *Science* 333, 843-850 (2011); Corti, D. et al. *Science* 333, 850-856 (2011)]. Unlike strain-specific antibodies, those antibodies are capable of neutralizing multiple antigenically distinct viruses, and hence inducing such antibodies has been a focus of next generation universal vaccine development [Nabel, G. J. et al. *Nat Med* 16, 1389-1391 (2010)]. However, robustly eliciting these antibodies with such heterologous neutralizing profile by vaccination has been difficult [Steel, J. et al. *M Bio* 1, e0018 (2010); Wang, T. T. et al. *PLoS Pathog* 6, e1000796 (2010); Wei, C. J. et al. *Science* 329, 1060-1064 (2010)]. Removal of the immunodominant head region of HA (which contains competing epitopes) and stabilization of the resulting stem domain through genetic manipulation is one potential way to improve the elicitation of these broadly neutralizing stem antibodies.

Current vaccine strategies for influenza use either a chemically inactivated or a live attenuated influenza virus. Both vaccines are generally produced in embryonated eggs which present major manufacturing limitations due to the time consuming process and limited production capacity. Another more critical limitation of current vaccines is its highly strain-specific efficacy. These challenges became glaring obvious during emergence of the 2009 H1N1 pandemic, thus validating the necessity for new vaccine platforms capable of overcoming these limitations. Virus-like particles represent one of such alternative approaches and are currently being evaluated in clinical trials [Roldao, A. et al. *Expert Rev Vaccines* 9, 1149-1176 (2010); Sheridan, C. *Nat Biotechnol* 27, 489-491 (2009)]. Instead of embryonated eggs, VLPs that often comprise HA, NA and matrix protein 1 (M1) can be mass-produced in mammalian or insect cell expression systems [Haynes, J. R. *Expert Rev Vaccines* 8, 435-445 (2009)]. The advantages of this approach are its particulate, multivalent nature and the authentic display of properly folded, trimeric HA spikes that faithfully mimic the infectious virion. In contrast, by the nature of its assembly, the enveloped VLPs contain a small but finite host cell component that may present potential safety, immunogenicity challenges following repeated use of this platform [Wu, C. Y. et al. *PLoS One* 5, e9784 (2010)]. Moreover, the immunity induced by the VLPs is essentially the same as current vaccines, and thus, will not likely significantly improve both potency and breadth of vaccine-induced protective immunity. In addition to VLPs, a recombinant HA protein has also been evaluated in humans [Treanor, J. J. et al. *Vaccine* 19, 1732-1737 (2001); Treanor, J. J. *JAMA* 297, 1577-1582 (2007)], though the ability to induce protective neutralizing antibody titers are limited. The recombinant HA proteins used in those trials were produced in insect cells and might not form native trimer preferentially [Stevens, J. *Science* 303, 1866-1870 (2004)].

Despite several alternatives to conventional influenza vaccines, advances in biotechnology in past decades have allowed engineering of biological materials to be exploited for the generation of novel vaccine platforms. Ferritin, an iron storage protein found in almost all living organisms, is an example which has been extensively studied and engineered for a number of potential biochemical/biomedical purposes [Iwahori, K. U.S. Patent 2009/0233377 (2009); Meldrum, F. C. et al. *Science* 257, 522-523 (1992); Naitou, M. et al. U.S. Patent 2011/0038025 (2011); Yamashita, I. *Biochem Biophys Acta* 1800, 846-857 (2010)], including a potential vaccine platform for displaying exogenous epitope peptides [Carter, D. C. et al. U.S. Patent 2006/0251679 (2006); Li, C. Q. et al. *Industrial Biotechnol* 2, 143-147 (2006)]. Its use as a vaccine platform is particularly interesting because of its self-assembly and multivalent presentation of antigen which induces stronger B cell responses than monovalent form as well as induce T-cell independent antibody responses [Bachmann, M. F. et al. Annu Rev Immunol 15, 235-270 (1997); Dintzis, H. M. et al. *Proc Natl Acad Sci USA* 73, 3671-3675 (1976)]. Further, the molecular architecture of ferritin, which consists of 24 subunits assembling into an octahedral cage with 432 symmetry has the potential to display multimeric antigens on its surface.

There remains a need for an efficacious influenza vaccine that provides robust protection against influenza virus. There particularly remains a need for an influenza vaccine that protects individuals from heterologous strains of influenza virus, including evolving seasonal and pandemic influenza virus strains of the future. The present invention meets this need by providing a novel nanoparticle-based vaccine consisting of a novel HA stabilized stem (SS) without the variable immunodominant head region genetically fused to the surface of nanoparticles (gen6 HA-SS np) resulting in an influenza vaccine that is easily manufactured, potent, and elicits antibodies that are broadly heterosubtypic protective.

BRIEF DESCRIPTION OF THE FIGURES

FIG. 5 shows the map of Gen6_H1NC99_ K394M/E446L/E448Q/R449W/D452L/Y437D/N438L_N19Q comprising SEQ ID NO: 266. FIG. 6 shows the map of Gen6_H1CA09_K394M/E446L/E448Q/R449W/D452L/Y437D/N438L_N19Q comprising SEQ ID NO: 273. FIG. 7 shows the map of Gen6_H2Sing57_K394M/M445L/E446L/E448Q/R449W/D452L/Y437D/N438L_N19Q comprising SEQ ID NO: 280. FIG. 8 shows the map of Gen6_H5Ind05 K394M/M445L/E446L/E448Q/R449W/D452L/Y437D/N438L/S49bW_N19Q comprising SEQ ID NO: 287. FIG. 9 shows the map of Gen6_H1NC99_K394M/E446L_N19Q comprising SEQ ID NO: 294. FIG. 10 shows the map of Gen6_H1NC99_K394M/E446L/Y437D/N438L_N19Q comprising SEQ ID NO: 301. FIG. 11 shows the map of Gen6_H1NC99_K3941/E4461/Y437D/N438L_N19Q comprising SEQ ID NO: 308. FIG. 12 shows the map of Gen6 H1NC99 K394L/E4461/Y437D/N438L_N19Q comprising SEQ ID NO: 315. FIG. 13 shows the map of Gen6_H1NC99_K394L/E446L/Y437D/N438L_N19Q comprising SEQ ID NO: 322. FIG. 14 shows the map of Gen6_H1NC99_K394M/E446M/Y437D/N438L_N19Q comprising SEQ ID NO: 329. FIG. 15 shows the map of Gen6 H1NC99 K394Q/E446Q/Y437D/N438L_N19Q comprising SEQ ID NO: 336. FIG. 16 shows the map of Gen6 H1NC99 K394M/E446L/Y437D/N438L/H45N/V47T_N19Q comprising SEQ ID NO: 343. FIG. 17 shows the map of Gen6 H1NC99 V361/K394M/L445M/E446L/E448Q/R449F/D452L/Y437D/N438L N19Q comprising SEQ ID NO: 350. FIG. 18 shows the map of Gen6_H1NC99_K394M/E446L/E448Q/R449W/D452L/S402aN/G402cT/S402dG/T402fA/Y437D/N438L_N19Q comprising SEQ ID NO: 357. FIG. 19 shows the map of Gen6_H1NC99_K394M/E446L/E448Q/R449W/D452L/S402bG/G402cN/S402eT/T402fA/Y437D/N438L_N19Q comprising SEQ ID NO: 364. FIG. 20 shows the map of Gen6_H1NC99_K394M/E446L/E448Q/R449W/D452L/S402eN/Y437D/N438L_N19Q comprising SEQ ID NO: 371. FIG. 21 shows the map of Gen6 H1NC99 K394M/E446L/E448Q/R449W/D452L/G402cN/G402eT/T402fA/Q370N/E372T/Y437D/N438L_S21T comprising SEQ ID NO: 378. FIG. 22 shows the map of Gen6_H1NC99_K394M/E446L/E448Q/R449W/D452L/G402cN/G402eT/T402fA/Q370N/E372T/Y437D/N438L_S21T/30 Q69N comprising SEQ ID NO: 386. FIG. 23 shows the map of Gen6_H1NC99_K394M/E446L/Y437D/N438L/4172-174 comprising SEQ ID NO: 392. FIG. 24 shows the map of Gen6_H1NC99_rpk3_Dloop2 comprising SEQ ID NO: 399.

SEQUENCE LISTING

Figure 1A:
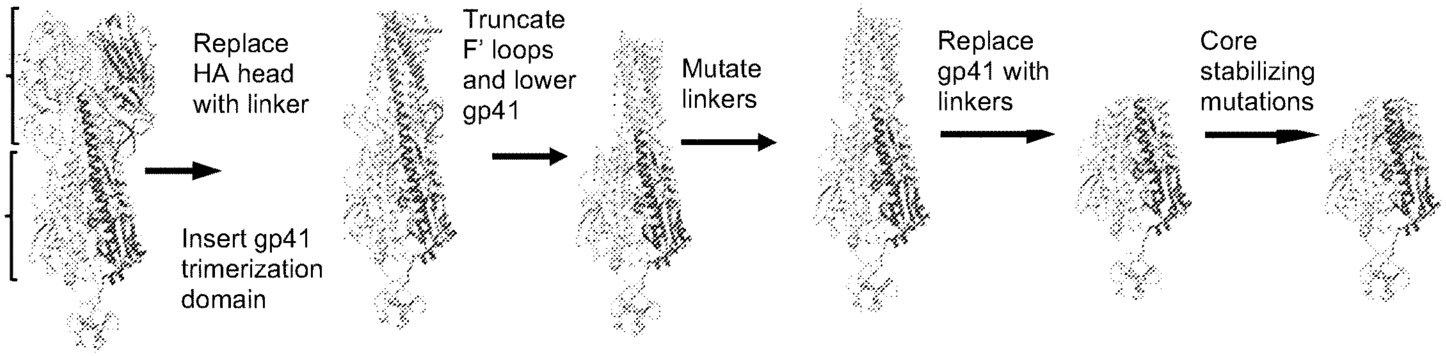
FIG. 1*a* shows the structure-based removal of the HA head allows for preservation of stem immunogen antigenicity. The ribbon models depict the HA-SS design pathway starting with the model of an HA ectodomain fused to a T4 foldon trimerization domain (in green below HA ectodomain) The last three HA-SS designs (Gen4-6) were genetically fused to ferritin nanoparticles (lower panel). One monomer of each HA trimer is shaded. The core stabilizing mutations for creating Gen6 are shown as spheres. The percent trimerization (including foldon) and antigenic affinity constants ($K_D$, M) to specified mAbs are shown below each HA-SS immunogen design. ND, not determined; NA, not applicable.
Figure 1A:
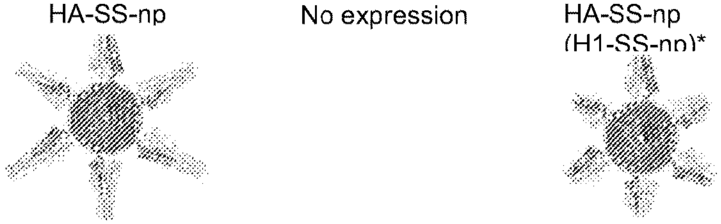

This application contains a Sequence Listing submitted as an XML file named "4239-104867-29_Sequence.xml", having a file size of 775,000 bytes, and created on Apr. 25, 2023. The information contained in this electronic file is hereby incorporated by reference in its entirety pursuant to 37 CFR § 1.52(e)(5).

DETAILED DESCRIPTION OF THE INVENTION

The present invention relates to a novel vaccine for influenza virus. More specifically, the present invention relates to novel, influenza HA protein-based vaccines that elicit an immune response against the stem region of the HA protein from a broad range of influenza viruses. It also relates to self-assembling nanoparticles that display immunogenic portions of the pre-fusion conformation of the stem region from the influenza HA protein on their surface. Such nanoparticles are useful for vaccinating individuals against influenza virus. Accordingly, the present invention also relates to protein constructs for producing such nanoparticles and nucleic acid molecules encoding such proteins. Additionally, the present invention relates to methods of producing nanoparticles of the present invention, and methods of using such nanoparticles to vaccinate individuals.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the claims.

It must be noted that as used herein and in the appended claims, the singular forms "a," "an," and "the" include plural referents unless the context clearly dictates otherwise. For example, a nucleic acid molecule refers to one or more nucleic acid molecules. As such, the terms "a", "an", "one or more" and "at least one" can be used interchangeably. Similarly the terms "comprising", "including" and "having" can be used interchangeably. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In addition to the above, unless specifically defined otherwise, the following terms and phrases, which are common to the various embodiments disclosed herein, are defined as follows:

As used herein, a protein construct is a protein made by the hand of man, in which two or more amino acid sequences have been covalently joined in a way not found in nature. The amino acid sequences being joined can be related or unrelated. As used herein, polypeptide sequences are unrelated, if their amino acid sequences are not normally found joined together via a covalent bond in their natural environment(s) (e.g., inside a cell). For example, the amino acid sequences of monomeric subunits that make up ferritin, and the amino acid sequences of influenza HA proteins are not normally found joined together via a covalent bond. Thus, such sequences are considered unrelated.

Protein constructs can also comprise related amino acid sequences. For example, the structure of the influenza HA protein is such that the head region amino acid sequence is flanked on both ends by stem region amino acid sequences. Through genetic means, it is possible to create a deletion version of an HA protein by removing amino acid residues from the middle of the head region, while maintaining a portion of the head region flanked by stem regions sequences. While the order of the sequences in the final molecule would remain the same, the spatial relationship between the amino acids would differ from the natural protein. Thus, such a molecule would be considered a protein construct. According to the present invention, protein constructs may also be referred to as fusion proteins.

Amino acid sequences in a protein construct can be joined directly to each other or they can be joined using a linker sequence. A linker sequence, peptide, or polypeptide, is a short (e.g., 2-20) amino acid sequence used to connect two proteins having a desired characteristic (e.g., structure, epitope, immunogenicity, activity, etc.). A linker sequence typically does not have its own activity and is usually used to allow other parts of the protein construct to assume a desired conformation. Linker sequences are typically made from small amino acid residues and/or runs thereof, such as, for examples, serine, alanine and glycine, although the use of other amino acid residues is not excluded.

As used herein, the term immunogenic refers to the ability of a specific protein, or a specific region thereof, to elicit an immune response to the specific protein, or to proteins comprising an amino acid sequence having a high degree of identity with the specific protein. According to the present invention, two proteins having a high degree of identity have amino acid sequences at least 80% identical, at least 85% identical, at least 87% identical, at least 90% identical, at least 92% identical, at least 93% identical, at least 94% identical, at least 95% identical, at least 96% identical, at least 97% identical, at least 98% identical or at least 99% identical. Methods of determining the percent identity between two amino acid or nucleic acid sequence are known in the art.

As used herein, an immune response to a vaccine, or nanoparticle, of the present invention is the development in a subject of a humoral and/or a cellular immune response to a HA protein present in the vaccine. For purposes of the present invention, a "humoral immune response" refers to an immune response mediated by antibody molecules, including secretory (IgA) or IgG molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A cellular immune response also refers to the production of cytokines, chemokines and other such molecules produced by activated T-cells and/or other white blood cells, including those derived from CD4+ and CD8+T-cells.

Thus, an immunological response may be one that stimulates CTLs, and/or the production or activation of helper T-cells. The production of chemokines and/or cytokines may also be stimulated. The vaccine may also elicit an antibody-mediated immune response. Hence, an immunological response may include one or more of the following effects: the production of antibodies (e.g., IgA or IgG) by B-cells; and/or the activation of suppressor, cytotoxic, or helper T-cells and/or T-cells directed specifically to an HA protein present in the vaccine. These responses may serve to neutralize infectivity (e.g., antibody-dependent protection), and/or mediate antibody-complement, or antibody dependent cell cytotoxicity (ADCC) to provide protection to an immunized individual. Such responses can be determined using standard immunoassays and neutralization assays, well known in the art.

As used herein, the term antigenic, antigenicity, and the like, refers to a protein that is bound by an antibody or a group of antibodies. Similarly, an antigenic portion of a protein is any portion that is recognized by an antibody or a group of antibodies. According to the present invention, recognition of a protein by an antibody means the antibody selectively binds to the protein. As used herein, the phrase selectively binds, selective binding, and the like, refer to the ability of an antibody to preferentially bind an HA protein as opposed to binding proteins unrelated to HA, or non-protein components in the sample or assay. An antibody that preferentially binds HA is one that binds HA but does not significantly bind other molecules or components that may be present in the sample or assay. Significant binding is considered, for example, binding of an anti-HA antibody to a non-HA molecule with an affinity or avidity great enough to interfere with the ability of the assay to detect and/or determine the level of anti-influenza antibodies, or HA protein, in the sample. Examples of other molecules and compounds that may be present in the sample, or the assay, include, but are not limited to, non-HA proteins, such as albumin, lipids and carbohydrates. According to the present invention, a non-HA protein is a protein having an amino acid sequence sharing less than 60% identity with the sequence of an influenza HA protein disclosed herein. In some embodiments, the antibody or antibodies provide broad heterosubtypic protection. In some embodiments, the antibody or antibodies are neutralizing.

As used herein, neutralizing antibodies are antibodies that prevent influenza virus from completing one round of replication. As defined herein, one round of replication refers the life cycle of the virus, starting with attachment of the virus to a host cell and ending with budding of newly formed virus from the host cell. This life cycle includes, but is not limited to, the steps of attaching to a cell, entering a cell, cleavage and rearrangement of the HA protein, fusion of the viral membrane with the endosomal membrane, release of viral ribonucleoproteins into the cytoplasm, formation of new viral particles and budding of viral particles from the host cell membrane. According to the present invention, a neutralizing antibody is one that inhibits one or more such steps.

As used herein, broadly neutralizing antibodies are antibodies that neutralize more than one type, subtype and/or strain of influenza virus. For example, broadly neutralizing antibodies elicited against an HA protein from a Type A influenza virus may neutralize a Type B or Type C virus. As a further example, broadly neutralizing antibodies elicited against an HA protein from Group I influenza virus may neutralize a Group 2 virus. As an additional example, broadly neutralizing antibodies elicited against an HA protein from one sub-type or strain of virus, may neutralize another sub-type or strain of virus. For example, broadly neutralizing antibodies elicited against an HA protein from an H1 influenza virus may neutralize viruses from one or more sub-types selected from the group consisting of H2, H3, H4, H5, H6, H7, H8, H8, H10, H11, H12, H13, H14, H15, H16, H17 or H18.

According to the present invention all nomenclature used to classify influenza virus is that commonly used by those skilled in the art. Thus, a Type, or Group, of influenza virus refers to influenza Type A, influenza Type B or influenza type C. It is understood by those skilled in the art that the designation of a virus as a specific Type relates to sequence difference in the respective M1 (matrix) protein or NP (nucleoprotein). Type A influenza viruses are further divided into Group1 and Group 2. These Groups are further divided into subtypes, which refers to classification of a virus based on the sequence of its HA protein. Examples of current commonly recognized subtypes are H1, H2, H3, H4, H5, H6, H7, H8, H8, H10, H11, H12, H13, H14, H15, H16, H17 or H18. Group 1 influenza subtypes are H1, H2, H5, H6, H8, H9, H11, H12, H13, H16, H17 and H18. Group 2 influenza subtypes are H3, H4, H7, H10, H14, and H15. Finally, the term strain refers to viruses within a subtype that differ from one another in that they have small, genetic variations in their genome.

As used herein, an influenza hemagglutinin protein, or HA protein, refers to a full-length influenza hemagglutinin protein or any portion thereof, that is useful for producing protein constructs and nanoparticles of the invention or that are capable of eliciting an immune response. Preferred HA proteins are those that are capable of forming a trimer. An epitope of a full-length influenza HA protein refers to a portion of such protein that can elicit an antibody response against the homologous influenza strain, i.e., a strain from which the HA is derived. In some embodiments, such an epitope can also elicit an antibody response against a heterologous influenza strain, i.e., a strain having an HA that is not identical to that of the HA of the immunogen. In some embodiments, the epitope elicits a broadly heterosubtypic protective response. In some embodiments, the epitope elicits neutralizing antibodies.

As used herein, a variant refers to a protein, or nucleic acid molecule, the sequence of which is similar, but not identical to, a reference sequence, wherein the activity of the variant protein (or the protein encoded by the variant nucleic acid molecule) is not significantly altered. These variations in sequence can be naturally occurring variations or they can be engineered through the use of genetic engineering technique known to those skilled in the art. Examples of such techniques are found in Sambrook J, Fritsch E F, Maniatis T et al., in Molecular Cloning—A Laboratory Manual, 2nd Edition, Cold Spring Harbor Laboratory Press, 1989, pp. 9.31-9.57), or in Current Protocols in Molecular Biology, John Wiley & Sons, N.Y. (1989), 6.3.1-6.3.6, both of which are incorporated herein by reference in their entirety.

With regard to variants, any type of alteration in the amino acid, or nucleic acid, sequence is permissible so long as the resulting variant protein retains the ability to elicit neutralizing or non-neutralizing antibodies against an influenza virus. Examples of such variations include, but are not limited to, deletions, insertions, substitutions and combinations thereof. For example, with regard to proteins, it is well understood by those skilled in the art that one or more (e.g., 2, 3, 4, 5, 6, 7, 8, 9 or 10), amino acids can often be removed from the amino and/or carboxy terminal ends of a protein without significantly affecting the activity of that protein. Similarly, one or more (e.g., 2, 3, 4, 5, 6, 7, 8, 9 or 10) amino acids can often be inserted into a protein without significantly affecting the activity of the protein. In variants into which insertions have been made, the inserted amino acids may be referred to by referencing the amino acid residue after which the insertion was made. For example, an insertion of four amino acid residues after amino acid residue 402 could be referred to as **402*a*-402*d***. Moreover, if one of those inserted amino acids are later substituted with another amino acid, such a change can be referred to by reference to the letter position. For example, substitution of an inserted glycine (in the further position of the insert) with a threonine can be referred to as S402dT.

As noted, variant proteins of the present invention can contain amino acid substitutions relative to the influenza HA proteins disclosed herein. Any amino acid substitution is permissible so long as the activity of the protein is not significantly affected. In this regard, it is appreciated in the art that amino acids can be classified into groups based on their physical properties. Examples of such groups include, but are not limited to, charged amino acids, uncharged amino acids, polar uncharged amino acids, and hydrophobic amino acids. Preferred variants that contain substitutions are those in which an amino acid is substituted with an amino acid from the same group. Such substitutions are referred to as conservative substitutions.

Naturally occurring residues may be divided into classes based on common side chain properties: 1) hydrophobic: Met, Ala, Val, Leu, Ile; 2) neutral hydrophilic: Cys, Ser, Thr; 3) acidic: Asp, Glu; 4) basic: Asn, Gln, His, Lys, Arg; 5) residues that influence chain orientation: Gly, Pro; and 6) aromatic: Trp, Tyr, Phe.

For example, non-conservative substitutions may involve the exchange of a member of one of these classes for a member from another class.

In making amino acid changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is generally understood in the art (Kyte et al., 1982, J. Mol. Biol. 157:105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological invention, as in the present case. The greatest local average hydrophilicity of a protein, as governed by the hydrophilicity of its adjacent amino acids, correlates with its immunogenicity and antigenicity, i.e., with a biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those within ±1 are particularly preferred, and those within ±0.5 are even more particularly preferred. One may also identify epitopes from primary amino acid sequences on the basis of hydrophilicity.

Desired amino acid substitutions (whether conservative or non-conservative) can be determined by those skilled in the art at the time such substitutions are desired. For example, amino acid substitutions can be used to identify important residues of the HA protein, or to increase or decrease the immunogenicity, solubility or stability of the HA proteins described herein. Exemplary amino acid substitutions are shown below in Table 1.

TABLE 1

Amino Acid Substitutions

| Original Amino Acid | Exemplary Substitutions |
|---|---|
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala |
| Leu | Ile, Val, Met, Ala |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

As used herein, the phrase significantly affect a proteins activity refers to a decrease in the activity of a protein by at least 10%, at least 20%, at least 30%, at least 40% or at least 50%. With regard to the present invention, such an activity may be measured, for example, as the ability of a protein to elicit protective antibodies against an influenza virus. Such activity may be measured by measuring the titer of such antibodies against influenza virus, the ability of such antibodies to protect against influenza infection or by measuring the number of types, subtypes or strains neutralized by the elicited antibodies. Methods of determining antibody titers, performing protection assays and performing virus neutralization assays are known to those skilled in the art. In addition to the activities described above, other activities that may be measured include the ability to agglutinate red blood cells and the binding affinity of the protein for a cell. Methods of measuring such activities are known to those skilled in the art.

The terms individual, subject, and patient are well-recognized in the art, and are herein used interchangeably to refer to any human or other animal susceptible to influenza infection. Examples include, but are not limited to, humans and other primates, including non-human primates such as chimpanzees and other apes and monkey species; farm animals such as cattle, sheep, pigs, seals, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The terms individual, subject, and patient by themselves, do not denote a particular age, sex, race, and the like. Thus, individuals of any age, whether male or female, are intended to be covered by the present disclosure and include, but are not limited to the elderly, adults, children, babies, infants, and toddlers. Likewise, the methods of the present invention can be applied to any race, including, for example, Caucasian (white), African-American (black), Native American, Native Hawaiian, Hispanic, Latino, Asian, and European. An infected subject is a subject that is known to have influenza virus in their body.

As used herein, a vaccinated subject is a subject that has been administered a vaccine that is intended to provide a protective effect against an influenza virus.

As used herein, the terms exposed, exposure, and the like, indicate the subject has come in contact with a person of animal that is known to be infected with an influenza virus.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

One embodiment of the present invention is a protein construct comprising an influenza HA protein wherein the head region of the influenza HA protein has been replaced with an amino acid sequence comprising less than 5 contiguous amino acid residues from the head region of the HA protein. As used herein, an HA protein, refers to a full-length influenza HA protein or any portion/portions and/or variants thereof, that is/are useful for producing protein constructs and nanoparticles of the invention. Accordingly, the present invention is drawn to molecules that are capable of eliciting an immune response to the stem region of influenza HA protein. In some embodiments, the sequence of the HA protein construct has been further altered (i.e., mutated) to stabilize the stem region of the protein in a form that can be presented to the immune system. Some representative examples of such HA proteins, and protein constructs made there from, are shown in Table 2 below.

TABLE 2

| PCT SEQ ID NO | Comments |
|---|---|
| | FERRITIN |
| 1 | Coding sequence for ferritin monomeric subunit protein from *H. pylori* |
| 2 | Amino acid sequence encoded by SEQ ID NO: 1 |
| 3 | Complement of SEQ ID NO1 |
| 4 | Nucleic acid sequence encoding amino acids 5-167 from SEQ ID NO: 2; Asn19 has been replaced with Gln |
| 5 | Amino acid sequence encoded by SEQ ID NO: 3 |
| 6 | Complement of SEQ ID NO3 |
| | FULL LENGTH HA |
| 7 | Nucleic acid sequence encoding full length hemagglutinin protein from A/New Caledonia/20/1999 (1999 NC, H1)(GenBank: AY289929) |
| 8 | Amino acid sequence encoded by SEQ ID NO: 7 (full length hemagglutinin protein from A/New Caledonia/20/1999 (1999 NC, H1)(GenBank: AY289929)) |
| 9 | Complement of SEQ ID NO: 7 |
| 10 | Nucleic acid sequence encoding full length hemagglutinin protein from A/California/4/2009 (H1) |
| 11 | Amino acid sequence encoded by SEQ ID NO: 10 |
| 12 | Complement of SEQ ID NO: 10 |
| 13 | Nucleic acid sequence encoding full length hemagglutinin protein from A/Singapore/1957 (H2) |
| 14 | Amino acid sequence encoded by SEQ ID NO: 13 |
| 15 | Complement of SEQ ID NO: 13 |
| 16 | Nucleic acid sequence encoding full length hemagglutinin protein from A/Indonesia/05/2005 (H5) |
| 17 | Amino acid sequence encoded by SEQ ID NO: 16 |
| 18 | Complement of SEQ ID NO: 16 |
| | STEM REGION FLANKS |
| 19 | Nucleic acid sequence encoding SEQ ID NO: 20 |
| 20 | Amino acid sequence flanking amino end of head region from H1 NC 1999 |
| 21 | Complement of SEQ ID NO: 19 |
| 22 | Nucleic acid sequence encoding SEQ ID NO: 24 |
| 23 | Amino acid sequence flanking carboxyl end of head region from H1 NC 1999. Contains internal loop region. Long version |
| 24 | Complement of SEQ ID NO: 22 |
| 25 | Nucleic acid sequence encoding SEQ ID NO: 27 |
| 26 | Amino acid sequence flanking carboxyl end of head region from H1 NC 1999. Internal loop region replaced with Ser-Gly loop. Long version |
| 27 | Complement of SEQ ID NO: 25 |
| 28 | Nucleic acid sequence encoding SEQ ID NO: 30 |
| 29 | Amino acid sequence flanking carboxyl end of head region from H1 NC 1999. Contains internal loop region. short version |
| 30 | Complement of SEQ ID NO: 28 |
| 31 | Nucleic acid sequence SEQ ID NO: 33 |

TABLE 2-continued

| PCT SEQ ID NO | Comments |
|---|---|
| 32 | Amino acid sequence flanking carboxyl end of head region from H1 NC 1999. Internal loop region replaced with Ser-Gly loop. short version |
| 33 | Complement of SEQ ID NO: 31 |
| 34 | Nucleic acid sequence encoding SEQ ID NO: 35 |
| 35 | Amino acid sequence flanking amino end of head region from H1 CA 2009 |
| 36 | Complement of SEQ ID NO: 34 |
| 37 | Nucleic acid sequence encoding SEQ ID NO: 38 |
| 38 | Amino acid sequence flanking carboxyl end of head region from H1 CA (2009). Contains internal loop region. Long version |
| 39 | Complement of SEQ ID NO: 37 |
| 40 | Nucleic acid sequence encoding SEQ ID NO: 31 |
| 41 | Amino acid sequence flanking carboxyl end of head region from H1 CA (2009). Internal loop region replaced with Ser-Gly loop. Long version |
| 42 | Complement of SEQ ID NO: 40 |
| 43 | Nucleic acid sequence encoding SEQ ID NO: 44 |
| 44 | Amino acid sequence flanking carboxyl end of head region from H1 CA (2009). Contains internal loop region. short version |
| 45 | Complement of SEQ ID NO: 43 |
| 46 | Nucleic acid sequence encoding SEQ ID NO: 47 |
| 47 | Amino acid sequence flanking carboxyl end of head region from H1 CA (2009). Internal loop region replaced with Ser-Gly loop. Short version |
| 48 | Complement of SEQ ID NO: 46 |
| 49 | Nucleic acid sequence encoding SEQ ID NO: 50 |
| 50 | Amino acid sequence flanking amino end of head region from H2 Sing 1957 |
| 51 | Complement of SEQ ID NO: 49 |
| 52 | Nucleic acid sequence encoding SEQ ID NO: 53 |
| 53 | Amino acid sequence flanking carboxyl end of head region from H2 Sing (1957) Contains internal loop region. Long version |
| 54 | Complement of SEQ ID NO: 52 |
| 55 | Nucleic acid sequence encoding SEQ ID NO: 56 |
| 56 | Amino acid sequence flanking carboxyl end of head region from H2 Sing (1957). Internal loop region replaced with Ser-Gly loop. Long version |
| 57 | Complement of SEQ ID NO: 55 |
| 58 | Nucleic acid sequence encoding SEQ ID NO: 59 |
| 59 | Amino acid sequence flanking carboxyl end of head region from H2 Sing (1957) Contains internal loop region. short version |
| 60 | Complement of SEQ ID NO: 58 |
| 61 | Nucleic acid sequence encoding SEQ ID NO: 62 |
| 62 | Amino acid sequence flanking carboxyl end of head region from H2 Sing (1957). Internal loop region replaced with Ser-Gly loop. short version |
| 63 | Complement of SEQ ID NO: 61 |
| 64 | Nucleic acid sequence encoding SEQ ID NO: 65 |
| 65 | Amino acid sequence flanking amino end of head region from H5 Indo (2005) |
| 66 | Complement of SEQ ID NO: 64 |
| 67 | Nucleic acid sequence encoding SEQ ID NO: 68 |
| 68 | Amino acid sequence flanking carboxyl end of head region from H5 Indo (2005) Contains internal loop region. Long version |
| 69 | Complement of SEQ ID NO: 67 |
| 70 | Nucleic acid sequence encoding SEQ ID NO: 71 |
| 71 | Amino acid sequence flanking carboxyl end of head region from H5 Indo (2005). Internal loop region replaced with Ser-Gly loop. Long version |
| 72 | Complement of SEQ ID NO: 70 |
| 73 | Nucleic acid sequence encoding SEQ ID NO: 74 |
| 74 | Amino acid sequence flanking carboxyl end of head region from H5 Indo (2005) Contains internal loop region. short version |
| 75 | Complement of SEQ ID NO: 73 |
| 76 | Nucleic acid sequence encoding SEQ ID NO: 77 |
| 77 | Amino acid sequence flanking carboxyl end of head region from H5 Indo (2005). Internal loop region replaced with Ser-Gly loop. short version |
| 78 | Complement of SEQ ID NO: 76 |
| | HA CONSTRUCTS 1 |
| 79 | Nucleic acid sequence encoding SEQ ID NO: 80 |
| 80 | Gen_H1NC99_01 (rpk-03) K394M/E446L/E448Q/R449W/D452L H1N1 A/New Caledonia/20/1999 |
| 81 | Complement of SEQ ID NO: 79 |
| 82 | Nucleic acid sequence encoding SEQ ID NO: 83 |
| 83 | Gen6_H1CA09_01 (rpk-3) K394M/E446L/E448Q/R449W/D452L H1N1 A/California/4/2009 |
| 84 | Complement of SEQ ID NO: 82 |
| 85 | Nucleic acid sequence encoding SEQ ID NO: 86 |
| 86 | Gen6_H2Sing57_01 (rpk-3) K394M/M445L/E446L/E448Q/R449W/D452L H2N2 A/Singapore/1957 |
| 87 | Complement of SEQ ID NO: 85 |
| 88 | Nucleic acid sequence encoding SEQ ID NO: 89 |

TABLE 2-continued

| PCT SEQ ID NO | Comments |
|---|---|
| 89 | Gen6_H5Ind05_01 (rpk-3) K394M/M445L/E446L/E448Q/R449W/D452L H5N1 A/Indonesia/05/2005 |
| 90 | Complement of SEQ ID NO: 88 |
| 91 | Nucleic acid sequence encoding SEQ ID NO: 92 |
| 92 | Gen6_H1NC99_02 (rpk-22) K394M/E446L H1N1 A/New Caledonia/20/1999 |
| 93 | Complement of SEQ ID NO: 91 |
| 94 | Nucleic acid sequence encoding SEQ ID NO: 95 |
| 95 | Gen6_H1NC99_03 (rpk-08) V36I/K394M/L445M/E446L/E448Q/W449F/D452L H1N1 A/New Caledonia/20/1999 |
| 96 | Complement of SEQ ID NO: 94 |
| 97 | Nucleic acid sequence encoding SEQ ID NO: 98 |
| 98 | Gen6_H1NC99_04 (rpk-3, gly1) S402bN/G402dT/S402eG/T450A H1N1 A/New Caledonia/20/1999 |
| 99 | Complement of SEQ ID NO: 97 |
| 100 | Nucleic acid sequence encoding SEQ ID NO: 101 |
| 101 | Gen6_H1NC99_05 (rpk-3, gly2) S402bG/G402cN/S402eT/T450A H1N1 A/New Caledonia/20/1999 |
| 102 | Complement of SEQ ID NO: 100 |
| 103 | Nucleic acid sequence encoding SEQ ID NO: 104 |
| 104 | Gen6_H1NC99_06 (rpk-3, gly3) S402eN H1N1 A/New Caledonia/20/1999 |
| 105 | Complement of SEQ ID NO: 103 |
| | HA-FERRITIN FUSIONS |
| 106 | Nucleic acid sequence encoding SEQ ID NO: 107 |
| 107 | Gen_H1NC99_01 (rpk-03) K394M/E446L/E448Q/R449W/D452L H1N1 A/New Caledonia/20/1999 |
| 108 | Complement of SEQ ID NO: 106 |
| 109 | Nucleic acid sequence encoding SEQ ID NO: 110 |
| 110 | Gen6_H1CA09_01 (rpk-3) K394M/E446L/E448Q/R449W/D452L H1N1 A/California/4/2009 |
| 111 | Complement of SEQ ID NO: 109 |
| 112 | Nucleic acid sequence encoding SEQ ID NO: 113 |
| 113 | Gen6_H2Sing57_01 (rpk-3) K394M/M445L/E446L/E448Q/R449W/D452L H2N2 A/Singapore/1957 |
| 114 | Complement of SEQ ID NO: 112 |
| 115 | Nucleic acid sequence encoding SEQ ID NO: 116 |
| 116 | Gen6_H5Ind05_01 (rpk-3) K394M/M445L/E446L/E448Q/R449W/D452L H5N1 A/Indonesia/05/2005 |
| 117 | Complement of SEQ ID NO: 115 |
| 118 | Nucleic acid sequence encoding SEQ ID NO: 119 |
| 119 | Gen6_H1NC99_02 (rpk-22) K394M/E446L H1N1 A/New Caledonia/20/1999 |
| 120 | Complement of SEQ ID NO: 118 |
| 121 | Nucleic acid sequence encoding SEQ ID NO: 122 |
| 122 | Gen6_H1NC99_03 (rpk-08) V36I/K394M/L445M/E446L/E448Q/W449F/D452L H1N1 A/New Caledonia/20/1999 |
| 123 | Complement of SEQ ID NO: 121 |
| 124 | Nucleic acid sequence encoding SEQ ID NO: 125 |
| 125 | Gen6_H1NC99_04 (rpk-3, gly1) S402bN/G402dT/S402eG/T450A H1N1 A/New Caledonia/20/1999 |
| 126 | Complement of SEQ ID NO: 124 |
| 127 | Nucleic acid sequence encoding SEQ ID NO: 128 |
| 128 | Gen6_H1NC99_05 (rpk-3, gly2) S402bG/G402cN/S402eT/T450A H1N1 A/New Caledonia/20/1999 |
| 129 | Complement of SEQ ID NO: 127 |
| 130 | Nucleic acid sequence encoding SEQ ID NO: 131 |
| 131 | Gen6_H1NC99_06 (rpk-3, gly3) S402eN H1N1 A/New Caledonia/20/1999 |
| 132 | Complement of SEQ ID NO: 130 |
| | INTERNAL LOOP SEQUENCES |
| 133 | Internal loop sequence From H1 NC NTQFTAVGKEFNKLERRMENLNKKVDDGFLDIW |
| 134 | NTQFTAVGKEFN; Fragment of SEQ ID NO: 133 |
| 135 | NKLERRMENLNK Fragment of SEQ ID NO: 133 |
| 136 | KKVDDGFLDIW Fragment of SEQ ID NO: 133 |
| 137 | Internal loop sequence from H1 CA 2009 NTQFTAVGKEFNHLEKRIENLNKKVDDGFLDIW |
| 138 | NTQFTAVGKEF; Fragment of SEQ ID NO: 137 |
| 139 | FNHLEKRIENL; Fragment of SEQ ID NO: 137 |
| 140 | LNKKVDDGFLDIW; Fragment of SEQ ID NO: 137 |
| 141 | Internal loop sequence from H5Sing 1957 NTQFEAVGKEFSNLERRLENLNKKMEDGFLDVW |
| 142 | NTQFEAVGKEF; Fragment of SEQ ID NO: 141 |
| 143 | FSNLERRLENLN; Fragment of SEQ ID NO: 141 |
| 144 | NKKMEDGFLDVW; Fragment of SEQ ID NO: 141 |

TABLE 2-continued

| PCT SEQ ID NO | Comments |
|---|---|
| 145 | Internal loop sequence from H5 Indo 2005 NTQFEAVGREFNNLERRIENLNKKMEDGFLDVW |
| 146 | NTQFEAVGREF; Fragment of SEQ ID NO: 145 |
| 147 | FNNLERRIENLN; Fragment of SEQ ID NO: 145 |
| 148 | NKKMEDGFLDVW; Fragment of SEQ ID NO: 145 |
| | MUTATION REGIONS |
| 149 | Mutation region for H1 NC 99 KVNSVIEKMNTQFTAVGKEFNKLERRMENLNKKVDDGFLDIWTYNAELLVLLE |
| 150 | KVNSVIEKMTYNAELLVLLE; SEQ ID NO149 minus internal loop |
| 151 | Mutation region for H1 CA 2009 KVNSVIEKMNTQFTAVGKEFNHLEKRIENLNKKVDDGFLDIWTYNAELLVLLE |
| 152 | KVNSVIEKMTYNAELLVLLE SEQ ID NO: 151 minus internal loop |
| 153 | Mutation region for H2 Sing 1957 KVNSVIEKMNTQFEAVGKEFSNLERRLENLNKKMEDGFLDVWTYNAELLVLME |
| 154 | KVNSVIEKMTYNAELLVLME; SEQ ID NO: 153 minus internal loop |
| 155 | Mutation region for H2 Indo 2005 KVNSIIDKMNTQFEAVGREFNNLERRIENLNKKMEDGFLDVWTYNAELLVLME |
| 156 | KVNSIIDKMTYNAELLVLME; SEQ ID NO: 155 minus internal loop |
| | ADDITIONAL CONSTRUCTS |
| 157 | Nucleic acid sequence encoding SEQ ID NO: 158 |
| 158 | Gen6_H1NC99_xx (rpk-22[MM]) K394M/E446M H1N1 A/New Caledonia/20/1999 HA Construct |
| 159 | Complement of SEQ ID NO: 157 |
| 160 | Nucleic acid sequence encoding SEQ ID NO: 161 |
| 161 | Gen6_H1NC99_xx (rpk-22[MM]) K394M/E446M H1N1 A/New Caledonia/20/1999 HA-Ferritin Construct |
| 162 | Complement of SEQ ID NO: 160 |
| 163 | Nucleic acid sequence encoding SEQ ID NO: 164 |
| 164 | Gen6_H1NC99_xx (rpk-22[II]) K394I/E446I H1N1 A/New Caledonia/20/1999 HA Construct |
| 165 | Complement of SEQ ID NO: 163 |
| 166 | Nucleic acid sequence encoding SEQ ID NO: 167 |
| 167 | Gen6_H1NC99_xx (rpk-22[II]) K394I/E446I H1N1 A/New Caledonia/20/1999 HA-Ferritin Construct |
| 168 | Complement of SEQ ID NO: 166 |
| 169 | Nucleic acid sequence encoding SEQ ID NO: 170 |
| 170 | Gen6_H1NC99_xx (rpk-22[LI]) K394I/E446I H1N1 A/New Caledonia/20/1999 HA Construct |
| 171 | Complement of SEQ ID NO: 169 |
| 172 | Nucleic acid sequence encoding SEQ ID NO: 173 |
| 173 | Gen6_H1NC99_xx (rpk-22[LI]) K394I/E446I H1N1 A/New Caledonia/20/1999 HA Ferritin Construct |
| 174 | Complement of SEQ ID NO: 172 |
| 175 | Nucleic acid sequence encoding SEQ ID NO: 176 |
| 176 | Gen6_H1NC99_xx (rpk-22[LL]) K394L/E446L H1N1 A/New Caledonia/20/1999 HA Construct |
| 177 | Complement of SEQ ID NO: 175 |
| 178 | Nucleic acid sequence encoding SEQ ID NO: 179 |
| 179 | Gen6_H1NC99_xx (rpk-22[LL]) K394L/E446L H1N1 A/New Caledonia/20/1999 HA-Ferritin Consruct |
| 180 | Complement of SEQ ID NO: 178 |
| 181 | Nucleic acid sequence encoding SEQ ID NO: 182 |
| 182 | GEN6_H1NC99_06 (RPK-3, GLY2-6-7(+ 3 GLY) H1N1 A/NEW CALEDONIA/20/1999 HA Construct |
| 183 | Complement of SEQ ID NO: 181 |
| 184 | Nucleic acid sequence encoding SEQ ID NO: 185 |
| 185 | GEN6_H1NC99_06 (RPK-3, GLY2-6-7 (+ 3 GLY) H1N1 A/NEW CALEDONIA/20/1999 HA-Ferritin Construct |
| 186 | Complement of SEQ ID NO: 184 |
| 187 | Nucleic acid sequence encoding SEQ ID NO: 188 |
| 188 | GEN6_H1NC99_06 (RPK-3, GLY2-5-6-7 (+ 4 GLY) H1N1 A/NEW CALEDONIA/20/1999 HA Construct |
| 189 | Complement of SEQ ID NO: 187 |
| 190 | Nucleic acid sequence encoding SEQ ID NO: 191 |
| 191 | GEN6_H1NC99_06 (RPK-3, GLY2-5-6-7 (+ 4 GLY) H1N1 A/NEW CALEDONIA/20/1999 HA-Ferritin Construct |
| 192 | Complement of SEQ ID NO: 190 |
| 193 | Nucleic acid sequence encoding SEQ ID NO: 194 |
| 194 | SP\|O66529\|RISB_AQUAE 6,7-DIMETHYL-8-RIBITYLLUMAZINE SYNTHASE OS = *AQUIFEX AEOLICUS* (STRAIN VF5) LUMAZINE SYNTHASE |
| 195 | Complement of SEQ ID NO: 193 |
| 196 | Nucleic acid sequence encoding SEQ ID NO: 197 |

TABLE 2-continued

| PCT SEQ ID NO | Comments |
|---|---|
| 197 | H1-NC99_GEN6_LS-01 HA Construct |
| 198 | Complement of SEQ ID NO: 196 |
| 199 | Nucleic acid sequence encoding SEQ ID NO: 200 |
| 200 | H1-NC99_GEN6_LS-01 HA-Lumazine Construct |
| 201 | Complement of SEQ ID NO: 199 |
| 202 | Nucleic acid sequence encoding SEQ ID NO: 203 |
| 203 | H1-NC99_GEN6_LS-02 HA Construct |
| 204 | Complement of SEQ ID NO: 202 |
| 205 | Nucleic acid sequence encoding SEQ ID NO: 206 |
| 206 | H1-NC99_GEN6_LS-02 HA-Lumazine Construct |
| 207 | Complement of SEQ ID NO: 205 |
| 208 | Nucleic acid sequence encoding SEQ ID NO: 209 |
| 209 | GEN6_H1NC99_K394M/E446L/E448Q/R449W/D452L/Y437D/N438L_N19Q (RPK-3 WT CLEAVAGE) H1N1 A/NEW CALEDONIA/20/1999 HA Construct |
| 210 | Complement of SEQ ID NO: 208 |
| 211 | Nucleic acid sequence encoding SEQ ID NO: 212 |
| 212 | GEN6_H1NC99_K394M/E446L/E448Q/R449W/D452L/Y437D/N438L_N19Q (RPK-3 WT CLEAVAGE) H1N1 A/NEW CALEDONIA/20/1999 HA-Ferritin Construct |
| 213 | Complement of SEQ ID NO: 211 |
| 214 | GEN6_H1CA09_K394M/E446L/E448Q/R449W/D452L/Y437D/N438L_N19Q (RPK-3 WT CLEAVAGE) H1N1 A/CALIFORNIA/4/2009 HA Construct |
| 215 | GEN6_H1CA09_K394M/E446L/E448Q/R449W/D452L/Y437D/N438L_N19Q (RPK-3 WT CLEAVAGE) H1N1 A/CALIFORNIA/4/2009 HA-Feritin Construct |
| 216 | Nucleic acid sequence encoding SEQ ID NO: 217 |
| 217 | GEN6_H1NC99_K394M/E446L/S339Q/I340R/Q341E/S342T_N19Q (RPK-22, DL→YN WT CLEAVAGE) H1N1 A/NEW CALEDONIA/20/1999 HA Construct |
| 218 | Complement of SEQ ID NO: 216 |
| 219 | Nucleic acid sequence encoding SEQ ID NO: 220 |
| 220 | GEN6_H1NC99_K394M/E446L/S339Q/I340R/Q341E/S342T_N19Q (RPK-22, DL→YN WT CLEAVAGE) H1N1 A/NEW CALEDONIA/20/1999 HA-Ferritin Construct |
| 221 | Complement of SEQ ID NO: 219 |
| 222 | GEN6_H1NC99_K394M/E446L/Y437D/N438L_N19Q (RPK-22, WT CLEAVAGE) H1N1 A/NEW CALEDONIA/20/1999 HA Construct |
| 223 | GEN6_H1NC99_K394M/E446L/Y437D/N438L_N19Q (RPK-22, WT CLEAVAGE) H1N1 A/NEW CALEDONIA/20/1999 HA-Ferritin Construct |
| 224 | GEN6_H1NC99_K394I/E446I/Y437D/N438L_N19Q (RPK-22 [II], WT CLEAVAGE) H1N1 A/NEW CALEDONIA/20/1999 HA Construct |
| 225 | GEN6_H1NC99_K394I/E446I/Y437D/N438L_N19Q (RPK-22 [II], WT CLEAVAGE) H1N1 A/NEW CALEDONIA/20/1999 HA-Ferritin Construct |
| 226 | GEN6_H1NC99_K394L/E446I/Y437D/N438L_N19Q (RPK-22 [LI], WT CLEAVAGE) H1N1 A/NEW CALEDONIA/20/1999 HA Construct |
| 227 | GEN6_H1NC99_K394L/E446I/Y437D/N438L_N19Q (RPK-22 [LI], WT CLEAVAGE) H1N1 A/NEW CALEDONIA/20/1999 HA-Ferritin Construct |
| 228 | GEN6_H1NC99_K394L/E446L/Y437D/N438L_N19Q (RPK-22 [LL], WT CLEAVAGE) H1N1 A/NEW CALEDONIA/20/1999 HA Construct |
| 229 | GEN6_H1NC99_K394L/E446L/Y437D/N438L_N19Q (RPK-22 [LL], WT CLEAVAGE) H1N1 A/NEW CALEDONIA/20/1999 HA-Ferritin Construct |
| 230 | GEN6_H1NC99_K394M/E446M/Y437D/N438L_N19Q (RPK-22 [MM], WT CLEAVAGE) H1N1 A/NEW CALEDONIA/20/1999 HA Construct |
| 231 | GEN6_H1NC99_K394M/E446M/Y437D/N438L_N19Q (RPK-22 [MM],WT CLEAVAGE) H1N1 A/NEW CALEDONIA/20/1999 HA-Ferritin Construct |
| 232 | GEN6_H1NC99_K394Q/E446Q/Y437D/N438L_N19Q (RPK-22 [QQ], WT CLEAVAGE) H1N1 A/NEW CALEDONIA/20/1999 HA Construct |
| 233 | GEN6_H1NC99_K394Q/E446Q/Y437D/N438L_N19Q (RPK-22 [QQ], WT CLEAVAGE) H1N1 A/NEW CALEDONIA/20/1999 HA-Ferritin Construct |
| 234 | Nucleic aicd sequence encoding SEQ ID NO: 235 |
| 235 | GEN6_H1NC99_K394M/E446L/Y437D/N438L/H45N/V47T_N19Q (RPK-22, H3-LIKE GLY, WT CLEAVAGE) H1N1 A/NEW CALEDONIA/20/1999 HA Construct |
| 236 | Complement of SEQ ID NO: 234 |
| 237 | Nucleic aicd sequence encoding SEQ ID NO: 238 |
| 238 | GEN6_H1NC99_K394M/E446L/Y437D/N438L/H45N/V47T_N19Q (RPK-22, H3-LIKE GLY, WT CLEAVAGE) H1N1 A/NEW CALEDONIA/20/1999 HA-Ferritin Construct |
| 239 | Complement of SEQ ID NO: 237 |
| 240 | GEN6_H1NC99_V36I/K394M/L445M/E446L/E448Q/R449F/D452L/Y437D/N438L_N19Q (RPK-08, WT CLEAVAGE) H1N1 A/NEW CALEDONIA/20/1999 HA Construct |
| 241 | GEN6_H1NC99_V36I/K394M/L445M/E446L/E448Q/R449F/D452L/Y437D/N438L_N19Q (RPK-08, WT CLEAVAGE) H1N1 A/NEW CALEDONIA/20/1999 HA-Ferritin Construct |
| 242 | Gen6_H1NC99_K394M/E446L/E448Q/R449W/D452L/S402bN/G402dT/S402eG/T402gA/Y437D/N438L_N19Q (rpk-3, gly1, wt cleavage) H1N1 A/New Caledonia/20/1999 HA Construct |
| 243 | Gen6_H1NC99_K394M/E446L/E448Q/R449W/D452L/S402bN/G402dT/S402eG/T402gA/Y437D/N438L_N19Q (rpk-3, gly1, wt cleavage) H1N1 A/New Caledonia/20/1999 HA-Ferritin construct |

TABLE 2-continued

Figure 5:
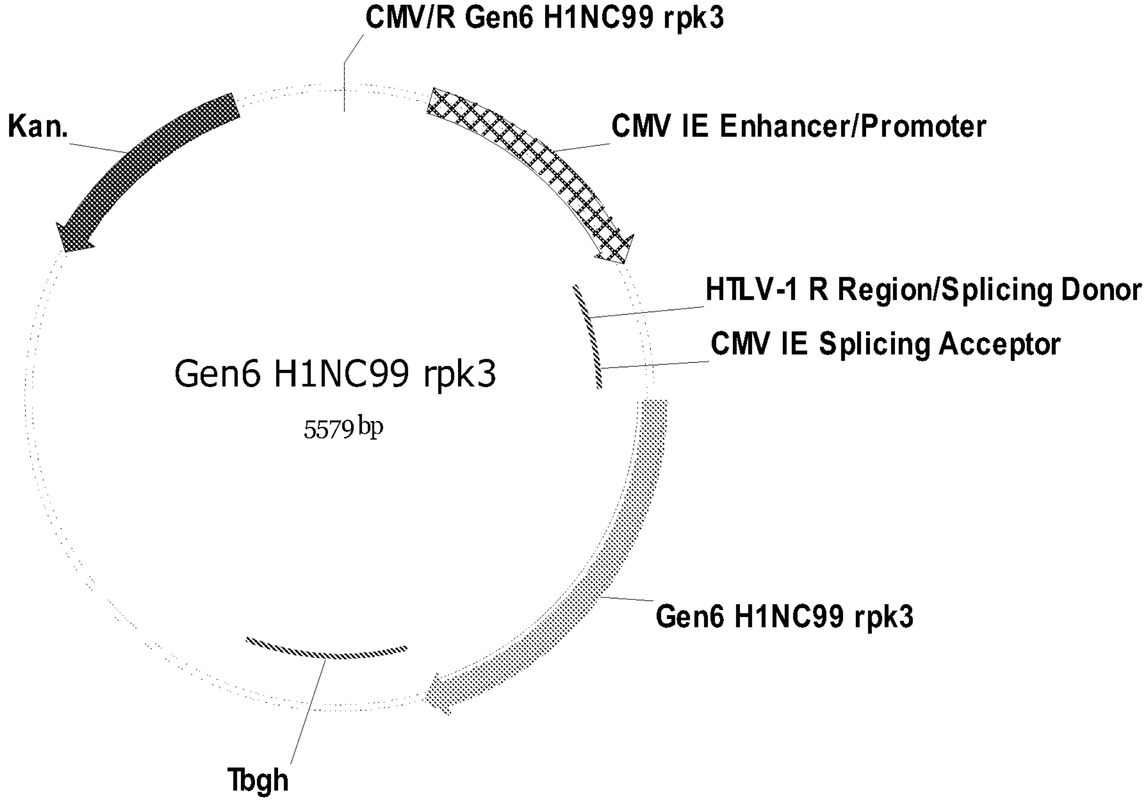
FIGS. 5-24 provide the plasmid map and sequences used in producing the peptide constructs of the present invention. As described in detail in Table 2 of this disclosure.
Figure 6:
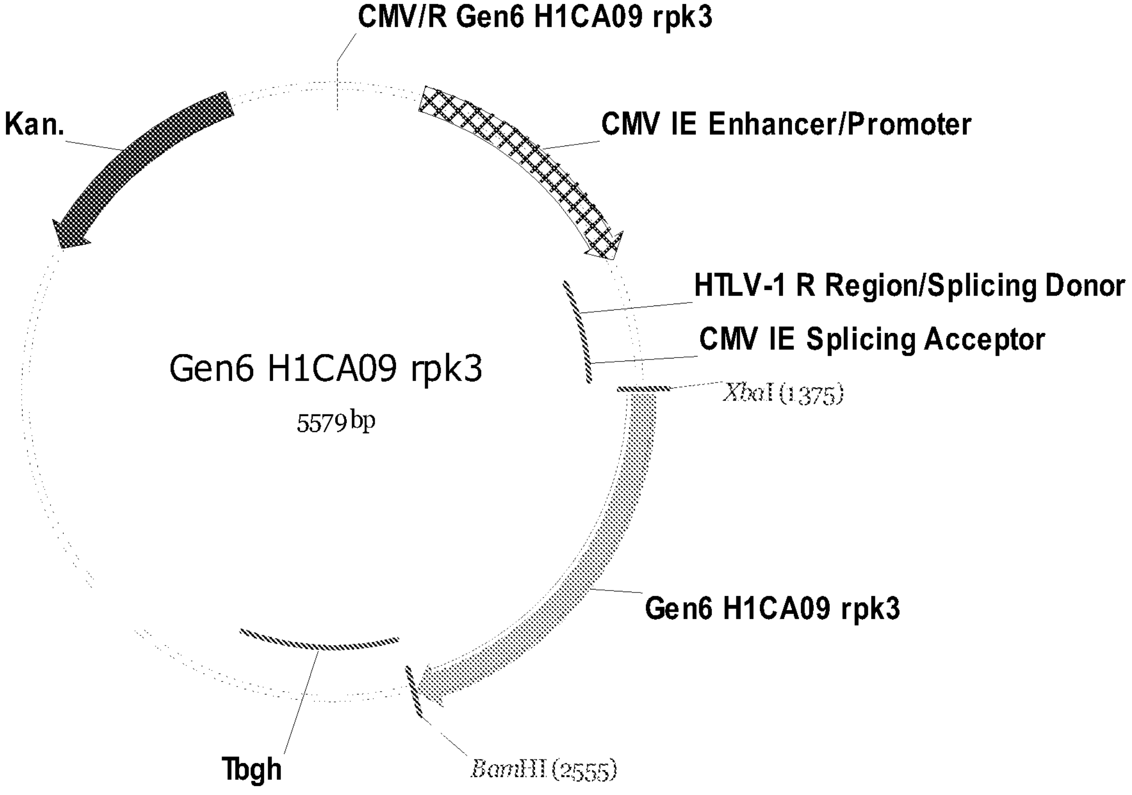
Figure 7:
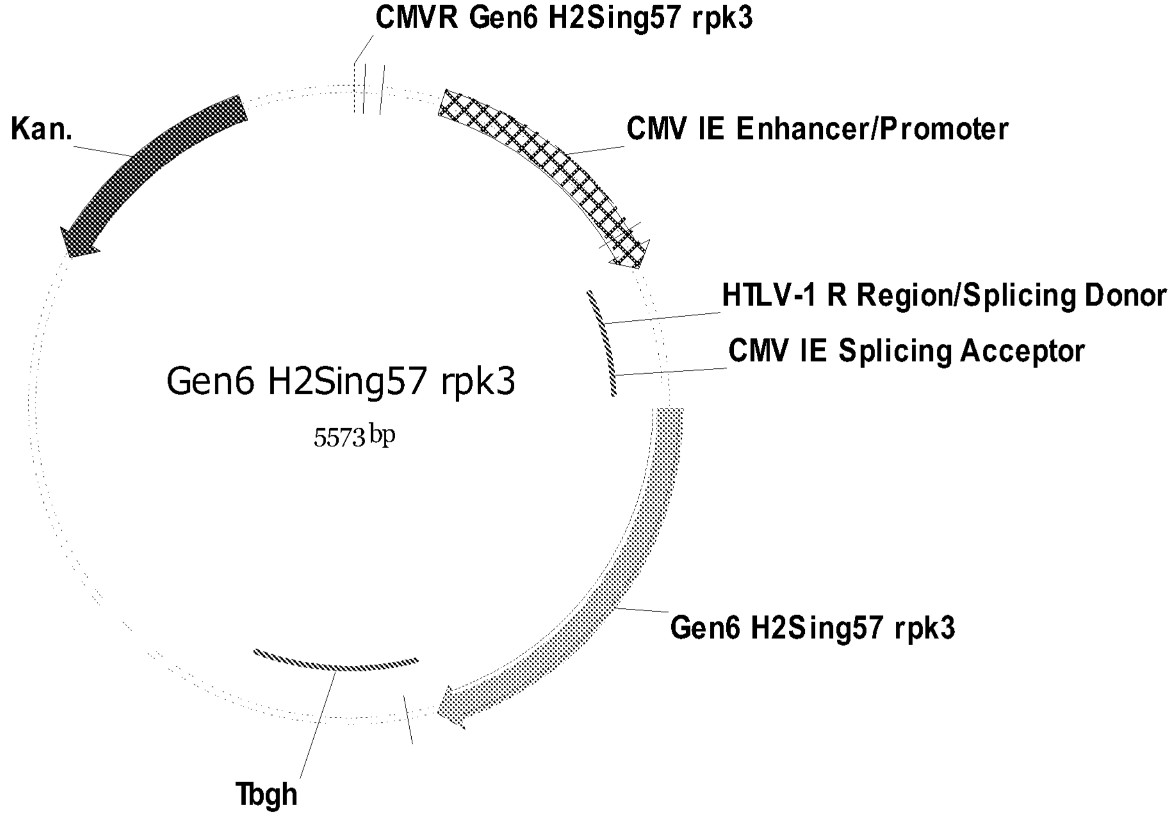
Figure 8:
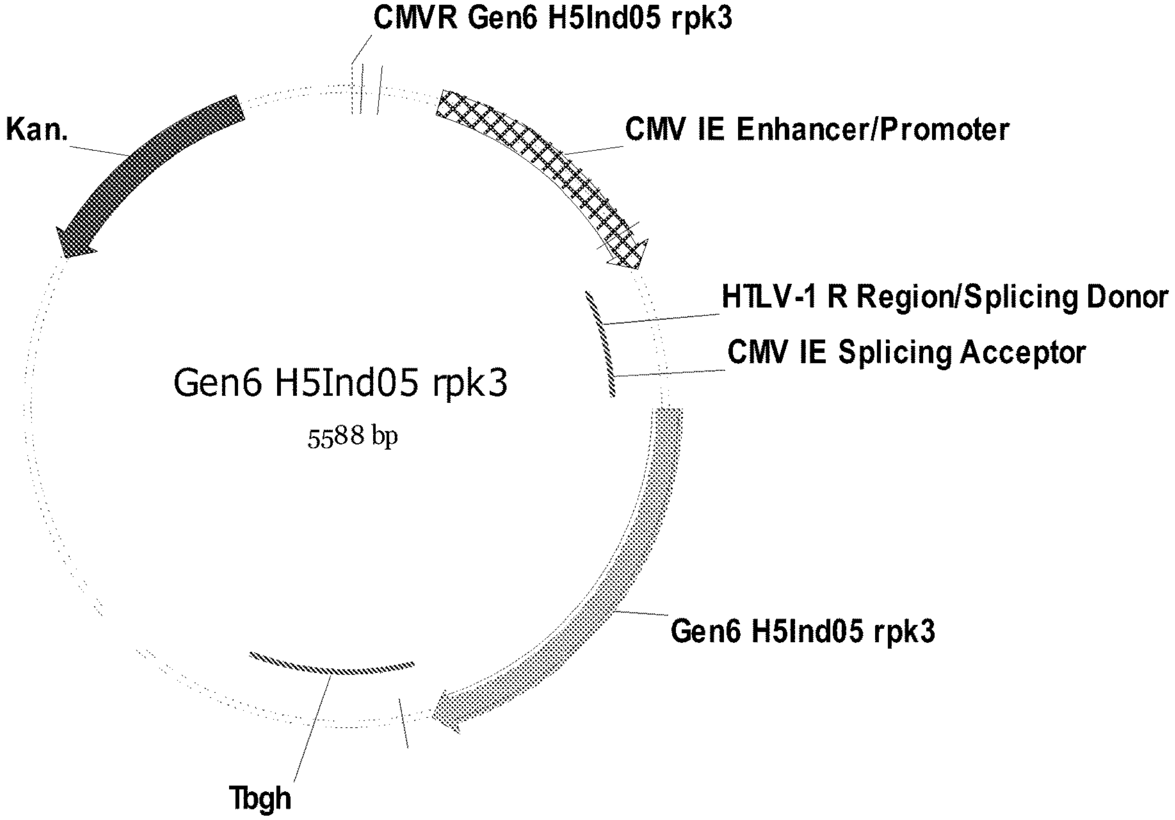

| PCT SEQ ID NO | Comments |
|---|---|
| 244 | Gen6_H1NC99_K394M/E446L/E448Q/R449W/D452L/S402bG/G402cN/S402eT/T402gA/Y437D/N438L_N19Q (rpk-3, gly2, wt cleavage) H1N1 A/New Caledonia/20/1999 HA Construct |
| 245 | Gen6_H1NC99_K394M/E446L/E448Q/R449W/D452L/S402bG/G402cN/S402eT/T402gA/Y437D/N438L_N19Q (rpk-3, gly2, wt cleavage) H1N1 A/New Caledonia/20/1999 HA-Ferritin Construct |
| 246 | GEN6_H1NC99_K394M/E446L/E448Q/R449W/D452L/S402EN/Y437D/N438L_N19Q (RPK-3, GLY3, WT CLEAVAGE) H1N1 A/NEW CALEDONIA/20/1999 HA Construct |
| 247 | GEN6_H1NC99_K394M/E446L/E448Q/R449W/D452L/S402EN/Y437D/N438L_N19Q (RPK-3, GLY3, WT CLEAVAGE) H1N1 A/NEW CALEDONIA/20/1999 HA-Ferritin Construct |
| 248 | Gen6_H1NC99_K394M/E446L/E448Q/R449W/D452L/G402cN/G402eT/T402gA/Q370N/E372T/Y437D/N438L_S21T (rpk-3, gly2-6-7, wt cleavage) H1N1 A/New Caledonia/20/1999 HA Construct |
| 249 | Gen6_H1NC99_K394M/E446L/E448Q/R449W/D452L/G402cN/G402eT/T402gA/Q370N/E372T/Y437D/N438L_S21T (rpk-3, gly2-6-7, wt cleavage) H1N1 A/New Caledonia/20/1999 HA-Ferritin Construct |
| 250 | Gen6_H1NC99_K394M/E446L/E448Q/R449W/D452L/G402cN/G402eT/T402gA/Q370N/E372T/Y437D/N438L_S21T/Q69N (rpk-3, gly2-5-6-7, wt cleavage) H1N1 A/New Caledonia/20/1999 HA Construct |
| 251 | Gen6_H1NC99_K394M/E446L/E448Q/R449W/D452L/G402cN/G402eT/T402gA/Q370N/E372T/Y437D/N438L_S21T/Q69N (rpk-3, gly2-5-6-7, wt cleavage) H1N1 A/New Caledonia/20/1999 HA-Ferritin Construct |
| 252 | GEN6_H1NC99_LS1_K394M/E446L/Y437D/N438L/A515-517 (RPK-22_LS1, WT CLEAVAGE) HA-Construct |
| 253 | GEN6_H1NC99_LS1_K394M/E446L/Y437D/N438L/A515-517 (RPK-22_LS1,WT CLEAVAGE)HA-Lumazine Construct |
| 254 | H1-NC99_GEN6_LS2_K394M/E446L/Y437D/N438L/A515-517 (RPK-22_LS2, WT CLEAVAGE) HA Construct |
| 255 | H1-NC99_GEN6_LS2_K394M/E446L/Y437D/N438L/A515-517 (RPK-22_LS2, WT CLEAVAGE) HA-Lumazine Construct |
| 256 | H1-NC99_GEN6_LS3_K394M/E446L/Y437D/N438L/A512-517 (RPK-22_LS3, WT CLEAVAGE) HA Construct |
| 257 | H1-NC99_GEN6_LS3_K394M/E446L/Y437D/N438L/A512-517 (RPK-22_LS3, WT CLEAVAGE) HA-Lumazine |
| 258 | H1-NC99_GEN6_LS4_K394M/E446L/Y437D/N438L/A512-517 (RPK-22_LS4, WT CLEAVAGE)HA Construct |
| 259 | H1-NC99_GEN6_LS4_K394M/E446L/Y437D/N438L/A512-517 (RPK-22_LS4, WT CLEAVAGE) HA-Lumazine Construct |
| 260 | Nucleic acid sequence encoding SEQ ID NO: 261 |
| 261 | Gen6_H1NC99_K394M/E446L/E448Q/R449W/D452L/Y437D/N438L_N19Q HA portion of insert |
| 262 | Complement of SEQ ID NO: 260 |
| 263 | Nucleic acid sequence encoding SEQ ID NO: 264 |
| 264 | Gen6_H1NC99_K394M/E446L/E448Q/R449W/D452L/Y437D/N438L_N19Q HA-Ferritin insert |
| 265 | Complement of SEQ ID NO: 263 |
| 266 | Sequence of entire plasmid from FIG. 5 |
| 267 | Nucleic acid sequence encoding SEQ ID NO: 268 |
| 268 | Gen6_H1CA09_K394M/E446L/E448Q/R449W/D452L/Y437D/N438L_N19Q HA portion of insert |
| 269 | Complement of SEQ ID NO: 267 |
| 270 | Nucleic acid sequence encoding SEQ ID NO: 271 |
| 271 | Gen6_H1CA09_K394M/E446L/E448Q/R449W/D452L/Y437D/N438L_N19Q HA-Ferritin insert |
| 272 | Complement of SEQ ID NO: 270 |
| 273 | Sequence of entire plasmid from FIG. 6 |
| 274 | Nucleic acid sequence encoding SEQ ID NO: 275 |
| 275 | Gen6_H2Sing57_K394M/M445L/E446L/E448Q/R449W/D452L/Y437D/N438L_N19Q HA portion of insert |
| 276 | Complement of SEQ ID NO: 274 |
| 277 | Nucleic acid sequence encoding SEQ ID NO: 278 |
| 278 | Gen6_H2Sing57_K394M/M445L/E446L/E448Q/R449W/D452L/Y437D/N438L_N19Q HA-Ferritin insert |
| 279 | Complement of SEQ ID NO: 277 |
| 280 | Sequence of entire plasmid from FIG. 7 |
| 281 | Nucleic acid sequence encoding SEQ ID NO: 282 |
| 282 | Gen6_H5Ind05_K394M/M445L/E446L/E448Q/R449W/D452L/Y437D/N438L/S49bW_N19Q HA portion of insert |
| 283 | Complement of SEQ ID NO: 281 |
| 284 | Nucleic acid sequence encoding SEQ ID NO: 285 |
| 285 | Gen6_H5Ind05_K394M/M445L/E446L/E448Q/R449W/D452L/Y437D/N438L/S49bW_N19Q HA-Ferritin insert |
| 286 | Complement of SEQ ID NO: 284 |
| 287 | Sequence of entire plasmid from FIG. 8 |
| 288 | Nucleic acid sequence encoding SEQ ID NO: 289 |

TABLE 2-continued

Figure 9:
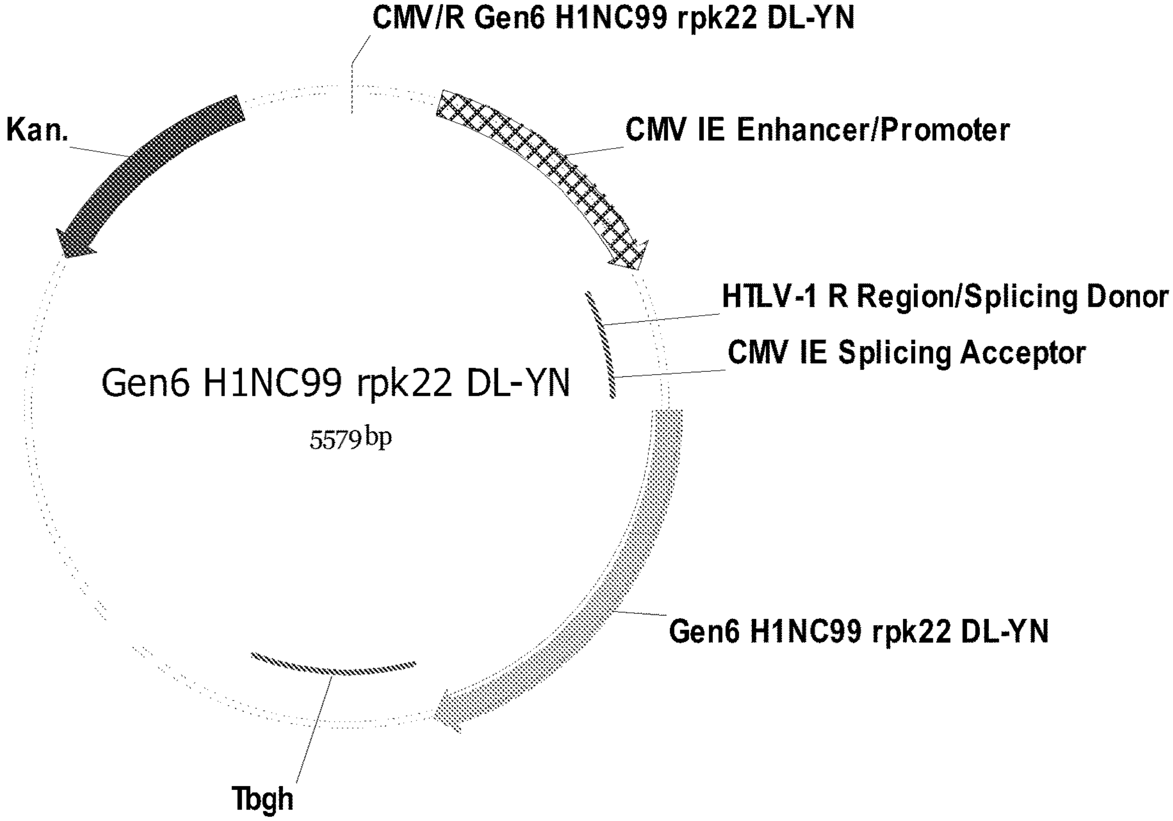
Figure 10:
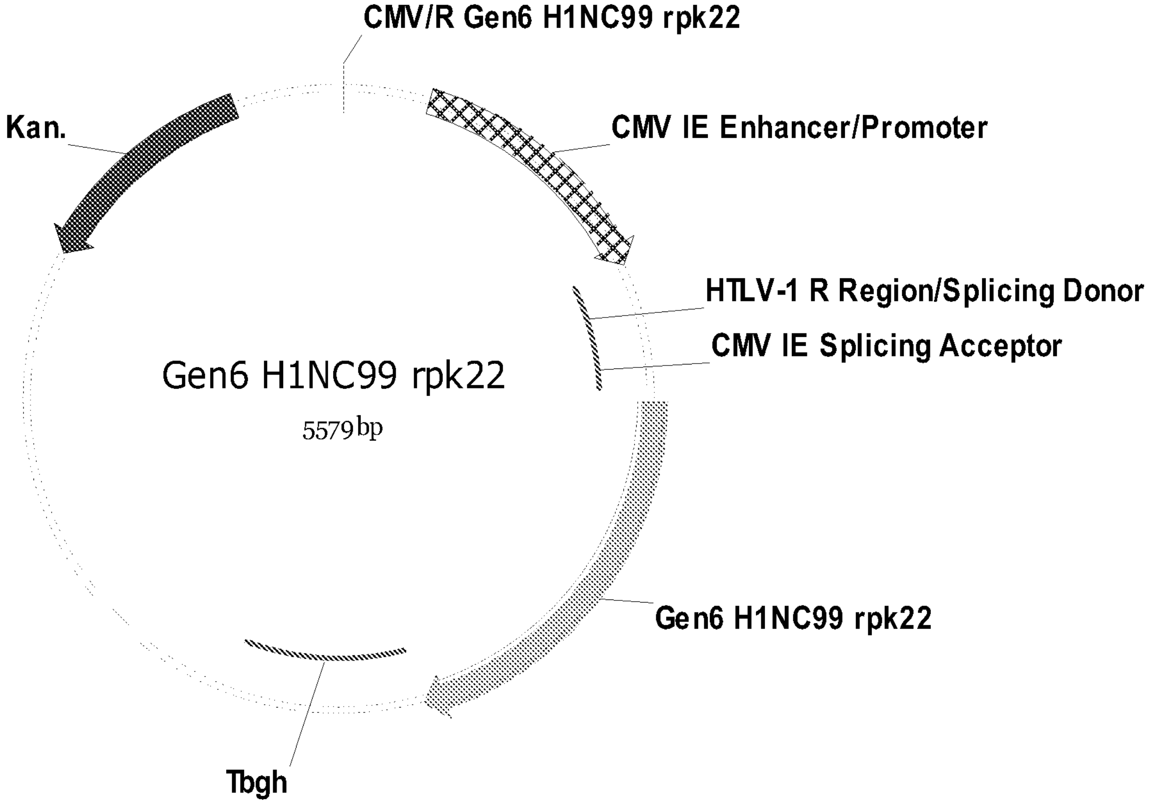
Figure 11:
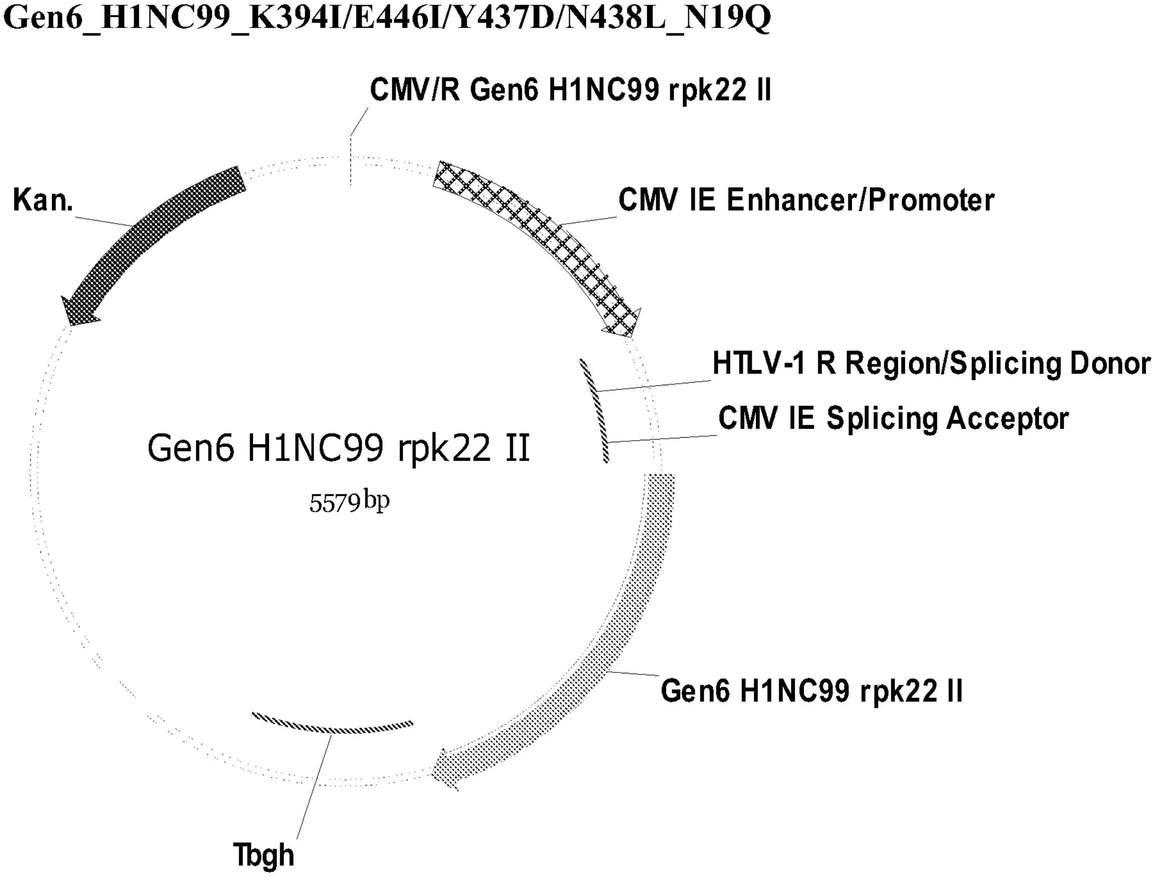
Figure 12:
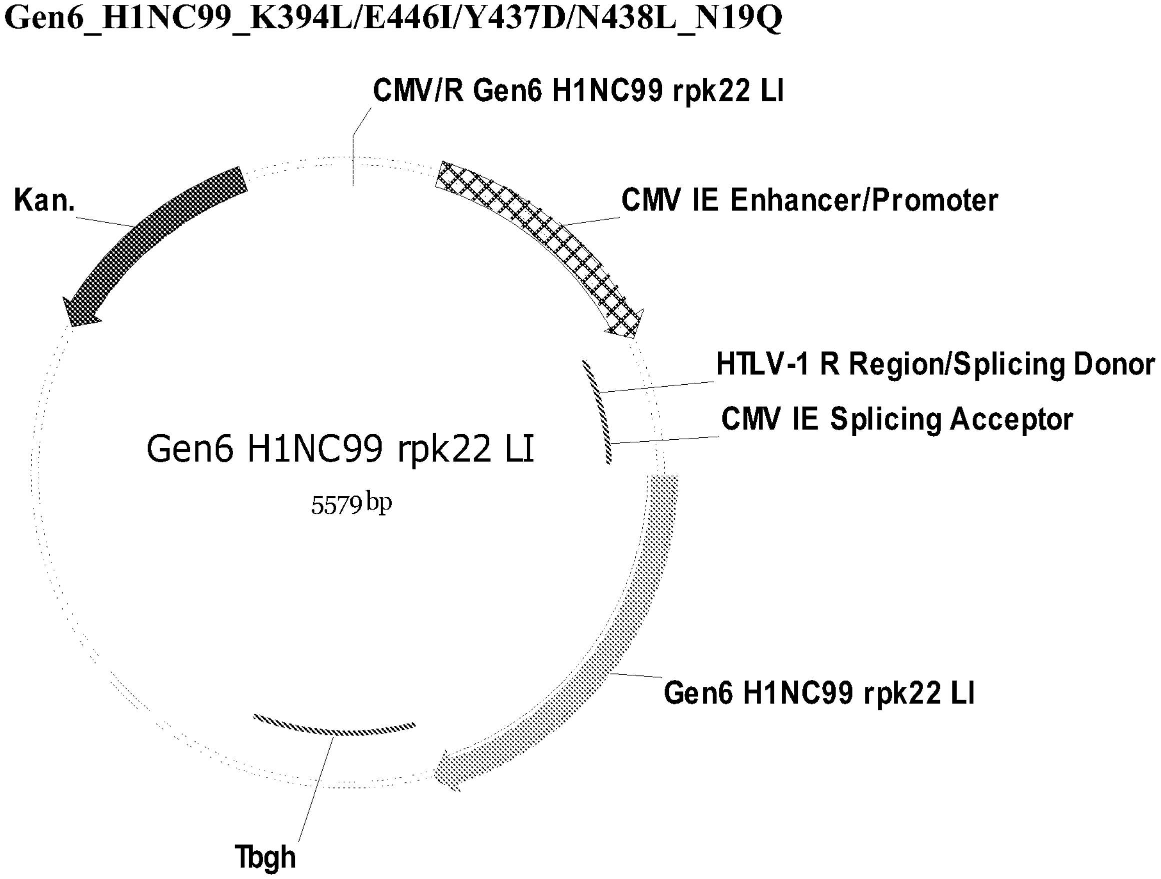
Figure 13:
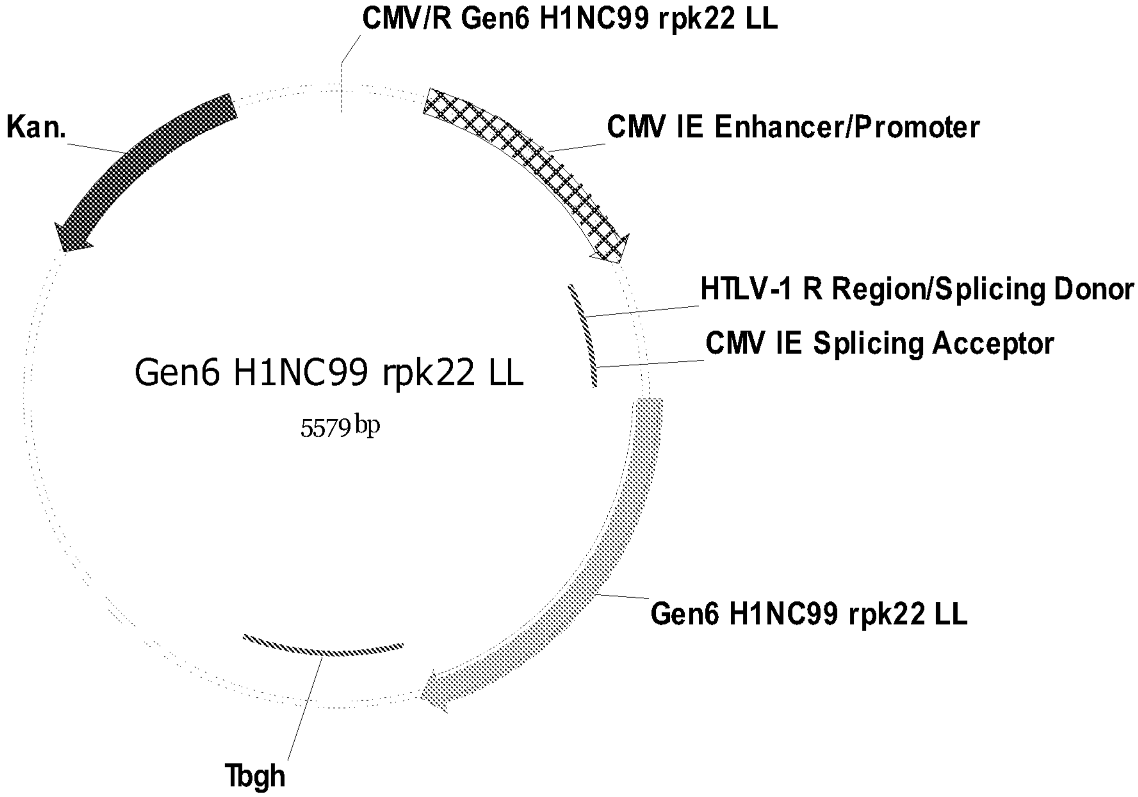
Figure 14:
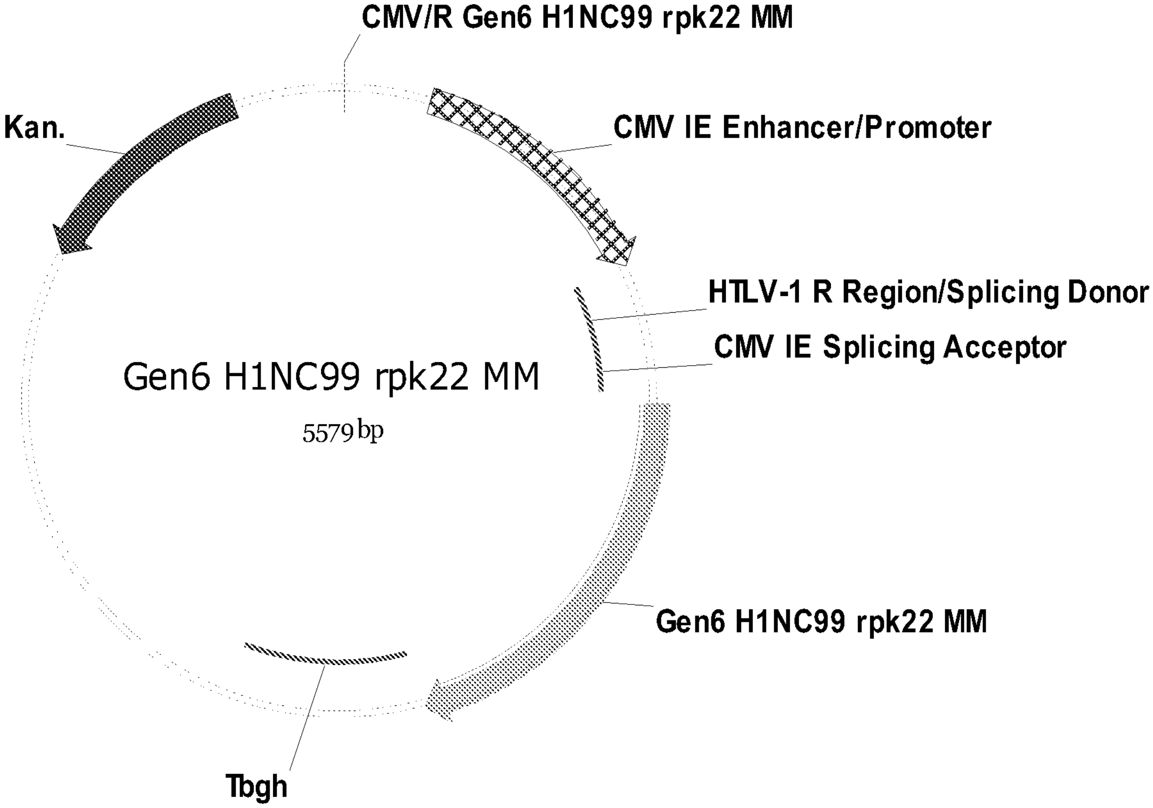
Figure 15:
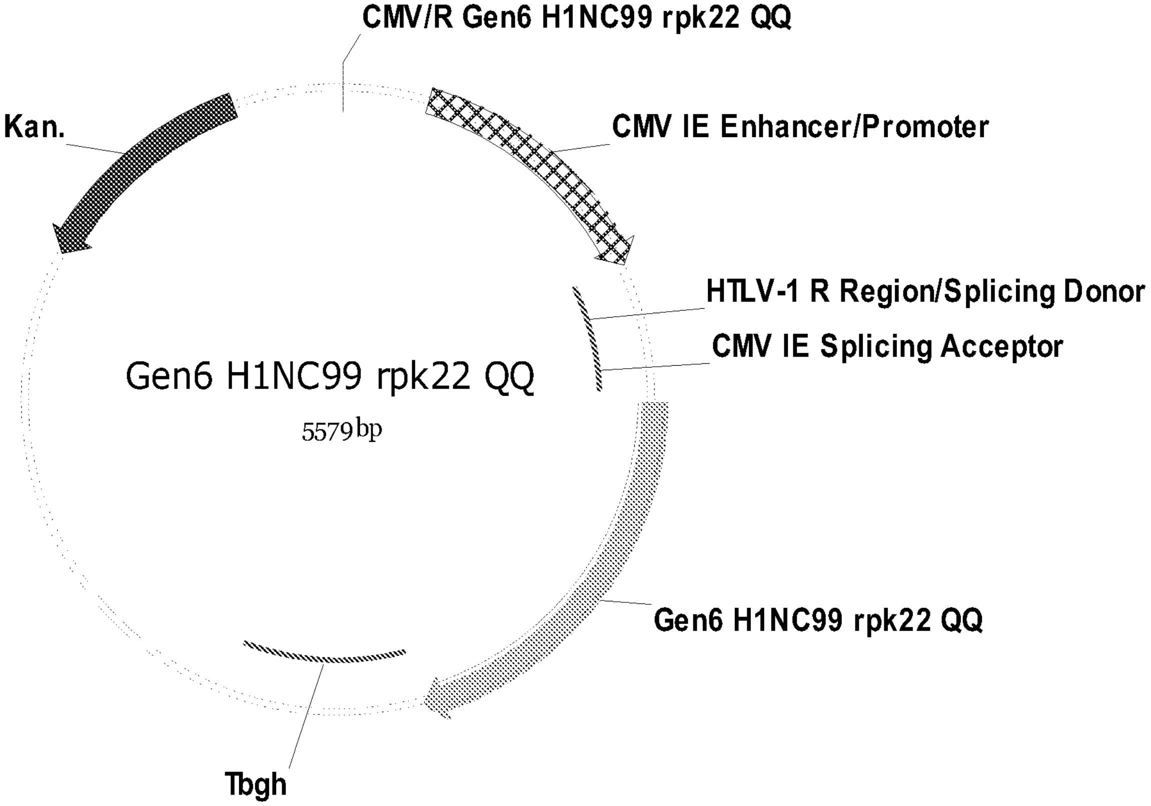
Figure 16:
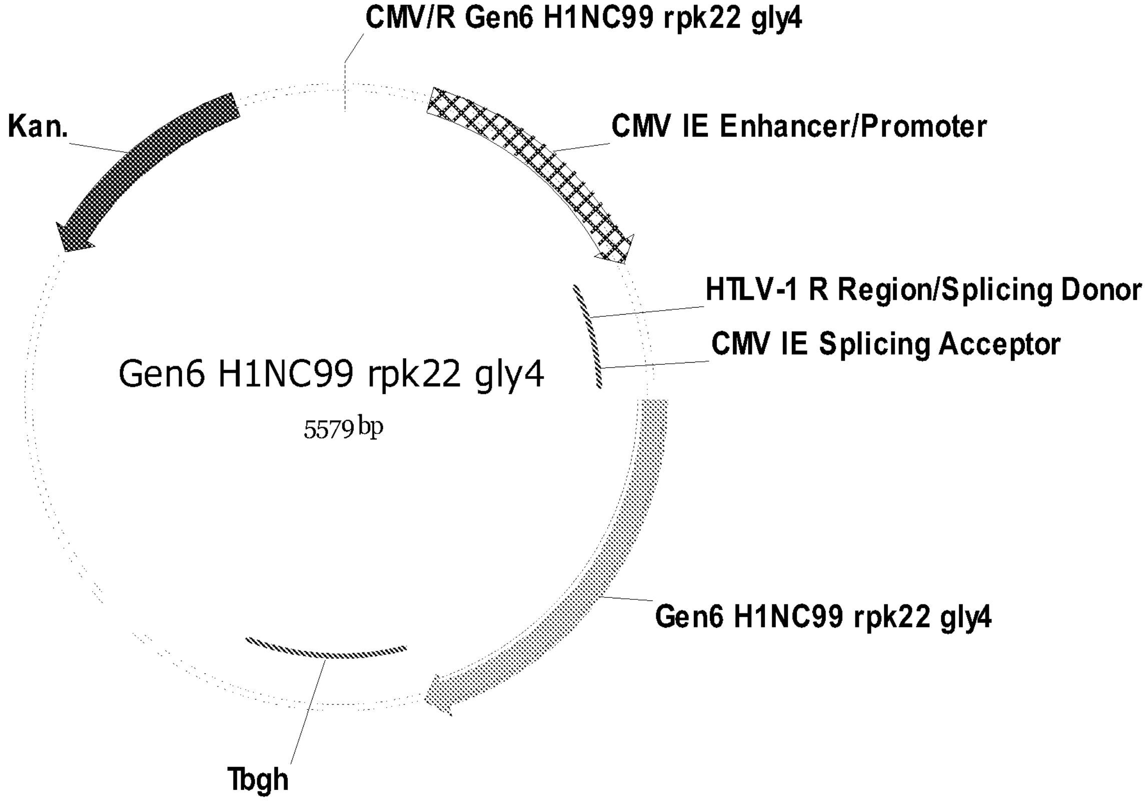
Figure 17:
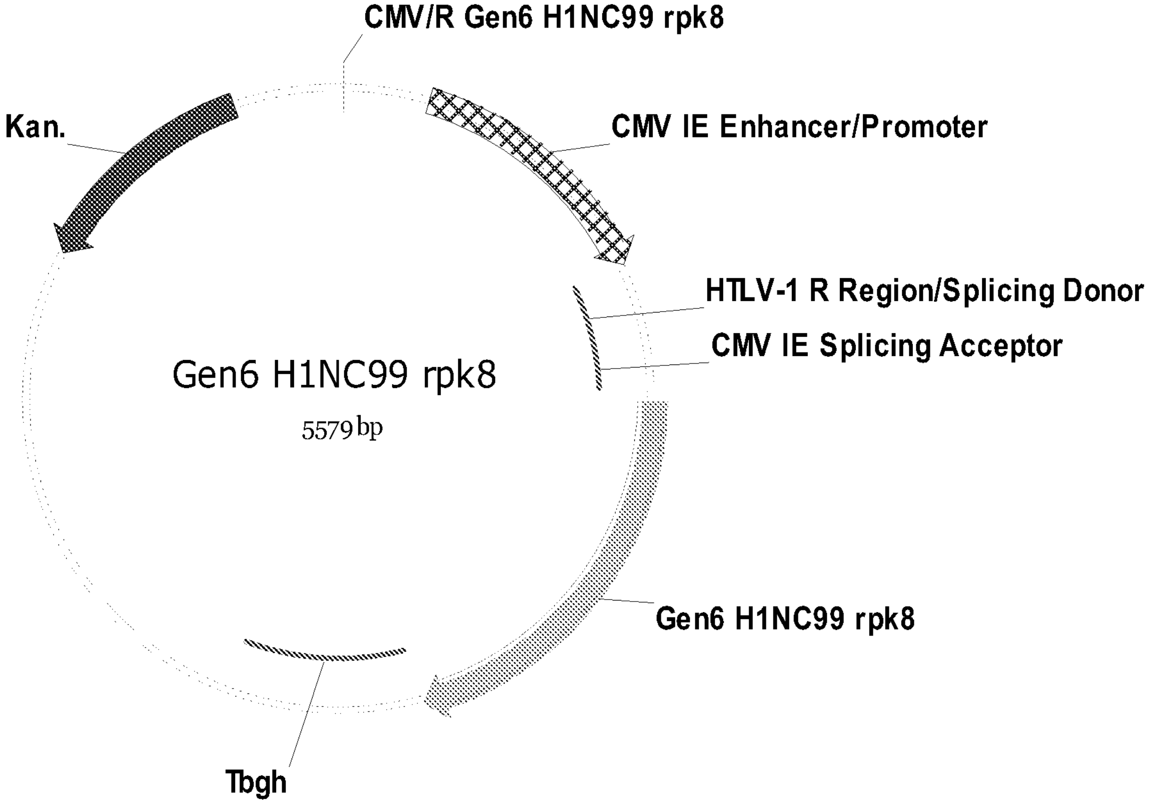
Figure 18:
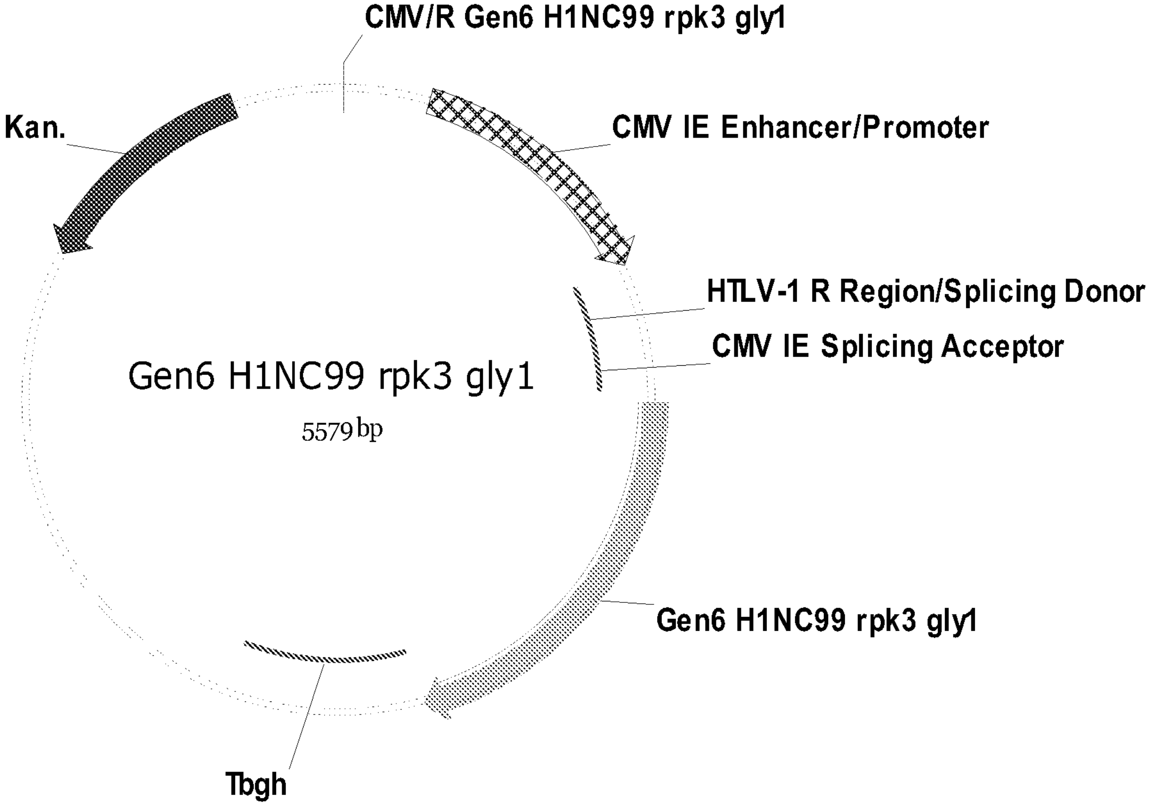

| PCT SEQ ID NO | Comments |
|---|---|
| 289 | Gen6_H1NC99_K394M/E446L_N19Q HA portion of insert |
| 290 | Complement of SEQ ID NO: 288 |
| 291 | Nucleic acid sequence encoding SEQ ID NO: 292 |
| 292 | Gen6_H1NC99_K394M/E446L_N19Q HA-Ferritin insert |
| 293 | Complement of SEQ ID NO: 291 |
| 294 | Sequence of entire plasmid from FIG. 9 |
| 295 | Nucleic acid sequence encoding SEQ ID NO: 296 |
| 296 | Gen6_H1NC99_K394M/E446L/Y437D/N438L_N19Q HA portion of insert |
| 297 | Compement of SEQ ID NO: 295 |
| 298 | Nucleic acid sequence encoding SEQ ID NO: 299 |
| 299 | Gen6_H1NC99_K394M/E446L/Y437D/N438L_N19Q HA-Ferritin insert |
| 300 | Complement of SEQ ID NO: 298 |
| 301 | Sequence of entire plasmid from FIG. 10 |
| 302 | Nucleic acid sequence encoding SEQ ID NO: 303 |
| 303 | Gen6_H1NC99_K394I/E446I/Y437D/N438L_N19Q HA portion of insert |
| 304 | Complement of SEQ ID NO: 302 |
| 305 | Nucleic acid sequence encoding SEQ ID NO: 306 |
| 306 | Gen6_H1NC99_K394I/E446I/Y437D/N438L_N19Q HA-Ferritin insert |
| 307 | Complement of SEQ ID NO: 305 |
| 308 | Sequence of entire plasmid from FIG. 11 |
| 309 | Nucleic acid sequence encoding SEQ ID NO: 310 |
| 310 | Gen6_H1NC99_K394L/E446I/Y437D/N438L_N19Q HA portion of insert |
| 311 | Complement of SEQ ID NO: 309 |
| 312 | Nucleic acid sequence encoding SEQ ID NO: 313 |
| 313 | Gen6_H1NC99_K394L/E446I/Y437D/N438L_N19Q HA-Ferritin Insert |
| 314 | Complement of SEQ ID NO: 312 |
| 315 | Sequence of entire plasmid from FIG. 12 |
| 316 | Nucleic acid sequence encoding SEQ ID NO: 317 |
| 317 | Gen6_H1NC99_K394L/E446L/Y437D/N438L_N19Q HA portion of Insert |
| 318 | Complement of SEQ ID NO: 316 |
| 319 | Nucleic acid sequence encoding SEQ ID NO: 320 |
| 320 | Gen6_H1NC99_K394L/E446L/Y437D/N438L_N19Q HA-Ferritin Insert |
| 321 | Complement of SEQ ID NO: 319 |
| 322 | Sequence of entire plasmid from FIG. 13 |
| 323 | Nucleic acid sequence encoding SEQ ID NO: 324 |
| 324 | Gen6_H1NC99_K394M/E446M/Y437D/N438L_N19Q HA portion of Insert |
| 325 | Complement of SEQ ID NO: 323 |
| 326 | Nucleic acid sequence encoding SEQ ID NO: 327 |
| 327 | Gen6_H1NC99_K394M/E446M/Y437D/N438L_N19Q HA-Ferritin Insert |
| 328 | Complement of SEQ ID NO: 326 |
| 329 | Sequence of entire plasmid from FIG. 14 |
| 330 | Nucleic acid sequence encoding SEQ ID NO: 331 |
| 331 | Gen6_H1NC99_K394Q/E446Q/Y437D/N438L_N19Q HA portion of Insert |
| 332 | Complement of SEQ ID NO: 330 |
| 333 | Nucleic acid sequence encoding SEQ ID NO: 334 |
| 334 | Gen6_H1NC99_K394Q/E446Q/Y437D/N438L_N19Q HA-Ferritin Insert |
| 335 | Complement of SEQ ID NO: 333 |
| 336 | Sequence of entire plasmid from FIG. 15 |
| 337 | Nucleic acid sequence encoding SEQ ID NO: 338 |
| 338 | Gen6_H1NC99_K394M/E446L/Y437D/N438L/H45N/V47T_N19Q HA portion of Insert |
| 339 | Complement of SEQ ID NO: 337 |
| 340 | Nucleic acid sequence encoding SEQ ID NO: 341 |
| 341 | Gen6_H1NC99_K394M/E446L/Y437D/N438L/H45N/V47T_N19Q HA-Ferritin Insert |
| 342 | Complement of SEQ ID NO: 340 |
| 343 | Sequence of entire plasmid from FIG. 16 |
| 344 | Nucleic acid sequence encoding SEQ ID NO: 345 |
| 345 | Gen6_H1NC99_V36I/K394M/L445M/E446L/E448Q/R449F/D452L/Y437D/N438L_N19Q HA portion of Insert |
| 346 | Complement of SEQ ID NO: 344 |
| 347 | Nucleic acid sequence encoding SEQ ID NO: 348 |
| 348 | Gen6_H1NC99_V36I/K394M/L445M/E446L/E448Q/R449F/D452L/Y437D/N438L_N19Q HA-Ferritin Insert |
| 349 | Complement of SEQ ID NO: 347 |
| 350 | Sequence of entire plasmid from FIG. 17 |
| 351 | Nucleic acid sequence encoding SEQ ID NO: 352 |
| 352 | Gen6_H1NC99_K394M/E446L/E448Q/R449W/D452L/S402bN/G402dT/S402eG/T402gA/Y437D/N438L_N19Q HA portion of Insert |
| 353 | Complement of SEQ ID NO: 351 |
| 354 | Nucleic acid sequence encoding SEQ ID NO: 355 |
| 355 | Gen6_H1NC99_K394M/E446L/E448Q/R449W/D452L/S402bN/G402dT/S402eG/T402gA/Y437D/N438L_N19Q HA-Ferritin Insert |
| 356 | Complement of SEQ ID NO: 354 |
| 357 | Sequence of entire plasmid from FIG. 18 |
| 358 | Nucleic acid sequence encoding SEQ ID NO: 359 |
| 359 | Gen6_H1NC99_K394M/E446L/E448Q/R449W/D452L/S402bG/G402cN/S402eT/T402gA/Y437D/N438L_N19Q HA portion of Insert |

TABLE 2-continued

Figure 19:
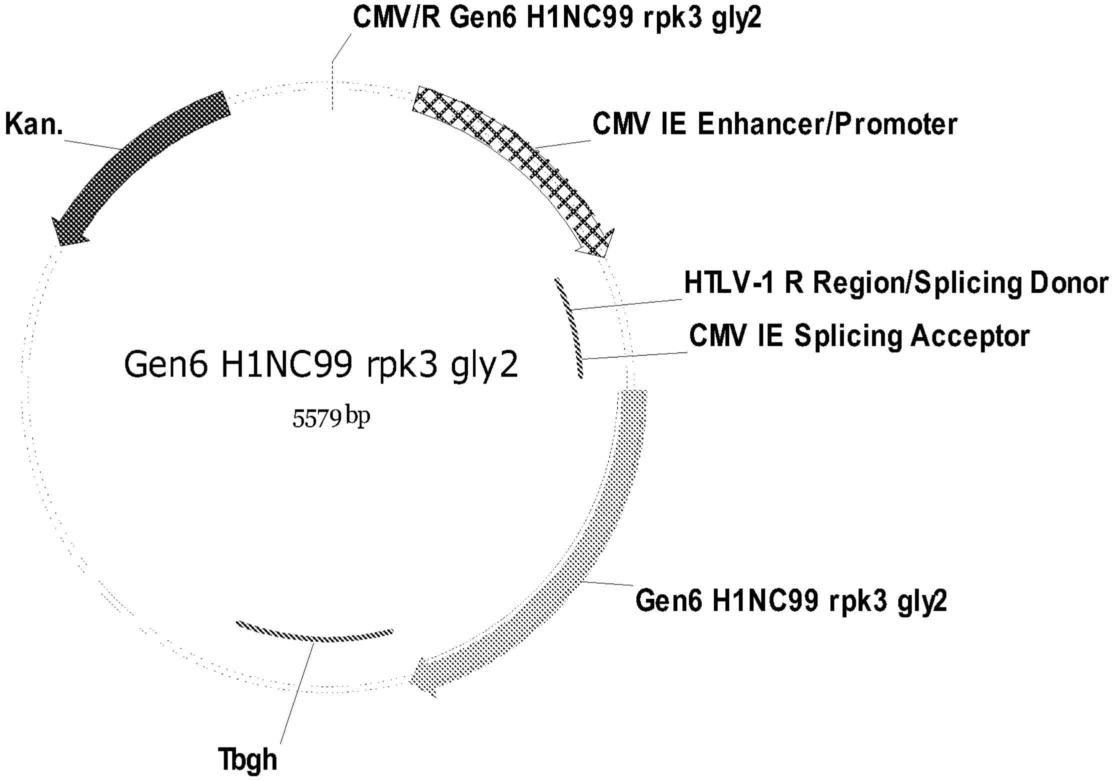
Figure 20:
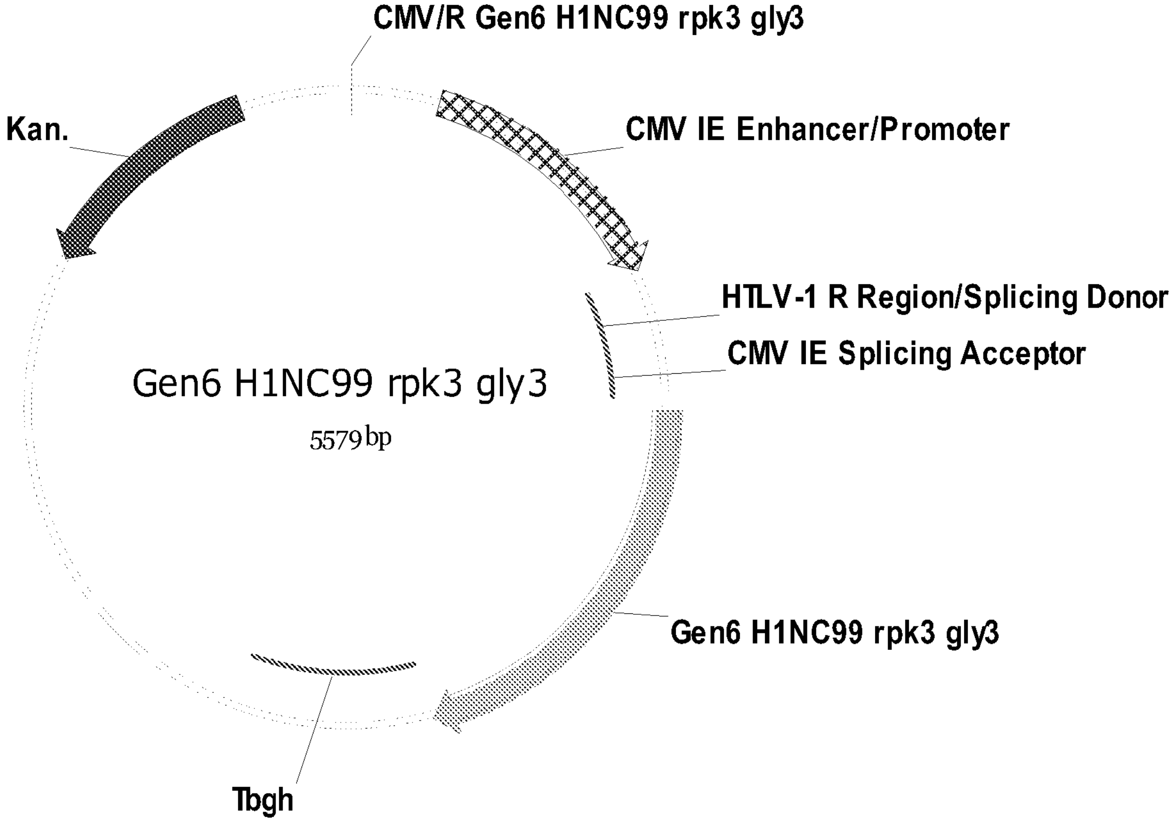
Figure 21:
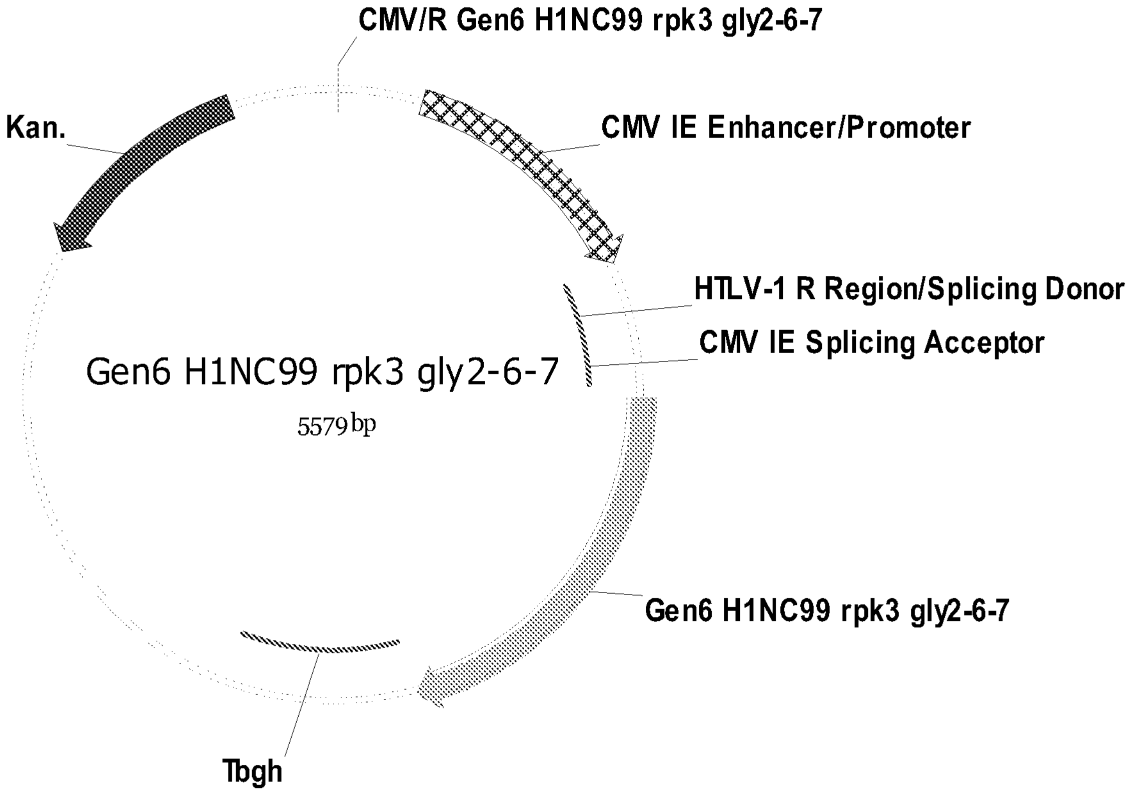
Figure 22:
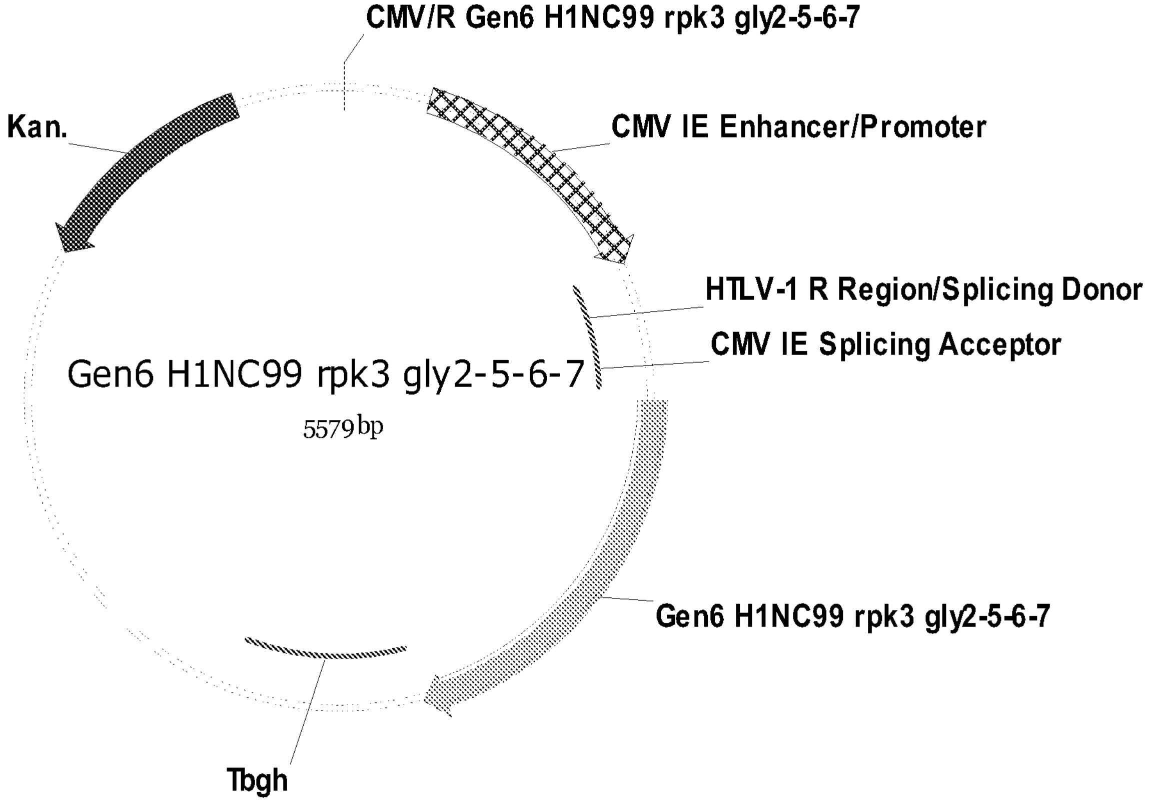
Figure 23:
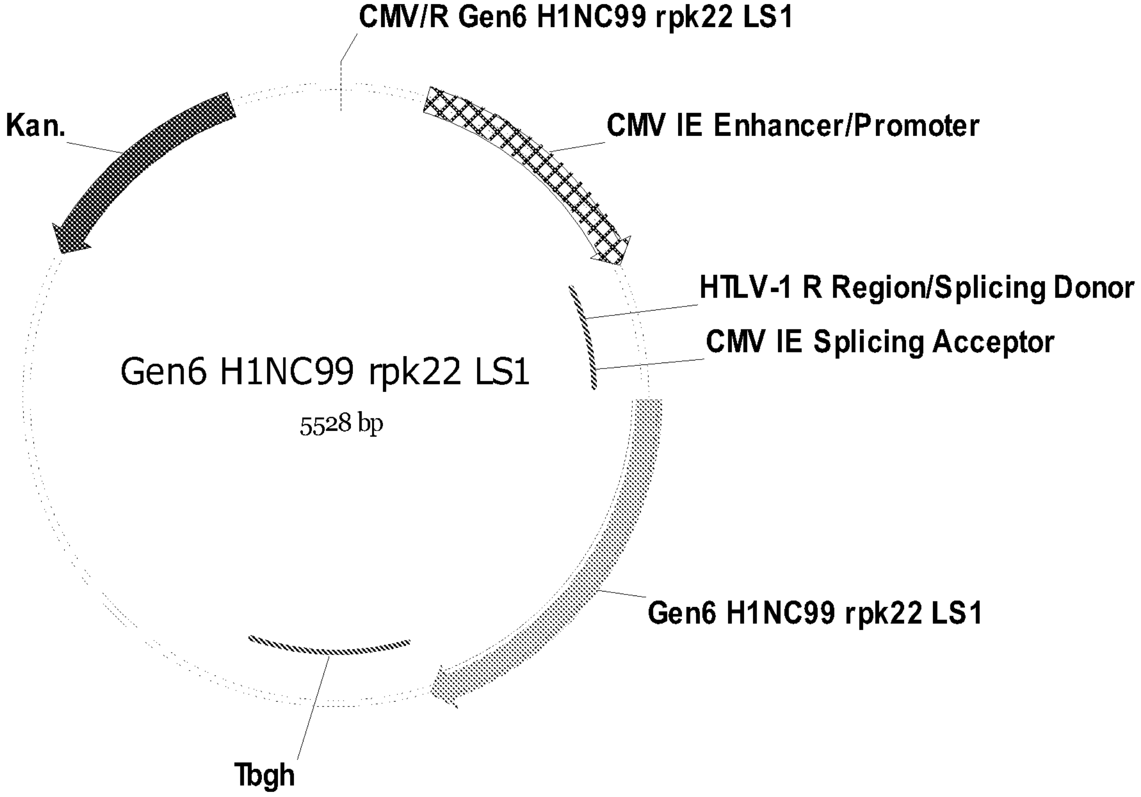
Figure 24:
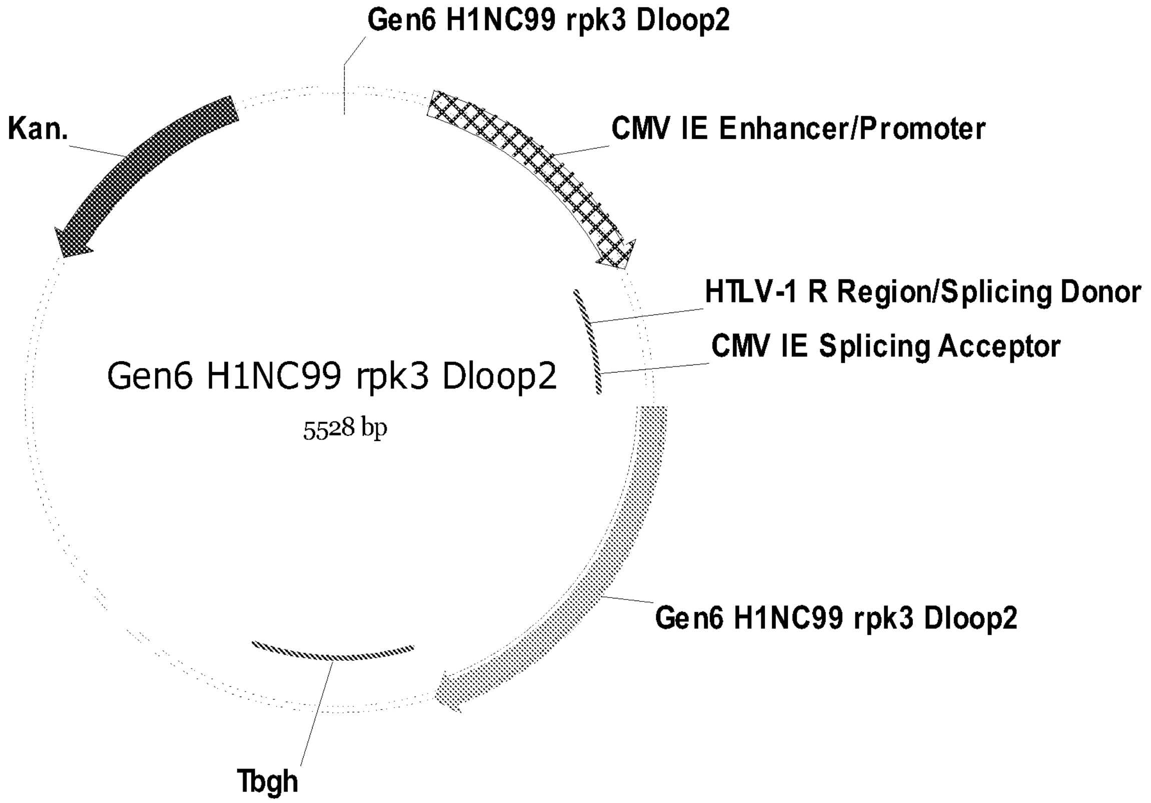

| PCT SEQ ID NO | Comments |
|---|---|
| 360 | Complement of SEQ ID NO: 358 |
| 361 | Nucleic acid sequence encoding SEQ ID NO: 362 |
| 362 | Gen6_H1NC99_K394M/E446L/E448Q/R449W/D452L/S402bG/G402cN/S402eT/T402gA/Y437D/N438L_N19Q HA-Ferritin Insert |
| 363 | Complement of SEQ ID NO: 361 |
| 364 | Sequence of entire plasmid from FIG. 19 |
| 365 | Nucleic acid sequence encoding SEQ ID NO: 366 |
| 366 | Gen6_H1NC99_K394M/E446L/E448Q/R449W/D452L/S402eN/Y437D/N438L_N19Q HA portion of Insert |
| 367 | Complement of SEQ ID NO: 365 |
| 368 | Nucleic acid sequence encoding SEQ ID NO: 369 |
| 369 | Gen6_H1NC99_K394M/E446L/E448Q/R449W/D452L/S402eN/Y437D/N438L_N19Q HA-Ferritin Insert |
| 370 | Complement of SEQ ID NO: 368 |
| 371 | Sequence of entire plasmid from FIG. 20 |
| 372 | Nucleic acid sequence encoding SEQ ID NO: 373 |
| 373 | Gen6_H1NC99_K394M/E446L/E448Q/R449W/D452L/G402dN/G402fT/T402gA/Q370N/E372T/Y437D/N438L_S21T HA portion of Insert |
| 374 | Complement of SEQ ID NO: 372 |
| 375 | Nucleic acid sequence encoding SEQ ID NO: 376 |
| 376 | Gen6_H1NC99_K394M/E446L/E448Q/R449W/D452L/G402dN/G402fT/T402gA/Q370N/E372T/Y437D/N438L_S21T HA-Ferritin Insert |
| 377 | Complement of SEQ ID NO: 375 |
| 378 | Sequence of entire plasmid from FIG. 21 |
| 379 | Nucleic acid sequence encoding SEQ ID NO: 380 |
| 380 | Gen6_H1NC99_K394M/E446L/E448Q/R449W/D452L/G402dN/G402fT/T402gA/Q370N/E372T/Y437D/N438L_S21T/Q69N HA portion of Insert |
| 381 | Complement of SEQ ID NO: 379 |
| 382 | Nucleic acid sequence encoding SEQ ID NO: 383 |
| 383 | Gen6_H1NC99_K394M/E446L/E448Q/R449W/D452L/G402dN/G402fT/T402gA/Q370N/E372T/Y437D/N438L_S21T/Q69N HA-Ferritin Insert |
| 384 | Complement of SEQ ID NO: 382 |
| 385 | Sequence of entire plasmid from FIG. 22 |
| 386 | Nucleic acid sequence encoding SEQ ID NO: 387 |
| 387 | Gen6_H1NC99_K394M/E446L/Y437D/N438L/Δ515-517 HA portion of insert |
| 388 | Complement of SEQ ID NO: 386 |
| 389 | Nucleic acid sequence encoding SEQ ID NO: 390 |
| 390 | Gen6_H1NC99_K394M/E446L/Y437D/N438L/Δ515-517 HA-Ferritin Insert |
| 391 | Complement of SEQ ID NO: 389 |
| 392 | Sequence of entire plasmid from FIG. 23 |
| 393 | Nucleic acid sequence encoding SEQ ID NO: 394 |
| 394 | Gen6_H1NC99_rpk3Dloop2 |
| 395 | Complement of SEQ ID NO: 393 |
| 396 | Nucleic acid sequence encoding SEQ ID NO: 397 |
| 397 | Gen6_H1NC99_rpk3Dloop2 |
| 398 | Complement of SEQ ID NO: 396 |
| 399 | Sequence of entire plasmid from FIG. 24 |
| 400 | Gen6_H1NC99_K394M/E446L/E448Q/R449W/D452L/Y437D/N438L/I337G/G355S/Δ338-354_N19Q (rpk-3, Dloop2) H1N1 A/New Caledonia/20/1999 HA Construct |
| 401 | Gen6_H1NC99_K394M/E446L/E448Q/R449W/D452L/Y437D/N438L/I337G/G355S/Δ338-354_N19Q (rpk-3, Dloop2) H1N1 A/New Caledonia/20/1999 HA-Ferritin Construct |

The trimeric HA protein on the surface of the virus comprises a globular head region and a stem, or stalk, region, which anchors the HA protein into the viral lipid envelope. The head region of influenza HA is formed exclusively from a major portion of the HA1 polypeptide, whereas the stalk region is made from segments of HA1 and HA2. According to the present invention, the head region consists of, approximately, the amino acids of an HA protein corresponding to amino acids 59-291 of the full-length HA protein of influenza H1N1 NC (SEQ ID NO:8). Similarly, as used herein, the stem region consists of, approximately, amino acids 1-58 and the amino acids of an HA protein corresponding to amino acids 328-564 of the full-length HA protein of influenza H1N1 NC (SEQ ID NO:8). As used herein, the term approximately, with regard to the head and stem regions means that the sequences cited above may vary in length by several amino acids without affecting the nature of the invention. Thus, for example, the head region may consist of amino acids 50-291, amino acids 59-296 or amino acids 59-285. Generally the head and stem region will not vary from the locations recited above by more than ten amino acids; however, in one embodiment the carboxy end of the head region can extend as far as an amino acid corresponding to amino acid 327 of SEQ ID NO:8. In one embodiment, the head region consists of the amino acid sequence between, and including, the amino acid residues corresponding to Cys59 and Cys291 of influenza A/New Caledonia/20/1999 (SEQ ID NO:8). With regard to HA proteins, it is understood by those skilled in the art that HA proteins from different influenza viruses may have different lengths due to mutations (insertions, deletions) in the protein. Thus, reference to a corresponding region refers to a region of another proteins that is identical, or nearly so (e.g., at least 90% identical, at least 95%, identical, at least 98% identical or at least 99% identical), in sequence, structure and/or function to the region being compared. For example, with regard to the stem region of an HA protein, the corresponding region in another HA protein may not have the same residue numbers, but will have a nearly identical sequence and will perform the same function. As an example, in the embodiment stated above, the head region of the HA protein from A/New Caledonia/20/1999 (SEQ ID NO:8) ends at amino acid C291. The corresponding amino acid at the end of the head region in A/California/4/2009 (H1) (SEQ ID NO:11) is cysteine 292. To better clarify sequences comparisons between viruses, numbering systems are used by those in the field, which relate amino acid positions to a reference sequence. Thus, corresponding amino acid residues in HA proteins from different strains of influenza may not have the same residue number with respect to their distance from the n-terminal amino acid of the protein. For example, using the H3 numbering system, reference to residue 100 in A/New Caledonia/20/1999 (1999 NC, H1) does not mean it is the 100th residue from the N-terminal amino acid. Instead, residue 100 of A/New Caledonia/20/1999 (1999 NC, H1) aligns with residue 100 of influenza H3N2 strain. The use of such numbering systems is understood by those skilled in the art. While the H3 numbering system can be used to identify the location of amino acids, unless otherwise noted, the location of amino acid residues in HA proteins will be identified by general reference to the position of a corresponding amino acid from a sequence disclosed herein.

The inventors have also discovered that by combining specific sequences of the influenza virus HA protein with unrelated molecules that are capable of presenting the HA protein to the immune system, immune responses to targeted regions of the HA protein can be elicited. One embodiment of the present invention is a protein construct comprising an influenza HA protein joined to at least a portion of a monomeric subunit protein, wherein the head region of the influenza HA protein has been replaced with an amino acid sequence comprising less than 5 contiguous amino acid residues from the head region of the HA protein, and wherein the protein construct is capable of forming a nanoparticle.

By joining at least a portion of the influenza HA protein to a monomeric subunit, protein constructs of the present invention are capable of assembling into nanoparticles expressing trimers of HA on their surface. It should be appreciated that the HA proteins making up such trimers are in a pre-fusion form and that connection to the monomeric subunit and expression on a nanoparticle stabilize the pre-fusion proteins in their trimeric form. This is significant since the HA protein is presented in a more native form meaning certain surfaces of the stem polypeptides are not exposed, thereby reducing the risk that the stem polypeptides may induce an unfavorable antibody response.

In one embodiment, the HA protein comprises at least one immunogenic portion from the stem region of influenza HA protein, wherein the protein elicits protective antibodies against an influenza virus. In one embodiment, the HA protein comprises at least one immunogenic portion from the stem region of an HA protein from a virus selected from the group consisting of influenza type A viruses, influenza type B viruses and influenza type C viruses, wherein the protein elicits protective antibodies against an influenza virus. In one embodiment, the HA protein comprises at least one immunogenic portion from the stem region of an HA protein selected from the group consisting of an H1 influenza virus HA protein, an H2 influenza virus HA protein, an influenza H3 virus HA protein, an influenza H4 virus HA protein, an influenza H5 virus HA protein, an influenza H6 virus HA protein, an H7 influenza virus HA protein, an H8 influenza virus HA protein, an H9 influenza virus HA protein, an H10 influenza virus HA protein HA protein, an H11 influenza virus HA protein, an H12 influenza virus HA protein, an H13 influenza virus HA protein, an H14 influenza virus HA protein, an H15 influenza virus HA protein, an H16 influenza virus HA protein, an H17 influenza virus HA protein, and an H18 influenza virus HA protein.

In one embodiment, the HA protein comprises at least one immunogenic portion from a protein comprising an amino acid sequence at least 80% identical to a sequence selected from the group consisting of SEQ ID NO:8, SEQ ID NO:11, SEQ ID NO:14 and SEQ ID NO:17. In one embodiment, the HA protein comprises at least one immunogenic portion from a protein comprising an amino acid sequence selected from the group consisting of SEQ ID NO:8, SEQ ID NO:11, SEQ ID NO:14 and SEQ ID NO:17. In one embodiment, the HA protein comprises at least one immunogenic portion from a protein comprising an amino acid sequence at least 80% identical to a sequence selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:150, SEQ ID NO:152, SEQ ID NO:154, SEQ ID NO:156, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400. In one embodiment, the HA protein comprises at least one immunogenic portion from a protein comprising an amino acid sequence selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:150, SEQ ID NO:152, SEQ ID NO:154, SEQ ID NO:156, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400. In one embodiment, such proteins comprising immunogenic portions of the HA protein elicit the production of broadly protective antibodies against influenza virus.

Immunogenic portions of proteins comprise epitopes, which are clusters of amino acid residues that are recognized by the immune system, thereby eliciting an immune response. Such epitopes may consist of contiguous amino acids residues (i.e., amino acid residues that are adjacent to one another in the protein), or they may consist of non-contiguous amino acid residues (i.e., amino acid residues that are not adjacent one another in the protein) but which are in close special proximity in the finally folded protein. It is well understood by those skilled in the art that epitopes require a minimum of six amino acid residues in order to be recognized by the immune system. Thus, in one embodiment the immunogenic portion from the influenza HA protein comprises at least one epitope. In one embodiment the HA protein comprises at least 6 amino acids, at least 10 amino acids, at least 25 amino acids, at least 50 amino acids, at least 75 amino acids or at least 100 amino acids from the stem region of influenza HA protein. In one embodiment the HA protein comprises at least 6 amino acids, at least 10 amino acids, at least 25 amino acids, at least 50 amino acids, at least 75 amino acids or at least 100 amino acids from the stem region of an HA protein from a virus selected from the group consisting of influenza type A viruses, influenza type B viruses and influenza type C viruses. In one embodiment the HA protein comprises at least 6 amino acids, at least 10 amino acids, at least 25 amino acids, at least 50 amino acids, at least 75 amino acids or at least 100 amino acids from the stem region of an HA protein selected from the group consisting an H1 influenza virus HA protein, an H2 influenza virus HA protein, an influenza H3 virus HA protein, an influenza H4 virus HA protein, an influenza H5 virus HA protein, an influenza H6 virus HA protein, an H7 influenza virus HA protein, an H8 influenza virus HA protein, an H9 influenza virus HA protein, an H10 influenza virus HA protein HA protein, an H11 influenza virus HA protein, an H12 influenza virus HA protein, an H13 influenza virus HA protein, an H14 influenza virus HA protein, an H15 influenza virus HA protein, an H16 influenza virus HA protein, an H17 influenza virus HA protein, and an H18 influenza virus HA protein. In one embodiment the HA protein comprises at least 6 amino acids, at least 10 amino acids, at least 25 amino acids, at least 50 amino acids, at least 75 amino acids or at least 100 amino acids from the stem region of an HA protein from a strain of virus selected from the group consisting of influenza A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), B/Brisbane/60/2008 (2008 Bris, B), and variants thereof. In one embodiment, the amino acids are contiguous amino acids from the stem region of the HA protein. In one embodiment, such proteins comprising at least 6 amino acids, at least 10 amino acids, at least 25 amino acids, at least 50 amino acids, at least 75 amino acids or at least 100 amino acids from the stem region of an HA protein elicit the production of broadly protective antibodies against influenza virus. One embodiment of the present invention is a protein construct comprising at least 6 amino acids, at least 10 amino acids, at least 25 amino acids, at least 50 amino acids, at least 75 amino acids or at least 100 amino acids from the stem region of an HA protein comprising an amino acid sequence selected from the group consisting of SEQ ID NO:8, SEQ ID NO:11, SEQ ID NO:14 and SEQ ID NO:17. One embodiment of the present invention is a protein construct comprising at least 6 amino acids, at least 10 amino acids, at least 25 amino acids, at least 50 amino acids, at least 75 amino acids or at least 100 amino acids from the stem region of an HA protein comprising an amino acid sequence selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:150, SEQ ID NO:152, SEQ ID NO:154, SEQ ID NO:156, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400. In one embodiment, the amino acids are contiguous amino acids from the stem region of the HA protein. In one embodiment, the amino acids are non-contiguous, but are in close spatial proximity in the final protein.

While the present application exemplifies the use of stem region sequences from several exemplary HA proteins, the invention may also be practiced using stem regions from proteins comprising variations of the disclosed HA sequences. Thus, in one embodiment, the HA protein is from a virus selected from the group consisting of influenza A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), B/Brisbane/60/2008 (2008 Bris, B), and variants thereof. In one embodiment of the HA protein comprises an amino acid sequence at least 80%, at least 85%, at least 90%, at least 92%, at least 94%, at least 96%, at least 98% or at least 99% identical the stem region of an HA protein comprising an amino acid sequence selected from the group consisting of SEQ ID NO:8, SEQ ID NO:, SEQ ID NO:11, SEQ ID NO:14, SEQ ID NO:17. In one embodiment the HA protein comprises an amino acid sequence selected from the group consisting of SEQ ID NO:8, SEQ ID NO:, SEQ ID NO:11, SEQ ID NO:14, SEQ ID NO:17.

In one embodiment, the head region sequence of the HA protein is replaced with a linker sequence. Any linker sequence may be used so long as the stem region sequences are able to form the desired structure. While any amino acids may be used to make the linker sequence, it is preferred to use amino acids lacking large or charged side chains. Preferred amino acids include, but are not limited to, serine, glycine and alanine. In one embodiment, the linker is made from serine and glycine residues. The length of the linker sequence may vary, but preferred embodiments use the shortest possible sequence in order to allow the stem sequences to form the desired structure. In one embodiment, the linker sequence is less than 10 amino acids in length. In one embodiment, the linker sequence is less than 5 amino acids in length. In preferred embodiments, the linker sequence lacks contiguous amino acid sequences from the head region of an HA protein. In one embodiment, the linker sequence comprises less than 5 contiguous amino acids from the head region of an HA protein.

As noted above, the HA sequence is linked to a portion of a monomeric subunit protein. As used herein, a monomeric subunit protein refers to a protein monomer that is capable of binding to other monomeric subunit proteins such that the monomeric subunit proteins self-assemble into a nanoparticle. Any monomeric subunit protein can be used to produce the protein construct of the present invention, so long as the protein construct is capable of forming a multimeric structure displaying HA protein on its surface. In one embodiment the monomeric subunit is ferritin.

Ferritin is a globular protein found in all animals, bacteria, and plants, that acts primarily to control the rate and location of polynuclear $Fe(III)_2O_3$ formation through the transportation of hydrated iron ions and protons to and from a mineralized core. The globular form of ferritin is made up of monomeric subunit proteins (also referred to as monomeric ferritin subunits), which are polypeptides having a molecule weight of approximately 17-20 kDa. An example of the sequence of one such monomeric ferritin subunit is represented by SEQ ID NO:2. Each monomeric ferritin subunit has the topology of a helix bundle which includes a four antiparallel helix motif, with a fifth shorter helix (the c-terminal helix) lying roughly perpendicular to the long axis of the 4 helix bundle. According to convention, the helices are labeled 'A, B, C, and D & E' from the N-terminus respectively. The N-terminal sequence lies adjacent to the nanoparticle three-fold axis and extends to the surface, while the E helices pack together at the four-fold axis with the C-terminus extending into the particle core. The consequence of this packing creates two pores on the nanoparticle surface. It is expected that one or both of these pores represent the point by which the hydrated iron diffuses into and out of the nanoparticle. Following production, these monomeric ferritin subunit proteins self-assemble into the globular ferritin protein. Thus, the globular form of ferritin comprises 24 monomeric, ferritin subunit proteins, and has a capsid-like structure having 432 symmetry.

According to the present invention, a monomeric ferritin subunit of the present invention is a full length, single polypeptide of a ferritin protein, or any portion thereof, which is capable of directing self-assembly of monomeric ferritin subunits into the globular form of the protein. Examples of such proteins include, but are not limited to SEQ ID NO:2 and SEQ ID NO:5 Amino acid sequences from monomeric ferritin subunits of any known ferritin protein can be used to produce protein constructs of the present invention, so long as the monomeric ferritin subunit is capable of self-assembling into a nanoparticle displaying HA on its surface. In one embodiment, the monomeric subunit is from a ferritin protein selected from the group consisting of a bacterial ferritin protein, a plant ferritin protein, an algal ferritin protein, an insect ferritin protein, a fungal ferritin protein and a mammalian ferritin protein. In one embodiment, the ferritin protein is from *Helicobacter pylori.*

Protein constructs of the present invention need not comprise the full-length sequence of a monomeric subunit polypeptide of a ferritin protein. Portions, or regions, of the monomeric ferritin subunit protein can be utilized so long as the portion comprises an amino acid sequence that directs self-assembly of monomeric ferritin subunits into the globular form of the protein. One example of such a region is located between amino acids 5 and 167 of the *Helicobacter pylori* ferritin protein. More specific regions are described in Zhang, Y. Self-Assembly in the Ferritin Nano-Cage Protein Super Family. 2011, Int. J. Mol. Sci., 12, 5406-5421, which is incorporated herein by reference in its entirety.

In one embodiment the HA protein is joined to at least 50, at least 100 or least 150 amino acids from ferritin, wherein the protein construct is capable of forming a nanoparticle. In one embodiment the HA protein is joined to at least 50, at least 100 or least 150 amino acids from SEQ ID NO:2 or SEQ ID NO:5, wherein the protein construct is capable of forming a nanoparticle. In one embodiment the HA protein is joined to a protein comprising an amino acid sequence at least 85%, at least 90% or at least 95% identical to the sequence of ferritin, wherein the protein construct is capable of forming a nanoparticle. In one embodiment the HA protein is joined to a protein comprising an amino acid sequence at least 85%, at least 90%, at least 95% identical to SEQ ID NO:2 or SEQ ID NO:5, wherein the protein construct is capable of forming a nanoparticle.

In one embodiment the monomeric subunit is lumazine synthase. In one embodiment the HA protein is joined to at least 50, at least 100 or least 150 amino acids from lumazine synthase, wherein the protein construct is capable of forming a nanoparticle. Thus, in one embodiment the HA protein is joined to a protein at least 85%, at least 90%, at least 95% identical to lumazine synthase, wherein the protein construct is capable of forming a nanoparticle.

As used herein, a nanoparticle of the present invention refers to a three-dimensional particle formed by self-assembly of protein constructs (fusion proteins) of the present invention. Nanoparticles of the present invention are generally spheroid in shape, although other shapes are not excluded, and are generally from about 20 nm to about 100 nm in diameter. Nanoparticles of the present invention may, but need not, comprise other molecules, such as proteins, lipids, carbohydrates, etc., than the protein constructs from which they are formed.

Protein constructs of the present invention can be made using recombinant technology to link together portions of HA proteins, linkers and monomeric subunits. In this way, protein constructs can be produced that comprise only those sequences necessary to produce nanoparticle vaccines. Thus, one embodiment of the present invention is a protein construct (also referred to as a fusion protein) comprising a first amino acid sequence from the stem region of an influenza virus HA protein and a second amino acid sequence from the stem region of an influenza virus HA protein, the first and second amino acid sequences being covalently linked by a linker sequence,

- wherein the first amino acid sequence comprises at least 20 contiguous amino acid residues from the amino acid sequence upstream of the amino-terminal end of the head region sequence;
- wherein the second amino acid sequence comprises at least 20 contiguous amino acid residues from the amino acid sequence downstream of the carboxyl-terminal end of the head region sequence; and,
- wherein the first or second amino acid sequence is joined to at least a portion of a monomeric subunit domain such that the protein construct is capable of forming a nanoparticle.

In one embodiment, the first amino acid sequence is from the stem region of an HA protein from a virus selected from the group consisting of influenza A viruses, influenza B viruses and influenza C viruses. In one embodiment, the first amino acid sequence is from the stem region of an HA protein from a virus selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus, an H16 influenza virus, an H17 influenza virus, and an H18 influenza virus. In one embodiment, the first amino acid sequence is from the stem region of an HA protein from a virus selected from the group consisting of influenza A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), B/Brisbane/60/2008 (2008 Bris, B). In one embodiment, the first amino acid sequence is from the stem region of an HA protein having an amino acid sequences at least 85%, at least 90%, at least 95% or at least 97% identical to a sequence selected from the group consisting of SEQ ID NO:8, SEQ ID NO:, SEQ ID NO:11, SEQ ID NO:14 and SEQ ID NO:17. In one embodiment, the first amino acid sequence is from the stem region of an HA protein comprising a sequence selected from the group consisting of SEQ ID NO:8, SEQ ID NO:11, SEQ ID NO:14 and SEQ ID NO:17. In one embodiment, the HA protein comprises at least one immunogenic portion from a protein comprising an amino acid sequence at least 85%, at least 90%, at least 95% or at least 97% identical to a sequence selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:150, SEQ ID NO:152, SEQ ID NO:154, SEQ ID NO:156, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400. In one embodiment, the HA protein comprises at least one immunogenic portion from a protein comprising an amino acid sequence selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:150, SEQ ID NO:152, SEQ ID NO:154, SEQ ID NO:156, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400.

In one embodiment, the second amino acid sequence is from the stem region of an HA protein from a virus selected from the group consisting of influenza A viruses, influenza B viruses and influenza C viruses. In one embodiment, the second amino acid sequence is from the stem region of an HA protein from a virus selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus, an H16 influenza virus, an H17 influenza virus, and an H18 influenza virus. In one embodiment, the second amino acid sequence is from the stem region of an HA protein from a virus selected from the group consisting of influenza A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), B/Brisbane/60/2008 (2008 Bris, B). In one embodiment, the second amino acid sequence is from the stem region of an HA protein having an amino acid sequences at least 85%, at least 90%, at least 95% or at least 97% identical to a sequence selected from the group consisting of SEQ ID NO:8, SEQ ID NO:11, SEQ ID NO:14 and SEQ ID NO:17. In one embodiment, the second amino acid sequence is from the stem region of an HA protein comprising a sequence selected from the group consisting of SEQ ID NO:8, SEQ ID NO:11, SEQ ID NO:14 and SEQ ID NO:17. In one embodiment, the HA protein comprises at least one immunogenic portion from a protein comprising an amino acid sequence at least 85%, at least 90%, at least 95% or at least 97% identical to a sequence selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:150, SEQ ID NO:152, SEQ ID NO:154, SEQ ID NO:156, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400. In one embodiment, the HA protein comprises at least one immunogenic portion from a protein comprising an amino acid sequence selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:150, SEQ ID NO:152, SEQ ID NO:154, SEQ ID NO:156, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400.

As noted above, the first amino acid sequence comprises at least 20 contiguous amino acid residues from the amino acid sequence upstream of the amino-terminal end of the head region sequence. According to the present invention, the term upstream refers to the entirety of the amino acid sequence linked to the amino-terminal end of the first amino acid residue of the head region. In one embodiment, the amino-terminal end of the head region is located at the amino acid residue corresponding to Cys59 of the HA protein of influenza A New Caledonia/20/1999 (H1) (SEQ ID NO:8) Thus, in one embodiment, the first amino acid sequence comprises at least 20 contiguous amino acid residues from the region of an HA protein corresponding to amino acid residues 1-58 of influenza A New Caledonia/20/1999 (H1) (SEQ ID NO:8). In one embodiment, the first amino acid sequence comprises at least 20 contiguous amino acid residues from a sequence at least 85%, at least 90%, at least 95% or at least 97% identical to a sequence selected from the group consisting of SEQ ID NO:20, SEQ ID NO: 35, SEQ ID NO:50 and SEQ ID NO:65. In one embodiment, the first amino acid sequence comprises at least 20 contiguous amino acid residues from a sequence selected from the group consisting of SEQ ID NO:20, SEQ ID NO: 35, SEQ ID NO:50 and SEQ ID NO:65.

In one embodiment, the first amino acid sequence comprises at least 40 contiguous amino acid residues from the amino acid region of an HA protein corresponding to amino acid residues 1-58 of influenza A New Caledonia/20/1999 (H1) (SEQ ID NO:8). In one embodiment, the first amino acid sequence comprises at least 40 contiguous amino acid residues from a sequence at least 85%, at least 90%, at least 95% or at least 97% identical to a sequence selected from the group consisting of SEQ ID NO:20, SEQ ID NO: 35, SEQ ID NO:50 and SEQ ID NO:65. In one embodiment, the first amino acid sequence comprises at least 40 contiguous amino acid residues from a sequence selected from the group consisting of SEQ ID NO:20, SEQ ID NO: 35, SEQ ID NO:50 and SEQ ID NO:65.

In one embodiment, the first amino acid sequence comprises a sequence at least 85%, at least 90%, at least 95% or at least 97% identical to a sequence selected from the group consisting of SEQ ID NO:20, SEQ ID NO: 35, SEQ ID NO:50 and SEQ ID NO:65. In one embodiment, the first amino acid sequence comprises a sequence selected from the group consisting of SEQ ID NO:20, SEQ ID NO: 35, SEQ ID NO:50 and SEQ ID NO:65.

In one embodiment, the second amino acid sequence is from the stem region of an HA protein from a virus selected from the group consisting of influenza A viruses, influenza B viruses and influenza C viruses. In one embodiment, the second amino acid sequence is from the stem region of an HA protein from a virus selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus, an H16 influenza virus, an H17 influenza virus, and an H18 influenza virus. In one embodiment, the second amino acid sequence is from the stem region of an HA protein from a virus selected from the group consisting of influenza A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), B/Brisbane/60/2008 (2008 Bris, B). In one embodiment, the second amino acid sequence is from the stem region of an HA protein having an amino acid sequences at least 85%, at least 90%, at least 95% or at least 97% identical to a sequence selected from the group consisting of SEQ ID NO:8, SEQ ID NO:11, SEQ ID NO:14 and SEQ ID NO:17. In one embodiment, the second amino acid sequence is from the stem region of an HA protein comprising a sequence selected from the group consisting of SEQ ID NO:8, SEQ ID NO:11, SEQ ID NO:14 and SEQ ID NO:17.

As noted above, the second amino acid sequence comprises at least 20 contiguous amino acid residues from the amino acid sequence downstream of the carboxyl-terminal end of the head region sequence. According to the present invention, the term downstream refers to the entire amino acid sequence linked to the carboxyl-terminal amino acid residue of the head region. In one embodiment, the carboxyl-terminal end of the head region is located at the amino acid position corresponding to Cys291 of the HA protein of influenza A New Caledonia/20/1999 (H1) (SEQ ID NO:8) Thus, in one embodiment, the second amino acid sequence comprises at least 20 contiguous amino acids from the amino acid region of an HA protein corresponding to amino acid residues 292-517 of influenza A New Caledonia/20/1999 (H1) (SEQ ID NO:8). In one embodiment, the second amino acid sequence comprises at least 20 contiguous amino acids from the amino acid region of an HA protein corresponding to amino acid residues 328-517 of influenza A New Caledonia/20/1999 (H1) (SEQ ID NO:8). In one embodiment, the second amino acid sequence comprises at least 20 contiguous amino acid residues from a sequence at least 85%, at least 90%, at least 95% or at least 97% identical to a sequence selected from the group consisting of SEQ ID NO:23, SEQ ID NO:26, SEQ ID NO:29, SEQ ID NO:32, SEQ ID NO:38, SEQ ID NO:41, SEQ ID NO:44, SEQ ID NO:47, SEQ ID NO:53, SEQ ID NO:56, SEQ ID NO:59, SEQ ID NO:62, SEQ ID NO:68, SEQ ID NO:71, SEQ ID NO:74 and SEQ ID NO:77. In one embodiment, the second amino acid sequence comprises at least 20 contiguous amino acid residues from a sequence selected from the group consisting of SEQ ID NO:23, SEQ ID NO:26, SEQ ID NO:29, SEQ ID NO:32, SEQ ID NO:38, SEQ ID NO:41, SEQ ID NO:44, SEQ ID NO:47, SEQ ID NO:53, SEQ ID NO:56, SEQ ID NO:59, SEQ ID NO:62, SEQ ID NO:68, SEQ ID NO:71, SEQ ID NO:74 and SEQ ID NO:77.

In one embodiment, the second amino acid sequence comprises at least 40, at least 60, at least 75, at least 100, or at least 150 contiguous amino acids from the amino acid sequence downstream of the carboxyl-terminal end of the head region sequence. In one embodiment, the second amino acid sequence comprises at least 40, at least 60, at least 75, at least 100, or at least 150 contiguous amino acids from the amino acid region of an HA protein corresponding to amino acid residues 292-517 of influenza A New Caledonia/20/1999 (H1) (SEQ ID NO:8). In one embodiment, the second amino acid sequence comprises at least 40, at least 60, at least 75, at least 100, or at least 150 contiguous amino acids from the amino acid region of an HA protein corresponding to amino acid residues 328-517 of influenza A New Caledonia/20/1999 (H1) (SEQ ID NO:8). In one embodiment, the second amino acid sequence comprises at least 40, at least 60, at least 75, at least 100, or at least 150 contiguous amino acids from a sequence at least 85%, at least 90%, at least 95% or at least 97% identical to a sequence selected from the group consisting of SEQ ID NO:23, SEQ ID NO:26, SEQ ID NO:29, SEQ ID NO:32, SEQ ID NO:38, SEQ ID NO:41, SEQ ID NO:44, SEQ ID NO:47, SEQ ID NO:53, SEQ ID NO:56, SEQ ID NO:59, SEQ ID NO:62, SEQ ID NO:68, SEQ ID NO:71, SEQ ID NO:74 and SEQ ID NO:77. In one embodiment, the second amino acid sequence comprises at least 40, at least 60, at least 75, at least 100, or at least 150 contiguous amino acids from the group consisting of SEQ ID NO:23, SEQ ID NO:26, SEQ ID NO:29, SEQ ID NO:32, SEQ ID NO:38, SEQ ID NO:41, SEQ ID NO:44, SEQ ID NO:47, SEQ ID NO:53, SEQ ID NO:56, SEQ ID NO:59, SEQ ID NO:62, SEQ ID NO:68, SEQ ID NO:71, SEQ ID NO:74 and SEQ ID NO:77. In one embodiment, the second amino acid sequence comprises an amino acid sequence at least 85%, at least 90%, at least 95% or at least 97% identical to a sequence selected from the group consisting of SEQ ID NO:23, SEQ ID NO:26, SEQ ID NO:29, SEQ ID NO:32, SEQ ID NO:38, SEQ ID NO:41, SEQ ID NO:44, SEQ ID NO:47, SEQ ID NO:53, SEQ ID NO:56, SEQ ID NO:59, SEQ ID NO:62, SEQ ID NO:68, SEQ ID NO:71, SEQ ID NO:74 and SEQ ID NO:77. In one embodiment, the second amino acid sequence comprises a sequence selected from the group consisting of SEQ ID NO:23, SEQ ID NO:26, SEQ ID NO:29, SEQ ID NO:32, SEQ ID NO:38, SEQ ID NO:41, SEQ ID NO:44, SEQ ID NO:47, SEQ ID NO:53, SEQ ID NO:56, SEQ ID NO:59, SEQ ID NO:62, SEQ ID NO:68, SEQ ID NO:71, SEQ ID NO:74 and SEQ ID NO:77.

As noted above, the first and second amino acid sequences of the protein construct can be joined by a linker sequence. Any linker sequence can be used as long as the linker sequence has less than five contiguous amino acid residues from the head region of an HA protein and so long as the first and second amino acids are able to form the desired conformation. In one embodiment, the linker sequence is less than 10 amino acids, less than 7 amino acids or less than 5 amino acids in length. In one embodiment, the linker sequence comprises glycine and serine. In one embodiment, the linker sequence joins the carboxyl-terminal end of the first amino acid sequence to the amino-terminal end of the second amino acid sequence. In one embodiment, the linker sequence joins the carboxyl-terminal end of the second amino acid sequence to the amino-terminal end of the first amino acid sequence.

As noted above, either the first or second amino acid sequence of the protein construct is joined to at least a portion of a monomeric subunit protein such that the protein construct is capable of forming a nanoparticle. In one embodiment, the at least a portion of the monomeric subunit protein is joined to the second amino acid sequence. In a preferred embodiment, the at least a portion of the monomeric subunit protein is joined to the carboxyl end of the second amino acid sequence. In one embodiment, the portion comprises at least 50, at least 100 or at least 150 amino acids from a monomeric subunit. In one embodiment, the monomeric subunit is ferritin. In one embodiment, the monomeric subunit is lumazine synthase. In one embodiment, the portion comprises at least 50, at least 100 or at least 150 amino acids from SEQ ID NO:2, SEQ ID NO:5 or SEQ ID NO:194. In one embodiment, the monomeric subunit comprises a sequence at least 85% identical, at least 90% identical or at least 95% identical to SEQ ID NO:2, SEQ ID NO:5 or SEQ ID NO:194. In one embodiment, the monomeric subunit comprises a sequence selected from the group consisting of SEQ ID NO:2, SEQ ID NO:5 and SEQ ID NO:194.

The inventors have discovered that modification of the influenza HA sequences of the heretofore described protein constructs leads to improved stability of the protein construct. For example, the inventors have found that deletion from an HA protein of the amino acid region corresponding to amino acids N403-W435 of the HA protein of influenza A New Caledonia/20/1999 (H1) (SEQ ID NO:8) results in a more stable protein construct. Upon deletion of this region, the amino acid sequences flanking this region can be joined together directly, or they can be joined with a linker sequence such as, for example, glycine-serine-glycine Thus, in one embodiment, the second amino acid sequence comprises a polypeptide sequence at least 85%, at least 90% or at least 95% identical to at least 100 contiguous amino acid residues from the amino acid sequence downstream of the carboxyl-terminal end of the head region sequence, wherein the polypeptide sequence lacks a region corresponding to SEQ ID NO:133, SEQ ID NO:134, SEQ ID NO:135 or SEQ ID NO:136 from the HA protein of influenza A/New Caledonia 1999 (SEQ ID NO:8). In one embodiment, the second amino acid sequence comprises at least 100 contiguous amino acid residues from the amino acid sequence downstream of the carboxyl-terminal end of the head region sequence, wherein the polypeptide sequence lacks a region corresponding to SEQ ID NO:133, SEQ ID NO:134, SEQ ID NO:135 or SEQ ID NO:136 of the HA protein of influenza A/New Caledonia 1999 (SEQ ID NO:8).

In one embodiment, the second amino acid sequence comprises a polypeptide sequence at least 85%, at least 90% or at least 95% identical to at least 100 contiguous amino acid residues from the amino acid sequence downstream of the carboxyl-terminal end of the head region sequence, wherein the polypeptide sequence lacks a region corresponding to SEQ ID NO:137, SEQ ID NO:138, SEQ ID NO:139 or SEQ ID NO:140 of the HA protein of influenza A/California/4/2009 (SEQ ID NO:10). In one embodiment, the second amino acid sequence comprises at least 100 contiguous amino acid residues from the amino acid sequence downstream of the carboxyl-terminal end of the head region sequence, wherein the polypeptide sequence lacks a region corresponding to SEQ ID NO:137, SEQ ID NO:138, SEQ ID NO:139 or SEQ ID NO:140 of the HA protein of influenza A/California/4/2009 (SEQ ID NO:10).

In one embodiment, the second amino acid sequence comprises an amino acid sequence at least 85%, at least 90% or at least 95% identical to at least 100 contiguous amino acid residues from the amino acid sequence downstream of the carboxyl-terminal end of the head region sequence, wherein the polypeptide sequence lacks a region corresponding to SEQ ID NO:141, SEQ ID NO:142, SEQ ID NO:143 or SEQ ID NO:144 of the HA protein of influenza A/Singapore/1957 (SEQ ID NO:12). In one embodiment, the second amino acid sequence comprises an amino acid sequence at least 85%, at least 90% or at least 95% identical to at least 100 contiguous amino acid residues from the amino acid sequence downstream of the carboxyl-terminal end of the head region sequence, wherein the polypeptide sequence lacks a region corresponding to SEQ ID NO:141, SEQ ID NO:142, SEQ ID NO:143 or SEQ ID NO:144 of the HA protein of influenza A/Singapore/1957 (SEQ ID NO:12).

In one embodiment, the second amino acid sequence comprises at least 100 contiguous amino acid residues from the amino acid sequence downstream of the carboxyl-terminal end of the head region sequence, wherein the polypeptide sequence lacks a region corresponding to SEQ ID NO:145, SEQ ID NO:146, SEQ ID NO:147 or SEQ ID NO:148 of the HA protein of influenza A/Indonesia/05/2005 (H5) (SEQ ID NO:16). In one embodiment, the second amino acid sequence comprises at least 100 contiguous amino acid residues from the amino acid sequence downstream of the carboxyl-terminal end of the head region sequence, wherein the polypeptide sequence lacks a region corresponding to SEQ ID NO:145, SEQ ID NO:146, SEQ ID NO:147 or SEQ ID NO:148 of the HA protein of influenza A/Indonesia/05/2005 (H5) (SEQ ID NO:16).

In one embodiment, the second amino acid sequence comprises a sequence at least 85%, at least 90% or at least 95% identical to 100 contiguous amino acids from SEQ ID NO:23, SEQ ID NO:26 or SEQ ID NO:29, wherein the 100 contiguous amino acids do not comprise a sequence selected from the group consisting of SEQ ID NO:133, SEQ ID NO:134, SEQ ID NO:135 and SEQ ID NO:136. In one embodiment, the second amino acid sequence comprises 100 contiguous amino acids from SEQ ID NO:23, SEQ ID NO:26 or SEQ ID NO:29, wherein the 100 contiguous amino acids do not comprise a sequence selected from the group consisting of SEQ ID NO:133, SEQ ID NO:134, SEQ ID NO:135 and SEQ ID NO:136.

In one embodiment, the second amino acid sequence comprises a sequence at least 85%, at least 90% or at least 95% identical to 100 contiguous amino acids from SEQ ID NO:38, SEQ ID NO:41 or SEQ ID NO:44, wherein the 100 contiguous amino acids do not comprise a sequence selected from the group consisting of SEQ ID NO:137, SEQ ID NO:138, SEQ ID NO:139 and SEQ ID NO:140. In one embodiment, the second amino acid sequence comprises 100 contiguous amino acids from SEQ ID NO:38, SEQ ID NO:41 or SEQ ID NO:44, wherein the 100 contiguous amino acids do not comprise a sequence selected from the group consisting of SEQ ID NO:137, SEQ ID NO:138, SEQ ID NO:139 and SEQ ID NO:140.

In one embodiment, the second amino acid sequence comprises a sequence at least 85%, at least 90% or at least 95% identical to 100 contiguous amino acids from SEQ ID NO:53, SEQ ID NO:56 or SEQ ID NO:59, wherein the 100 contiguous amino acids do not comprise a sequence selected from the group consisting of SEQ ID NO:141, SEQ ID NO:142, SEQ ID NO:143 and SEQ ID NO:144. In one embodiment, the second amino acid sequence comprises 100 contiguous amino acids from SEQ ID NO:53, SEQ ID NO:56 or SEQ ID NO:59, wherein the 100 contiguous amino acids do not comprise a sequence selected from the group consisting of SEQ ID NO:141, SEQ ID NO:142, SEQ ID NO:143 and SEQ ID NO:144.

In one embodiment, the second amino acid sequence comprises a sequence at least 85%, at least 90% or at least 95% identical to 100 contiguous amino acids from SEQ ID NO:68, SEQ ID NO:71 or SEQ ID NO:74, wherein the 100 contiguous amino acids do not comprise a sequence selected from the group consisting of SEQ ID NO:145, SEQ ID NO:146, SEQ ID NO:147 and SEQ ID NO:148. In one embodiment, the second amino acid sequence comprises 100 contiguous amino acids from SEQ ID NO:68, SEQ ID NO:71 or SEQ ID NO:74, wherein the 100 contiguous amino acids do not comprise a sequence selected from the group consisting of SEQ ID NO:145, SEQ ID NO:146, SEQ ID NO:147 and SEQ ID NO:148.

In one embodiment, the second amino acid sequence comprises a sequence at least 85%, at least 90% or at least 95% identical to 100 contiguous amino acids from a sequence selected from the group consisting of SEQ ID NO:26, SEQ ID NO:28, SEQ ID NO:32, SEQ ID NO:41, SEQ ID NO:44, SEQ ID NO:47, SEQ ID NO:56, SEQ ID NO:59, SEQ ID NO:62, SEQ ID NO:71 and SEQ ID NO:77. In one embodiment, the second amino acid sequence comprises at least 100 contiguous amino acids from a sequence selected from the group consisting of SEQ ID NO:26, SEQ ID NO:32, SEQ ID NO:41, SEQ ID NO:47, SEQ ID NO:56, SEQ ID NO:62, SEQ ID NO:71 and SEQ ID NO:77. In one embodiment, the second amino acid sequence comprises a sequence selected from the group consisting of SEQ ID NO:26, SEQ ID NO:32, SEQ ID NO:41, SEQ ID NO:47, SEQ ID NO:56, SEQ ID NO:62, SEQ ID NO:71, SEQ ID NO:74 and SEQ ID NO:77

The inventors have also discovered that alteration of the sequence of the HA stem region sequence results in a more stable protein construct. For example, in the folded HA protein, the amino acid residues corresponding to K394 and E446 of influenza A New Caledonia/20/1999 (H1) (corresponding to K1 and E53 of SEQ ID NO:149) form a salt bridge, helping to stabilize the folded protein. The inventors have discovered that by substituting the lysine and glutamic acid residues with the appropriate amino acids, the interaction between the two amino acid residues can be strengthened, which improves the stability of the molecule and allows more extensive manipulation thereto. Thus, one embodiment of the present invention is a protein construct comprising a first amino acid sequence from the stem region of an influenza virus HA protein and a second amino acid sequence from the stem region of an influenza virus HA protein, the first and second amino acid sequences being covalently linked by a linker sequence, wherein the first amino acid sequence comprises at least 20 contiguous amino acid residues from the amino acid sequence upstream of the amino-terminal end of the head region sequence, wherein the second amino acid sequence comprises at least 60 contiguous amino acids from the amino acid sequence downstream of the carboxyl-terminal end of the head region sequence, wherein the 60 contiguous amino acids comprise a polypeptide sequence corresponding to the sequence of SEQ ID NO:149 or SEQ ID NO:150 from A/New Caledonia/20/1999, and wherein the amino acid residue in the polypeptide sequence that corresponds to K1 of SEQ ID NO:149 or K1 of SEQ ID NO:150 is substituted with an amino acid other than lysine, and the amino acid residue corresponding to E53 of SEQ ID NO:149 or E20 of SEQ ID NO:150 is substituted with an amino acid residue other than glutamic acid, such that the strength of the interaction between the substituted amino acid residues is greater than the strength of the interaction in the wild-type protein.

As noted above, the amino acid residues corresponding to K394 and E446 of influenza A New Caledonia/20/1999 (H1) form a salt bridge, which is a type of bond. It is known in the art that other types of bonds between amino acids exist, the strength of which vary depending on the type of bond. Examples of such bonds include, but are not limited to, a hydrophobic bond and a hydrogen bond, both of which are generally stronger than a salt bridge. Thus, in one embodiment, the amino acid residue in the polypeptide corresponding to K1 of SEQ ID NO:149 or K1 of SEQ ID NO:150 and the amino acid residue in the polypeptide corresponding to E53 of SEQ ID NO:149 or E20 of SEQ ID NO:150 are altered so that they form a hydrogen bond in the final folded protein. In one embodiment, the amino acid residue in the polypeptide corresponding to K1 of SEQ ID NO:149 or K1 of SEQ ID NO:150 and the amino acid residue in the polypeptide corresponding to E53 of SEQ ID NO:149 or E20 of SEQ ID NO:150 are altered so that they form a hydrophobic bond in the final folded protein.

The amino acids corresponding to K1 of SEQ ID NO:149, K1 of SEQ ID NO:150, E53 of SEQ ID NO:149 or E20 of SEQ ID NO:150 can be substituted with any amino acid residue, as long as the resulting interaction between the two amino acids is stronger than the salt-bridge in the unaltered protein. Examples of substitutions that increase the strength of the interaction between the amino acids corresponding to K394 and E446 of influenza A New Caledonia/20/1999 (H1) (K1 and E53 of SEQ ID NO:149) include, but are not limited to:

wherein the amino acid residue in the polypeptide sequence that corresponds to K1 of SEQ ID NO:149 is substituted with methionine, and the amino acid residue corresponding to E53 of SEQ ID NO:149 is substituted with a leucine;

wherein the amino acid residue in the polypeptide sequence that corresponds to K1 of SEQ ID NO:149 is substituted with methionine, and the amino acid residue corresponding to E53 of SEQ ID NO:149 is substituted with a methionine;

wherein the amino acid residue in the polypeptide sequence that corresponds to K1 of SEQ ID NO:149 is substituted with leucine, and the amino acid residue corresponding to E53 of SEQ ID NO:149 is substituted with a leucine;

wherein the amino acid residue in the polypeptide sequence that corresponds to K1 of SEQ ID NO:149 is substituted with isoleucine, and the amino acid residue corresponding to E53 of SEQ ID NO:149 is substituted with a isoleucine;

wherein the amino acid residue in the polypeptide sequence that corresponds to K1 of SEQ ID NO:149 is substituted with leucine, and the amino acid residue corresponding to E53 of SEQ ID NO:149 is substituted with an isoleucine;

wherein the amino acid residue in the polypeptide sequence that corresponds to K1 of SEQ ID NO:149 is substituted with glutamine, and the amino acid residue corresponding to E53 of SEQ ID NO:149 is substituted with a glutamine.

In one embodiment, the first amino acid sequence is from the stem region of an HA protein from a virus selected from the group consisting of influenza A viruses, influenza B viruses and influenza C viruses. In one embodiment, the first amino acid sequence is from the stem region of an HA protein from a virus selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus, an H16 influenza virus, an H17 influenza virus, and an H18 influenza virus. In one embodiment, the first amino acid sequence is from the stem region of an HA protein from a virus selected from the group consisting of influenza A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), B/Brisbane/60/2008 (2008 Bris, B). In one embodiment, the first amino acid sequence is from the stem region of an HA protein having an amino acid sequences at least 85%, at least 90%, at least 95% or at least 97% identical to a sequence selected from the group consisting of SEQ ID NO:8, SEQ ID NO:11, SEQ ID NO:14 and SEQ ID NO:17. In one embodiment, the first amino acid sequence is from the stem region of an HA protein comprising a sequence selected from the group consisting of SEQ ID NO:8, SEQ ID NO:11, SEQ ID NO:14 and SEQ ID NO:17.

In one embodiment, the second amino acid sequence is from the stem region of an HA protein from a virus selected from the group consisting of influenza A viruses, influenza B viruses and influenza C viruses. In one embodiment, the second amino acid sequence is from the stem region of an HA protein from a virus selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus, an H16 influenza virus, an H17 influenza virus, and an H18 influenza virus. In one embodiment, the second amino acid sequence is from the stem region of an HA protein from a virus selected from the group consisting of influenza A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), B/Brisbane/60/2008 (2008 Bris, B). In one embodiment, the second amino acid sequence is from the stem region of an HA protein having an amino acid sequences at least 85%, at least 90%, at least 95% or at least 97% identical to a sequence selected from the group consisting of SEQ ID NO:8, SEQ ID NO:11, SEQ ID NO:14 and SEQ ID NO:17. In one embodiment, the second amino acid sequence is from the stem region of an HA protein comprising a sequence selected from the group consisting of SEQ ID NO:8, SEQ ID NO:11, SEQ ID NO:14 and SEQ ID NO:17.

In one embodiment, the first amino acid sequence comprises at least 20 contiguous amino acid residues from the region of an HA protein corresponding to amino acid residues 1-58 of influenza A New Caledonia/20/1999 (H1) (SEQ ID NO:8). In one embodiment, the first amino acid sequence comprises at least 20 contiguous amino acid residues from a sequence at least 85%, at least 90%, at least 95% or at least 97% identical to a sequence selected from the group consisting of SEQ ID NO:20, SEQ ID NO: 35, SEQ ID NO:50 and SEQ ID NO:65. In one embodiment, the first amino acid sequence comprises at least 20 contiguous amino acid residues from a sequence selected from the group consisting of SEQ ID NO:20, SEQ ID NO: 35, SEQ ID NO:50 and SEQ ID NO:65.

In one embodiment, the first amino acid sequence comprises at least 40 contiguous amino acid residues from the amino acid region of an HA protein corresponding to amino acid residues 1-58 of influenza A New Caledonia/20/1999 (H1) (SEQ ID NO:8). In one embodiment, the first amino acid sequence comprises at least 40 contiguous amino acid residues from a sequence at least 85%, at least 90%, at least 95% or at least 97% identical to a sequence selected from the group consisting of SEQ ID NO:20, SEQ ID NO: 35, SEQ ID NO:50 and SEQ ID NO:65. In one embodiment, the first amino acid sequence comprises at least 40 contiguous amino acid residues from a sequence selected from the group consisting of SEQ ID NO:20, SEQ ID NO: 35, SEQ ID NO:50 and SEQ ID NO:65. In one embodiment, the first amino acid sequence comprises a sequence at least 85%, at least 90% or at least 95% identical to a sequence selected from the group consisting of SEQ ID NO:20, SEQ ID NO: 35, SEQ ID NO:50 and SEQ ID NO:65. In one embodiment, the first amino acid sequence comprises a sequence selected from the group consisting of SEQ ID NO:20, SEQ ID NO: 35, SEQ ID NO:50 and SEQ ID NO:65.

In one embodiment, the second amino acid sequence is from the stem region of an HA protein from a virus selected from the group consisting of influenza A viruses, influenza B viruses and influenza C viruses. In one embodiment, the second amino acid sequence is from the stem region of an HA protein from a virus selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus, an H16 influenza virus, an H17 influenza virus, and an H18 influenza virus. In one embodiment, the second amino acid sequence is from the stem region of an HA protein from a virus selected from the group consisting of influenza A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), B/Brisbane/60/2008 (2008 Bris, B). In one embodiment, the second amino acid sequence is from the stem region of an HA protein having an amino acid sequences at least 85%, at least 90%, at least 95% or at least 97% identical to a sequence selected from the group consisting of SEQ ID NO:8, SEQ ID NO:11, SEQ ID NO:14 and SEQ ID NO:17. In one embodiment, the second amino acid sequence is from the stem region of an HA protein comprising a sequence selected from the group consisting of SEQ ID NO:8, SEQ ID NO:11, SEQ ID NO:14 and SEQ ID NO:17.

In one embodiment, the at least 60 contiguous amino acids of the second amino acid sequence are from the amino acid region of an HA protein corresponding to amino acid residues 292-517 of influenza A New Caledonia/20/1999 (H1) (SEQ ID NO:8). In one embodiment, the at least 60 contiguous amino acids of the second amino acid sequence are from the amino acid region of an HA protein corresponding to amino acid residues 328-517 of influenza A New Caledonia/20/1999 (H1) (SEQ ID NO:8). In one embodiment, the at least 60 contiguous amino acids of the second amino acid sequence are from a sequence at least 85%, at least 90%, at least 95% or at least 97% identical to a sequence selected from the group consisting of SEQ ID NO:23, SEQ ID NO:26, SEQ ID NO:29, SEQ ID NO:32, SEQ ID NO:38, SEQ ID NO:41, SEQ ID NO:44, SEQ ID NO:47, SEQ ID NO:53, SEQ ID NO:56, SEQ ID NO:59, SEQ ID NO:62, SEQ ID NO:68, SEQ ID NO:71, SEQ ID NO:74 and SEQ ID NO:77. In one embodiment, the at least 60 contiguous amino acids of the second amino acid sequence are from a sequence selected from the group consisting of SEQ ID NO:23, SEQ ID NO:26, SEQ ID NO:29, SEQ ID NO:32, SEQ ID NO:38, SEQ ID NO:41, SEQ ID NO:44, SEQ ID NO:47, SEQ ID NO:53, SEQ ID NO:56, SEQ ID NO:59, SEQ ID NO:62, SEQ ID NO:68, SEQ ID NO:71, SEQ ID NO:74 and SEQ ID NO:77.

In one embodiment, the second amino acid sequence comprises at least 75, at least 100, at least 150 or at least 200 contiguous amino acids from the amino acid sequence downstream of the carboxyl-terminal end of the head region sequence, wherein the at least 75, at least 100, at least 150 or at least 200 contiguous amino acids comprise a polypeptide sequence corresponding to the sequence of SEQ ID NO:149 or SEQ ID NO:150 of H1N1 NC, and wherein the amino acid residue in the polypeptide sequence corresponding to K1 of SEQ ID NO:149 or K1 of SEQ ID NO:150, and the amino acid residue in the polypeptide sequence that corresponds to E53 of SEQ ID NO:149 or E20 of SEQ ID NO:150 have been substituted with amino acids other than lysine and glutamic acid, respectively, such that the strength of the interaction between the substituted amino acid residues is greater than the strength of the interaction in the wild-type protein. In one embodiment, the second amino acid sequence comprises at least 75, at least 100, at least 150 or at least 200 contiguous amino acids from the amino acid region of an HA protein corresponding to amino acid residues 292-517 of influenza A New Caledonia/20/1999 (H1) (SEQ ID NO:8), wherein the at least 75, at least 100, at least 150 or at least 200 contiguous amino acids comprise a polypeptide sequence corresponding to the sequence of SEQ ID NO:149 or SEQ ID NO:150 of H1N1 NC, and wherein the amino acid residue in the polypeptide sequence corresponding to K1 of SEQ ID NO:149 or K1 of SEQ ID NO:150, and the amino acid residue in the polypeptide sequence that corresponds to E53 of SEQ ID NO:149 or E20 of SEQ ID NO:150 have been substituted with amino acids other than lysine and glutamic acid, respectively, such that the strength of the interaction between the substituted amino acid residues is greater than the strength of the interaction in the wild-type protein. In one embodiment, the second amino acid sequence comprises at least 75, at least 100, at least 150 or at least 200 contiguous amino acids from the amino acid region of an HA protein corresponding to amino acid residues 328-517 of influenza A New Caledonia/20/1999 (H1) (SEQ ID NO:8), wherein the at least 75, at least 100, at least 150 or at least 200 contiguous amino acids comprise a polypeptide sequence corresponding to the sequence of SEQ ID NO:149 or SEQ ID NO:150 of H1N1 NC, and wherein the amino acid residue in the polypeptide sequence corresponding to K1 of SEQ ID NO:149 or K1 of SEQ ID NO:150, and the amino acid residue in the polypeptide sequence that corresponds to E53 of SEQ ID NO:149 or E20 of SEQ ID NO:150 have been substituted with amino acids other than lysine and glutamic acid, respectively, such that the strength of the interaction between the substituted amino acid residues is greater than the strength of the interaction in the wild-type protein. In one embodiment, the second amino acid sequence comprises at least 75, at least 100, at least 150 or at least 200 contiguous amino acids from a sequence at least 85%, at least 90%, at least 95% or at least 97% identical to a sequence selected from the group consisting of SEQ ID NO:23, SEQ ID NO:26, SEQ ID NO:29, SEQ ID NO:32, SEQ ID NO:38, SEQ ID NO:41, SEQ ID NO:44, SEQ ID NO:47, SEQ ID NO:53, SEQ ID NO:56, SEQ ID NO:59, SEQ ID NO:62, SEQ ID NO:68, SEQ ID NO:71, SEQ ID NO:74 and SEQ ID NO:77, wherein the at least 75, at least 100, at least 150 or at least 200 contiguous amino acids comprise a polypeptide sequence corresponding to the sequence of SEQ ID NO:149 or SEQ ID NO:150 of H1N1 NC, and wherein the amino acid residue in the polypeptide sequence corresponding to K1 of SEQ ID NO:149 or K1 of SEQ ID NO:150, and the amino acid residue in the polypeptide sequence that corresponds to E53 of SEQ ID NO:149 or E20 of SEQ ID NO:150 have been substituted with amino acids other than lysine and glutamic acid, respectively, such that the strength of the interaction between the substituted amino acid residues is greater than the strength of the interaction in the wild-type protein. In one embodiment, the second amino acid sequence comprises at least 75, at least 100, at least 150, or at least 200 contiguous amino acids from the group consisting of SEQ ID NO:23, SEQ ID NO:26, SEQ ID NO:29, SEQ ID NO:32, SEQ ID NO:38, SEQ ID NO:41, SEQ ID NO:44, SEQ ID NO:47, SEQ ID NO:53, SEQ ID NO:56, SEQ ID NO:59, SEQ ID NO:62, SEQ ID NO:68, SEQ ID NO:71, SEQ ID NO:74 and SEQ ID NO:77, wherein the at least 75, at least 100, at least 150 or at least 200 contiguous amino acids comprise a polypeptide sequence corresponding to the sequence of SEQ ID NO:149 or SEQ ID NO:150 of H1N1 NC, and wherein the amino acid residue in the polypeptide sequence corresponding to K1 of SEQ ID NO:149 or K1 of SEQ ID NO:150, and the amino acid residue in the polypeptide sequence that corresponds to E53 of SEQ ID NO:149 or E20 of SEQ ID NO:150 have been substituted with amino acids other than lysine and glutamic acid, respectively, such that the strength of the interaction between the substituted amino acid residues is greater than the strength of the interaction in the wild-type protein.

Protein constructs containing the specified site-specific mutations can be used to make nanoparticles of the present invention by joining them to monomeric subunits. Thus, in one embodiment, the protein construct containing the disclosed site-specific mutations (e.g., K1 of SEQ ID NO:149 or SEQ ID NO:150 and E53 of SEQ ID NO149 or E20 of SEQ ID NO:150) is joined to at least a portion of a monomeric subunit protein, wherein the portion of the monomeric subunit protein is capable of directing self-assembly of protein constructs. In one embodiment, the at least a portion of the monomeric subunit protein is joined to the second amino acid sequence. In a preferred embodiment, the at least a portion of the monomeric subunit protein is joined to the carboxyl end of the second amino acid sequence. In one embodiment, the portion comprises at least 50, at least 100 or at least 150 amino acids from a monomeric subunit. In one embodiment, the monomeric subunit is ferritin. In one embodiment, the monomeric subunit is lumazine synthase. In one embodiment, the monomeric subunit comprises a sequence at least 85% identical, at least 90% identical or at least 95% identical to SEQ ID NO:2, SEQ ID NO:5 or SEQ ID NO:194. In one embodiment, the monomeric subunit comprises a sequence selected from the group consisting of SEQ ID NO:2, SEQ ID NO:5 and SEQ ID NO:194.

While the modifications made to the HA proteins disclosed herein have been described as separate embodiments, it should be appreciated that all such modification may be contained in a single protein construct. For example, a protein construct could be made in which a first amino acid sequence is joined by a linker to a second amino acid sequence, wherein the second amino acid sequence comprises amino acid sequence from the region downstream of the carboxyl-terminal end of the head region but lacks the internal loop sequence represented by SEQ ID NOs:133-148, and wherein amino acids in the second amino acid sequence corresponding to K1 of SEQ ID NO:149 or K1 of SEQ ID NO:50 and E53 of SEQ ID NO:149 or E20 of SEQ ID NO:150 have been substituted with amino acids other than lysine and glutamic acid, respectively, in order to increase the strength of the interaction between these amino acid residues in the folded protein. Thus, one embodiment of the present invention is a protein construct comprising a first amino acid sequence from the stem region of an influenza virus HA protein and a second amino acid sequence from the stem region of an influenza virus HA protein, the first and second amino acid sequences being covalently linked by a linker sequence,

- wherein the first amino acid sequence comprises at least 20 contiguous amino acid residues from the amino acid sequence upstream of the amino-terminal end of the head region sequence;
- wherein the second amino acid sequence comprises a polypeptide sequence at least 85%, at least 90% or at least 95% identical to at least 100 contiguous amino acid residues from the amino acid sequence downstream of the carboxyl-terminal end of the head region sequence,
- wherein the polypeptide sequence comprises a sequence corresponding to the sequence in influenza A New Caledonia/20/1999 (H1) represented by SEQ ID NO:150, the sequence in influenza A California/2009 (H1) represented by SEQ ID NO:152, the sequence in influenza A Singapore/1957 (H2) represented by SEQ ID NO:154, and the sequence in influenza A Indonesia/2005 H5) represented by SEQ ID NO:156; and,
- wherein the amino acid residue in the polypeptide sequence that corresponds to K1 of SEQ ID NO:150 has been substituted with an amino acid other than lysine and the amino acid residue corresponding to E20 of SEQ ID NO:150 has been substituted with an amino acid other than glutamic acid.

In one embodiment, the polypeptide comprises at least 100 contiguous amino acids from the amino acid sequence downstream of the carboxyl-terminal end of the head region sequence. In one embodiment, the at least 100 contiguous amino acids comprise SEQ ID NO:150. In one embodiment, the at least 100 contiguous amino acids comprise SEQ ID NO:152. In one embodiment, the at least 100 contiguous amino acids sequence comprise SEQ ID NO:154. In one embodiment, the at least 100 contiguous amino acids comprise SEQ ID NO:156. It should be appreciated that in the above-described constructs, when the internal loop region is removed, the respective ends of the remaining HA protein can be directly joined together. However, in some cases, such direct linkage may reduce the flexibility of the peptide backbone. Thus, in some cases, it may be beneficial to replace the internal loop region with a linker sequence. As an example, if a six amino acid linker sequence were inserted into SEQ ID NO:150, the final sequence may appear as follows: VNSVIEKMGSGGSGTYNAELLVLL.

Accordingly, in one embodiment, the polypeptide sequence of the protein construct comprises SEQ ID NO:150, into which is inserted a short linker sequence. In one embodiment, the polypeptide sequence of the protein construct comprises SEQ ID NO:152, into which is inserted a short linker sequence. In one embodiment, the polypeptide sequence of the protein construct comprises SEQ ID NO:154, into which is inserted a short linker sequence. In one embodiment, the polypeptide sequence of the protein construct comprises SEQ ID NO:156, into which is inserted a short linker sequence. In one embodiment, the linker is made from serine and glycine residues. In one embodiment, the linker is less than ten amino acids in length. In one embodiment, the linker is less than 5 amino acids in length. In one embodiment, the linker is less than three amino acids in length.

While the protein constructs described heretofore can be used to produce nanoparticles capable of generating an immune response against one or more influenza viruses, in some embodiments, it may be useful to engineer further mutations into the amino acid sequences of proteins of the present invention. For example, it may be useful to alter sites such as enzyme recognition sites or glycosylation sites in the monomeric subunit protein, the trimerization domain, or linker sequences, in order to give the protein beneficial properties (e.g., solubility, half-life, mask portions of the protein from immune surveillance). In this regard, it is known that the monomeric subunit of ferritin is not glycosylated naturally. However, it can be glycosylated if it is expressed as a secreted protein in mammalian or yeast cells. Thus, in one embodiment, potential N-linked glycosylation sites in the amino acid sequences from the monomeric ferritin subunit are mutated so that the mutated ferritin subunit sequences are no longer glycosylated at the mutated site. One such sequence of a mutated monomeric ferritin subunit is represented by SEQ ID NO:5.

Protein construct sequences can also be altered to include further useful mutations. For example, in some instances, it may be desirable to block the production of an immune response against certain amino acid sequences in the protein construct. This may be done by adding a glycosylation site near the site to be blocked such that the glycans sterically hinder the ability of the immune system to reach the blocked site. Thus, in one embodiment, the sequence of the protein construct has been altered to include one or more glycosylation sites. Examples of such sites include, but are not limited to, Asn-X-Ser, Asn-X-Thr and Asn-X-Cys. In some instances, the glycosylation site can be introduced into a linker sequence. Further examples of useful sites at which to introduce glycosylation sites include, but are not limited to, the amino acid corresponding to amino acids 45-47, or amino acids 370-372 from the HA protein of influenza A New Caledonia/20/1999 (H1). Methods of introducing glycosylation sites are known to those skilled in the art.

The disclosure herein demonstrates that mutations at specific locations in the HA or monomeric subunit protein produce useful protein constructs and consequently nanoparticles of the present invention. Examples of useful locations in a ferritin protein at which to introduce mutations include an amino acid corresponding to an amino acid position selected from the group consisting of amino acid position 18, amino acid position 20 and amino acid position 68 of SEQ ID NO:2. Examples of useful locations at which to introduce mutations include an amino acid in the HA protein corresponding to an amino acid position selected from the group consisting of amino acid position 36, amino acid position 45, amino acid position 47, amino acid position 49, amino acid position 339, amino acid position 340, amino acid position 341, amino acid position 342, amino acid position 361, amino acid position 372, amino acid position 394, amino acid position 402, amino acid position 437, amino acid position 438, amino acid position 445, amino acid position 446, amino acid position 448, amino acid 449, amino acid position 450 and amino acid position 452 of HA protein of influenza A New Caledonia/20/1999 (H1) (SEQ ID NO:8). Some examples of such mutations are listed in Table 2. In one embodiment, the HA portion of the protein construct comprises an isoleucine, or an amino acid residue having similar properties thereto, at the position corresponding to amino acid position 36 of HA protein of influenza A New Caledonia/20/1999 (H1). In one embodiment, the HA portion of the protein construct comprises an asparagine, or an amino acid residue having similar properties thereto, at the position corresponding to amino acid position 45 of HA protein of influenza A New Caledonia/20/1999 (H1). In one embodiment, the HA portion of the protein construct comprises a threonine, or an amino acid residue having similar properties thereto, at the position corresponding to amino acid position 47 of HA protein of influenza A New Caledonia/20/1999 (H1). In one embodiment, the HA portion of the protein construct comprises a tryptophan, or an amino acid residue having similar properties thereto, at the position corresponding to amino acid position 49 of HA protein of influenza A New Caledonia/20/1999 (H1). In one embodiment, the HA portion of the protein construct comprises an glutamine, or an amino acid residue having similar properties thereto, at the position corresponding to amino acid position 339 of HA protein of influenza A New Caledonia/20/1999 (H1). In one embodiment, the HA portion of the protein construct comprises an arginine, or an amino acid residue having similar properties thereto, at the position corresponding to amino acid position 340 of HA protein of influenza A New Caledonia/20/1999 (H1). In one embodiment, the HA portion of the protein construct comprises a glutamic acid, or an amino acid residue having similar properties thereto, at the position corresponding to amino acid position 341 of HA protein of influenza A New Caledonia/20/1999 (H1). In one embodiment, the HA portion of the protein construct comprises a threonine, or an amino acid residue having similar properties thereto, at the position corresponding to amino acid position 342 of HA protein of influenza A New Caledonia/20/1999 (H1). In one embodiment, the HA portion of the protein construct comprises a threonine, or an amino acid residue having similar properties thereto, at the position corresponding to amino acid position 372 of HA protein of influenza A New Caledonia/20/1999 (H1). In one embodiment, the HA portion of the protein construct comprises a methionine, an isoleucine, a leucine, a glutamine, or an amino acid residue having similar properties thereto, at the position corresponding to amino acid position 394 of HA protein of influenza A New Caledonia/20/1999 (H1). In one embodiment, the HA portion of the protein construct comprises an asparagine, a threonine, a glycine, an asparagine, or an amino acid residue having similar properties thereto, at the position corresponding to amino acid position 402 of HA protein of influenza A New Caledonia/20/1999 (H1). In one embodiment, the HA portion of the protein construct comprises an aspartic acid, or an amino acid residue having similar properties thereto, at the position corresponding to amino acid position 437 of HA protein of influenza A New Caledonia/20/1999 (H1). In one embodiment, the HA portion of the protein construct comprises a leucine, or an amino acid residue having similar properties thereto, at the position corresponding to amino acid position 438 of HA protein of influenza A New Caledonia/20/1999 (H1). In one embodiment, the HA portion of the protein construct comprises a leucine, a methionine, or an amino acid residue having similar properties thereto, at the position corresponding to amino acid position 445 of HA protein of influenza A New Caledonia/20/1999 (H1). In one embodiment, the HA portion of the protein construct comprises an isoleucine, a leucine, a methionine, a glutamine, or an amino acid residue having similar properties thereto, at the position corresponding to amino acid position 446 of HA protein of influenza A New Caledonia/20/1999 (H1). In one embodiment, the HA portion of the protein construct comprises a glutamine, or an amino acid residue having similar properties thereto, at the position corresponding to amino acid position 448 of HA protein of influenza A New Caledonia/20/1999 (H1). In one embodiment, the HA portion of the protein construct comprises a tryptophan, a phenylalanine, or an amino acid residue having similar properties thereto, at the position corresponding to amino acid position 449 of HA protein of influenza A New Caledonia/20/1999 (H1). In one embodiment, the HA portion of the protein construct comprises an alanine, or an amino acid residue having similar properties thereto, at the position corresponding to amino acid position 450 of HA protein of influenza A New Caledonia/20/1999 (H1). In one embodiment, the HA portion of the protein construct comprises a leucine, or an amino acid residue having similar properties thereto, at the position corresponding to amino acid position 452 of HA protein of influenza A New Caledonia/20/1999 (H1). In one embodiment, the HA portion of the protein construct lacks one or more amino acids corresponding to amino acids 515-517 of the HA protein of influenza A New Caledonia/20/1999 (H1).

One embodiment of the present invention is a protein construct comprising an amino acid sequence at least 85%, at least 90%, at least 95% or at least 97% identical to a sequence selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400.

In one embodiment, the amino acid residue corresponding to K1 of SEQ ID NO:149 or K1 of SEQ ID NO:150 is substituted with an amino acid other than lysine, and the amino acid residue corresponding to E53 of SEQ ID NO:149 or E20 of SEQ ID NO:20 is substituted with an amino acid other than glutamic acid, such that the strength of the interaction between the substituted amino acids is increased in the folded protein.

One embodiment of the present invention is a protein construct comprising a sequence selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400. In one embodiment, the protein construct is capable of forming a nanoparticle when linked to a monomeric subunit protein, wherein the nanoparticle is capable of eliciting an immune response against an influenza virus.

As has been discussed previously, protein constructs made from influenza HA protein can be used to make nanoparticles of the present invention by joining them to monomeric subunits. Thus, in one embodiment, the protein construct is joined to at least a portion of a monomeric subunit protein, wherein the portion of the monomeric subunit protein is capable of directing self-assembly of protein constructs. In one embodiment, the at least a portion of the monomeric subunit protein is joined to the second amino acid sequence. In a preferred embodiment, the at least a portion of the monomeric subunit protein is joined to the carboxyl end of the second amino acid sequence. In one embodiment, the portion comprises at least 50, at least 100 or at least 150 amino acids from a monomeric subunit. In one embodiment, the monomeric subunit is ferritin. In one embodiment, the monomeric subunit is lumazine synthase. In one embodiment, the monomeric subunit comprises a sequence at least 85% identical, at least 90% identical or at least 95% identical to SEQ ID NO:2, SEQ ID NO:5 or SEQ ID NO:194. In one embodiment, the monomeric subunit comprises a sequence selected from the group consisting of SEQ ID NO:2, SEQ ID NO:5 and SEQ ID NO:194.

One embodiment of the present invention is a protein construct comprising an amino acid sequence at least 85%, at least 90%, at least 95% or at least 97% identical to a sequence selected from the group consisting of SEQ ID NO:107, SEQ ID NO:110, SEQ ID NO:113, SEQ ID NO:116, SEQ ID NO:119, SEQ ID NO:122, SEQ ID NO:125, SEQ ID NO:128, SEQ ID NO:131, SEQ ID NO:161, SEQ ID NO:167, SEQ ID NO:173, SEQ ID NO:179, SEQ ID NO:185, SEQ ID NO:191, SEQ ID NO:200, SEQ ID NO:206, SEQ ID NO:212, SEQ ID NO:215, SEQ ID NO:220, SEQ ID NO:223, SEQ ID NO:225, SEQ ID NO:227, SEQ ID NO:229, SEQ ID NO:231, SEQ ID NO:233, SEQ ID NO:238, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:264, SEQ ID NO:271, SEQ ID NO:278, SEQ ID NO:285, SEQ ID NO:292, SEQ ID NO:299, SEQ ID NO:306, SEQ ID NO:313, SEQ ID NO:320, SEQ ID NO:327, SEQ ID NO:334, SEQ ID NO:341, SEQ ID NO:348, SEQ ID NO:355, SEQ ID NO:362, SEQ ID NO:369, SEQ ID NO:376, SEQ ID NO:383, SEQ ID NO:390 and SEQ ID NO:397. In one embodiment, the amino acid residue corresponding to K1 of SEQ ID NO:149 or K1 of SEQ ID NO:150 is substituted with an amino acid other than lysine, and the amino acid residue corresponding to E53 of SEQ ID NO:149 or E20 of SEQ ID NO:20 is substituted with an amino acid other than glutamic acid, such that the strength of the interaction between the substituted amino acids is increased in the folded protein. In one embodiment, the HA portion of the protein construct comprises an isoleucine, or an amino acid residue having similar properties thereto, at the position corresponding to amino acid position 36 of HA protein of influenza A New Caledonia/20/1999 (H1). In one embodiment, the HA portion of the protein construct comprises an asparagine, or an amino acid residue having similar properties thereto, at the position corresponding to amino acid position 45 of HA protein of influenza A New Caledonia/20/1999 (H1). In one embodiment, the HA portion of the protein construct comprises a threonine, or an amino acid residue having similar properties thereto, at the position corresponding to amino acid position 47 of HA protein of influenza A New Caledonia/20/1999 (H1). In one embodiment, the HA portion of the protein construct comprises a tryptophan, or an amino acid residue having similar properties thereto, at the position corresponding to amino acid position 49 of HA protein of influenza A New Caledonia/20/1999 (H1). In one embodiment, the HA portion of the protein construct comprises an glutamine, or an amino acid residue having similar properties thereto, at the position corresponding to amino acid position 339 of HA protein of influenza A New Caledonia/20/1999 (H1). In one embodiment, the HA portion of the protein construct comprises an arginine, or an amino acid residue having similar properties thereto, at the position corresponding to amino acid position 340 of HA protein of influenza A New Caledonia/20/1999 (H1). In one embodiment, the HA portion of the protein construct comprises a glutamic acid, or an amino acid residue having similar properties thereto, at the position corresponding to amino acid position 341 of HA protein of influenza A New Caledonia/20/1999 (H1). In one embodiment, the HA portion of the protein construct comprises a threonine, or an amino acid residue having similar properties thereto, at the position corresponding to amino acid position 342 of HA protein of influenza A New Caledonia/20/1999 (H1). In one embodiment, the HA portion of the protein construct comprises a threonine, or an amino acid residue having similar properties thereto, at the position corresponding to amino acid position 372 of HA protein of influenza A New Caledonia/20/1999 (H1). In one embodiment, the HA portion of the protein construct comprises a methionine, an isoleucine, a leucine, a glutamine, or an amino acid residue having similar properties thereto, at the position corresponding to amino acid position 394 of HA protein of influenza A New Caledonia/20/1999 (H1). In one embodiment, the HA portion of the protein construct comprises an asparagine, a threonine, a glycine, an asparagine, or an amino acid residue having similar properties thereto, at the position corresponding to amino acid position 402 of HA protein of influenza A New Caledonia/20/1999 (H1). In one embodiment, the HA portion of the protein construct comprises an aspartic acid, or an amino acid residue having similar properties thereto, at the position corresponding to amino acid position 437 of HA protein of influenza A New Caledonia/20/1999 (H1). In one embodiment, the HA portion of the protein construct comprises a leucine, or an amino acid residue having similar properties thereto, at the position corresponding to amino acid position 438 of HA protein of influenza A New Caledonia/20/1999 (H1). In one embodiment, the HA portion of the protein construct comprises a leucine, a methionine, or an amino acid residue having similar properties thereto, at the position corresponding to amino acid position 445 of HA protein of influenza A New Caledonia/20/1999 (H1). In one embodiment, the HA portion of the protein construct comprises an isoleucine, a leucine, a methionine, a glutamine, or an amino acid residue having similar properties thereto, at the position corresponding to amino acid position 446 of HA protein of influenza A New Caledonia/20/1999 (H1). In one embodiment, the HA portion of the protein construct comprises a glutamine, or an amino acid residue having similar properties thereto, at the position corresponding to amino acid position 448 of HA protein of influenza A New Caledonia/20/1999 (H1). In one embodiment, the HA portion of the protein construct comprises a tryptophan, a phenylalanine, or an amino acid residue having similar properties thereto, at the position corresponding to amino acid position 449 of HA protein of influenza A New Caledonia/20/1999 (H1). In one embodiment, the HA portion of the protein construct comprises an alanine, or an amino acid residue having similar properties thereto, at the position corresponding to amino acid position 450 of HA protein of influenza A New Caledonia/20/1999 (H1). In one embodiment, the HA portion of the protein construct comprises a leucine, or an amino acid residue having similar properties thereto, at the position corresponding to amino acid position 452 of HA protein of influenza A New Caledonia/20/1999 (H1). In one embodiment, the HA portion of the protein construct lacks one or more amino acids corresponding to amino acids 515-517 of the HA protein of influenza A New Caledonia/20/1999 (H1).

One embodiment of the present invention is a protein construct comprising a sequence selected from the group consisting of SEQ ID NO:107, SEQ ID NO:110, SEQ ID NO:113, SEQ ID NO:116, SEQ ID NO:119, SEQ ID NO:122, SEQ ID NO:125, SEQ ID NO:128, SEQ ID NO:131, SEQ ID NO:161, SEQ ID NO:167, SEQ ID NO:173, SEQ ID NO:179, SEQ ID NO:185, SEQ ID NO:191, SEQ ID NO:200, SEQ ID NO:206, SEQ ID NO:212, SEQ ID NO:215, SEQ ID NO:220, SEQ ID NO:223, SEQ ID NO:225, SEQ ID NO:227, SEQ ID NO:229, SEQ ID NO:231, SEQ ID NO:233, SEQ ID NO:238, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:264, SEQ ID NO:271, SEQ ID NO:278, SEQ ID NO:285, SEQ ID NO:292, SEQ ID NO:299, SEQ ID NO:306, SEQ ID NO:313, SEQ ID NO:320, SEQ ID NO:327, SEQ ID NO:334, SEQ ID NO:341, SEQ ID NO:348, SEQ ID NO:355, SEQ ID NO:362, SEQ ID NO:369, SEQ ID NO:376, SEQ ID NO:383, SEQ ID NO:390 and SEQ ID NO:397.

One embodiment of the present invention is a protein construct encoded by a nucleic acid molecule comprising a nucleic acid sequence at least 85%, at least 90%, at least 95% or at least 97% identical to a sequence selected from the group consisting of SEQ ID NO:266, SEQ ID NO:273, SEQ ID NO: SEQ ID NO:280, SEQ ID NO:287, SEQ ID NO:294, SEQ ID NO:301, SEQ ID NO:308, SEQ ID NO:315, SEQ ID NO:322, SEQ ID NO:329, SEQ ID NO:336, SEQ ID NO:343, SEQ ID NO:350, SEQ ID NO:357, SEQ ID NO:364, SEQ ID NO:371, SEQ ID NO:378, SEQ ID NO:385 SEQ ID NO:392 and SEQ ID NO:399. One embodiment of the present invention is a protein construct encoded by a nucleic acid molecule comprising a nucleic acid sequence selected from the group consisting of SEQ ID NO:266, SEQ ID NO:273, SEQ ID NO: SEQ ID NO:280, SEQ ID NO:287, SEQ ID NO:294, SEQ ID NO:301, SEQ ID NO:308, SEQ ID NO:315, SEQ ID NO:322, SEQ ID NO:329, SEQ ID NO:336, SEQ ID NO:343, SEQ ID NO:350, SEQ ID NO:357, SEQ ID NO:364, SEQ ID NO:371, SEQ ID NO:378, SEQ ID NO:385 SEQ ID NO:392 and SEQ ID NO:399.

Proteins and protein constructs of the present invention are encoded by nucleic acid molecules of the present invention. In addition, they are expressed by nucleic acid constructs of the present invention. As used herein a nucleic acid construct is a recombinant expression vector, i.e., a vector linked to a nucleic acid molecule encoding a protein such that the nucleic acid molecule can effect expression of the protein when the nucleic acid construct is administered to, for example, a subject or an organ, tissue or cell. The vector also enables transport of the nucleic acid molecule to a cell within an environment, such as, but not limited to, an organism, tissue, or cell culture. A nucleic acid construct of the present disclosure is produced by human intervention. The nucleic acid construct can be DNA, RNA or variants thereof. The vector can be a DNA plasmid, a viral vector, or other vector. In one embodiment, a vector can be a cytomegalovirus (CMV), retrovirus, adenovirus, adeno-associated virus, herpes virus, vaccinia virus, poliovirus, sindbis virus, or any other DNA or RNA virus vector. In one embodiment, a vector can be a pseudotyped lentiviral or retroviral vector. In one embodiment, a vector can be a DNA plasmid. In one embodiment, a vector can be a DNA plasmid comprising viral components and plasmid components to enable nucleic acid molecule delivery and expression. Methods for the construction of nucleic acid constructs of the present disclosure are well known. See, for example, *Molecular Cloning: a Laboratory Manual, 3rd* edition, Sambrook et al. 2001 Cold Spring Harbor Laboratory Press, and *Current Protocols in Molecular Biology*, Ausubel et al. eds., John Wiley & Sons, 1994. In one embodiment, the vector is a DNA plasmid, such as a CMV/R plasmid such as CMV/R or CMV/R 8 KB (also referred to herein as CMV/R 8 kb). Examples of CMV/R and CMV/R 8 kb are provided herein. CMV/R is also described in U.S. Pat. No. 7,094,598 B2, issued Aug. 22, 2006.

As used herein, a nucleic acid molecule comprises a nucleic acid sequence that encodes a protein construct of the present invention. A nucleic acid molecule can be produced recombinantly, synthetically, or by a combination of recombinant and synthetic procedures. A nucleic acid molecule of the disclosure can have a wild-type nucleic acid sequence or a codon-modified nucleic acid sequence to, for example, incorporate codons better recognized by the human translation system. In one embodiment, a nucleic acid molecule can be genetically-engineered to introduce, or eliminate, codons encoding different amino acids, such as to introduce codons that encode an N-linked glycosylation site. Methods to produce nucleic acid molecules of the disclosure are known in the art, particularly once the nucleic acid sequence is know. It is to be appreciated that a nucleic acid construct can comprise one nucleic acid molecule or more than one nucleic acid molecule. It is also to be appreciated that a nucleic acid molecule can encode one protein or more than one protein.

One embodiment is a nucleic acid molecule encoding an influenza HA protein comprising an amino acid sequence at least 80%, at least 85%, at least 90%, at least 92%, at least 94%, at least 96%, at least 98% or at least 99% identical to a sequence selected from the group consisting of SEQ ID NO:150, SEQ ID N0152, SEQ ID NO:154 and SEQ ID NO:156. One embodiment is a nucleic acid molecule encoding an influenza HA protein comprising an amino acid sequence selected from the group consisting of SEQ ID NO:150, SEQ ID N0152, SEQ ID NO:154 and SEQ ID NO:156.

In one embodiment the nucleic acid molecule encodes an influenza HA protein comprising an amino acid sequence at least 80%, at least 85%, at least 90%, at least 92%, at least 94%, at least 96%, at least 98% or at least 99% identical to a sequence selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400. In one embodiment the nucleic acid molecule encodes an influenza HA protein comprising an amino acid selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400.

One embodiment of the present invention is a nucleic acid molecule comprising a nucleic acid sequence comprising an amino acid sequence at least 80%, at least 85%, at least 90%, at least 92%, at least 94%, at least 96%, at least 98% or at least 99% identical to a sequence selected from the group consisting of SEQ ID NO:79, SEQ ID NO:82, SEQ ID NO:85, SEQ ID NO:88, SEQ ID NO:91, SEQ ID NO:94, SEQ ID NO:97, SEQ ID NO:100, SEQ ID NO:103, SEQ ID NO:157, SEQ ID NO:163, SEQ ID NO:169, SEQ ID NO:175, SEQ ID NO:181, SEQ ID NO:187, SEQ ID NO:196, SEQ ID NO:202, SEQ ID NO:208, SEQ ID NO:216, SEQ ID NO:234, SEQ ID NO:260, SEQ ID NO:267, SEQ ID NO:274, SEQ ID NO:281, SEQ ID NO:288, SEQ ID NO:295, SEQ ID NO:302, SEQ ID NO:309, SEQ ID NO:316, SEQ ID NO:323, SEQ ID NO:330, SEQ ID NO:337, SEQ ID NO:344, SEQ ID NO:351, SEQ ID NO:358, SEQ ID NO:365, SEQ ID NO:372, SEQ ID NO:379, SEQ ID NO:386 and SEQ ID NO:393. One embodiment of the present invention is a nucleic acid molecule comprising a nucleic acid sequence selected from the group consisting of SEQ ID NO:79, SEQ ID NO:82, SEQ ID NO:85, SEQ ID NO:88, SEQ ID NO:91, SEQ ID NO:94, SEQ ID NO:97, SEQ ID NO:100, SEQ ID NO:103, SEQ ID NO:157, SEQ ID NO:163, SEQ ID NO:169, SEQ ID NO:175, SEQ ID NO:181, SEQ ID NO:187, SEQ ID NO:196, SEQ ID NO:202, SEQ ID NO:208, SEQ ID NO:216, SEQ ID NO:234, SEQ ID NO:260, SEQ ID NO:267, SEQ ID NO:274, SEQ ID NO:281, SEQ ID NO:288, SEQ ID NO:295, SEQ ID NO:302, SEQ ID NO:309, SEQ ID NO:316, SEQ ID NO:323, SEQ ID NO:330, SEQ ID NO:337, SEQ ID NO:344, SEQ ID NO:351, SEQ ID NO:358, SEQ ID NO:365, SEQ ID NO:372, SEQ ID NO:379, SEQ ID NO:386 and SEQ ID NO:393.

Preferred nucleic acid molecules are those that encode a monomeric subunit, a HA protein, and/or a protein construct comprising a monomeric subunit protein joined to an influenza HA protein. Thus, one embodiment of the present invention is a nucleic acid molecule comprising a nucleic acid sequence encoding a protein that comprises a monomeric subunit of a ferritin protein joined to an influenza HA protein. In one embodiment, the monomeric subunit comprises an amino acid sequence at least 80%, at least 85%, at least 90%, at least 92%, at least 94%, at least 96%, at least 98% or at least 99% identical to a sequence selected from the group consisting of SEQ ID NO:2 and SEQ ID NO:5. In one embodiment, the monomeric subunit comprises an amino acid sequence selected from the group consisting of SEQ ID NO:2 and SEQ ID NO:5.

One embodiment of the present invention is a nucleic acid molecule comprising a nucleic acid sequence encoding a protein that comprises a monomeric subunit of lumazine synthase joined to an influenza HA protein. In one embodiment, the monomeric subunit comprises an amino acid sequence at least 80%, at least 85%, at least 90%, at least 92%, at least 94%, at least 96%, at least 98% or at least 99% identical to SEQ ID NO:194. In one embodiment, the monomeric subunit comprises SEQ ID NO:194.

One embodiment of the present invention is a nucleic acid molecule encoding a protein construct comprising an amino acid sequence at least 80%, at least 85%, at least 90%, at least 92%, at least 94%, at least 96%, at least 98% or at least 99% identical to a sequence selected from the group consisting of SEQ ID NO:107, SEQ ID NO:110, SEQ ID NO:113, SEQ ID NO:116, SEQ ID NO:119, SEQ ID NO:122, SEQ ID NO:125, SEQ ID NO:128, SEQ ID NO:131, SEQ ID NO:161, SEQ ID NO:167, SEQ ID NO:173, SEQ ID NO:179, SEQ ID NO:185, SEQ ID NO:191, SEQ ID NO:200, SEQ ID NO:206, SEQ ID NO:212, SEQ ID NO:215, SEQ ID NO:220, SEQ ID NO:223, SEQ ID NO:225, SEQ ID NO:227, SEQ ID NO:229, SEQ ID NO:231, SEQ ID NO:233, SEQ ID NO:238, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:264, SEQ ID NO:271, SEQ ID NO:278, SEQ ID NO:285, SEQ ID NO:292, SEQ ID NO:299, SEQ ID NO:306, SEQ ID NO:313, SEQ ID NO:320, SEQ ID NO:327, SEQ ID NO:334, SEQ ID NO:341, SEQ ID NO:348, SEQ ID NO:355, SEQ ID NO:362, SEQ ID NO:369, SEQ ID NO:376, SEQ ID NO:383, SEQ ID NO:390 and SEQ ID NO:397. One embodiment of the resent invention is a nucleic acid molecule encoding a protein construct comprising a sequence selected from the group consisting of SEQ ID NO:107, SEQ ID NO:110, SEQ ID NO:113, SEQ ID NO:116, SEQ ID NO:119, SEQ ID NO:122, SEQ ID NO:125, SEQ ID NO:128, SEQ ID NO:131, SEQ ID NO:161, SEQ ID NO:167, SEQ ID NO:173, SEQ ID NO:179, SEQ ID NO:185, SEQ ID NO:191, SEQ ID NO:200, SEQ ID NO:206, SEQ ID NO:212, SEQ ID NO:215, SEQ ID NO:220, SEQ ID NO:223, SEQ ID NO:225, SEQ ID NO:227, SEQ ID NO:229, SEQ ID NO:231, SEQ ID NO:233, SEQ ID NO:238, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:264, SEQ ID NO:271, SEQ ID NO:278, SEQ ID NO:285, SEQ ID NO:292, SEQ ID NO:299, SEQ ID NO:306, SEQ ID NO:313, SEQ ID NO:320, SEQ ID NO:327, SEQ ID NO:334, SEQ ID NO:341, SEQ ID NO:348, SEQ ID NO:355, SEQ ID NO:362, SEQ ID NO:369, SEQ ID NO:376, SEQ ID NO:383, SEQ ID NO:390 and SEQ ID NO:397.

One embodiment of the present invention is a nucleic acid molecule comprising a nucleic acid sequence at least 80%, at least 85%, at least 90%, at least 92%, at least 94%, at least 96%, at least 98% or at least 99% identical to a sequence selected from the group consisting of SEQ ID NO:106, SEQ ID NO:109, SEQ ID NO:112, SEQ ID NO:115, SEQ ID NO:118, SEQ ID NO:121, SEQ ID NO:124, SEQ ID NO:127, SEQ ID NO:130, SEQ ID NO:160, SEQ ID NO:166, SEQ ID NO:172, SEQ ID NO:178, SEQ ID NO:184, SEQ ID NO:190, SEQ ID NO:199, SEQ ID NO:205, SEQ ID NO:211, SEQ ID NO:219, SEQ ID NO:237, SEQ ID NO:263, SEQ ID NO:270, SEQ ID NO:277, SEQ ID NO:284, SEQ ID NO:291, SEQ ID NO:298, SEQ ID NO:305, SEQ ID NO:312, SEQ ID NO:319, SEQ ID NO:326, SEQ ID NO:333, SEQ ID NO:340, SEQ ID NO:347, SEQ ID NO:354, SEQ ID NO:361, SEQ ID NO:368, SEQ ID NO:375, SEQ ID NO:382, SEQ ID NO:389 and SEQ ID NO:396. One embodiment of the present invention is a nucleic acid molecule comprising a nucleic acid sequence selected from the group consisting of SEQ ID NO:106, SEQ ID NO:109, SEQ ID NO:112, SEQ ID NO:115, SEQ ID NO:118, SEQ ID NO:121, SEQ ID NO:124, SEQ ID NO:127, SEQ ID NO:130, SEQ ID NO:160, SEQ ID NO:166, SEQ ID NO:172, SEQ ID NO:178, SEQ ID NO:184, SEQ ID NO:190, SEQ ID NO:199, SEQ ID NO:205, SEQ ID NO:211, SEQ ID NO:219, SEQ ID NO:237, SEQ ID NO:263, SEQ ID NO:270, SEQ ID NO:277, SEQ ID NO:284, SEQ ID NO:291, SEQ ID NO:298, SEQ ID NO:305, SEQ ID NO:312, SEQ ID NO:319, SEQ ID NO:326, SEQ ID NO:333, SEQ ID NO:340, SEQ ID NO:347, SEQ ID NO:354, SEQ ID NO:361, SEQ ID NO:368, SEQ ID NO:375, SEQ ID NO:382, SEQ ID NO:389 and SEQ ID NO:396.

Also encompassed by the present invention are expression systems for producing protein constructs of the present invention. In one embodiment, nucleic acid molecules of the present invention are operationally linked to a promoter. As used herein, operationally linked means that proteins encoded by the linked nucleic acid molecules can be expressed when the linked promoter is activated. Promoters useful for practicing the present invention are known to those skilled in the art. One embodiment of the present invention is a nucleic acid molecule comprising a nucleic acid sequence at least 85%, at least 90%, at least 95% or at least 97% identical to a sequence selected from the group consisting of SEQ ID NO:266, SEQ ID NO:273, SEQ ID NO: SEQ ID NO:280, SEQ ID NO:287, SEQ ID NO:294, SEQ ID NO:301, SEQ ID NO:308, SEQ ID NO:315, SEQ ID NO:322, SEQ ID NO:329, SEQ ID NO:336, SEQ ID NO:343, SEQ ID NO:350, SEQ ID NO:357, SEQ ID NO:364, SEQ ID NO:371, SEQ ID NO:378, SEQ ID NO:385 SEQ ID NO:392 and SEQ ID NO:399. One embodiment of the present invention is a nucleic acid molecule comprising a nucleic acid sequence selected from the group consisting of SEQ ID NO:266, SEQ ID NO:273, SEQ ID NO: SEQ ID NO:280, SEQ ID NO:287, SEQ ID NO:294, SEQ ID NO:301, SEQ ID NO:308, SEQ ID NO:315, SEQ ID NO:322, SEQ ID NO:329, SEQ ID NO:336, SEQ ID NO:343, SEQ ID NO:350, SEQ ID NO:357, SEQ ID NO:364, SEQ ID NO:371, SEQ ID NO:378, SEQ ID NO:385 SEQ ID NO:392 and SEQ ID NO:399.

One embodiment of the present invention is a recombinant cell comprising a nucleic acid molecule of the present invention. One embodiment of the present invention is a recombinant virus comprising a nucleic acid molecule of the present invention.

As indicated above, the recombinant production of the protein constructs of the present invention can be accomplished using any suitable conventional recombinant technology currently known in the field. For example, production of a nucleic acid molecule encoding a fusion protein can be carried out in *E. coli* using a nucleic acid molecule encoding a suitable monomeric subunit protein, such as the *Helicobacter pylori* ferritin monomeric subunit, ad fusing it to a nucleic acid molecule encoding a suitable influenza protein disclosed herein. The construct may then be transformed into protein expression cells, grown to suitable size, and induced to produce the fusion protein.

As has been described, because protein constructs of the present invention comprise a monomeric subunit protein, they can self-assemble. According to the present invention, the supramolecule resulting from such self-assembly is referred to as an HA expressing, monomeric subunit-based nanoparticle. For ease of discussion, the HA expressing, monomeric subunit-based nanoparticle will simply be referred to as a, or the, nanoparticle (np). Nanoparticles of the present invention have similar structural characteristics as the nanoparticles of the monomeric protein from which they are made. For example, with regard to ferritin, a ferritin-based nanoparticle contains 24 subunits and has 432 symmetry. In the case of nanoparticles of the present invention, the subunits are the protein constructs comprising a monomeric subunit (e.g., ferritin, lumazine synthase, etc.) joined to an influenza HA protein. Such nanoparticles display at least a portion of the HA protein on their surface as HA trimers. In such a construction, the HA trimer is accessible to the immune system and thus can elicit an immune response. Thus, one embodiment of the present invention is a nanoparticle comprising a protein construct of the present invention, wherein the protein construct comprises amino acids from the stem region of an HA protein joined to a monomeric subunit protein. In one embodiment, the nanoparticle displays the HA protein on its surface as a HA trimer. In one embodiment, the influenza HA protein is capable of eliciting protective antibodies to an influenza virus.

In one embodiment of the present invention, the nanoparticle comprises a protein construct comprising a first amino acid sequence from the stem region of an influenza virus HA protein and a second amino acid sequence from the stem region of an influenza virus HA protein, the first and second amino acid sequences being covalently linked by a linker sequence, wherein the first amino acid sequence comprises at least 20 contiguous amino acid residues from the amino acid sequence upstream of the amino-terminal end of the head region sequence;

wherein the second amino acid sequence comprises at least 20 contiguous amino acid residues from the amino acid sequence downstream of the carboxyl-terminal end of the head region sequence; and, wherein the first or second amino acid sequence is joined to at least a portion of a monomeric subunit domain.

In one embodiment of the present invention, the nanoparticle comprises a protein construct comprising a first amino acid sequence from the stem region of an influenza virus HA protein and a second amino acid sequence from the stem region of an influenza virus HA protein, the first and second amino acid sequences being covalently linked by a linker sequence, wherein the first amino acid sequence comprises at least 20 contiguous amino acid residues from the amino acid sequence upstream of the amino-terminal end of the head region sequence;

wherein the second amino acid sequence comprises a polypeptide sequence at least 85%, at least 90% or at least 95% identical to at least 100 contiguous amino acid residues from the amino acid sequence downstream of the carboxyl-terminal end of the head region sequence, wherein the polypeptide sequence comprises a sequence corresponding to the sequence in influenza A New Caledonia/20/1999 (H1) represented by SEQ ID NO:150, the sequence in influenza A California/2009 (H1) represented by SEQ ID NO:152, the sequence in influenza A Singapore/1957 (H2) represented by SEQ ID NO:154, and the sequence in influenza A Indonesia/2005 H5) represented by SEQ ID NO:156; and, wherein the first or second amino acid sequence is joined to a monomeric subunit protein.

In a further embodiment, the amino acid residue in the polypeptide sequence that corresponds to K1 of SEQ ID NO:150 has been substituted with an amino acid other than lysine and the amino acid residue corresponding to E20 of SEQ ID NO:150 has been substituted with an amino acid other than glutamic acid.

In one embodiment, additional mutations have been made in the monomeric subunit portion and/or the first and/or second amino acid sequences of the protein construct that makes up the nanoparticle. Examples of useful locations in a ferritin protein at which to introduce mutations include an amino acid corresponding to an amino acid position selected from the group consisting of amino acid position 18, amino acid position 20 and amino acid position 68 of SEQ ID NO:2. In one embodiment, the protein construct comprises a mutation at an amino acid position corresponding to an amino acid position selected from the group consisting of amino acid position 36, amino acid position 45, amino acid position 47, amino acid position 49, amino acid position 339, amino acid position 340, amino acid position 341, amino acid position 342, amino acid position 361, amino acid position 372, amino acid position 394, amino acid position 402, amino acid position 437, amino acid position 438, amino acid position 445, amino acid position 446, amino acid position 448, amino acid 449, amino acid position 450 and amino acid position 452 of HA protein of influenza A New Caledonia/20/1999 (H1) (SEQ ID NO:8). In one embodiment, the HA portion of the protein construct comprises an isoleucine, or an amino acid residue having similar properties thereto, at the position corresponding to amino acid position 36 of HA protein of influenza A New Caledonia/20/1999 (H1). In one embodiment, the HA portion of the protein construct comprises an asparagine, or an amino acid residue having similar properties thereto, at the position corresponding to amino acid position 45 of HA protein of influenza A New Caledonia/20/1999 (H1). In one embodiment, the HA portion of the protein construct comprises a threonine, or an amino acid residue having similar properties thereto, at the position corresponding to amino acid position 47 of HA protein of influenza A New Caledonia/20/1999 (H1). In one embodiment, the HA portion of the protein construct comprises a tryptophan, or an amino acid residue having similar properties thereto, at the position corresponding to amino acid position 49 of HA protein of influenza A New Caledonia/20/1999 (H1). In one embodiment, the HA portion of the protein construct comprises an glutamine, or an amino acid residue having similar properties thereto, at the position corresponding to amino acid position 339 of HA protein of influenza A New Caledonia/20/1999 (H1). In one embodiment, the HA portion of the protein construct comprises an arginine, or an amino acid residue having similar properties thereto, at the position corresponding to amino acid position 340 of HA protein of influenza A New Caledonia/20/1999 (H1). In one embodiment, the HA portion of the protein construct comprises a glutamic acid, or an amino acid residue having similar properties thereto, at the position corresponding to amino acid position 341 of HA protein of influenza A New Caledonia/20/1999 (H1). In one embodiment, the HA portion of the protein construct comprises a threonine, or an amino acid residue having similar properties thereto, at the position corresponding to amino acid position 342 of HA protein of influenza A New Caledonia/20/1999 (H1). In one embodiment, the HA portion of the protein construct comprises a threonine, or an amino acid residue having similar properties thereto, at the position corresponding to amino acid position 372 of HA protein of influenza A New Caledonia/20/1999 (H1). In one embodiment, the HA portion of the protein construct comprises a methionine, an isoleucine, a leucine, a glutamine, or an amino acid residue having similar properties thereto, at the position corresponding to amino acid position 394 of HA protein of influenza A New Caledonia/20/1999 (H1). In one embodiment, the HA portion of the protein construct comprises an asparagine, a threonine, a glycine, an asparagine, or an amino acid residue having similar properties thereto, at the position corresponding to amino acid position 402 of HA protein of influenza A New Caledonia/20/1999 (H1). In one embodiment, the HA portion of the protein construct comprises an aspartic acid, or an amino acid residue having similar properties thereto, at the position corresponding to amino acid position 437 of HA protein of influenza A New Caledonia/20/1999 (H1). In one embodiment, the HA portion of the protein construct comprises a leucine, or an amino acid residue having similar properties thereto, at the position corresponding to amino acid position 438 of HA protein of influenza A New Caledonia/20/1999 (H1). In one embodiment, the HA portion of the protein construct comprises a leucine, a methionine, or an amino acid residue having similar properties thereto, at the position corresponding to amino acid position 445 of HA protein of influenza A New Caledonia/20/1999 (H1). In one embodiment, the HA portion of the protein construct comprises an isoleucine, a leucine, a methionine, a glutamine, or an amino acid residue having similar properties thereto, at the position corresponding to amino acid position 446 of HA protein of influenza A New Caledonia/20/1999 (H1). In one embodiment, the HA portion of the protein construct comprises a glutamine, or an amino acid residue having similar properties thereto, at the position corresponding to amino acid position 448 of HA protein of influenza A New Caledonia/20/1999 (H1). In one embodiment, the HA portion of the protein construct comprises a tryptophan, a phenylalanine, or an amino acid residue having similar properties thereto, at the position corresponding to amino acid position 449 of HA protein of influenza A New Caledonia/20/1999 (H1). In one embodiment, the HA portion of the protein construct comprises an alanine, or an amino acid residue having similar properties thereto, at the position corresponding to amino acid position 450 of HA protein of influenza A New Caledonia/20/1999 (H1). In one embodiment, the HA portion of the protein construct comprises a leucine, or an amino acid residue having similar properties thereto, at the position corresponding to amino acid position 452 of HA protein of influenza A New Caledonia/20/1999 (H1). In one embodiment, the HA portion of the protein construct lacks one or more amino acids corresponding to amino acids 515-517 of the HA protein of influenza A New Caledonia/20/1999 (H1).

In one embodiment, a nanoparticle of the present invention comprises a monomeric subunit protein comprising at least 50 amino acids, at least 100 amino acids, or at least 150 amino acids from lumazine synthase. In one embodiment, the monomeric subunit protein comprises at least 50 amino acids, at least 100 amino acids, or at least 150 amino acids from an amino acid sequence selected from SEQ ID NO:194, and/or comprises an amino acid sequence at least 85%, at least 90%, at least 95%, at least 97% at least 99% identical to SEQ ID NO:194. In one embodiment, the monomeric subunit comprises SEQ ID NO:194.

In one embodiment, the monomeric subunit protein comprises at least 50 amino acids, at least 100 amino acids, or at least 150 amino acids from a ferritin protein. In one embodiment, the monomeric subunit protein comprises at least 50 amino acids, at least 100 amino acids, or at least 150 amino acids from an amino acid sequence selected from the group consisting of SEQ ID NO:2 and SEQ ID NO:5, and/or comprises an amino acid sequence at least 85%, at least 90%, at least 95%, at least 97% at least 99% identical to an amino acid sequence selected from the group consisting of SEQ ID NO:2 and SEQ ID NO:5. In one embodiment, the monomeric ferritin subunit comprises SEQ ID NO:2 or SEQ ID NO:5.

In one embodiment, the nanoparticle comprises a protein construct comprising a monomeric protein of the present invention joined to at least one immunogenic portion of an HA protein from a virus selected from the group consisting of influenza type A viruses, influenza type B viruses and influenza type C viruses. In one embodiment the protein construct comprises a monomeric protein of the present invention joined to at least one immunogenic portion of an HA protein selected from the group consisting of an H1 influenza virus HA protein, an H2 influenza virus HA protein, H3 influenza virus HA protein, an H4 influenza virus HA protein, an H5 influenza virus HA protein, an H6 influenza virus HA protein, an H7 virus influenza HA protein, an H8 influenza virus HA protein, an H9 influenza virus HA protein, an H10 influenza virus HA protein, an H11 influenza virus HA protein, an H12 influenza virus HA protein, an H13 influenza virus HA protein, an H14 influenza virus HA protein, an H15 influenza virus HA protein, an H16 influenza virus HA protein, an H17 influenza virus HA protein, and an H18 influenza virus HA protein. In, one embodiment the immunogenic portion comprises at least one epitope.

In one embodiment, the nanoparticle comprises a protein construct comprising a monomeric protein of the present invention joined to amino acid sequence at least about 80%, at least about 85%, at least about 90%, at least about 95%, at least about 97% or at least about 99% identical to a sequence selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400, wherein the protein construct is capable of selectively binding anti-influenza antibodies. In one embodiment, the nanoparticle comprises a protein construct comprising a monomeric protein of the present invention joined to amino acid sequence selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400, wherein the protein construct is capable of selectively binding anti-influenza antibodies.

In one embodiment of the present invention, the nanoparticle comprises a protein construct comprising an amino acid sequence at least 80%, at least about 85%, at least about 90%, at least about 95%, at least about 97% or at least about 99% identical to a sequence selected from the group consisting of SEQ ID NO:107, SEQ ID NO:110, SEQ ID NO:113, SEQ ID NO:116, SEQ ID NO:119, SEQ ID NO:122, SEQ ID NO:125, SEQ ID NO:128, SEQ ID NO:131, SEQ ID NO:161, SEQ ID NO:167, SEQ ID NO:173, SEQ ID NO:179, SEQ ID NO:185, SEQ ID NO:191, SEQ ID NO:200, SEQ ID NO:206, SEQ ID NO:212, SEQ ID NO:215, SEQ ID NO:220, SEQ ID NO:223, SEQ ID NO:225, SEQ ID NO:227, SEQ ID NO:229, SEQ ID NO:231, SEQ ID NO:233, SEQ ID NO:238, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:264, SEQ ID NO:271, SEQ ID NO:278, SEQ ID NO:285, SEQ ID NO:292, SEQ ID NO:299, SEQ ID NO:306, SEQ ID NO:313, SEQ ID NO:320, SEQ ID NO:327, SEQ ID NO:334, SEQ ID NO:341, SEQ ID NO:348, SEQ ID NO:355, SEQ ID NO:362, SEQ ID NO:369, SEQ ID NO:376, SEQ ID NO:383, SEQ ID NO:390 and SEQ ID NO:397, wherein the protein construct is capable of selectively binding anti-influenza antibodies. In one embodiment of the present invention, the nanoparticle comprises a protein construct comprising an amino acid sequence selected from the group consisting of SEQ ID NO:107, SEQ ID NO:110, SEQ ID NO:113, SEQ ID NO:116, SEQ ID NO:119, SEQ ID NO:122, SEQ ID NO:125, SEQ ID NO:128, SEQ ID NO:131, SEQ ID NO:161, SEQ ID NO:167, SEQ ID NO:173, SEQ ID NO:179, SEQ ID NO:185, SEQ ID NO:191, SEQ ID NO:200, SEQ ID NO:206, SEQ ID NO:212, SEQ ID NO:215, SEQ ID NO:220, SEQ ID NO:223, SEQ ID NO:225, SEQ ID NO:227, SEQ ID NO:229, SEQ ID NO:231, SEQ ID NO:233, SEQ ID NO:238, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:264, SEQ ID NO:271, SEQ ID NO:278, SEQ ID NO:285, SEQ ID NO:292, SEQ ID NO:299, SEQ ID NO:306, SEQ ID NO:313, SEQ ID NO:320, SEQ ID NO:327, SEQ ID NO:334, SEQ ID NO:341, SEQ ID NO:348, SEQ ID NO:355, SEQ ID NO:362, SEQ ID NO:369, SEQ ID NO:376, SEQ ID NO:383, SEQ ID NO:390 and SEQ ID NO:397.

In one embodiment, a nanoparticle of the invention comprises a protein construct encoded by a nucleic acid molecule comprising a nucleic acid sequence at least 85%, at least 90%, at least 95% or at least 97% identical to a sequence selected from the group consisting of SEQ ID NO:266, SEQ ID NO:273, SEQ ID NO: SEQ ID NO:280, SEQ ID NO:287, SEQ ID NO:294, SEQ ID NO:301, SEQ ID NO:308, SEQ ID NO:315, SEQ ID NO:322, SEQ ID NO:329, SEQ ID NO:336, SEQ ID NO:343, SEQ ID NO:350, SEQ ID NO:357, SEQ ID NO:364, SEQ ID NO:371, SEQ ID NO:378, SEQ ID NO:385 SEQ ID NO:392 and SEQ ID NO:399. In one embodiment, a nanoparticle of the invention comprises a protein construct encoded by a nucleic acid molecule comprising a nucleic acid sequence selected from the group consisting of SEQ ID NO:266, SEQ ID NO:273, SEQ ID NO: SEQ ID NO:280, SEQ ID NO:287, SEQ ID NO:294, SEQ ID NO:301, SEQ ID NO:308, SEQ ID NO:315, SEQ ID NO:322, SEQ ID NO:329, SEQ ID NO:336, SEQ ID NO:343, SEQ ID NO:350, SEQ ID NO:357, SEQ ID NO:364, SEQ ID NO:371, SEQ ID NO:378, SEQ ID NO:385 SEQ ID NO:392 and SEQ ID NO:399.

Nanoparticles of the present invention can be used to elicit an immune response to influenza virus. One type of immune response is a B-cell response, which results in the production of antibodies against the antigen that elicited the immune response. Thus, in one embodiment that the nanoparticle elicits antibodies that bind to the stem region of influenza HA protein from a virus selected from the group consisting of influenza A viruses, influenza B viruses and influenza C viruses. One embodiment of the present invention is a nanoparticle that elicits antibodies that bind to the stem region of influenza HA protein selected from the group consisting of an H1 influenza virus HA protein, an H2 influenza virus HA protein, an influenza H3 virus HA protein, an influenza H4 virus HA protein, an influenza H5 virus HA protein, an influenza H6 virus HA protein, an H7 influenza virus HA protein, an H8 influenza virus HA protein, an H9 influenza virus HA protein, an H10 influenza virus HA protein HA protein, an H11 influenza virus HA protein, an H12 influenza virus HA protein, an H13 influenza virus HA protein, an H14 influenza virus HA protein, an H15 influenza virus HA protein, an H16 influenza virus HA protein, an H17 influenza virus HA protein, and an H18 influenza virus HA protein. One embodiment of the present invention is a nanoparticle that elicits antibodies that bind to the stem region of influenza HA protein from a strain of virus selected from the group consisting of influenza A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), B/Brisbane/60/2008 (2008 Bris, B), and variants thereof.

While all antibodies are capable of binding to the antigen which elicited the immune response that resulted in antibody production, preferred antibodies are those that provide broad heterosubtypic protection against influenza virus. Thus, one embodiment of the present invention is a nanoparticle that elicits protective antibodies that bind to the stem region of influenza HA protein from a virus selected from the group consisting of influenza A viruses, influenza B viruses and influenza C viruses. One embodiment of the present invention is a protein that elicits protective antibodies that bind to the stem region of influenza HA protein selected from the group consisting of an H1 influenza virus HA protein, an H2 influenza virus HA protein, an influenza H3 virus HA protein, an influenza H4 virus HA protein, an influenza H5 virus HA protein, an influenza H6 virus HA protein, an H7 influenza virus HA protein, an H8 influenza virus HA protein, an H9 influenza virus HA protein, an H10 influenza virus HA protein HA protein, an H11 influenza virus HA protein, an H12 influenza virus HA protein, an H13 influenza virus HA protein, an H14 influenza virus HA protein, an H15 influenza virus HA protein, an H16 influenza virus HA protein, an H17 influenza virus HA protein, and an H18 influenza virus HA protein. One embodiment of the present invention is a nanoparticle that elicits antibodies against a virus selected from the group consisting of influenza A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1) and B/Brisbane/60/2008 (2008 Bris, B). One embodiment of the present invention is a nanoparticle that elicits antibodies that bind to a protein comprising an amino acid sequence at least 80% identical to a sequence selected from the group consisting of SEQ ID NO:8, SEQ ID NO:11, SEQ ID NO:14 and SEQ ID NO:17. One embodiment of the present invention is a nanoparticle that elicits antibodies that bind to a protein comprising an amino acid sequence selected from the group consisting of SEQ ID NO:8, SEQ ID NO:11, SEQ ID NO:14 and SEQ ID NO:17.

Protective antibodies elicited by proteins of the present invention can protect against viral infections by affecting any step in the life cycle of the virus. For example, protective antibodies may prevent an influenza virus from attaching to a cell, entering a cell, releasing viral ribonucleoproteins into the cytoplasm, forming new viral particles in the infected cell and budding new viral particles from the infected host cell membrane. In one embodiment, protective antibodies elicited by proteins of the present invention prevent influenza virus from entering the host cell. In one embodiment, protective antibodies elicited by proteins of the present invention prevent fusion of viral membranes with endosomal membranes. In one embodiment, protective antibodies elicited by proteins of the present invention prevent release of ribonucleoproteins into the cytoplasm of the host cell. In one embodiment, protective antibodies elicited by proteins of the present invention prevent assembly of new virus in the infected host cell. In one embodiment, protective antibodies elicited by proteins of the present invention prevent release of newly formed virus from the infected host cell.

Because the amino acid sequence of the stem region of influenza virus is highly conserved, protective antibodies elicited by nanoparticles of the present invention may be broadly protective. That is, protective antibodies elicited by nanoparticles of the present invention may protect against influenza viruses of more than one type, subtype and/or strain, Thus, one embodiment of the present invention is a protein that elicits broadly protective antibodies that bind the stem region of influenza HA protein. One embodiment is a nanoparticle that elicits antibodies that bind the stem region of an HA protein from more than one type of influenza virus selected from the group consisting of influenza type A viruses, influenza type B viruses and influenza type C viruses. One embodiment is a nanoparticle that elicits antibodies that bind the stem region of an HA protein from more than one sub-type of influenza virus selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus, an H16 influenza virus, an H17 influenza virus, and an H18 influenza virus. One embodiment is a nanoparticle that elicits antibodies that bind the stem region of an HA protein from more than strain of influenza virus. One embodiment of the present invention is a nanoparticle that elicits antibodies that bind more than one protein comprising an amino acid sequence at least 80% identical to a sequence selected from the group consisting of SEQ ID NO:8, SEQ ID NO:11, SEQ ID NO:14 and SEQ ID NO:17. One embodiment of the present invention is a nanoparticle that elicits antibodies that bind to more than one protein comprising an amino acid sequence selected from the group consisting of SEQ ID NO:8, SEQ ID NO:11, SEQ ID NO:14 and SEQ ID NO:17.

Because nanoparticles of the present invention can elicit an immune response to an influenza virus, they are useful as vaccines to protect individuals against infection by influenza virus. Thus, one embodiment of the present invention is a vaccine comprising a nanoparticle of the present invention. Vaccines of the present invention can also contain other components such as adjuvants, buffers and the like. Although any adjuvant can be used, preferred embodiments can contain: chemical adjuvants such as aluminum phosphate, benzyalkonium chloride, ubenimex, and QS21; genetic adjuvants such as the IL-2 gene or fragments thereof, the granulocyte macrophage colony-stimulating factor (GM-CSF) gene or fragments thereof, the IL-18 gene or fragments thereof, the chemokine (C—C motif) ligand 21 (CCL21) gene or fragments thereof, the IL-6 gene or fragments thereof, CpG, LPS, TLR agonists, and other immune stimulatory genes; protein adjuvants such IL-2 or fragments thereof, the granulocyte macrophage colony-stimulating factor (GM-CSF) or fragments thereof, IL-18 or fragments thereof, the chemokine (C—C motif) ligand 21 (CCL21) or fragments thereof, IL-6 or fragments thereof, CpG, LPS, TLR agonists and other immune stimulatory cytokines or fragments thereof; lipid adjuvants such as cationic liposomes, N3 (cationic lipid), monophosphoryl lipid A (MPL1); other adjuvants including cholera toxin, enterotoxin, Fms-like tyrosine kinase-3 ligand (Flt-3L), bupivacaine, marcaine, and levamisole.

One embodiment of the present invention is a nanoparticle vaccine that includes more than one influenza HA protein. Such a vaccine can include a combination of different influenza HA proteins, either on a single nanoparticle or as a mixture of nanoparticles, at least two of which have unique influenza HA proteins. A multivalent vaccine can comprise as many influenza HA proteins as necessary in order to result in production of the immune response necessary to protect against a desired breadth of virus strains. In one embodiment, the vaccine comprises an HA protein from at least two different influenza strains (bi-valent). In one embodiment, the vaccine comprises a HA protein from at least three different influenza strains (tri-valent). In one embodiment, the vaccine comprises an HA protein from at least four different influenza strains (tetra-valent). In one embodiment, the vaccine comprises an HA protein from at least five different influenza strains (penta-valent). In one embodiment, the vaccine comprises an HA protein from at least six different influenza strains (hexa-valent). In various embodiments, a vaccine comprises an HA protein from each of 7, 8, 9, or 10 different strains of influenza virus. An example of such a combination is a nanoparticle vaccine that comprises influenza A group 1 HA protein, an influenza A group 2 HA protein, and an influenza B HA protein. In one embodiment, the influenza HA proteins are H1 HA, H3 HA, and B HA. In one embodiment, the influenza HA proteins are those included in the 2011-2012 influenza vaccine. Another example of a multivalent vaccine is a nanoparticle vaccine that comprises HA proteins from four different influenza viruses. In one embodiment, the multivalent vaccine comprises HA proteins from influenza A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1) and B/Brisbane/60/2008 (2008 Bris, B).

One embodiment of the present invention is a method to vaccinate an individual against influenza virus, the method comprising administering a nanoparticle to an individual such that an immune response against influenza virus is produced in the individual, wherein the nanoparticle comprises a monomeric subunit protein joined to an influenza HA protein, and wherein the nanoparticle displays the influenza HA on its surface. In one embodiment, the nanoparticle is a monovalent nanoparticle. In one embodiment, the nanoparticle is multivalent nanoparticle. Another embodiment of the present invention is a method to vaccinate an individual against infection with influenza virus, the method comprising:

a) obtaining a nanoparticle comprising monomeric subunits, wherein the monomeric subunits are joined to an influenza hemagglutinin protein, and wherein the nanoparticle displays the influenza HA on its surface; and,
b) administering the nanoparticle to an individual such that an immune response against an influenza virus is produced.

One embodiment of the present invention is a method to vaccinate an individual against influenza virus, the method comprising administering a vaccine of the embodiments to an individual such that an immune response against influenza virus is produced in the individual, wherein the vaccine comprises at least one nanoparticle comprising a monomeric subunit joined to an influenza HA protein, and wherein the nanoparticle displays the influenza HA on its surface. In one embodiment, the vaccine is a monovalent vaccine. In one embodiment, the vaccine is multivalent vaccine. Another embodiment of the present invention is a method to vaccinate an individual against infection with influenza virus, the method comprising:

a) obtaining a vaccine comprising at least one nanoparticle comprising a protein construct of the present invention, wherein the protein construct comprises a monomeric subunit protein joined to an influenza HA protein, and wherein the nanoparticle displays the influenza HA on its surface; and,
b) administering the vaccine to an individual such that an immune response against an influenza virus is produced.

In one embodiment, the nanoparticle is a monovalent nanoparticle. In one embodiment, the nanoparticle is multivalent nanoparticle.

In one embodiment, the nanoparticle has octahedral symmetry. In one embodiment, the influenza HA protein is capable of eliciting antibodies to an influenza virus. In one embodiment, the influenza HA protein is capable of eliciting broadly antibodies to an influenza virus. In preferred embodiments the elicited antibodies are protective antibodies. In a preferred embodiment, the elicited antibodies are broadly heterosubtypic protective.

Vaccines of the present invention can be used to vaccinate individuals using a prime/boost protocol. Such a protocol is described in U.S. Patent Publication No. 20110177122, which is incorporated herein by reference in its entirety. In such a protocol, a first vaccine composition may be administered to the individual (prime) and then after a period of time, a second vaccine composition may be administered to the individual (boost). Administration of the boosting composition is generally weeks or months after administration of the priming composition, preferably about 2-3 weeks or 4 weeks, or 8 weeks, or 16 weeks, or 20 weeks, or 24 weeks, or 28 weeks, or 32 weeks. In one embodiment, the boosting composition is formulated for administration about 1 week, or 2 weeks, or 3 weeks, or 4 weeks, or 5 weeks, or 6 weeks, or 7 weeks, or 8 weeks, or 9 weeks, or 16 weeks, or 20 weeks, or 24 weeks, or 28 weeks, or 32 weeks after administration of the priming composition The first and second vaccine compositions can be, but need not be, the same composition. Thus, in one embodiment of the present invention, the step of administering the vaccine comprises administering a first vaccine composition, and then at a later time, administering a second vaccine composition. In one embodiment, the first vaccine composition comprises a nanoparticle of the present invention. In one embodiment, the first vaccine composition comprises a nanoparticle comprising amino acid sequences from the HA protein of an influenza virus selected from the group consisting of A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005

(2005 Indo, H5), B/Florida/4/2006 (2006 Flo, B), A/Perth/16/2009 (2009 Per, H3), A/Brisbane/59/2007 (2007 Bris, H1), B/Brisbane/60/2008 (2008 Bris, B).

In one embodiment, the individual being vaccinated has been exposed to influenza virus. As used herein, the terms exposed, exposure, and the like, indicate the subject has come in contact with a person of animal that is known to be infected with an influenza virus. Vaccines of the present invention may be administered using techniques well known to those in the art. Techniques for formulation and administration may be found, for example, in "Remington's Pharmaceutical Sciences", 18th ed., 1990, Mack Publishing Co., Easton, PA. Vaccines may be administered by means including, but not limited to, traditional syringes, needleless injection devices, or microprojectile bombardment gene guns. Suitable routes of administration include, but are not limited to, parenteral delivery, such as intramuscular, intradermal, subcutaneous, intramedullary injections, as well as, intrathecal, direct intraventricular, intravenous, intraperitoneal, intranasal, or intraocular injections, just to name a few. For injection, the compounds of one embodiment of the invention may be formulated in aqueous solutions, preferably in physiologically compatible buffers such as Hanks' solution, Ringer's solution, or physiological saline buffer.

In one embodiment, vaccines, or nanoparticles, of the present invention can be used to protect an individual against infection by heterologous influenza virus. That is, a vaccine made using HA protein from one strain of influenza virus is capable of protecting an individual against infection by different strains of influenza. For example, a vaccine made using HA protein from influenza A/New Caledonia/20/1999 (1999 NC, H1), can be used to protect an individual against infection by an influenza virus including, but not limited to A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 indo, H5), A/Perth/16/2009 (2009 Per, H3), and/or A/Brisbane/59/2007 (2007 Bris, H1).

In one embodiment, vaccines, or nanoparticles, of the present invention can be used to protect an individual against infection by an antigenically divergent influenza virus. Antigenically divergent refers to the tendency of a strain of influenza virus to mutate over time, thereby changing the amino acids that are displayed to the immune system. Such mutation over time is also referred to as antigenic drift. Thus, for example, a vaccine made using HA protein from a A/New Caledonia/20/1999 (1999 NC, H1) strain of influenza virus is capable of protecting an individual against infection by earlier, antigenically divergent New Caledonia strains of influenza, and by evolving (or diverging) influenza strains of the future.

Because nanoparticles of the present invention display HA proteins that are antigenically similar to an intact HA, they can be used in assays for detecting antibodies against influenza virus (anti-influenza antibodies).

Thus, one embodiment of the present invention is a method for detecting anti-influenza virus antibodies using nanoparticles of the present invention. A detection method of the present invention can generally be accomplished by:

a. contacting at least a portion of a sample being tested for the presence of anti-influenza antibodies with a nanoparticle of the present invention; and,
b. detecting the presence of a nanoparticle/antibody complex;

wherein the presence of a nanoparticle/antibody complex indicates that the sample contains anti-influenza antibodies.

In one embodiment of the present invention, a sample is obtained, or collected, from an individual to be tested for the presence of anti-influenza virus antibodies. The individual may or may not be suspected of having anti-influenza antibodies or of having been exposed to influenza virus. A sample is any specimen obtained from the individual that can be used to test for the presence of anti-influenza virus antibodies. A preferred sample is a body fluid that can be used to detect the presence of anti-influenza virus antibodies. Examples of body fluids that may be used to practice the present method include, but are not limited to, blood, plasma, serum, lacrimal fluid and saliva. Those skilled in the art can readily identify samples appropriate for practicing the disclosed methods.

Blood, or blood-derived fluids such as plasma, serum, and the like, are particularly suitable as the sample. Such samples can be collected and prepared from individuals using methods known in the art. The sample may be refrigerated or frozen before assay.

Any nanoparticle of the present invention can be used to practice the disclosed method as long as the nanoparticle binds to anti-influenza virus antibodies. Useful nanoparticles, and methods of their production, have been described in detail herein. In a preferred embodiment, the nanoparticle comprises a protein construct, wherein the protein construct comprises at least 25, at least 50, at least 75, at least 100, or at least 150 contiguous amino acids from a monomeric subunit protein joined to (fused to) at least one epitope from an influenza HA protein such that the nanoparticle comprises trimers of the influenza virus HA protein epitope on its surface, and wherein the protein construct is capable of self-assembling into nanoparticles.

As used herein, the term contacting refers to the introduction of a sample being tested for the presence of anti-influenza antibodies to a nanoparticle of the present invention, for example, by combining or mixing the sample and the nanoparticle of the present invention, such that the nanoparticle is able to come into physical contact with antibodies in the sample, if present. When anti-influenza virus antibodies are present in the sample, an antibody/nanoparticle complex is then formed. Such complex formation refers to the ability of an anti-influenza virus antibodies to selectively bind to the HA portion of the protein construct in the nanoparticle in order to form a stable complex that can be detected. Binding of anti-influenza virus antibodies in the sample to the nanoparticle is accomplished under conditions suitable to form a complex. Such conditions (e.g., appropriate concentrations, buffers, temperatures, reaction times) as well as methods to optimize such conditions are known to those skilled in the art. Binding can be measured using a variety of methods standard in the art including, but not limited to, agglutination assays, precipitation assays, enzyme immunoassays (e.g., ELISA), immunoprecipitation assays, immunoblot assays and other immunoassays as described, for example, in Sambrook et al., Molecular Cloning: A Laboratory Manual, (Cold Spring Harbor Labs Press, 1989), and Harlow et al., Antibodies, a Laboratory Manual (Cold Spring Harbor Labs Press, 1988), both of which are incorporated by reference herein in their entirety. These references also provide examples of complex formation conditions.

As used herein, the phrases selectively binds HA, selective binding to HA, and the like, refer to the ability of an antibody to preferentially bind a HA protein as opposed to binding proteins unrelated to HA, or non-protein components in the sample or assay. An antibody that selectively binds HA is one that binds HA but does not significantly bind other molecules or components that may be present in the sample or assay. Significant binding, is considered, for example, binding of an anti-HA antibody to a non-HA molecule with an affinity or avidity great enough to interfere with the ability of the assay to detect and/or determine the level of, anti-influenza antibodies in the sample. Examples of other molecules and compounds that may be present in the sample, or the assay, include, but are not limited to, non-HA proteins, such as albumin, lipids and carbohydrates.

In one embodiment, an anti-influenza virus antibody/nanoparticle complex, also referred to herein as an antibody/nanoparticle complex, can be formed in solution. In one embodiment an antibody/nanoparticle complex can be formed in which the nanoparticle is immobilized on (e.g., coated onto) a substrate. Immobilization techniques are known to those skilled in the art. Suitable substrate materials include, but are not limited to, plastic, glass, gel, celluloid, fabric, paper, and particulate materials. Examples of substrate materials include, but are not limited to, latex, polystyrene, nylon, nitrocellulose, agarose, cotton, PVDF (polyvinylidene-fluoride), and magnetic resin. Suitable shapes for substrate material include, but are not limited to, a well (e.g., microtiter dish well), a microtiter plate, a dipstick, a strip, a bead, a lateral flow apparatus, a membrane, a filter, a tube, a dish, a celluloid-type matrix, a magnetic particle, and other particulates. Particularly preferred substrates include, for example, an ELISA plate, a dipstick, an immunodot strip, a radioimmunoassay plate, an agarose bead, a plastic bead, a latex bead, a cotton thread, a plastic chip, an immunoblot membrane, an immunoblot paper and a flow-through membrane. In one embodiment, a substrate, such as a particulate, can include a detectable marker. For descriptions of examples of substrate materials, see, for example, Kemeny, D. M. (1991) A Practical Guide to ELISA, Pergamon Press, Elmsford, NY pp 33-44, and Price, C. and Newman, D. eds. Principles and Practice of Immunoassay, 2nd edition (1997) Stockton Press, NY, NY, both of which are incorporated herein by reference in their entirety.

In accordance with the present invention, once formed, an anti-influenza virus antibody/nanoparticle complex is detected. Detection can be qualitative, quantitative, or semi-quantitative. As used herein, the phrases detecting complex formation, detecting the complex, and the like, refer to identifying the presence of anti-influenza virus antibody complexed with the nanoparticle. If complexes are formed, the amount of complexes formed can, but need not be, quantified. Complex formation, or selective binding, between a putative anti-influenza virus antibody and a nanoparticle can be measured (i.e., detected, determined) using a variety of methods standard in the art (see, for example, Sambrook et al. supra.), examples of which are disclosed herein. A complex can be detected in a variety of ways including, but not limited to use of one or more of the following assays: a hemagglutination inhibition assay, a radial diffusion assay, an enzyme-linked immunoassay, a competitive enzyme-linked immunoassay, a radioimmunoassay, a fluorescence immunoassay, a chemiluminescent assay, a lateral flow assay, a flow-through assay, a particulate-based assay (e.g., using particulates such as, but not limited to, magnetic particles or plastic polymers, such as latex or polystyrene beads), an immunoprecipitation assay, a BioCoreJ assay (e.g., using colloidal gold), an immunodot assay (e.g., CMG=s Immunodot System, Fribourg, Switzerland), and an immunoblot assay (e.g., a western blot), an phosphorescence assay, a flow-through assay, a chromatography assay, a PAGe-based assay, a surface plasmon resonance assay, a spectrophotometric assay, and an electronic sensory assay. Such assays are well known to those skilled in the art.

Assays can be used to give qualitative or quantitative results depending on how they are used. Some assays, such as agglutination, particulate separation, and precipitation assays, can be observed visually (e.g., either by eye or by a machines, such as a densitometer or spectrophotometer) without the need for a detectable marker.

In other assays, conjugation (i.e., attachment) of a detectable marker to the nanoparticle, or to a reagent that selectively binds to the nanoparticle, aids in detecting complex formation. A detectable marker can be conjugated to the nanoparticle, or nanoparticle-binding reagent, at a site that does not interfere with ability of the nanoparticle to bind to an anti-influenza virus antibody. Methods of conjugation are known to those of skill in the art. Examples of detectable markers include, but are not limited to, a radioactive label, a fluorescent label, a chemiluminescent label, a chromophoric label, an enzyme label, a phosphorescent label, an electronic label; a metal sol label, a colored bead, a physical label, or a ligand. A ligand refers to a molecule that binds selectively to another molecule. Preferred detectable markers include, but are not limited to, fluorescein, a radioisotope, a phosphatase (e.g., alkaline phosphatase), biotin, avidin, a peroxidase (e.g., horseradish peroxidase), beta-galactosidase, and biotin-related compounds or avidin-related compounds (e.g., streptavidin or ImmunoPure7 NeutrAvidin).

In one embodiment, an antibody/nanoparticle complex can be detected by contacting a sample with a specific compound, such as an antibody, that binds to an anti-influenza antibody, ferritin, or to the antibody/nanoparticle complex, conjugated to a detectable marker. A detectable marker can be conjugated to the specific compound in such a manner as not to block the ability of the compound to bind to the complex being detected. Preferred detectable markers include, but are not limited to, fluorescein, a radioisotope, a phosphatase (e.g., alkaline phosphatase), biotin, avidin, a peroxidase (e.g., horseradish peroxidase), beta-galactosidase, and biotin-related compounds or avidin-related compounds (e.g., streptavidin or ImmunoPure7 NeutrAvidin).

In another embodiment, a complex is detected by contacting the complex with an indicator molecule. Suitable indicator molecules include molecules that can bind to the anti-influenza virus antibody/nanoparticle complex, the anti-influenza virus antibody, or the nanoparticle. As such, an indicator molecule can comprise, for example, a reagent that binds the anti-influenza virus antibody, such as an antibody that recognizes immunoglobulins. Preferred indicator molecules that are antibodies include, for example, antibodies reactive with the antibodies from species of individual in which the anti-influenza virus antibodies are produced. An indicator molecule itself can be attached to a detectable marker of the present invention. For example, an antibody can be conjugated to biotin, horseradish peroxidase, alkaline phosphatase or fluorescein.

The present invention can further comprise one or more layers and/or types of secondary molecules or other binding molecules capable of detecting the presence of an indicator molecule. For example, an untagged (i.e., not conjugated to a detectable marker) secondary antibody that selectively binds to an indicator molecule can be bound to a tagged (i.e., conjugated to a detectable marker) tertiary antibody that selectively binds to the secondary antibody. Suitable secondary antibodies, tertiary antibodies and other secondary or tertiary molecules can be readily selected by those skilled in the art. Preferred tertiary molecules can also be selected by those skilled in the art based upon the characteristics of the secondary molecule. The same strategy can be applied for subsequent layers.

Preferably, the indicator molecule is conjugated to a detectable marker. A developing agent is added, if required, and the substrate is submitted to a detection device for analysis. In some protocols, washing steps are added after one or both complex formation steps in order to remove excess reagents. If such steps are used, they involve conditions known to those skilled in the art such that excess reagents are removed but the complex is retained.

Because assays of the present invention can detect anti-influenza virus antibodies in a sample, including a blood sample, such assays can be used to identify individuals having anti-influenza antibodies. Thus, one embodiment of the present invention is a method to identify an individual having anti-influenza virus antibodies, the method comprising:

a. contacting a sample from an individual being tested for anti-influenza antibodies with a nanoparticle of the present invention; and, b. analyzing the contacted sample for the presence of a nanoparticle/antibody complex wherein the presence of a nanoparticle/antibody complex indicates the individual has anti-influenza antibodies.

Any of the disclosed assay formats can be used to conduct the disclosed method. Examples of useful assay formats include, but are not limited to, a radial diffusion assay, an enzyme-linked immunoassay, a competitive enzyme-linked immunoassay, a radioimmunoassay, a fluorescence immunoassay, a chemiluminescent assay, a lateral flow assay, a flow-through assay, a particulate-based assay (e.g., using particulates such as, but not limited to, magnetic particles or plastic polymers, such as latex or polystyrene beads), an immunoprecipitation assay, a BioCoreJ assay (e.g., using colloidal gold), an immunodot assay (e.g., CMG=s Immunodot System, Fribourg, Switzerland), and an immunoblot assay (e.g., a western blot), an phosphorescence assay, a flow-through assay, a chromatography assay, a PAGe-based assay, a surface plasmon resonance assay, bio-layer interferometry assay, a spectrophotometric assay, and an electronic sensory assay.

If no anti-influenza antibodies are detected in the sample, such a result indicates the individual does not have anti-influenza virus antibodies. The individual being tested may or may not be suspected of having antibodies to influenza virus. The disclosed methods may also be used to determine if an individual has been exposed to one or more specific type, group, sub-group or strain of influenza virus. To make such a determination, a sample is obtained from an individual that has tested negative for antibodies (i.e., lacked antibodies) to one or more specific type, group, sub-group or strain of influenza virus sometime in their past (e.g., greater than about 1 year, greater than about 2 years, greater than about 3 years, greater than about 4 years, greater than about 5 years, etc.). The sample is then tested for the presence of anti-influenza virus antibodies to one or more type, group, sub-group or strain, of influenza virus using a nanoparticle-based assay of the present invention. If the assay indicates the presence of such antibodies, the individual is then identified as having been exposed to one or more type, group sub-group or strain, of influenza virus sometime after the test identifying them as negative for anti-influenza antibodies. Thus, one embodiment of the present invention is method to identify an individual that has been exposed to influenza virus, the method comprising:

a. contacting at least a portion of a sample from an individual being tested for anti-influenza antibodies with a nanoparticle of the present invention; and, b. analyzing the contacted sample for the presence or level of a antibody/nanoparticle complex, wherein the presence or level of antibody/nanoparticle complex indicates the presence or level of recent anti-influenza antibodies;

c. comparing the recent anti-influenza antibody level with a past anti-influenza antibody level;

wherein an increase in the recent anti-influenza antibody level over the past anti-influenza antibody level indicates the individual has been exposed to influenza virus subsequent to determination of the past anti-influenza antibody level.

Methods of the present invention are also useful for determining the response of an individual to a vaccine. Thus, one embodiment is a method for measuring the response of an individual to an influenza vaccine, the method comprising:

a. administering to the individual a vaccine for influenza virus;

b. contacting at least a portion of a sample from the individual with a nanoparticle of the present invention;

c. analyzing the contacted sample for the presence or level of a antibody/nanoparticle complex, wherein the presence or level of antibody/nanoparticle complex indicates the presence or level of recent anti-influenza antibodies wherein an increase in the level of antibody in the sample over the pre-vaccination level of antibody in the individual indicates the vaccine induced an immune response in the individual.

The influenza vaccine administered to the individual may, but need not, comprise a vaccine of the present invention, as long as the nanoparticle comprises an HA protein that can bind an anti-influenza antibody induced by the administered vaccine. Methods of administering influenza vaccines are known to those of skill in the art.

Analysis of the sample obtained from the individual may be performed using any of the disclosed assay formats. In one embodiment, analysis of the sample is performed using an assay format selected from the group consisting of, a radial diffusion assay, an enzyme-linked immunoassay, a competitive enzyme-linked immunoassay, a radioimmunoassay, a fluorescence immunoassay, a chemiluminescent assay, a lateral flow assay, a flow-through assay, a particulate-based assay (e.g., using particulates such as, but not limited to, magnetic particles or plastic polymers, such as latex or polystyrene beads), an immunoprecipitation assay, a BioCoreJ assay (e.g., using colloidal gold), an immunodot assay (e.g., CMG=s Immunodot System, Fribourg, Switzerland), and an immunoblot assay (e.g., a western blot), an phosphorescence assay, a flow-through assay, a chromatography assay, a PAGE-based assay, a surface plasmon resonance assay, bio-layer interferometry assay, a spectrophotometric assay, and an electronic sensory assay.

In one embodiment, the method includes a step of determining the level of anti-influenza antibody present in the individual prior to administering the vaccine. However, it is also possible to determine the level of anti-influenza antibody present in the individual from prior medical records, if such information is available.

While not necessary to perform the disclosed method, it may be preferable to wait some period of time between the step of administering the vaccine and the step of determining the level of anti-influenza antibody in the individual. In one embodiment, determination of the level of anti-influenza antibodies present in the individual is performed at least 1 day, at least 2 days, at least 3 days, at least 4 days, at least 5 days, at least 6 days, at least one week, at least two weeks, at least three weeks, at least four weeks, at least two months, at least three months or at least six months, following administration of the vaccine.

The present invention also includes kits suitable for detecting anti-influenza antibodies. Suitable means of detection include the techniques disclosed herein, utilizing nanoparticles of the present invention. Kits may also comprise a detectable marker, such as an antibody that selectively binds to the nanoparticle, or other indicator molecules. The kit can also contain associated components, such as, but not limited to, buffers, labels, containers, inserts, tubings, vials, syringes and the like.

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, and temperature is in degrees Celsius. Standard abbreviations are used.

Example 1: Iterative Structure-Based Design of HA Stabilized-Stem (HA-SS) Constructs This example shows the six iterative cycles of structure-based design (Gen1-Gen6) used to produce the HA stabilized-stem (HA-SS) immunogens that lack the immunodominant head domain.

Influenza A viruses comprise 18 HA subtypes of which two, H1 and H3, currently cause the majority of human infections. Seasonal influenza vaccines provide some protection against circulating H1 and H3 strains, but little protection against the divergent H5, H7, and H9 subtypes that cause occasional outbreaks of human infection as zoonoses from avian and/or swine reservoirs. The inventors hypothesized that an immune response focused on the conserved hemagglutinin (HA) stem could potentially elicit broad heterosubtypic influenza protection against diverse strains. The inventors therefore used iterative structure-based design to develop HA stabilized-stem (HA-SS) glycoproteins, which lack the immunodominant HA head region (FIG. 1).

The ectodomain sequence of A/New Caledonia/20/1999 (1999 NC) HA and the crystal structure (PDB ID 1GBN) of A/South Carolina/1/1918 (1918 SC) were used as design templates, and each generation of HA-SS variant was evaluated for expression as soluble trimers, and for antigenicity based on stem-specific monoclonal antibody (mAb) reactivity similar to wild-type (wt) HA trimer.

Plasmids encoding full-length HA and neuraminidase (NA) from 1999 NC, 1986 SG, 2009 CA, H2 2005 CAN, H5 2005 IND and H5 2004 VN were synthesized using human-preferred codons. Various versions of HA-SS were generated by overlapping PCR and site-directed mutagenesis. All HA, HA-SS proteins and mAbs were expressed in freestyle 293 (293F; Life Technologies) cells or 293 GnTI$^{-/-}$ cells (for Gen4 HA-SS crystallization) and purified as previously described (Wei, C. J., et al. Elicitation of broadly neutralizing influenza antibodies in animals with previous influenza exposure. Sci. Transl. Med. 4, 147ra114 (2012)). Construction, purification, and characterization of HA-np and Gen1-Gen6 HA-SS and Gen4-6 HA-SS-np were performed as described (Kanekiyo, M., et al. *Nature* 499, 102-106 (2013)).

The first generation design (Gen1 HA-SS) replaced the receptor-binding domain (residues HA1 51-277, H3 numbering) with a GSG linker (FIG. 1). The HA ectodomain trimer and all trimeric HA-SS designs were each generated with the C-terminal transmembrane and cytoplasmic residues HA2 175-220 (H3 numbering) replaced with a short linker, T4 foldon, thrombin cleavage site and His tag. The HA1/HA2 cleavage site was mutated to prevent cleavage. To model the structures of the HA-SS designs, 1918 SC HA (PDB ID 1GBN) and the bacteriophage T4 foldon trimer (PDB ID 1RFO) were used as templates, loops and connections were designed using LOOPY (Xiang, et. al. *Proc. Natl. Acad. Sci. U.S.A.* 99, 7432-7437 (2002)), side chains were mutated using SCAP (Xiang, et al., *J. Mol. Biol.* 311, 421-430 (2001)) and structural superpositions were performed using LSQMAN (Kleywegt, et al., in International Tables for Crystallography, Vol. F, 353-367 (Kluwer Academic Publishers, Dordrecht, The Netherlands, 2001)). The energetics of particular mutations were assessed computationally using the Rosetta program DDG_MONOMER (Kellogg, et al., *Proteins* 79, 830-838 (2011)). Chimera (Pettersen, E. F., et al. *Journal of Computational Chemistry* 25, 1605-1612 (2004)) was used to perform surface area calculations. Approximately 700 trimeric structures in the Protein Data Bank (PDB) were examined to find a suitable trimerization domain to further stabilize HA-SS immunogen. This search revealed HIV-1 gp41 (PDB ID 1SZT) to be optimal for (i) its size (less than 70 amino acids per monomer), (ii) its thermostability ($T_m$=70° C.), (iii) ease of transplantation, with N- and C-termini located at the same end of the trimer, and (iv) structural complementarity between the C-terminal ends of the inner heptad repeat 1 (HR1) helices of gp41 and the inner C helices of the HA-SS trimer. Gen1 HA-SS failed to express as a trimer, despite the presence of a C-terminal foldon trimerization domain.

To increase trimer stability in the second generation, the inventors replaced HA2 residues 66-85 at the membrane-distal region of the HA-SS with a thermostable HIV-1 gp41 trimerization domain (see Tan, et al., *Proc. Natl. Acad. Sci. U.S.A.* 94, 12303-12308 (1997)) in which the inner heptad repeat 1 (HR1) helices are structurally complementary with the inner C helices of the HA stem. Connecting gp41 and HA-SS necessitated circular permutation of gp41 helices HR1 and HR2, which were reversed in order and reconnected with a glycine-rich linker (FIG. 1). To insert the six-helix bundle of the post-fusion form of HIV-1 gp41 into Gen2 HA-SS, residues 28-32 (residues 573-577, HXBc2 numbering) from the three inner helices of gp41 were superimposed onto HA inner helix residues HA2 81-85 (from PDB ID 1RU7) with a root mean square deviation (RMSD) of 1.41 Å for 15 Ca atoms. HA2 residues 66-85 were replaced with the gp41 heptad repeat (HR) 2 helix (residues 628-654, HXBc2 numbering) followed by a six-residue glycine rich linker (NGTGGG) containing the sequon for an N-linked glycosylation site and the gp41 HR1 helix (residues 548-577). HR1 was designed to be in frame with helix C of HA2 to generate a long central chimeric helix. Efforts to stabilize the membrane distal portion of the F' region through the addition of salt bridges, shortening loops and reducing its hydrophobicity did not improve the trimerization or antigenicity of the Gen2 HA-SS design. Expression of Gen2 HA-SS resulted in 29% trimerization.

To improve trimerization in the third generation, a 44-residue portion of the HA1F' region with irregular secondary structure was removed, and the inner helix C of HA-SS was truncated by six residues for better complementarity between gp41 and HA2. This resulted in a soluble Gen3 HA-SS with 77% trimerization, which was recognized by HA stem broadly neutralizing mAbs (bNAbs) with affinities similar overall to those of the soluble HA trimer (FIG. 1). In Gen3 HA-SS HA2 residues 43-50, and 278-313 of the F' region were replaced with a GWG linker, and HA2 residues 60-65 and 86-92 were removed. To realign gp41 with a lower region of the HA stem, residues 30-34 (575-579 Hxbc2 numbering) from the three inner helices of gp41 were superimposed onto HA inner helix residues HA2 90-94 with an RMSD of 0.59 Å for 15 Cα atoms. Faster off-rates were observed for CR6261 and 70-5B03 which may be due in part to the loss of the HA F' region that can make limited contact with the CR6261 heavy chain.

To characterize the Gen3 HA-SS at the atomic-level, the inventors determined the crystal structure of Gen3 HA-SS in complex with the antigen-binding fragment (Fab) of the murine bNAb C179 (see Okuno, Y., et al. J. Virol. 67, 2552-2558 (1993)) at 3.19 Å resolution (FIG. 2*a*, left panel); the C179 antibody was the first broadly neutralizing HA stem-directed antibody to be discovered with heterosubtypic neutralization.

C179 harvested from hybridoma cells was cleaved into Fabs as previously described (Ofek, G., et al. *J. Virol.* 78, 10724-10737 (2004)) with the following modifications: LysC (Roche) was used at a ratio of 1:20,000 (w/w) to C179 and the crystallizable fragment (Fc) was removed from the digestion solution by passing through a mercapto-ethyl-pyridine column (Pall Life Sciences) in 50 mM Tris pH 8.0 and the C179 Fab was eluted with 50 mM NaAc pH 5.0.

The complex of Gen3 HA-SS (expressed in 293 $GnTI^{-/-}$ cells) with C179 Fab was obtained by passing a 1:1.25 (Gen3 HA-SS/C179 molar ratio) mixture through a Superdex 200 26/60 (GE Healthcare) gel filtration column and collecting the peak eluting at 152.0 mLs. The complex was concentrated to 10 mg/ml in 150 mM NaCl, 10 mM Tris HCl pH 7.5 and crystallized at 20° C. by hanging drop vapor diffusion in 15% (W/V) polyethylene glycol 1500, 5% (V/V) 2-methyl-2,4-pentanediol, 200 mM $NH_4Cl$ and 100 mM Tris HCl pH 8.5, derived from the precipitant synergy crystallization screen (Majeed, S., et al. Structure 11, 1061-1070 (2003)). Crystals were cryocooled without any additional cryoprotectant and stored in liquid nitrogen prior to data collection.

X-ray data was collected to 3.19 Å resolution at a temperature of 100K using a wavelength of 1.000 Å at the Southeast Regional Collaborative Access Team (SER-CAT) 22-BM beamline at the Advanced Photon Source (APS), Argonne National Laboratory. X-ray data was processed with HKL2000 in the trigonal space group H3 and the structure of the complex was determined by molecular replacement using five separate search models. PHASER (Mccoy, A. J., et al. *J. Appl. Crystallogr.* 40, 658-674 (2007)) was used to search with the HA stem monomer from the structure of 1934 PR8 (PDB ID 1RU7, residues 5-36, 315-323 HA1 chain A and residues 514-559, 590-660 HA2 chain B), the HIV-1 gp41 monomer (PDB ID 1SZT, residues 3-29, 42-67), the heavy chain variable domain of the murine antibody S25-2 (PDB ID 1Q9K, residues 1-111), and the light chain variable domain of the murine antibody MN16C13F4 (PDB ID 1UWX, residues 3-108). MOLREP (Collaborative Computational Project. *Acta Crystallogr. D Biol. Crystallogr.* 50, 760-763 (1994)) was used to locate the T4 foldon monomer (PDB ID 1RFO, chain A) which confirmed an independent fitting by hand. The C179 Fab constant domains were fit into Fo-Fc density by eye prior to refinement using the constant domains of the above Abs (PDB IDs 1Q9K and 1UWX) as templates. Model building and refinement were performed using COOT (Emsley, P. & Cowtan, K. Coot: *D Biol. Crystallogr.* 60, 2126-2132 (2004)) and PHENIX (Adams, P. D., et al. *Acta Crystallogr. D Biol. Crystallogr.* 58, 1948-1954 (2002)) with riding hydrogens, respectively. All of the residues of the Gen3 HA-SS were modeled into electron density except for the HA cleavage loop (residues 48-52), the glycine rich loop connecting the gp41 helices (residues 139-144), the linker connecting HA-SS to the foldon (residues 256-259) and the thrombin cleavage site and His tag C-terminal to the foldon domain (residues 286-302). Carbohydrates were observed and built on Asn residues 23, 119 and 236. The C179 structure included heavy chain residues 1-213 and light chain residues 1-214. The Ramachandran statistics as determined by PHENIX revealed 91.64% of residues in favored regions, 7.49% in allowed and 0.86% as outliers.

Figure 2A:
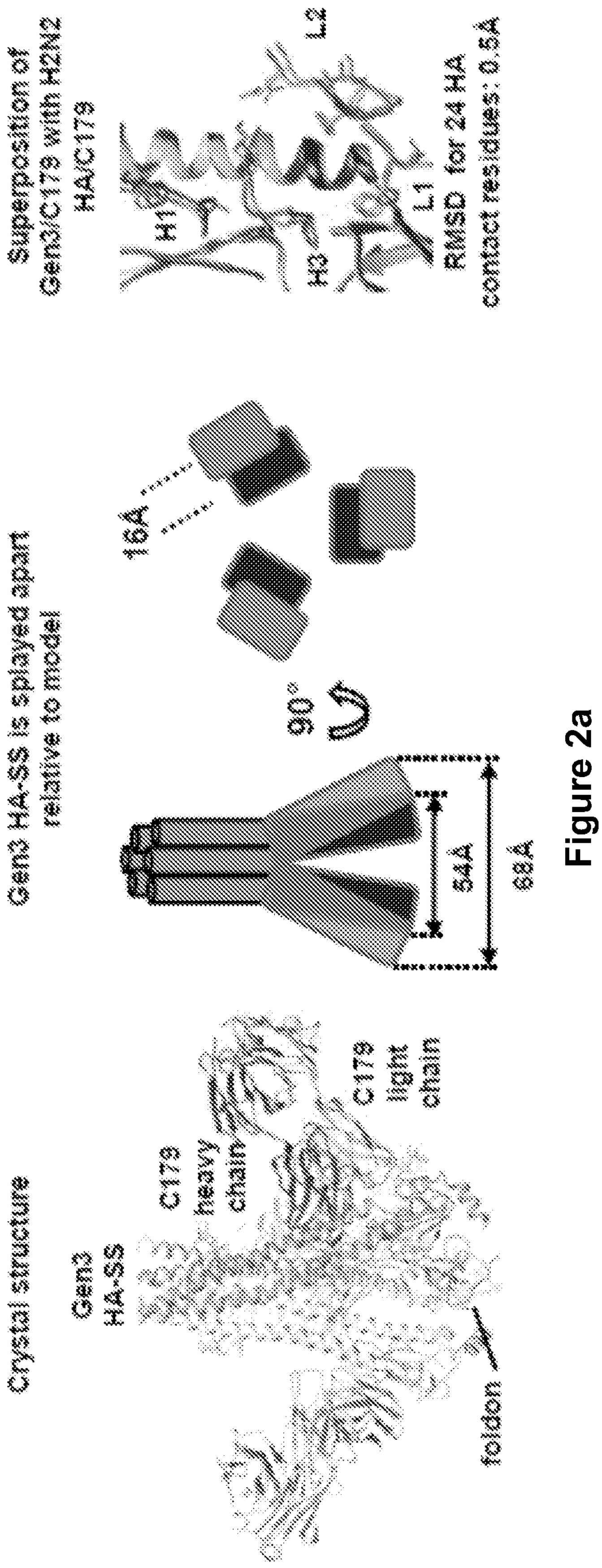
FIG. 2*a* shows that the trimeric, but not nanoparticle stem immunogens, display HA stem splaying. The left panel depicts a ribbon diagram of the crystal structure of the complex between Gen3 HA-SS (dark and gray) and mAb C179 (labeled). The middle panel of FIG. 2*a* shows a cartoon comparing the splaying of the crystal structure (light) with the model (dark) in two different views (side and bottom). The right panel of FIG. 2*a* shows a superposition of the Gen3 HA-SS/C179 binding interface with a 1957 H2N2 HA/C179 binding interface (PDB ID 4HLZ). Antibody CDR loops are labeled by "H" for heavy chain and "L" for light chain. The heavy chain framework 3 loop is labeled FR3. RMSD, root mean square deviation.

The co-crystal structure revealed C179 recognition of Gen3 HA-SS to be similar to the recognition of an H2N2 trimeric HA in the recently published co-crystal structure of C179 with an A/Japan/305/1957 (1957 JP) HA (see Dreyfus, et al., *J. Virol.* 87, 7149-7154 (2013). (FIG. 2*a*, right panel). While these findings confirmed the preservation of the stem epitope on the Gen3 HA-SS; the overall structure revealed several unexpected differences (FIG. 2*a*, left and middle panel). First, the stem trimer subunits were splayed apart at their C-termini by approximately 15 Å relative to HA (FIG. 2*a*, middle panel). Second, the C-terminal foldon trimerization domain was inverted and tucked inside the stem trimer into the splayed region (FIG. 2*a*, left panel). Finally, the outer helix A of the HA stem forms a continuous helix with the outer HR2 helix of the gp41 six-helix bundle, rather than forming two separate helices separated by a glycine linker.

Figure 1B:
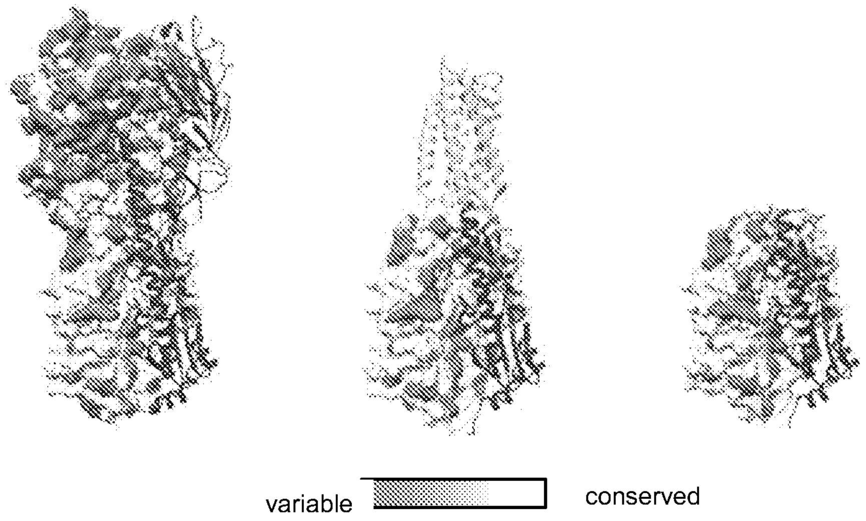
FIG. 1*b* shows the surface representations of the HA portions of H1N1 HA ectodomain (PDB ID 1GBN), Gen4 HA-SS and Gen6 HA-SS respectively without the foldon domains, shaded by sequence conservation with H5N1 2004 VN (dark gray, variable; white, conserved). The HA stem percentage of the immunogens without foldon domains increase for Gen4 and Gen6 HA-SS respectively. *This immunogen was evaluated further and is referred to as H1-SS-np in the Examples section of this disclosure.
Figure 1C:
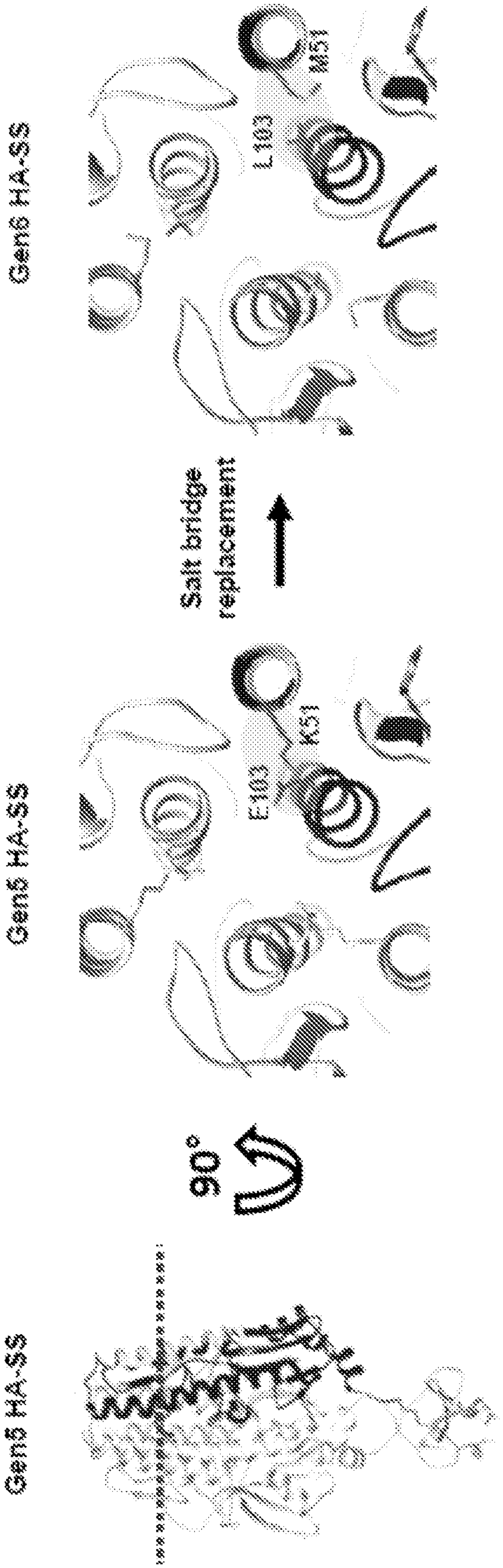
FIG. 1*c* show a ribbon representation depicting a cross-sectional view of the replacement of the Glu103-Lys51 salt bridge with the Leu103-Met51 hydrophobic pair in Gen6 HA-SS. The dotted line (left) indicates the location of the cross-section.
Figure 1D:
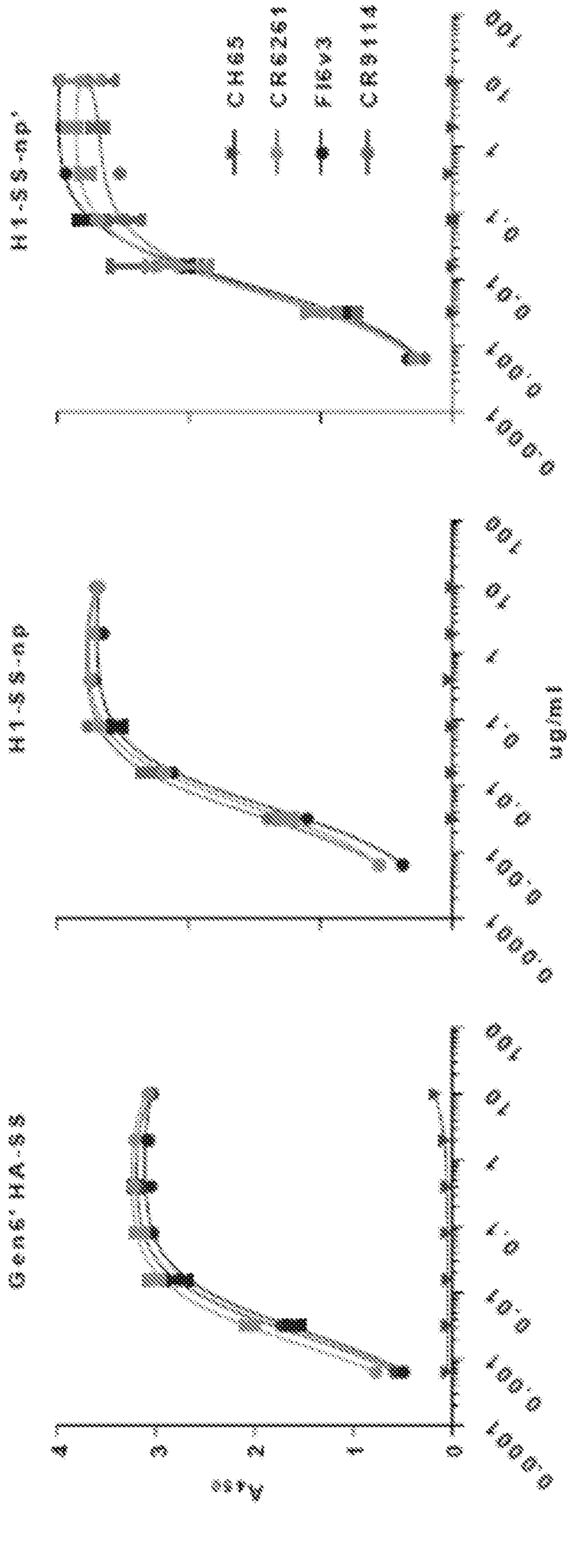
FIG. 1*d* shows the antigenicity of Gen6 HA-SS presented in its soluble and nanoparticle formats. The three panels show ELISA binding of one head (CH65) and three stem-specific antibodies (CR6261, CR9114, FI6v3) to Gen6' HA-SS (left panel), H1-SS-np (middle panel), and H1-SS-np' (right panel). ELISA binding of antibodies ranging in concentration from 10-6.40×$10^{-4}$ μg/mL.
Figure 1E:
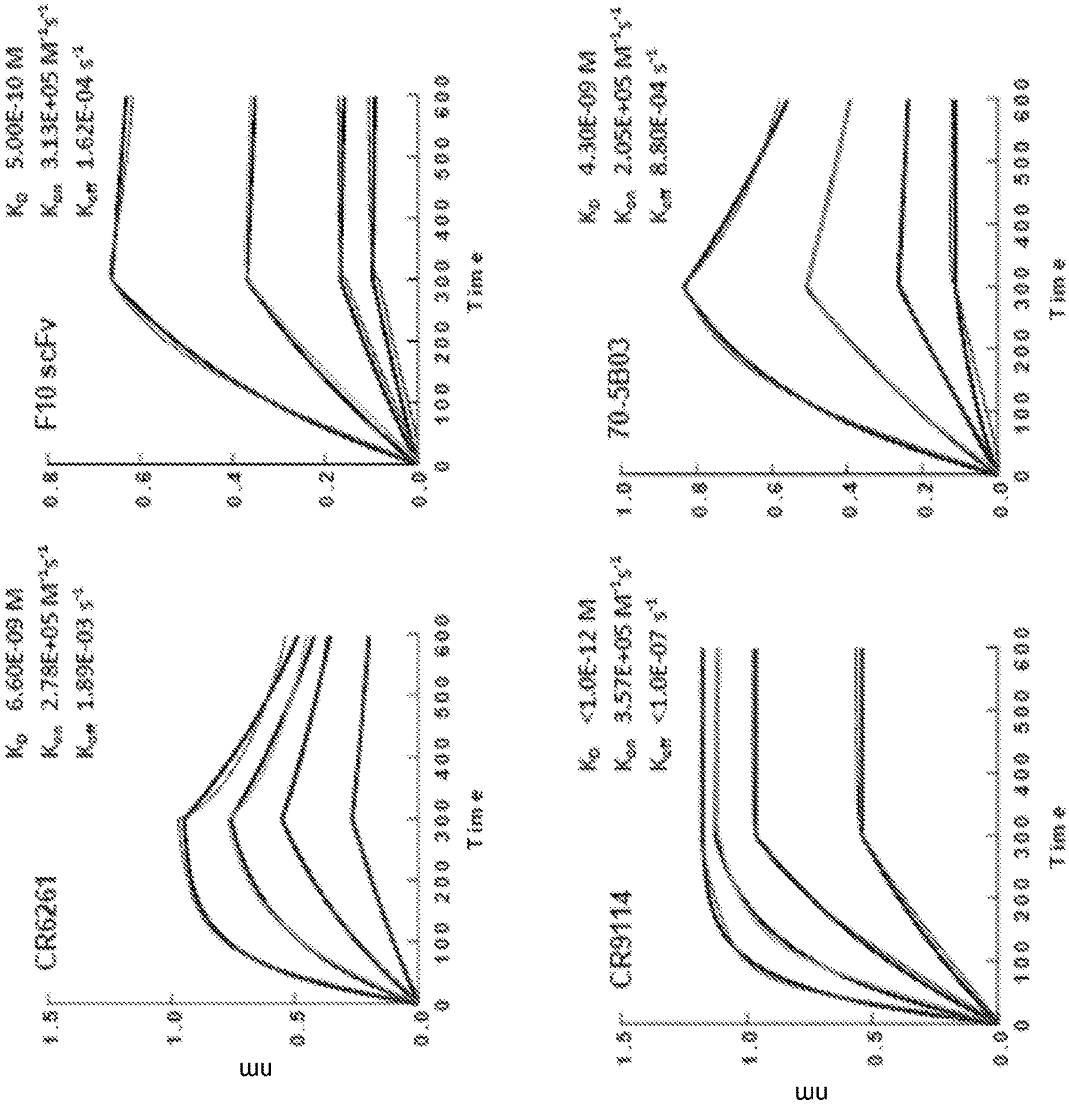
FIG. 1*e* and Figure if show the Octet sensorgrams of H1-SS-np (FIG. 1*e*) and H1-SS-np' (FIG. 1*f*) binding to HA stem-directed bNAbs. H1-SS-np was immobilized onto an Octet probe and incubated with varying concentrations of antibody binding fragments Fab or scFv stem-directed antibodies, which are indicated on top of each sensorgram.
Figure 1F:
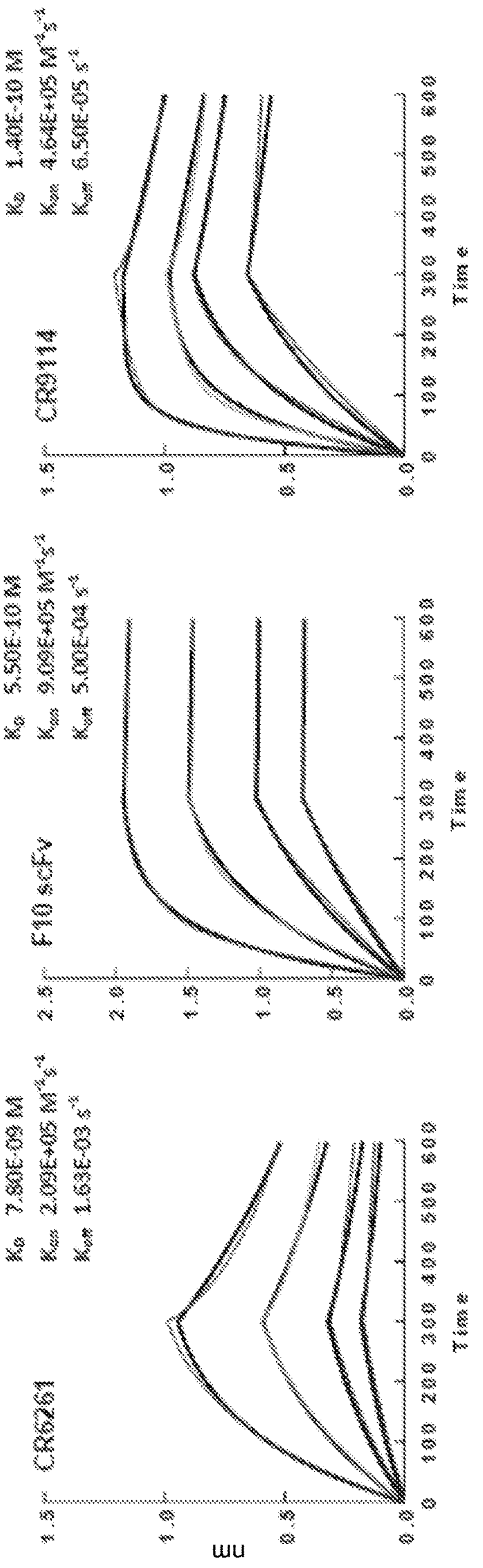
FIG. 1*g* shows the stimulation of wild-type IGHV1-69 v-gene reverted CR6261 BCR (left panel) vs. double Ile53Ala/Phe54Ala CDRH2 mutant BCR (right panel) by anti-IgM (=total receptor activity), empty np, HA-np (with HA containing a Y98F mutation to abolish nonspecific binding to sialic acid), and H1-SS-np' was measured by flow cytometry as the ratio of the Ca2+ bound/unbound states of the Ca2+ sensitive dye FuraRed.
Figure 1G:
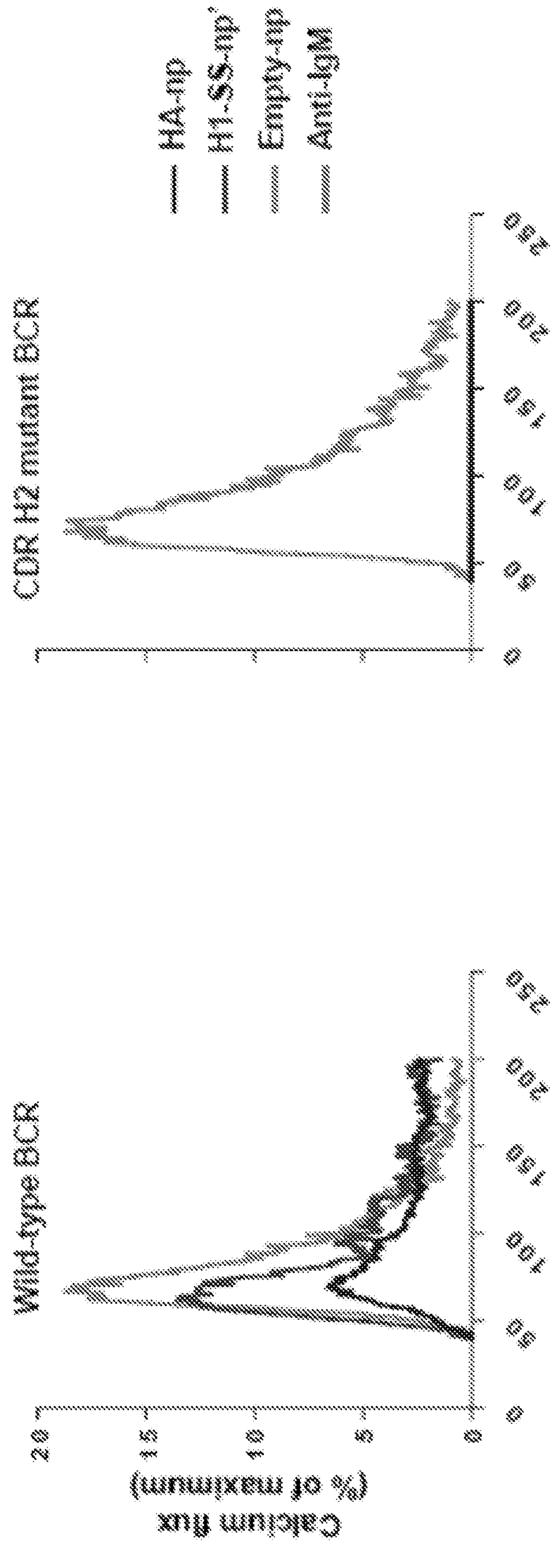
Figure 2B:
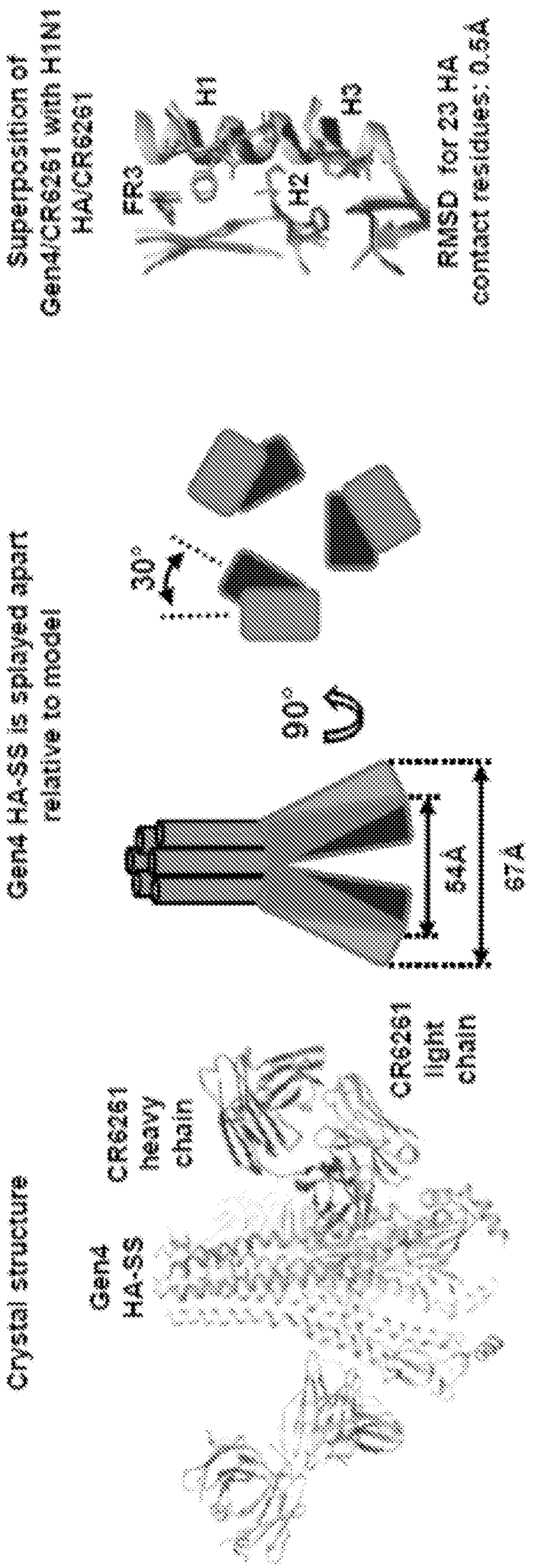
FIG. 2*b* depicts the same panel format as in FIG. 2*a*, showing Gen4 HA-SS and in the right panel a superposition of the Gen4 HA-SS/CR6261 heavy chain binding interface with the 1918 H1N1 HA/CR6261 binding interface (PDB ID 3GBN).
Figure 2C:
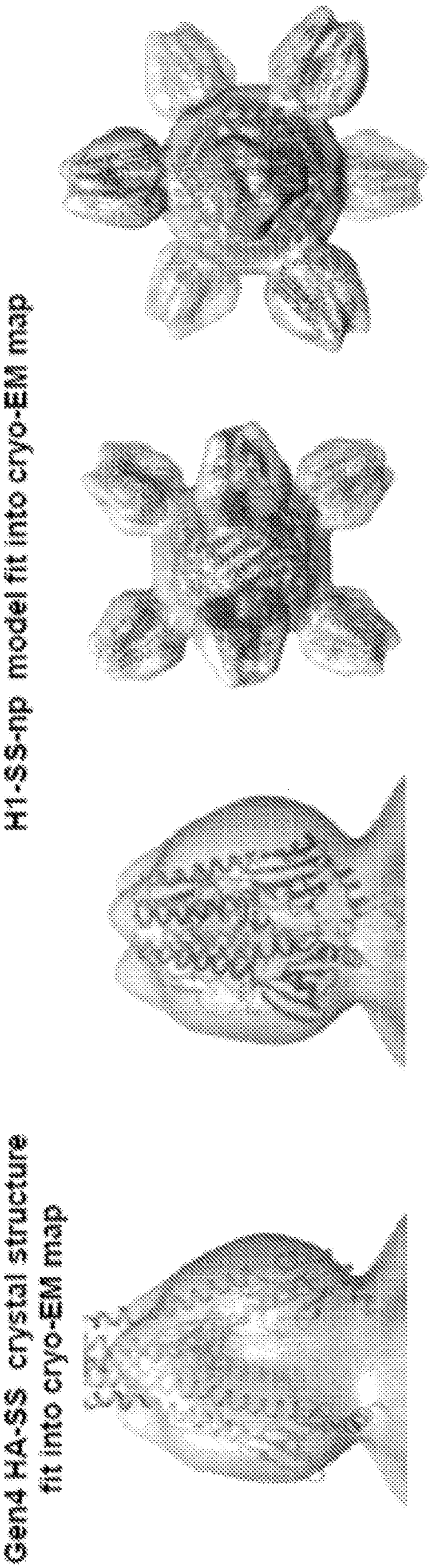
FIG. 2*c* shows the H1-SS-np cryo-electron microscopy analysis. The first two panels show the Gen4 HA-SS crystal structure (cropped) and the H1-SS-np model, respectively, fit into the cryo-electron microscopy map for one H1-SS-np spike. The next two panels of FIG. 2*c* show two different views of the entire H1-SS-np model fit into the H1-SS-np cryo-electron microscopy map.
Figure 2D:
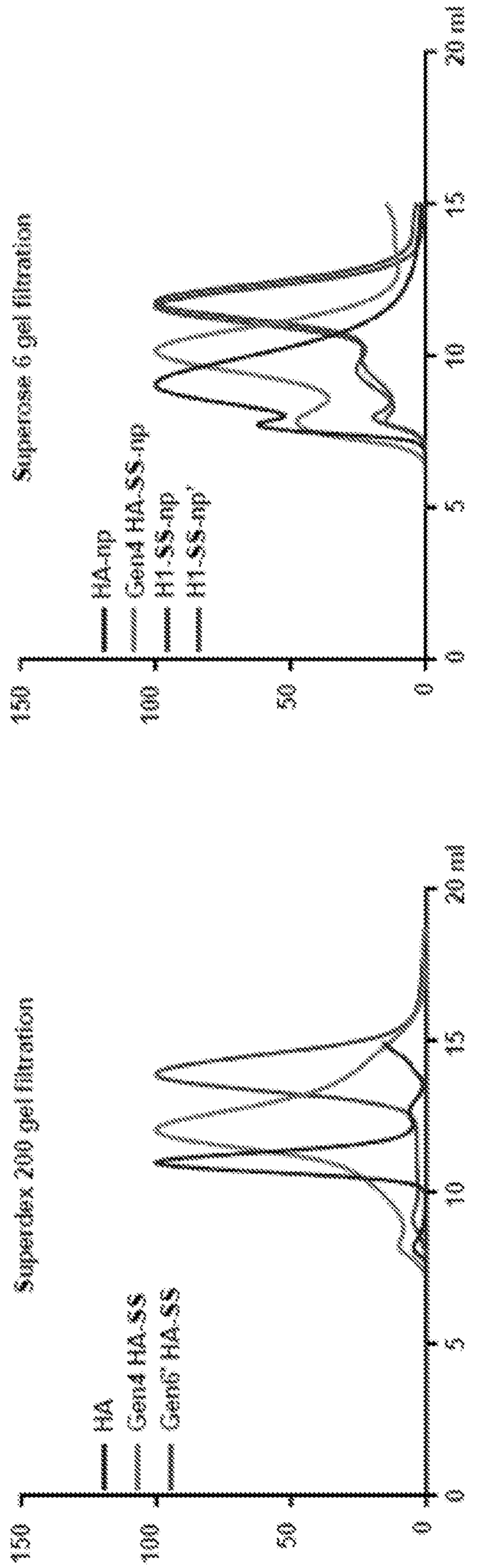
FIG. 2*d* shows the characterization of influenza virus HA and HA-SS insoluble and nanoparticle formats in the size exclusion chromatogram of HA, Gen4 HA-SS and H1-SS-np' (left panel), and HA np, Gen4 HA-SS-np and H1-SS-np' and H1-SS-np (right panel) with a Superdex 20010/300 and Superose 610/300 column, respectively.
Figure 2E:
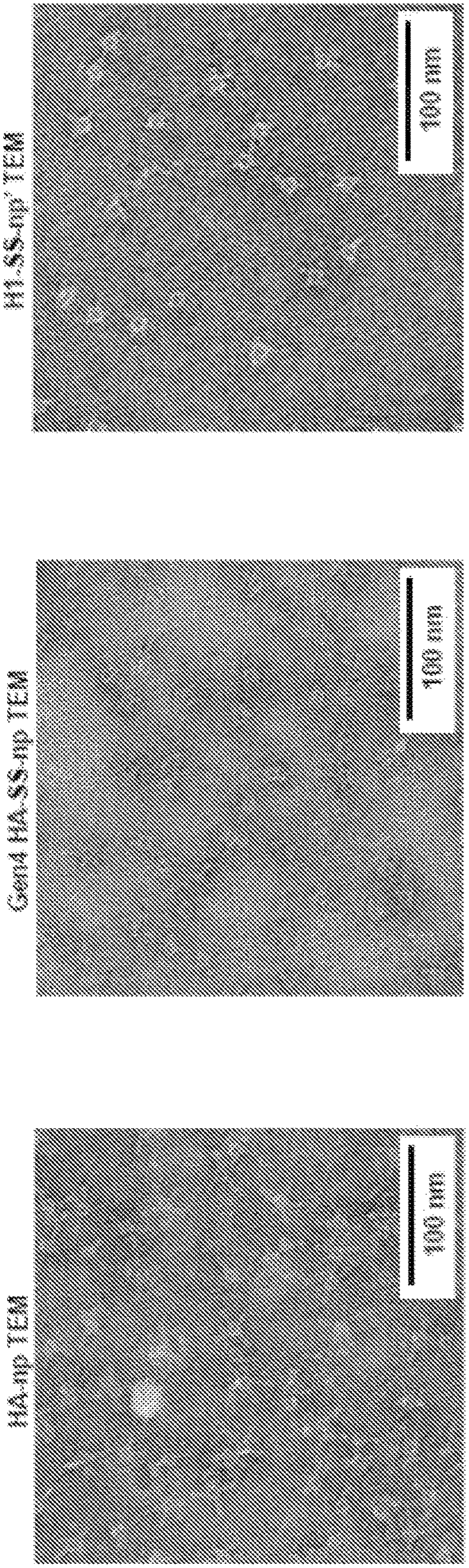
FIG. 2*e* negatively stained transmission electron microscopy images of HA-np (left panel) and Gen4 HA-SS-np (middle panel) and H1-SS-np (right panel). Images were originally recorded at 67,000× magnification.
Figure 2F:
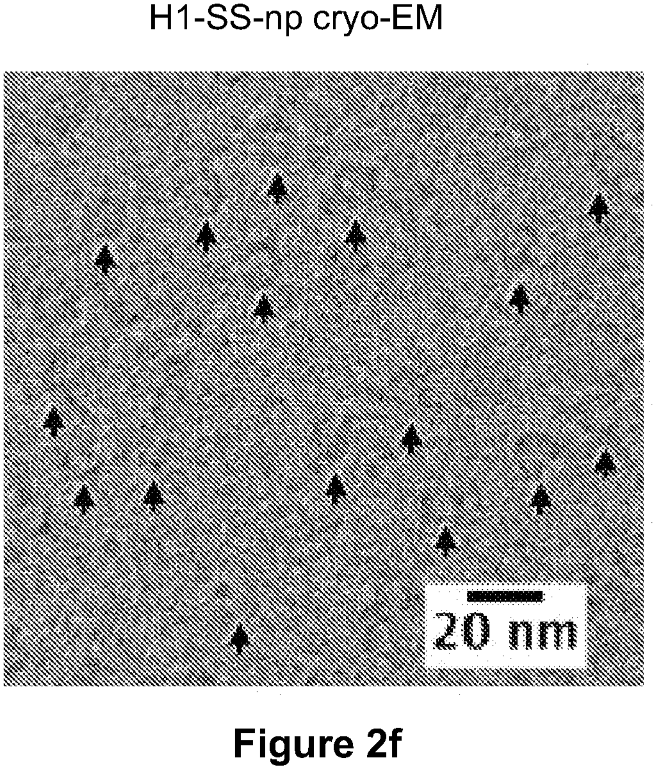
FIG. 2*f* shows a cryo-EM image of a field of H1-SS-np. Arrows depict some ring-like nanoparticles; scalebar is 20 nm.
Figure 2G:
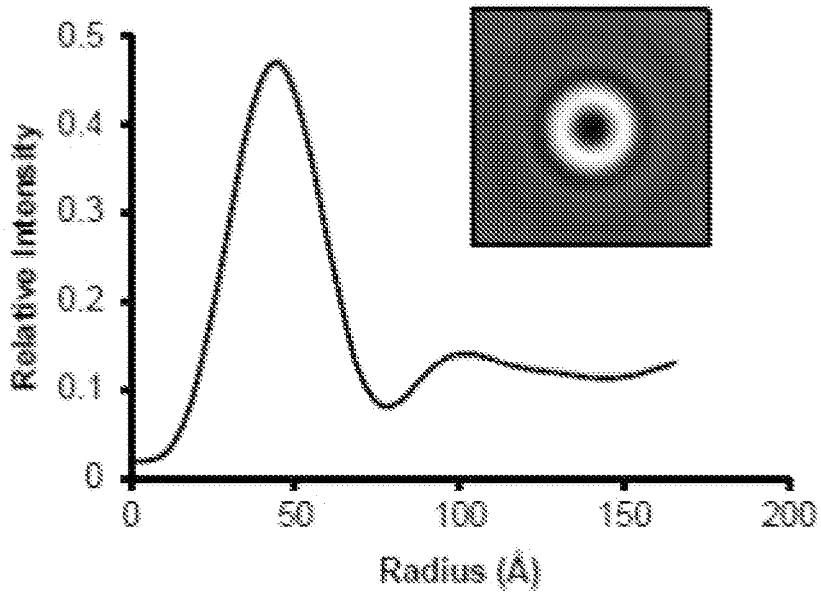
FIG. 2*g* shows a size analysis of H1-SS-np by 2D radial density profile (curve) of the global circular average of nanoparticles (inset). The profile illustrates a two-layered structure with a base peak centered at about 40 Å from the particle center and a second peak spanning the range of about 80 Å to 140 Å. The difference in peak heights is consistent for a more continuous protein layer topped by a layer containing a few discrete spikes.
Figure 2H:
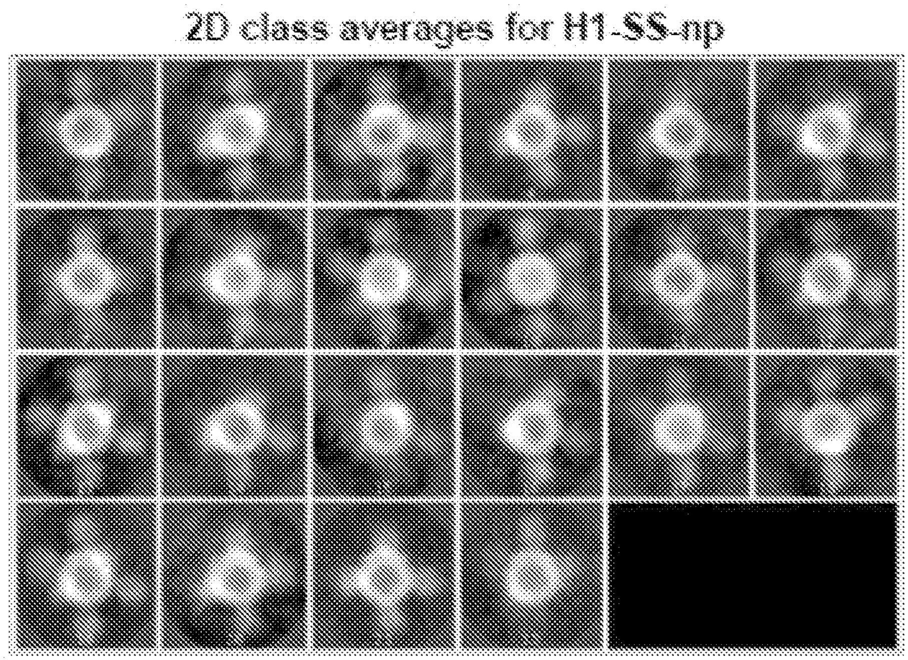
FIG. 2*h* shows the reference-free 2D class averages of H1-SS-np with no symmetry imposed. Classes indicate distinct views of a particle with a protein shell and protruding spike densities and views are consistent with expected octahedral symmetry.
Figure 2I:
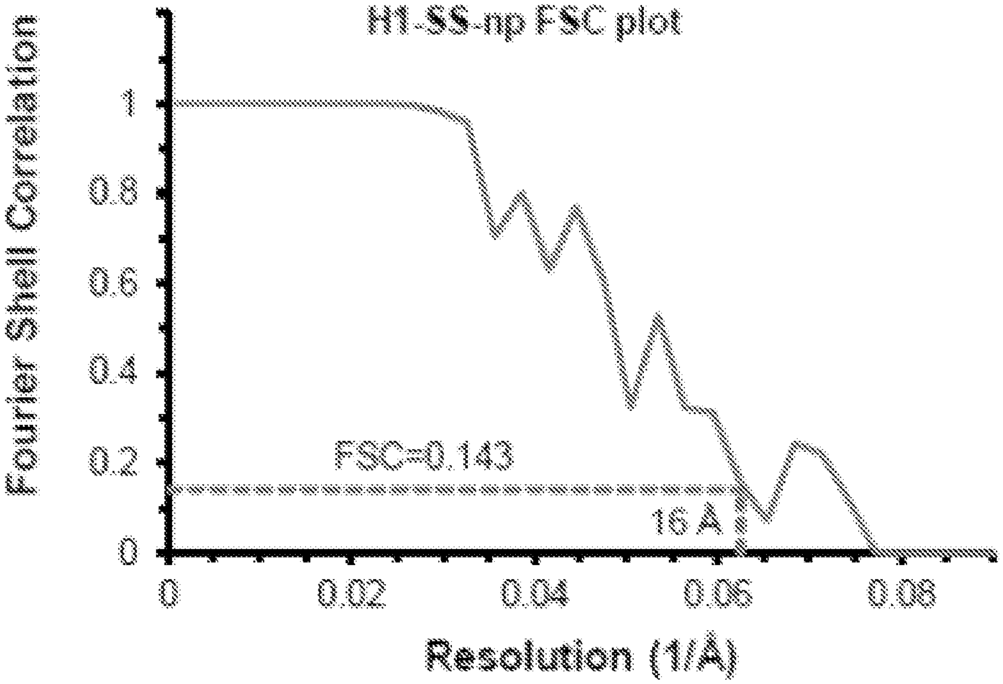
FIG. 2*i* resolution assessment of the H1-SS-np 3D reconstruction by Fourier shell correlation (FSC) plot. FSC (0.143) was used as the cut-off following the gold-standard procedure as implemented in the RELION software package.

To address these issues, a fourth generation HA-SS was created containing three mutations (outlined in FIG. 1) in an effort to remove potential side chain clashes and disrupt the continuous helix between helix B of HA2 and the gp41 HR2 (FIG. 2*b*).

To crystalize the Gen4 HA-SS/CR6261 complex, the Gen4 HA-SS (expressed in 293 $GnTI^{-/-}$ cells) was deglycosylated by incubating with endoglycosidase H (77 U/μg Gen4 HA-SS) for 4 hrs. at 37° C. followed by passage through a concanavalin A column (Sigma) to remove protein with uncleaved N-linked glycans. The complex with CR6261 Fab was obtained by passing a 1:1.25 (Gen4 HA-SS/CR6261 molar ratio) mixture through a Superdex 200 10/300 (GE Healthcare) gel filtration column and collecting the peak eluting at 12.5 mLs. The complex was concentrated to 11 mg/ml in 150 mM NaCl, 10 mM Tris HCl pH 7.5 and crystallized at 20° C. by hanging drop vapor diffusion in 7% (w/v) polyethylene glycol 4000, 4.5% (v/v) isopropanol, 100 mM imidazole pH 6.5. The crystal was soaked in a reservoir solution containing an additional 5% (v/v) 2R,3R butanediol (Sigma) for six hours at room temperature followed by a brief 30 second transfer to a reservoir solution containing 15% 2R,3R butanediol before flash cooling.

X-ray data was collected to 4.30 Å resolution at a temperature of 100K using a wavelength of 1.000 Å at the SER-CAT BM-22 beamline of APS. Data was processed with HKL2000 (ref 37) in the space group H3 and the structure of the complex was determined by molecular replacement using three separate search models. PHASER was used to search with the HA stem monomer from the structure of 1934 PR8, the HIV-1 gp41 monomer (same models as above), and the variable and constant domains of CR6261 (PDB ID 3GBM). Model building and refinement were performed using COOT and PHENIX, respectively. All of the residues of the Gen4 HA-SS were modeled into electron density except for the HA cleavage loop (residues 48-52), the glycine rich loop connecting the gp41 helices (residues 137-145), and the C-terminal foldon (residues 256-259), the thrombin cleavage site and His tag C-terminal to the foldon domain (residues 286-302). While density was visible inside of the HA stem in the same region observed in the Gen3 HA-SS structure, it was not sufficient to uniquely place or stably refine a foldon domain. The CR6261 Fab structure included heavy chain residues 1-213 and light chain residues 3-107 and 113-215. The Ramachandran statistics as determined by PHENIX revealed 93.19% of residues in favored regions, 6.09% in allowed and 1.06% as outliers.

For cryo-electron microscopy analysis, particles were vitrified over holey carbon films (Quantfoil, GroBlobichau, Germany) using a Vitrobot Mark IV (FEI Company, Hillsboro, OR). Cryo-images of particles were collected on a Titan Krios electron microscope (FEI Company, Hillsboro, OR), operated at liquid nitrogen temperatures and operated at 300 kV. Images were collected on a 4,096×4,096 charge-coupled-device (CCD) camera (Gatan Inc., Warrendale, PA) at a pixel size of 1.2 Å with defocus values ranging from approx. 2.8 to approx. 6 μm, and at doses ranging from approx. 10 to 20 e–/$Å^2$. Observed defocus values were fit using ctffind3 (Mindell, J. A. & Grigorieff, N. *J Struct Biol* 142, 334-347 (2003)), and images that exhibited drift or astigmatism were excluded from further analysis. Particles (13,464) were manually picked from images. Reference-free 2D classification indicated octahedral symmetry, which was imposed during 3D refinement. A smooth, spike less, low-pass filtered ferritin (PDB ID 2JD6) was used as a staring model. After removal of overlapping particles during the refinement process, the reconstruction (3D map) was calculated from 6,540 particles. All image analyses (2D and 3D) were carried out with the Relion package (Scheres, S. H. W. *J. Mol. Biol.* 415, 406-418 (2012).). Visualization and molecular docking of model coordinates were performed with Chimera.

Atomic coordinates and structure factors for Gen3 HA-SS in complex with C179 and Gen4 HA-SS complex with CR6261 have been deposited under PDB codes 4MKD and 4MKE respectively. The cryo-electron microscopy map for H1-SS-np has been deposited under the EMDB code EMD-6332.

The co-crystal structure at 4.30 Å resolution of Gen4 HA-SS complexed with a Fab of the bNAb CR6261 (see Ekiert, D. C., et al. *Science* 324, 246-251 (2009)) revealed that the splaying relative to gp41 persists, with an additional rotation of ~19° (FIG. 2*b*, middle panel). However, the level of trimerization (83%), preservation of stem-epitope conformation, and HA stem bNAb binding (nM to four bNAbs) were near optimal in the Gen4 HA-SS (FIGS. 1*a* and 2*b*).

The inventors were concerned about the implications of an immunogenic HIV-1 gp41 region, and therefore sought to replace gp41 with a short glycine-rich linker (FIG. 1*a*), as this would also increase the percentage of the HA stem on the immunogen surface (FIG. 1*b*). The gp41 replacement was carried out in two contexts, a Gen5 HA-SS, which retained the Gen4 stabilized-stem region, and a Gen 6 HA-SS, in which an internal salt bridge comprising Lys51-Glu103 (HA2, H3 numbering) was replaced by a nearly isosteric Met-Leu hydrophobic pair (Gen6 HA-SS, FIG. 1*c*).

The Gen5 HA-SS was created by completely removing the gp41 trimerization domain, connecting HA2 residues 58-93 with a GSGGSG loop and introducing the HA2 mutations Y94D and N95L.

To design Gen6 HA-SS, five mutations were initially created to stabilize the inner core of the HA stem HA2: K51M, E103L, E105Q, R106W, and D109L (referred to as Gen6' HA-SS). Trimerization and recognition by HA stem antibodies were preserved for all three immunogens (FIG. 1*a*). The intermediate version of Gen6 HA-SS (referred to as Gen6' HA-SS) containing three additional internal stabilizing mutations displayed similar antigenicity (FIG. 1*d*), but mutations E105Q, R106W, and D109L were ultimately observed not to be required for stabilization of Gen6 HA-SS and fusion with ferritin and were not used in the final H1-SS-np construct (FIG. 1*c*).

Example 2: Creation of Self-Assembling Ferritin Nanoparticles

This example describes the fusion of Gen4, Gen5, Gen6', and Gen6 HA-SS to the self-assembling ferritin nanoparticle through their respective HA C-termini.

Immunogenicity of HA is substantially increased in the context of a self-assembling nanoparticle (HA-np) (see Kanekiyo, M., et al., *Nature* 499, 102-106 (2013)). Moreover, the inventors speculated that a C-terminal fusion to the nanoparticle might reduce the splaying of the membrane-proximal regions of the stem. The inventors therefore genetically fused Gen4, Gen5, Gen6', and Gen6 HA-SS through their respective HA C-termini (replacing the foldon) to the self-assembling ferritin nanoparticle of *H. pylori* to create HA-SS-nanoparticles (HA-SS-np).

Gen4-6 HA-SS were fused to *H. pylori* ferritin N-terminus (residues 5-167) with a SGG linker to produce HA-SS ferritin nanoparticles (Gen4 HA-SS-np, H1-SS-np and H1-SS-np') as described (Kanekiyo, M., et al. *Nature* 499, 102-106 (2013)).

A fortéBio Octet Red384 instrument was used to measure binding kinetics of HA and HA-SS molecules to mAbs CR6261, CR9114, F10 scFv and 70-5B03. All the assays were performed at 30° C. with agitation set to 1,000 rpm in PBS supplemented with 1% BSA in order to minimize nonspecific interactions. The final volume for all the solutions was 100 μl/well. Assays were performed at 30° C. in solid black 96-well plates (Geiger Bio-One). HA or HA-SS with a C-terminal biotinylated Avi-Tag (25 μg/ml) and HA-np or HA-SS-np in 10 mM acetate pH 5.0 buffer were used to load streptavidin and amine-reactive biosensor probes respectively for 300 s. Typical capture levels were between 0.8 and 1 nm, and variability within a row of eight tips did not exceed 0.1 nm. Biosensor tips were equilibrated for 300 s in PBS/1% BSA buffer prior to binding measurements of the Fabs or F10 scFv in solution (0.01 to 0.5 μM). Upon antibody addition, association was allowed to proceed for 300 s; binding was then allowed to dissociate for 300 s. Dissociation wells were used only once to prevent contamination. Parallel correction to subtract systematic baseline drift was carried out by subtracting the measurements recorded for a sensor loaded with HA or HA-SS molecules incubated in PBS/1% BSA. To remove nonspecific binding responses, a biotinylated gp120 resurfaced core molecule was loaded onto the streptavidin probe and incubated with anti-stem antibodies, and the nonspecific responses were subtracted from HA and HA-SS response data. Data analysis and curve fitting were carried out using Octet software, version 7.0. Experimental data were fitted with the binding equations describing a 1:1 interaction. Global analyses of the complete data sets assuming binding was reversible (full dissociation) were carried out using nonlinear least-squares fitting allowing a single set of binding parameters to be obtained simultaneously for all concentrations used in each experiment.

ELISA, hemagglutination inhibition (HA1) assay and pseudotype neutralization assays were performed as previously described (Wei, C. J., et al. *Science* 329:1060-1064 (2010)). The recombinant HA/NA lentiviral vectors expressing a luciferase reporter gene were produced as described (Wei, C. J., et al. *Sci. Transl. Med.* 2, 24ra21 (2010)). All influenza viruses were obtained from Centers for Disease Control and Prevention (CDC; Atlanta, GA).

Gen4, Gen6 and Gen6' HA-SS-np each expressed as nanoparticles as confirmed by transmission electron microscopic analysis and gel filtration (FIG. 2). However, Gen5 HA-SS-np failed to express. Gen6 and Gen6' HA-SS-np were selected for further evaluation and hereafter are referred to in these Examples as H1-SS-np and H1-SS-np' respectively. Cryo-electron microscopy (EM) analysis of H1-SS-np performed to a resolution of 16 Å revealed symmetrical, spherical particles, each with eight spikes protruding from the surface (FIG. 2*c*). Notably, the membrane-proximal region of the Gen6 HA-SS stem fits better into electron density than Gen4 HA-SS, suggesting that the splaying is either mitigated or no longer present (FIG. 2*c*, left panel). Moreover, both H1-SS-np and H1-SS-np' had the desired antigenic properties, being recognized by CR6261, CR9114, F10, and 70-5B03 (see, Ekiert, D. C., et al. *Science* 324, 246-251 (2009); Sui, J., et al. *Nat. Struct. Mol. Biol.* 16, 265-273 (2009); Dreyfus, C., et al. *Science* 337, 1343-1348 (2012); Wrammert, J., et al. *J. Exp. Med.* 208, 181-193 (2011)) in ELISA and biolayer interferometry measurements, indicating the authentic HA-SS structure was preserved upon fusion to ferritin (FIGS. 1*a*, 1*e* and 1*f*).

Example 3: Assessing Vaccine Efficacy

This example demonstrates the characterization of various measures of vaccine efficacy for the ferritin nanoparticles fused to the HA constructs.

The inventors assessed the capacity of H1-SS-np to trigger signaling by membrane-anchored germline-reverted CR6261 B cell receptor (BCR) compared to full length HA-np using a calcium flux assay (Novak, et. al. Cytometry 17, 135-141 (1994)).

For the BCR activation assay, germline CR6261 BCRs (wild type and double 153A/F54A mutant) were stably expressed by lentiviral transfection (FEEKW vector; Luo, X. M., et al. Blood 113, 1422-1431 (2009)) of light chain and membrane-anchored IgM heavy chain into a surface IgM negative clone of Ramos B cell line. Germline CR6261 BCR positive cells were then sorted by flow cytometry (BD FACSAria; BD Biosciences) and amplified. Cells expressing >95% positivity for germline CR6261 BCR (wild type or 153A/F54A mutant) were assessed for surface expression and correct HA antigenicity. For signaling, 2500 nM of either H1-SS-np, HA np (with HA containing Y98F mutation to abolish nonspecific binding to sialic acid) or empty np was presented to $1\times10^6$ Ramos B cells expressing germline CR6261 BCRs. The kinetics of calcium flux in response to BCR stimulation was measured by flow cytometry as the ratio of the Ca' bound/unbound states of the dye Fura Red. This ratio for Ca' flux is presented 10 seconds after exposure to ligand. A 30 second baseline was acquired prior to stimulation. Ratiometric measures for individual cells were averaged and smoothened by Kinetic analysis, FlowJo software. Functionality between germline CR6261 BCR versus germline CR6261 BCR with I53A/F54A mutation was compared by Ca' flux following exposure to 0.5 μg/μl anti-human IgM $F(ab')_2$ (Southern Biotech).

In contrast to empty ferritin particles, H1-SS-np induced effective signaling through wild-type BCR as did full-length HA-np to a lesser extent, and no signaling was observed through a BCR mutated in two critical contact residues in the second heavy chain complementarity determining region (CDR H2) (FIG. 1*g*). This finding confirms the ability of H1-SS-np to engage the IGHV1-69 germline precursor of CR6261 and stimulate naïve B cells through CDR H2-dependent recognition, characteristic of broadly neutralizing stem-directed antibodies found in humans.

To evaluate H1-SS-np vaccine efficacy the inventors immunized mice and ferrets using the Sigma Adjuvant System (SAS) as SAS has been reported to induce HA responses similar to MF59, another squalene-based adjuvant approved for use in humans.

For the immunization studies, a total of three animal experiments, two in mice and one in ferrets, were performed for this study. In the first mouse experiment, female BALB/c mice (6-8 weeks old, Jackson Laboratories) were immunized intramuscularly with 2 μg H1-SS-np, 2 μg of empty ferritin np, 0.2 μg of H5 2005 IND HA-np or TIV (HA molar equivalent) at week 0 and 4. Blood was collected 14 days after each immunization and serum was isolated. For the second mouse immunization experiment, female BALB/c mice were immunized three times with 3 μg of H1-SS-np or empty ferritin np at weeks 0, 8, and 12. For ferret immunization, 6 month old male Fitch ferrets (Triple F Farms, Sayre, PA), seronegative for exposure to currently circulating pandemic H1N1, seasonal H1N1, H3N2, and B influenza strains, were housed and cared for at BIOQUAL, Inc. (Rockville, MD). These facilities are accredited by the American Association for the Accreditation of Laboratory Animal Care International and meet NIH standards as set forth in the *Guide for the Care and Use of Laboratory Animals*. Ferrets were immunized intramuscularly with 20 μg of H1-SS-np', or empty ferritin np or TIV (equivalent to 2.5 μg of H1 HA) in 500 μl of PBS at weeks 0 and 4. Ferrets in the positive control group were immunized with 250 μg plasmid DNA expressing H5 2005 IND followed by 2.5 μg HA of H5N1 2005 IND MIV at weeks 0 and 4. The vaccine was administered via intramuscular injections into the upper thigh muscle. Sigma Adjuvant System (SAS, Sigma) was used for all protein or np-based immunization. Blood was collected 14 days after each immunization and serum was isolated Animal experiments were conducted in full compliance with all relevant federal regulations and NIH guidelines.

For the passive transfer studies, 150 mice were first vaccinated with H1-SS-np protein (2 μg/dose with SAS) at weeks 0 and 4, to generate HA-SS immune Ig, and sera were collected at weeks 1, 2, and 3 (terminal) post boost. Ig from immune sera was purified with protein G (Life Technologies) using the manufacturer protocol. 24 hour before challenge, two groups of BALB/c mice (n=10/group, Taconic inc.) received either naïve (Molecular innovations) or immune Ig via an intraperitoneal route. Sera were collected from infused animals 24 hours post passive transfer for serological analysis.

For virus challenge studies, the H5N1 strain, A/Vietnam/1203/04, was obtained from the Centers for Disease Control and Prevention (Atlanta, GA) (CDC #2004706280, E1/E3 (1/19/07) and amplified in 10-day old embryonated hen's eggs (Charles River, North Franklin, CT) at BIOQUAL Inc. The challenge stock has an infectious titer of 1010 $TCID_{50}$/ml. For blood collection, bleeds, and challenge procedure, the animals were anesthetized with a solution of ketamine/dexmedetomidine formulated to provide doses of 25 mg/kg ketamine and 0.001 mg/kg dexmedetomidine to each animal Mice were inoculated intranasally with 50 μl of virus, approximately 25 μl to each nostril and ferrets were inoculated intranasally with 500 μl of virus, approximately 250 μl to each nostril. The challenge dose was 25 $LD_{50}$ in mice and 1000 $TCID_{50}$ in ferrets. Based on previous studies these challenge doses were expected to result in 100% lethality in naïve control mice and ferrets respectively. Clinical signs of infection, weight, and temperatures were recorded twice daily for ferrets. Activity scores were assigned as follows: 0, alert and playful; 1, alert but playful only when stimulated; 2, alert, but not playful when stimulated; and 3, neither alert nor playful when stimulated. Ferrets that showed signs of severe disease (prolonged fever; diarrhea; nasal discharge interfering with eating, drinking, or breathing; severe lethargy; or neurological signs) or had >20% weight loss were euthanized immediately.

Figure 3A:
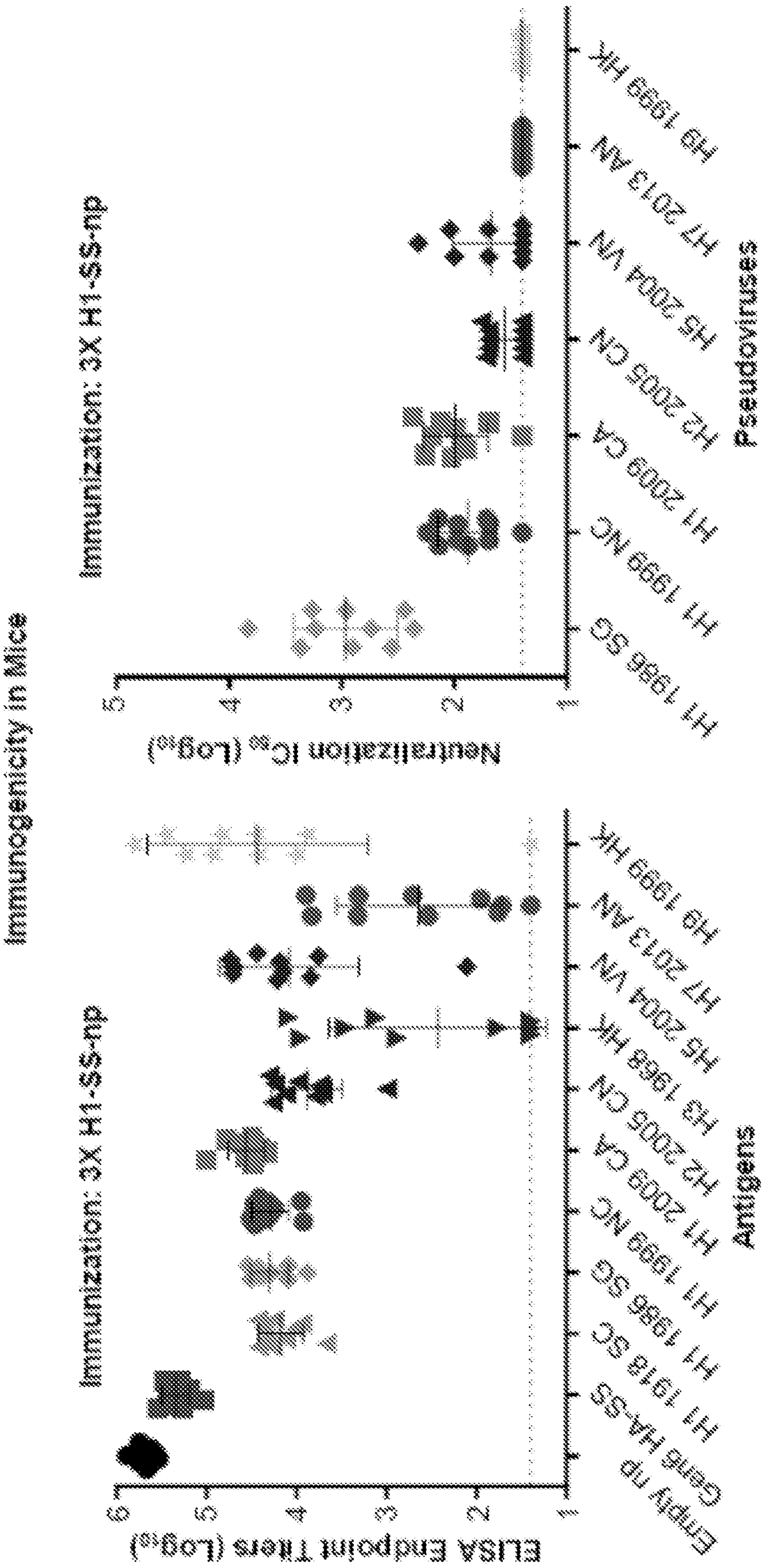
FIG. 3*a* shows the immune responses of immunized mice and ferrets. The left panel shows the antibody endpoint titers to diverse HA proteins and the right panel shows the neutralization titers of sera from mice (n=10 per group) immunized with SAS-adjuvanted H1-SS-np.
Figure 3B:
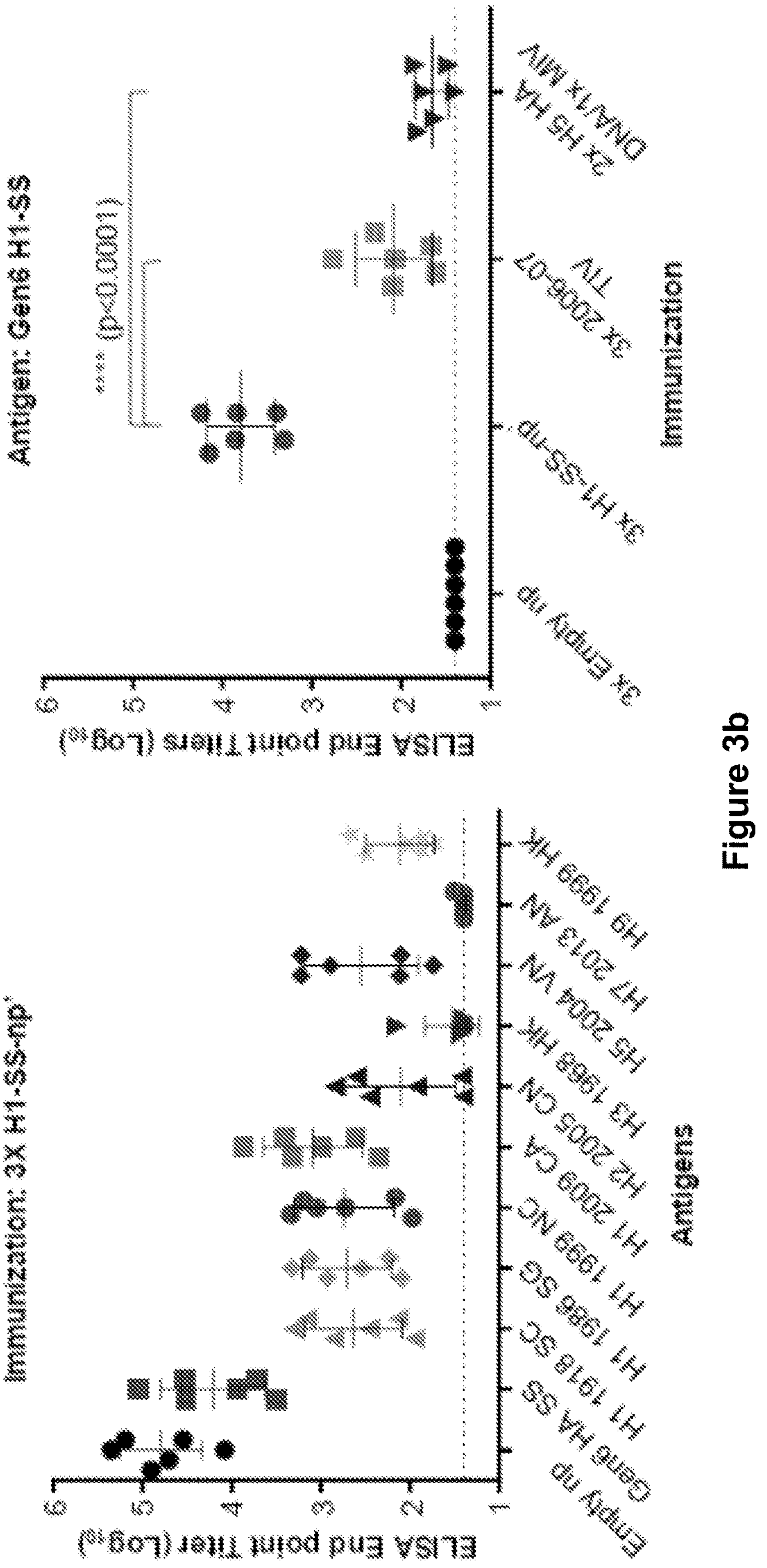
FIG. 3*b* shows the immune responses of ferrets immunized with SAS-adjuvanted empty np (n=5), H1-SS-np' (n=6), 2006-07 TIV (n=6) or with H5 HA (2×DNA/lx MIV; n=6). The left panel of FIG. 3*b* shows the antibody endpoint titers of H1-SS-np' immune sera to diverse HA proteins and the right panel shows the HA stem reactivity of sera from the four immunization regimens.
Figure 3C:
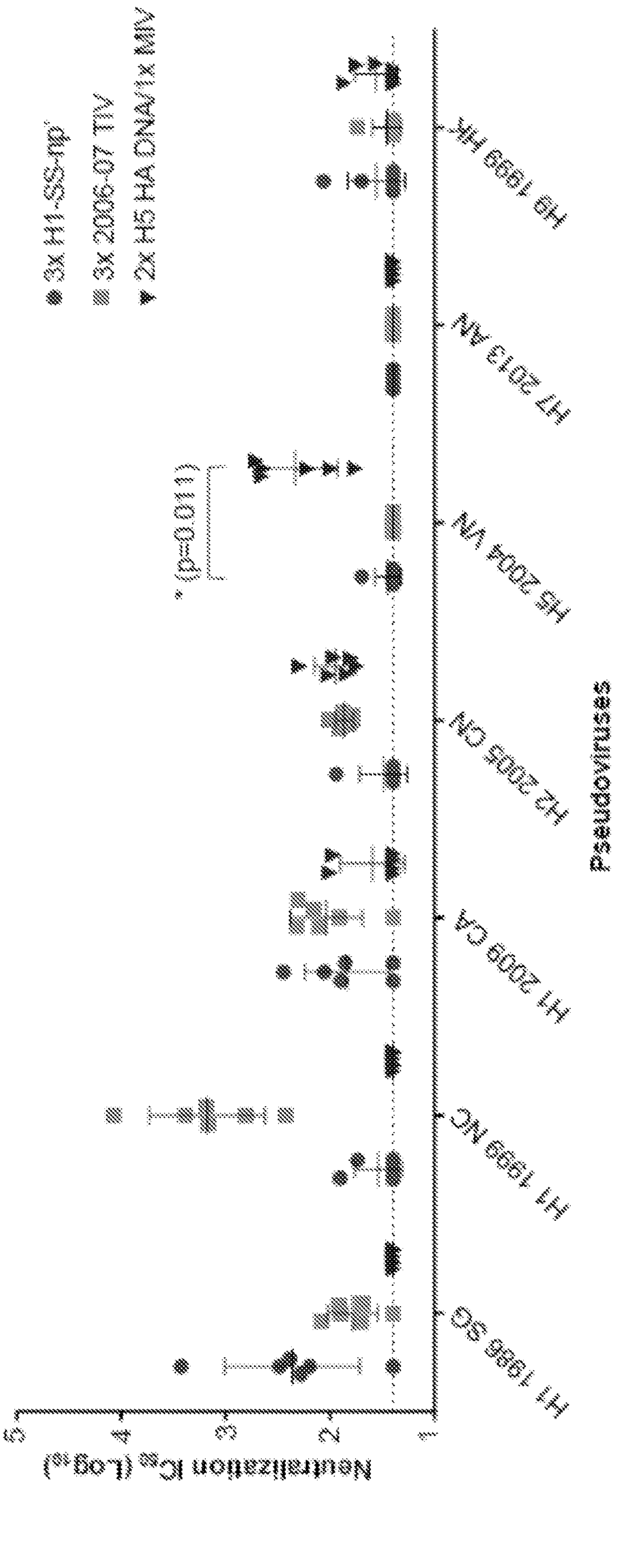
FIG. 3*c* shows the neutralization titers of sera from ferrets immunized with three administration regimens. Antibody endpoint and $IC_{50}$ titers are shown for each individual animal two weeks post boost. The dotted line indicates the baseline (1:25 dilution) for both ELISA and pseudotyped lentiviral reporter assays. Error bars represent mean±s.d.; statistical analysis was performed using a two-tailed student's t-test.

H1-SS-np and H1-SS-np' elicited broad antibody responses against group 1 HA subtypes (seasonal and pandemic H1, H2, H5 and H9) in both mice and ferrets respectively (FIGS. 3*a*, 3*b* and 3C). Furthermore, H1-SS-np induced substantial group 2 (H3 and H7) responses equivalent to those of H2 and H5 in half of the mice (FIG. 3*a*, left panel). The antibody response to HA stem elicited by H1-SS-np was significantly higher than that of trivalent inactivated influenza vaccine (TIV) in both mice and ferrets (FIG. 3*b*, right panel). Although a considerable response to ferritin was also observed (FIGS. 3*a* and 3*b*, left panel), previous studies have shown that immunization with bacterial ferritin does not induce immunity to autologous ferritin in mice, nor does it mitigate HA-specific antibody responses to subsequent immunizations. Measurement of serum neutralization activity (NT) using a highly sensitive HA-NA lentiviral reporter assay (Wei, C. J., et al. *Sci. Transl. Med.* 2, 24ra21 (2010)) revealed appreciable activity against the divergent H1N1 strains A/California/04/2009 (2009 CA) and A/Singapore/6/1986 (1986 SG) and the homologous 1999 NC strain in both mice and ferrets. However, NT against heterosubtypic H5N1 A/Vietnam/1203/2004 (H5N1 2004 VN), human origin H2N2 A/Canada/720/2005 (H2N2 2005 CA), H7N9 A/Anhui/1/2013 (H7N9 2013 AN) and H9N2 A/Hong Kong/1074/1999 (H9N2 1999 HK) was low or undetectable in both mice and ferrets (FIGS. 3*a* and 3*c*). The minimal heterosubtypic neutralization observed despite strong heterosubtypic antibody reactivity is likely due to the precise targeting of a single epitope region required for stem neutralization, making it more sensitive to minor structural differences than other parts of the HA stem which is 20-fold greater in surface area. TIV-immunized animals had the highest NT against homologous 1999 NC, detectable NT against the heterologous H1N1 strains, and no NT against heterosubtypic H5N1 in both mice and ferrets (FIG. 3*b*). As expected, TIV-immunized animals had significant hemagglutination inhibition (HA1) titers and NT activity elicited by H1-SS-np and H1-SS-np' was not associated with HA1.

Figure 4A:
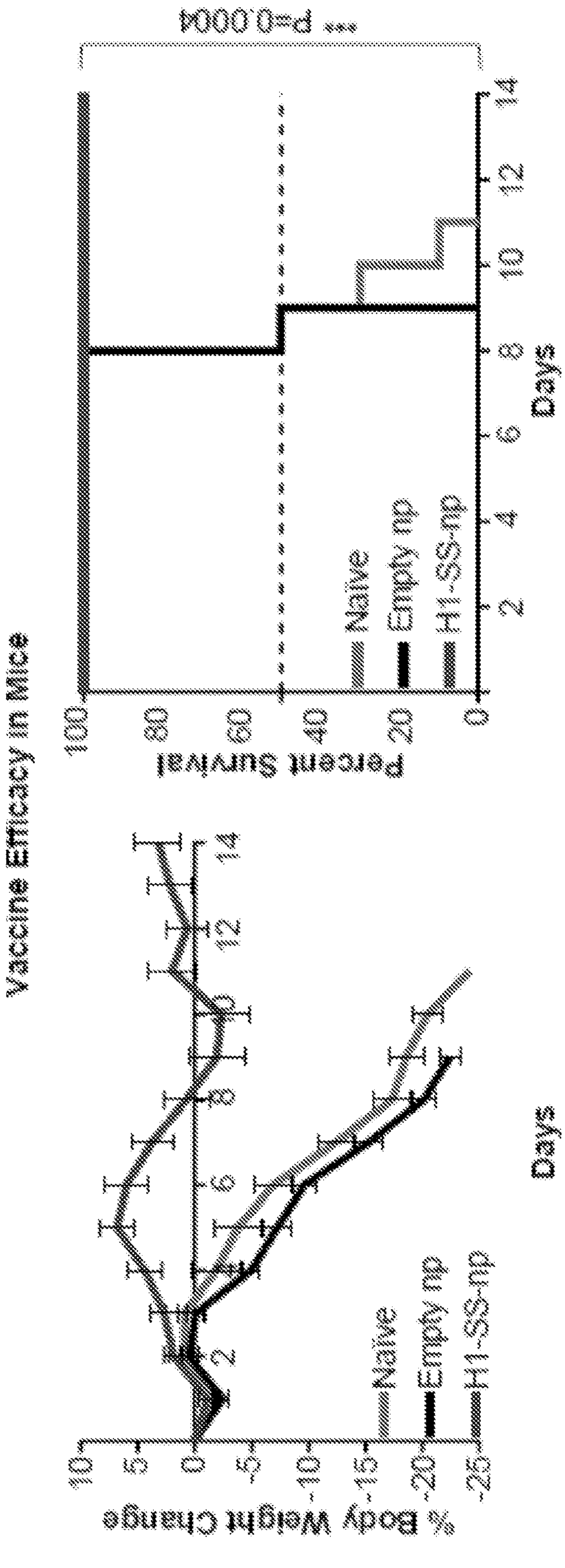
FIG. 4*a* shows the immune protection conferred against lethal H5N1 2004 VN influenza virus challenge in mice and ferrets. BALB/c mice (n=10 per group) were vaccinated three times with SAS-adjuvanted empty np or H1-SS-np at weeks 0, 8, and 11 or left unvaccinated (naïve). Four weeks post final vaccination, mice were challenged with high dose (25 LD50) of H5N1 2004 VN virus and monitored for body weight loss (left panel) and survival (right panel) for 14 days.
Figure 4B:
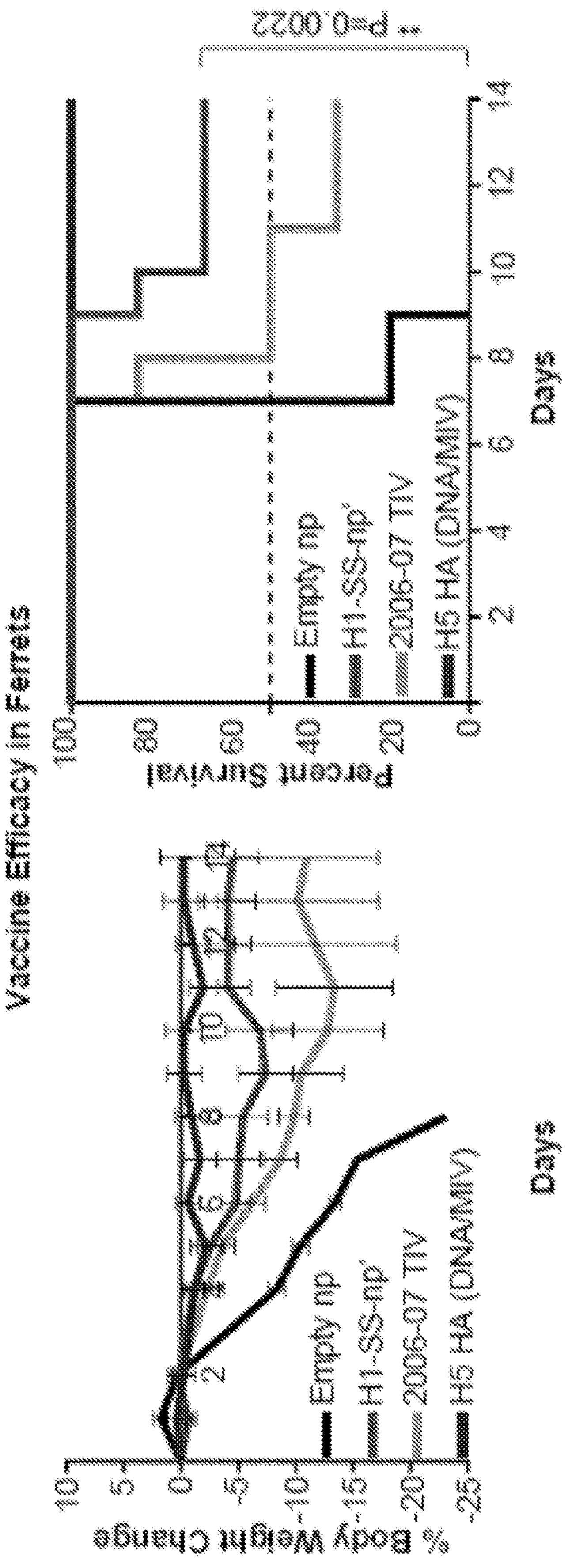
FIG. 4*b* shows ferrets vaccinated three times with SAS-adjuvanted empty np (n=5), H1-SS-np' (n=6), 2006-07 TIV (n=6), or H5 HA (DNA/MIV; n=6) and challenged six weeks after the final immunization with 1000 $TCID_{50}$ of H5N1 2004 V N. Body weight loss (left panel) and survival (right panel) were monitored for 14 days.

To assess protection, immunized mice and ferrets were challenged with a high lethal dose of highly pathogenic H5N1 2004 VN virus. All naïve mice and those immunized with empty np died and notably, all those immunized with H1-SS-np survived (FIG. 4*a*). All ferrets immunized with empty ferritin nanoparticles succumbed to infection, and all ferrets immunized with an H5N1 HA DNA/monovalent inactivated vaccine (MIV) prime-boost survived (FIG. 4*b*). Consistent with the mouse study, four out of six H1N1-based H1-SS-np'-immunized ferrets survived H5N1 challenge. Although two out of six TIV-immunized ferrets survived, one of the two survivors experienced severe weight loss (FIG. 4*a*), and there was no evidence of H5 serological response in the other survivor which had minimal weight loss, suggesting infection did not occur. Apart from one seronegative animal, the TIV-immunized group was not different in weight loss or fever compared to empty ferritin-np controls and showed greater illness as evidenced by post challenge activity scores than the H1-SS-np'-immunized ferrets. There was a considerable reduction in day 6 weight loss, fever and illness based on activity scores in the H1-SS-np'-immunized ferrets compared to empty ferritin-immunized controls (FIG. 4). The HA1 titers to H5N1 2004 VN present at day 14 post-challenge in the surviving ferrets indicates that while H1-SS-np' was able to protect against illness, it did not prevent infection. Tables 3 and 4 provide the summary of these immunization studies in the mice and ferrets.

TABLE 3

Post challenge sera HAI antibody titers to H1N1 1999 NC and H5N1 2004 VN in mice immunized with H1-SS-np.

| | H1-SS-np | |
|---|---|---|
| Mouse # | H1N1 1999 NC (Post challenge) | H5N1 2004 VN (Postchallenge) |
| 1 | <10 | 40 |
| 2 | <10 | 80 |
| 3 | <10 | 10 |
| 4 | <10 | 160 |
| 5* | N/A | N/A |
| 6 | <10 | 160 |
| 7 | <10 | <10 |
| 8 | <10 | <10 |
| 9 | <10 | 160 |
| 10 | <10 | <10 |

*This mouse died one day before challenge.

TABLE 4

Pre challenge HAI antibody titer to homologous H1N1 1999 NC and post challenge HAI antibody titer to challenge strain H5N1 2004 VN in ferrets immunized with indicated regimens.

| | H1N1 1999 NC (Pre Challenge) | | | | H5N1 2004 VN (post challenge) | | | |
|---|---|---|---|---|---|---|---|---|
| Ferret # | Empty np | H1-SS-np' | H5 HA (DNA/MIV) | 2006-07 TIV | Empty np | H1-SS-np' | H5 HA (DNA/MIV) | 2006-07 TIV |
| 1 | 10 | 10 | 10 | 640 | N/A | ≥1280 | <10 | 640 |
| 2 | 10 | 10 | 10 | 1280 | N/A | N/A | <10 | N/A |

TABLE 4-continued

Pre challenge HAI antibody titer to homologous H1N1 1999 NC and post challenge HAI antibody titer to challenge strain H5N1 2004 VN in ferrets immunized with indicated regimens.

| | H1N1 1999 NC (Pre Challenge) | | | | H5N1 2004 VN (post challenge) | | | |
|---|---|---|---|---|---|---|---|---|
| Ferret # | Empty np | H1-SS-np' | H5 HA (DNA/MIV) | 2006-07 TIV | Empty np | H1-SS-np' | H5 HA (DNA/MIV) | 2006-07 TIV |
| 3 | 10 | 10 | 10 | 2560 | N/A | ≥1280 | <10 | <10 |
| 4 | 10 | 10 | 10 | 1280 | N/A | ≥1280 | ≥1280 | N/A |
| 5 | 10 | 10 | 10 | 2560 | N/A | 640 | ≥1280 | N/A |
| 6 | N/A | 10 | 10 | 2560 | NA | N/A | ≥1280 | N/A |

Figure 4C:
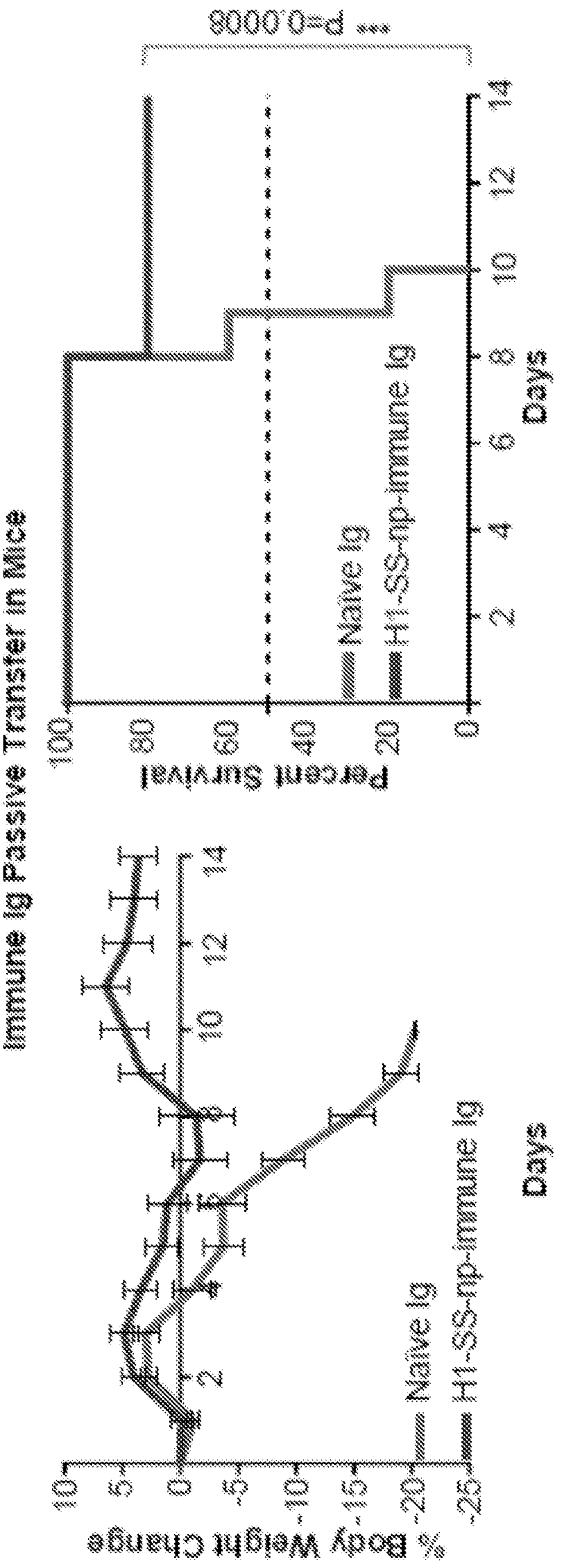
FIG. 4*c* shows BALB/c mice (n=10 per group) passively immunized (intraperitoneal) with 10 mg Ig from either naïve or H1-SS-np-immune animals 24 hours before challenge with a high dose (25 $LD_{50}$) of H5N1 2004 VN influenza virus. Body weight loss (left panel) and survival (right panel) were monitored for 14 days. In each of FIGS. 4*a*, 4*b* and 4*c*, the black dotted line (right panels) indicate 50% survival. Statistical analysis was performed with a Log-Rank (Mantel-Cox) test.
Figure 4D:
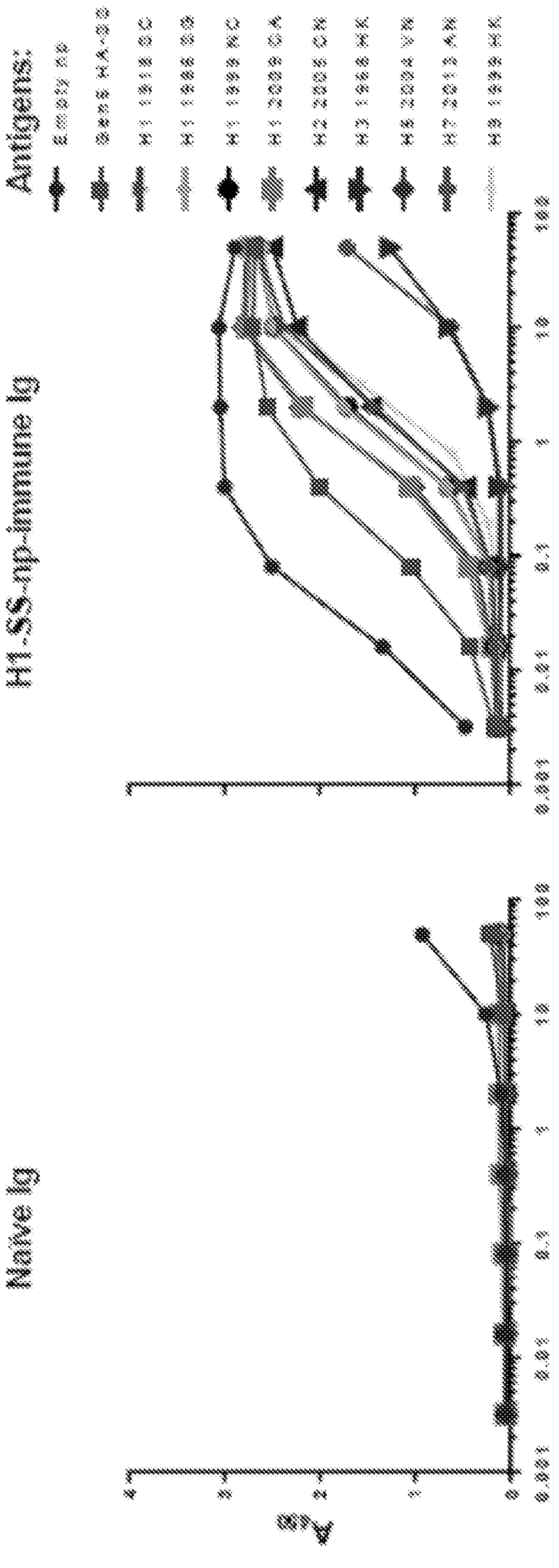
FIG. 4*d* shows the characterization of naïve and H1-SS-np-immune Ig. By ELISA binding of naïve Ig (left) and H1-SS-np-immune Ig (right) to empty ferritin np and various HA proteins.
Figure 4E:
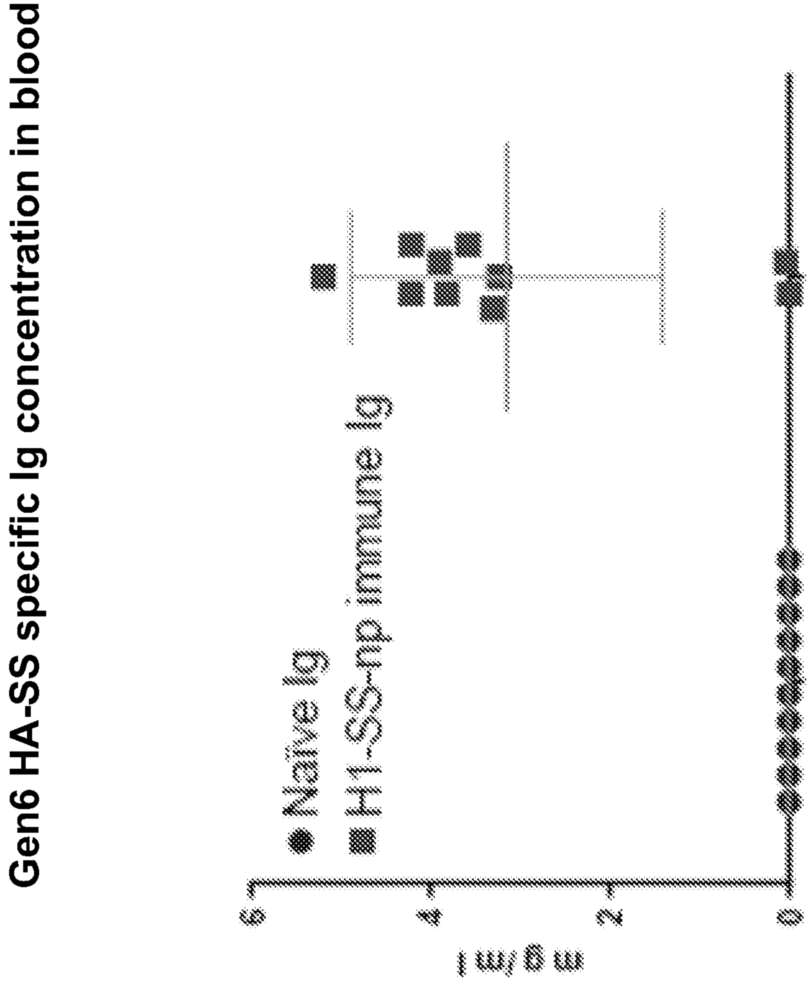
FIG. 4*e* shows the estimated concentration of Gen6 HA-SS specific Ig in mice sera 24 hours post infusion with polyclonal Ig.

The negligible H5N1 NT activity elicited by H1-SS-np' (FIG. 3*c*) does not explain the heterosubtypic protection observed. However, there was a correlation between HA stem antibody titer and survival as well as between antibody titers and body weight in the H1-SS-np'-immunized ferrets. To further investigate this correlation, the inventors passively transferred H1-SS-np-immune Ig to naïve mice (10 mg/animal) 24 hour before challenge with a high lethal dose of H5N1 2004 VN virus. The transferred Ig had strong reactivity with the group 1 HA subtypes (H1, H2, H5, and H9), weaker binding to group 2 subtypes (H3 and H7), and minimal NT activity (FIGS. 4*d* and 4*e*). The IC50 neutralization titer of H1-SS-np immune Ig to diverse influenza pseudoviruses is shown in Table 5.

TABLE 5

$IC_{50}$ pseudovirus neutralization titer of H1-SS-np-immune Ig.

| Virus | H1N1 1986 SG | H1N1 1999 NC | H1N1 2009 CA | H2N2 2004 CN | H5N1 2004 VN | H7N9 2013 AN | H9N2 1999 HK |
|---|---|---|---|---|---|---|---|
| IC50 | 11 mg/ml | >50 mg/ml | >50 mg/ml | >50 mg/ml | >50 mg/ml | >50 mg/ml | >50 mg/ml |

While all the mice that received naïve Ig died from infection, eight out of ten mice that received immune Ig were completely protected from lethal H5N1 heterosubtypic challenge. Low sera reactivity to homologous H1 1999 NC HA in the two mice that died in the immune Ig group indicate they may not have received the appropriate Ig administration (FIG. 4*c*).

Together, these data show that antibody-mediated protection based on functional mechanisms other than neutralization such as antibody-dependent cell-mediated cytotoxicity (ADCC) or antibody-dependent complement-mediated lysis are responsible for protection elicited by H1-SS-np and H1-SS-np' immunizations. Influenza protection in mice by broadly neutralizing HA stem antibodies have been reported to be dependent on Fc interactions (DiLillo, et. al. *Nat Med* 20, 143-151 (2014)) and cross-reactive ADCC against influenza HA in the absence of neutralization has been reported in both human and macaque plasma (Jegaskanda, S., et al. *J Immunol* 190, 1837-1848 (2013); Jegaskanda, et al. J. Virol. 87, 5512-5522 (2013); Jegaskanda, et al. *J Immunol* 193, 469-475 (2014)). Consistent with these reports, the results presented herein suggest that HA stem-based influenza vaccines need not necessarily be focused on neutralizing epitopes to induce broad protection.

Using structure-based design and avoiding immunodominant responses to the HA head domain, combined with a nanoparticle antigen display platform, the inventors have successfully generated an HA stem-only nanoparticle vaccine immunogen that elicits antibody-mediated heterosubtypic protective immunity against H5N1 disease in ferrets. These results demonstrate that elicitation of non-neutralizing antibodies by an HA-stem-only nanoparticle vaccine can provide broad protection against severe disease and should be used to develop universal influenza vaccines.

SEQUENCE LISTING

```
Sequence total quantity: 401
SEQ ID NO: 1            moltype = DNA  length = 504
FEATURE                 Location/Qualifiers
source                  1..504
                        mol_type = unassigned DNA
                        organism = Helicobacter pylori
SEQUENCE: 1
atgctgtccg acatcatcaa gctgctgaac gaacaggtga acaaggagat gcagagctcc  60
```

-continued

```
aacctgtaca tgagtatgtc tagttggtgt tatacacact cactggacgg cgctgggctg  120
ttcctgtttg atcacgcagc cgaggaatac gaacatgcaa agaaactgat catttttcctg 180
aatgagaaca atgtgcccgt ccagctgact tcaatcagcg cccctgaaca taagttcgag  240
ggcctgaccc agatctttca gaaagcttac gaacacgagc agcatatttc cgaatctatc  300
aacaatattg tggaccacgc cattaagagc aaagatcatg ctaccttcaa ctttctgcag  360
tggtacgtgg ccgagcagca cgaggaggag gtcctgttta aggacatcct ggataaaatc  420
gaactgattg gaaacgagaa tcatggcctg tacctggcag atcagtatgt gaagggcatt  480
gccaagtcca gaaaaagtgg gtca                                          504

SEQ ID NO: 2           moltype = AA  length = 168
FEATURE                Location/Qualifiers
source                 1..168
                       mol_type = protein
                       organism = Helicobacter pylori
SEQUENCE: 2
MLSDIIKLLN EQVNKEMQSS NLYMSMSSWC YTHSLDGAGL FLFDHAAEEY EHAKKLIIFL  60
NENNVPVQLT SISAPEHKFE GLTQIFQKAY EHEQHISESI NNIVDHAIKS KDHATFNFLQ  120
WYVAEQHEEE VLFKDILDKI ELIGNENHGL YLADQYVKGI AKSRKSGS                168

SEQ ID NO: 3           moltype = DNA  length = 504
FEATURE                Location/Qualifiers
source                 1..504
                       mol_type = unassigned DNA
                       organism = Helicobacter pylori
SEQUENCE: 3
tgacccactt tttctggact tggcaatgcc cttcacatac tgatctgcca ggtacaggcc  60
atgattctcg tttccaatca gttcgatttt atccaggatg tccttaaaca ggacctcctc  120
ctcgtgctgc tcggccacgt accactgcag aaagttgaag gtagcatgat ctttgctctt  180
aatggcgtgg tccacaatat tgttgataga ttcggaaata tgctgctcgt gttcgtaagc  240
tttctgaaag atctgggtca ggccctcgaa cttatgttca ggggcgctga ttgaagtcag  300
ctggacgggc acattgttct cattcaggaa aatgatcagt ttctttgcat gttcgtattc  360
ctcggctgcg tgatcaaaca ggaacagccc agcgccgtcc agtgagtgtg tataacacca  420
actagacata ctcatgtaca ggttggagct ctgcatctcc ttgttcacct gttcgttcag  480
cagcttgatg atgtcggaca gcat                                          504

SEQ ID NO: 4           moltype = DNA  length = 492
FEATURE                Location/Qualifiers
source                 1..492
                       mol_type = unassigned DNA
                       organism = Influenza A virus
SEQUENCE: 4
atcatcaagc tgctgaacga acaggtgaac aaggagatgc agagctccaa cctgtacatg  60
agtatgtcta gttggtgtta tacacactca ctggacggcg ctgggctgtt cctgtttgat  120
cacgcagccg aggaatacga acatgcaaag aaactgatca ttttcctgaa tgagaacaat  180
gtgcccgtcc agctgacttc aatcagcgcc cctgaacata agttcgaggg cctgacccag  240
atctttcaga aagcttacga acacgagcag catatttccg aatctatcaa caatattgtg  300
gaccacgcca ttaagagcaa agatcatgct accttcaact ttctgcagtg gtacgtggcc  360
gagcagcacg aggaggaggt cctgtttaag gacatcctgg ataaaatcga actgattgga  420
aacgagaatc atggcctgta cctggcagat cagtatgtga agggcattgc caagtccaga  480
aaaagtgggt ca                                                       492

SEQ ID NO: 5           moltype = AA  length = 165
FEATURE                Location/Qualifiers
source                 1..165
                       mol_type = protein
                       organism = Influenza A virus
SEQUENCE: 5
DIIKLLNEQV NKEMQSSNLY MSMSSWCYTH SLDGAGLFLF DHAAEEYEHA KKLIIFLNEN  60
NVPVQLTSIS APEHKFEGLT QIFQKAYEHE QHISESINNI VDHAIKSKDH ATFNFLQWYV  120
AEQHEEEVLF KDILDKIELI GNENHGLYLA DQYVKGIAKS RKSGS                   165

SEQ ID NO: 6           moltype = DNA  length = 492
FEATURE                Location/Qualifiers
source                 1..492
                       mol_type = unassigned DNA
                       organism = Influenza A virus
SEQUENCE: 6
tgacccactt tttctggact tggcaatgcc cttcacatac tgatctgcca ggtacaggcc  60
atgattctcg tttccaatca gttcgatttt atccaggatg tccttaaaca ggacctcctc  120
ctcgtgctgc tcggccacgt accactgcag aaagttgaag gtagcatgat ctttgctctt  180
aatggcgtgg tccacaatat tgttgataga ttcggaaata tgctgctcgt gttcgtaagc  240
tttctgaaag atctgggtca ggccctcgaa cttatgttca ggggcgctga ttgaagtcag  300
ctggacgggc acattgttct cattcaggaa aatgatcagt ttctttgcat gttcgtattc  360
ctcggctgcg tgatcaaaca ggaacagccc agcgccgtcc agtgagtgtg tataacacca  420
actagacata ctcatgtaca ggttggagct ctgcatctcc ttgttcacct gttcgttcag  480
cagcttgatg at                                                       492

SEQ ID NO: 7           moltype = DNA  length = 1695
FEATURE                Location/Qualifiers
```

```
source                  1..1695
                        mol_type = unassigned DNA
                        organism = Influenza A virus
SEQUENCE: 7
atgaaggcca aactgctggt gctgctgtgt acctttaccg ccacctacgc cgacacaatc  60
tgtatcggct accacgccaa caatagcacc gacaccgtgg atacagtgct ggagaagaac  120
gtgaccgtga cccactctgt gaacctgctg gaggacagcc acaatggcaa gctgtgtctg  180
ctgaaaggca ttgcccctct gcagctgggc aattgttctg tggccggatg gattctgggc  240
aaccccgagt gtgagctgct gatttctaag gagagctgga gctacatcgt ggagaccccc  300
aatcctgaga atggcacctg ctaccctggc tacttcgccg attacgagga gctgcgcgag  360
cagctgtcta gcgtgtccag cttcgagaga ttcgagatct tccccaagga gtccagctgg  420
cctaatcaca cagtgacagg cgtgtctgcc agctgtagcc acaacggcaa aagcagcttc  480
taccggaacc tgctgtggct gacaggcaag aatggcctgt accccaacct gagcaagagc  540
tacgtgaaca acaaggaaaa ggaagtgctg gtgctgtggg gagtgcacca ccctcccaac  600
atcggaaatc agcgggccct gtaccacaca gagaacgcct atgtgagcgt ggtgtccagc  660
cactacagca gaagattcac ccccgagatc gccaagagac ccaaagtgag agaccaggag  720
ggccggatca attactactg gaccctgctg gagcctggcg ataccatcat cttcgaggcc  780
aacggcaatc tgatcgcccc ttggtatgcc tttgccctga gcagaggctt tggcagcggc  840
atcatcacaa gcaacgcccc catggatgag tgtgatgcca agtgccagac acctcagggc  900
gccatcaata gcagcctgcc cttccagaat gtgcaccctg tgaccatcgg cgagtgcccc  960
aagtatgtga gaagcgccaa gctgagaatg gtgaccggcc tgagaaacat ccctagcatc  1020
cagagcagag gactgtttgg agccatcgcc ggattcatcg agggaggatg gacaggcatg  1080
gtggatggct ggtacggcta ccaccaccag aatgagcagg gctctggata tgccgccgat  1140
cagaagtcta cccagaacgc catcaacggc atcaccaaca aggtgaacag cgtgatcgag  1200
aagatgaaca cccagtttac cgctgtgggc aaggagttca acaagctgga gcggaggatg  1260
gagaacctga acaagaaggt ggacgacggc tttctggaca tctggaccta caatgccgaa  1320
ctcctggtcc tcctcgagaa tgagaggacc ctggacttcc acgacagcaa cgtgaagaac  1380
ctgtatgaga aggtgaagag ccagctgaag aacaacgcca aggagatcgg caacggctgc  1440
ttcgagttct accacaagtg taacaacgag tgtatggaga gcgtgaagaa cggcacctac  1500
gactacccta agtacagcga ggagagcaag ctgaaccggg agaagatcga tggcgtgaag  1560
ctggagagca tgggcgtgta tcagatcctg gccatctaca gcacagtggc ctcttctctg  1620
gtgctgctgg tgtctctggg cgccatctcc ttttggatgt gctccaacgg cagcctgcag  1680
tgcaggatct gtatc                                                 1695

SEQ ID NO: 8            moltype = AA  length = 565
FEATURE                 Location/Qualifiers
source                  1..565
                        mol_type = protein
                        organism = Influenza A virus
SEQUENCE: 8
MKAKLLVLLC TFTATYADTI CIGYHANNST DTVDTVLEKN VTVTHSVNLL EDSHNGKLCL  60
LKGIAPLQLG NCSVAGWILG NPECELLISK ESWSYIVETP NPENGTCYPG YFADYEELRE  120
QLSSVSSFER FEIFPKESSW PNHTVTGVSA SCSHNGKSSF YRNLLWLTGK NGLYPNLSKS  180
YVNNKEKEVL VLWGVHHPPN IGNQRALYHT ENAYVSVVSS HYSRRFTPEI AKRPKVRDQE  240
GRINYYWTLL EPGDTIIFEA NGNLIAPWYA FALSRGFGSG IITSNAPMDE CDAKCQTPQG  300
AINSSLPFQN VHPVTIGECP KYVRSAKLRM VTGLRNIPSI QSRGLFGAIA GFIEGGWTGM  360
VDGWYGYHHQ NEQGSGYAAD QKSTQNAING ITNKVNSVIE KMNTQFTAVG KEFNKLERRM  420
ENLNKKVDDG FLDIWTYNAE LLVLLENERT LDFHDSNVKN LYEKVKSQLK NNAKEIGNGC  480
FEFYHKCNNE CMESVKNGTY DYPKYSEESK LNREKIDGVK LESMGVYQIL AIYSTVASSL  540
VLLVSLGAIS FWMCSNGSLQ CRICI                                      565

SEQ ID NO: 9            moltype = DNA  length = 1695
FEATURE                 Location/Qualifiers
source                  1..1695
                        mol_type = unassigned DNA
                        organism = Influenza A virus
SEQUENCE: 9
gatacagatc ctgcactgca ggctgccgtt ggagcacatc caaaaggaga tggcgcccag  60
agacaccagc agcaccagag aagaggccac tgtgctgtag atggccagga tctgatacac  120
gcccatgctc tccagcttca cgccatcgat cttctcccgg ttcagcttgc tctcctcgct  180
gtacttaggg tagtcgtagg tgccgttctt cacgctctcc atacactcgt tgttacactt  240
gtggtagaac tcgaagcagc cgttgccgat ctccttggcg ttgttcttca gctggctctt  300
caccttctca tacaggttct tcacgttgct gtcgtggaag tccagggtcc tctcattctc  360
gaggaggacc aggagttcgg cattgtaggt ccagatgtcc agaaagccgt cgtccacctt  420
cttgttcagg ttctccatcc tccgctccag cttgttgaac tccttgccca cagcggtaaa  480
ctgggtgttc atcttctcga tcacgctgtt caccttgttg gtgatgccgt tgatggcgtt  540
ctgggtagac ttctgatcgg cggcatatcc agagccctgc tcattctggt ggtggtagcc  600
gtaccagcca tccaccatgc ctgtccatcc tccctcgatg aatccggcga tggctccaaa  660
cagtcctctg ctctggatgc tagggatgtt tctcaggccg gtcaccattc tcagcttggc  720
gcttctcaca tacttggggc actcgccgat ggtcacaggg tgcacattct ggaagggcag  780
gctgctattg atggcgccct gaggtgtctg gcacttggca tcacactcat ccatgggggc  840
gttgcttgtg atgatgccgc tgccaaagcc tctgctcagg gcaaaggcat accaaggggc  900
gatcagattg ccgttggcct cgaagatgat ggtatcgcca ggctccagca gggtccagta  960
gtaattgatc cggccctcct ggtctctcac tttgggtctc ttggcgatct cgggggtgaa  1020
tcttctgctg tagtggctgg acaccacgct cacataggcg ttctctgtgt ggtacagggc  1080
ccgctgattt ccgatgttgg gagggtggtg cactccccac agcaccagca cttccttttc  1140
cttgttgttc acgtagctct tgctcaggtt ggggtacagg ccattcttgc ctgtcagcca  1200
cagcaggttc cggtagaagc tgcttttgcc gttgtggcta cagctggcag acacgcctgt  1260
cactgtgtga ttaggccagc tggactcctt ggggaagatc tcgaatctct cgaagctgga  1320
```

-continued

```
cacgctagac agctgctcgc gcagctcctc gtaatcggcg aagtagccag ggtagcaggt  1380
gccattctca ggattggggg tctccacgat gtagctccag ctctccttag aaatcagcag  1440
ctcacactcg gggttgccca gaatccatcc ggccacagaa caattgccca gctgcagagg  1500
ggcaatgcct ttcagcagac acagcttgcc attgtggctg tcctccagca ggttcacaga  1560
gtgggtcacg gtcacgttct tctccagcac tgtatccacg gtgtcggtgc tattgttggc  1620
gtggtagccg atacagattg tgtcggcgta ggtggcggta aaggtacaca gcagcaccag  1680
cagtttggcc ttcat                                                   1695

SEQ ID NO: 10          moltype = DNA  length = 1698
FEATURE                Location/Qualifiers
source                 1..1698
                       mol_type = unassigned DNA
                       organism = Influenza A virus
SEQUENCE: 10
atgaaggcta ttttggtcgt gctcctgtac acctttgcca cagccaatgc cgataccctt  60
tgtattggct accatgcaaa caactctacc gatacggtcg acacggtgct cgaaaagaat  120
gttactgtca cccactctgt gaacttgctg gaggataaac acaatggcaa gctctgcaaa  180
ctgcgagggg tggctcccct gcatctggga aaatgtaata ttgccggctg gatactgggt  240
aatccagaat gcgaatcctt gagtacggca tccagttggt cctatatcgt cgagaccccg  300
tcaagtgaca atgggacctg ctacccaggc gacttcattg attatgaaga gctgagggag  360
cagttgtcat ccgtaagcag cttcgaaagg tttgagattt tcccgaaaac tagctcctgg  420
cccaatcatg actctaacaa aggagttact gcagcctgtc ctcatgcggg cgcgaaaagc  480
ttctacaaga acctgatatg gctcgtgaag aaaggcaatt catacccaaa actgtctaag  540
agctacataa acgataaagg gaaagaggtt ctggtgcttt ggggcataca ccacccatct  600
acctcagccg accagcagtc tctgtatcag aacgccgaca catacgtgtt tgtgggcagc  660
tcccgctatt ctaagaagtt caaacccgag atcgccatca gaccaaaggt gagagaccag  720
gaaggaagga tgaattatta ctggaccttg gtcgaacctg gcgataagat aacgtttgag  780
gctacgggca acctggtcgt gccgagatat gcttttgcca tggagaggaa tgcggggagc  840
ggaattatca tcagcgacac tccagttcat gactgtaata ccacatgtca gacaccgaag  900
ggcgccatca acacgagctt gccctttcag aatatacatc caatcacaat cggaaaatgc  960
cccaagtacg tgaaaagcac taaactgaga ctcgccaccg gactcaggaa tatcccaagc  1020
atccagtcac ggggtctgtt cggcgctatc gccggattta ttgaaggcgg ctggacgggg  1080
atggtggacg gttggtacgg ctaccatcat caaaatgagc agggctccgg atacgccgct  1140
gacctgaaat ctacgcagaa tgccatagat gagatcacaa acaaggtcaa tagtgtgata  1200
gaaaaaatga atactcagtt cacagctgtt ggaaaggagt ttaaccacct cgagaagcga  1260
attgagaacc tgaacaagaa ggtggacgat ggctttttgg atatctggac gtataacgct  1320
gagctgcttg ttctgctgga gaacgaaaga accottgact accacgattc caacgtgaag  1380
aatctgtatg agaaagtgcg aagccagttg aaaaacaacg caaaagaaat aggcaacggc  1440
tgtttcgagt tctaccacaa atgcgataac acctgcatgg agagtgtgaa gaacggaacg  1500
tacgattatc caaaatactc cgaggaggcc aaactcaata gggaggagat agacggtgtt  1560
aagctggagt ccacacgcat ctatcagatt ctggcgatct actctactgt ggcttccagc  1620
ctggtgctgg tcgtttccct tggggcgatc agcttctgga tgtgcagcaa tggctccctg  1680
caatgccgca tctgcatc                                                 1698

SEQ ID NO: 11          moltype = AA  length = 566
FEATURE                Location/Qualifiers
source                 1..566
                       mol_type = protein
                       organism = Influenza A virus
SEQUENCE: 11
MKAILVVLLY TFATANADTL CIGYHANNST DTVDTVLEKN VTVTHSVNLL EDKHNGKLCK  60
LRGVAPLHLG KCNIAGWILG NPECESLSTA SSWSYIVETP SSDNGTCYPG DFIDYEELRE  120
QLSSVSSFER FEIFPKTSSW PNHDSNKGVT AACPHAGAKS FYKNLIWLVK KGNSYPKLSK  180
SYINDKGKEV LVLWGIHHPS TSADQQSLYQ NADTYVFVGS SRYSKKFKPE IAIRPKVRDQ  240
EGRMNYYWTL VEPGDKITFE ATGNLVVPRY AFAMERNAGS GIIISDTPVH DCNTTCQTPK  300
GAINTSLPFQ NIHPITIGKC PKYVKSTKLR LATGLRNIPS IQSRGLFGAI AGFIEGGWTG  360
MVDGWYGYHH QNEQGSGYAA DLKSTQNAID EITNKVNSVI EKMNTQFTAV GKEFNHLEKR  420
IENLNKKVDD GFLDIWTYNA ELLVLLENER TLDYHDSNVK NLYEKVRSQL KNNAKEIGNG  480
CFEFYHKCDN TCMESVKNGT YDYPKYSEEA KLNREEIDGV KLESTRIYQI LAIYSTVASS  540
LVLVVSLGAI SFWMCSNGSL QCRICI                                        566

SEQ ID NO: 12          moltype = DNA  length = 1698
FEATURE                Location/Qualifiers
source                 1..1698
                       mol_type = unassigned DNA
                       organism = Influenza A virus
SEQUENCE: 12
gatgcagatg cggcattgca gggagccatt gctgcacatc cagaagctga tcgccccaag  60
ggaaacgacc agcaccaggc tggaagccac agtagagtag atcgccagaa tctgatagat  120
gcgtgtggac tccagcttaa caccgtctat ctcctcccta ttgagtttgg cctcctcgga  180
gtattttgga taatcgtacg ttccgttctt cacactctcc atgcaggtgt tatcgcattt  240
gtggtagaac tcgaaacagc cgttgcctat ttcttttgcg ttgtttttca actggcttcg  300
cactttctca tacagattct tcacgttgga atcgtggtag tcaagggttc tttcgttctc  360
cagcagaaca agcagctcag cgttatacgt ccagatatcc aaaaagccat cgtccacctt  420
cttgttcagg ttctcaattc gcttctcgag gtggttaaac tcctttccaa cagctgtgaa  480
ctgagtattc atttttttcta tcacactatt gaccttgttt gtgatctcat ctatggcatt  540
ctgcgtagat ttcaggtcag cggcgtatcc ggagccctgc tcattttgat gatggtagcc  600
gtaccaaccg tccaccatcc ccgtccagcc gccttcaata aatccggcga tagcgccgaa  660
cagaccccgt gactggatgc ttgggatatt cctgagtccg gtggcgagtc tcagtttagt  720
```

-continued

```
gcttttcacg tacttggggc attttccgat tgtgattgga tgtatattct gaaagggcaa  780
gctcgtgttg atggcgccct tcggtgtctg acatgtggta ttacagtcat gaactggagt  840
gtcgctgatg ataattccgc tccccgcatt cctctccatg gcaaaagcat atctcggcac  900
gaccaggttg cccgtagcct caaacgttat cttatcgcca ggttcgacca aggtccagta  960
ataattcatc cttccttcct ggtctctcac ctttggtctg atggcgatct cgggtttgaa  1020
cttcttagaa tagcgggagc tgcccacaaa cacgtatgtg tcggcgttct gatacagaga  1080
ctgctggtcg gctgaggtag atgggtggtg tatgccccaa agcaccagaa cctctttccc  1140
tttatcgttt atgtagctct tagacagttt tgggtatgaa ttgcctttct tcacgagcca  1200
tatcaggttc ttgtagaagc ttttcgcgcc cgcatgagga caggctgcag taactccttt  1260
gttagagtca tgattgggcc aggagctagt tttcgggaaa atctcaaacc tttcgaagct  1320
gcttacggat gacaactgct ccctcagctc ttcataatca atgaagtcgc ctgggtagca  1380
ggtcccattg tcacttgacg gggtctcgac gatataggac caactggatg ccgtactcaa  1440
ggattcgcat tctggattac ccagtatcca gccggcaata ttacattttc ccagatgcag  1500
gggagccacc cctcgcagtt tgcagagctt gccattgtgt ttatcctcca gcaagttcac  1560
agagtgggtg acagtaacat tcttttcgag caccgtgtcg accgtatcgg tagagttgtt  1620
tgcatggtag ccaatacaaa gggtatcggc attggctgtg gcaaaggtgt acaggagcac  1680
gaccaaaata gccttcat                                                1698

SEQ ID NO: 13          moltype = DNA  length = 1683
FEATURE                Location/Qualifiers
source                 1..1683
                       mol_type = unassigned DNA
                       organism = Influenza A virus
SEQUENCE: 13
atggccatca tctacctgat cctgctgttt acagctgtga gaggcgacca gatctgtatc  60
ggctaccacg ccaacaatag caccgagaag gtggacacca tcctggagag aaacgtgaca  120
gtgacccacg ccaaggacat cctggaaaag acccacaacg gcaagctgtg taagctgaac  180
ggcatccctc ctctggaact gggcgattgt tctatcgccg gatggctgct gggaaacccc  240
gagtgtgata ggctgctgtc tgtgcctgag tggagctaca tcatggagaa ggagaaccct  300
agggacggcc tgtgttaccc tggcagcttc aacgattacg aggagctgaa gcacctgctg  360
tctagcgtga agcacttcga gaaggtgaag atcctgccca aggacagatg gacccagcac  420
acaacaacag gaggaagcag agcctgcgcc gtgtctggca accccagctt cttccggaat  480
atggtgtggc tgaccaagaa gggcagcaat taccctgtgg cccagggcag ctacaataat  540
accagcggcg agcagatgct gatcatctgg ggagtgcacc accctaatga cgagaccgag  600
cagagaaccc tgtaccagaa tgtgggcacc tacgtgtctg tgggcaccag caccctgaat  660
aagagaagca cccccgagat tgccacaaga cccaaggtga acggccaggg aggaagaatg  720
gagttcagct ggaccctgct ggatatgtgg gacaccatca actttgagag caccggcaat  780
ctgatcgccc ctgagtacgg cttcaagatc agcaagagag gcagcagcgg catcatgaaa  840
accgagggca ccctggagaa ttgtgagacc aagtgccaga cacctctggg cgccatcaat  900
accaccctgc ccttccacaa tgtgcaccct ctgaccatcg gcgagtgccc taagtatgtg  960
aagagcgaga agctggtgct ggccacagga ctgagaaacg tgccccagat cgagagcaga  1020
ggcctgtttg gagccatcgc cggattcatc gagggaggat ggcagggaat ggtcgatggc  1080
tggtacggct accaccacag caatgatcag ggctctggct atgccgccga taaggagtct  1140
acccagaagg cctttgacgg catcaccaac aaggtgaaca gcgtgatcga gaagatgaac  1200
acccagtttg aggctgtggg caaggagttt agcaacctgg agcggagact ggagaacctg  1260
aacaagaaga tggaggacgg cttcctggat gtgtggacct acaatgccga actgctggtg  1320
ctgatggaga atgagcggac cctggacttc cacgacagca acgtgaagaa cctgtacgac  1380
aaagtgagga tgcagctgag ggacaacgtg aaggaactgg gcaatggctg cttcgagttc  1440
taccacaagt gtgacgacga gtgtatgaac tccgtgaaga acggcaccta cgactaccct  1500
aagtacgagg aggagagcaa gctgaaccgg aacgagatca agggcgtgaa gctgtctagc  1560
atgggcgtgt atcagatcct ggccatctat gccacagtgg ccggatctct gagcctggca  1620
attatgatgg ctggaatcag cttctggatg tgctccaatg gcagcctgca gtgccggatc  1680
tgt                                                                1683

SEQ ID NO: 14          moltype = AA  length = 564
FEATURE                Location/Qualifiers
source                 1..564
                       mol_type = protein
                       organism = Influenza A virus
SEQUENCE: 14
MAIIYLILLF TAVRGDQICI GYHANNSTEK VDTILERNVT VTHAKDILEK THNGKLCKLN  60
GIPPLELGDC SIAGWLLGNP ECDRLLSVPE WSYIMEKENP RDGLCYPGSF NDYEELKHLL  120
SSVKHFEKVK ILPKDRWTQH TTTGGSRACA VSGNPSFFRN MVWLTKKGSN YPVAKGSYNN  180
TSGEQMLIIW GVHHPNDETE QRTLYQNVGT YVSVGTSTLN KRSTPDYHIA TRPKVNGQGG  240
RMEFSWTLLD MWDTINFEST GNLIAPEYGF KISKRGSSGI MKTEGTLENC ETKCQTPLGA  300
INTTLPFHNV HPLTIGECPK YVKSEKLVLA TGLRNVPQIE SRGLFGAIAG FIEGGWQGMV  360
DGWYGYHHSN DQGSGYAADK ESTQKAFDGI TNKVNSVIEK MNTQFEAVGK EFSNLERRLE  420
NLNKKMEDGF LDVWTYNAEL LVLMENERTL DFHDSNVKNL YDKVRMQLRD NVKELGNGCF  480
EFYHKCDDEC MNSVKNGTYD YPKYEEESKL NRNEIKGVKL SSMGVYQILA IYATVAGSLS  540
LAIMMAGISF WMCSNGSLQC RICI                                         564

SEQ ID NO: 15          moltype = DNA  length = 1683
FEATURE                Location/Qualifiers
source                 1..1683
                       mol_type = unassigned DNA
                       organism = Influenza A virus
SEQUENCE: 15
acagatccgg cactgcaggc tgccattgga gcacatccag aagctgattc cagccatcat  60
aattgccagg ctcagagatc cggccactgt ggcatagatg gccaggatct gatacacgcc  120
```

```
catgctagac agcttcacgc ccttgatctc gttccggttc agcttgctct cctcctcgta  180
cttagggtag tcgtaggtgc cgttcttcac ggagttcata cactcgtcgt cacacttgtg  240
gtagaactcg aagcagccat tgcccagttc cttcacgttg tccctcagct gcatcctcac  300
tttgtcgtac aggttcttca cgttgctgtc gtggaagtcc agggtccgct cattctccat  360
cagcaccagc agttcggcat tgtaggtcca cacatccagg aagccgtcct ccatcttctt  420
gttcaggttc tccagtctcc gctccaggtt gctaaactcc ttgcccacag cctcaaactg  480
ggtgttcatc ttctcgatca cgctgttcac cttgttggtg atgccgtcaa aggccttctg  540
ggtagactcc ttatcggcgg catagccaga gccctgatca ttgctgtggt ggtagccgta  600
ccagccatcg accattccct gccatcctcc ctcgatgaat ccggcgatgg ctccaaacag  660
gcctctgctc tcgatctggg gcacgtttct cagtcctgtg gccagcacca gcttctcgct  720
cttcacatac ttagggcact cgccgatggt cagagggtgc acattgtgga agggcagggt  780
ggtattgatg gcgcccagag gtgtctggca cttggtctca caattctcca gggtgccctc  840
ggttttcatg atgccgctgc tgcctctctt gctgatcttg aagccgtact caggggcgat  900
cagattgccg gtgctctcaa agttgatggt gtcccacata tccagcaggg tccagctgaa  960
ctccattctt cctccctggc cgttcacctt gggtcttgtg gcaatctcgg gggtgcttct  1020
cttattcagg gtgctggtgc ccacagacac gtaggtgccc acattctggt acagggttct  1080
ctgctcggtc tcgtcattag ggtggtgcac tccccagatg atcagcatct gctcgccgct  1140
ggtattattg tagctgccct gggccacagg gtaattgctg cccttcttgg tcagccacac  1200
catattccgg aagaagctgg ggttgccaga cacggcgcag gctctgcttc ctcctgttgt  1260
tgtgtgctgg gtccatctgt ccttgggcag gatcttcacc ttctcgaagt gcttcacgct  1320
agacagcagg tgcttcagct cctcgtaatc gttgaagctg ccagggtaac acaggccgtc  1380
cctagggttc tccttctcca tgatgtagct ccactcaggc acagacagca gcctatcaca  1440
ctcggggttt cccagcagcc atccggcgat agaacaatcg cccagttcca gaggagggat  1500
gccgttcagc ttacacagct tgccgttgtg ggtcttttcc aggatgtcct tggcgtgggt  1560
cactgtcacg tttctctcca ggatggtgtc caccttctcg gtgctattgt tggcgtggta  1620
gccgatacag atctggtcgc ctctcacagc tgtaaacagc aggatcaggt agatgatggc  1680
cat                                                                1683

SEQ ID NO: 16          moltype = DNA  length = 1704
FEATURE                Location/Qualifiers
source                 1..1704
                       mol_type = unassigned DNA
                       organism = Influenza A virus
SEQUENCE: 16
atggaaaaga tcgtgctgct gctggccatt gtgagcctgg tgaagagcga ccagatctgc  60
attggctacc acgccaacaa tagcacagag caggtggaca ccatcatgga aaaaaacgtg  120
accgtgaccc acgctcagga catcctggaa aagacccaca acggcaagct gtgtgatctg  180
gacggcgtga agcctctgat cctgagagat tgtagcgtgg ctggatggct gctgggcaac  240
cctatgtgcg acgagttcat caacgtgccc gagtggagct atatcgtgga gaaggccaac  300
cccaccaacg atctgtgtta ccccggcagc ttcaacgatt acgaggaact gaagcacctg  360
ctgtcccgga tcaaccactt cgagaagatc cagatcatcc ccaagtcctc ttggagcgat  420
cacgaagcct ctagcggagt gtctagcgcc tgtccttacc tgggcagccc cagcttcttc  480
agaaacgtgg tgtggctgat caagaagaac agcacctacc ccaccatcaa gaagagctac  540
aacaacacca accaggaaga tctgctggtc ctgtggggaa tccaccaccc taatgatgcc  600
gccgagcaga ccagactgta ccagaacccc accacctata tcagcatcgg caccagcacc  660
ctgaatcaga gactggtgcc caagatcgcc accagatcca aggtgaacgg ccagagcggc  720
aggatggaat tcttctggac catcctgaag cccaacgacg ccatcaactt cgagagcaac  780
ggcaacttta tcgcccctga gtacgcctac aagatcgtga agaagggcga cagcgccatc  840
atgaagagcg agctggaata cggcaactgc aacaccaagt gccagacacc tatgggcgcc  900
atcaacagca gcatgccctt ccacaacatc caccctctga ccatcggcga gtgccctaag  960
tacgtgaaga gcaacagact ggtgctggcc acaggcctga gaaatagccc ccagcgggag  1020
agcagaagaa agaagagggg cctgtttgga gccatcgccg gctttattga aggcggctgg  1080
cagggaatgg tggatggctg gtacggctac caccacagca atgagcaggg ctctggatat  1140
gccgccgaca aagagtctac ccagaaggcc atcgacggcg tcaccaacaa ggtgaacagc  1200
atcatcgaca agatgaacac ccagttcgag gctgtgggca gagagttcaa caacctggaa  1260
cggcggatcg agaacctgaa caagaaaatg gaagatggct tcctggatgt gtggacctac  1320
aatgccgaac tgctggtgct gatggaaaac gagcggaccc tggacttcca cgacagcaac  1380
gtgaagaacc tgtacgacaa agtgcggctg cagctgagag acaacgccaa agagctgggc  1440
aacggctgct tcgagttcta ccacaagtgc gacaacgagt gcatggaaag catccggaac  1500
ggcacctaca actaccctca gtacagcgag gaagccaggc tgaagaggga agagatcagc  1560
ggcgtgaaac tggaatccat cggcacctac cagatcctga gcatctacag cacagtggcc  1620
tcttctctgg ccctggccat tatgatggcc ggactgagcc tgtggatgtg cagcaatggc  1680
agcctgcagt gcaggatctg catc                                         1704

SEQ ID NO: 17          moltype = AA  length = 568
FEATURE                Location/Qualifiers
source                 1..568
                       mol_type = protein
                       organism = Influenza A virus
SEQUENCE: 17
MEKIVLLLAI VSLVKSDQIC IGYHANNSTE QVDTIMEKNV TVTHAQDILE KTHNGKLCDL  60
DGVKPLILRD CSVAGWLLGN PMCDEFINVP EWSYIVEKAN PTNDLCYPGS FNDYEELKHL  120
LSRINHFEKI QIIPKSSWSD HEASSGVSSA CPYLGSPSFF RNVVWLIKKN STYPTIKKSY  180
NNTNQEDLLV LWGIHHPNDA AEQTRLYQNP TTYISIGTST LNQRLVPKIA TRSKVNGQSG  240
RMEFFWTILK PNDAINFESN GNFIAPEYAY KIVKKGDSAI MKSELEYGNC NTKCQTPMGA  300
INSSMPFHNI HPLTIGECPK YVKSNRLVLA TGLRNSPQRE SRRKKRGLFG AIAGFIEGGW  360
QGMVDGWYGY HHSNEQGSGY AADKESTQKA IDGVTNKVNS IIDKMNTQFE AVGREFNNLE  420
RRIENLNKKM EDGFLDVWTY NAELLVLMEN ERTLDFHDSN VKNLYDKVRL QLRDNAKELG  480
NGCFEFYHKC DNECMESIRN GTYNYPQYSE EARLKREEIS GVKLESIGTY QILSIYSTVA  540
```

-continued

```
SSLALAIMMA GLSLWMCSNG SLQCRICI                                   568

SEQ ID NO: 18          moltype = DNA  length = 1704
FEATURE                Location/Qualifiers
source                 1..1704
                       mol_type = unassigned DNA
                       organism = Influenza A virus
SEQUENCE: 18
gatgcagatc ctgcactgca ggctgccatt gctgcacatc cacaggctca gtccggccat  60
cataatggcc agggccagag aagaggccac tgtgctgtag atgctcagga tctggtaggt  120
gccgatggat tccagtttca cgccgctgat ctcttccctc ttcagcctgg cttcctcgct  180
gtactgaggg tagttgtagg tgccgttccg gatgctttcc atgcactcgt tgtcgcactt  240
gtggtagaac tcgaagcagc cgttgcccag ctctttggcg ttgtctctca gctgcagccg  300
cactttgtcg tacaggttct tcacgttgct gtcgtggaag tccagggtcc gctcgttttc  360
catcagcacc agcagttcgg cattgtaggt ccacacatcc aggaagccat cttccatttt  420
cttgttcagg ttctcgatcc gccgttccag gttgttgaac tctctgccca cagcctcgaa  480
ctgggtgttc atcttgtcga tgatgctgtt caccttgttg gtgacgccgt cgatggcctt  540
ctgggtagac tctttgtcgg cggcatatcc agagccctgc tcattgctgt ggtggtagcc  600
gtaccagcca tccaccattc cctgccagcc gccttcaata aagccggcga tggctccaaa  660
caggcccctc ttctttcttc tgctctcccg ctgggggcta tttctcaggc ctgtggccag  720
caccagtctg ttgctcttca cgtacttagg gcactcgccg atggtcagag ggtggatgtt  780
gtggaagggc atgctgctgt tgatggcgcc cataggtgtc tggcacttgg tgttgcagtt  840
gccgtattcc agctcgctct tcatgatggc gctgtcgccc ttcttcacga tcttgtaggc  900
gtactcaggg gcgataaagt tgccgttgct ctcgaagttg atggcgtcgt tgggcttcag  960
gatggtccag aagaattcca tcctgccgct ctggccgttc accttggatc tggtggcgat  1020
cttgggcacc agtctctgat tcagggtgct ggtgccgatg ctgatatagg tggtggggtt  1080
ctggtacagt ctggtctgct cggcggcatc attagggtgg tggattcccc acaggaccag  1140
cagatcttcc tggttggtgt tgttgtagct cttcttgatg gtggggtagg tgctgttctt  1200
cttgatcagc cacaccacgt ttctgaagaa gctggggctg cccaggtaag gacaggcgct  1260
agacactccg ctagaggctt cgtgatcgct ccaagaggac ttggggatga tctggatctt  1320
ctcgaagtgg ttgatccggg acagcaggtg cttcagttcc tcgtaatcgt tgaagctgcc  1380
ggggtaacac agatcgttgg tggggttggc cttctccacg atatagctcc actcgggcac  1440
gttgatgaac tcgtcgcaca tagggttgcc cagcagccat ccagccacgc tacaatctct  1500
caggatcaga ggcttcacgc cgtccagatc acacagcttg ccgttgtggg tcttttccag  1560
gatgtcctga gcgtgggtca cggtcacgtt tttttccatg atggtgtcca cctgctctgt  1620
gctattgttg gcgtggtagc caatgcagat ctggtcgctc ttcaccaggc tcacaatggc  1680
cagcagcagc acgatctttt ccat                                       1704

SEQ ID NO: 19          moltype = DNA  length = 147
FEATURE                Location/Qualifiers
source                 1..147
                       mol_type = unassigned DNA
                       organism = Influenza A virus
SEQUENCE: 19
atgaaggcca aactgctggt gctgctgtgt acctttaccg ccacctacgc cgacacaatc  60
tgtatcggct accacgccaa caatagcacc gacaccgtgg atacagtgct ggagaagaac  120
gtgaccgtga cccactctgt gaacctg                                    147

SEQ ID NO: 20          moltype = AA  length = 49
FEATURE                Location/Qualifiers
source                 1..49
                       mol_type = protein
                       organism = Influenza A virus
SEQUENCE: 20
MKAKLLVLLC TFTATYADTI CIGYHANNST DTVDTVLEKN VTVTHSVNL            49

SEQ ID NO: 21          moltype = DNA  length = 147
FEATURE                Location/Qualifiers
source                 1..147
                       mol_type = unassigned DNA
                       organism = Influenza A virus
SEQUENCE: 21
caggttcaca gagtgggtca cggtcacgtt cttctccagc actgtatcca cggtgtcggt  60
gctattgttg gcgtggtagc cgatacagat tgtgtcggcg taggtggcgg taaaggtaca  120
cagcagcacc agcagtttgg ccttcat                                    147

SEQ ID NO: 22          moltype = DNA  length = 678
FEATURE                Location/Qualifiers
source                 1..678
                       mol_type = unassigned DNA
                       organism = Influenza A virus
SEQUENCE: 22
gatgccaagt gccagacacc tcagggcgcc atcaatagca gcctgccctt ccagaatgtg  60
caccctgtga ccatcggcga gtgccccaag tatgtgagaa gcgccaagct gagaatggtg  120
accggcctga gaaacatccc tagcatccag agcagaggac tgtttggagc catcgccgga  180
ttcatcgagg gaggatggac aggcatggtg gatggctggt acggctacca ccaccagaat  240
gagcagggct ctggatatgc cgccgatcag aagtctaccc agaacgccat caacggcatc  300
accaacaagg tgaacagcgt gatcgagaag atgaacaccc agtttaccgc tgtgggcaag  360
gagttcaaca agctggagcg gaggatggag aacctgaaca agaaggtgga cgacggcttt  420
```

```
ctggacatct ggacctacaa tgccgaactc ctggtcctcc tcgagaatga gaggaccctg  480
gacttccacg acagcaacgt gaagaacctg tatgagaagg tgaagagcca gctgaagaac  540
aacgccaagg agatcggcaa cggctgcttc gagttctacc acaagtgtaa caacgagtgt  600
atggagagcg tgaagaacgg cacctacgac taccctaagt acagcgagga gagcaagctg  660
aaccgggaga agatcgat                                                678

SEQ ID NO: 23          moltype = AA  length = 226
FEATURE                Location/Qualifiers
source                 1..226
                       mol_type = protein
                       organism = Influenza A virus
SEQUENCE: 23
DAKCQTPQGA INSSLPFQNV HPVTIGECPK YVRSAKLRMV TGLRNIPSIQ SRGLFGAIAG  60
FIEGGWTGMV DGWYGYHHQN EQGSGYAADQ KSTQNAINGI TNKVNSVIEK MNTQFTAVGK  120
EFNKLERRME NLNKKVDDGF LDIWTYNAEL LVLLENERTL DFHDSNVKNL YEKVKSQLKN  180
NAKEIGNGCF EFYHKCNNEC MESVKNGTYD YPKYSEESKL NREKID                 226

SEQ ID NO: 24          moltype = DNA  length = 678
FEATURE                Location/Qualifiers
source                 1..678
                       mol_type = unassigned DNA
                       organism = Influenza A virus
SEQUENCE: 24
atcgatcttc tcccggttca gcttgctctc ctcgctgtac ttagggtagt cgtaggtgcc  60
gttcttcacg ctctccatac actcgttgtt acacttgtgg tagaactcga agcagccgtt  120
gccgatctcc ttggcgttgt tcttcagctg gctcttcacc ttctcataca ggttcttcac  180
gttgctgtcg tggaagtcca gggtcctctc attctcgagg aggaccagga gttcggcatt  240
gtaggtccag atgtccagaa agccgtcgtc caccttcttg ttcaggttct ccatcctccg  300
ctccagcttg ttgaactcct tgcccacagc ggtaaactgg gtgttcatct tctcgatcac  360
gctgttcacc ttgttggtga tgccgttgat ggcgttctgg gtagacttct gatcggcggc  420
atatccagag ccctgctcat tctggtggtg gtagccgtac cagccatcca ccatgcctgt  480
ccatcctccc tcgatgaatc cggcgatggc tccaaacagt cctctgctct ggatgctagg  540
gatgtttctc aggccggtca ccattctcag cttggcgctt ctcacatact tggggcactc  600
gccgatggtc acagggtgca cattctggaa gggcaggctg ctattgatgg cgccctgagg  660
tgtctggcac ttggcatc                                                678

SEQ ID NO: 25          moltype = DNA  length = 576
FEATURE                Location/Qualifiers
source                 1..576
                       mol_type = unassigned DNA
                       organism = Influenza A virus
SEQUENCE: 25
gatgccaagt gccagacacc tcagggcgcc atcaatagca gcctgccctt ccagaatgtg  60
caccctgtga ccatcggcga gtgccccaag tatgtgagaa gcgccaagct gagaatggtg  120
accggcctga gaaacatccc tagcatccag agcagaggac tgtttggagc catcgccgga  180
ttcatcgagg gaggatggac aggcatggtg gatggctggt acggctacca ccaccagaat  240
gagcagggct ctggatatgc cgccgatcag aagtctaccc agaacgccat caacggcatc  300
accaacaagg tgaacagcgt gatcgagaag atgtacaatg ccgaactcct ggtcctcctc  360
gagaatgaga ggaccctgga cttccacgac agcaacgtga agaacctgta tgagaaggtg  420
aagagccagc tgaagaacaa cgccaaggag atcggcaacg gctgcttcga gttctaccac  480
aagtgtaaca acgagtgtat ggagagcgtg aagaacggca cctacgacta ccctaagtac  540
agcgaggaga gcaagctgaa ccgggagaag atcgat                            576

SEQ ID NO: 26          moltype = AA  length = 193
FEATURE                Location/Qualifiers
source                 1..193
                       mol_type = protein
                       organism = Influenza A virus
SEQUENCE: 26
DAKCQTPQGA INSSLPFQNV HPVTIGECPK YVRSAKLRMV TGLRNIPSIQ SRGLFGAIAG  60
FIEGGWTGMV DGWYGYHHQN EQGSGYAADQ KSTQNAINGI TNKVNSVIEK MTYNAELLVL  120
LENERTLDFH DSNVKNLYEK VKSQLKNNAK EIGNGCFEFY HKCNNECMES VKNGTYDYPK  180
YSEESKLNRE KID                                                     193

SEQ ID NO: 27          moltype = DNA  length = 576
FEATURE                Location/Qualifiers
source                 1..576
                       mol_type = unassigned DNA
                       organism = Influenza A virus
SEQUENCE: 27
atcgatcttc tcccggttca gcttgctctc ctcgctgtac ttagggtagt cgtaggtgcc  60
gttcttcacg ctctccatac actcgttgtt acacttgtgg tagaactcga agcagccgtt  120
gccgatctcc ttggcgttgt tcttcagctg gctcttcacc ttctcataca ggttcttcac  180
gttgctgtcg tggaagtcca gggtcctctc attctcgagg aggaccagga gttcggcatt  240
gtacatcttc tcgatcacgc tgttcacctt gttggtgatg ccgttgatgg cgttctgggt  300
agacttctga tcggcggcat atccagagcc ctgctcattc tggtggtggt agccgtacca  360
gccatccacc atgcctgtcc atcctccctc gatgaatccg gcgatggctc caaacagtcc  420
tctgctctgg atgctaggga tgtttctcag gccggtcacc attctcagct tggcgcttct  480
cacatacttg gggcactcgc cgatggtcac agggtgcaca ttctggaagg gcaggctgct  540
```

```
attgatggcg ccctgaggtg tctggcactt ggcatc                            576

SEQ ID NO: 28          moltype = DNA  length = 570
FEATURE                Location/Qualifiers
source                 1..570
                       mol_type = unassigned DNA
                       organism = Influenza A virus
SEQUENCE: 28
ctgagaatgg tgaccggcct gagaaacatc cctagcatcc agagcagagg actgtttgga  60
gccatcgccg gattcatcga gggaggatgg acaggcatgg tggatggctg gtacggctac  120
caccaccaga atgagcaggg ctctggatat gccgccgatc agaagtctac ccagaacgcc  180
atcaacggca tcaccaacaa ggtgaacagc gtgatcgaga agatgaacac ccagtttacc  240
gctgtgggca aggagttcaa caagctggag cggaggatgg agaacctgaa caagaaggtg  300
gacgacggct ttctggacat ctggacctac aatgccgaac tcctggtcct cctcgagaat  360
gagaggaccc tggacttcca cgacagcaac gtgaagaacc tgtatgagaa ggtgaagagc  420
cagctgaaga acaacgccaa ggagatcggc aacggctgct tcgagttcta ccacaagtgt  480
aacaacgagt gtatggagag cgtgaagaac ggcacctacg actaccctaa gtacagcgag  540
gagagcaagc tgaaccggga gaagatcgat                                   570

SEQ ID NO: 29          moltype = AA  length = 194
FEATURE                Location/Qualifiers
source                 1..194
                       mol_type = protein
                       organism = Influenza A virus
SEQUENCE: 29
LRMVTGLRNI PQRETSIQSR GLFGAIAGFI EGGWTGMVDG WYGYHHQNEQ GSGYAADQKS  60
TQNAINGITN KVNSVIEKMN TQFTAVGKEF NKLERRMENL NKKVDDGFLD IWTYNAELLV  120
LLENERTLDF HDSNVKNLYE KVKSQLKNNA KEIGNGCFEF YHKCNNECME SVKNGTYDYP  180
KYSEESKLNR EKID                                                    194

SEQ ID NO: 30          moltype = DNA  length = 570
FEATURE                Location/Qualifiers
source                 1..570
                       mol_type = unassigned DNA
                       organism = Influenza A virus
SEQUENCE: 30
atcgatcttc tcccggttca gcttgctctc ctcgctgtac ttagggtagt cgtaggtgcc  60
gttcttcacg ctctccatac actcgttgtt acacttgtgg tagaactcga agcagccgtt  120
gccgatctcc ttggcgttgt tcttcagctg gctcttcacc ttctcataca ggttcttcac  180
gttgctgtcg tggaagtcca gggtcctctc attctcgagg aggaccagga gttcggcatt  240
gtaggtccag atgtccagaa agccgtcgtc caccttcttg ttcaggttct ccatcctccg  300
ctccagcttg ttgaactcct tgcccacagc ggtaaactgg gtgttcatct tctcgatcac  360
gctgttcacc ttgttggtga tgccgttgat ggcgttctgg gtagacttct gatcggcggc  420
atatccagag ccctgctcat tctggtggtg gtagccgtac cagccatcca ccatgcctgt  480
ccatcctccc tcgatgaatc cggcgatggc tccaaacagt cctctgctct ggatgctagg  540
gatgtttctc aggccggtca ccattctcag                                   570

SEQ ID NO: 31          moltype = DNA  length = 468
FEATURE                Location/Qualifiers
source                 1..468
                       mol_type = unassigned DNA
                       organism = Influenza A virus
SEQUENCE: 31
ctgagaatgg tgaccggcct gagaaacatc cctagcatcc agagcagagg actgtttgga  60
gccatcgccg gattcatcga gggaggatgg acaggcatgg tggatggctg gtacggctac  120
caccaccaga atgagcaggg ctctggatat gccgccgatc agaagtctac ccagaacgcc  180
atcaacggca tcaccaacaa ggtgaacagc gtgatcgaga agatgtacaa tgccgaactc  240
ctggtcctcc tcgagaatga gaggaccctg gacttccacg acagcaacgt gaagaacctg  300
tatgagaagg tgaagagcca gctgaagaac aacgccaagg agatcggcaa cggctgcttc  360
gagttctacc acaagtgtaa caacgagtgt atggagagcg tgaagaacgg cacctacgac  420
taccctaagt acagcgagga gagcaagctg aaccgggaga agatcgat               468

SEQ ID NO: 32          moltype = AA  length = 157
FEATURE                Location/Qualifiers
source                 1..157
                       mol_type = protein
                       organism = Influenza A virus
SEQUENCE: 32
LRMVTGLRNI PQRETRGLFG AIAGFIEGGW TGMVDGWYGY HHQNEQGSGY AADQKSTQNA  60
INGITNKVNS VIEKMTYNAE LLVLLENERT LDFHDSNVKN LYEKVKSQLK NNAKEIGNGC  120
FEFYHKCNNE CMESVKNGTY DYPKYSEESK LNREKID                           157

SEQ ID NO: 33          moltype = DNA  length = 468
FEATURE                Location/Qualifiers
source                 1..468
                       mol_type = unassigned DNA
                       organism = Influenza A virus
SEQUENCE: 33
atcgatcttc tcccggttca gcttgctctc ctcgctgtac ttagggtagt cgtaggtgcc  60
```

-continued

```
gttcttcacg ctctccatac actcgttgtt acacttgtgg tagaactcga agcagccgtt  120
gccgatctcc ttggcgttgt tcttcagctg gctcttcacc ttctcataca ggttcttcac  180
gttgctgtcg tggaagtcca gggtcctctc attctcgagg aggaccagga gttcggcatt  240
gtacatcttc tcgatcacgc tgttcacctt gttggtgatg ccgttgatgg cgttctgggt  300
agacttctga tcggcggcat atccagagcc ctgctcattc tggtggtggt agccgtacca  360
gccatccacc atgcctgtcc atcctccctc gatgaatccg gcgatggctc caaacagtcc  420
tctgctctgg atgctaggga tgtttctcag gccggtcacc attctcag              468

SEQ ID NO: 34          moltype = DNA  length = 147
FEATURE                Location/Qualifiers
source                 1..147
                       mol_type = unassigned DNA
                       organism = Influenza A virus
SEQUENCE: 34
atgaaggcta ttttggtcgt gctcctgtac acctttgcca cagccaatgc cgataccctt  60
tgtattggct accatgcaaa caactctacc gatacggtcg acacggtgct cgaaaagaat  120
gttactgtca cccactctgt gaacttg                                     147

SEQ ID NO: 35          moltype = AA  length = 49
FEATURE                Location/Qualifiers
source                 1..49
                       mol_type = protein
                       organism = Influenza A virus
SEQUENCE: 35
MKAILVVLLY TFATANADTL CIGYHANNST DTVDTVLEKN VTVTHSVNL              49

SEQ ID NO: 36          moltype = DNA  length = 147
FEATURE                Location/Qualifiers
source                 1..147
                       mol_type = unassigned DNA
                       organism = Influenza A virus
SEQUENCE: 36
caagttcaca gagtgggtga cagtaacatt cttttcgagc accgtgtcga ccgtatcggt  60
agagttgttt gcatggtagc caatacaaag ggtatcggca ttggctgtgg caaaggtgta  120
caggagcacg accaaaatag ccttcat                                     147

SEQ ID NO: 37          moltype = DNA  length = 672
FEATURE                Location/Qualifiers
source                 1..672
                       mol_type = unassigned DNA
                       organism = Influenza A virus
SEQUENCE: 37
acatgtcaga caccgaaggg cgccatcaac acgagcttgc cctttcagaa tatacatcca  60
atcacaatcg gaaaatgccc caagtacgtg aaaagcacta aactgagact cgccaccgga  120
ctcaggaata tcccaagcat ccagtcacgg ggtctgttcg gcgctatcgc cggatttatt  180
gaaggcggct ggacggggat ggtggacggt tggtacggct accatcatca aaatgagcag  240
ggctccggat acgccgctga cctgaaatct acgcagaatg ccatagatga gatcacaaac  300
aaggtcaata gtgtgataga aaaaatgaat actcagttca cagctgttgg aaaggagttt  360
aaccacctcg agaagcgaat tgagaacctg aacaagaagg tggacgatgg ctttttggat  420
atctggacgt ataacgctga gctgcttgtt ctgctggaga acgaaagaac ccttgactac  480
cacgattcca acgtgaagaa tctgtatgag aaagtgcgaa gccagttgaa aaacaacgca  540
aaagaaatag gcaacggctg tttcgagttc taccacaaat gcgataacac ctgcatggag  600
agtgtgaaga acggaacgta cgattatcca aaatactccg aggaggccaa actcaatagg  660
gaggagatag ac                                                     672

SEQ ID NO: 38          moltype = AA  length = 224
FEATURE                Location/Qualifiers
source                 1..224
                       mol_type = protein
                       organism = Influenza A virus
SEQUENCE: 38
TCQTPKGAIN TSLPFQNIHP ITIGKCPKYV KSTKLRLATG LRNIPSIQSR GLFGAIAGFI  60
EGGWTGMVDG WYGYHHQNEQ GSGYAADLKS TQNAIDEITN KVNSVIEKMN TQFTAVGKEF  120
NHLEKRIENL NKKVDDGFLD IWTYNAELLV LLENERTLDY HDSNVKNLYE KVRSQLKNNA  180
KEIGNGCFEF YHKCDNTCME SVKNGTYDYP KYSEEAKLNR EEID                  224

SEQ ID NO: 39          moltype = DNA  length = 672
FEATURE                Location/Qualifiers
source                 1..672
                       mol_type = unassigned DNA
                       organism = Influenza A virus
SEQUENCE: 39
gtctatctcc tccctattga gtttggcctc ctcggagtat tttggataat cgtacgttcc  60
gttcttcaca ctctccatgc aggtgttatc gcatttgtgg tagaactcga aacagccgtt  120
gcctatttct tttgcgttgt ttttcaactg gcttcgcact ttctcataca gattcttcac  180
gttggaatcg tggtagtcaa gggttctttc gttctccagc agaacaagca gctcagcgtt  240
atacgtccag atatccaaaa agccatcgtc caccttcttg ttcaggttct caattcgctt  300
ctcgaggtgg ttaaactcct ttccaacagc tgtgaactga gtattcattt tttctatcac  360
actattgacc ttgtttgtga tctcatctat ggcattctgc gtagatttca ggtcagcggc  420
```

-continued

```
gtatccggag ccctgctcat tttgatgatg gtagccgtac caaccgtcca ccatccccgt  480
ccagccgcct tcaataaatc cggcgatagc gccgaacaga ccccgtgact ggatgcttgg  540
gatattcctg agtccggtgg cgagtctcag tttagtgctt ttcacgtact tggggcattt  600
tccgattgtg attggatgta tattctgaaa gggcaagctc gtgttgatgg cgcccttcgg  660
tgtctgacat gt                                                      672

SEQ ID NO: 40          moltype = DNA  length = 573
FEATURE                Location/Qualifiers
source                 1..573
                       mol_type = unassigned DNA
                       organism = Influenza A virus
SEQUENCE: 40
acatgtcaga caccgaaggg cgccatcaac acgagcttgc cctttcagaa tatacatcca  60
atcacaatcg gaaaatgccc caagtacgtg aaaagcacta aactgagact cgccaccgga  120
ctcaggaata tcccaagcat ccagtcacgg ggtctgttcg gcgctatcgc cggatttatt  180
gaaggcggct ggacggggat ggtggacggt tggtacggct accatcatca aaatgagcag  240
ggctccggat acgccgctga cctgaaatct acgcagaatg ccatagatga gatcacaaac  300
aaggtcaata gtgtgataga aaaaatgacg tataacgctg agctgcttgt tctgctggag  360
aacgaaagaa cccttgacta ccacgattcc aacgtgaaga atctgtatga gaaagtgcga  420
agccagttga aaaacaacgc aaaagaaata ggcaacggct gtttcgagtt ctaccacaaa  480
tgcgataaca cctgcatgga gagtgtgaag aacggaacgt acgattatcc aaaatactcc  540
gaggaggcca aactcaatag ggaggagata gac                               573

SEQ ID NO: 41          moltype = AA  length = 191
FEATURE                Location/Qualifiers
source                 1..191
                       mol_type = protein
                       organism = Influenza A virus
SEQUENCE: 41
TCQTPKGAIN TSLPFQNIHP ITIGKCPKYV KSTKLRLATG LRNIPSIQSR GLFGAIAGFI  60
EGGWTGMVDG WYGYHHQNEQ GSGYAADLKS TQNAIDEITN KVNSVIEKMT YNAELLVLLE  120
NERTLDYHDS NVKNLYEKVR SQLKNNAKEI GNGCFEFYHK CDNTCMESVK NGTYDYPKYS  180
EEAKLNREEI D                                                       191

SEQ ID NO: 42          moltype = DNA  length = 573
FEATURE                Location/Qualifiers
source                 1..573
                       mol_type = unassigned DNA
                       organism = Influenza A virus
SEQUENCE: 42
gtctatctcc tccctattga gtttggcctc ctcggagtat tttggataat cgtacgttcc  60
gttcttcaca ctctccatgc aggtgttatc gcatttgtgg tagaactcga aacagccgtt  120
gcctatttct tttgcgttgt ttttcaactg gcttcgcact ttctcataca gattcttcac  180
gttggaatcg tggtagtcaa gggttctttc gttctccagc agaacaagca gctcagcgtt  240
atacgtcatt ttttctatca cactattgac cttgtttgtg atctcatcta tggcattctg  300
cgtagatttc aggtcagcgg cgtatccgga gccctgctca ttttgatgat ggtagccgta  360
ccaaccgtcc accatccccg tccagccgcc ttcaataaat ccggcgatag cgccgaacag  420
accccgtgac tggatgcttg ggatattcct gagtccggtg gcgagtctca gtttagtgct  480
tttcacgtac ttggggcatt ttccgattgt gattggatgt atattctgaa agggcaagct  540
cgtgttgatg gcgcccttcg gtgtctgaca tgt                               573

SEQ ID NO: 43          moltype = DNA  length = 507
FEATURE                Location/Qualifiers
source                 1..507
                       mol_type = unassigned DNA
                       organism = Influenza A virus
SEQUENCE: 43
ctgagactcg ccaccggact caggaatatc ccaagcatcc agtcacgggg tctgttcggc  60
gctatcgccg gatttattga aggcggctgg acggggatgg tggacggttg gtacggctac  120
catcatcaaa atgagcaggg ctccggatac gccgctgacc tgaaatctac gcagaatgcc  180
atagatgaga tcacaaacaa ggtcaatagt gtgatagaaa aaatgaatac tcagttcaca  240
gctgttggaa aggagtttaa ccacctcgag aagcgaattg agaacctgaa caagaaggtg  300
gacgatggct ttttggatat ctggacgtat aacgctgagc tgcttgttct gctggagaac  360
gaaagaaccc ttgactacca cgattccaac gtgaagaatc tgtatgagaa agtgcgaagc  420
cagttgaaaa acaacgcaaa agaaataggc aacggctgtt tcgagttcta ccacaaatgc  480
gataacacct gcatggagag tgtgaag                                      507

SEQ ID NO: 44          moltype = AA  length = 190
FEATURE                Location/Qualifiers
source                 1..190
                       mol_type = protein
                       organism = Influenza A virus
SEQUENCE: 44
LRLATGLRNI PSIQSRGLFG AIAGFIEGGW TGMVDGWYGY HHQNEQGSGY AADLKSTQNA  60
IDEITNKVNS VIEKMNTQFT AVGKEFNHLE KRIENLNKKV DDGFLDIWTY NAELLVLLEN  120
ERTLDYHDSN VKNLYEKVRS QLKNNAKEIG NGCFEFYHKC DNTCMESVKN GTYDYPKYSE  180
EAKLNREEID                                                         190

SEQ ID NO: 45          moltype = DNA  length = 507
```

-continued

```
FEATURE                Location/Qualifiers
source                 1..507
                       mol_type = unassigned DNA
                       organism = Influenza A virus
SEQUENCE: 45
cttcacactc tccatgcagg tgttatcgca tttgtggtag aactcgaaac agccgttgcc  60
tatttctttt gcgttgtttt tcaactggct tcgcactttc tcatacagat tcttcacgtt  120
ggaatcgtgg tagtcaaggg ttctttcgtt ctccagcaga acaagcagct cagcgttata  180
cgtccagata tccaaaaagc catcgtccac cttcttgttc aggttctcaa ttcgcttctc  240
gaggtggtta aactcctttc caacagctgt gaactgagta ttcatttttt ctatcacact  300
attgaccttg tttgtgatct catctatggc attctgcgta gatttcaggt cagcggcgta  360
tccggagccc tgctcatttt gatgatggta gccgtaccaa ccgtccacca tccccgtcca  420
gccgccttca ataaatccgg cgatagcgcc gaacagaccc cgtgactgga tgcttgggat  480
attcctgagt ccggtggcga gtctcag                                       507

SEQ ID NO: 46          moltype = DNA  length = 471
FEATURE                Location/Qualifiers
source                 1..471
                       mol_type = unassigned DNA
                       organism = Influenza A virus
SEQUENCE: 46
ctgagactcg ccaccggact caggaatatc ccaagcatcc agtcacgggg tctgttcggc  60
gctatcgccg gatttattga aggcggctgg acggggatgg tggacggttg gtacggctac  120
catcatcaaa atgagcaggg ctccggatac gccgctgacc tgaaatctac gcagaatgcc  180
atagatgaga tcacaaacaa ggtcaatagt gtgatagaaa aatgacgta taacgctgag   240
ctgcttgttc tgctggagaa cgaaagaacc cttgactacc acgattccaa cgtgaagaat  300
ctgtatgaga aagtgcgaag ccagttgaaa aacaacgcaa aagaaatagg caacggctgt  360
ttcgagttct accacaaatg cgataacacc tgcatggaga gtgtgaagaa cggaacgtac  420
gattatccaa aatactccga ggaggccaaa ctcaataggg aggagataga c            471

SEQ ID NO: 47          moltype = AA  length = 157
FEATURE                Location/Qualifiers
source                 1..157
                       mol_type = protein
                       organism = Influenza A virus
SEQUENCE: 47
LRLATGLRNI PSIQSRGLFG AIAGFIEGGW TGMVDGWYGY HHQNEQGSGY AADLKSTQNA  60
IDEITNKVNS VIEKMTYNAE LLVLLENERT LDYHDSNVKN LYEKVRSQLK NNAKEIGNGC  120
FEFYHKCDNT CMESVKNGTY DYPKYSEEAK LNREEID                            157

SEQ ID NO: 48          moltype = DNA  length = 471
FEATURE                Location/Qualifiers
source                 1..471
                       mol_type = unassigned DNA
                       organism = Influenza A virus
SEQUENCE: 48
gtctatctcc tccctattga gtttggcctc ctcggagtat tttggataat cgtacgttcc  60
gttcttcaca ctctccatgc aggtgttatc gcatttgtgg tagaactcga aacagccgtt  120
gcctatttct tttgcgttgt ttttcaactg gcttcgcact ttctcataca gattcttcac  180
gttggaatcg tggtagtcaa gggttctttc gttctccagc agaacaagca gctcagcgtt  240
atacgtcatt ttttctatca cactattgac cttgtttgtg atctcatcta tggcattctg  300
cgtagatttc aggtcagcgg cgtatccgga gccctgctca ttttgatgat ggtagccgta  360
ccaaccgtcc accatccccg tccagccgcc ttcaataaat ccggcgatag cgccgaacag  420
accccgtgac tggatgcttg ggatattcct gagtccggtg gcgagtctca g            471

SEQ ID NO: 49          moltype = DNA  length = 141
FEATURE                Location/Qualifiers
source                 1..141
                       mol_type = unassigned DNA
                       organism = Influenza A virus
SEQUENCE: 49
atggccatca tctacctgat cctgctgttt acagctgtga gaggcgacca gatctgtatc  60
ggctaccacg ccaacaatag caccgagaag gtggacacca tcctggagag aaacgtgaca  120
gtgacccacg ccaaggacat c                                             141

SEQ ID NO: 50          moltype = AA  length = 47
FEATURE                Location/Qualifiers
source                 1..47
                       mol_type = protein
                       organism = Influenza A virus
SEQUENCE: 50
MAIIYLILLF TAVRGDQICI GYHANNSTEK VDTILERNVT VTHAKDI                 47

SEQ ID NO: 51          moltype = DNA  length = 141
FEATURE                Location/Qualifiers
source                 1..141
                       mol_type = unassigned DNA
                       organism = Influenza A virus
SEQUENCE: 51
```

-continued

```
gatgtccttg gcgtgggtca ctgtcacgtt tctctccagg atggtgtcca ccttctcggt  60
gctattgttg gcgtggtagc cgatacagat ctggtcgcct ctcacagctg taaacagcag  120
gatcaggtag atgatggcca t                                            141

SEQ ID NO: 52          moltype = DNA  length = 672
FEATURE                Location/Qualifiers
source                 1..672
                       mol_type = unassigned DNA
                       organism = Influenza A virus
SEQUENCE: 52
aagtgccaga cacctctggg cgccatcaat accaccctgc ccttccacaa tgtgcaccct  60
ctgaccatcg gcgagtgccc taagtatgtg aagagcgaga agctggtgct ggccacagga  120
ctgagaaacg tgccccagat cgagagcaga ggcctgtttg gagccatcgc cggattcatc  180
gagggaggat ggcagggaat ggtcgatggc tggtacggct accaccacag caatgatcag  240
ggctctggct atgccgccga taaggagtct acccagaagg cctttgacgg catcaccaac  300
aaggtgaaca gcgtgatcga gaagatgaac acccagtttg aggctgtggg caaggagttt  360
agcaacctgg agcggagact ggagaacctg aacaagaaga tggaggacgg cttcctggat  420
gtgtggacct acaatgccga actgctggtg ctgatggaga atgagcggac cctggacttc  480
cacgacagca acgtgaagaa cctgtacgac aaagtgagga tgcagctgag ggacaacgtg  540
aaggaactgg gcaatggctg cttcgagttc taccacaagt gtgacgacga gtgtatgaac  600
tccgtgaaga acggcaccta cgactaccct aagtacgagg aggagagcaa gctgaaccgg  660
aacgagatca ag                                                      672

SEQ ID NO: 53          moltype = AA  length = 224
FEATURE                Location/Qualifiers
source                 1..224
                       mol_type = protein
                       organism = Influenza A virus
SEQUENCE: 53
KCQTPLGAIN TTLPFHNVHP LTIGECPKYV KSEKLVLATG LRNVPQIESR GLFGAIAGFI  60
EGGWQGMVDG WYGYHHSNDQ GSGYAADKES TQKAFDGITN KVNSVIEKMN TQFEAVGKEF  120
SNLERRLENL NKKMEDGFLD VWTYNAELLV LMENERTLDF HDSNVKNLYD KVRMQLRDNV  180
KELGNGCFEF YHKCDDECMN SVKNGTYDYP KYEEESKLNR NEIK                   224

SEQ ID NO: 54          moltype = DNA  length = 672
FEATURE                Location/Qualifiers
source                 1..672
                       mol_type = unassigned DNA
                       organism = Influenza A virus
SEQUENCE: 54
cttgatctcg ttccggttca gcttgctctc ctcctcgtac ttagggtagt cgtaggtgcc  60
gttcttcacg gagttcatac actcgtcgtc acacttgtgg tagaactcga agcagccatt  120
gcccagttcc ttcacgttgt ccctcagctg catcctcact ttgtcgtaca ggttcttcac  180
gttgctgtcg tggaagtcca gggtccgctc attctccatc agcaccagca gttcggcatt  240
gtaggtccac acatccagga agccgtcctc catcttcttg ttcaggttct ccagtctccg  300
ctccaggttg ctaaactcct tgcccacagc ctcaaactgg gtgttcatct tctcgatcac  360
gctgttcacc ttgttggtga tgccgtcaaa ggccttctgg gtagactcct tatcggcggc  420
atagccagag ccctgatcat tgctgtggtg gtagccgtac cagccatcga ccattccctg  480
ccatcctccc tcgatgaatc cggcgatggc tccaaacagg cctctgctct cgatctgggg  540
cacgtttctc agtcctgtgg ccagcaccag cttctcgctc ttcacatact tagggcactc  600
gccgatggtc agagggtgca cattgtggaa gggcagggtg gtattgatgg cgcccagagg  660
tgtctggcac tt                                                      672

SEQ ID NO: 55          moltype = DNA  length = 573
FEATURE                Location/Qualifiers
source                 1..573
                       mol_type = unassigned DNA
                       organism = Influenza A virus
SEQUENCE: 55
aagtgccaga cacctctggg cgccatcaat accaccctgc ccttccacaa tgtgcaccct  60
ctgaccatcg gcgagtgccc taagtatgtg aagagcgaga agctggtgct ggccacagga  120
ctgagaaacg tgccccagat cgagagcaga ggcctgtttg gagccatcgc cggattcatc  180
gagggaggat ggcagggaat ggtcgatggc tggtacggct accaccacag caatgatcag  240
ggctctggct atgccgccga taaggagtct acccagaagg cctttgacgg catcaccaac  300
aaggtgaaca gcgtgatcga gaagatgacc tacaatgccg aactgctggt gctgatggag  360
aatgagcgga ccctggactt ccacgacagc aacgtgaaga acctgtacga caaagtgagg  420
atgcagctga gggacaacgt gaaggaactg ggcaatggct gcttcgagtt ctaccacaag  480
tgtgacgacg agtgtatgaa ctccgtgaag aacggcacct acgactaccc taagtacgag  540
gaggagagca agctgaaccg gaacgagatc aag                               573

SEQ ID NO: 56          moltype = AA  length = 191
FEATURE                Location/Qualifiers
source                 1..191
                       mol_type = protein
                       organism = Influenza A virus
SEQUENCE: 56
KCQTPLGAIN TTLPFHNVHP LTIGECPKYV KSEKLVLATG LRNVPQIESR GLFGAIAGFI  60
EGGWQGMVDG WYGYHHSNDQ GSGYAADKES TQKAFDGITN KVNSVIEKMT YNAELLVLME  120
NERTLDFHDS NVKNLYDKVR MQLRDNVKEL GNGCFEFYHK CDDECMNSVK NGTYDYPKYE  180
```

-continued

```
EESKLNRNEI K                                                      191

SEQ ID NO: 57          moltype = DNA  length = 573
FEATURE                Location/Qualifiers
source                 1..573
                       mol_type = unassigned DNA
                       organism = Influenza A virus
SEQUENCE: 57
cttgatctcg ttccggttca gcttgctctc ctcctcgtac ttagggtagt cgtaggtgcc  60
gttcttcacg gagttcatac actcgtcgtc acacttgtgg tagaactcga agcagccatt  120
gcccagttcc ttcacgttgt ccctcagctg catcctcact ttgtcgtaca ggttcttcac  180
gttgctgtcg tggaagtcca gggtccgctc attctccatc agcaccagca gttcggcatt  240
gtaggtcatc ttctcgatca cgctgttcac cttgttggtg atgccgtcaa aggccttctg  300
ggtagactcc ttatcggcgg catagccaga gccctgatca ttgctgtggt ggtagccgta  360
ccagccatcg accattccct gccatcctcc ctcgatgaat ccggcgatgg ctccaaacag  420
gcctctgctc tcgatctggg gcacgtttct cagtcctgtg gccagcacca gcttctcgct  480
cttcacatac ttagggcact cgccgatggt cagagggtgc acattgtgga agggcagggt  540
ggtattgatg gcgcccagag gtgtctggca ctt                               573

SEQ ID NO: 58          moltype = DNA  length = 570
FEATURE                Location/Qualifiers
source                 1..570
                       mol_type = unassigned DNA
                       organism = Influenza A virus
SEQUENCE: 58
ctggtgctgg ccacaggact gagaaacgtg ccccagatcg agagcagagg cctgtttgga  60
gccatcgccg gattcatcga gggaggatgg cagggaatgg tcgatggctg gtacggctac  120
caccacagca atgatcaggg ctctggctat gccgccgata aggagtctac ccagaaggcc  180
tttgacggca tcaccaacaa ggtgaacagc gtgatcgaga agatgaacac ccagtttgag  240
gctgtgggca aggagtttag caacctggag cggagactgg agaacctgaa caagaagatg  300
gaggacggct tcctggatgt gtggacctac aatgccgaac tgctggtgct gatggagaat  360
gagcggaccc tggacttcca cgacagcaac gtgaagaacc tgtacgacaa agtgaggatg  420
cagctgaggg acaacgtgaa ggaactgggc aatggctgct tcgagttcta ccacaagtgt  480
gacgacgagt gtatgaactc cgtgaagaac ggcacctacg actaccctaa gtacgaggag  540
gagagcaagc tgaaccggaa cgagatcaag                                   570

SEQ ID NO: 59          moltype = AA  length = 190
FEATURE                Location/Qualifiers
source                 1..190
                       mol_type = protein
                       organism = Influenza A virus
SEQUENCE: 59
LVLATGLRNV PQIESRGLFG AIAGFIEGGW QGMVDGWYGY HHSNDQGSGY AADKESTQKA  60
FDGITNKVNS VIEKMNTQFE AVGKEFSNLE RRLENLNKKM EDGFLDVWTY NAELLVLMEN  120
ERTLDFHDSN VKNLYDKVRM QLRDNVKELG NGCFEFYHKC DDECMNSVKN GTYDYPKYEE  180
ESKLNRNEIK                                                         190

SEQ ID NO: 60          moltype = DNA  length = 570
FEATURE                Location/Qualifiers
source                 1..570
                       mol_type = unassigned DNA
                       organism = Influenza A virus
SEQUENCE: 60
cttgatctcg ttccggttca gcttgctctc ctcctcgtac ttagggtagt cgtaggtgcc  60
gttcttcacg gagttcatac actcgtcgtc acacttgtgg tagaactcga agcagccatt  120
gcccagttcc ttcacgttgt ccctcagctg catcctcact ttgtcgtaca ggttcttcac  180
gttgctgtcg tggaagtcca gggtccgctc attctccatc agcaccagca gttcggcatt  240
gtaggtccac acatccagga agccgtcctc catcttcttg ttcaggttct ccagtctccg  300
ctccaggttg ctaaactcct tgcccacagc ctcaaactgg gtgttcatct tctcgatcac  360
gctgttcacc ttgttggtga tgccgtcaaa ggccttctgg gtagactcct tatcggcggc  420
atagccagag ccctgatcat tgctgtggtg gtagccgtac cagccatcga ccattccctg  480
ccatcctccc tcgatgaatc cggcgatggc tccaaacagg cctctgctct cgatctgggg  540
cacgtttctc agtcctgtgg ccagcaccag                                   570

SEQ ID NO: 61          moltype = DNA  length = 471
FEATURE                Location/Qualifiers
source                 1..471
                       mol_type = unassigned DNA
                       organism = Influenza A virus
SEQUENCE: 61
ctggtgctgg ccacaggact gagaaacgtg ccccagatcg agagcagagg cctgtttgga  60
gccatcgccg gattcatcga gggaggatgg cagggaatgg tcgatggctg gtacggctac  120
caccacagca atgatcaggg ctctggctat gccgccgata aggagtctac ccagaaggcc  180
tttgacggca tcaccaacaa ggtgaacagc gtgatcgaga agatgaccta caatgccgaa  240
ctgctggtgc tgatggagaa tgagcggacc ctggacttcc acgacagcaa cgtgaagaac  300
ctgtacgaca aagtgaggat gcagctgagg gacaacgtga aggaactggg caatggctgc  360
ttcgagttct accacaagtg tgacgacgag tgtatgaact ccgtgaagaa cggcacctac  420
gactacccta agtacgagga ggagagcaag ctgaaccgga acgagatcaa g          471
```

-continued

```
SEQ ID NO: 62          moltype = AA  length = 157
FEATURE                Location/Qualifiers
source                 1..157
                       mol_type = protein
                       organism = Influenza A virus
SEQUENCE: 62
LVLATGLRNV PQIESRGLFG AIAGFIEGGW QGMVDGWYGY HHSNDQGSGY AADKESTQKA  60
FDGITNKVNS VIEKMTYNAE LLVLMENERT LDFHDSNVKN LYDKVRMQLR DNVKELGNGC  120
FEFYHKCDDE CMNSVKNGTY DYPKYEEESK LNRNEIK                           157

SEQ ID NO: 63          moltype = DNA  length = 471
FEATURE                Location/Qualifiers
source                 1..471
                       mol_type = unassigned DNA
                       organism = Influenza A virus
SEQUENCE: 63
cttgatctcg ttccggttca gcttgctctc ctcctcgtac ttagggtagt cgtaggtgcc  60
gttcttcacg gagttcatac actcgtcgtc acacttgtgg tagaactcga agcagccatt  120
gcccagttcc ttcacgttgt ccctcagctg catcctcact ttgtcgtaca ggttcttcac  180
gttgctgtcg tggaagtcca gggtccgctc attctccatc agcaccagca gttcggcatt  240
gtaggtcatc ttctcgatca cgctgttcac cttgttggtg atgccgtcaa aggccttctg  300
ggtagactcc ttatcggcgg catagccaga gccctgatca ttgctgtggt ggtagccgta  360
ccagccatcg accattccct gccatcctcc ctcgatgaat ccggcgatgg ctccaaacag  420
gcctctgctc tcgatctggg gcacgtttct cagtcctgtg gccagcacca g           471

SEQ ID NO: 64          moltype = DNA  length = 150
FEATURE                Location/Qualifiers
source                 1..150
                       mol_type = unassigned DNA
                       organism = Influenza A virus
SEQUENCE: 64
gccaccatgg aaaagatcgt gctgctgctg gccattgtga gcctggtgaa gagcgaccag  60
atctgcattg gctaccacgc caacaatagc acagagcagg tggacaccat catggaaaaa  120
aacgtgaccg tgacccacgc tcaggacatc                                  150

SEQ ID NO: 65          moltype = AA  length = 48
FEATURE                Location/Qualifiers
source                 1..48
                       mol_type = protein
                       organism = Influenza A virus
SEQUENCE: 65
MEKIVLLLAI VSLVKSDQIC IGYHANNSTE QVDTIMEKNV TVTHAQDI               48

SEQ ID NO: 66          moltype = DNA  length = 150
FEATURE                Location/Qualifiers
source                 1..150
                       mol_type = unassigned DNA
                       organism = Influenza A virus
SEQUENCE: 66
gatgtcctga gcgtgggtca cggtcacgtt tttttccatg atggtgtcca cctgctctgt  60
gctattgttg gcgtggtagc caatgcagat ctggtcgctc ttcaccaggc tcacaatggc  120
cagcagcagc acgatctttt ccatggtggc                                  150

SEQ ID NO: 67          moltype = DNA  length = 681
FEATURE                Location/Qualifiers
source                 1..681
                       mol_type = unassigned DNA
                       organism = Influenza A virus
SEQUENCE: 67
aagtgccaga cacctatggg cgccatcaac agcagcatgc ccttccacaa catccaccct  60
ctgaccatcg gcgagtgccc taagtacgtg aagagcaaca gactggtgct ggccacaggc  120
ctgagaaata gcccccagcg ggagagcaga agaaagaaga ggggcctgtt tggagccatc  180
gccggcttta ttgaaggcgg ctggcaggga atggtggatg gctggtacgg ctaccaccac  240
agcaatgagc agggctctgg atatgccgcc gacaaagagt ctacccagaa ggccatcgac  300
ggcgtcacca acaaggtgaa cagcatcatc gacaagatga acacccagtt cgaggctgtg  360
ggcagagagt tcaacaacct ggaacggcgg atcgagaacc tgaacaagaa aatggaagat  420
ggcttcctgg atgtgtggac ctacaatgcc gaactgctgg tgctgatgga aaacgagcgg  480
accctggact tccacgacag caacgtgaag aacctgtacg acaaagtgcg gctgcagctg  540
agagacaacg ccaaagagct gggcaacggc tgcttcgagt tctaccacaa gtgcgacaac  600
gagtgcatgg aaagcatccg gaacggcacc tacaactacc ctcagtacag cgaggaagcc  660
aggctgaaga gggaagagat c                                           681

SEQ ID NO: 68          moltype = AA  length = 227
FEATURE                Location/Qualifiers
source                 1..227
                       mol_type = protein
                       organism = Influenza A virus
SEQUENCE: 68
KCQTPMGAIN SSMPFHNIHP LTIGECPKYV KSNRLVLATG LRNSPQRESR RKKRGLFGAI  60
```

-continued

```
AGFIEGGWQG MVDGWYGYHH SNEQGSGYAA DKESTQKAID GVTNKVNSII DKMNTQFEAV  120
GREFNNLERR IENLNKKMED GFLDVWTYNA ELLVLMENER TLDFHDSNVK NLYDKVRLQL  180
RDNAKELGNG CFEFYHKCDN ECMESIRNGT YNYPQYSEEA RLKREEI                227

SEQ ID NO: 69          moltype = DNA  length = 681
FEATURE                Location/Qualifiers
source                 1..681
                       mol_type = unassigned DNA
                       organism = Influenza A virus
SEQUENCE: 69
gatctcttcc ctcttcagcc tggcttcctc gctgtactga gggtagttgt aggtgccgtt  60
ccggatgctt tccatgcact cgttgtcgca cttgtggtag aactcgaagc agccgttgcc  120
cagctctttg gcgttgtctc tcagctgcag ccgcactttg tcgtacaggt tcttcacgtt  180
gctgtcgtgg aagtccaggg tccgctcgtt ttccatcagc accagcagtt cggcattgta  240
ggtccacaca tccaggaagc catcttccat tttcttgttc aggttctcga tccgccgttc  300
caggttgttg aactctctgc ccacagcctc gaactgggtg ttcatcttgt cgatgatgct  360
gttcaccttg ttggtgacgc cgtcgatggc cttctgggta gactctttgt cggcggcata  420
tccagagccc tgctcattgc tgtggtggta gccgtaccag ccatccacca ttccctgcca  480
gccgccttca ataaagccgg cgatggctcc aaacaggccc ctcttctttc ttctgctctc  540
ccgctggggg ctatttctca ggcctgtggc cagcaccagt ctgttgctct tcacgtactt  600
agggcactcg ccgatggtca gagggtggat gttgtggaag ggcatgctgc tgttgatggc  660
gcccataggt gtctggcact t                                            681

SEQ ID NO: 70          moltype = DNA  length = 582
FEATURE                Location/Qualifiers
source                 1..582
                       mol_type = unassigned DNA
                       organism = Influenza A virus
SEQUENCE: 70
aagtgccaga cacctatggg cgccatcaac agcagcatgc ccttccacaa catccaccct  60
ctgaccatcg gcgagtgccc taagtacgtg aagagcaaca gactggtgct ggccacaggc  120
ctgagaaata gcccccagcg ggagagcaga agaaagaaga ggggcctgtt tggagccatc  180
gccggcttta ttgaaggcgg ctggcaggga atggtggatg gctggtacgg ctaccaccac  240
agcaatgagc agggctctgg atatgccgcc gacaaagagt ctacccagaa ggccatcgac  300
ggcgtcacca acaaggtgaa cagcatcatc gacaagatga cctacaatgc cgaactgctg  360
gtgctgatgg aaaacgagcg gaccctggac ttccacgaca gcaacgtgaa gaacctgtac  420
gacaaagtgc ggctgcagct gagagacaac gccaaagagc tgggcaacgg ctgcttcgag  480
ttctaccaca agtgcgacaa cgagtgcatg gaaagcatcc ggaacggcac ctacaactac  540
cctcagtaca gcgaggaagc caggctgaag agggaagaga tc                     582

SEQ ID NO: 71          moltype = AA  length = 194
FEATURE                Location/Qualifiers
source                 1..194
                       mol_type = protein
                       organism = Influenza A virus
SEQUENCE: 71
KCQTPMGAIN SSMPFHNIHP LTIGECPKYV KSNRLVLATG LRNSPQRESR RKKRGLFGAI  60
AGFIEGGWQG MVDGWYGYHH SNEQGSGYAA DKESTQKAID GVTNKVNSII DKMTYNAELL  120
VLMENERTLD FHDSNVKNLY DKVRLQLRDN AKELGNGCFE FYHKCDNECM ESIRNGTYNY  180
PQYSEEARLK REEI                                                    194

SEQ ID NO: 72          moltype = DNA  length = 582
FEATURE                Location/Qualifiers
source                 1..582
                       mol_type = unassigned DNA
                       organism = Influenza A virus
SEQUENCE: 72
gatctcttcc ctcttcagcc tggcttcctc gctgtactga gggtagttgt aggtgccgtt  60
ccggatgctt tccatgcact cgttgtcgca cttgtggtag aactcgaagc agccgttgcc  120
cagctctttg gcgttgtctc tcagctgcag ccgcactttg tcgtacaggt tcttcacgtt  180
gctgtcgtgg aagtccaggg tccgctcgtt ttccatcagc accagcagtt cggcattgta  240
ggtcatcttg tcgatgatgc tgttcacctt gttggtgacg ccgtcgatgg ccttctgggt  300
agactctttg tcggcggcat atccagagcc ctgctcattg ctgtggtggt agccgtacca  360
gccatccacc attccctgcc agccgccttc aataaagccg gcgatggctc caaacaggcc  420
cctcttcttt cttctgctct cccgctgggg gctatttctc aggcctgtgg ccagcaccag  480
tctgttgctc ttcacgtact tagggcactc gccgatggtc agagggtgga tgttgtggaa  540
gggcatgctg ctgttgatgg cgcccatagg tgtctggcac tt                     582

SEQ ID NO: 73          moltype = DNA  length = 579
FEATURE                Location/Qualifiers
source                 1..579
                       mol_type = unassigned DNA
                       organism = Influenza A virus
SEQUENCE: 73
ctggtgctgg ccacaggcct gagaaatagc cccccagcggg agagcagaag aaagaagagg  60
ggcctgtttg gagccatcgc cggctttatt gaaggcggct ggcagggaat ggtggatggc  120
tggtacggct accaccacag caatgagcag ggctctggat atgccgccga caaagagtct  180
acccagaagg ccatcgacgg cgtcaccaac aaggtgaaca gcatcatcga caagatgaac  240
acccagttcg aggctgtggg cagagagttc aacaacctgg aacggcggat cgagaacctg  300
```

```
aacaagaaaa tggaagatgg cttcctggat gtgtggacct acaatgccga actgctggtg  360
ctgatggaaa acgagcggac cctggacttc cacgacagca acgtgaagaa cctgtacgac  420
aaagtgcggc tgcagctgag agacaacgcc aaagagctgg gcaacggctg cttcgagttc  480
taccacaagt gcgacaacga gtgcatggaa agcatccgga acggcaccta caactaccct  540
cagtacagcg aggaagccag gctgaagagg gaagagatc                         579

SEQ ID NO: 74          moltype = AA  length = 193
FEATURE                Location/Qualifiers
source                 1..193
                       mol_type = protein
                       organism = Influenza A virus
SEQUENCE: 74
LVLATGLRNS PQRESRRKKR GLFGAIAGFI EGGWQGMVDG WYGYHHSNEQ GSGYAADKES  60
TQKAIDGVTN KVNSIIDKMN TQFEAVGREF NNLERRIENL NKKMEDGFLD VWTYNAELLV  120
LMENERTLDF HDSNVKNLYD KVRLQLRDNA KELGNGCFEF YHKCDNECME SIRNGTYNYP  180
QYSEEARLKR EEI                                                     193

SEQ ID NO: 75          moltype = DNA  length = 579
FEATURE                Location/Qualifiers
source                 1..579
                       mol_type = unassigned DNA
                       organism = Influenza A virus
SEQUENCE: 75
gatctcttcc ctcttcagcc tggcttcctc gctgtactga gggtagttgt aggtgccgtt  60
ccggatgctt tccatgcact cgttgtcgca cttgtggtag aactcgaagc agccgttgcc  120
cagctctttg gcgttgtctc tcagctgcag ccgcactttg tcgtacaggt tcttcacgtt  180
gctgtcgtgg aagtccaggg tccgctcgtt ttccatcagc accagcagtt cggcattgta  240
ggtccacaca tccaggaagc catcttccat tttcttgttc aggttctcga tccgccgttc  300
caggttgttg aactctctgc ccacagcctc gaactgggtg ttcatcttgt cgatgatgct  360
gttcaccttg ttggtgacgc cgtcgatggc cttctgggta gactctttgt cggcggcata  420
tccagagccc tgctcattgc tgtggtggta gccgtaccag ccatccacca ttccctgcca  480
gccgccttca ataaagccgg cgatggctcc aaacaggccc ctcttctttc ttctgctctc  540
ccgctggggg ctatttctca ggcctgtggc cagcaccag                         579

SEQ ID NO: 76          moltype = DNA  length = 480
FEATURE                Location/Qualifiers
source                 1..480
                       mol_type = unassigned DNA
                       organism = Influenza A virus
SEQUENCE: 76
ctggtgctgg ccacaggcct gagaaatagc ccccagcggg agagcagaag aaagaagagg  60
ggcctgtttg gagccatcgc cggctttatt gaaggcggct ggcagggaat ggtggatggc  120
tggtacggct accaccacag caatgagcag ggctctggat atgccgccga caaagagtct  180
acccagaagg ccatcgacgg cgtcaccaac aaggtgaaca gcatcatcga caagatgacc  240
tacaatgccg aactgctggt gctgatggaa aacgagcgga ccctggactt ccacgacagc  300
aacgtgaaga acctgtacga caaagtgcgg ctgcagctga gagacaacgc caaagagctg  360
ggcaacggct gcttcgagtt ctaccacaag tgcgacaacg agtgcatgga aagcatccgg  420
aacggcacct acaactaccc tcagtacagc gaggaagcca ggctgaagag ggaagagatc  480

SEQ ID NO: 77          moltype = AA  length = 160
FEATURE                Location/Qualifiers
source                 1..160
                       mol_type = protein
                       organism = Influenza A virus
SEQUENCE: 77
LVLATGLRNS PQRESRRKKR GLFGAIAGFI EGGWQGMVDG WYGYHHSNEQ GSGYAADKES  60
TQKAIDGVTN KVNSIIDKMT YNAELLVLME NERTLDFHDS NVKNLYDKVR LQLRDNAKEL  120
GNGCFEFYHK CDNECMESIR NGTYNYPQYS EEARLKREEI                        160

SEQ ID NO: 78          moltype = DNA  length = 480
FEATURE                Location/Qualifiers
source                 1..480
                       mol_type = unassigned DNA
                       organism = Influenza A virus
SEQUENCE: 78
gatctcttcc ctcttcagcc tggcttcctc gctgtactga gggtagttgt aggtgccgtt  60
ccggatgctt tccatgcact cgttgtcgca cttgtggtag aactcgaagc agccgttgcc  120
cagctctttg gcgttgtctc tcagctgcag ccgcactttg tcgtacaggt tcttcacgtt  180
gctgtcgtgg aagtccaggg tccgctcgtt ttccatcagc accagcagtt cggcattgta  240
ggtcatcttg tcgatgatgc tgttcacctt gttggtgacg ccgtcgatgg ccttctgggt  300
agactctttg tcggcggcat atccagagcc ctgctcattg ctgtggtggt agccgtacca  360
gccatccacc attccctgcc agccgccttc aataaagccg gcgatggctc caaacaggcc  420
cctcttcttt cttctgctct cccgctgggg gctatttctc aggcctgtgg ccagcaccag  480

SEQ ID NO: 79          moltype = DNA  length = 645
FEATURE                Location/Qualifiers
misc_feature           1..645
                       note = Synthetic
source                 1..645
```

```
                        mol_type = other DNA
                        organism = synthetic construct
SEQUENCE: 79
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcagcgga ggctccggaa cagacctggc tgagctgctg  420
gtgctgctgc tgaaccagtg gactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                  645

SEQ ID NO: 80           moltype = AA  length = 215
FEATURE                 Location/Qualifiers
REGION                  1..215
                        note = Synthetic
source                  1..215
                        mol_type = protein
                        organism = synthetic construct
SEQUENCE: 80
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGSG GSGTDLAELL VLLLNQWTLL FHDSNVKNLY EKVKSQLKNN AKEIGNGCFE  180
FYHKCNNECM ESVKNGTYDY PKYSEESKLN REKID                             215

SEQ ID NO: 81           moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 81
gtcaatttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaacagca gagtccactg gttcagcagc agcaccagca gctcagccag  240
gtctgttccg gagcctccgc tgcccatttt ttcgatgaca gaattcacca tgttagtaat  300
gccattgatt gcgttctgtg tagacttctg atcagcggcg tagccgctgc cctgctcatt  360
ctgatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat                  645

SEQ ID NO: 82           moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 82
atgaaggcaa tcctggtcgt cctgctgtat actttcgcta ccgctaacgc tgacaccctg  60
tgcatcggct atcacgctaa caactcaacc gacacagtgg atactgtcct ggagaagaac  120
gtgactgtca cccactctgt gaatctgggc agtggactga ggctggcaac tggactgcga  180
aacatcccac agcgggaaac cagaggactg ttcggcgcta tcgcagggtt tattgagggc  240
gggtggacag gaatggtgga cgggtggtac ggctaccacc atcagaacga gcagggatca  300
ggctacgccg ctgacctgaa gagcacacag aatgcaatcg atgaaattac taacatggtg  360
aattccgtca tcgagaaaat gggcagcgga ggctccggaa ccgacctggc agaactgctg  420
gtgctgctgc tgaaccagtg gacactgctg taccacgata gtaacgtgaa gaatctgtat  480
gagaaagtcc gatcacagct gaagaacaat gctaaagaaa tcgggaatgg atgcttcgag  540
ttttaccata agtgcgacaa cacctgtatg gagagcgtga aaaatggcac atacgattat  600
cccaagtatt ccgaggaagc caaactgaac agagaggaaa ttgac                  645

SEQ ID NO: 83           moltype = AA  length = 215
FEATURE                 Location/Qualifiers
REGION                  1..215
                        note = Synthetic
source                  1..215
                        mol_type = protein
                        organism = synthetic construct
SEQUENCE: 83
MKAKLLVLLC TFTATYADTL CIGYHANNST DTVDTVLEKN VTVTHSVNLG SGLRLATGLR  60
NIPQRETRGL FGAIAGFIEG GWTGMVDGWY GYHHQNEQGS GYAADLKSTQ NAIDEITNMV  120
NSVIEKMGSG GSGTDLAELL VLLLNQWTLL YHDSNVKNLY EKVRSQLKNN AKEIGNGCFE  180
```

-continued

```
FYHKCDNTCM ESVKNGTYDY PKYSEEAKLN REEID                        215

SEQ ID NO: 84          moltype = DNA  length = 645
FEATURE                Location/Qualifiers
misc_feature           1..645
                       note = Synthetic
source                 1..645
                       mol_type = other DNA
                       organism = synthetic construct
SEQUENCE: 84
gtcaatttcc tctctgttca gtttggcttc ctcggaatac ttgggataat cgtatgtgcc  60
atttttcacg ctctccatac aggtgttgtc gcacttatgg taaaactcga agcatccatt  120
cccgatttct ttagcattgt tcttcagctg tgatcggact ttctcataca gattcttcac  180
gttactatcg tggtacagca gtgtccactg gttcagcagc agcaccagca gttctgccag  240
gtcggttccg gagcctccgc tgcccatttt ctcgatgacg gaattcacca tgttagtaat  300
ttcatcgatt gcattctgtg tgctcttcag gtcagcggcg tagcctgatc cctgctcgtt  360
ctgatggtgg tagccgtacc acccgtccac cattcctgtc cacccgccct caataaaccc  420
tgcgatagcg ccgaacagtc ctctggtttc ccgctgtggg atgtttcgca gtccagttgc  480
cagcctcagt ccactgccca gattcacaga gtgggtgaca gtcacgttct tctccaggac  540
agtatccact gtgtcggttg agttgttagc gtgatagccg atgcacaggg tgtcagcgtt  600
agcggtagcg aaagtataca gcaggacgac caggattgcc ttcat             645

SEQ ID NO: 85          moltype = DNA  length = 639
FEATURE                Location/Qualifiers
misc_feature           1..639
                       note = Synthetic
source                 1..639
                       mol_type = other DNA
                       organism = synthetic construct
SEQUENCE: 85
atggctatca tctacctgat cctgctgttc actgctgtgc ggggggacca gatttgcatc  60
ggctaccacg ctaataattc aactgagaag gtggatacta tcctggagcg gaacgtgacc  120
gtcacacacg ctaaagacat tggcagcgga ctggtgctgg caaccggact gaggaatgtc  180
ccacagatcg agtcccgcgg actgttcggc gctatcgcag ggtttattga aggcgggtgg  240
cagggaatga ttgatgggtg gtacggctac caccattcta acgaccaagg aagtggctac  300
gccgctgata aggagagtac tcagaaagcc ttcgatggca tcaccaacat ggtgaattca  360
gtcattgaga agatgggcag cggaggctcc ggaaccgacc tggcagaact gctggtgctg  420
ctgctgaatc agtggacact gctgtttcac gactctaacg tgaagaatct gtatgataaa  480
gtccggatgc agctgagaga caacgtgaag gagctgggga atggatgctt cgaattttac  540
cataagtgcg acgatgagtg tatgaacagt gtcaaaaatg gcacatacga ttatcccaag  600
tatgaggaag agtcaaaact gaaccgaaat gaaatcaag                    639

SEQ ID NO: 86          moltype = AA  length = 213
FEATURE                Location/Qualifiers
REGION                 1..213
                       note = Synthetic
source                 1..213
                       mol_type = protein
                       organism = synthetic construct
SEQUENCE: 86
MAIIYLILLF TAVRGDQICI GYHANNSTEK VDTILERNVT VTHAKDIGSG LVLATGLRNV  60
PQIESRGLFG AIAGFIEGGW QGMIDGWYGY HHSNDQGSGY AADKESTQKA FDGITNMVNS  120
VIEKMGSGGS GTDLAELLVL LLNQWTLLFH DSNVKNLYDK VRMQLRDNVK ELGNGCFEFY  180
HKCDDECMNS VKNGTYDYPK YEEESKLNRN EIK                          213

SEQ ID NO: 87          moltype = DNA  length = 639
FEATURE                Location/Qualifiers
misc_feature           1..639
                       note = Synthetic
source                 1..639
                       mol_type = other DNA
                       organism = synthetic construct
SEQUENCE: 87
cttgatttca tttcggttca gttttgactc ttcctcatac ttgggataat cgtatgtgcc  60
atttttgaca ctgttcatac actcatcgtc gcacttatgg taaaattcga agcatccatt  120
ccccagctcc ttcacgttgt ctctcagctg catccggact ttatcataca gattcttcac  180
gttagagtcg tgaaacagca gtgtccactg attcagcagc agcaccagca gttctgccag  240
gtcggttccg gagcctccgc tgcccatctt ctcaatgact gaattcacca tgttggtgat  300
gccatcgaag gctttctgag tactctcctt atcagcggcg tagccacttc cttggtcgtt  360
agaatggtgg tagccgtacc acccatcaat cattccctgc cacccgcctt caataaaccc  420
tgcgatagcg ccgaacagtc cgcgggactc gatctgtggg acattcctca gtccggttgc  480
cagcaccagt ccgctgccaa tgtctttagc gtgtgtgacg gtcacgttcc gctccaggat  540
agtatccacc ttctcagttg aattattagc gtggtagccg atgcaaatct ggtccccccg  600
cacagcagtg aacagcagga tcaggtagat gatagccat                    639

SEQ ID NO: 88          moltype = DNA  length = 651
FEATURE                Location/Qualifiers
misc_feature           1..651
                       note = Synthetic
```

-continued

```
source                  1..651
                        mol_type = other DNA
                        organism = synthetic construct
SEQUENCE: 88
atggaaaaaa tcgtgctgct gctggctatc gtgtccctgg tgaagtccga ccagatctgt  60
attgggtatc atgctaacaa ctccacagaa caggtggata ctatcatgga gaagaacgtg  120
accgtcacac acgctcagga cattggatgg ggactggtcc tggcaaccgg actgagaaat  180
tcaccacaga gggaaagccg gagaaagaaa cgcggactgt tcggcgctat cgcagggttt  240
attgagggcg ggtggcaggg aatggtggat gggtggtacg gctaccacca ttccaacgaa  300
cagggatctg gctacgccgc tgataaggag tctactcaga aagctatcga cggcgtgacc  360
aacatggtca atagtatcat tgataagatg ggctctggag gcagtggaac cgacctggca  420
gagctgctgg tgctgctgct gaaccagtgg acactgctgt tccacgactc taacgtgaag  480
aatctgtatg ataaagtccg actgcagctg cgggacaacg ccaaggaact ggggaatgga  540
tgcttcgagt tctaccataa gtgcgataac gaatgtatgg agagcatccg aaacggcaca  600
tacaattatc cccagtattc cgaggaagct aggctgaaac gcgaggaaat t           651

SEQ ID NO: 89           moltype = AA  length = 217
FEATURE                 Location/Qualifiers
REGION                  1..217
                        note = Synthetic
source                  1..217
                        mol_type = protein
                        organism = synthetic construct
SEQUENCE: 89
MEKIVLLLAI VSLVKSDQIC IGYHANNSTE QVDTIMEKNV TVTHAQDIGW GLVLATGLRN  60
SPQRESRRKK RGLFGAIAGF IEGGWQGMVD GWYGYHHSNE QGSGYAADKE STQKAIDGVT  120
NMVNSIIDKM GSGGSGTDLA ELLVLLLNQW TLLFHDSNVK NLYDKVRLQL RDNAKELGNG  180
CFEFYHKCDN ECMESIRNGT YNYPQYSEEA RLKREEI                          217

SEQ ID NO: 90           moltype = DNA  length = 651
FEATURE                 Location/Qualifiers
misc_feature            1..651
                        note = Synthetic
source                  1..651
                        mol_type = other DNA
                        organism = synthetic construct
SEQUENCE: 90
aatttcctcg cgtttcagcc tagcttcctc ggaatactgg ggataattgt atgtgccgtt  60
tcggatgctc tccatacatt cgttatcgca cttatggtag aactcgaagc atccattccc  120
cagttccttg gcgttgtccc gcagctgcag tcggacttta tcatacagat tcttcacgtt  180
agagtcgtgg aacagcagtg tccactggtt cagcagcagc accagcagct ctgccaggtc  240
ggttccactg cctccagagc ccatcttatc aatgatacta ttgaccatgt tggtcacgcc  300
gtcgatagct ttctgagtag actccttatc agcggcgtag ccagatccct gttcgttgga  360
atggtggtag ccgtaccacc catccaccat tccctgccac ccgccctcaa taaaccctgc  420
gatagcgccg aacagtccgc gtttctttct ccggctttcc ctctgtggtg aatttctcag  480
tccggttgcc aggaccagtc cccatccaat gtcctgagcg tgtgtgacgg tcacgttctt  540
ctccatgata gtatccacct gttctgtgga gttgttagca tgatacccaa tacagatctg  600
gtcggacttc accagggaca cgatagccag cagcagcacg attttttcca t           651

SEQ ID NO: 91           moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 91
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcagcgga ggctccggaa cagacctggc tgagctgctg  420
gtgctgctgc tgaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                  645

SEQ ID NO: 92           moltype = AA  length = 215
FEATURE                 Location/Qualifiers
REGION                  1..215
                        note = Synthetic
source                  1..215
                        mol_type = protein
                        organism = synthetic construct
SEQUENCE: 92
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
```

-continued

```
NSVIEKMGSG GSGTDLAELL VLLLNERTLD FHDSNVKNLY EKVKSQLKNN AKEIGNGCFE  180
FYHKCNNECM ESVKNGTYDY PKYSEESKLN REKID                            215

SEQ ID NO: 93          moltype = DNA  length = 645
FEATURE                Location/Qualifiers
misc_feature           1..645
                       note = Synthetic
source                 1..645
                       mol_type = other DNA
                       organism = synthetic construct
SEQUENCE: 93
gtcaattttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaaatcca gagtccgctc gttcagcagc agcaccagca gctcagccag  240
gtctgttccg gagcctccgc tgcccatttt ttcgatgaca gaattcacca tgttagtaat  300
gccattgatt gcgttctgtg tagacttctg atcagcggcg tagccgctgc cctgctcatt  360
ctgatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat                 645

SEQ ID NO: 94          moltype = DNA  length = 645
FEATURE                Location/Qualifiers
misc_feature           1..645
                       note = Synthetic
source                 1..645
                       mol_type = other DNA
                       organism = synthetic construct
SEQUENCE: 94
atgaaggcca aactgctggt cctgctgtgt acttttaccg caacctacgc tgacactatc  60
tgcatcggct atcacgcaaa caactccacc gacacagtgg ataccattct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcagcgga ggctccggaa cagacctggc tgagctgctg  420
gtgctgatgc tgaaccagtt cactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                 645

SEQ ID NO: 95          moltype = AA  length = 215
FEATURE                Location/Qualifiers
REGION                 1..215
                       note = Synthetic
source                 1..215
                       mol_type = protein
                       organism = synthetic construct
SEQUENCE: 95
MKAKLLVLLC TFTATYADTI CIGYHANNST DTVDTILEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGSG GSGTDLAELL VLMLNQFTLL FHDSNVKNLY EKVKSQLKNN AKEIGNGCFE  180
FYHKCNNECM ESVKNGTYDY PKYSEESKLN REKID                            215

SEQ ID NO: 96          moltype = DNA  length = 645
FEATURE                Location/Qualifiers
misc_feature           1..645
                       note = Synthetic
source                 1..645
                       mol_type = other DNA
                       organism = synthetic construct
SEQUENCE: 96
gtcaattttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaacagca gagtgaactg gttcagcatc agcaccagca gctcagccag  240
gtctgttccg gagcctccgc tgcccatttt ttcgatgaca gaattcacca tgttagtaat  300
gccattgatt gcgttctgtg tagacttctg atcagcggcg tagccgctgc cctgctcatt  360
ctgatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccagaat  540
ggtatccact gtgtcggtgg agttgtttgc gtgatagccg atgcagatag tgtcagcgta  600
ggttgcggta aaagtacaca gcaggaccag cagtttggcc ttcat                 645

SEQ ID NO: 97          moltype = DNA  length = 645
FEATURE                Location/Qualifiers
misc_feature           1..645
```

```
                        note = Synthetic
source                  1..645
                        mol_type = other DNA
                        organism = synthetic construct
SEQUENCE: 97
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcaatgga acaggcggag ctgacctggc tgagctgctg  420
gtgctgctgc tgaaccagtg gactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                  645

SEQ ID NO: 98           moltype = AA  length = 215
FEATURE                 Location/Qualifiers
REGION                  1..215
                        note = Synthetic
source                  1..215
                        mol_type = protein
                        organism = synthetic construct
SEQUENCE: 98
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGNG TGGADLAELL VLLLNQWTLL FHDSNVKNLY EKVKSQLKNN AKEIGNGCFE  180
FYHKCNNECM ESVKNGTYDY PKYSEESKLN REKID                             215

SEQ ID NO: 99           moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 99
gtcaatttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaacagca gagtccactg gttcagcagc agcaccagca gctcagccag  240
gtcagctccg cctgttccat tgcccatttt ttcgatgaca gaattcacca tgttagtaat  300
gccattgatt gcgttctgtg tagacttctg atcagcggcg tagccgctgc cctgctcatt  360
ctgatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat                  645

SEQ ID NO: 100          moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 100
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcggaaat ggcactggag ctgacctggc tgagctgctg  420
gtgctgctgc tgaaccagtg gactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                  645

SEQ ID NO: 101          moltype = AA  length = 215
FEATURE                 Location/Qualifiers
REGION                  1..215
                        note = Synthetic
source                  1..215
                        mol_type = protein
                        organism = synthetic construct
SEQUENCE: 101
MKAKLLVLLC TFTATYADTI CIGYHANNST DTVDTVLEKN VTVTHSVNLG SGLRMVTGLR  60
```

```
NIPQRETRGL FGAIAGFIEG GWTGMVDGWY GYHHQNEQGS GYAADQKSTQ NAINGITNMV  120
NSVIEKMGGN GTGADLAELL VLLLNQWTLL FHDSNVKNLY EKVKSQLKNN AKEIGNGCFE  180
FYHKCNNECM ESVKNGTYDY PKYSEESKLN REKID                             215

SEQ ID NO: 102         moltype = DNA  length = 645
FEATURE                Location/Qualifiers
misc_feature           1..645
                       note = Synthetic
source                 1..645
                       mol_type = other DNA
                       organism = synthetic construct
SEQUENCE: 102
gtcaatttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaacagca gagtccactg gttcagcagc agcaccagca gctcagccag  240
gtcagctcca gtgccatttc cgcccatttt ttcgatgaca gaattcacca tgttagtaat  300
gccattgatt gcgttctgtg tagacttctg atcagcggcg tagccgctgc cctgctcatt  360
ctgatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat                  645

SEQ ID NO: 103         moltype = DNA  length = 645
FEATURE                Location/Qualifiers
misc_feature           1..645
                       note = Synthetic
source                 1..645
                       mol_type = other DNA
                       organism = synthetic construct
SEQUENCE: 103
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcagcgga ggcaacggaa cagacctggc tgagctgctg  420
gtgctgctgc tgaaccagtg gactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                  645

SEQ ID NO: 104         moltype = AA  length = 215
FEATURE                Location/Qualifiers
REGION                 1..215
                       note = Synthetic
source                 1..215
                       mol_type = protein
                       organism = synthetic construct
SEQUENCE: 104
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGSG GNGTDLAELL VLLLNQWTLL FHDSNVKNLY EKVKSQLKNN AKEIGNGCFE  180
FYHKCNNECM ESVKNGTYDY PKYSEESKLN REKID                             215

SEQ ID NO: 105         moltype = DNA  length = 645
FEATURE                Location/Qualifiers
misc_feature           1..645
                       note = Synthetic
source                 1..645
                       mol_type = other DNA
                       organism = synthetic construct
SEQUENCE: 105
gtcaatttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaacagca gagtccactg gttcagcagc agcaccagca gctcagccag  240
gtctgttccg ttgcctccgc tgcccatttt ttcgatgaca gaattcacca tgttagtaat  300
gccattgatt gcgttctgtg tagacttctg atcagcggcg tagccgctgc cctgctcatt  360
ctgatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat                  645

SEQ ID NO: 106         moltype = DNA  length = 1149
FEATURE                Location/Qualifiers
```

```
misc_feature            1..1149
                        note = Synthetic
source                  1..1149
                        mol_type = other DNA
                        organism = synthetic construct
SEQUENCE: 106
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcagcgga ggctccggaa cagacctggc tgagctgctg  420
gtgctgctgc tgaaccagtg gactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgacagtgg gggcgacatc  660
atcaagctgc tgaacgaaca ggtgaacaag gagatgcaga gctccaacct gtacatgagt  720
atgtctagtt ggtgttatac acactcactg gacggcgctg ggctgttcct gtttgatcac  780
gcagccgagg aatacgaaca tgcaaagaaa ctgatcattt tcctgaatga gaacaatgtg  840
cccgtccagc tgacttcaat cagcgcccct gaacataagt tcgagggcct gacccagatc  900
tttcagaaag cttacgaaca cgagcagcat atttccgaat ctatcaacaa tattgtggac  960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtca                                                          1149

SEQ ID NO: 107          moltype = AA  length = 383
FEATURE                 Location/Qualifiers
REGION                  1..383
                        note = Synthetic
source                  1..383
                        mol_type = protein
                        organism = synthetic construct
SEQUENCE: 107
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGSG GSGTDLAELL VLLLNQWTLL FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                          383

SEQ ID NO: 108          moltype = DNA  length = 1149
FEATURE                 Location/Qualifiers
misc_feature            1..1149
                        note = Synthetic
source                  1..1149
                        mol_type = other DNA
                        organism = synthetic construct
SEQUENCE: 108
tgacccactt tttctggact tggcaatgcc cttcacatac tgatctgcca ggtacaggcc  60
atgattctcg tttccaatca gttcgatttt atccaggatg tccttaaaca ggacctcctc  120
ctcgtgctgc tcggccacgt accactgcag aaagttgaag gtagcatgat ctttgctctt  180
aatggcgtgg tccacaatat tgttgataga ttcggaaata tgctgctcgt gttcgtaagc  240
tttctgaaag atctgggtca ggccctcgaa cttatgttca ggggcgctga ttgaagtcag  300
ctggacgggc acattgttct cattcaggaa aatgatcagt ttctttgcat gttcgtattc  360
ctcggctgcg tgatcaaaca ggaacagccc agcgccgtcc agtgagtgtg tataacacca  420
actagacata ctcatgtaca ggttggagct ctgcatctcc ttgttcacct gttcgttcag  480
cagcttgatg atgtcgcccc cactgtcaat tttctctcga ttcagcttac tctcttcaga  540
atatttggga tagtcgtaag tgccgttctt cacagactcc atacattcat tgttgcactt  600
atggtaaaac tcgaagcatc cattcccgat ttctttggca ttgttcttca gctgggattt  660
gaccttctca tacagattct tcacgttgct atcgtggaac agcagagtcc actggttcag  720
cagcagcacc agcagctcag ccaggtctgt tccggagcct ccgctgccca tttttttcgat  780
gacagaattc accatgttag taatgccatt gattgcgttc tgtgtagact tctgatcagc  840
ggcgtagccg ctgccctgct cattctgatg gtggtagccg taccacccgt ccaccattcc  900
tgtccacccg ccctcaataa accctgcgat agcgccgaac agtcctcttg tttcccgctg  960
tgggatgttg cgcagtccgg tgaccatcct cagtccgctg cccagattca ctgagtgggt  1020
gacagtcacg ttcttctcca ggacggtatc cactgtgtcg gtggagttgt ttgcgtgata  1080
gccgatgcag atagtgtcag cgtaggttgc ggtaaaagta cacagcagga ccagcagttt  1140
ggccttcat                                                          1149

SEQ ID NO: 109          moltype = DNA  length = 1149
FEATURE                 Location/Qualifiers
misc_feature            1..1149
                        note = Synthetic
source                  1..1149
                        mol_type = other DNA
                        organism = synthetic construct
```

SEQUENCE: 109
atgaaggcaa tcctggtcgt cctgctgtat actttcgcta ccgctaacgc tgacaccctg 60
tgcatcggct atcacgctaa caactcaacc gacacagtgg atactgtcct ggagaagaac 120
gtgactgtca cccactctgt gaatctgggc agtggactga ggctggcaac tggactgcga 180
aacatcccac agcgggaaac cagaggactg ttcggcgcta tcgcagggtt tattgagggc 240
gggtggacag gaatggtgga cgggtggtac ggctaccacc atcagaacga gcagggatca 300
ggctacgccg ctgacctgaa gagcacacag aatgcaatcg atgaaattac taacatggtg 360
aattccgtca tcgagaaaat gggcagcgga ggctccggaa ccgacctggc agaactgctg 420
gtgctgctgc tgaaccagtg gacactgctg taccacgata gtaacgtgaa gaatctgtat 480
gagaaagtcc gatcacagct gaagaacaat gctaaagaaa tcgggaatgg atgcttcgag 540
ttttaccata agtgcgacaa cacctgtatg gagagcgtga aaaatggcac atacgattat 600
cccaagtatt ccgaggaagc caaactgaac agagaggaaa ttgactctgg gggcgacatc 660
atcaagctgc tgaacgaaca ggtcaacaag gagatgcaga gctccaatct gtacatgtcc 720
atgtctagtt ggtgttatac ccactctctg gacggcgctg ggctgttcct gtttgatcac 780
gcagccgagg aatacgaaca tgcaaagaaa ctgatcattt tcctgaacga gaacaatgtg 840
cccgtccagc tgacatcaat cagcgcccct gaacataagt tcgagggcct gactcagatc 900
tttcagaaag cttacgaaca cgagcagcat atttccgaat ctatcaacaa tattgtggac 960
cacgccatta agagtaaaga tcatgctacc ttcaattttc tgcagtggta cgtggccgag 1020
cagcacgagg aggaggtcct gtttaaggac atcctggata aaatcgaact gattggaaac 1080
gagaatcatg gcctgtacct ggcagatcag tatgtgaagg gcattgccaa gagccggaaa 1140
agtgggtca 1149

SEQ ID NO: 110 moltype = AA length = 383
FEATURE Location/Qualifiers
REGION 1..383
note = Synthetic
source 1..383
mol_type = protein
organism = synthetic construct
SEQUENCE: 110
MKAKLLVLLC TFTATYADTL CIGYHANNST DTVDTVLEKN VTVTHSVNLG SGLRLATGLR 60
NIPQRETRGL FGAIAGFIEG GWTGMVDGWY GYHHQNEQGS GYAADLKSTQ NAIDEITNMV 120
NSVIEKMGSG GSGTDLAELL VLLLNQWTLL YHDSNVKNLY EKVRSQLKNN AKEIGNGCFE 180
FYHKCDNTCM ESVKNGTYDY PKYSEEAKLN REKIDSGGDI IKLLNEQVNK EMQSSNLYMS 240
MSSWCYTHSL DGAGLFLFDH AAEEYEHAKK LIIFLNENNV PVQLTSISAP EHKFEGLTQI 300
FQKAYEHEQH ISESINNIVD HAIKSKDHAT FNFLQWYVAE QHEEEVLFKD ILDKIELIGN 360
ENHGLYLADQ YVKGIAKSRK SGS 383

SEQ ID NO: 111 moltype = DNA length = 1149
FEATURE Location/Qualifiers
misc_feature 1..1149
note = Synthetic
source 1..1149
mol_type = other DNA
organism = synthetic construct
SEQUENCE: 111
tgacccactt ttccggctct tggcaatgcc cttcacatac tgatctgcca ggtacaggcc 60
atgattctcg tttccaatca gttcgatttt atccaggatg tccttaaaca ggacctcctc 120
ctcgtgctgc tcggccacgt accactgcag aaaattgaag gtagcatgat ctttactctt 180
aatggcgtgg tccacaatat tgttgataga ttcggaaata tgctgctcgt gttcgtaagc 240
tttctgaaag atctgagtca ggccctcgaa cttatgttca ggggcgctga ttgatgtcag 300
ctggacgggc acattgttct cgttcaggaa aatgatcagt ttctttgcat gttcgtattc 360
ctcggctgcg tgatcaaaca ggaacagccc agcgccgtcc agagagtggg tataacacca 420
actagacatg gacatgtaca gattggagct ctgcatctcc ttgttgacct gttcgttcag 480
cagcttgatg atgtcgcccc cagagtcaat ttcctctctg ttcagtttgg cttcctcgga 540
atacttggga taatcgtatg tgccattttt cacgctctcc atacaggtgt tgtcgcactt 600
atggtaaaac tcgaagcatc cattcccgat ttctttagca ttgttcttca gctgtgatcg 660
gactttctca tacagattct tcacgttact atcgtggtac agcagtgtcc actggttcag 720
cagcagcacc agcagttctg ccaggtcggt tccggagcct ccgctgccca ttttctcgat 780
gacggaattc accatgttag taatttcatc gattgcattc tgtgtgctct tcaggtcagc 840
ggcgtagcct gatccctgct cgttctgatg gtggtagccg taccacccgt ccaccattcc 900
tgtccacccg ccctcaataa accctgcgat agcgccgaac agtcctctgg tttcccgctg 960
tgggatgttt cgcagtccag ttgccagcct cagtccactg cccagattca cagagtgggt 1020
gacagtcacg ttcttctcca ggacagtatc cactgtgtcg gttgagttgt tagcgtgata 1080
gccgatgcac agggtgtcag cgttagcggt agcgaaagta tacagcagga cgaccaggat 1140
tgccttcat 1149

SEQ ID NO: 112 moltype = DNA length = 1143
FEATURE Location/Qualifiers
misc_feature 1..1143
note = Synthetic
source 1..1143
mol_type = other DNA
organism = synthetic construct
SEQUENCE: 112
atggctatca tctacctgat cctgctgttc actgctgtgc ggggggacca gatttgcatc 60
ggctaccacg ctaataattc aactgagaag gtggatacta tcctggagcg gaacgtgacc 120
gtcacacacg ctaaagacat tggcagcgga ctggtgctgg caaccggact gaggaatgtc 180
ccacagatcg agtcccgcgg actgttcggc gctatcgcag ggtttattga aggcgggtgg 240

```
cagggaatga ttgatgggtg gtacggctac caccattcta acgaccaagg aagtggctac  300
gccgctgata aggagagtac tcagaaagcc ttcgatggca tcaccaacat ggtgaattca  360
gtcattgaga agatgggcag cggaggctcc ggaaccgacc tggcagaact gctggtgctg  420
ctgctgaatc agtggacact gctgtttcac gactctaacg tgaagaatct gtatgataaa  480
gtccggatgc agctgagaga caacgtgaag gagctgggga atggatgctt cgaattttac  540
cataagtgcg acgatgagtg tatgaacagt gtcaaaaatg gcacatacga ttatcccaag  600
tatgaggaag agtcaaaact gaaccgaaat gaaatcaaga gcgggggcga catcatcaag  660
ctgctgaacg agcaagtgaa taaggaaatg cagagctcca acctgtacat gtccatgtct  720
agttggtgtt atactcactc tctggatggc gccgggctgt tcctgtttga ccacgcagcc  780
gaagagtacg agcatgctaa gaaactgatc attttcctga acgaaaacaa cgtgcccgtc  840
cagctgacat caatcagcgc acctgagcat aagttcgaag gcctgactca gatctttcag  900
aaagcttacg agcacgaaca gcatatttcc gagtctatca acaatattgt ggaccacgcc  960
atcaagagca aagatcatgc taccttcaac tttctgcagt ggtacgtggc cgagcagcac  1020
gaagaggaag tcctgtttaa ggacatcctg gataaaatcg agctgattgg aaacgaaaat  1080
catggcctgt acctggcaga ccagtatgtg aagggcattg ccaagtccag aaaaagtggg  1140
tca                                                                1143
```

```
SEQ ID NO: 113         moltype = AA  length = 381
FEATURE                Location/Qualifiers
REGION                 1..381
                       note = Synthetic
source                 1..381
                       mol_type = protein
                       organism = synthetic construct
SEQUENCE: 113
MAIIYLILLF TAVRGDQICI GYHANNSTEK VDTILERNVT VTHAKDIGSG LVLATGLRNV  60
PQIESRGLFG AIAGFIEGGW QGMIDGWYGY HHSNDQGSGY AADKESTQKA FDGITNMVNS  120
VIEKMGSGGS GTDLAELLVL LLNQWTLLFH DSNVKNLYDK VRMQLRDNVK ELGNGCFEFY  180
HKCDDECMNS VKNGTYDYPK YEEESKLNRN EIKSGGDIIK LLNEQVNKEM QSSNLYMSMS  240
SWCYTHSLDG AGLFLFDHAA EEYEHAKKLI IFLNENNVPV QLTSISAPEH KFEGLTQIFQ  300
KAYEHEQHIS ESINNIVDHA IKSKDHATFN FLQWYVAEQH EEEVLFKDIL DKIELIGNEN  360
HGLYLADQYV KGIAKSRKSG S                                            381
```

```
SEQ ID NO: 114         moltype = DNA  length = 1143
FEATURE                Location/Qualifiers
misc_feature           1..1143
                       note = Synthetic
source                 1..1143
                       mol_type = other DNA
                       organism = synthetic construct
SEQUENCE: 114
tgacccactt tttctggact tggcaatgcc cttcacatac tggtctgcca ggtacaggcc  60
atgattttcg tttccaatca gctcgatttt atccaggatg tccttaaaca ggacttcctc  120
ttcgtgctgc tcggccacgt accactgcag aaagttgaag gtagcatgat ctttgctctt  180
gatggcgtgg tccacaatat tgttgataga ctcggaaata tgctgttcgt gctcgtaagc  240
tttctgaaag atctgagtca ggccttcgaa cttatgctca ggtgcgctga ttgatgtcag  300
ctggacgggc acgttgtttt cgttcaggaa aatgatcagt ttcttagcat gctcgtactc  360
ttcggctgcg tggtcaaaca ggaacagccc ggcgccatcc agagagtgag tataacacca  420
actagacatg gacatgtaca ggttggagct ctgcatttcc ttattcactt gctcgttcag  480
cagcttgatg atgtcgcccc cgctcttgat ttcatttcgg ttcagttttg actcttcctc  540
atacttggga taatcgtatg tgccattttt gacactgttc atacactcat cgtcgcactt  600
atggtaaaat tcgaagcatc cattccccag ctccttcacg ttgtctctca gctgcatccg  660
gactttatca tacagattct tcacgttaga gtcgtgaaac agcagtgtcc actgattcag  720
cagcagcacc agcagttctg ccaggtcggt tccggagcct ccgctgccca tcttctcaat  780
gactgaattc accatgttgg tgatgccatc gaaggctttc tgagtactct ccttatcagc  840
ggcgtagcca cttccttggt cgttagaatg gtggtagccg taccacccat caatcattcc  900
ctgccacccg ccttcaataa accctgcgat agcgccgaac agtccgcggg actcgatctg  960
tgggacattc ctcagtccgg ttgccagcac cagtccgctg ccaatgtctt tagcgtgtgt  1020
gacggtcacg ttccgctcca ggatagtatc caccttctca gttgaattat tagcgtggta  1080
gccgatgcaa atctggtccc cccgcacagc agtgaacagc aggatcaggt agatgatagc  1140
cat                                                                1143
```

```
SEQ ID NO: 115         moltype = DNA  length = 1158
FEATURE                Location/Qualifiers
misc_feature           1..1158
                       note = Synthetic
source                 1..1158
                       mol_type = other DNA
                       organism = synthetic construct
SEQUENCE: 115
atggaaaaaa tcgtgctgct gctggctatc gtgtccctgg tgaagtccga ccagatctgt  60
attgggtatc atgctaacaa ctccacagaa caggtggata ctatcatgga gaagaacgtg  120
accgtcacac acgctcagga cattggatgg ggactggtcc tggcaaccgg actgagaaat  180
tcaccacaga gggaaagccg gagaaagaaa cgcggactgt tcggcgctat cgcagggttt  240
attgagggcg ggtggcaggg aatggtggat gggtggtacg gctaccacca ttccaacgaa  300
cagggatctg gctacgccgc tgataaggag tctactcaga aagctatcga cggcgtgacc  360
aacatggtca atagtatcat tgataagatg ggctctggag gcagtggaac cgacctggca  420
gagctgctgg tgctgctgct gaaccagtgg acactgctgt tccacgactc taacgtgaag  480
aatctgtatg ataaagtccg actgcagctg cgggacaacg ccaaggaact ggggaatgga  540
```

```
tgcttcgagt tctaccataa gtgcgataac gaatgtatgg agagcatccg aaacggcaca  600
tacaattatc cccagtattc cgaggaagct aggctgaaac gcgaggaaat tagctccggg  660
ggagacatca ttaagctgct gaacgaacag gtgaacaagg agatgcagtc tagtaacctg  720
tacatgagta tgtcaagctg gtgttatact cactcactgg atggcgccgg gctgttcctg  780
tttgaccacg cagccgagga atacgaacat gctaagaaac tgatcatttt cctgaatgag  840
aacaatgtgc ccgtccagct gacatccatc tctgcacctg aacataagtt cgagggcctg  900
actcagatct ttcagaaagc ctacgaacac gagcagcata ttagtgagtc aatcaacaat  960
attgtggacc acgccatcaa gagcaaagat catgctacct tcaattttct gcagtggtac  1020
gtggccgagc agcacgagga agaggtcctg tttaaggaca tcctggataa aatcgaactg  1080
attggaaacg agaatcatgg cctgtacctg gcagaccagt atgtgaaggg cattgccaag  1140
tccaggaaaa gcgggtcc                                                1158

SEQ ID NO: 116          moltype = AA  length = 386
FEATURE                 Location/Qualifiers
REGION                  1..386
                        note = Synthetic
source                  1..386
                        mol_type = protein
                        organism = synthetic construct
SEQUENCE: 116
MEKIVLLLAI VSLVKSDQIC IGYHANNSTE QVDTIMEKNV TVTHAQDIGW GLVLATGLRN  60
SPQRESRRKK RGLFGAIAGF IEGGWQGMVD GWYGYHHSNE QGSGYAADKE STQKAIDGVT  120
NMVNSIIDKM GSGGSGTDLA ELLVLLLNQW TLLFHDSNVK NLYDKVRLQL RDNAKELGNG  180
CFEFYHKCDN ECMESIRNGT YNYPQYSEEA RLKREEISSG GDIIKLLNEQ VNKEMQSSNL  240
YMSMSSWCYT HSLDGAGLFL FDHAAEEYEH AKKLIIFLNE NNVPVQLTSI SAPEHKFEGL  300
TQIFQKAYEH EQHISESINN IVDHAIKSKD HATFNFLQWY VAEQHEEEVL FKDILDKIEL  360
IGNENHGLYL ADQYVKGIAK SRKSGS                                       386

SEQ ID NO: 117          moltype = DNA  length = 1158
FEATURE                 Location/Qualifiers
misc_feature            1..1158
                        note = Synthetic
source                  1..1158
                        mol_type = other DNA
                        organism = synthetic construct
SEQUENCE: 117
ggacccgctt ttcctggact tggcaatgcc cttcacatac tggtctgcca ggtacaggcc  60
atgattctcg tttccaatca gttcgatttt atccaggatg tccttaaaca ggacctcttc  120
ctcgtgctgc tcggccacgt accactgcag aaaattgaag gtagcatgat ctttgctctt  180
gatggcgtgg tccacaatat tgttgattga ctcactaata tgctgctcgt gttcgtaggc  240
tttctgaaag atctgagtca ggccctcgaa cttatgttca ggtgcagaga tggatgtcag  300
ctggacgggc acattgttct cattcaggaa aatgatcagt ttcttagcat gttcgtattc  360
ctcggctgcg tggtcaaaca ggaacagccc ggcgccatcc agtgagtgag tataacacca  420
gcttgacata ctcatgtaca ggttactaga ctgcatctcc ttgttcacct gttcgttcag  480
cagcttaatg atgtctcccc cggagctaat ttcctcgcgt ttcagcctag cttcctcgga  540
atactgggga taattgtatg tgccgtttcg gatgctctcc atacattcgt tatcgcactt  600
atggtagaac tcgaagcatc cattccccag ttccttggcg ttgtcccgca gctgcagtcg  660
gactttatca tacagattct tcacgttaga gtcgtggaac agcagtgtcc actggttcag  720
cagcagcacc agcagctctg ccaggtcggt tccactgcct ccagagccca tcttatcaat  780
gatactattg accatgttgg tcacgccgtc gatagctttc tgagtagact ccttatcagc  840
ggcgtagcca gatccctgtt cgttggaatg gtggtagccg taccacccat ccaccattcc  900
ctgccacccg ccctcaataa accctgcgat agcgccgaac agtccgcgtt tctttctccg  960
gctttccctc tgtggtgaat ttctcagtcc ggttgccagg accagtcccc atccaatgtc  1020
ctgagcgtgt gtgacggtca cgttcttctc catgatagta tccacctgtt ctgtggagtt  1080
gttagcatga tacccaatac agatctggtc ggacttcacc agggacacga tagccagcag  1140
cagcacgatt ttttccat                                                1158

SEQ ID NO: 118          moltype = DNA  length = 1149
FEATURE                 Location/Qualifiers
misc_feature            1..1149
                        note = Synthetic
source                  1..1149
                        mol_type = other DNA
                        organism = synthetic construct
SEQUENCE: 118
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcagcgga ggctccggaa cagacctggc tgagctgctg  420
gtgctgctgc tgaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgacagtgg gggcgacatc  660
atcaagctgc tgaacgaaca ggtgaacaag gagatgcaga gctccaacct gtacatgagt  720
atgtctagtt ggtgttatac acactcactg gacggcgctg ggctgttcct gtttgatcac  780
gcagccgagg aatacgaaca tgcaaagaaa ctgatcattt tcctgaatga gaacaatgtg  840
```

```
cccgtccagc tgacttcaat cagcgcccct gaacataagt tcgagggcct gacccagatc  900
tttcagaaag cttacgaaca cgagcagcat atttccgaat ctatcaacaa tattgtggac  960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtca                                                          1149

SEQ ID NO: 119          moltype = AA  length = 383
FEATURE                 Location/Qualifiers
REGION                  1..383
                        note = Synthetic
source                  1..383
                        mol_type = protein
                        organism = synthetic construct
SEQUENCE: 119
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                          383

SEQ ID NO: 120          moltype = DNA  length = 1149
FEATURE                 Location/Qualifiers
misc_feature            1..1149
                        note = Synthetic
source                  1..1149
                        mol_type = other DNA
                        organism = synthetic construct
SEQUENCE: 120
tgacccactt tttctggact tggcaatgcc cttcacatac tgatctgcca ggtacaggcc  60
atgattctcg tttccaatca gttcgatttt atccaggatg tccttaaaca ggacctcctc  120
ctcgtgctgc tcggccacgt accactgcag aaagttgaag gtagcatgat ctttgctctt  180
aatggcgtgg tccacaatat tgttgataga ttcggaaata tgctgctcgt gttcgtaagc  240
tttctgaaag atctgggtca ggccctcgaa cttatgttca ggggcgctga ttgaagtcag  300
ctggacgggc acattgttct cattcaggaa aatgatcagt ttctttgcat gttcgtattc  360
ctcggctgcg tgatcaaaca ggaacagccc agcgccgtcc agtgagtgtg tataacacca  420
actagacata ctcatgtaca ggttggagct ctgcatctcc ttgttcacct gttcgttcag  480
cagcttgatg atgtcgcccc cactgtcaat ttctctcgat ttcagcttac tctcttcaga  540
atatttggga tagtcgtaag tgccgttctt cacagactcc atacattcat tgttgcactt  600
atggtaaaac tcgaagcatc cattcccgat ttctttggca ttgttcttca gctgggattt  660
gaccttctca tacagattct tcacgttgct atcgtggaaa tccagagtcc gctcgttcag  720
cagcagcacc agcagctcag ccaggtctgt tccggagcct ccgctgccca ttttttcgat  780
gacagaattc accatgttag taatgccatt gattgcgttc tgtgtagact tctgatcagc  840
ggcgtagccg ctgccctgct cattctgatg gtggtagccg taccacccgt ccaccattcc  900
tgtccacccg ccctcaataa accctgcgat agcgccgaac agtcctcttg tttcccgctg  960
tgggatgttg cgcagtccgg tgaccatcct cagtccgctg cccagattca ctgagtgggt  1020
gacagtcacg ttcttctcca ggacggtatc cactgtgtcg gtggagttgt ttgcgtgata  1080
gccgatgcag atagtgtcag cgtaggttgc ggtaaaagta cacagcagga ccagcagttt  1140
ggccttcat                                                          1149

SEQ ID NO: 121          moltype = DNA  length = 1149
FEATURE                 Location/Qualifiers
misc_feature            1..1149
                        note = Synthetic
source                  1..1149
                        mol_type = other DNA
                        organism = synthetic construct
SEQUENCE: 121
atgaaggcca aactgctggt cctgctgtgt acttttaccg caacctacgc tgacactatc  60
tgcatcggct atcacgcaaa caactccacc gacacagtgg ataccattct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcagcgga ggctccggaa cagacctggc tgagctgctg  420
gtgctgatgc tgaaccagtt cactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgacagtgg gggcgacatc  660
atcaagctgc tgaacgaaca ggtgaacaag gagatgcaga gctccaacct gtacatgagt  720
atgtctagtt ggtgttatac acactcactg gacggcgctg ggctgttcct gtttgatcac  780
gcagccgagg aatacgaaca tgcaaagaaa ctgatcattt tcctgaatga gaacaatgtg  840
cccgtccagc tgacttcaat cagcgcccct gaacataagt tcgagggcct gacccagatc  900
tttcagaaag cttacgaaca cgagcagcat atttccgaat ctatcaacaa tattgtggac  960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
```

-continued

```
agtgggtca                                                             1149

SEQ ID NO: 122          moltype = AA  length = 383
FEATURE                 Location/Qualifiers
REGION                  1..383
                        note = Synthetic
source                  1..383
                        mol_type = protein
                        organism = synthetic construct
SEQUENCE: 122
MKAKLLVLLC TFTATYADTI CIGYHANNST DTVDTILEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGSG GSGTDLAELL VLMLNQFTLL FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                             383

SEQ ID NO: 123          moltype = DNA  length = 1149
FEATURE                 Location/Qualifiers
misc_feature            1..1149
                        note = Synthetic
source                  1..1149
                        mol_type = other DNA
                        organism = synthetic construct
SEQUENCE: 123
tgacccactt tttctggact tggcaatgcc cttcacatac tgatctgcca ggtacaggcc  60
atgattctcg tttccaatca gttcgatttt atccaggatg tccttaaaca ggacctcctc  120
ctcgtgctgc tcggccacgt accactgcag aaagttgaag gtagcatgat ctttgctctt  180
aatggcgtgg tccacaatat tgttgataga ttcggaaata tgctgctcgt gttcgtaagc  240
tttctgaaag atctgggtca ggccctcgaa cttatgttca ggggcgctga ttgaagtcag  300
ctggacgggc acattgttct cattcaggaa aatgatcagt ttctttgcat gttcgtattc  360
ctcggctgcg tgatcaaaca ggaacagccc agcgccgtcc agtgagtgtg tataacacca  420
actagacata ctcatgtaca ggttggagct ctgcatctcc ttgttcacct gttcgttcag  480
cagcttgatg atgtcgcccc cactgtcaat ttctctcgga ttcagcttac tctcttcaga  540
atatttggga tagtcgtaag tgccgttctt cacagactcc atacattcat tgttgcactt  600
atggtaaaac tcgaagcatc cattcccgat ttctttggca ttgttcttca gctgggattt  660
gaccttctca tacagattct tcacgttgct atcgtggaac agcagagtga actggttcag  720
catcagcacc agcagctcag ccaggtctgt tccggagcct ccgctgccca ttttttcgat  780
gacagaattc accatgttag taatgccatt gattgcgttc tgtgtagact tctgatcagc  840
ggcgtagccg ctgccctgct cattctgatg gtggtagccg taccacccgt ccaccattcc  900
tgtccacccg ccctcaataa accctgcgat agcgccgaac agtcctcttg tttcccgctg  960
tgggatgttg cgcagtccgg tgaccatcct cagtccgctg cccagattca ctgagtgggt  1020
gacagtcacg ttcttctcca gaatggtatc cactgtgtcg gtggagttgt ttgcgtgata  1080
gccgatgcag atagtgtcag cgtaggttgc ggtaaaagta cacagcagga ccagcagttt  1140
ggccttcat                                                             1149

SEQ ID NO: 124          moltype = DNA  length = 1149
FEATURE                 Location/Qualifiers
misc_feature            1..1149
                        note = Synthetic
source                  1..1149
                        mol_type = other DNA
                        organism = synthetic construct
SEQUENCE: 124
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcaatgga acaggcggag ctgacctggc tgagctgctg  420
gtgctgctgc tgaaccagtg gactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgacagtgg gggcgacatc  660
atcaagctgc tgaacgaaca ggtgaacaag gagatgcaga gctccaacct gtacatgagt  720
atgtctagtt ggtgttatac acactcactg gacggcgctg ggctgttcct gtttgatcac  780
gcagccgagg aatacgaaca tgcaaagaaa ctgatcattt tcctgaatga gaacaatgtg  840
cccgtccagc tgacttcaat cagcgcccct gaacataagt tcgagggcct gacccagatc  900
tttcagaaag cttacgaaca cgagcagcat atttccgaat ctatcaacaa tattgtggac  960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtca                                                             1149

SEQ ID NO: 125          moltype = AA  length = 383
FEATURE                 Location/Qualifiers
REGION                  1..383
```

```
                         note = Synthetic
source                   1..383
                         mol_type = protein
                         organism = synthetic construct
SEQUENCE: 125
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGNG TGGADLAELL VLLLNQWTLL FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                         383

SEQ ID NO: 126           moltype = DNA  length = 1149
FEATURE                  Location/Qualifiers
misc_feature             1..1149
                         note = Synthetic
source                   1..1149
                         mol_type = other DNA
                         organism = synthetic construct
SEQUENCE: 126
tgacccactt tttctggact tggcaatgcc cttcacatac tgatctgcca ggtacaggcc  60
atgattctcg tttccaatca gttcgatttt atccaggatg tccttaaaca ggacctcctc  120
ctcgtgctgc tcggccacgt accactgcag aaagttgaag gtagcatgat ctttgctctt  180
aatggcgtgg tccacaatat tgttgataga ttcggaaata tgctgctcgt gttcgtaagc  240
tttctgaaag atctgggtca ggccctcgaa cttatgttca ggggcgctga ttgaagtcag  300
ctggacgggc acattgttct cattcaggaa aatgatcagt ttctttgcat gttcgtattc  360
ctcggctgcg tgatcaaaca ggaacagccc agcgccgtcc agtgagtgtg tataacacca  420
actagacata ctcatgtaca ggttggagct ctgcatctcc ttgttcacct gttcgttcag  480
cagcttgatg atgtcgcccc cactgtcaat ttctctcgga ttcagcttac tctcttcaga  540
atatttggga tagtcgtaag tgccgttctt cacagactcc atacattcat tgttgcactt  600
atggtaaaac tcgaagcatc cattcccgat ttctttggca ttgttcttca gctgggattt  660
gaccttctca tacagattct tcacgttgct atcgtggaac agcagagtcc actggttcag  720
cagcagcacc agcagctcag ccaggtcagc tccgcctgtt ccattgccca ttttttcgat  780
gacagaattc accatgttag taatgccatt gattgcgttc tgtgtagact tctgatcagc  840
ggcgtagccg ctgccctgct cattctgatg gtggtagccg taccacccgt ccaccattcc  900
tgtccacccg ccctcaataa accctgcgat agcgccgaac agtcctcttg tttcccgctg  960
tgggatgttg cgcagtccgg tgaccatcct cagtccgctg cccagattca ctgagtgggt  1020
gacagtcacg ttcttctcca ggacggtatc cactgtgtcg gtggagttgt ttgcgtgata  1080
gccgatgcag atagtgtcag cgtaggttgc ggtaaaagta cacagcagga ccagcagttt  1140
ggccttcat                                                         1149

SEQ ID NO: 127           moltype = DNA  length = 1149
FEATURE                  Location/Qualifiers
misc_feature             1..1149
                         note = Synthetic
source                   1..1149
                         mol_type = other DNA
                         organism = synthetic construct
SEQUENCE: 127
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcggaaat ggcactggag ctgacctggc tgagctgctg  420
gtgctgctgc tgaaccagtg gactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgacagtgg gggcgacatc  660
atcaagctgc tgaacgaaca ggtgaacaag gagatgcaga gctccaacct gtacatgagt  720
atgtctagtt ggtgttatac acactcactg gacggcgctg ggctgttcct gtttgatcac  780
gcagccgagg aatacgaaca tgcaaagaaa ctgatcattt tcctgaatga gaacaatgtg  840
cccgtccagc tgacttcaat cagcgcccct gaacataagt tcgagggcct gacccagatc  900
tttcagaaag cttacgaaca cgagcagcat atttccgaat ctatcaacaa tattgtggac  960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtca                                                         1149

SEQ ID NO: 128           moltype = AA  length = 383
FEATURE                  Location/Qualifiers
REGION                   1..383
                         note = Synthetic
source                   1..383
                         mol_type = protein
                         organism = synthetic construct
SEQUENCE: 128
```

-continued

```
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGGN GTGADLAELL VLLLNQWTLL FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                         383

SEQ ID NO: 129          moltype = DNA  length = 1149
FEATURE                 Location/Qualifiers
misc_feature            1..1149
                        note = Synthetic
source                  1..1149
                        mol_type = other DNA
                        organism = synthetic construct
SEQUENCE: 129
tgacccactt tttctggact tggcaatgcc cttcacatac tgatctgcca ggtacaggcc  60
atgattctcg tttccaatca gttcgatttt atccaggatg tccttaaaca ggacctcctc  120
ctcgtgctgc tcggccacgt accactgcag aaagttgaag gtagcatgat ctttgctctt  180
aatggcgtgg tccacaatat tgttgataga ttcggaaata tgctgctcgt gttcgtaagc  240
tttctgaaag atctgggtca ggccctcgaa cttatgttca ggggcgctga ttgaagtcag  300
ctggacgggc acattgttct cattcaggaa aatgatcagt ttctttgcat gttcgtattc  360
ctcggctgcg tgatcaaaca ggaacagccc agcgccgtcc agtgagtgtg tataacacca  420
actagacata ctcatgtaca ggttggagct ctgcatctcc ttgttcacct gttcgttcag  480
cagcttgatg atgtcgcccc cactgtcaat ttctctcga ttcagcttac tctcttcaga  540
atatttggga tagtcgtaag tgccgttctt cacagactcc atacattcat tgttgcactt  600
atggtaaaac tcgaagcatc cattcccgat ttctttggca ttgttcttca gctgggattt  660
gaccttctca tacagattct tcacgttgct atcgtggaac agcagagtcc actggttcag  720
cagcagcacc agcagctcag ccaggtcagc tccagtgcca tttccgccca ttttttcgat  780
gacagaattc accatgttag taatgccatt gattgcgttc tgtgtagact tctgatcagc  840
ggcgtagccg ctgccctgct cattctgatg gtggtagccg taccacccgt ccaccattcc  900
tgtccacccg ccctcaataa accctgcgat agcgccgaac agtcctcttg tttcccgctg  960
tgggatgttg cgcagtccgg tgaccatcct cagtccgctg cccagattca ctgagtgggt  1020
gacagtcacg ttcttctcca ggacggtatc cactgtgtcg gtggagttgt ttgcgtgata  1080
gccgatgcag atagtgtcag cgtaggttgc ggtaaaagta cacagcagga ccagcagttt  1140
ggccttcat                                                         1149

SEQ ID NO: 130          moltype = DNA  length = 1149
FEATURE                 Location/Qualifiers
misc_feature            1..1149
                        note = Synthetic
source                  1..1149
                        mol_type = other DNA
                        organism = synthetic construct
SEQUENCE: 130
atgaaggcca aactgctggt cctgctgtgt actttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcagcgga ggcaacggaa cagacctggc tgagctgctg  420
gtgctgctgc tgaaccagtg gactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgacagtgg gggcgacatc  660
atcaagctgc tgaacgaaca ggtgaacaag gagatgcaga gctccaacct gtacatgagt  720
atgtctagtt ggtgttatac acactcactg gacggcgctg ggctgttcct gtttgatcac  780
gcagccgagg aatacgaaca tgcaaagaaa ctgatcattt tcctgaatga gaacaatgtg  840
cccgtccagc tgacttcaat cagcgcccct gaacataagt tcgagggcct gacccagatc  900
tttcagaaag cttacgaaca cgagcagcat atttccgaat ctatcaacaa tattgtggac  960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtca                                                         1149

SEQ ID NO: 131          moltype = AA  length = 383
FEATURE                 Location/Qualifiers
REGION                  1..383
                        note = Synthetic
source                  1..383
                        mol_type = protein
                        organism = synthetic construct
SEQUENCE: 131
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGSG GNGTDLAELL VLLLNQWTLL FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
```

```
FQKAYEHEQH ISESINNIVD HAIKSKDHAT FNFLQWYVAE QHEEEVLFKD ILDKIELIGN  360
ENHGLYLADQ YVKGIAKSRK SGS                                          383

SEQ ID NO: 132          moltype = DNA  length = 1149
FEATURE                 Location/Qualifiers
misc_feature            1..1149
                        note = Synthetic
source                  1..1149
                        mol_type = other DNA
                        organism = synthetic construct
SEQUENCE: 132
tgacccactt tttctggact tggcaatgcc cttcacatac tgatctgcca ggtacaggcc  60
atgattctcg tttccaatca gttcgatttt atccaggatg tccttaaaca ggacctcctc  120
ctcgtgctgc tcggccacgt accactgcag aaagttgaag gtagcatgat ctttgctctt  180
aatggcgtgg tccacaatat tgttgataga ttcggaaata tgctgctcgt gttcgtaagc  240
tttctgaaag atctgggtca ggccctcgaa cttatgttca ggggcgctga ttgaagtcag  300
ctggacgggc acattgttct cattcaggaa aatgatcagt ttctttgcat gttcgtattc  360
ctcggctgcg tgatcaaaca ggaacagccc agcgccgtcc agtgagtgtg tataacacca  420
actagacata ctcatgtaca ggttggagct ctgcatctcc ttgttcacct gttcgttcag  480
cagcttgatg atgtcgcccc cactgtcaat tttctctcga ttcagcttac tctcttcaga  540
atatttggga tagtcgtaag tgccgttctt cacagactcc atacattcat tgttgcactt  600
atggtaaaac tcgaagcatc cattcccgat ttctttggca ttgttcttca gctgggattt  660
gaccttctca tacagattct tcacgttgct atcgtggaac agcagagtcc actggttcag  720
cagcagcacc agcagctcag ccaggtctgt tccgttgcct ccgctgccca ttttttcgat  780
gacagaattc accatgttag taatgccatt gattgcgttc tgtgtagact tctgatcagc  840
ggcgtagccg ctgccctgct cattctgatg gtggtagccg taccacccgt ccaccattcc  900
tgtccacccg ccctcaataa accctgcgat agcgccgaac agtcctcttg tttcccgctg  960
tgggatgttg cgcagtccgg tgaccatcct cagtccgctg cccagattca ctgagtgggt  1020
gacagtcacg ttcttctcca ggacggtatc cactgtgtcg gtggagttgt ttgcgtgata  1080
gccgatgcag atagtgtcag cgtaggttgc ggtaaaagta cacagcagga ccagcagttt  1140
ggccttcat                                                          1149

SEQ ID NO: 133          moltype = AA  length = 33
FEATURE                 Location/Qualifiers
source                  1..33
                        mol_type = protein
                        organism = Influenza A virus
SEQUENCE: 133
NTQFTAVGKE FNKLERRMEN LNKKVDDGFL DIW                               33

SEQ ID NO: 134          moltype = AA  length = 12
FEATURE                 Location/Qualifiers
source                  1..12
                        mol_type = protein
                        organism = Influenza A virus
SEQUENCE: 134
NTQFTAVGKE FN                                                      12

SEQ ID NO: 135          moltype = AA  length = 12
FEATURE                 Location/Qualifiers
source                  1..12
                        mol_type = protein
                        organism = Influenza A virus
SEQUENCE: 135
NKLERRMENL NK                                                      12

SEQ ID NO: 136          moltype = AA  length = 11
FEATURE                 Location/Qualifiers
source                  1..11
                        mol_type = protein
                        organism = Influenza A virus
SEQUENCE: 136
KKVDDGFLDI W                                                       11

SEQ ID NO: 137          moltype = AA  length = 33
FEATURE                 Location/Qualifiers
source                  1..33
                        mol_type = protein
                        organism = Influenza A virus
SEQUENCE: 137
NTQFTAVGKE FNHLEKRIEN LNKKVDDGFL DIW                               33

SEQ ID NO: 138          moltype = AA  length = 11
FEATURE                 Location/Qualifiers
source                  1..11
                        mol_type = protein
                        organism = Influenza A virus
SEQUENCE: 138
NTQFTAVGKE F                                                       11
```

-continued

```
SEQ ID NO: 139          moltype = AA  length = 11
FEATURE                 Location/Qualifiers
source                  1..11
                        mol_type = protein
                        organism = Influenza A virus
SEQUENCE: 139
FNHLEKRIEN L                                                  11

SEQ ID NO: 140          moltype = AA  length = 13
FEATURE                 Location/Qualifiers
source                  1..13
                        mol_type = protein
                        organism = Influenza A virus
SEQUENCE: 140
LNKKVDDGFL DIW                                                13

SEQ ID NO: 141          moltype = AA  length = 33
FEATURE                 Location/Qualifiers
source                  1..33
                        mol_type = protein
                        organism = Influenza A virus
SEQUENCE: 141
NTQFEAVGKE FSNLERRLEN LNKKMEDGFL DVW                          33

SEQ ID NO: 142          moltype = AA  length = 11
FEATURE                 Location/Qualifiers
source                  1..11
                        mol_type = protein
                        organism = Influenza A virus
SEQUENCE: 142
NTQFEAVGKE F                                                  11

SEQ ID NO: 143          moltype = AA  length = 12
FEATURE                 Location/Qualifiers
source                  1..12
                        mol_type = protein
                        organism = Influenza A virus
SEQUENCE: 143
FSNLERRLEN LN                                                 12

SEQ ID NO: 144          moltype = AA  length = 12
FEATURE                 Location/Qualifiers
source                  1..12
                        mol_type = protein
                        organism = Influenza A virus
SEQUENCE: 144
NKKMEDGFLD VW                                                 12

SEQ ID NO: 145          moltype = AA  length = 33
FEATURE                 Location/Qualifiers
source                  1..33
                        mol_type = protein
                        organism = Influenza A virus
SEQUENCE: 145
NTQFEAVGRE FNNLERRIEN LNKKMEDGFL DVW                          33

SEQ ID NO: 146          moltype = AA  length = 11
FEATURE                 Location/Qualifiers
source                  1..11
                        mol_type = protein
                        organism = Influenza A virus
SEQUENCE: 146
NTQFEAVGRE F                                                  11

SEQ ID NO: 147          moltype = AA  length = 12
FEATURE                 Location/Qualifiers
source                  1..12
                        mol_type = protein
                        organism = Influenza A virus
SEQUENCE: 147
FNNLERRIEN LN                                                 12

SEQ ID NO: 148          moltype = AA  length = 12
FEATURE                 Location/Qualifiers
source                  1..12
                        mol_type = protein
                        organism = Influenza A virus
SEQUENCE: 148
```

```
NKKMEDGFLD VW                                                    12

SEQ ID NO: 149          moltype = AA  length = 53
FEATURE                 Location/Qualifiers
source                  1..53
                        mol_type = protein
                        organism = Influenza A virus
SEQUENCE: 149
KVNSVIEKMN TQFTAVGKEF NKLERRMENL NKKVDDGFLD IWTYNAELLV LLE         53

SEQ ID NO: 150          moltype = AA  length = 20
FEATURE                 Location/Qualifiers
source                  1..20
                        mol_type = protein
                        organism = Influenza A virus
SEQUENCE: 150
KVNSVIEKMT YNAELLVLLE                                            20

SEQ ID NO: 151          moltype = AA  length = 53
FEATURE                 Location/Qualifiers
source                  1..53
                        mol_type = protein
                        organism = Influenza A virus
SEQUENCE: 151
KVNSVIEKMN TQFTAVGKEF NHLEKRIENL NKKVDDGFLD IWTYNAELLV LLE         53

SEQ ID NO: 152          moltype = AA  length = 20
FEATURE                 Location/Qualifiers
source                  1..20
                        mol_type = protein
                        organism = Influenza A virus
SEQUENCE: 152
KVNSVIEKMT YNAELLVLLE                                            20

SEQ ID NO: 153          moltype = AA  length = 53
FEATURE                 Location/Qualifiers
source                  1..53
                        mol_type = protein
                        organism = Influenza A virus
SEQUENCE: 153
KVNSVIEKMN TQFEAVGKEF SNLERRLENL NKKMEDGFLD VWTYNAELLV LME         53

SEQ ID NO: 154          moltype = AA  length = 20
FEATURE                 Location/Qualifiers
source                  1..20
                        mol_type = protein
                        organism = Influenza A virus
SEQUENCE: 154
KVNSVIEKMT YNAELLVLME                                            20

SEQ ID NO: 155          moltype = AA  length = 53
FEATURE                 Location/Qualifiers
source                  1..53
                        mol_type = protein
                        organism = Influenza A virus
SEQUENCE: 155
KVNSIIDKMN TQFEAVGREF NNLERRIENL NKKMEDGFLD VWTYNAELLV LME         53

SEQ ID NO: 156          moltype = AA  length = 20
FEATURE                 Location/Qualifiers
source                  1..20
                        mol_type = protein
                        organism = Influenza A virus
SEQUENCE: 156
KVNSIIDKMT YNAELLVLME                                            20

SEQ ID NO: 157          moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 157
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
```

```
ggctacgccg ctgatcagaa gtctacacag aacgcaatca atggcattac taacatggtg  360
aattctgtca tcgaaaaaat gggcagcgga ggctccggaa cagacctggc tgagctgctg  420
gtgctgctga tgaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                   645

SEQ ID NO: 158         moltype = AA  length = 215
FEATURE                Location/Qualifiers
REGION                 1..215
                       note = Synthetic
source                 1..215
                       mol_type = protein
                       organism = synthetic construct
SEQUENCE: 158
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGSG GSGTDLAELL VLLMNERTLD FHDSNVKNLY EKVKSQLKNN AKEIGNGCFE  180
FYHKCNNECM ESVKNGTYDY PKYSEESKLN REKID                              215

SEQ ID NO: 159         moltype = DNA  length = 645
FEATURE                Location/Qualifiers
misc_feature           1..645
                       note = Synthetic
source                 1..645
                       mol_type = other DNA
                       organism = synthetic construct
SEQUENCE: 159
gtcaatttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaaatcca gagtccgctc gttcatcagc agcaccagca gctcagccag  240
gtctgttccg gagcctccgc tgcccatttt ttcgatgaca gaattcacca tgttagtaat  300
gccattgatt gcgttctgtg tagacttctg atcagcggcg tagccgctgc cctgctcatt  360
ctgatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat                   645

SEQ ID NO: 160         moltype = DNA  length = 1149
FEATURE                Location/Qualifiers
misc_feature           1..1149
                       note = Synthetic
source                 1..1149
                       mol_type = other DNA
                       organism = synthetic construct
SEQUENCE: 160
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcagcgga ggctccggaa cagacctggc tgagctgctg  420
gtgctgctga tgaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgacagtgg gggcgacatc  660
atcaagctgc tgaacgaaca ggtgaacaag gagatgcaga gctccaacct gtacatgagt  720
atgtctagtt ggtgttatac acactcactg gacggcgctg ggctgttcct gtttgatcac  780
gcagccgagg aatacgaaca tgcaaagaaa ctgatcattt tcctgaatga gaacaatgtg  840
cccgtccagc tgacttcaat cagcgcccct gaacataagt tcgagggcct gacccagatc  900
tttcagaaag cttacgaaca cgagcagcat atttccgaat ctatcaacaa tattgtggac  960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtca                                                           1149

SEQ ID NO: 161         moltype = AA  length = 383
FEATURE                Location/Qualifiers
REGION                 1..383
                       note = Synthetic
source                 1..383
                       mol_type = protein
                       organism = synthetic construct
SEQUENCE: 161
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
```

-continued

```
NSVIEKMGSG GSGTDLAELL VLLMNERTLD FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                         383

SEQ ID NO: 162          moltype = DNA  length = 1149
FEATURE                 Location/Qualifiers
misc_feature            1..1149
                        note = Synthetic
source                  1..1149
                        mol_type = other DNA
                        organism = synthetic construct
SEQUENCE: 162
tgacccactt tttctggact tggcaatgcc cttcacatac tgatctgcca ggtacaggcc  60
atgattctcg tttccaatca gttcgatttt atccaggatg tccttaaaca ggacctcctc  120
ctcgtgctgc tcggccacgt accactgcag aaagttgaag gtagcatgat ctttgctctt  180
aatggcgtgg tccacaatat tgttgataga ttcggaaata tgctgctcgt gttcgtaagc  240
tttctgaaag atctgggtca ggccctcgaa cttatgttca ggggcgctga ttgaagtcag  300
ctggacgggc acattgttct cattcaggaa aatgatcagt ttctttgcat gttcgtattc  360
ctcggctgcg tgatcaaaca ggaacagccc agcgccgtcc agtgagtgtg tataacacca  420
actagacata ctcatgtaca ggttggagct ctgcatctcc ttgttcacct gttcgttcag  480
cagcttgatg atgtcgcccc cactgtcaat ttctctcga ttcagcttac tctcttcaga  540
atatttggga tagtcgtaag tgccgttctt cacagactcc atacattcat tgttgcactt  600
atggtaaaac tcgaagcatc cattcccgat ttctttggca ttgttcttca gctgggattt  660
gaccttctca tacagattct tcacgttgct atcgtggaaa tccagagtcc gctcgttcat  720
cagcagcacc agcagctcag ccaggtctgt tccggagcct ccgctgccca ttttttcgat  780
gacagaattc accatgttag taatgccatt gattgcgttc tgtgtagact tctgatcagc  840
ggcgtagccg ctgccctgct cattctgatg gtggtagccg taccacccgt ccaccattcc  900
tgtccacccg ccctcaataa accctgcgat agcgccgaac agtcctcttg tttcccgctg  960
tgggatgttg cgcagtccgg tgaccatcct cagtccgctg cccagattca ctgagtgggt  1020
gacagtcacg ttcttctcca ggacggtatc cactgtgtcg gtggagttgt ttgcgtgata  1080
gccgatgcag atagtgtcag cgtaggttgc ggtaaaagta cacagcagga ccagcagttt  1140
ggccttcat                                                         1149

SEQ ID NO: 163          moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 163
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatcgtg  360
aattctgtca tcgaaaaaat gggcagcgga ggctccggaa cagacctggc tgagctgctg  420
gtgctgctga tcaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                 645

SEQ ID NO: 164          moltype = AA  length = 215
FEATURE                 Location/Qualifiers
REGION                  1..215
                        note = Synthetic
source                  1..215
                        mol_type = protein
                        organism = synthetic construct
SEQUENCE: 164
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNIV  120
NSVIEKMGSG GSGTDLAELL VLLINERTLD FHDSNVKNLY EKVKSQLKNN AKEIGNGCFE  180
FYHKCNNECM ESVKNGTYDY PKYSEESKLN REKID                            215

SEQ ID NO: 165          moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 165
gtcaatttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
```

-continued

```
gttgctatcg tggaaatcca gagtccgctc gttgatcagc agcaccagca gctcagccag  240
gtctgttccg gagcctccgc tgcccatttt ttcgatgaca gaattcacga tgttagtaat  300
gccattgatt gcgttctgtg tagacttctg atcagcggcg tagccgctgc cctgctcatt  360
ctgatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat                   645

SEQ ID NO: 166         moltype = DNA  length = 1149
FEATURE                Location/Qualifiers
misc_feature           1..1149
                       note = Synthetic
source                 1..1149
                       mol_type = other DNA
                       organism = synthetic construct
SEQUENCE: 166
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatcgtg  360
aattctgtca tcgaaaaaat gggcagcgga ggctccggaa cagacctggc tgagctgctg  420
gtgctgctga tcaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgacagtgg gggcgacatc  660
atcaagctgc tgaacgaaca ggtgaacaag gagatgcaga gctccaacct gtacatgagt  720
atgtctagtt ggtgttatac acactcactg gacggcgctg ggctgttcct gtttgatcac  780
gcagccgagg aatacgaaca tgcaaagaaa ctgatcattt tcctgaatga gaacaatgtg  840
cccgtccagc tgacttcaat cagcgcccct gaacataagt tcgagggcct gacccagatc  900
tttcagaaag cttacgaaca cgagcagcat atttccgaat ctatcaacaa tattgtggac  960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtca                                                           1149

SEQ ID NO: 167         moltype = AA  length = 383
FEATURE                Location/Qualifiers
REGION                 1..383
                       note = Synthetic
source                 1..383
                       mol_type = protein
                       organism = synthetic construct
SEQUENCE: 167
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNIV  120
NSVIEKMGSG GSGTDLAELL VLLINERTLD FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                           383

SEQ ID NO: 168         moltype = DNA  length = 1149
FEATURE                Location/Qualifiers
misc_feature           1..1149
                       note = Synthetic
source                 1..1149
                       mol_type = other DNA
                       organism = synthetic construct
SEQUENCE: 168
tgacccactt tttctggact tggcaatgcc cttcacatac tgatctgcca ggtacaggcc  60
atgattctcg tttccaatca gttcgatttt atccaggatg tccttaaaca ggacctcctc  120
ctcgtgctgc tcggccacgt accactgcag aaagttgaag gtagcatgat ctttgctctt  180
aatggcgtgg tccacaatat tgttgataga ttcggaaata tgctgctcgt gttcgtaagc  240
tttctgaaag atctgggtca ggccctcgaa cttatgttca ggggcgctga ttgaagtcag  300
ctggacgggc acattgttct cattcaggaa aatgatcagt ttctttgcat gttcgtattc  360
ctcggctgcg tgatcaaaca ggaacagccc agcgccgtcc agtgagtgtg tataacacca  420
actagacata ctcatgtaca ggttggagct ctgcatctcc ttgttcacct gttcgttcag  480
cagcttgatg atgtcgcccc cactgtcaat tttctctcga ttcagcttac tctcttcaga  540
atatttggga tagtcgtaag tgccgttctt cacagactcc atacattcat tgttgcactt  600
atggtaaaac tcgaagcatc cattcccgat ttctttggca ttgttcttca gctgggattt  660
gaccttctca tacagattct tcacgttgct atcgtggaaa tccagagtcc gctcgttgat  720
cagcagcacc agcagctcag ccaggtctgt tccggagcct ccgctgccca tttttcgat  780
gacagaattc acgatgttag taatgccatt gattgcgttc tgtgtagact tctgatcagc  840
ggcgtagccg ctgccctgct cattctgatg gtggtagccg taccacccgt ccaccattcc  900
tgtccacccg ccctcaataa accctgcgat agcgccgaac agtcctcttg tttcccgctg  960
tgggatgttg cgcagtccgg tgaccatcct cagtccgctg cccagattca ctgagtgggt  1020
```

-continued

```
gacagtcacg ttcttctcca ggacggtatc cactgtgtcg gtggagttgt ttgcgtgata  1080
gccgatgcag atagtgtcag cgtaggttgc ggtaaaagta cacagcagga ccagcagttt  1140
ggccttcat                                                          1149

SEQ ID NO: 169         moltype = DNA  length = 645
FEATURE                Location/Qualifiers
misc_feature           1..645
                       note = Synthetic
source                 1..645
                       mol_type = other DNA
                       organism = synthetic construct
SEQUENCE: 169
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacctggtg  360
aattctgtca tcgaaaaaat gggcagcgga ggctccggaa cagacctggc tgagctgctg  420
gtgctgctga tcaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                  645

SEQ ID NO: 170         moltype = AA  length = 215
FEATURE                Location/Qualifiers
REGION                 1..215
                       note = Synthetic
source                 1..215
                       mol_type = protein
                       organism = synthetic construct
SEQUENCE: 170
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNLV  120
NSVIEKMGSG GSGTDLAELL VLLINERTLD FHDSNVKNLY EKVKSQLKNN AKEIGNGCFE  180
FYHKCNNECM ESVKNGTYDY PKYSEESKLN REKID                              215

SEQ ID NO: 171         moltype = DNA  length = 645
FEATURE                Location/Qualifiers
misc_feature           1..645
                       note = Synthetic
source                 1..645
                       mol_type = other DNA
                       organism = synthetic construct
SEQUENCE: 171
gtcaatttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaaatcca gagtccgctc gttgatcagc agcaccagca gctcagccag  240
gtctgttccg gagcctccgc tgcccatttt ttcgatgaca gaattcacca ggttagtaat  300
gccattgatt gcgttctgtg tagacttctg atcagcggcg tagccgctgc cctgctcatt  360
ctgatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat                  645

SEQ ID NO: 172         moltype = DNA  length = 1149
FEATURE                Location/Qualifiers
misc_feature           1..1149
                       note = Synthetic
source                 1..1149
                       mol_type = other DNA
                       organism = synthetic construct
SEQUENCE: 172
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacctggtg  360
aattctgtca tcgaaaaaat gggcagcgga ggctccggaa cagacctggc tgagctgctg  420
gtgctgctga tcaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgacagtgg gggcgacatc  660
atcaagctgc tgaacgaaca ggtgaacaag gagatgcaga gctccaacct gtacatgagt  720
atgtctagtt ggtgttatac acactcactg gacggcgctg ggctgttcct gtttgatcac  780
gcagccgagg aatacgaaca tgcaaagaaa ctgatcattt tcctgaatga gaacaatgtg  840
```

-continued

```
cccgtccagc tgacttcaat cagcgcccct gaacataagt tcgagggcct gacccagatc  900
tttcagaaag cttacgaaca cgagcagcat atttccgaat ctatcaacaa tattgtggac  960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtca                                                         1149

SEQ ID NO: 173         moltype = AA  length = 383
FEATURE                Location/Qualifiers
REGION                 1..383
                       note = Synthetic
source                 1..383
                       mol_type = protein
                       organism = synthetic construct
SEQUENCE: 173
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNLV  120
NSVIEKMGSG GSGTDLAELL VLLINERTLD FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                         383

SEQ ID NO: 174         moltype = DNA  length = 1149
FEATURE                Location/Qualifiers
misc_feature           1..1149
                       note = Synthetic
source                 1..1149
                       mol_type = other DNA
                       organism = synthetic construct
SEQUENCE: 174
tgacccactt tttctggact tggcaatgcc cttcacatac tgatctgcca ggtacaggcc  60
atgattctcg tttccaatca gttcgatttt atccaggatg tccttaaaca ggacctcctc  120
ctcgtgctgc tcggccacgt accactgcag aaagttgaag gtagcatgat ctttgctctt  180
aatggcgtgg tccacaatat tgttgataga ttcggaaata tgctgctcgt gttcgtaagc  240
tttctgaaag atctgggtca ggccctcgaa cttatgttca ggggcgctga ttgaagtcag  300
ctggacgggc acattgttct cattcaggaa aatgatcagt ttctttgcat gttcgtattc  360
ctcggctgcg tgatcaaaca ggaacagccc agcgccgtcc agtgagtgtg tataacacca  420
actagacata ctcatgtaca ggttggagct ctgcatctcc ttgttcacct gttcgttcag  480
cagcttgatg atgtcgcccc cactgtcaat tttctctcga ttcagcttac tctcttcaga  540
atatttggga tagtcgtaag tgccgttctt cacagactcc atacattcat tgttgcactt  600
atggtaaaac tcgaagcatc cattcccgat ttctttggca ttgttcttca gctgggattt  660
gaccttctca tacagattct tcacgttgct atcgtggaaa tccagagtcc gctcgttgat  720
cagcagcacc agcagctcag ccaggtctgt tccggagcct ccgctgccca ttttttcgat  780
gacagaattc accaggttag taatgccatt gattgcgttc tgtgtagact tctgatcagc  840
ggcgtagccg ctgccctgct cattctgatg gtggtagccg taccacccgt ccaccattcc  900
tgtccacccg ccctcaataa accctgcgat agcgccgaac agtcctcttg tttcccgctg  960
tgggatgttg cgcagtccgg tgaccatcct cagtccgctg cccagattca ctgagtgggt  1020
gacagtcacg ttcttctcca ggacggtatc cactgtgtcg gtggagttgt ttgcgtgata  1080
gccgatgcag atagtgtcag cgtaggttgc ggtaaaagta cacagcagga ccagcagttt  1140
ggccttcat                                                         1149

SEQ ID NO: 175         moltype = DNA  length = 645
FEATURE                Location/Qualifiers
misc_feature           1..645
                       note = Synthetic
source                 1..645
                       mol_type = other DNA
                       organism = synthetic construct
SEQUENCE: 175
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacctggtg  360
aattctgtca tcgaaaaaat gggcagcgga ggctccggaa cagacctggc tgagctgctg  420
gtgctgctgc tgaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                  645

SEQ ID NO: 176         moltype = AA  length = 215
FEATURE                Location/Qualifiers
REGION                 1..215
                       note = Synthetic
source                 1..215
                       mol_type = protein
                       organism = synthetic construct
```

SEQUENCE: 176
MKAKLLVLLC TFTATYADTI CIGYHANNST DTVDTVLEKN VTVTHSVNLG SGLRMVTGLR 60
NIPQRETRGL FGAIAGFIEG GWTGMVDGWY GYHHQNEQGS GYAADQKSTQ NAINGITNLV 120
NSVIEKMGSG GSGTDLAELL VLLLNERTLD FHDSNVKNLY EKVKSQLKNN AKEIGNGCFE 180
FYHKCNNECM ESVKNGTYDY PKYSEESKLN REKID 215

SEQ ID NO: 177 moltype = DNA length = 645
FEATURE Location/Qualifiers
misc_feature 1..645
note = Synthetic
source 1..645
mol_type = other DNA
organism = synthetic construct
SEQUENCE: 177
gtcaatttc tctcgattca gcttactctc ttcagaatat ttgggatagt cgtaagtgcc 60
gttcttcaca gactccatac attcattgtt gcacttatgg taaaactcga agcatccatt 120
cccgatttct ttggcattgt tcttcagctg ggatttgacc ttctcataca gattcttcac 180
gttgctatcg tggaaatcca gagtccgctc gttcagcagc agcaccagca gctcagccag 240
gtctgttccg gagcctccgc tgcccatttt ttcgatgaca gaattcacca ggttagtaat 300
gccattgatt gcgttctgtg tagacttctg atcagcggcg tagccgctgc cctgctcatt 360
ctgatggtgg tagccgtacc acccgtccac cattcctgtc cacccgccct caataaaccc 420
tgcgatagcg ccgaacagtc ctcttgtttc ccgctgtggg atgttgcgca gtccggtgac 480
catcctcagt ccgctgccca gattcactga gtgggtgaca gtcacgttct tctccaggac 540
ggtatccact gtgtcggtgg agttgtttgc gtgatagccg atgcagatag tgtcagcgta 600
ggttgcggta aaagtacaca gcaggaccag cagtttggcc ttcat 645

SEQ ID NO: 178 moltype = DNA length = 1149
FEATURE Location/Qualifiers
misc_feature 1..1149
note = Synthetic
source 1..1149
mol_type = other DNA
organism = synthetic construct
SEQUENCE: 178
atgaaggcca aactgctggt cctgctgtgt acttttaccg caacctacgc tgacactatc 60
tgcatcggct atcacgcaaa caactccacc gacacagtgg ataccgtcct ggagaagaac 120
gtgactgtca cccactcagt gaatctgggc agcggactga ggatggtcac cggactgcgc 180
aacatcccac agcgggaaac aagaggactg ttcggcgcta tcgcaggggtt tattgagggc 240
gggtggacag gaatggtgga cgggtggtac ggctaccacc atcagaatga gcagggcagc 300
ggctacgccg ctgatcagaa gtctacacag aacgcaatca atggcattac taacctggtg 360
aattctgtca tcgaaaaaat gggcagcgga ggctccggaa cagacctggc tgagctgctg 420
gtgctgctgc tgaacgagcg gactctggat ttccacgata gcaacgtgaa gaatctgtat 480
gagaaggtca aatcccagct gaagaacaat gccaaagaaa tcgggaatgg atgcttcgag 540
ttttaccata agtgcaacaa tgaatgtatg gagtctgtga agaacggcac ttacgactat 600
cccaaatatt ctgaagagag taagctgaat cgagagaaaa ttgacagtgg gggcgacatc 660
atcaagctgc tgaacgaaca ggtgaacaag gagatgcaga gctccaacct gtacatgagt 720
atgtctagtt ggtgttatac acactcactg gacggcgctg ggctgttcct gtttgatcac 780
gcagccgagg aatacgaaca tgcaaagaaa ctgatcattt tcctgaatga gaacaatgtg 840
cccgtccagc tgacttcaat cagcgcccct gaacataagt tcgagggcct gacccagatc 900
tttcagaaag cttacgaaca cgagcagcat atttccgaat ctatcaacaa tattgtggac 960
cacgccatta agagcaaaga tcatgctacc ttcaactttc tgcagtggta cgtggccgag 1020
cagcacgagg aggaggtcct gtttaaggac atcctggata aaatcgaact gattggaaac 1080
gagaatcatg gcctgtacct ggcagatcag tatgtgaagg gcattgccaa gtccagaaaa 1140
agtgggtca 1149

SEQ ID NO: 179 moltype = AA length = 383
FEATURE Location/Qualifiers
REGION 1..383
note = Synthetic
source 1..383
mol_type = protein
organism = synthetic construct
SEQUENCE: 179
MKAKLLVLLC TFTATYADTI CIGYHANNST DTVDTVLEKN VTVTHSVNLG SGLRMVTGLR 60
NIPQRETRGL FGAIAGFIEG GWTGMVDGWY GYHHQNEQGS GYAADQKSTQ NAINGITNLV 120
NSVIEKMGSG GSGTDLAELL VLLLNERTLD FHDSNVKNLY EKVKSQLKNN AKEIGNGCFE 180
FYHKCNNECM ESVKNGTYDY PKYSEESKLN REKIDSGGDI IKLLNEQVNK EMQSSNLYMS 240
MSSWCYTHSL DGAGLFLFDH AAEEYEHAKK LIIFLNENNV PVQLTSISAP EHKFEGLTQI 300
FQKAYEHEQH ISESINNIVD HAIKSKDHAT FNFLQWYVAE QHEEEVLFKD ILDKIELIGN 360
ENHGLYLADQ YVKGIAKSRK SGS 383

SEQ ID NO: 180 moltype = DNA length = 1149
FEATURE Location/Qualifiers
misc_feature 1..1149
note = Synthetic
source 1..1149
mol_type = other DNA
organism = synthetic construct
SEQUENCE: 180

-continued

```
tgacccactt tttctggact tggcaatgcc cttcacatac tgatctgcca ggtacaggcc  60
atgattctcg tttccaatca gttcgatttt atccaggatg tccttaaaca ggacctcctc  120
ctcgtgctgc tcggccacgt accactgcag aaagttgaag gtagcatgat ctttgctctt  180
aatggcgtgg tccacaatat tgttgataga ttcggaaata tgctgctcgt gttcgtaagc  240
tttctgaaag atctgggtca ggccctcgaa cttatgttca ggggcgctga ttgaagtcag  300
ctggacgggc acattgttct cattcaggaa aatgatcagt ttctttgcat gttcgtattc  360
ctcggctgcg tgatcaaaca ggaacagccc agcgccgtcc agtgagtgtg tataacacca  420
actagacata ctcatgtaca ggttggagct ctgcatctcc ttgttcacct gttcgttcag  480
cagcttgatg atgtcgcccc cactgtcaat tttctctcga ttcagcttac tctcttcaga  540
atatttggga tagtcgtaag tgccgttctt cacagactcc atacattcat tgttgcactt  600
atggtaaaac tcgaagcatc cattcccgat ttctttggca ttgttcttca gctgggattt  660
gaccttctca tacagattct tcacgttgct atcgtggaaa tccagagtcc gctcgttcag  720
cagcagcacc agcagctcag ccaggtctgt tccggagcct ccgctgccca tttttcgat  780
gacagaattc accaggttag taatgccatt gattgcgttc tgtgtagact tctgatcagc  840
ggcgtagccg ctgccctgct cattctgatg gtggtagccg taccacccgt ccaccattcc  900
tgtccacccg ccctcaataa accctgcgat agcgccgaac agtcctcttg tttcccgctg  960
tgggatgttg cgcagtccgg tgaccatcct cagtccgctg cccagattca ctgagtgggt  1020
gacagtcacg ttcttctcca ggacggtatc cactgtgtcg gtggagttgt ttgcgtgata  1080
gccgatgcag atagtgtcag cgtaggttgc ggtaaaagta cacagcagga ccagcagttt  1140
ggccttcat                                                         1149

SEQ ID NO: 181          moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 181
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc ataacaatac ccagggcagc  300
ggctacgccg ctgatcagaa gtctacacag aacgcaatca atggcattac taacatggtg  360
aattctgtca tcgaaaaaat gggcggaaat ggcactggag ctgacctggc tgagctgctg  420
gtgctgctgc tgaaccagtg gactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                 645

SEQ ID NO: 182          moltype = AA  length = 215
FEATURE                 Location/Qualifiers
REGION                  1..215
                        note = Synthetic
source                  1..215
                        mol_type = protein
                        organism = synthetic construct
SEQUENCE: 182
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHNNTQGS GYAADQKSTQ NAINGITNMV  120
NSVIEKMGGN GTGADLAELL VLLLNQWTLL FHDSNVKNLY EKVKSQLKNN AKEIGNGCFE  180
FYHKCNNECM ESVKNGTYDY PKYSEESKLN REKID                            215

SEQ ID NO: 183          moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 183
gtcaattttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaacagca gagtccactg gttcagcagc agcaccagca gctcagccag  240
gtcagctcca gtgccatttc cgcccatttt ttcgatgaca gaattcacca tgttagtaat  300
gccattgatt gcgttctgtg tagacttctg atcagcggcg tagccgctgc cctgggtatt  360
gttatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat                 645

SEQ ID NO: 184          moltype = DNA  length = 1149
FEATURE                 Location/Qualifiers
misc_feature            1..1149
                        note = Synthetic
source                  1..1149
```

mol_type = other DNA
organism = synthetic construct
SEQUENCE: 184
atgaaggcca aactgctggt cctgctgtgt acttttaccg caacctacgc tgacactatc 60
tgcatcggct atcacgcaaa caactccacc gacacagtgg ataccgtcct ggagaagaac 120
gtgactgtca cccactcagt gaatctgggc agcggactga ggatggtcac cggactgcgc 180
aacatcccac agcgggaaac aagaggactg ttcggcgcta tcgcagggtt tattgagggc 240
gggtggacag gaatggtgga cgggtggtac ggctaccacc ataacaatac ccagggcagc 300
ggctacgccg ctgatcagaa gtctacacag aacgcaatca atggcattac taacatggtg 360
aattctgtca tcgaaaaaat gggcggaaat ggcactggag ctgacctggc tgagctgctg 420
gtgctgctgc tgaaccagtg gactctgctg ttccacgata gcaacgtgaa gaatctgtat 480
gagaaggtca aatcccagct gaagaacaat gccaaagaaa tcgggaatgg atgcttcgag 540
ttttaccata agtgcaacaa tgaatgtatg gagtctgtga agaacggcac ttacgactat 600
cccaaatatt ctgaagagag taagctgaat cgagagaaaa ttgacagtgg gggcgacatc 660
atcaagctgc tgaacgaaca ggtgaacaag gagatgaaca gcaccaacct gtacatgagt 720
atgtctagtt ggtgttatac acactcactg gacggcgctg ggctgttcct gtttgatcac 780
gcagccgagg aatacgaaca tgcaaagaaa ctgatcattt tcctgaatga gaacaatgtg 840
cccgtccagc tgacttcaat cagcgcccct gaacataagt tcgagggcct gacccagatc 900
tttcagaaag cttacgaaca cgagcagcat atttccgaat ctatcaacaa tattgtggac 960
cacgccatta agagcaaaga tcatgctacc ttcaactttc tgcagtggta cgtggccgag 1020
cagcacgagg aggaggtcct gtttaaggac atcctggata aaatcgaact gattggaaac 1080
gagaatcatg gcctgtacct ggcagatcag tatgtgaagg gcattgccaa gtccagaaaa 1140
agtgggtca 1149

SEQ ID NO: 185 moltype = AA length = 383
FEATURE Location/Qualifiers
REGION 1..383
note = Synthetic
source 1..383
mol_type = protein
organism = synthetic construct
SEQUENCE: 185
MKAKLLVLLC TFTATYADTI CIGYHANNST DTVDTVLEKN VTVTHSVNLG SGLRMVTGLR 60
NIPQRETRGL FGAIAGFIEG GWTGMVDGWY GYHHNNTQGS GYAADQKSTQ NAINGITNMV 120
NSVIEKMGGN GTGADLAELL VLLLNQWTLL FHDSNVKNLY EKVKSQLKNN AKEIGNGCFE 180
FYHKCNNECM ESVKNGTYDY PKYSEESKLN REKIDSGGDI IKLLNEQVNK EMNSTNLYMS 240
MSSWCYTHSL DGAGLFLFDH AAEEYEHAKK LIIFLNENNV PVQLTSISAP EHKFEGLTQI 300
FQKAYEHEQH ISESINNIVD HAIKSKDHAT FNFLQWYVAE QHEEEVLFKD ILDKIELIGN 360
ENHGLYLADQ YVKGIAKSRK SGS 383

SEQ ID NO: 186 moltype = DNA length = 1149
FEATURE Location/Qualifiers
misc_feature 1..1149
note = Synthetic
source 1..1149
mol_type = other DNA
organism = synthetic construct
SEQUENCE: 186
tgacccactt tttctggact tggcaatgcc cttcacatac tgatctgcca ggtacaggcc 60
atgattctcg tttccaatca gttcgatttt atccaggatg tccttaaaca ggacctcctc 120
ctcgtgctgc tcggccacgt accactgcag aaagttgaag gtagcatgat ctttgctctt 180
aatggcgtgg tccacaatat tgttgataga ttcggaaata tgctgctcgt gttcgtaagc 240
tttctgaaag atctgggtca ggccctcgaa cttatgttca ggggcgctga ttgaagtcag 300
ctggacgggc acattgttct cattcaggaa aatgatcagt ttctttgcat gttcgtattc 360
ctcggctgcg tgatcaaaca ggaacagccc agcgccgtcc agtgagtgtg tataacacca 420
actagacata ctcatgtaca ggttggtgct gttcatctcc ttgttcacct gttcgttcag 480
cagcttgatg atgtcgcccc cactgtcaat tttctctcga ttcagcttac tctcttcaga 540
atatttggga tagtcgtaag tgccgttctt cacagactcc atacattcat tgttgcactt 600
atggtaaaac tcgaagcatc cattcccgat ttctttggca ttgttcttca gctgggattt 660
gaccttctca tacagattct tcacgttgct atcgtggaac agcagagtcc actggttcag 720
cagcagcacc agcagctcag ccaggtcagc tccagtgcca tttccgccca tttttttcgat 780
gacagaattc accatgttag taatgccatt gattgcgttc tgtgtagact tctgatcagc 840
ggcgtagccg ctgccctggg tattgttatg gtggtagccg taccacccgt ccaccattcc 900
tgtccacccg ccctcaataa accctgcgat agcgccgaac agtcctcttg tttcccgctg 960
tgggatgttg cgcagtccgg tgaccatcct cagtccgctg cccagattca ctgagtgggt 1020
gacagtcacg ttcttctcca ggacggtatc cactgtgtcg gtggagttgt ttgcgtgata 1080
gccgatgcag atagtgtcag cgtaggttgc ggtaaaagta cacagcagga ccagcagttt 1140
ggccttcat 1149

SEQ ID NO: 187 moltype = DNA length = 645
FEATURE Location/Qualifiers
misc_feature 1..645
note = Synthetic
source 1..645
mol_type = other DNA
organism = synthetic construct
SEQUENCE: 187
atgaaggcca aactgctggt cctgctgtgt acttttaccg caacctacgc tgacactatc 60
tgcatcggct atcacgcaaa caactccacc gacacagtgg ataccgtcct ggagaagaac 120

```
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc ataacaatac ccagggcagc  300
ggctacgccg ctgatcagaa gtctacacag aacgcaatca atggcattac taacatggtg  360
aattctgtca tcgaaaaaat gggcggaaat ggcactggag ctgacctggc tgagctgctg  420
gtgctgctgc tgaaccagtg gactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                   645

SEQ ID NO: 188         moltype = AA  length = 215
FEATURE                Location/Qualifiers
REGION                 1..215
                       note = Synthetic
source                 1..215
                       mol_type = protein
                       organism = synthetic construct
SEQUENCE: 188
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHNNTQGS GYAADQKSTQ NAINGITNMV  120
NSVIEKMGGN GTGADLAELL VLLLNQWTLL FHDSNVKNLY EKVKSQLKNN AKEIGNGCFE  180
FYHKCNNECM ESVKNGTYDY PKYSEESKLN REKID                              215

SEQ ID NO: 189         moltype = DNA  length = 645
FEATURE                Location/Qualifiers
misc_feature           1..645
                       note = Synthetic
source                 1..645
                       mol_type = other DNA
                       organism = synthetic construct
SEQUENCE: 189
gtcaatttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaacagca gagtccactg gttcagcagc agcaccagca gctcagccag  240
gtcagctcca gtgccatttc cgcccatttt ttcgatgaca gaattcacca tgttagtaat  300
gccattgatt gcgttctgtg tagacttctg atcagcggcg tagccgctgc cctgggtatt  360
gttatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat                   645

SEQ ID NO: 190         moltype = DNA  length = 1149
FEATURE                Location/Qualifiers
misc_feature           1..1149
                       note = Synthetic
source                 1..1149
                       mol_type = other DNA
                       organism = synthetic construct
SEQUENCE: 190
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc ataacaatac ccagggcagc  300
ggctacgccg ctgatcagaa gtctacacag aacgcaatca atggcattac taacatggtg  360
aattctgtca tcgaaaaaat gggcggaaat ggcactggag ctgacctggc tgagctgctg  420
gtgctgctgc tgaaccagtg gactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgacagtgg gggcgacatc  660
atcaagctgc tgaacgaaca ggtgaacaag gagatgaaca gcaccaacct gtacatgagt  720
atgtctagtt ggtgttatac acactcactg gacggcgctg ggctgttcct gtttgatcac  780
gcagccgagg aatacgaaca tgcaaagaaa ctgatcattt tcctgaatga gaacaatgtg  840
cccgtcaacc tgacttcaat cagcgcccct gaacataagt tcgagggcct gacccagatc  900
tttcagaaag cttacgaaca cgagcagcat atttccgaat ctatcaacaa tattgtggac  960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtca                                                            1149

SEQ ID NO: 191         moltype = AA  length = 383
FEATURE                Location/Qualifiers
REGION                 1..383
                       note = Synthetic
source                 1..383
                       mol_type = protein
                       organism = synthetic construct
```

```
SEQUENCE: 191
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHNNTQGS GYAADQKSTQ NAINGITNMV  120
NSVIEKMGGN GTGADLAELL VLLLNQWTLL FHDSNVKNLY EKVKSQLKNN AKEIGNGCFE  180
FYHKCNNECM ESVKNGTYDY PKYSEESKLN REKIDSGGDI IKLLNEQVNK EMNSTNLYMS  240
MSSWCYTHSL DGAGLFLFDH AAEEYEHAKK LIIFLNENNV PVNLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                         383

SEQ ID NO: 192         moltype = DNA  length = 1149
FEATURE                Location/Qualifiers
misc_feature           1..1149
                       note = Synthetic
source                 1..1149
                       mol_type = other DNA
                       organism = synthetic construct
SEQUENCE: 192
tgacccactt tttctggact tggcaatgcc cttcacatac tgatctgcca ggtacaggcc  60
atgattctcg tttccaatca gttcgatttt atccaggatg tccttaaaca ggacctcctc  120
ctcgtgctgc tcggccacgt accactgcag aaagttgaag gtagcatgat ctttgctctt  180
aatggcgtgg tccacaatat tgttgataga ttcggaaata tgctgctcgt gttcgtaagc  240
tttctgaaag atctgggtca ggccctcgaa cttatgttca ggggcgctga ttgaagtcag  300
gttgacgggc acattgttct cattcaggaa aatgatcagt ttctttgcat gttcgtattc  360
ctcggctgcg tgatcaaaca ggaacagccc agcgccgtcc agtgagtgtg tataacacca  420
actagacata ctcatgtaca ggttggtgct gttcatctcc ttgttcacct gttcgttcag  480
cagcttgatg atgtcgcccc cactgtcaat ttctctcgga ttcagcttac tctcttcaga  540
atatttggga tagtcgtaag tgccgttctt cacagactcc atacattcat tgttgcactt  600
atggtaaaac tcgaagcatc cattcccgat ttctttggca ttgttcttca gctgggattt  660
gaccttctca tacagattct tcacgttgct atcgtggaac agcagagtcc actggttcag  720
cagcagcacc agcagctcag ccaggtcagc tccagtgcca tttccgccca ttttttcgat  780
gacagaattc accatgttag taatgccatt gattgcgttc tgtgtagact tctgatcagc  840
ggcgtagccg ctgccctggg tattgttatg gtggtagccg taccacccgt ccaccattcc  900
tgtccacccg ccctcaataa accctgcgat agcgccgaac agtcctcttg tttcccgctg  960
tgggatgttg cgcagtccgg tgaccatcct cagtccgctg cccagattca ctgagtgggt  1020
gacagtcacg ttcttctcca ggacggtatc cactgtgtcg gtggagttgt ttgcgtgata  1080
gccgatgcag atagtgtcag cgtaggttgc ggtaaaagta cacagcagga ccagcagttt  1140
ggccttcat                                                         1149

SEQ ID NO: 193         moltype = DNA  length = 465
FEATURE                Location/Qualifiers
source                 1..465
                       mol_type = unassigned DNA
                       organism = Aquifex aeolicus
SEQUENCE: 193
atgcaaattt acgaagggaa actaaccgct gaagggctga ggttcggtat agtggcttcc  60
aggttcaacc acgcactcgt ggatagacta gttgagggag ctatagactg catagtaaga  120
cacgggggaa gggaagaaga cataacgctc gttagagtgc cgggctcctg ggaaattccc  180
gtggctgcgg gagagcttgc gagaaaagag gacatagacg ctgtgatagc gataggagtt  240
ctaataaggg ggctactcc ccactttgat tacatagcct ctgaagtgtc aaaagggctt  300
gcgaaccttt ccttagaact gagaaaaccc ataaccttcg gtgttataac tgcggacacc  360
ttggagcagg cgatagaaag ggcgggaaca aagcacggga ataagggctg ggaagctgca  420
ctttccgcaa tagaaatggc aaacttattt aagagtctga gatga                 465

SEQ ID NO: 194         moltype = AA  length = 154
FEATURE                Location/Qualifiers
source                 1..154
                       mol_type = protein
                       organism = Aquifex aeolicus
SEQUENCE: 194
MQIYEGKLTA EGLRFGIVAS RFNHALVDRL VEGAIDCIVR HGGREEDITL VRVPGSWEIP  60
VAAGELARKE DIDAVIAIGV LIRGATPHFD YIASEVSKGL ANLSLELRKP ITFGVITADT  120
LEQAIERAGT KHGNKGWEAA LSAIEMANLF KSLR                             154

SEQ ID NO: 195         moltype = DNA  length = 465
FEATURE                Location/Qualifiers
source                 1..465
                       mol_type = unassigned DNA
                       organism = Aquifex aeolicus
SEQUENCE: 195
tcatctcaga ctcttaaata agtttgccat ttctattgcg gaaagtgcag cttcccagcc  60
cttattcccg tgctttgttc ccgccctttc tatcgcctgc tccaaggtgt ccgcagttat  120
aacaccgaag gttatgggtt ttctcagttc taaggaaagg ttcgcaagcc cttttgacac  180
ttcagaggct atgtaatcaa agtggggagt agccccctt attagaactc ctatcgctat  240
cacagcgtct atgtcctctt ttctcgcaag ctctcccgca gccacgggaa tttcccagga  300
gcccggcact ctaacgagcg ttatgtcttc ttcccttccc ccgtgtctta ctatgcagtc  360
tatagctccc tcaactagtc tatccacgag tgcgtggttg aacctggaag ccactatacc  420
gaacctcagc ccttcagcgg ttagtttccc ttcgtaaatt tgcat                 465

SEQ ID NO: 196         moltype = DNA  length = 642
```

```
FEATURE                Location/Qualifiers
misc_feature           1..642
                       note = Synthetic
source                 1..642
                       mol_type = other DNA
                       organism = synthetic construct
SEQUENCE: 196
atgaaggcca agctgctggt gctcctgtgc accttcaccg ccacctacgc cgacaccatc  60
tgcatcggct accacgccaa caacagcacc gacaccgtgg ataccgtgct ggaaaagaac  120
gtgaccgtga cccacagcgt gaacctgggc agcggcctgc ggatggtgac aggcctgcgg  180
aacatccccc agagagagac acggggcctg ttcggcgcca ttgccggctt tatcgagggc  240
ggctggaccg gcatggtgga cgggtggtac ggctaccacc accagaacga gcagggcagc  300
ggctacgccg ccgaccagaa gtccacccag aacgccatca acggcatcac caacatggtg  360
aacagcgtga tcgagaagat gggctccggc ggcagcggca ccgatctggc tgaactgctg  420
gtcctgctgc tgaacgagcg gaccctggac ttccacgaca gcaacgtgaa gaacctgtac  480
gagaaagtga agtcccagct gaagaacaac gccaaagaga tcggcaacgg ctgcttcgag  540
ttctaccaca agtgcaacaa cgagtgcatg gaaagcgtga agaacggcac ctacgactac  600
cccaagtaca gcgaggaaag caagctgaac cgcgagggag gc                     642

SEQ ID NO: 197         moltype = AA  length = 214
FEATURE                Location/Qualifiers
REGION                 1..214
                       note = Synthetic
source                 1..214
                       mol_type = protein
                       organism = synthetic construct
SEQUENCE: 197
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLN REGG                              214

SEQ ID NO: 198         moltype = DNA  length = 642
FEATURE                Location/Qualifiers
misc_feature           1..642
                       note = Synthetic
source                 1..642
                       mol_type = other DNA
                       organism = synthetic construct
SEQUENCE: 198
gcctccctcg cggttcagct tgctttcctc gctgtacttg ggtagtcgt aggtgccgtt  60
cttcacgctt tccatgcact cgttgttgca cttgtggtag aactcgaagc agccgttgcc  120
gatctctttg gcgttgttct tcagctggga cttcactttc tcgtacaggt tcttcacgtt  180
gctgtcgtgg aagtccaggg tccgctcgtt cagcagcagg accagcagtt cagccagatc  240
ggtgccgctg ccgccggagc ccatcttctc gatcacgctg ttcaccatgt tggtgatgcc  300
gttgatggcg ttctgggtgg acttctggtc ggcggcgtag ccgctgccct gctcgttctg  360
gtggtggtag ccgtaccacc cgtccaccat gccggtccag ccgccctcga taaagccggc  420
aatggcgccg aacaggcccc gtgtctctct ctgggggatg ttccgcaggc ctgtcaccat  480
ccgcaggccg ctgcccaggt tcacgctgtg ggtcacggtc acgttctttt ccagcacggt  540
atccacggtg tcggtgctgt tgttggcgtg gtagccgatg cagatggtgt cggcgtaggt  600
ggcggtgaag gtgcacagga gcaccagcag cttggccttc at                     642

SEQ ID NO: 199         moltype = DNA  length = 1104
FEATURE                Location/Qualifiers
misc_feature           1..1104
                       note = Synthetic
source                 1..1104
                       mol_type = other DNA
                       organism = synthetic construct
SEQUENCE: 199
atgaaggcca agctgctggt gctcctgtgc accttcaccg ccacctacgc cgacaccatc  60
tgcatcggct accacgccaa caacagcacc gacaccgtgg ataccgtgct ggaaaagaac  120
gtgaccgtga cccacagcgt gaacctgggc agcggcctgc ggatggtgac aggcctgcgg  180
aacatccccc agagagagac acggggcctg ttcggcgcca ttgccggctt tatcgagggc  240
ggctggaccg gcatggtgga cgggtggtac ggctaccacc accagaacga gcagggcagc  300
ggctacgccg ccgaccagaa gtccacccag aacgccatca acggcatcac caacatggtg  360
aacagcgtga tcgagaagat gggctccggc ggcagcggca ccgatctggc tgaactgctg  420
gtcctgctgc tgaacgagcg gaccctggac ttccacgaca gcaacgtgaa gaacctgtac  480
gagaaagtga agtcccagct gaagaacaac gccaaagaga tcggcaacgg ctgcttcgag  540
ttctaccaca agtgcaacaa cgagtgcatg gaaagcgtga agaacggcac ctacgactac  600
cccaagtaca gcgaggaaag caagctgaac cgcgagggag gcatgcaaat ctacgagggc  660
aagctgacag ccgagggcct gagattcggc atcgtggcca gccggttcaa ccacgccctg  720
gtggacagac tggtggaagg cgccatcgac tgcatcgtgc ggcacggcgg cagagaagag  780
gacatcaccc tggtccgcgt gcccggcagc tgggaaattc ctgtggctgc cggcgagctg  840
gcccggaaag aggatatcga cgccgtcatc gccatcggcg tgctgatcag aggcgccacc  900
ccccacttcg actatatcgc cagcgaggtg tccaagggcc tggccaacct gagcctggaa  960
ctgcggaagc ccatcacctt cggagtgatc accgccgaca ccctggaaca ggccatcgag  1020
agagccggca ccaagcacgg caacaaggga tgggaagccg ccctgagcgc catcgagatg  1080
gccaatctgt tcaagagcct gcgc                                         1104
```

```
SEQ ID NO: 200         moltype = AA  length = 368
FEATURE                Location/Qualifiers
REGION                 1..368
                       note = Synthetic
source                 1..368
                       mol_type = protein
                       organism = synthetic construct
SEQUENCE: 200
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLN REGGMQIYEG KLTAEGLRFG IVASRFNHAL  240
VDRLVEGAID CIVRHGGREE DITLVRVPGS WEIPVAAGEL ARKEDIDAVI AIGVLIRGAT  300
PHFDYIASEV SKGLANLSLE LRKPITFGVI TADTLEQAIE RAGTKHGNKG WEAALSAIEM  360
ANLFKSLR                                                          368

SEQ ID NO: 201         moltype = DNA  length = 1104
FEATURE                Location/Qualifiers
misc_feature           1..1104
                       note = Synthetic
source                 1..1104
                       mol_type = other DNA
                       organism = synthetic construct
SEQUENCE: 201
gcgcaggctc ttgaacagat tggccatctc gatggcgctc agggcggctt cccatccctt  60
gttgccgtgc ttggtgccgg ctctctcgat ggcctgttcc agggtgtcgg cggtgatcac  120
tccgaaggtg atgggcttcc gcagttccag gctcaggttg gccaggccct tggacacctc  180
gctggcgata tagtcgaagt gggggggtggc gcctctgatc agcacgccga tggcgatgac  240
ggcgtcgata tcctctttcc gggccagctc gccggcagcc acaggaattt cccagctgcc  300
gggcacgcgg accagggtga tgtcctcttc tctgccgccg tgccgcacga tgcagtcgat  360
ggcgccttcc accagtctgt ccaccagggc gtggttgaac cggctggcca cgatgccgaa  420
tctcaggccc tcggctgtca gcttgccctc gtagatttgc atgcctccct cgcggttcag  480
cttgctttcc tcgctgtact tggggtagtc gtaggtgccg ttcttcacgc tttccatgca  540
ctcgttgttg cacttgtggt agaactcgaa gcagccgttg ccgatctctt tggcgttgtt  600
cttcagctgg gacttcactt tctcgtacag gttcttcacg ttgctgtcgt ggaagtccag  660
ggtccgctcg ttcagcagca ggaccagcag ttcagccaga tcggtgccgc tgccgccgga  720
gcccatcttc tcgatcacgc tgttcaccat gttggtgatg ccgttgatgg cgttctgggt  780
ggacttctgg tcggcggcgt agccgctgcc ctgctcgttc tggtggtggt agccgtacca  840
cccgtccacc atgccggtcc agccgccctc gataaagccg gcaatggcgc cgaacaggcc  900
ccgtgtctct ctctggggga tgttccgcag gcctgtcacc atccgcaggc cgctgcccag  960
gttcacgctg tgggtcacgg tcacgttctt ttccagcacg gtatccacgg tgtcggtgct  1020
gttgttggcg tggtagccga tgcagatggt gtcggcgtag gtggcggtga aggtgcacag  1080
gagcaccagc agcttggcct tcat                                        1104

SEQ ID NO: 202         moltype = DNA  length = 645
FEATURE                Location/Qualifiers
misc_feature           1..645
                       note = Synthetic
source                 1..645
                       mol_type = other DNA
                       organism = synthetic construct
SEQUENCE: 202
atgaaggcca agctgctggt gctcctgtgc accttcaccg ccacctacgc cgacaccatc  60
tgcatcggct accacgccaa caacagcacc gacaccgtgg ataccgtgct ggaaaagaac  120
gtgaccgtga cccacagcgt gaacctgggc agcggcctgc ggatggtgac aggcctgcgg  180
aacatccccc agagagagac acggggcctg ttcggcgcca ttgccggctt tatcgagggc  240
ggctggaccg gcatggtgga cgggtggtac ggctaccacc accagaacga gcagggcagc  300
ggctacgccg ccgaccagaa gtccacccag aacgccatca acggcatcac caacatggtg  360
aacagcgtga tcgagaagat gggctccggc ggcagcggca ccgatctggc tgaactgctg  420
gtcctgctgc tgaacgagcg gaccctggac ttccacgaca gcaacgtgaa gaacctgtac  480
gagaaagtga agtcccagct gaagaacaac gccaaagaga tcggcaacgg ctgcttcgag  540
ttctaccaca agtgcaacaa cgagtgcatg gaaagcgtga agaacggcac ctacgactac  600
cccaagtaca gcgaggaaag caagctgaac cgcgagggaa gcggc                 645

SEQ ID NO: 203         moltype = AA  length = 215
FEATURE                Location/Qualifiers
REGION                 1..215
                       note = Synthetic
source                 1..215
                       mol_type = protein
                       organism = synthetic construct
SEQUENCE: 203
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLN REGSG                           215

SEQ ID NO: 204         moltype = DNA  length = 645
```

-continued

```
FEATURE                Location/Qualifiers
misc_feature           1..645
                       note = Synthetic
source                 1..645
                       mol_type = other DNA
                       organism = synthetic construct
SEQUENCE: 204
gccgcttccc tcgcggttca gcttgctttc ctcgctgtac ttggggtagt cgtaggtgcc  60
gttcttcacg ctttccatgc actcgttgtt gcacttgtgg tagaactcga agcagccgtt  120
gccgatctct ttggcgttgt tcttcagctg ggacttcact ttctcgtaca ggttcttcac  180
gttgctgtcg tggaagtcca gggtccgctc gttcagcagc aggaccagca gttcagccag  240
atcggtgccg ctgccgccgg agcccatctt ctcgatcacg ctgttcacca tgttggtgat  300
gccgttgatg gcgttctggg tggacttctg gtcggcggcg tagccgctgc cctgctcgtt  360
ctggtggtgg tagccgtacc acccgtccac catgccggtc cagccgccct cgataaagcc  420
ggcaatggcg ccgaacaggc cccgtgtctc tctctggggg atgttccgca ggcctgtcac  480
catccgcagg ccgctgccca ggttcacgct gtgggtcacg gtcacgttct tttccagcac  540
ggtatccacg gtgtcggtgc tgttgttggc gtggtagccg atgcagatgg tgtcggcgta  600
ggtggcggtg aaggtgcaca ggagcaccag cagcttggcc ttcat                  645

SEQ ID NO: 205         moltype = DNA  length = 1107
FEATURE                Location/Qualifiers
misc_feature           1..1107
                       note = Synthetic
source                 1..1107
                       mol_type = other DNA
                       organism = synthetic construct
SEQUENCE: 205
atgaaggcca agctgctggt gctcctgtgc accttcaccg ccacctacgc cgacaccatc  60
tgcatcggct accacgccaa caacagcacc gacaccgtgg ataccgtgct ggaaaagaac  120
gtgaccgtga cccacagcgt gaacctgggc agcggcctgc ggatggtgac aggcctgcgg  180
aacatccccc agagagagac acggggcctg ttcggcgcca ttgccggctt tatcgagggc  240
ggctggaccg gcatggtgga cgggtggtac ggctaccacc accagaacga gcagggcagc  300
ggctacgccg ccgaccagaa gtccacccag aacgccatca acggcatcac caacatggtg  360
aacagcgtga tcgagaagat gggctccggc ggcagcggca ccgatctggc tgaactgctg  420
gtcctgctgc tgaacgagcg gaccctggac ttccacgaca gcaacgtgaa gaacctgtac  480
gagaaagtga agtcccagct gaagaacaac gccaaagaga tcggcaacgg ctgcttcgag  540
ttctaccaca agtgcaacaa cgagtgcatg gaaagcgtga agaacggcac ctacgactac  600
cccaagtaca gcgaggaaag caagctgaac cgcgagggaa gcggcatgca aatctacgag  660
ggcaagctga cagccgaggg cctgagattc ggcatcgtgg ccagccggtt caaccacgcc  720
ctggtggaca gactggtgga aggcgccatc gactgcatcg tgcggcacgg cggcagagaa  780
gaggacatca ccctggtccg cgtgcccggc agctgggaaa ttcctgtggc tgccggcgag  840
ctggcccgga aagaggatat cgacgccgtc atcgccatcg gcgtgctgat cagaggcgcc  900
accccccact tcgactatat cgccagcgag gtgtccaagg gcctggccaa cctgagcctg  960
gaactgcgga agcccatcac cttcggagtg atcaccgccg acaccctgga acaggccatc  1020
gagagagccg gcaccaagca cggcaacaag ggatgggaag ccgccctgag cgccatcgag  1080
atggccaatc tgttcaagag cctgcgc                                      1107

SEQ ID NO: 206         moltype = AA  length = 369
FEATURE                Location/Qualifiers
REGION                 1..369
                       note = Synthetic
source                 1..369
                       mol_type = protein
                       organism = synthetic construct
SEQUENCE: 206
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLN REGSGMQIYE GKLTAEGLRF GIVASRFNHA  240
LVDRLVEGAI DCIVRHGGRE EDITLVRVPG SWEIPVAAGE LARKEDIDAV IAIGVLIRGA  300
TPHFDYIASE VSKGLANLSL ELRKPITFGV ITADTLEQAI ERAGTKHGNK GWEAALSAIE  360
MANLFKSLR                                                          369

SEQ ID NO: 207         moltype = DNA  length = 1107
FEATURE                Location/Qualifiers
misc_feature           1..1107
                       note = Synthetic
source                 1..1107
                       mol_type = other DNA
                       organism = synthetic construct
SEQUENCE: 207
gcgcaggctc ttgaacagat tggccatctc gatggcgctc agggcggctt cccatccctt  60
gttgccgtgc ttggtgccgg ctctctcgat ggcctgttcc agggtgtcgg cggtgatcac  120
tccgaaggtg atgggcttcc gcagttccag gctcaggttg gccaggccct tggacacctc  180
gctggcgata tagtcgaagt ggggggtggc gcctctgatc agcacgccga tggcgatgac  240
ggcgtcgata tcctctttcc gggccagctc gccggcagcc acaggaattt cccagctgcc  300
gggcacgcgg accagggtga tgtcctcttc tctgccgccg tgccgcacga tgcagtcgat  360
ggcgccttcc accagtctgt ccaccagggc gtggttgaac cggctggcca cgatgccgaa  420
tctcaggccc tcggctgtca gcttgccctc gtagatttgc atgccgcttc cctcgcggtt  480
```

```
cagcttgctt tcctcgctgt acttggggta gtcgtaggtg ccgttcttca cgctttccat  540
gcactcgttg ttgcacttgt ggtagaactc gaagcagccg ttgccgatct ctttggcgtt  600
gttcttcagc tgggacttca ctttctcgta caggttcttc acgttgctgt cgtggaagtc  660
cagggtccgc tcgttcagca gcaggaccag cagttcagcc agatcggtgc cgctgccgcc  720
ggagcccatc ttctcgatca cgctgttcac catgttggtg atgccgttga tggcgttctg  780
ggtggacttc tggtcggcgg cgtagccgct gccctgctcg ttctggtggt ggtagccgta  840
ccacccgtcc accatgccgg tccagccgcc ctcgataaag ccggcaatgg cgccgaacag  900
gccccgtgtc tctctctggg ggatgttccg caggcctgtc accatccgca ggccgctgcc  960
caggttcacg ctgtgggtca cggtcacgtt cttttccagc acggtatcca cggtgtcggt  1020
gctgttgttg gcgtggtagc cgatgcagat ggtgtcggcg taggtggcgg tgaaggtgca  1080
caggagcacc agcagcttgg ccttcat                                     1107

SEQ ID NO: 208         moltype = DNA  length = 645
FEATURE                Location/Qualifiers
misc_feature           1..645
                       note = Synthetic
source                 1..645
                       mol_type = other DNA
                       organism = synthetic construct
SEQUENCE: 208
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccaa gcatccagag cagaggactg ttcggcgcta tcgcaggtt tattgagggc   240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcagcgga ggctccggaa cagacctggc tgagctgctg  420
gtgctgctgc tgaaccagtg gactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                 645

SEQ ID NO: 209         moltype = AA  length = 215
FEATURE                Location/Qualifiers
REGION                 1..215
                       note = Synthetic
source                 1..215
                       mol_type = protein
                       organism = synthetic construct
SEQUENCE: 209
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNMV  120
NSVIEKMGSG GSGTDLAELL VLLLNQWTLL FHDSNVKNLY EKVKSQLKNN AKEIGNGCFE  180
FYHKCNNECM ESVKNGTYDY PKYSEESKLN REKID                            215

SEQ ID NO: 210         moltype = DNA  length = 645
FEATURE                Location/Qualifiers
misc_feature           1..645
                       note = Synthetic
source                 1..645
                       mol_type = other DNA
                       organism = synthetic construct
SEQUENCE: 210
gtcaattttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaacagca gagtccactg gttcagcagc agcaccagca gctcagccag  240
gtctgttccg gagcctccgc tgcccatttt ttcgatgaca gaattcacca tgttagtaat  300
gccattgatt gcgttctgtg tagacttctg atcagcggcg tagccgctgc cctgctcatt  360
ctgatggtgg tagccgtacc acccgtccac cattcctgtc cacccgccct caataaaccc  420
tgcgatagcg ccgaacagtc ctctgctctg gatgcttggg atgttgcgca gtccggtgac  480
catcctcagt ccgctgccca gattcactga gtgggtgaca gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat                 645

SEQ ID NO: 211         moltype = DNA  length = 1149
FEATURE                Location/Qualifiers
misc_feature           1..1149
                       note = Synthetic
source                 1..1149
                       mol_type = other DNA
                       organism = synthetic construct
SEQUENCE: 211
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccaa gcatccagag cagaggactg ttcggcgcta tcgcaggtt tattgagggc   240
gggtggacag gaatggtgga cgggtggtac ggctaccacc atcagaatga gcagggcagc  300
ggctacgccg ctgatcagaa gtctacacag aacgcaatca atggcattac taacatggtg  360
```

-continued

```
aattctgtca tcgaaaaaat gggcagcgga ggctccggaa cagacctggc tgagctgctg  420
gtgctgctgc tgaaccagtg gactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgacagtgg gggcgacatc  660
atcaagctgc tgaacgaaca ggtgaacaag gagatgcaga gctccaacct gtacatgagt  720
atgtctagtt ggtgttatac acactcactg gacggcgctg ggctgttcct gtttgatcac  780
gcagccgagg aatacgaaca tgcaaagaaa ctgatcattt tcctgaatga gaacaatgtg  840
cccgtccagc tgacttcaat cagcgcccct gaacataagt tcgagggcct gacccagatc  900
tttcagaaag cttacgaaca cgagcagcat atttccgaat ctatcaacaa tattgtggac  960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtca                                                          1149

SEQ ID NO: 212          moltype = AA  length = 383
FEATURE                 Location/Qualifiers
REGION                  1..383
                        note = Synthetic
source                  1..383
                        mol_type = protein
                        organism = synthetic construct
SEQUENCE: 212
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNMV  120
NSVIEKMGSG GSGTDLAELL VLLLNQWTLL FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                          383

SEQ ID NO: 213          moltype = DNA  length = 1149
FEATURE                 Location/Qualifiers
misc_feature            1..1149
                        note = Synthetic
source                  1..1149
                        mol_type = other DNA
                        organism = synthetic construct
SEQUENCE: 213
tgacccactt tttctggact tggcaatgcc cttcacatac tgatctgcca ggtacaggcc  60
atgattctcg tttccaatca gttcgatttt atccaggatg tccttaaaca ggacctcctc  120
ctcgtgctgc tcggccacgt accactgcag aaagttgaag gtagcatgat ctttgctctt  180
aatggcgtgg tccacaatat tgttgataga ttcggaaata tgctgctcgt gttcgtaagc  240
tttctgaaag atctgggtca ggccctcgaa cttatgttca ggggcgctga ttgaagtcag  300
ctggacgggc acattgttct cattcaggaa aatgatcagt ttctttgcat gttcgtattc  360
ctcggctgcg tgatcaaaca ggaacagccc agcgccgtcc agtgagtgtg tataacacca  420
actagacata ctcatgtaca ggttggagct ctgcatctcc ttgttcacct gttcgttcag  480
cagcttgatg atgtcgcccc cactgtcaat tttctctcga ttcagcttac tctcttcaga  540
atatttggga tagtcgtaag tgccgttctt cacagactcc atacattcat tgttgcactt  600
atggtaaaac tcgaagcatc cattcccgat ttctttggca ttgttcttca gctgggattt  660
gaccttctca tacagattct tcacgttgct atcgtggaac agcagagtcc actggttcag  720
cagcagcacc agcagctcag ccaggtctgt tccggagcct ccgctgccca tttttttcgat  780
gacagaattc accatgttag taatgccatt gattgcgttc tgtgtagact tctgatcagc  840
ggcgtagccg ctgccctgct cattctgatg gtggtagccg taccacccgt ccaccattcc  900
tgtccacccg ccctcaataa accctgcgat agcgccgaac agtcctctgc tctggatgct  960
tgggatgttg cgcagtccgg tgaccatcct cagtccgctg cccagattca ctgagtgggt  1020
gacagtcacg ttcttctcca ggacggtatc cactgtgtcg gtggagttgt ttgcgtgata  1080
gccgatgcag atagtgtcag cgtaggttgc ggtaaaagta cacagcagga ccagcagttt  1140
ggccttcat                                                          1149

SEQ ID NO: 214          moltype = AA  length = 215
FEATURE                 Location/Qualifiers
REGION                  1..215
                        note = Synthetic
source                  1..215
                        mol_type = protein
                        organism = synthetic construct
SEQUENCE: 214
MKAKLLVLLC TFTATYADTL CIGYHANNST DTVDTVLEKN VTVTHSVNLG SGLRLATGLR  60
NIPSIQSRGL FGAIAGFIEG GWTGMVDGWY GYHHQNEQGS GYAADLKSTQ NAIDEITNMV  120
NSVIEKMGSG GSGTDLAELL VLLLNQWTLL YHDSNVKNLY EKVRSQLKNN AKEIGNGCFE  180
FYHKCDNTCM ESVKNGTYDY PKYSEEAKLN REKID                             215

SEQ ID NO: 215          moltype = AA  length = 383
FEATURE                 Location/Qualifiers
REGION                  1..383
                        note = Synthetic
source                  1..383
                        mol_type = protein
```

```
                         organism = synthetic construct
SEQUENCE: 215
MKAKLLVLLC TFTATYADTL CIGYHANNST DTVDTVLEKN VTVTHSVNLG SGLRLATGLR  60
NIPSIQSRGL FGAIAGFIEG GWTGMVDGWY GYHHQNEQGS GYAADLKSTQ NAIDEITNMV  120
NSVIEKMGSG GSGTDLAELL VLLLNQWTLL YHDSNVKNLY EKVRSQLKNN AKEIGNGCFE  180
FYHKCDNTCM ESVKNGTYDY PKYSEEAKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                          383

SEQ ID NO: 216           moltype = DNA  length = 645
FEATURE                  Location/Qualifiers
misc_feature             1..645
                         note = Synthetic
source                   1..645
                         mol_type = other DNA
                         organism = synthetic construct
SEQUENCE: 216
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcagcgga ggctccggaa catacaacgc tgagctgctg  420
gtgctgctgc tgaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                  645

SEQ ID NO: 217           moltype = AA  length = 215
FEATURE                  Location/Qualifiers
REGION                   1..215
                         note = Synthetic
source                   1..215
                         mol_type = protein
                         organism = synthetic construct
SEQUENCE: 217
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNMV  120
NSVIEKMGSG GSGTYNAELL VLLLNERTLD FHDSNVKNLY EKVKSQLKNN AKEIGNGCFE  180
FYHKCNNECM ESVKNGTYDY PKYSEESKLN REKID                              215

SEQ ID NO: 218           moltype = DNA  length = 645
FEATURE                  Location/Qualifiers
misc_feature             1..645
                         note = Synthetic
source                   1..645
                         mol_type = other DNA
                         organism = synthetic construct
SEQUENCE: 218
gtcaatttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaaatcca gagtccgctc gttcagcagc agcaccagca gctcagcgtt  240
gtatgttccg gagcctccgc tgcccatttt ttcgatgaca gaattcacca tgttagtaat  300
gccattgatt gcgttctgtg tagacttctg atcagcggcg tagccgctgc cctgctcatt  360
ctgatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat                  645

SEQ ID NO: 219           moltype = DNA  length = 1149
FEATURE                  Location/Qualifiers
misc_feature             1..1149
                         note = Synthetic
source                   1..1149
                         mol_type = other DNA
                         organism = synthetic construct
SEQUENCE: 219
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcagcgga ggctccggaa catacaacgc tgagctgctg  420
gtgctgctgc tgaacgagcg gactctggat ttccacgata gcaacgtgaa gaatctgtat  480
```

-continued

```
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgacagtgg gggcgacatc  660
atcaagctgc tgaacgaaca ggtgaacaag gagatgcaga gctccaacct gtacatgagt  720
atgtctagtt ggtgttatac acactcactg gacggcgctg ggctgttcct gtttgatcac  780
gcagccgagg aatacgaaca tgcaaagaaa ctgatcattt tcctgaatga gaacaatgtg  840
cccgtccagc tgacttcaat cagcgcccct gaacataagt tcgagggcct gacccagatc  900
tttcagaaag cttacgaaca cgagcagcat atttccgaat ctatcaacaa tattgtggac  960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtca                                                         1149

SEQ ID NO: 220          moltype = AA  length = 383
FEATURE                 Location/Qualifiers
REGION                  1..383
                        note = Synthetic
source                  1..383
                        mol_type = protein
                        organism = synthetic construct
SEQUENCE: 220
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNMV  120
NSVIEKMGSG GSGTYNAELL VLLLNERTLD FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                         383

SEQ ID NO: 221          moltype = DNA  length = 1151
FEATURE                 Location/Qualifiers
misc_feature            1..1151
                        note = Synthetic
source                  1..1151
                        mol_type = other DNA
                        organism = synthetic construct
SEQUENCE: 221
rctgacccac tttttctgga cttggcaatg cccttcacat actgatctgc caggtacagg  60
ccatgattct cgtttccaat cagttcgatt ttatccagga tgtccttaaa caggacctcc  120
tcctcgtgct gctcggccac gtaccactgc agaaagttga aggtagcatg atctttgctc  180
ttaatggcgt ggtccacaat attgttgata gattcggaaa tatgctgctc gtgttcgtaa  240
gctttctgaa agatctgggt caggccctcg aacttatgtt caggggcgct gattgaagtc  300
agctggacgg gcacattgtt ctcattcagg aaaatgatca gtttctttgc atgttcgtat  360
tcctcggctg cgtgatcaaa caggaacagc ccagcgccgt ccagtgagtg tgtataacac  420
caactagaca tactcatgta caggttggag ctctgcatct ccttgttcac ctgttcgttc  480
agcagcttga tgatgtcgcc cccactgtca attttctctc gattcagctt actctcttca  540
gaatatttgg gatagtcgta agtgccgttc ttcacagact ccatacattc attgttgcac  600
ttatggtaaa actcgaagca tccattcccg atttctttgg cattgttctt cagctgggat  660
ttgaccttct catacagatt cttcacgttg ctatcgtgga aatccagagt ccgctcgttc  720
agcagcagca ccagcagctc agcgttgtat gttccggagc ctccgctgcc catttttttcg  780
atgacagaat tcaccatgtt agtaatgcca ttgattgcgt tctgtgtaga cttctgatca  840
gcggcgtagc cgctgccctg ctcattctga tggtggtagc cgtaccaccc gtccaccatt  900
cctgtccacc cgccctcaat aaaccctgcg atagcgccga acagtcctct tgtttcccgc  960
tgtgggatgt tgcgcagtcc ggtgaccatc ctcagtccgc tgcccagatt cactgagtgg  1020
gtgacagtca cgttcttctc caggacggta tccactgtgt cggtggagtt gtttgcgtga  1080
tagccgatgc agatagtgtc agcgtaggtt gcggtaaaag tacacagcag gaccagcagt  1140
ttggccttca t                                                      1151

SEQ ID NO: 222          moltype = AA  length = 215
FEATURE                 Location/Qualifiers
REGION                  1..215
                        note = Synthetic
source                  1..215
                        mol_type = protein
                        organism = synthetic construct
SEQUENCE: 222
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNMV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLN REKID                            215

SEQ ID NO: 223          moltype = AA  length = 383
FEATURE                 Location/Qualifiers
REGION                  1..383
                        note = Synthetic
source                  1..383
                        mol_type = protein
                        organism = synthetic construct
SEQUENCE: 223
```

-continued

```
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNMV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                         383

SEQ ID NO: 224         moltype = AA  length = 215
FEATURE                Location/Qualifiers
REGION                 1..215
                       note = Synthetic
source                 1..215
                       mol_type = protein
                       organism = synthetic construct
SEQUENCE: 224
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNIV  120
NSVIEKMGSG GSGTDLAELL VLLINERTLD FHDSNVKNLY EKVKSQLKNN AKEIGNGCFE  180
FYHKCNNECM ESVKNGTYDY PKYSEESKLN REKID                            215

SEQ ID NO: 225         moltype = AA  length = 383
FEATURE                Location/Qualifiers
REGION                 1..383
                       note = Synthetic
source                 1..383
                       mol_type = protein
                       organism = synthetic construct
SEQUENCE: 225
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNIV  120
NSVIEKMGSG GSGTDLAELL VLLINERTLD FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                         383

SEQ ID NO: 226         moltype = AA  length = 215
FEATURE                Location/Qualifiers
REGION                 1..215
                       note = Synthetic
source                 1..215
                       mol_type = protein
                       organism = synthetic construct
SEQUENCE: 226
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNLV  120
NSVIEKMGSG GSGTDLAELL VLLINERTLD FHDSNVKNLY EKVKSQLKNN AKEIGNGCFE  180
FYHKCNNECM ESVKNGTYDY PKYSEESKLN REKID                            215

SEQ ID NO: 227         moltype = AA  length = 383
FEATURE                Location/Qualifiers
REGION                 1..383
                       note = Synthetic
source                 1..383
                       mol_type = protein
                       organism = synthetic construct
SEQUENCE: 227
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNLV  120
NSVIEKMGSG GSGTDLAELL VLLINERTLD FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                         383

SEQ ID NO: 228         moltype = AA  length = 215
FEATURE                Location/Qualifiers
REGION                 1..215
                       note = Synthetic
source                 1..215
                       mol_type = protein
                       organism = synthetic construct
SEQUENCE: 228
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNLV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLN REKID                            215
```

-continued

```
SEQ ID NO: 229          moltype = AA  length = 383
FEATURE                 Location/Qualifiers
REGION                  1..383
                        note = Synthetic
source                  1..383
                        mol_type = protein
                        organism = synthetic construct
SEQUENCE: 229
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNLV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                         383

SEQ ID NO: 230          moltype = AA  length = 215
FEATURE                 Location/Qualifiers
REGION                  1..215
                        note = Synthetic
source                  1..215
                        mol_type = protein
                        organism = synthetic construct
SEQUENCE: 230
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNMV  120
NSVIEKMGSG GSGTDLAELL VLLMNERTLD FHDSNVKNLY EKVKSQLKNN AKEIGNGCFE  180
FYHKCNNECM ESVKNGTYDY PKYSEESKLN REKID                             215

SEQ ID NO: 231          moltype = AA  length = 383
FEATURE                 Location/Qualifiers
REGION                  1..383
                        note = Synthetic
source                  1..383
                        mol_type = protein
                        organism = synthetic construct
SEQUENCE: 231
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNMV  120
NSVIEKMGSG GSGTDLAELL VLLMNERTLD FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                         383

SEQ ID NO: 232          moltype = AA  length = 215
FEATURE                 Location/Qualifiers
REGION                  1..215
                        note = Synthetic
source                  1..215
                        mol_type = protein
                        organism = synthetic construct
SEQUENCE: 232
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNQV  120
NSVIEKMGSG GSGTDLAELL VLLQNERTLD FHDSNVKNLY EKVKSQLKNN AKEIGNGCFE  180
FYHKCNNECM ESVKNGTYDY PKYSEESKLN REKID                             215

SEQ ID NO: 233          moltype = AA  length = 383
FEATURE                 Location/Qualifiers
REGION                  1..383
                        note = Synthetic
source                  1..383
                        mol_type = protein
                        organism = synthetic construct
SEQUENCE: 233
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNQV  120
NSVIEKMGSG GSGTDLAELL VLLQNERTLD FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                         383

SEQ ID NO: 234          moltype = DNA  length = 645
FEATURE                 Location/Qualifiers
misc_feature            1..645
                        note = Synthetic
source                  1..645
```

```
                         mol_type = other DNA
                         organism = synthetic construct
SEQUENCE: 234
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca ccaactcaac taatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcagcgga ggctccggaa cagacctggc tgagctgctg  420
gtgctgctgc tgaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                 645

SEQ ID NO: 235           moltype = AA  length = 215
FEATURE                  Location/Qualifiers
REGION                   1..215
                         note = Synthetic
source                   1..215
                         mol_type = protein
                         organism = synthetic construct
SEQUENCE: 235
MKAKLLVLLC TFTATYADTI CIGYHANNST DTVDTVLEKN VTVTNSTNLG SGLRMVTGLR  60
NIPSIQSRGL FGAIAGFIEG GWTGMVDGWY GYHHQNEQGS GYAADQKSTQ NAINGITNMV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLN REKID                            215

SEQ ID NO: 236           moltype = DNA  length = 645
FEATURE                  Location/Qualifiers
misc_feature             1..645
                         note = Synthetic
source                   1..645
                         mol_type = other DNA
                         organism = synthetic construct
SEQUENCE: 236
gtcaattttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaaatcca gagtccgctc gttcagcagc agcaccagca gctcagccag  240
gtctgttccg gagcctccgc tgcccatttt ttcgatgaca gaattcacca tgttagtaat  300
gccattgatt gcgttctgtg tagacttctg atcagcggcg tagccgctgc cctgctcatt  360
ctgatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattagttga gttggtgaca gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat                 645

SEQ ID NO: 237           moltype = DNA  length = 1149
FEATURE                  Location/Qualifiers
misc_feature             1..1149
                         note = Synthetic
source                   1..1149
                         mol_type = other DNA
                         organism = synthetic construct
SEQUENCE: 237
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca ccaactcaac taatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcagcgga ggctccggaa cagacctggc tgagctgctg  420
gtgctgctgc tgaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgacagtgg gggcgacatc  660
atcaagctgc tgaacgaaca ggtgaacaag gagatgcaga gctccaacct gtacatgagt  720
atgtctagtt ggtgttatac acactcactg gacggcgctg ggctgttcct gtttgatcac  780
gcagccgagg aatacgaaca tgcaaagaaa ctgatcattt tcctgaatga gaacaatgtg  840
cccgtccagc tgacttcaat cagcgcccct gaacataagt tcgagggcct gacccagatc  900
tttcagaaag cttacgaaca cgagcagcat atttccgaat ctatcaacaa tattgtggac  960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtca                                                         1149

SEQ ID NO: 238           moltype = AA  length = 383
FEATURE                  Location/Qualifiers
```

```
REGION                  1..383
                        note = Synthetic
source                  1..383
                        mol_type = protein
                        organism = synthetic construct
SEQUENCE: 238
MKAKLLVLLC TFTATYADTI CIGYHANNST DTVDTVLEKN VTVTNSTNLG SGLRMVTGLR  60
NIPSIQSRGL FGAIAGFIEG GWTGMVDGWY GYHHQNEQGS GYAADQKSTQ NAINGITNMV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                          383

SEQ ID NO: 239          moltype = DNA  length = 1149
FEATURE                 Location/Qualifiers
misc_feature            1..1149
                        note = Synthetic
source                  1..1149
                        mol_type = other DNA
                        organism = synthetic construct
SEQUENCE: 239
tgacccactt tttctggact tggcaatgcc cttcacatac tgatctgcca ggtacaggcc  60
atgattctcg tttccaatca gttcgatttt atccaggatg tccttaaaca ggacctcctc  120
ctcgtgctgc tcggccacgt accactgcag aaagttgaag gtagcatgat ctttgctctt  180
aatggcgtgg tccacaatat tgttgataga ttcggaaata tgctgctcgt gttcgtaagc  240
tttctgaaag atctgggtca ggccctcgaa cttatgttca ggggcgctga ttgaagtcag  300
ctggacgggc acattgttct cattcaggaa aatgatcagt ttctttgcat gttcgtattc  360
ctcggctgcg tgatcaaaca ggaacagccc agcgccgtcc agtgagtgtg tataacacca  420
actagacata ctcatgtaca ggttggagct ctgcatctcc ttgttcacct gttcgttcag  480
cagcttgatg atgtcgcccc cactgtcaat tttctctcga ttcagcttac tctcttcaga  540
atatttggga tagtcgtaag tgccgttctt cacagactcc atacattcat tgttgcactt  600
atggtaaaac tcgaagcatc cattcccgat ttctttggca ttgttcttca gctgggattt  660
gaccttctca tacagattct tcacgttgct atcgtggaaa tccagagtcc gctcgttcag  720
cagcagcacc agcagctcag ccaggtctgt tccggagcct ccgctgccca ttttttcgat  780
gacagaattc accatgttag taatgccatt gattgcgttc tgtgtagact tctgatcagc  840
ggcgtagccg ctgccctgct cattctgatg gtggtagccg taccacccgt ccaccattcc  900
tgtccacccg ccctcaataa accctgcgat agcgccgaac agtcctcttg tttcccgctg  960
tgggatgttg cgcagtccgg tgaccatcct cagtccgctg cccagattag ttgagttggt  1020
gacagtcacg ttcttctcca ggacggtatc cactgtgtcg gtggagttgt ttgcgtgata  1080
gccgatgcag atagtgtcag cgtaggttgc ggtaaaagta cacagcagga ccagcagttt  1140
ggccttcat                                                          1149

SEQ ID NO: 240          moltype = AA  length = 215
FEATURE                 Location/Qualifiers
REGION                  1..215
                        note = Synthetic
source                  1..215
                        mol_type = protein
                        organism = synthetic construct
SEQUENCE: 240
MKAKLLVLLC TFTATYADTI CIGYHANNST DTVDTILEKN VTVTHSVNLG SGLRMVTGLR  60
NIPSIQSRGL FGAIAGFIEG GWTGMVDGWY GYHHQNEQGS GYAADQKSTQ NAINGITNMV  120
NSVIEKMGSG GSGTDLAELL VLMLNQFTLL FHDSNVKNLY EKVKSQLKNN AKEIGNGCFE  180
FYHKCNNECM ESVKNGTYDY PKYSEESKLN REKID                             215

SEQ ID NO: 241          moltype = AA  length = 383
FEATURE                 Location/Qualifiers
REGION                  1..383
                        note = Synthetic
source                  1..383
                        mol_type = protein
                        organism = synthetic construct
SEQUENCE: 241
MKAKLLVLLC TFTATYADTI CIGYHANNST DTVDTILEKN VTVTHSVNLG SGLRMVTGLR  60
NIPSIQSRGL FGAIAGFIEG GWTGMVDGWY GYHHQNEQGS GYAADQKSTQ NAINGITNMV  120
NSVIEKMGSG GSGTDLAELL VLMLNQFTLL FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                          383

SEQ ID NO: 242          moltype = AA  length = 215
FEATURE                 Location/Qualifiers
REGION                  1..215
                        note = Synthetic
source                  1..215
                        mol_type = protein
                        organism = synthetic construct
```

-continued

```
SEQUENCE: 242
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNMV  120
NSVIEKMGNG TGGADLAELL VLLLNQWTLL FHDSNVKNLY EKVKSQLKNN AKEIGNGCFE  180
FYHKCNNECM ESVKNGTYDY PKYSEESKLN REKID                            215

SEQ ID NO: 243          moltype = AA  length = 383
FEATURE                 Location/Qualifiers
REGION                  1..383
                        note = Synthetic
source                  1..383
                        mol_type = protein
                        organism = synthetic construct
SEQUENCE: 243
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNMV  120
NSVIEKMGNG TGGADLAELL VLLLNQWTLL FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                         383

SEQ ID NO: 244          moltype = AA  length = 215
FEATURE                 Location/Qualifiers
REGION                  1..215
                        note = Synthetic
source                  1..215
                        mol_type = protein
                        organism = synthetic construct
SEQUENCE: 244
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNMV  120
NSVIEKMGGN GTGADLAELL VLLLNQWTLL FHDSNVKNLY EKVKSQLKNN AKEIGNGCFE  180
FYHKCNNECM ESVKNGTYDY PKYSEESKLN REKID                            215

SEQ ID NO: 245          moltype = AA  length = 383
FEATURE                 Location/Qualifiers
REGION                  1..383
                        note = Synthetic
source                  1..383
                        mol_type = protein
                        organism = synthetic construct
SEQUENCE: 245
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNMV  120
NSVIEKMGGN GTGADLAELL VLLLNQWTLL FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                         383

SEQ ID NO: 246          moltype = AA  length = 215
FEATURE                 Location/Qualifiers
REGION                  1..215
                        note = Synthetic
source                  1..215
                        mol_type = protein
                        organism = synthetic construct
SEQUENCE: 246
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNMV  120
NSVIEKMGSG GNGTDLAELL VLLLNQWTLL FHDSNVKNLY EKVKSQLKNN AKEIGNGCFE  180
FYHKCNNECM ESVKNGTYDY PKYSEESKLN REKID                            215

SEQ ID NO: 247          moltype = AA  length = 383
FEATURE                 Location/Qualifiers
REGION                  1..383
                        note = Synthetic
source                  1..383
                        mol_type = protein
                        organism = synthetic construct
SEQUENCE: 247
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNMV  120
NSVIEKMGSG GNGTDLAELL VLLLNQWTLL FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                         383
```

-continued

```
SEQ ID NO: 248          moltype = AA  length = 215
FEATURE                 Location/Qualifiers
REGION                  1..215
                        note = Synthetic
source                  1..215
                        mol_type = protein
                        organism = synthetic construct
SEQUENCE: 248
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHNNTQGS GYAADQKSTQ NAINGITNMV  120
NSVIEKMGGN GTGADLAELL VLLLNQWTLL FHDSNVKNLY EKVKSQLKNN AKEIGNGCFE  180
FYHKCNNECM ESVKNGTYDY PKYSEESKLN REKID                            215

SEQ ID NO: 249          moltype = AA  length = 383
FEATURE                 Location/Qualifiers
REGION                  1..383
                        note = Synthetic
source                  1..383
                        mol_type = protein
                        organism = synthetic construct
SEQUENCE: 249
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHNNTQGS GYAADQKSTQ NAINGITNMV  120
NSVIEKMGGN GTGADLAELL VLLLNQWTLL FHDSNVKNLY EKVKSQLKNN AKEIGNGCFE  180
FYHKCNNECM ESVKNGTYDY PKYSEESKLN REKIDSGGDI IKLLNEQVNK EMNSTNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                         383

SEQ ID NO: 250          moltype = AA  length = 215
FEATURE                 Location/Qualifiers
REGION                  1..215
                        note = Synthetic
source                  1..215
                        mol_type = protein
                        organism = synthetic construct
SEQUENCE: 250
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHNNTQGS GYAADQKSTQ NAINGITNMV  120
NSVIEKMGGN GTGADLAELL VLLLNQWTLL FHDSNVKNLY EKVKSQLKNN AKEIGNGCFE  180
FYHKCNNECM ESVKNGTYDY PKYSEESKLN REKID                            215

SEQ ID NO: 251          moltype = AA  length = 383
FEATURE                 Location/Qualifiers
REGION                  1..383
                        note = Synthetic
source                  1..383
                        mol_type = protein
                        organism = synthetic construct
SEQUENCE: 251
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHNNTQGS GYAADQKSTQ NAINGITNMV  120
NSVIEKMGGN GTGADLAELL VLLLNQWTLL FHDSNVKNLY EKVKSQLKNN AKEIGNGCFE  180
FYHKCNNECM ESVKNGTYDY PKYSEESKLN REKIDSGGDI IKLLNEQVNK EMNSTNLYMS  240
MSSWCYTHSL DGAGLFLFDH AAEEYEHAKK LIIFLNENNV PVNLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                         383

SEQ ID NO: 252          moltype = AA  length = 214
FEATURE                 Location/Qualifiers
REGION                  1..214
                        note = Synthetic
source                  1..214
                        mol_type = protein
                        organism = synthetic construct
SEQUENCE: 252
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNMV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLN REGG                             214

SEQ ID NO: 253          moltype = AA  length = 368
FEATURE                 Location/Qualifiers
REGION                  1..368
                        note = Synthetic
source                  1..368
                        mol_type = protein
                        organism = synthetic construct
```

```
SEQUENCE: 253
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNMV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLN REGGMQIYEG KLTAEGLRFG IVASRFNHAL  240
VDRLVEGAID CIVRHGGREE DITLVRVPGS WEIPVAAGEL ARKEDIDAVI AIGVLIRGAT  300
PHFDYIASEV SKGLANLSLE LRKPITFGVI TADTLEQAIE RAGTKHGNKG WEAALSAIEM  360
ANLFKSLR                                                          368

SEQ ID NO: 254         moltype = AA  length = 215
FEATURE                Location/Qualifiers
REGION                 1..215
                       note = Synthetic
source                 1..215
                       mol_type = protein
                       organism = synthetic construct
SEQUENCE: 254
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNMV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLN REGSG                            215

SEQ ID NO: 255         moltype = AA  length = 369
FEATURE                Location/Qualifiers
REGION                 1..369
                       note = Synthetic
source                 1..369
                       mol_type = protein
                       organism = synthetic construct
SEQUENCE: 255
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNMV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLN REGSGMQIYE GKLTAEGLRF GIVASRFNHA  240
LVDRLVEGAI DCIVRHGGRE EDITLVRVPG SWEIPVAAGE LARKEDIDAV IAIGVLIRGA  300
TPHFDYIASE VSKGLANLSL ELRKPITFGV ITADTLEQAI ERAGTKHGNK GWEAALSAIE  360
MANLFKSLR                                                         369

SEQ ID NO: 256         moltype = AA  length = 211
FEATURE                Location/Qualifiers
REGION                 1..211
                       note = Synthetic
source                 1..211
                       mol_type = protein
                       organism = synthetic construct
SEQUENCE: 256
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNMV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLG G                                211

SEQ ID NO: 257         moltype = AA  length = 364
FEATURE                Location/Qualifiers
REGION                 1..364
                       note = Synthetic
source                 1..364
                       mol_type = protein
                       organism = synthetic construct
SEQUENCE: 257
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNMV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLG GQIYEGKLTA EGLRFGIVAS RFNHALVDRL  240
VEGAIDCIVR HGGREEDITL VRVPGSWEIP VAAGELARKE DIDAVIAIGV LIRGATPHFD  300
YIASEVSKGL ANLSLELRKP ITFGVITADT LEQAIERAGT KHGNKGWEAA LSAIEMANLF  360
KSLR                                                              364

SEQ ID NO: 258         moltype = AA  length = 212
FEATURE                Location/Qualifiers
REGION                 1..212
                       note = Synthetic
source                 1..212
                       mol_type = protein
                       organism = synthetic construct
SEQUENCE: 258
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNMV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLG SG                               212
```

-continued

```
SEQ ID NO: 259          moltype = AA  length = 365
FEATURE                 Location/Qualifiers
REGION                  1..365
                        note = Synthetic
source                  1..365
                        mol_type = protein
                        organism = synthetic construct
SEQUENCE: 259
MKAKLLVLLC TFTATYADTI CIGYHANNST DTVDTVLEKN VTVTHSVNLG SGLRMVTGLR  60
NIPSIQSRGL FGAIAGFIEG GWTGMVDGWY GYHHQNEQGS GYAADQKSTQ NAINGITNMV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLG SGQIYEGKLT AEGLRFGIVA SRFNHALVDR  240
LVEGAIDCIV RHGGREEDIT LVRVPGSWEI PVAAGELARK EDIDAVIAIG VLIRGATPHF  300
DYIASEVSKG LANLSLELRK PITFGVITAD TLEQAIERAG TKHGNKGWEA ALSAIEMANL  360
FKSLR                                                             365

SEQ ID NO: 260          moltype = DNA  length = 645
FEATURE                 Location/Qualifiers
misc_feature            1..645
                        note = Synthetic
source                  1..645
                        mol_type = other DNA
                        organism = synthetic construct
CDS                     1..645
SEQUENCE: 260
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcagcgga ggctccggaa cagacctggc tgagctgctg  420
gtgctgctgc tgaaccagtg gactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                 645

SEQ ID NO: 261          moltype = AA  length = 215
FEATURE                 Location/Qualifiers
REGION                  1..215
                        note = Synthetic Construct
source                  1..215
                        mol_type = protein
                        organism = synthetic construct
SEQUENCE: 261
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGSG GSGTDLAELL VLLLNQWTLL FHDSNVKNLY EKVKSQLKNN AKEIGNGCFE  180
FYHKCNNECM ESVKNGTYDY PKYSEESKLN REKID                            215

SEQ ID NO: 262          moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 262
gtcaattttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaacagca gagtccactg gttcagcagc agcaccagca gctcagccag  240
gtctgttccg gagcctccgc tgcccatttt ttcgatgaca gaattcacca tgttagtaat  300
gccattgatt gcgttctgtg tagacttctg atcagcggcg tagccgctgc cctgctcatt  360
ctgatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat                 645

SEQ ID NO: 263          moltype = DNA  length = 1155
FEATURE                 Location/Qualifiers
misc_feature            1..1155
                        note = Synthetic
source                  1..1155
                        mol_type = other DNA
                        organism = synthetic construct
CDS                     1..1155
```

SEQUENCE: 263
atgaaggcca aactgctggt cctgctgtgt acttttaccg caacctacgc tgacactatc 60
tgcatcggct atcacgcaaa caactccacc gacacagtgg ataccgtcct ggagaagaac 120
gtgactgtca cccactcagt gaatctgggc agcggactga ggatggtcac cggactgcgc 180
aacatcccac agcgggaaac aagaggactg ttcggcgcta tcgcagggtt tattgagggc 240
gggtggacag gaatggtgga cgggtggtac ggctaccacc atcagaatga gcagggcagc 300
ggctacgccg ctgatcagaa gtctacacag aacgcaatca atggcattac taacatggtg 360
aattctgtca tcgaaaaaat gggcagcgga ggctccggaa cagacctggc tgagctgctg 420
gtgctgctgc tgaaccagtg gactctgctg ttccacgata gcaacgtgaa gaatctgtat 480
gagaaggtca aatcccagct gaagaacaat gccaaagaaa tcgggaatgg atgcttcgag 540
ttttaccata agtgcaacaa tgaatgtatg gagtctgtga agaacggcac ttacgactat 600
cccaaatatt ctgaagagag taagctgaat cgagagaaaa ttgacagtgg gggcgacatc 660
atcaagctgc tgaacgaaca ggtgaacaag gagatgcaga gctccaacct gtacatgagt 720
atgtctagtt ggtgttatac acactcactg gacggcgctg ggctgttcct gtttgatcac 780
gcagccgagg aatacgaaca tgcaaagaaa ctgatcattt tcctgaatga gaacaatgtg 840
cccgtccagc tgacttcaat cagcgcccct gaacataagt tcgagggcct gacccagatc 900
tttcagaaag cttacgaaca cgagcagcat atttccgaat ctatcaacaa tattgtggac 960
cacgccatta agagcaaaga tcatgctacc ttcaactttc tgcagtggta cgtggccgag 1020
cagcacgagg aggaggtcct gtttaaggac atcctggata aaatcgaact gattggaaac 1080
gagaatcatg gcctgtacct ggcagatcag tatgtgaagg gcattgccaa gtccagaaaa 1140
agtgggtcat gatga 1155

SEQ ID NO: 264 moltype = AA length = 383
FEATURE Location/Qualifiers
REGION 1..383
note = Synthetic Construct
source 1..383
mol_type = protein
organism = synthetic construct
SEQUENCE: 264
MKAKLLVLLC TFTATYADTI CIGYHANNST DTVDTVLEKN VTVTHSVNLG SGLRMVTGLR 60
NIPQRETRGL FGAIAGFIEG GWTGMVDGWY GYHHQNEQGS GYAADQKSTQ NAINGITNMV 120
NSVIEKMGSG GSGTDLAELL VLLLNQWTLL FHDSNVKNLY EKVKSQLKNN AKEIGNGCFE 180
FYHKCNNECM ESVKNGTYDY PKYSEESKLN REKIDSGGDI IKLLNEQVNK EMQSSNLYMS 240
MSSWCYTHSL DGAGLFLFDH AAEEYEHAKK LIIFLNENNV PVQLTSISAP EHKFEGLTQI 300
FQKAYEHEQH ISESINNIVD HAIKSKDHAT FNFLQWYVAE QHEEEVLFKD ILDKIELIGN 360
ENHGLYLADQ YVKGIAKSRK SGS 383

SEQ ID NO: 265 moltype = DNA length = 1155
FEATURE Location/Qualifiers
misc_feature 1..1155
note = Synthetic
source 1..1155
mol_type = other DNA
organism = synthetic construct
SEQUENCE: 265
tcatcatgac ccactttttc tggacttggc aatgcccttc acatactgat ctgccaggta 60
caggccatga ttctcgtttc caatcagttc gattttatcc aggatgtcct taaacaggac 120
ctcctcctcg tgctgctcgg ccacgtacca ctgcagaaag ttgaaggtag catgatcttt 180
gctcttaatg gcgtggtcca caatattgtt gatagattcg gaaatatgct gctcgtgttc 240
gtaagctttc tgaaagatct gggtcaggcc ctcgaactta tgttcagggg cgctgattga 300
agtcagctgg acgggcacat tgttctcatt caggaaaatg atcagtttct ttgcatgttc 360
gtattcctcg gctgcgtgat caaacaggaa cagcccagcg ccgtccagtg agtgtgtata 420
acaccaacta gacatactca tgtacaggtt ggagctctgc atctccttgt tcacctgttc 480
gttcagcagc ttgatgatgt cgcccccact gtcaattttc tctcgattca gcttactctc 540
ttcagaatat ttgggatagt cgtaagtgcc gttcttcaca gactccatac attcattgtt 600
gcacttatgg taaaactcga agcatccatt cccgatttct ttggcattgt tcttcagctg 660
ggatttgacc ttctcataca gattcttcac gttgctatcg tggaacagca gagtccactg 720
gttcagcagc agcaccagca gctcagccag gtctgttccg gagcctccgc tgcccatttt 780
ttcgatgaca gaattcacca tgttagtaat gccattgatt gcgttctgtg tagacttctg 840
atcagcggcg tagccgctgc cctgctcatt ctgatggtgg tagccgtacc acccgtccac 900
cattcctgtc cacccgccct caataaaccc tgcgatagcg ccgaacagtc ctcttgtttc 960
ccgctgtggg atgttgcgca gtccggtgac catcctcagt ccgctgccca gattcactga 1020
gtgggtgaca gtcacgttct tctccaggac ggtatccact gtgtcggtgg agttgtttgc 1080
gtgatagccg atgcagatag tgtcagcgta ggttgcggta aaagtacaca gcaggaccag 1140
cagtttggcc ttcat 1155

SEQ ID NO: 266 moltype = DNA length = 5579
FEATURE Location/Qualifiers
misc_feature 1..5579
note = Synthetic
source 1..5579
mol_type = other DNA
organism = synthetic construct
SEQUENCE: 266
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240

-continued

```
ctattggcca ttgcatacgt tgtatccata tcataatatg tacatttata ttggctcatg  300
tccaacatta ccgccatgtt gacattgatt attgactagt tattaatagt aatcaattac  360
ggggtcatta gttcatagcc catatatgga gttccgcgtt acataactta cggtaaatgg  420
cccgcctggc tgaccgccca acgacccccg cccattgacg tcaataatga cgtatgttcc  480
catagtaacg ccaataggga ctttccattg acgtcaatgg gtggagtatt tacggtaaac  540
tgcccacttg gcagtacatc aagtgtatca tatgccaagt acgcccccta ttgacgtcaa  600
tgacggtaaa tggcccgcct ggcattatgc ccagtacatg accttatggg actttcctac  660
ttggcagtac atctacgtat tagtcatcgc tattaccatg gtgatgcggt tttggcagta  720
catcaatggg cgtggatagc ggtttgactc acggggattt ccaagtctcc accccattga  780
cgtcaatggg agtttgtttt ggcaccaaaa tcaacgggac tttccaaaat gtcgtaacaa  840
ctccgcccca ttgacgcaaa tgggcggtag gcgtgtacgg tgggaggtct atataagcag  900
agctcgttta gtgaaccgtc agatcgcctg gagacgccat ccacgctgtt ttgacctcca  960
tagaagacac cgggaccgat ccagcctcca tcggctcgca tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctcaggtc gagaccgggc  1140
ctttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgcggc cgctctagag  1380
atatcgccac catgaaggcc aaactgctgg tcctgctgtg tacttttacc gcaacctacg  1440
ctgacactat ctgcatcggc tatcacgcaa acaactccac cgacacagtg gataccgtcc  1500
tggagaagaa cgtgactgtc acccactcag tgaatctggg cagcggactg aggatggtca  1560
ccggactgcg caacatccca cagcgggaaa caagaggact gttcggcgct atcgcagggt  1620
ttattgaggg cgggtggaca ggaatggtgg acgggtggta cggctaccac catcagaatg  1680
agcagggcag cggctacgcc gctgatcaga agtctacaca gaacgcaatc aatggcatta  1740
ctaacatggt gaattctgtc atcgaaaaaa tgggcagcgg aggctccgga acagacctgg  1800
ctgagctgct ggtgctgctg ctgaaccagt ggactctgct gttccacgat agcaacgtga  1860
agaatctgta tgagaaggtc aaatcccagc tgaagaacaa tgccaaagaa atcgggaatg  1920
gatgcttcga gttttaccat aagtgcaaca atgaatgtat ggagtctgtg aagaacggca  1980
cttacgacta tcccaaatat tctgaagaga gtaagctgaa tcgagagaaa attgacagtg  2040
ggggcgacat catcaagctg ctgaacgaac aggtgaacaa ggagatgcag agctccaacc  2100
tgtacatgag tatgtctagt tggtgttata cacactcact ggacggcgct gggctgttcc  2160
tgtttgatca cgcagccgag gaatacgaac atgcaaagaa actgatcatt ttcctgaatg  2220
agaacaatgt gcccgtccag ctgacttcaa tcagcgcccc tgaacataag ttcgagggcc  2280
tgacccagat ctttcagaaa gcttacgaac acgagcagca tatttccgaa tctatcaaca  2340
atattgtgga ccacgccatt aagagcaaag atcatgctac cttcaacttt ctgcagtggt  2400
acgtggccga gcagcacgag gaggaggtcc tgtttaagga catcctggat aaaatcgaac  2460
tgattggaaa cgagaatcat ggcctgtacc tggcagatca gtatgtgaag ggcattgcca  2520
agtccagaaa aagtgggtca tgatgaacac gtgggatcca gatctgctgt gccttctagt  2580
tgccagccat ctgttgtttg cccctccccc gtgccttcct tgaccctgga aggtgccact  2640
cccactgtcc tttcctaata aaatgaggaa attgcatcgc attgtctgag taggtgtcat  2700
tctattctgg ggggtggggt ggggcaggac agcaaggggg aggattggga agacaatagc  2760
aggcatgctg gggatgcggt gggctctatg ggtacccagg tgctgaagaa ttgacccggt  2820
tcctcctggg ccagaaagaa gcaggcacat ccccttctct gtgacacacc ctgtccacgc  2880
ccctggttct tagttccagc cccactcata ggacactcat agctcaggag ggctccgcct  2940
tcaatcccac ccgctaaagt acttggagcg gtctctccct ccctcatcag cccaccaaac  3000
caaacctagc ctccaagagt gggaagaaat taaagcaaga taggctatta agtgcagagg  3060
gagagaaaat gcctccaaca tgtgaggaag taatgagaga aatcatagaa ttttaaggcc  3120
atgatttaag gccatcatgg ccttaatctt ccgcttcctc gctcactgac tcgctgcgct  3180
cggtcgttcg gctgcggcga gcggtatcag ctcactcaaa ggcggtaata cggttatcca  3240
cagaatcagg ggataacgca ggaaagaaca tgtgagcaaa aggccagcaa aaggccagga  3300
accgtaaaaa ggccgcgttg ctggcgtttt tccataggct ccgcccccct gacgagcatc  3360
acaaaaatcg acgctcaagt cagaggtggc gaaacccgac aggactataa agataccagg  3420
cgtttccccc tggaagctcc ctcgtgcgct ctcctgttcc gaccctgccg cttaccggat  3480
acctgtccgc ctttctccct tcgggaagcg tggcgctttc tcatagctca cgctgtaggt  3540
atctcagttc ggtgtaggtc gttcgctcca agctgggctg tgtgcacgaa ccccccgttc  3600
agcccgaccg ctgcgcctta tccggtaact atcgtcttga gtccaacccg gtaagacacg  3660
acttatcgcc actggcagca gccactggta acaggattag cagagcgagg tatgtaggcg  3720
gtgctacaga gttcttgaag tggtggccta actacggcta cactagaaga acagtatttg  3780
gtatctgcgc tctgctgaag ccagttacct tcggaaaaag agttggtagc tcttgatccg  3840
gcaaacaaac caccgctggt agcggtggtt tttttgtttg caagcagcag attacgcgca  3900
gaaaaaaagg atctcaagaa gatcctttga tcttttctac ggggtctgac gctcagtgga  3960
acgaaaactc acgttaaggg attttggtca tgagattatc aaaaaggatc ttcacctaga  4020
tccttttaaa ttaaaaatga agttttaaat caatctaaag tatatatgag taaacttggt  4080
ctgacagtta ccaatgctta atcagtgagg cacctatctc agcgatctgt ctatttcgtt  4140
catccatagt tgcctgactc gggggggggg ggcgctgagg tctgcctcgt gaagaaggtg  4200
ttgctgactc ataccaggcc tgaatcgccc catcatccag ccagaaagtg agggagccac  4260
ggttgatgag agctttgttg taggtggacc agttggtgat tttgaacttt tgctttgcca  4320
cggaacggtc tgcgttgtcg ggaagatgcg tgatctgatc cttcaactca gcaaaagttc  4380
gatttattca acaaagccgc cgtcccgtca agtcagcgta atgctctgcc agtgttacaa  4440
ccaattaacc aattctgatt agaaaaactc atcgagcatc aaatgaaact gcaatttatt  4500
catatcagga ttatcaatac catatttttg aaaaagccgt ttctgtaatg aaggagaaaa  4560
ctcaccgagg cagttccata ggatggcaag atcctggtat cggtctgcga ttccgactcg  4620
tccaacatca atacaaccta ttaatttccc ctcgtcaaaa ataaggttat caagtgagaa  4680
atcaccatga gtgacgactg aatccggtga gaatggcaaa agcttatgca tttctttcca  4740
gacttgttca acaggccagc cattacgctc gtcatcaaaa tcactcgcat caaccaaacc  4800
gttattcatt cgtgattgcg cctgagcgag acgaaatacg cgatcgctgt taaaaggaca  4860
attacaaaca ggaatcgaat gcaaccggcg caggaacact gccagcgcat caacaatatt  4920
ttcacctgaa tcaggatatt cttctaatac ctggaatgct gttttcccgg ggatcgcagt  4980
```

-continued

```
ggtgagtaac catgcatcat caggagtacg gataaaatgc ttgatggtcg gaagaggcat  5040
aaattccgtc agccagttta gtctgaccat ctcatctgta acatcattgg caacgctacc  5100
tttgccatgt ttcagaaaca actctggcgc atcgggcttc ccatacaatc gatagattgt  5160
cgcacctgat tgcccgacat tatcgcgagc ccatttatac ccatataaat cagcatccat  5220
gttggaattt aatcgcggcc tcgagcaaga cgtttcccgt tgaatatggc tcataacacc  5280
ccttgtatta ctgtttatgt aagcagacag ttttattgtt catgatgata tatttttatc  5340
ttgtgcaatg taacatcaga gattttgaga cacaacgtgg ctttcccccc cccccccatta  5400
ttgaagcatt tatcagggtt attgtctcat gagcggatac atatttgaat gtatttagaa  5460
aaataaacaa ataggggttc cgcgcacatt tccccgaaaa gtgccacctg acgtctaaga  5520
aaccattatt atcatgacat taacctataa aaataggcgt atcacgaggc cctttcgtc   5579

SEQ ID NO: 267          moltype = DNA  length = 645
FEATURE                 Location/Qualifiers
misc_feature            1..645
                        note = Synthetic
source                  1..645
                        mol_type = other DNA
                        organism = synthetic construct
CDS                     1..645
SEQUENCE: 267
atgaaggcaa tcctggtcgt cctgctgtat actttcgcta ccgctaacgc tgacaccctg  60
tgcatcggct atcacgctaa caactcaacc gacacagtgg atactgtcct ggagaagaac  120
gtgactgtca cccactctgt gaatctgggc agtggactga ggctggcaac tggactgcga  180
aacatcccac agcgggaaac cagaggactg ttcggcgcta tcgcagggtt tattgagggc  240
gggtggacag gaatggtgga cgggtggtac ggctaccacc atcagaacga gcagggatca  300
ggctacgccg ctgacctgaa gagcacacag aatgcaatcg atgaaattac taacatggtg  360
aattccgtca tcgagaaaat gggcagcgga ggctccggaa ccgacctggc agaactgctg  420
gtgctgctgc tgaaccagtg gacactgctg taccacgata gtaacgtgaa gaatctgtat  480
gagaaagtcc gatcacagct gaagaacaat gctaaagaaa tcgggaatgg atgcttcgag  540
ttttaccata agtgcgacaa cacctgtatg gagagcgtga aaaatggcac atacgattat  600
cccaagtatt ccgaggaagc caaactgaac agagaggaaa ttgac                 645

SEQ ID NO: 268          moltype = AA  length = 215
FEATURE                 Location/Qualifiers
REGION                  1..215
                        note = Synthetic Construct
source                  1..215
                        mol_type = protein
                        organism = synthetic construct
SEQUENCE: 268
MKAILVVLLY TFATANADTL CIGYHANNST DTVDTVLEKN VTVTHSVNLG SGLRLATGLR  60
NIPQRETRGL FGAIAGFIEG GWTGMVDGWY GYHHQNEQGS GYAADLKSTQ NAIDEITNMV  120
NSVIEKMGSG GSGTDLAELL VLLLNQWTLL YHDSNVKNLY EKVRSQLKNN AKEIGNGCFE  180
FYHKCDNTCM ESVKNGTYDY PKYSEEAKLN REEID                            215

SEQ ID NO: 269          moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 269
gtcaatttcc tctctgttca gtttggcttc ctcggaatac ttgggataat cgtatgtgcc  60
atttttcacg ctctccatac aggtgttgtc gcacttatgg taaaactcga agcatccatt  120
cccgatttct ttagcattgt tcttcagctg tgatcggact ttctcataca gattcttcac  180
gttactatcg tggtacagca gtgtccactg gttcagcagc agcaccagca gttctgccag  240
gtcggttccg gagcctccgc tgcccatttt ctcgatgacg gaattcacca tgttagtaat  300
ttcatcgatt gcattctgtg tgctcttcag gtcagcggcg tagcctgatc cctgctcgtt  360
ctgatggtgg tagccgtacc acccgtccac cattcctgtc cacccgccct caataaaccc  420
tgcgatagcg ccgaacagtc ctctggtttc ccgctgtggg atgtttcgca gtccagttgc  480
cagcctcagt ccactgccca gattcacaga gtgggtgaca gtcacgttct tctccaggac  540
agtatccact gtgtcggttg agttgttagc gtgatagccg atgcacaggg tgtcagcgtt  600
agcggtagcg aaagtataca gcaggacgac caggattgcc ttcat                 645

SEQ ID NO: 270          moltype = DNA  length = 1155
FEATURE                 Location/Qualifiers
misc_feature            1..1155
                        note = Synthetic
source                  1..1155
                        mol_type = other DNA
                        organism = synthetic construct
CDS                     1..1155
SEQUENCE: 270
atgaaggcaa tcctggtcgt cctgctgtat actttcgcta ccgctaacgc tgacaccctg  60
tgcatcggct atcacgctaa caactcaacc gacacagtgg atactgtcct ggagaagaac  120
gtgactgtca cccactctgt gaatctgggc agtggactga ggctggcaac tggactgcga  180
aacatcccac agcgggaaac cagaggactg ttcggcgcta tcgcagggtt tattgagggc  240
gggtggacag gaatggtgga cgggtggtac ggctaccacc atcagaacga gcagggatca  300
```

```
ggctacgccg ctgacctgaa gagcacacag aatgcaatcg atgaaattac taacatggtg  360
aattccgtca tcgagaaaat gggcagcgga ggctccggaa ccgacctggc agaactgctg  420
gtgctgctgc tgaaccagtg gacactgctg taccacgata gtaacgtgaa gaatctgtat  480
gagaaagtcc gatcacagct gaagaacaat gctaaagaaa tcgggaatgg atgcttcgag  540
ttttaccata agtgcgacaa cacctgtatg gagagcgtga aaaatggcac atacgattat  600
cccaagtatt ccgaggaagc caaactgaac agagaggaaa ttgactctgg gggcgacatc  660
atcaagctgc tgaacgaaca ggtcaacaag gagatgcaga gctccaatct gtacatgtcc  720
atgtctagtt ggtgttatac ccactctctg gacggcgctg ggctgttcct gtttgatcac  780
gcagccgagg aatacgaaca tgcaaagaaa ctgatcattt tcctgaacga gaacaatgtg  840
cccgtccagc tgacatcaat cagcgcccct gaacataagt tcgagggcct gactcagatc  900
tttcagaaag cttacgaaca cgagcagcat atttccgaat ctatcaacaa tattgtggac  960
cacgccatta agagtaaaga tcatgctacc ttcaattttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gagccggaaa  1140
agtgggtcat gatga                                                  1155

SEQ ID NO: 271          moltype = AA  length = 383
FEATURE                 Location/Qualifiers
REGION                  1..383
                        note = Synthetic Construct
source                  1..383
                        mol_type = protein
                        organism = synthetic construct
SEQUENCE: 271
MKAILVVLLY TFATANADTL CIGYHANNST DTVDTVLEKN VTVTHSVNLG SGLRLATGLR  60
NIPQRETRGL FGAIAGFIEG GWTGMVDGWY GYHHQNEQGS GYAADLKSTQ NAIDEITNMV  120
NSVIEKMGSG GSGTDLAELL VLLLNQWTLL YHDSNVKNLY EKVRSQLKNN AKEIGNGCFE  180
FYHKCDNTCM ESVKNGTYDY PKYSEEAKLN REEIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                         383

SEQ ID NO: 272          moltype = DNA  length = 1155
FEATURE                 Location/Qualifiers
misc_feature            1..1155
                        note = Synthetic
source                  1..1155
                        mol_type = other DNA
                        organism = synthetic construct
SEQUENCE: 272
tcatcatgac ccacttttcc ggctcttggc aatgcccttc acatactgat ctgccaggta  60
caggccatga ttctcgtttc caatcagttc gattttatcc aggatgtcct taaacaggac  120
ctcctcctcg tgctgctcgg ccacgtacca ctgcagaaaa ttgaaggtag catgatcttt  180
actcttaatg gcgtggtcca caatattgtt gatagattcg gaaatatgct gctcgtgttc  240
gtaagctttc tgaaagatct gagtcaggcc ctcgaactta tgttcagggg cgctgattga  300
tgtcagctgg acgggcacat tgttctcgtt caggaaaatg atcagtttct ttgcatgttc  360
gtattcctcg gctgcgtgat caaacaggaa cagcccagcg ccgtccagag agtgggtata  420
acaccaacta gacatggaca tgtacagatt ggagctctgc atctccttgt tgacctgttc  480
gttcagcagc ttgatgatgt cgcccccaga gtcaatttcc tctctgttca gtttggcttc  540
ctcggaatac ttgggataat cgtatgtgcc atttttcacg ctctccatac aggtgttgtc  600
gcacttatgg taaaactcga agcatccatt cccgatttct ttagcattgt tcttcagctg  660
tgatcggact ttctcataca gattcttcac gttactatcg tggtacagca gtgtccactg  720
gttcagcagc agcaccagca gttctgccag gtcggttccg gagcctccgc tgcccatttt  780
ctcgatgacg gaattcacca tgttagtaat ttcatcgatt gcattctgtg tgctcttcag  840
gtcagcggcg tagcctgatc cctgctcgtt ctgatggtgg tagccgtacc acccgtccac  900
cattcctgtc cacccgccct caataaaccc tgcgatagcg ccgaacagtc ctctggtttc  960
ccgctgtggg atgtttcgca gtccagttgc cagcctcagt ccactgccca gattcacaga  1020
gtgggtgaca gtcacgttct tctccaggac agtatccact gtgtcggttg agttgttagc  1080
gtgatagccg atgcacaggg tgtcagcgtt agcggtagcg aaagtataca gcaggacgac  1140
caggattgcc ttcat                                                  1155

SEQ ID NO: 273          moltype = DNA  length = 5579
FEATURE                 Location/Qualifiers
misc_feature            1..5579
                        note = Synthetic
source                  1..5579
                        mol_type = other DNA
                        organism = synthetic construct
SEQUENCE: 273
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcagattgg  240
ctattggcca ttgcatacgt tgtatccata tcataatatg tacatttata ttggctcatg  300
tccaacatta ccgccatgtt gacattgatt attgactagt tattaatagt aatcaattac  360
ggggtcatta gttcatagcc catatatgga gttccgcgtt acataactta cggtaaatgg  420
cccgcctggc tgaccgccca acgacccccg cccattgacg tcaataatga cgtatgttcc  480
catagtaacg ccaataggga ctttccattg acgtcaatgg gtggagtatt tacggtaaac  540
tgcccacttg gcagtacatc aagtgtatca tatgccaagt acgcccccta ttgacgtcaa  600
```

-continued

```
tgacggtaaa tggcccgcct ggcattatgc ccagtacatg accttatggg actttcctac  660
ttggcagtac atctacgtat tagtcatcgc tattaccatg gtgatgcggt tttggcagta  720
catcaatggg cgtggatagc ggtttgactc acggggattt ccaagtctcc accccattga  780
cgtcaatggg agtttgtttt ggcaccaaaa tcaacgggac tttccaaaat gtcgtaacaa  840
ctccgcccca ttgacgcaaa tgggcggtag gcgtgtacgg tgggaggtct atataagcag  900
agctcgttta gtgaaccgtc agatcgcctg gagacgccat ccacgctgtt ttgacctcca  960
tagaagacac cgggaccgat ccagcctcca tcggctcgca tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctcaggtc gagaccgggc  1140
ctttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgcggc cgctctagag  1380
atatcgccac catgaaggca atcctggtcg tcctgctgta tactttcgct accgctaacg  1440
ctgacaccct gtgcatcggc tatcacgcta acaactcaac cgacacagtg gatactgtcc  1500
tggagaagaa cgtgactgtc acccactctg tgaatctggg cagtggactg aggctggcaa  1560
ctggactgcg aaacatccca cagcgggaaa ccagaggact gttcggcgct atcgcagggt  1620
ttattgaggg cgggtggaca ggaatggtgg acgggtggta cggctaccac catcagaacg  1680
agcagggatc aggctacgcc gctgacctga agagcacaca gaatgcaatc gatgaaatta  1740
ctaacatggt gaattccgtc atcgagaaaa tgggcagcgg aggctccgga accgacctgg  1800
cagaactgct ggtgctgctg ctgaaccagt ggacactgct gtaccacgat agtaacgtga  1860
agaatctgta tgagaaagtc cgatcacagc tgaagaacaa tgctaaagaa atcgggaatg  1920
gatgcttcga gttttaccat aagtgcgaca acacctgtat ggagagcgtg aaaaatggca  1980
catacgatta tcccaagtat tccgaggaag ccaaactgaa cagagaggaa attgactctg  2040
ggggcgacat catcaagctg ctgaacgaac aggtcaacaa ggagatgcag agctccaatc  2100
tgtacatgtc catgtctagt tggtgttata cccactctct ggacggcgct gggctgttcc  2160
tgtttgatca cgcagccgag gaatacgaac atgcaaagaa actgatcatt ttcctgaacg  2220
agaacaatgt gcccgtccag ctgacatcaa tcagcgcccc tgaacataag ttcgagggcc  2280
tgactcagat ctttcagaaa gcttacgaac acgagcagca tatttccgaa tctatcaaca  2340
atattgtgga ccacgccatt aagagtaaag atcatgctac cttcaatttt ctgcagtggt  2400
acgtggccga gcagcacgag gaggaggtcc tgtttaagga catcctggat aaaatcgaac  2460
tgattggaaa cgagaatcat ggcctgtacc tggcagatca gtatgtgaag ggcattgcca  2520
agagccggaa aagtgggtca tgatgaacac gtgggatcca gatctgctgt gccttctagt  2580
tgccagccat ctgttgtttg cccctccccc gtgccttcct tgaccctgga aggtgccact  2640
cccactgtcc tttcctaata aaatgaggaa attgcatcgc attgtctgag taggtgtcat  2700
tctattctgg ggggtggggt ggggcaggac agcaaggggg aggattggga agacaatagc  2760
aggcatgctg gggatgcggt gggctctatg ggtacccagg tgctgaagaa ttgacccggt  2820
tcctcctggg ccagaaagaa gcaggcacat ccccttctct gtgacacacc ctgtccacgc  2880
ccctggttct tagttccagc cccactcata ggacactcat agctcaggag ggctccgcct  2940
tcaatcccac ccgctaaagt acttggagcg gtctctccct ccctcatcag cccaccaaac  3000
caaacctagc ctccaagagt gggaagaaat taaagcaaga taggctatta agtgcagagg  3060
gagagaaaat gcctccaaca tgtgaggaag taatgagaga aatcatagaa ttttaaggcc  3120
atgatttaag gccatcatgg ccttaatctt ccgcttcctc gctcactgac tcgctgcgct  3180
cggtcgttcg gctgcggcga gcggtatcag ctcactcaaa ggcggtaata cggttatcca  3240
cagaatcagg ggataacgca ggaaagaaca tgtgagcaaa aggccagcaa aaggccagga  3300
accgtaaaaa ggccgcgttg ctggcgtttt tccataggct ccgcccccct gacgagcatc  3360
acaaaaatcg acgctcaagt cagaggtggc gaaacccgac aggactataa agataccagg  3420
cgtttccccc tggaagctcc ctcgtgcgct ctcctgttcc gaccctgccg cttaccggat  3480
acctgtccgc ctttctccct tcgggaagcg tggcgctttc tcatagctca cgctgtaggt  3540
atctcagttc ggtgtaggtc gttcgctcca agctgggctg tgtgcacgaa ccccccgttc  3600
agcccgaccg ctgcgcctta tccggtaact atcgtcttga gtccaacccg gtaagacacg  3660
acttatcgcc actggcagca gccactggta acaggattag cagagcgagg tatgtaggcg  3720
gtgctacaga gttcttgaag tggtggccta actacggcta cactagaaga acagtatttg  3780
gtatctgcgc tctgctgaag ccagttacct tcggaaaaag agttggtagc tcttgatccg  3840
gcaaacaaac caccgctggt agcggtggtt tttttgtttg caagcagcag attacgcgca  3900
gaaaaaaagg atctcaagaa gatcctttga tcttttctac ggggtctgac gctcagtgga  3960
acgaaaactc acgttaaggg attttggtca tgagattatc aaaaaggatc ttcacctaga  4020
tccttttaaa ttaaaaatga agttttaaat caatctaaag tatatatgag taaacttggt  4080
ctgacagtta ccaatgctta atcagtgagg cacctatctc agcgatctgt ctatttcgtt  4140
catccatagt tgcctgactc gggggggggg ggcgctgagg tctgcctcgt gaagaaggtg  4200
ttgctgactc ataccaggcc tgaatcgccc catcatccag ccagaaagtg agggagccac  4260
ggttgatgag agctttgttg taggtggacc agttggtgat tttgaacttt tgctttgcca  4320
cggaacggtc tgcgttgtcg ggaagatgcg tgatctgatc cttcaactca gcaaaagttc  4380
gatttattca acaaagccgc cgtcccgtca agtcagcgta atgctctgcc agtgttacaa  4440
ccaattaacc aattctgatt agaaaaactc atcgagcatc aaatgaaact gcaatttatt  4500
catatcagga ttatcaatac catatttttg aaaaagccgt ttctgtaatg aaggagaaaa  4560
ctcaccgagg cagttccata ggatggcaag atcctggtat cggtctgcga ttccgactcg  4620
tccaacatca atacaaccta ttaatttccc ctcgtcaaaa ataaggttat caagtgagaa  4680
atcaccatga gtgacgactg aatccggtga gaatggcaaa agcttatgca tttctttcca  4740
gacttgttca acaggccagc cattacgctc gtcatcaaaa tcactcgcat caaccaaacc  4800
gttattcatt cgtgattgcg cctgagcgag acgaaatacg cgatcgctgt taaaaggaca  4860
attacaaaca ggaatcgaat gcaaccggcg caggaacact gccagcgcat caacaatatt  4920
ttcacctgaa tcaggatatt cttctaatac ctggaatgct gttttcccgg ggatcgcagt  4980
ggtgagtaac catgcatcat caggagtacg gataaaatgc ttgatggtcg gaagaggcat  5040
aaattccgtc agccagttta gtctgaccat ctcatctgta acatcattgg caacgctacc  5100
tttgccatgt ttcagaaaca actctggcgc atcgggcttc ccatacaatc gatagattgt  5160
cgcacctgat tgcccgacat tatcgcgagc ccatttatac ccatataaat cagcatccat  5220
gttggaattt aatcgcggcc tcgagcaaga cgtttcccgt tgaatatggc tcataacacc  5280
ccttgtatta ctgtttatgt aagcagacag ttttattgtt catgatgata tatttttatc  5340
```

```
ttgtgcaatg taacatcaga gattttgaga cacaacgtgg ctttcccccc ccccccatta  5400
ttgaagcatt tatcagggtt attgtctcat gagcggatac atatttgaat gtatttagaa  5460
aaataaacaa ataggggttc cgcgcacatt tccccgaaaa gtgccacctg acgtctaaga  5520
aaccattatt atcatgacat taacctataa aaataggcgt atcacgaggc cctttcgtc   5579

SEQ ID NO: 274         moltype = DNA  length = 639
FEATURE                Location/Qualifiers
misc_feature           1..639
                       note = Synthetic
source                 1..639
                       mol_type = other DNA
                       organism = synthetic construct
CDS                    1..639
SEQUENCE: 274
atggctatca tctacctgat cctgctgttc actgctgtgc ggggggacca gatttgcatc  60
ggctaccacg ctaataattc aactgagaag gtggatacta tcctggagcg gaacgtgacc  120
gtcacacacg ctaaagacat tggcagcgga ctggtgctgg caaccggact gaggaatgtc  180
ccacagatcg agtcccgcgg actgttcggc gctatcgcag ggtttattga aggcgggtgg  240
cagggaatga ttgatgggtg gtacggctac caccattcta acgaccaagg aagtggctac  300
gccgctgata aggagagtac tcagaaagcc ttcgatggca tcaccaacat ggtgaattca  360
gtcattgaga agatgggcag cggaggctcc ggaaccgacc tggcagaact gctggtgctg  420
ctgctgaatc agtggacact gctgtttcac gactctaacg tgaagaatct gtatgataaa  480
gtccggatgc agctgagaga caacgtgaag gagctgggga atggatgctt cgaattttac  540
cataagtgcg acgatgagtg tatgaacagt gtcaaaaatg gcacatacga ttatcccaag  600
tatgaggaag agtcaaaact gaaccgaaat gaaatcaag                        639

SEQ ID NO: 275         moltype = AA  length = 213
FEATURE                Location/Qualifiers
REGION                 1..213
                       note = Synthetic Construct
source                 1..213
                       mol_type = protein
                       organism = synthetic construct
SEQUENCE: 275
MAIIYLILLF TAVRGDQICI GYHANNSTEK VDTILERNVT VTHAKDIGSG LVLATGLRNV  60
PQIESRGLFG AIAGFIEGGW QGMIDGWYGY HHSNDQGSGY AADKESTQKA FDGITNMVNS  120
VIEKMGSGGS GTDLAELLVL LLNQWTLLFH DSNVKNLYDK VRMQLRDNVK ELGNGCFEFY  180
HKCDDECMNS VKNGTYDYPK YEEESKLNRN EIK                                213

SEQ ID NO: 276         moltype = DNA  length = 639
FEATURE                Location/Qualifiers
misc_feature           1..639
                       note = Synthetic
source                 1..639
                       mol_type = other DNA
                       organism = synthetic construct
SEQUENCE: 276
cttgatttca tttcggttca gttttgactc ttcctcatac ttgggataat cgtatgtgcc  60
atttttgaca ctgttcatac actcatcgtc gcacttatgg taaaattcga agcatccatt  120
ccccagctcc ttcacgttgt ctctcagctg catccggact ttatcataca gattcttcac  180
gttagagtcg tgaaacagca gtgtccactg attcagcagc agcaccagca gttctgccag  240
gtcggttccg gagcctccgc tgcccatctt ctcaatgact gaattcacca tgttggtgat  300
gccatcgaag gctttctgag tactctcctt atcagcggcg tagccacttc cttggtcgtt  360
agaatggtgg tagccgtacc acccatcaat cattccctgc cacccgcctt caataaaccc  420
tgcgatagcg ccgaacagtc cgcgggactc gatctgtggg acattcctca gtccggttgc  480
cagcaccagt ccgctgccaa tgtctttagc gtgtgtgacg gtcacgttcc gctccaggat  540
agtatccacc ttctcagttg aattattagc gtggtagccg atgcaaatct ggtccccccg  600
cacagcagtg aacagcagga tcaggtagat gatagccat                        639

SEQ ID NO: 277         moltype = DNA  length = 1149
FEATURE                Location/Qualifiers
misc_feature           1..1149
                       note = Synthetic
source                 1..1149
                       mol_type = other DNA
                       organism = synthetic construct
CDS                    1..1149
SEQUENCE: 277
atggctatca tctacctgat cctgctgttc actgctgtgc ggggggacca gatttgcatc  60
ggctaccacg ctaataattc aactgagaag gtggatacta tcctggagcg gaacgtgacc  120
gtcacacacg ctaaagacat tggcagcgga ctggtgctgg caaccggact gaggaatgtc  180
ccacagatcg agtcccgcgg actgttcggc gctatcgcag ggtttattga aggcgggtgg  240
cagggaatga ttgatgggtg gtacggctac caccattcta acgaccaagg aagtggctac  300
gccgctgata aggagagtac tcagaaagcc ttcgatggca tcaccaacat ggtgaattca  360
gtcattgaga agatgggcag cggaggctcc ggaaccgacc tggcagaact gctggtgctg  420
ctgctgaatc agtggacact gctgtttcac gactctaacg tgaagaatct gtatgataaa  480
gtccggatgc agctgagaga caacgtgaag gagctgggga atggatgctt cgaattttac  540
cataagtgcg acgatgagtg tatgaacagt gtcaaaaatg gcacatacga ttatcccaag  600
tatgaggaag agtcaaaact gaaccgaaat gaaatcaaga gcgggggcga catcatcaag  660
```

-continued

```
ctgctgaacg agcaagtgaa taaggaaatg cagagctcca acctgtacat gtccatgtct  720
agttggtgtt atactcactc tctggatggc gccgggctgt tcctgtttga ccacgcagcc  780
gaagagtacg agcatgctaa gaaactgatc attttcctga acgaaaacaa cgtgcccgtc  840
cagctgacat caatcagcgc acctgagcat aagttcgaag gcctgactca gatctttcag  900
aaagcttacg agcacgaaca gcatatttcc gagtctatca acaatattgt ggaccacgcc  960
atcaagagca aagatcatgc taccttcaac tttctgcagt ggtacgtggc cgagcagcac  1020
gaagaggaag tcctgtttaa ggacatcctg gataaaatcg agctgattgg aaacgaaaat  1080
catggcctgt acctggcaga ccagtatgtg aagggcattg ccaagtccag aaaaagtggg  1140
tcatgatga                                                          1149

SEQ ID NO: 278         moltype = AA  length = 381
FEATURE                Location/Qualifiers
REGION                 1..381
                       note = Synthetic Construct
source                 1..381
                       mol_type = protein
                       organism = synthetic construct
SEQUENCE: 278
MAIIYLILLF TAVRGDQICI GYHANNSTEK VDTILERNVT VTHAKDIGSG LVLATGLRNV  60
PQIESRGLFG AIAGFIEGGW QGMIDGWYGY HHSNDQGSGY AADKESTQKA FDGITNMVNS  120
VIEKMGSGGS GTDLAELLVL LLNQWTLLFH DSNVKNLYDK VRMQLRDNVK ELGNGCFEFY  180
HKCDDECMNS VKNGTYDYPK YEEESKLNRN EIKSGGDIIK LLNEQVNKEM QSSNLYMSMS  240
SWCYTHSLDG AGLFLFDHAA EEYEHAKKLI IFLNENNVPV QLTSISAPEH KFEGLTQIFQ  300
KAYEHEQHIS ESINNIVDHA IKSKDHATFN FLQWYVAEQH EEEVLFKDIL DKIELIGNEN  360
HGLYLADQYV KGIAKSRKSG S                                            381

SEQ ID NO: 279         moltype = DNA  length = 1149
FEATURE                Location/Qualifiers
misc_feature           1..1149
                       note = Synthetic
source                 1..1149
                       mol_type = other DNA
                       organism = synthetic construct
SEQUENCE: 279
tcatcatgac ccactttttc tggacttggc aatgcccttc acatactggt ctgccaggta  60
caggccatga ttttcgtttc caatcagctc gattttatcc aggatgtcct taaacaggac  120
ttcctcttcg tgctgctcgg ccacgtacca ctgcagaaag ttgaaggtag catgatcttt  180
gctcttgatg gcgtggtcca caatattgtt gatagactcg gaaatatgct gttcgtgctc  240
gtaagctttc tgaaagatct gagtcaggcc ttcgaactta tgctcaggtg cgctgattga  300
tgtcagctgg acgggcacgt tgttttcgtt caggaaaatg atcagtttct tagcatgctc  360
gtactcttcg gctgcgtggt caaacaggaa cagcccggcg ccatccagag agtgagtata  420
acaccaacta gacatggaca tgtacaggtt ggagctctgc atttccttat tcacttgctc  480
gttcagcagc ttgatgatgt cgccccccgct cttgatttca tttcggttca gttttgactc  540
ttcctcatac ttgggataat cgtatgtgcc atttttgaca ctgttcatac actcatcgtc  600
gcacttatgg taaaattcga agcatccatt ccccagctcc ttcacgttgt ctctcagctg  660
catccggact ttatcataca gattcttcac gttagagtcg tgaaacagca gtgtccactg  720
attcagcagc agcaccagca gttctgccag gtcggttccg gagcctccgc tgcccatctt  780
ctcaatgact gaattcacca tgttggtgat gccatcgaag gctttctgag tactctcctt  840
atcagcggcg tagccacttc cttggtcgtt agaatggtgg tagccgtacc acccatcaat  900
cattccctgc cacccgcctt caataaaccc tgcgatagcg ccgaacagtc cgcgggactc  960
gatctgtggg acattcctca gtccggttgc cagcaccagt ccgctgccaa tgtctttagc  1020
gtgtgtgacg gtcacgttcc gctccaggat agtatccacc ttctcagttg aattattagc  1080
gtggtagccg atgcaaatct ggtccccccg cacagcagtg aacagcagga tcaggtagat  1140
gatagccat                                                          1149

SEQ ID NO: 280         moltype = DNA  length = 5573
FEATURE                Location/Qualifiers
misc_feature           1..5573
                       note = Synthetic
source                 1..5573
                       mol_type = other DNA
                       organism = synthetic construct
SEQUENCE: 280
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcagattgg  240
ctattggcca ttgcatacgt tgtatccata tcataatatg tacatttata ttggctcatg  300
tccaacatta ccgccatgtt gacattgatt attgactagt tattaatagt aatcaattac  360
ggggtcatta gttcatagcc catatatgga gttccgcgtt acataactta cggtaaatgg  420
cccgcctggc tgaccgccca acgacccccg cccattgacg tcaataatga cgtatgttcc  480
catagtaacg ccaataggga ctttccattg acgtcaatgg gtggagtatt tacggtaaac  540
tgcccacttg gcagtacatc aagtgtatca tatgccaagt acgcccccta ttgacgtcaa  600
tgacggtaaa tggcccgcct ggcattatgc ccagtacatg accttatggg actttcctac  660
ttggcagtac atctacgtat tagtcatcgc tattaccatg gtgatgcggt tttggcagta  720
catcaatggg cgtggatagc ggtttgactc acggggattt ccaagtctcc accccattga  780
cgtcaatggg agtttgtttt ggcaccaaaa tcaacgggac tttccaaaat gtcgtaacaa  840
ctccgcccca ttgacgcaaa tgggcggtag gcgtgtacgg tgggaggtct atataagcag  900
agctcgttta gtgaaccgtc agatcgcctg gagacgccat ccacgctgtt ttgacctcca  960
```

-continued

```
tagaagacac cgggaccgat ccagcctcca tcggctcgca tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctcaggtc gagaccgggc  1140
ctttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgcggc cgctctagag  1380
atatcgccac catggctatc atctacctga tcctgctgtt cactgctgtg cggggggacc  1440
agatttgcat cggctaccac gctaataatt caactgagaa ggtggatact atcctggagc  1500
ggaacgtgac cgtcacacac gctaaagaca ttggcagcgg actggtgctg gcaaccggac  1560
tgaggaatgt cccacagatc gagtcccgcg gactgttcgg cgctatcgca gggtttattg  1620
aaggcgggtg gcagggaatg attgatgggt ggtacggcta ccaccattct aacgaccaag  1680
gaagtggcta cgccgctgat aaggagagta ctcagaaagc cttcgatggc atcaccaaca  1740
tggtgaattc agtcattgag aagatgggca gcggaggctc cggaaccgac ctggcagaac  1800
tgctggtgct gctgctgaat cagtggacac tgctgtttca cgactctaac gtgaagaatc  1860
tgtatgataa agtccggatg cagctgagag acaacgtgaa ggagctgggg aatggatgct  1920
tcgaatttta ccataagtgc gacgatgagt gtatgaacag tgtcaaaaat ggcacatacg  1980
attatcccaa gtatgaggaa gagtcaaaac tgaaccgaaa tgaaatcaag agcgggggcg  2040
acatcatcaa gctgctgaac gagcaagtga ataaggaaat gcagagctcc aacctgtaca  2100
tgtccatgtc tagttggtgt tatactcact ctctggatgg cgccgggctg ttcctgtttg  2160
accacgcagc cgaagagtac gagcatgcta agaaactgat cattttcctg aacgaaaaca  2220
acgtgcccgt ccagctgaca tcaatcagcg cacctgagca taagttcgaa ggcctgactc  2280
agatctttca gaaagcttac gagcacgaac agcatatttc cgagtctatc aacaatattg  2340
tggaccacgc catcaagagc aaagatcatg ctaccttcaa ctttctgcag tggtacgtgg  2400
ccgagcagca cgaagaggaa gtcctgttta aggacatcct ggataaaatc gagctgattg  2460
gaaacgaaaa tcatggcctg tacctggcag accagtatgt gaagggcatt gccaagtcca  2520
gaaaaagtgg gtcatgatga acacgtggga tccagatctg ctgtgccttc tagttgccag  2580
ccatctgttg tttgcccctc ccccgtgcct tccttgaccc tggaaggtgc cactcccact  2640
gtcctttcct aataaaatga ggaaattgca tcgcattgtc tgagtaggtg tcattctatt  2700
ctggggggtg gggtggggca ggacagcaag ggggaggatt gggaagacaa tagcaggcat  2760
gctggggatg cggtgggctc tatgggtacc caggtgctga agaattgacc cggttcctcc  2820
tgggccagaa agaagcaggc acatcccctt ctctgtgaca caccctgtcc acgcccctgg  2880
ttcttagttc cagccccact cataggacac tcatagctca ggagggctcc gccttcaatc  2940
ccacccgcta aagtacttgg agcggtctct ccctccctca tcagcccacc aaaccaaacc  3000
tagcctccaa gagtgggaag aaattaaagc aagataggct attaagtgca gagggagaga  3060
aaatgcctcc aacatgtgag gaagtaatga gagaaatcat agaattttaa ggccatgatt  3120
taaggccatc atggccttaa tcttccgctt cctcgctcac tgactcgctg cgctcggtcg  3180
ttcggctgcg gcgagcggta tcagctcact caaaggcggt aatacggtta tccacagaat  3240
caggggataa cgcaggaaag aacatgtgag caaaaggcca gcaaaaggcc aggaaccgta  3300
aaaaggccgc gttgctggcg tttttccata ggctccgccc ccctgacgag catcacaaaa  3360
atcgacgctc aagtcagagg tggcgaaacc cgacaggact ataaagatac caggcgtttc  3420
cccctggaag ctccctcgtg cgctctcctg ttccgaccct gccgcttacc ggatacctgt  3480
ccgcctttct cccttcggga agcgtggcgc tttctcatag ctcacgctgt aggtatctca  3540
gttcggtgta ggtcgttcgc tccaagctgg gctgtgtgca cgaacccccc gttcagcccg  3600
accgctgcgc cttatccggt aactatcgtc ttgagtccaa cccggtaaga cacgacttat  3660
cgccactggc agcagccact ggtaacagga ttagcagagc gaggtatgta ggcggtgcta  3720
cagagttctt gaagtggtgg cctaactacg gctacactag aagaacagta tttggtatct  3780
gcgctctgct gaagccagtt accttcggaa aaagagttgg tagctcttga tccggcaaac  3840
aaaccaccgc tggtagcggt ggtttttttg tttgcaagca gcagattacg cgcagaaaaa  3900
aaggatctca agaagatcct ttgatctttt ctacggggtc tgacgctcag tggaacgaaa  3960
actcacgtta agggattttg gtcatgagat tatcaaaaag gatcttcacc tagatccttt  4020
taaattaaaa atgaagtttt aaatcaatct aaagtatata tgagtaaact tggtctgaca  4080
gttaccaatg cttaatcagt gaggcaccta tctcagcgat ctgtctattt cgttcatcca  4140
tagttgcctg actcgggggg ggggggcgct gaggtctgcc tcgtgaagaa ggtgttgctg  4200
actcatacca ggcctgaatc gccccatcat ccagccagaa agtgagggag ccacggttga  4260
tgagagcttt gttgtaggtg gaccagttgg tgattttgaa cttttgcttt gccacggaac  4320
ggtctgcgtt gtcgggaaga tgcgtgatct gatccttcaa ctcagcaaaa gttcgattta  4380
ttcaacaaag ccgccgtccc gtcaagtcag cgtaatgctc tgccagtgtt acaaccaatt  4440
aaccaattct gattagaaaa actcatcgag catcaaatga aactgcaatt tattcatatc  4500
aggattatca ataccatatt tttgaaaaag ccgtttctgt aatgaaggag aaaactcacc  4560
gaggcagttc cataggatgg caagatcctg gtatcggtct gcgattccga ctcgtccaac  4620
atcaatacaa cctattaatt tcccctcgtc aaaaataagg ttatcaagtg agaaatcacc  4680
atgagtgacg actgaatccg gtgagaatgg caaaagctta tgcatttctt tccagacttg  4740
ttcaacaggc cagccattac gctcgtcatc aaaatcactc gcatcaacca aaccgttatt  4800
cattcgtgat tgcgcctgag cgagacgaaa tacgcgatcg ctgttaaaag gacaattaca  4860
aacaggaatc gaatgcaacc ggcgcaggaa cactgccagc gcatcaacaa tattttcacc  4920
tgaatcagga tattcttcta atacctggaa tgctgttttc ccggggatcg cagtggtgag  4980
taaccatgca tcatcaggag tacggataaa atgcttgatg gtcggaagag gcataaattc  5040
cgtcagccag tttagtctga ccatctcatc tgtaacatca ttggcaacgc tacctttgcc  5100
atgtttcaga aacaactctg gcgcatcggg cttcccatac aatcgataga ttgtcgcacc  5160
tgattgcccg acattatcgc gagcccattt atacccatat aaatcagcat ccatgttgga  5220
atttaatcgc ggcctcgagc aagacgtttc ccgttgaata tggctcataa cacccccttgt 5280
attactgttt atgtaagcag acagttttat tgttcatgat gatatatttt tatcttgtgc  5340
aatgtaacat cagagatttt gagacacaac gtggctttcc cccccccccc attattgaag  5400
catttatcag ggttattgtc tcatgagcgg atacatattt gaatgtattt agaaaaataa  5460
acaaataggg gttccgcgca catttccccg aaaagtgcca cctgacgtct aagaaaccat  5520
tattatcatg acattaacct ataaaaatag gcgtatcacg aggccctttc gtc         5573
```

SEQ ID NO: 281 moltype = DNA length = 654

```
FEATURE                Location/Qualifiers
misc_feature           1..654
                       note = Synthetic
source                 1..654
                       mol_type = other DNA
                       organism = synthetic construct
CDS                    1..654
SEQUENCE: 281
atggaaaaaa tcgtgctgct gctggctatc gtgtccctgg tgaagtccga ccagatctgt  60
attgggtatc atgctaacaa ctccacagaa caggtggata ctatcatgga gaagaacgtg  120
accgtcacac acgctcagga cattggatgg ggactggtcc tggcaaccgg actgagaaat  180
tcaccacaga gggaaagccg gagaaagaaa cgcggactgt tcggcgctat cgcagggttt  240
attgagggcg ggtggcaggg aatggtggat gggtggtacg gctaccacca ttccaacgaa  300
cagggatctg gctacgccgc tgataaggag tctactcaga aagctatcga cggcgtgacc  360
aacatggtca atagtatcat tgataagatg ggctctggag gcagtggaac cgacctggca  420
gagctgctgg tgctgctgct gaaccagtgg acactgctgt tccacgactc taacgtgaag  480
aatctgtatg ataaagtccg actgcagctg cgggacaacg ccaaggaact ggggaatgga  540
tgcttcgagt tctaccataa gtgcgataac gaatgtatgg agagcatccg aaacggcaca  600
tacaattatc cccagtattc cgaggaagct aggctgaaac gcgaggaaat tagc        654

SEQ ID NO: 282         moltype = AA  length = 218
FEATURE                Location/Qualifiers
REGION                 1..218
                       note = Synthetic Construct
source                 1..218
                       mol_type = protein
                       organism = synthetic construct
SEQUENCE: 282
MEKIVLLLAI VSLVKSDQIC IGYHANNSTE QVDTIMEKNV TVTHAQDIGW GLVLATGLRN  60
SPQRESRRKK RGLFGAIAGF IEGGWQGMVD GWYGYHHSNE QGSGYAADKE STQKAIDGVT  120
NMVNSIIDKM GSGGSGTDLA ELLVLLLNQW TLLFHDSNVK NLYDKVRLQL RDNAKELGNG  180
CFEFYHKCDN ECMESIRNGT YNYPQYSEEA RLKREEIS                          218

SEQ ID NO: 283         moltype = DNA  length = 654
FEATURE                Location/Qualifiers
misc_feature           1..654
                       note = Synthetic
source                 1..654
                       mol_type = other DNA
                       organism = synthetic construct
SEQUENCE: 283
gctaatttcc tcgcgtttca gcctagcttc ctcggaatac tggggataat tgtatgtgcc  60
gtttcggatg ctctccatac attcgttatc gcacttatgg tagaactcga agcatccatt  120
ccccagttcc ttggcgttgt cccgcagctg cagtcggact ttatcataca gattcttcac  180
gttagagtcg tggaacagca gtgtccactg gttcagcagc agcaccagca gctctgccag  240
gtcggttcca ctgcctccag agcccatctt atcaatgata ctattgacca tgttggtcac  300
gccgtcgata gctttctgag tagactcctt atcagcggcg tagccagatc cctgttcgtt  360
ggaatggtgg tagccgtacc acccatccac cattccctgc cacccgccct caataaaccc  420
tgcgatagcg ccgaacagtc cgcgtttctt tctccggctt tccctctgtg gtgaatttct  480
cagtccggtt gccaggacca gtccccatcc aatgtcctga gcgtgtgtga cggtcacgtt  540
cttctccatg atagtatcca cctgttctgt ggagttgtta gcatgatacc caatacagat  600
ctggtcggac ttcaccaggg acacgatagc cagcagcagc acgatttttt ccat        654

SEQ ID NO: 284         moltype = DNA  length = 1164
FEATURE                Location/Qualifiers
misc_feature           1..1164
                       note = Synthetic
source                 1..1164
                       mol_type = other DNA
                       organism = synthetic construct
CDS                    1..1164
SEQUENCE: 284
atggaaaaaa tcgtgctgct gctggctatc gtgtccctgg tgaagtccga ccagatctgt  60
attgggtatc atgctaacaa ctccacagaa caggtggata ctatcatgga gaagaacgtg  120
accgtcacac acgctcagga cattggatgg ggactggtcc tggcaaccgg actgagaaat  180
tcaccacaga gggaaagccg gagaaagaaa cgcggactgt tcggcgctat cgcagggttt  240
attgagggcg ggtggcaggg aatggtggat gggtggtacg gctaccacca ttccaacgaa  300
cagggatctg gctacgccgc tgataaggag tctactcaga aagctatcga cggcgtgacc  360
aacatggtca atagtatcat tgataagatg ggctctggag gcagtggaac cgacctggca  420
gagctgctgg tgctgctgct gaaccagtgg acactgctgt tccacgactc taacgtgaag  480
aatctgtatg ataaagtccg actgcagctg cgggacaacg ccaaggaact ggggaatgga  540
tgcttcgagt tctaccataa gtgcgataac gaatgtatgg agagcatccg aaacggcaca  600
tacaattatc cccagtattc cgaggaagct aggctgaaac gcgaggaaat tagctccggg  660
ggagacatca ttaagctgct gaacgaacag gtgaacaagg agatgcagtc tagtaacctg  720
tacatgagta tgtcaagctg gtgttatact cactcactgg atggcgccgg gctgttcctg  780
tttgaccacg cagccgagga atacgaacat gctaagaaac tgatcatttt cctgaatgag  840
aacaatgtgc ccgtccagct gacatccatc tctgcacctg aacataagtt cgagggcctg  900
actcagatct ttcagaaagc ctacgaacac gagcagcata ttagtgagtc aatcaacaat  960
attgtggacc acgccatcaa gagcaaagat catgctacct tcaattttct gcagtggtac  1020
```

-continued

```
gtggccgagc agcacgagga agaggtcctg tttaaggaca tcctggataa aatcgaactg  1080
attggaaacg agaatcatgg cctgtacctg gcagaccagt atgtgaaggg cattgccaag  1140
tccaggaaaa gcgggtcctg atga                                         1164

SEQ ID NO: 285         moltype = AA  length = 386
FEATURE                Location/Qualifiers
REGION                 1..386
                       note = Synthetic Construct
source                 1..386
                       mol_type = protein
                       organism = synthetic construct
SEQUENCE: 285
MEKIVLLLAI VSLVKSDQIC IGYHANNSTE QVDTIMEKNV TVTHAQDIGW GLVLATGLRN  60
SPQRESRRKK RGLFGAIAGF IEGGWQGMVD GWYGYHHSNE QGSGYAADKE STQKAIDGVT  120
NMVNSIIDKM GSGGSGTDLA ELLVLLLNQW TLLFHDSNVK NLYDKVRLQL RDNAKELGNG  180
CFEFYHKCDN ECMESIRNGT YNYPQYSEEA RLKREEISSG GDIIKLLNEQ VNKEMQSSNL  240
YMSMSSWCYT HSLDGAGLFL FDHAAEEYEH AKKLIIFLNE NNVPVQLTSI SAPEHKFEGL  300
TQIFQKAYEH EQHISESINN IVDHAIKSKD HATFNFLQWY VAEQHEEEVL FKDILDKIEL  360
IGNENHGLYL ADQYVKGIAK SRKSGS                                       386

SEQ ID NO: 286         moltype = DNA  length = 1164
FEATURE                Location/Qualifiers
misc_feature           1..1164
                       note = Synthetic
source                 1..1164
                       mol_type = other DNA
                       organism = synthetic construct
SEQUENCE: 286
tcatcaggac ccgcttttcc tggacttggc aatgcccttc acatactggt ctgccaggta  60
caggccatga ttctcgtttc caatcagttc gattttatcc aggatgtcct taaacaggac  120
ctcttcctcg tgctgctcgg ccacgtacca ctgcagaaaa ttgaaggtag catgatcttt  180
gctcttgatg gcgtggtcca caatattgtt gattgactca ctaatatgct gctcgtgttc  240
gtaggctttc tgaaagatct gagtcaggcc ctcgaactta tgttcaggtg cagagatgga  300
tgtcagctgg acgggcacat tgttctcatt caggaaaatg atcagtttct tagcatgttc  360
gtattcctcg gctgcgtggt caaacaggaa cagcccggcg ccatccagtg agtgagtata  420
acaccagctt gacatactca tgtacaggtt actagactgc atctccttgt tcacctgttc  480
gttcagcagc ttaatgatgt ctcccccgga gctaatttcc tcgcgtttca gcctagcttc  540
ctcggaatac tggggataat tgtatgtgcc gtttcggatg ctctccatac attcgttatc  600
gcacttatgg tagaactcga agcatccatt ccccagttcc ttggcgttgt cccgcagctg  660
cagtcggact ttatcataca gattcttcac gttagagtcg tggaacagca gtgtccactg  720
gttcagcagc agcaccagca gctctgccag gtcggttcca ctgcctccag agcccatctt  780
atcaatgata ctattgacca tgttggtcac gccgtcgata gctttctgag tagactcctt  840
atcagcggcg tagccagatc cctgttcgtt ggaatggtgg tagccgtacc acccatccac  900
cattccctgc cacccgccct caataaaccc tgcgatagcg ccgaacagtc cgcgtttctt  960
tctccggctt tccctctgtg gtgaatttct cagtccggtt gccaggacca gtccccatcc  1020
aatgtcctga gcgtgtgtga cggtcacgtt cttctccatg atagtatcca cctgttctgt  1080
ggagttgtta gcatgatacc caatacagat ctggtcggac ttcaccaggg acacgatagc  1140
cagcagcagc acgatttttt ccat                                         1164

SEQ ID NO: 287         moltype = DNA  length = 5588
FEATURE                Location/Qualifiers
misc_feature           1..5588
                       note = Synthetic
source                 1..5588
                       mol_type = other DNA
                       organism = synthetic construct
SEQUENCE: 287
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcagattgg  240
ctattggcca ttgcatacgt tgtatccata tcataatatg tacatttata ttggctcatg  300
tccaacatta ccgccatgtt gacattgatt attgactagt tattaatagt aatcaattac  360
ggggtcatta gttcatagcc catatatgga gttccgcgtt acataactta cggtaaatgg  420
cccgcctggc tgaccgccca acgacccccg cccattgacg tcaataatga cgtatgttcc  480
catagtaacg ccaataggga ctttccattg acgtcaatgg gtggagtatt tacggtaaac  540
tgcccacttg gcagtacatc aagtgtatca tatgccaagt acgcccccta ttgacgtcaa  600
tgacggtaaa tggcccgcct ggcattatgc ccagtacatg accttatggg actttcctac  660
ttggcagtac atctacgtat tagtcatcgc tattaccatg gtgatgcggt tttggcagta  720
catcaatggg cgtggatagc ggtttgactc acggggattt ccaagtctcc accccattga  780
cgtcaatggg agtttgtttt ggcaccaaaa tcaacgggac tttccaaaat gtcgtaacaa  840
ctccgcccca ttgacgcaaa tgggcggtag gcgtgtacgg tgggaggtct atataagcag  900
agctcgttta gtgaaccgtc agatcgcctg gagacgccat ccacgctgtt ttgacctcca  960
tagaagacac cgggaccgat ccagcctcca tcggctcgca tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctcaggtc gagaccgggc  1140
ctttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
```

-continued

```
ggtcttttct gcagtcaccg tcgtcgacac gtgtgatcag atatcgcggc cgctctagag  1380
atatcgccac catggaaaaa atcgtgctgc tgctggctat cgtgtccctg gtgaagtccg  1440
accagatctg tattgggtat catgctaaca actccacaga acaggtggat actatcatgg  1500
agaagaacgt gaccgtcaca cacgctcagg acattggatg gggactggtc ctggcaaccg  1560
gactgagaaa ttcaccacag agggaaagcc ggagaaagaa acgcggactg ttcggcgcta  1620
tcgcagggtt tattgagggc gggtggcagg gaatggtgga tgggtggtac ggctaccacc  1680
attccaacga acagggatct ggctacgccg ctgataagga gtctactcag aaagctatcg  1740
acggcgtgac caacatggtc aatagtatca ttgataagat gggctctgga ggcagtggaa  1800
ccgacctggc agagctgctg gtgctgctgc tgaaccagtg gacactgctg ttccacgact  1860
ctaacgtgaa gaatctgtat gataaagtcc gactgcagct gcgggacaac gccaaggaac  1920
tggggaatgg atgcttcgag ttctaccata agtgcgataa cgaatgtatg gagagcatcc  1980
gaaacggcac atacaattat ccccagtatt ccgaggaagc taggctgaaa cgcgaggaaa  2040
ttagctccgg gggagacatc attaagctgc tgaacgaaca ggtgaacaag gagatgcagt  2100
ctagtaacct gtacatgagt atgtcaagct ggtgttatac tcactcactg gatggcgccg  2160
ggctgttcct gtttgaccac gcagccgagg aatacgaaca tgctaagaaa ctgatcattt  2220
tcctgaatga gaacaatgtg cccgtccagc tgacatccat ctctgcacct gaacataagt  2280
tcgagggcct gactcagatc tttcagaaag cctacgaaca cgagcagcat attagtgagt  2340
caatcaacaa tattgtggac cacgccatca agagcaaaga tcatgctacc ttcaattttc  2400
tgcagtggta cgtggccgag cagcacgagg aagaggtcct gtttaaggac atcctggata  2460
aaatcgaact gattggaaac gagaatcatg gcctgtacct ggcagaccag tatgtgaagg  2520
gcattgccaa gtccaggaaa agcgggtcct gatgaacacg tgggatccag atctgctgtg  2580
ccttctagtt gccagccatc tgttgtttgc ccctcccccg tgccttcctt gaccctggaa  2640
ggtgccactc ccactgtcct ttcctaataa aatgaggaaa ttgcatcgca ttgtctgagt  2700
aggtgtcatt ctattctggg gggtggggtg gggcaggaca gcaaggggga ggattgggaa  2760
gacaatagca ggcatgctgg ggatgcggtg ggctctatgg gtacccaggt gctgaagaat  2820
tgacccggtt cctcctgggc cagaaagaag caggcacatc cccttctctg tgacacaccc  2880
tgtccacgcc cctggttctt agttccagcc ccactcatag gacactcata gctcaggagg  2940
gctccgcctt caatcccacc cgctaaagta cttggagcgg tctctccctc cctcatcagc  3000
ccaccaaacc aaacctagcc tccaagagtg ggaagaaatt aaagcaagat aggctattaa  3060
gtgcagaggg agagaaaatg cctccaacat gtgaggaagt aatgagagaa atcatagaat  3120
tttaaggcca tgatttaagg ccatcatggc cttaatcttc cgcttcctcg ctcactgact  3180
cgctgcgctc ggtcgttcgg ctgcggcgag cggtatcagc tcactcaaag gcggtaatac  3240
ggttatccac agaatcaggg gataacgcag gaaagaacat gtgagcaaaa ggccagcaaa  3300
aggccaggaa ccgtaaaaag gccgcgttgc tggcgttttt ccataggctc cgcccccctg  3360
acgagcatca caaaaatcga cgctcaagtc agaggtggcg aaacccgaca ggactataaa  3420
gataccaggc gtttccccct ggaagctccc tcgtgcgctc tcctgttccg accctgccgc  3480
ttaccggata cctgtccgcc tttctccctt cgggaagcgt ggcgctttct catagctcac  3540
gctgtaggta tctcagttcg gtgtaggtcg ttcgctccaa gctgggctgt gtgcacgaac  3600
cccccgttca gcccgaccgc tgcgccttat ccggtaacta tcgtcttgag tccaacccgg  3660
taagacacga cttatcgcca ctggcagcag ccactggtaa caggattagc agagcgaggt  3720
atgtaggcgg tgctacagag ttcttgaagt ggtggcctaa ctacggctac actagaagaa  3780
cagtatttgg tatctgcgct ctgctgaagc cagttacctt cggaaaaaga gttggtagct  3840
cttgatccgg caaacaaacc accgctggta gcggtggttt ttttgtttgc aagcagcaga  3900
ttacgcgcag aaaaaaagga tctcaagaag atcctttgat cttttctacg gggtctgacg  3960
ctcagtggaa cgaaaactca cgttaaggga ttttggtcat gagattatca aaaaggatct  4020
tcacctagat ccttttaaat taaaaatgaa gttttaaatc aatctaaagt atatatgagt  4080
aaacttggtc tgacagttac caatgcttaa tcagtgaggc acctatctca gcgatctgtc  4140
tatttcgttc atccatagtt gcctgactcg gggggggggg gcgctgaggt ctgcctcgtg  4200
aagaaggtgt tgctgactca taccaggcct gaatcgcccc atcatccagc cagaaagtga  4260
gggagccacg gttgatgaga gctttgttgt aggtggacca gttggtgatt ttgaactttt  4320
gctttgccac ggaacggtct gcgttgtcgg gaagatgcgt gatctgatcc ttcaactcag  4380
caaaagttcg atttattcaa caaagccgcc gtcccgtcaa gtcagcgtaa tgctctgcca  4440
gtgttacaac caattaacca attctgatta gaaaaactca tcgagcatca aatgaaactg  4500
caatttattc atatcaggat tatcaatacc atatttttga aaaagccgtt tctgtaatga  4560
aggagaaaac tcaccgaggc agttccatag gatggcaaga tcctggtatc ggtctgcgat  4620
tccgactcgt ccaacatcaa tacaacctat taatttcccc tcgtcaaaaa taaggttatc  4680
aagtgagaaa tcaccatgag tgacgactga atccggtgag aatggcaaaa gcttatgcat  4740
ttctttccag acttgttcaa caggccagcc attacgctcg tcatcaaaat cactcgcatc  4800
aaccaaaccg ttattcattc gtgattgcgc ctgagcgaga cgaaatacgc gatcgctgtt  4860
aaaaggacaa ttacaaacag gaatcgaatg caaccggcgc aggaacactg ccagcgcatc  4920
aacaatattt tcacctgaat caggatattc ttctaatacc tggaatgctg ttttcccggg  4980
gatcgcagtg gtgagtaacc atgcatcatc aggagtacgg ataaaatgct tgatggtcgg  5040
aagaggcata aattccgtca gccagtttag tctgaccatc tcatctgtaa catcattggc  5100
aacgctacct ttgccatgtt tcagaaacaa ctctggcgca tcgggcttcc catacaatcg  5160
atagattgtc gcacctgatt gcccgacatt atcgcgagcc catttatacc catataaatc  5220
agcatccatg ttggaattta atcgcggcct cgagcaagac gtttcccgtt gaatatggct  5280
cataacaccc cttgtattac tgtttatgta agcagacagt tttattgttc atgatgatat  5340
atttttatct tgtgcaatgt aacatcagag attttgagac acaacgtggc tttccccccc  5400
cccccattat tgaagcattt atcagggtta ttgtctcatg agcggataca tatttgaatg  5460
tatttagaaa aataaacaaa taggggttcc gcgcacattt ccccgaaaag tgccacctga  5520
cgtctaagaa accattatta tcatgacatt aacctataaa aataggcgta tcacgaggcc  5580
ctttcgtc                                                           5588
```

```
SEQ ID NO: 288          moltype = DNA  length = 645
FEATURE                 Location/Qualifiers
misc_feature            1..645
                        note = Synthetic
source                  1..645
                        mol_type = other DNA
```

-continued

```
                         organism = synthetic construct
CDS                      1..645
SEQUENCE: 288
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcagcgga ggctccggaa catacaacgc tgagctgctg  420
gtgctgctgc tgaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                 645

SEQ ID NO: 289           moltype = AA  length = 215
FEATURE                  Location/Qualifiers
REGION                   1..215
                         note = Synthetic Construct
source                   1..215
                         mol_type = protein
                         organism = synthetic construct
SEQUENCE: 289
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGSG GSGTYNAELL VLLLNERTLD FHDSNVKNLY EKVKSQLKNN AKEIGNGCFE  180
FYHKCNNECM ESVKNGTYDY PKYSEESKLN REKID                            215

SEQ ID NO: 290           moltype = DNA  length = 645
FEATURE                  Location/Qualifiers
misc_feature             1..645
                         note = Synthetic
source                   1..645
                         mol_type = other DNA
                         organism = synthetic construct
SEQUENCE: 290
gtcaatttc  tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaaatcca gagtccgctc gttcagcagc agcaccagca gctcagcgtt  240
gtatgttccg gagcctccgc tgcccatttt ttcgatgaca gaattcacca tgttagtaat  300
gccattgatt gcgttctgtg tagacttctg atcagcggcg tagccgctgc cctgctcatt  360
ctgatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat                 645

SEQ ID NO: 291           moltype = DNA  length = 1155
FEATURE                  Location/Qualifiers
misc_feature             1..1155
                         note = Synthetic
source                   1..1155
                         mol_type = other DNA
                         organism = synthetic construct
CDS                      1..1155
SEQUENCE: 291
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcagcgga ggctccggaa catacaacgc tgagctgctg  420
gtgctgctgc tgaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgacagtgg gggcgacatc  660
atcaagctgc tgaacgaaca ggtgaacaag gagatgcaga gctccaacct gtacatgagt  720
atgtctagtt ggtgttatac acactcactg gacggcgctg ggctgttcct gtttgatcac  780
gcagccgagg aatacgaaca tgcaaagaaa ctgatcattt tcctgaatga gaacaatgtg  840
cccgtccagc tgacttcaat cagcgcccct gaacataagt tcgagggcct gacccagatc  900
tttcagaaag cttacgaaca cgagcagcat atttccgaat ctatcaacaa tattgtggac  960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtcat gatga                                                  1155

SEQ ID NO: 292           moltype = AA  length = 383
```

```
FEATURE                Location/Qualifiers
REGION                 1..383
                       note = Synthetic Construct
source                 1..383
                       mol_type = protein
                       organism = synthetic construct
SEQUENCE: 292
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGSG GSGTYNAELL VLLLNERTLD FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                          383

SEQ ID NO: 293         moltype = DNA  length = 1155
FEATURE                Location/Qualifiers
misc_feature           1..1155
                       note = Synthetic
source                 1..1155
                       mol_type = other DNA
                       organism = synthetic construct
SEQUENCE: 293
tcatcatgac ccacttttc tggacttggc aatgcccttc acatactgat ctgccaggta  60
caggccatga ttctcgtttc caatcagttc gattttatcc aggatgtcct taaacaggac  120
ctcctcctcg tgctgctcgg ccacgtacca ctgcagaaag ttgaaggtag catgatcttt  180
gctcttaatg gcgtggtcca caatattgtt gatagattcg gaaatatgct gctcgtgttc  240
gtaagctttc tgaaagatct gggtcaggcc ctcgaactta tgttcagggg cgctgattga  300
agtcagctgg acgggcacat tgttctcatt caggaaaatg atcagtttct ttgcatgttc  360
gtattcctcg gctgcgtgat caaacaggaa cagcccagcg ccgtccagtg agtgtgtata  420
acaccaacta gacatactca tgtacaggtt ggagctctgc atctccttgt tcacctgttc  480
gttcagcagc ttgatgatgt cgcccccact gtcaattttc tctcgattca gcttactctc  540
ttcagaatat ttgggatagt cgtaagtgcc gttcttcaca gactccatac attcattgtt  600
gcacttatgg taaaactcga agcatccatt cccgatttct ttggcattgt tcttcagctg  660
ggatttgacc ttctcataca gattcttcac gttgctatcg tggaaatcca gagtccgctc  720
gttcagcagc agcaccagca gctcagcgtt gtatgttccg gagcctccgc tgcccatttt  780
ttcgatgaca gaattcacca tgttagtaat gccattgatt gcgttctgtg tagacttctg  840
atcagcggcg tagccgctgc cctgctcatt ctgatggtgg tagccgtacc acccgtccac  900
cattcctgtc cacccgccct caataaaccc tgcgatagcg ccgaacagtc ctcttgtttc  960
ccgctgtggg atgttgcgca gtccggtgac catcctcagt ccgctgccca gattcactga  1020
gtgggtgaca gtcacgttct tctccaggac ggtatccact gtgtcggtgg agttgtttgc  1080
gtgatagccg atgcagatag tgtcagcgta ggttgcggta aaagtacaca gcaggaccag  1140
cagtttggcc ttcat                                                   1155

SEQ ID NO: 294         moltype = DNA  length = 5579
FEATURE                Location/Qualifiers
misc_feature           1..5579
                       note = Synthetic
source                 1..5579
                       mol_type = other DNA
                       organism = synthetic construct
SEQUENCE: 294
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcagattgg  240
ctattggcca ttgcatacgt tgtatccata tcataatatg tacatttata ttggctcatg  300
tccaacatta ccgccatgtt gacattgatt attgactagt tattaatagt aatcaattac  360
ggggtcatta gttcatagcc catatatgga gttccgcgtt acataactta cggtaaatgg  420
cccgcctggc tgaccgccca acgacccccg cccattgacg tcaataatga cgtatgttcc  480
catagtaacg ccaataggga ctttccattg acgtcaatgg gtggagtatt tacggtaaac  540
tgcccacttg gcagtacatc aagtgtatca tatgccaagt acgcccccta ttgacgtcaa  600
tgacggtaaa tggcccgcct ggcattatgc ccagtacatg accttatggg actttcctac  660
ttggcagtac atctacgtat tagtcatcgc tattaccatg gtgatgcggt tttggcagta  720
catcaatggg cgtggatagc ggtttgactc acggggattt ccaagtctcc accccattga  780
cgtcaatggg agtttgtttt ggcaccaaaa tcaacgggac tttccaaaat gtcgtaacaa  840
ctccgcccca ttgacgcaaa tgggcggtag gcgtgtacgg tgggaggtct atataagcag  900
agctcgttta gtgaaccgtc agatcgcctg gagacgccat ccacgctgtt ttgacctcca  960
tagaagacac cgggaccgat ccagcctcca tcggctcgca tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctcaggtc gagaccgggc  1140
ctttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgcggc cgctctagag  1380
atatcgccac catgaaggcc aaactgctgg tcctgctgtg tacttttacc gcaacctacg  1440
ctgacactat ctgcatcggc tatcacgcaa acaactccac cgacacagtg gataccgtcc  1500
tggagaagaa cgtgactgtc acccactcag tgaatctggg cagcggactg aggatggtca  1560
ccggactgcg caacatccca cagcgggaaa caagaggact gttcggcgct atcgcagggt  1620
```

-continued ttattgaggg cgggtggaca ggaatggtgg acgggtggta cggctaccac catcagaatg 1680
agcagggcag cggctacgcc gctgatcaga agtctacaca gaacgcaatc aatggcatta 1740
ctaacatggt gaattctgtc atcgaaaaaa tgggcagcgg aggctccgga acatacaacg 1800
ctgagctgct ggtgctgctg ctgaacgagc ggactctgga tttccacgat agcaacgtga 1860
agaatctgta tgagaaggtc aaatcccagc tgaagaacaa tgccaaagaa atcgggaatg 1920
gatgcttcga gttttaccat aagtgcaaca atgaatgtat ggagtctgtg aagaacggca 1980
cttacgacta tcccaaatat tctgaagaga gtaagctgaa tcgagagaaa attgacagtg 2040
ggggcgacat catcaagctg ctgaacgaac aggtgaacaa ggagatgcag agctccaacc 2100
tgtacatgag tatgtctagt tggtgttata cacactcact ggacggcgct gggctgttcc 2160
tgtttgatca cgcagccgag gaatacgaac atgcaaagaa actgatcatt ttcctgaatg 2220
agaacaatgt gcccgtccag ctgacttcaa tcagcgcccc tgaacataag ttcgagggcc 2280
tgacccagat ctttcagaaa gcttacgaac acgagcagca tatttccgaa tctatcaaca 2340
atattgtgga ccacgccatt aagagcaaag atcatgctac cttcaacttt ctgcagtggt 2400
acgtggccga gcagcacgag gaggaggtcc tgtttaagga catcctggat aaaatcgaac 2460
tgattggaaa cgagaatcat ggcctgtacc tggcagatca gtatgtgaag ggcattgcca 2520
agtccagaaa aagtgggtca tgatgaacac gtgggatcca gatctgctgt gccttctagt 2580
tgccagccat ctgttgtttg cccctccccc gtgccttcct tgaccctgga aggtgccact 2640
cccactgtcc tttcctaata aaatgaggaa attgcatcgc attgtctgag taggtgtcat 2700
tctattctgg ggggtggggt ggggcaggac agcaaggggg aggattggga agacaatagc 2760
aggcatgctg gggatgcggt gggctctatg ggtacccagg tgctgaagaa ttgacccggt 2820
tcctcctggg ccagaaagaa gcaggcacat ccccttctct gtgacacacc ctgtccacgc 2880
ccctggttct tagttccagc cccactcata ggacactcat agctcaggag ggctccgcct 2940
tcaatcccac ccgctaaagt acttggagcg gtctctccct ccctcatcag cccaccaaac 3000
caaacctagc ctccaagagt gggaagaaat taaagcaaga taggctatta agtgcagagg 3060
gagagaaaat gcctccaaca tgtgaggaag taatgagaga aatcatagaa ttttaaggcc 3120
atgatttaag gccatcatgg ccttaatctt ccgcttcctc gctcactgac tcgctgcgct 3180
cggtcgttcg gctgcggcga gcggtatcag ctcactcaaa ggcggtaata cggttatcca 3240
cagaatcagg ggataacgca ggaaagaaca tgtgagcaaa aggccagcaa aaggccagga 3300
accgtaaaaa ggccgcgttg ctggcgtttt tccataggct ccgcccccct gacgagcatc 3360
acaaaaatcg acgctcaagt cagaggtggc gaaacccgac aggactataa agataccagg 3420
cgtttccccc tggaagctcc ctcgtgcgct ctcctgttcc gaccctgccg cttaccggat 3480
acctgtccgc ctttctccct tcgggaagcg tggcgctttc tcatagctca cgctgtaggt 3540
atctcagttc ggtgtaggtc gttcgctcca agctgggctg tgtgcacgaa ccccccgttc 3600
agcccgaccg ctgcgcctta tccggtaact atcgtcttga gtccaacccg gtaagacacg 3660
acttatcgcc actggcagca gccactggta acaggattag cagagcgagg tatgtaggcg 3720
gtgctacaga gttcttgaag tggtggccta actacggcta cactagaaga acagtatttg 3780
gtatctgcgc tctgctgaag ccagttacct tcggaaaaag agttggtagc tcttgatccg 3840
gcaaacaaac caccgctggt agcggtggtt tttttgtttg caagcagcag attacgcgca 3900
gaaaaaaagg atctcaagaa gatcctttga tcttttctac ggggtctgac gctcagtgga 3960
acgaaaactc acgttaaggg attttggtca tgagattatc aaaaaggatc ttcacctaga 4020
tccttttaaa ttaaaaatga agttttaaat caatctaaag tatatatgag taaacttggt 4080
ctgacagtta ccaatgctta atcagtgagg cacctatctc agcgatctgt ctatttcgtt 4140
catccatagt tgcctgactc ggggggggggg ggcgctgagg tctgcctcgt gaagaaggtg 4200
ttgctgactc ataccaggcc tgaatcgccc catcatccag ccagaaagtg agggagccac 4260
ggttgatgag agctttgttg taggtggacc agttggtgat tttgaacttt tgctttgcca 4320
cggaacggtc tgcgttgtcg ggaagatgcg tgatctgatc cttcaactca gcaaaagttc 4380
gatttattca acaaagccgc cgtcccgtca agtcagcgta atgctctgcc agtgttacaa 4440
ccaattaacc aattctgatt agaaaaactc atcgagcatc aaatgaaact gcaatttatt 4500
catatcagga ttatcaatac catatttttg aaaaagccgt ttctgtaatg aaggagaaaa 4560
ctcaccgagg cagttccata ggatggcaag atcctggtat cggtctgcga ttccgactcg 4620
tccaacatca atacaaccta ttaatttccc ctcgtcaaaa ataaggttat caagtgagaa 4680
atcaccatga gtgacgactg aatccggtga gaatggcaaa agcttatgca tttctttcca 4740
gacttgttca acaggccagc cattacgctc gtcatcaaaa tcactcgcat caaccaaacc 4800
gttattcatt cgtgattgcg cctgagcgag acgaaatacg cgatcgctgt taaaaggaca 4860
attacaaaca ggaatcgaat gcaaccggcg caggaacact gccagcgcat caacaatatt 4920
ttcacctgaa tcaggatatt cttctaatac ctggaatgct gttttcccgg ggatcgcagt 4980
ggtgagtaac catgcatcat caggagtacg gataaaatgc ttgatggtcg gaagaggcat 5040
aaattccgtc agccagttta gtctgaccat ctcatctgta acatcattgg caacgctacc 5100
tttgccatgt ttcagaaaca actctggcgc atcgggcttc ccatacaatc gatagattgt 5160
cgcacctgat tgcccgacat tatcgcgagc ccatttatac ccatataaat cagcatccat 5220
gttggaattt aatcgcggcc tcgagcaaga cgtttcccgt tgaatatggc tcataacacc 5280
ccttgtatta ctgtttatgt aagcagacag ttttattgtt catgatgata tatttttatc 5340
ttgtgcaatg taacatcaga gattttgaga cacaacgtgg ctttcccccc ccccccatta 5400
ttgaagcatt tatcagggtt attgtctcat gagcggatac atatttgaat gtatttagaa 5460
aaataaacaa ataggggttc cgcgcacatt tccccgaaaa gtgccacctg acgtctaaga 5520
aaccattatt atcatgacat taacctataa aaataggcgt atcacgaggc cctttcgtc 5579

SEQ ID NO: 295 moltype = DNA length = 645
FEATURE Location/Qualifiers
misc_feature 1..645
note = Synthetic
source 1..645
mol_type = other DNA
organism = synthetic construct
CDS 1..645
SEQUENCE: 295
atgaaggcca aactgctggt cctgctgtgt acttttaccg caacctacgc tgacactatc 60
tgcatcggct atcacgcaaa caactccacc gacacagtgg ataccgtcct ggagaagaac 120
gtgactgtca cccactcagt gaatctgggc agcggactga ggatggtcac cggactgcgc 180

```
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcagcgga ggctccggaa cagacctggc tgagctgctg  420
gtgctgctgc tgaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                  645

SEQ ID NO: 296         moltype = AA  length = 215
FEATURE                Location/Qualifiers
REGION                 1..215
                       note = Synthetic Construct
source                 1..215
                       mol_type = protein
                       organism = synthetic construct
SEQUENCE: 296
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLN REKID                             215

SEQ ID NO: 297         moltype = DNA  length = 645
FEATURE                Location/Qualifiers
misc_feature           1..645
                       note = Synthetic
source                 1..645
                       mol_type = other DNA
                       organism = synthetic construct
SEQUENCE: 297
gtcaattttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaaatcca gagtccgctc gttcagcagc agcaccagca gctcagccag  240
gtctgttccg gagcctccgc tgcccatttt ttcgatgaca gaattcacca tgttagtaat  300
gccattgatt gcgttctgtg tagacttctg atcagcggcg tagccgctgc cctgctcatt  360
ctgatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat                  645

SEQ ID NO: 298         moltype = DNA  length = 1155
FEATURE                Location/Qualifiers
misc_feature           1..1155
                       note = Synthetic
source                 1..1155
                       mol_type = other DNA
                       organism = synthetic construct
CDS                    1..1155
SEQUENCE: 298
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcagcgga ggctccggaa cagacctggc tgagctgctg  420
gtgctgctgc tgaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgacagtgg gggcgacatc  660
atcaagctgc tgaacgaaca ggtgaacaag gagatgcaga gctccaacct gtacatgagt  720
atgtctagtt ggtgttatac acactcactg gacggcgctg ggctgttcct gtttgatcac  780
gcagccgagg aatacgaaca tgcaaagaaa ctgatcattt tcctgaatga gaacaatgtg  840
cccgtccagc tgacttcaat cagcgcccct gaacataagt tcgagggcct gacccagatc  900
tttcagaaag cttacgaaca cgagcagcat atttccgaat ctatcaacaa tattgtggac  960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtcat gatga                                                   1155

SEQ ID NO: 299         moltype = AA  length = 383
FEATURE                Location/Qualifiers
REGION                 1..383
                       note = Synthetic Construct
source                 1..383
                       mol_type = protein
                       organism = synthetic construct
```

```
SEQUENCE: 299
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                        383

SEQ ID NO: 300          moltype = DNA  length = 1155
FEATURE                 Location/Qualifiers
misc_feature            1..1155
                        note = Synthetic
source                  1..1155
                        mol_type = other DNA
                        organism = synthetic construct
SEQUENCE: 300
tcatcatgac ccactttttc tggacttggc aatgcccttc acatactgat ctgccaggta  60
caggccatga ttctcgtttc caatcagttc gattttatcc aggatgtcct taaacaggac  120
ctcctcctcg tgctgctcgg ccacgtacca ctgcagaaag ttgaaggtag catgatcttt  180
gctcttaatg gcgtggtcca caatattgtt gatagattcg gaaatatgct gctcgtgttc  240
gtaagctttc tgaaagatct gggtcaggcc ctcgaactta tgttcagggg cgctgattga  300
agtcagctgg acgggcacat tgttctcatt caggaaaatg atcagtttct ttgcatgttc  360
gtattcctcg gctgcgtgat caaacaggaa cagcccagcg ccgtccagtg agtgtgtata  420
acaccaacta gacatactca tgtacaggtt ggagctctgc atctccttgt tcacctgttc  480
gttcagcagc ttgatgatgt cgcccccact gtcaattttc tctcgattca gcttactctc  540
ttcagaatat ttgggatagt cgtaagtgcc gttcttcaca gactccatac attcattgtt  600
gcacttatgg taaaactcga agcatccatt cccgatttct ttggcattgt tcttcagctg  660
ggatttgacc ttctcataca gattcttcac gttgctatcg tggaaatcca gagtccgctc  720
gttcagcagc agcaccagca gctcagccag gtctgttccg gagcctccgc tgcccatttt  780
ttcgatgaca gaattcacca tgttagtaat gccattgatt gcgttctgtg tagacttctg  840
atcagcggcg tagccgctgc cctgctcatt ctgatggtgg tagccgtacc acccgtccac  900
cattcctgtc cacccgccct caataaaccc tgcgatagcg ccgaacagtc ctcttgtttc  960
ccgctgtggg atgttgcgca gtccggtgac catcctcagt ccgctgccca gattcactga  1020
gtgggtgaca gtcacgttct tctccaggac ggtatccact gtgtcggtgg agttgtttgc  1080
gtgatagccg atgcagatag tgtcagcgta ggttgcggta aaagtacaca gcaggaccag  1140
cagtttggcc ttcat                                                 1155

SEQ ID NO: 301          moltype = DNA  length = 5579
FEATURE                 Location/Qualifiers
misc_feature            1..5579
                        note = Synthetic
source                  1..5579
                        mol_type = other DNA
                        organism = synthetic construct
SEQUENCE: 301
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcagattgg  240
ctattggcca ttgcatacgt tgtatccata tcataatatg tacatttata ttggctcatg  300
tccaacatta ccgccatgtt gacattgatt attgactagt tattaatagt aatcaattac  360
ggggtcatta gttcatagcc catatatgga gttccgcgtt acataactta cggtaaatgg  420
cccgcctggc tgaccgccca acgacccccg cccattgacg tcaataatga cgtatgttcc  480
catagtaacg ccaataggga ctttccattg acgtcaatgg gtggagtatt tacggtaaac  540
tgcccacttg gcagtacatc aagtgtatca tatgccaagt acgcccccta ttgacgtcaa  600
tgacggtaaa tggcccgcct ggcattatgc ccagtacatg accttatggg actttcctac  660
ttggcagtac atctacgtat tagtcatcgc tattaccatg gtgatgcggt tttggcagta  720
catcaatggg cgtggatagc ggtttgactc acggggattt ccaagtctcc accccattga  780
cgtcaatggg agtttgtttt ggcaccaaaa tcaacgggac tttccaaaat gtcgtaacaa  840
ctccgcccca ttgacgcaaa tgggcggtag gcgtgtacgg tgggaggtct atataagcag  900
agctcgttta gtgaaccgtc agatcgcctg gagacgccat ccacgctgtt ttgacctcca  960
tagaagacac cgggaccgat ccagcctcca tcggctcgca tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctcaggtc gagaccgggc  1140
ctttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgcggc cgctctagag  1380
atatcgccac catgaaggcc aaactgctgg tcctgctgtg tacttttacc gcaacctacg  1440
ctgacactat ctgcatcggc tatcacgcaa acaactccac cgacacagtg gataccgtcc  1500
tggagaagaa cgtgactgtc acccactcag tgaatctggg cagcggactg aggatggtca  1560
ccggactgcg caacatccca cagcgggaaa caagaggact gttcggcgct atcgcagggt  1620
ttattgaggg cgggtggaca ggaatggtgg acgggtggta cggctaccac catcagaatg  1680
agcagggcag cggctacgcc gctgatcaga agtctacaca gaacgcaatc aatggcatta  1740
ctaacatggt gaattctgtc atcgaaaaaa tgggcagcgg aggctccgga acagacctgg  1800
ctgagctgct ggtgctgctg ctgaacgagc ggactctgga tttccacgat agcaacgtga  1860
agaatctgta tgagaaggtc aaatcccagc tgaagaacaa tgccaaagaa atcgggaatg  1920
gatgcttcga gttttaccat aagtgcaaca atgaatgtat ggagtctgtg aagaacggca  1980
```

```
cttacgacta tcccaaatat tctgaagaga gtaagctgaa tcgagagaaa attgacagtg  2040
ggggcgacat catcaagctg ctgaacgaac aggtgaacaa ggagatgcag agctccaacc  2100
tgtacatgag tatgtctagt tggtgttata cacactcact ggacggcgct gggctgttcc  2160
tgtttgatca cgcagccgag gaatacgaac atgcaaagaa actgatcatt ttcctgaatg  2220
agaacaatgt gcccgtccag ctgacttcaa tcagcgcccc tgaacataag ttcgagggcc  2280
tgacccagat ctttcagaaa gcttacgaac acgagcagca tatttccgaa tctatcaaca  2340
atattgtgga ccacgccatt aagagcaaag atcatgctac cttcaacttt ctgcagtggt  2400
acgtggccga gcagcacgag gaggaggtcc tgtttaagga catcctggat aaaatcgaac  2460
tgattggaaa cgagaatcat ggcctgtacc tggcagatca gtatgtgaag ggcattgcca  2520
agtccagaaa aagtgggtca tgatgaacac gtgggatcca gatctgctgt gccttctagt  2580
tgccagccat ctgttgtttg cccctccccc gtgccttcct tgaccctgga aggtgccact  2640
cccactgtcc tttcctaata aaatgaggaa attgcatcgc attgtctgag taggtgtcat  2700
tctattctgg ggggtggggt ggggcaggac agcaaggggg aggattggga agacaatagc  2760
aggcatgctg gggatgcggt gggctctatg ggtacccagg tgctgaagaa ttgacccggt  2820
tcctcctggg ccagaaagaa gcaggcacat ccccttctct gtgacacacc ctgtccacgc  2880
ccctggttct tagttccagc cccactcata ggacactcat agctcaggag ggctccgcct  2940
tcaatcccac ccgctaaagt acttggagcg gtctctccct ccctcatcag cccaccaaac  3000
caaacctagc ctccaagagt gggaagaaat taaagcaaga taggctatta agtgcagagg  3060
gagagaaaat gcctccaaca tgtgaggaag taatgagaga aatcatagaa ttttaaggcc  3120
atgatttaag gccatcatgg ccttaatctt ccgcttcctc gctcactgac tcgctgcgct  3180
cggtcgttcg gctgcggcga gcggtatcag ctcactcaaa ggcggtaata cggttatcca  3240
cagaatcagg ggataacgca ggaaagaaca tgtgagcaaa aggccagcaa aaggccagga  3300
accgtaaaaa ggccgcgttg ctggcgtttt tccataggct ccgcccccct gacgagcatc  3360
acaaaaatcg acgctcaagt cagaggtggc gaaacccgac aggactataa agataccagg  3420
cgtttccccc tggaagctcc ctcgtgcgct ctcctgttcc gaccctgccg cttaccggat  3480
acctgtccgc ctttctccct tcgggaagcg tggcgctttc tcatagctca cgctgtaggt  3540
atctcagttc ggtgtaggtc gttcgctcca agctgggctg tgtgcacgaa ccccccgttc  3600
agcccgaccg ctgcgcctta tccggtaact atcgtcttga gtccaacccg gtaagacacg  3660
acttatcgcc actggcagca gccactggta acaggattag cagagcgagg tatgtaggcg  3720
gtgctacaga gttcttgaag tggtggccta actacggcta cactagaaga acagtatttg  3780
gtatctgcgc tctgctgaag ccagttacct tcggaaaaag agttggtagc tcttgatccg  3840
gcaaacaaac caccgctggt agcggtggtt tttttgtttg caagcagcag attacgcgca  3900
gaaaaaaagg atctcaagaa gatcctttga tcttttctac ggggtctgac gctcagtgga  3960
acgaaaactc acgttaaggg attttggtca tgagattatc aaaaaggatc ttcacctaga  4020
tccttttaaa ttaaaaatga agttttaaat caatctaaag tatatatgag taaacttggt  4080
ctgacagtta ccaatgctta atcagtgagg cacctatctc agcgatctgt ctatttcgtt  4140
catccatagt tgcctgactc gggggggggg ggcgctgagg tctgcctcgt gaagaaggtg  4200
ttgctgactc ataccaggcc tgaatcgccc catcatccag ccagaaagtg agggagccac  4260
ggttgatgag agctttgttg taggtggacc agttggtgat tttgaacttt tgctttgcca  4320
cggaacggtc tgcgttgtcg ggaagatgcg tgatctgatc cttcaactca gcaaaagttc  4380
gatttattca acaaagccgc cgtcccgtca agtcagcgta atgctctgcc agtgttacaa  4440
ccaattaacc aattctgatt agaaaaactc atcgagcatc aaatgaaact gcaatttatt  4500
catatcagga ttatcaatac catatttttg aaaaagccgt ttctgtaatg aaggagaaaa  4560
ctcaccgagg cagttccata ggatggcaag atcctggtat cggtctgcga ttccgactcg  4620
tccaacatca atacaaccta ttaatttccc ctcgtcaaaa ataaggttat caagtgagaa  4680
atcaccatga gtgacgactg aatccggtga gaatggcaaa agcttatgca tttctttcca  4740
gacttgttca acaggccagc cattacgctc gtcatcaaaa tcactcgcat caaccaaacc  4800
gttattcatt cgtgattgcg cctgagcgag acgaaatacg cgatcgctgt taaaaggaca  4860
attacaaaca ggaatcgaat gcaaccggcg caggaacact gccagcgcat caacaatatt  4920
ttcacctgaa tcaggatatt cttctaatac ctggaatgct gttttcccgg ggatcgcagt  4980
ggtgagtaac catgcatcat caggagtacg gataaaatgc ttgatggtcg gaagaggcat  5040
aaattccgtc agccagttta gtctgaccat ctcatctgta acatcattgg caacgctacc  5100
tttgccatgt ttcagaaaca actctggcgc atcgggcttc ccatacaatc gatagattgt  5160
cgcacctgat tgcccgacat tatcgcgagc ccatttatac ccatataaat cagcatccat  5220
gttggaattt aatcgcggcc tcgagcaaga cgtttcccgt tgaatatggc tcataacacc  5280
ccttgtatta ctgtttatgt aagcagacag ttttattgtt catgatgata tatttttatc  5340
ttgtgcaatg taacatcaga gattttgaga cacaacgtgg ctttcccccc ccccccatta  5400
ttgaagcatt tatcagggtt attgtctcat gagcggatac atatttgaat gtatttagaa  5460
aaataaacaa ataggggttc cgcgcacatt tccccgaaaa gtgccacctg acgtctaaga  5520
aaccattatt atcatgacat taacctataa aaataggcgt atcacgaggc cctttcgtc   5579
```

```
SEQ ID NO: 302          moltype = DNA  length = 645
FEATURE                 Location/Qualifiers
misc_feature            1..645
                        note = Synthetic
source                  1..645
                        mol_type = other DNA
                        organism = synthetic construct
CDS                     1..645
SEQUENCE: 302
atgaaggcca aactgctggt cctgctgtgt actttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatcgtg  360
aattctgtca tcgaaaaaat gggcagcgga ggctccggaa cagacctggc tgagctgctg  420
gtgctgctga tcaacgagcg gactctggat ttccacgata gcaacgtgaa gaatctgtat  480
gagaaggtca aatcccagct gaagaacaat gccaaagaaa tcgggaatgg atgcttcgag  540
```

-continued

```
ttttaccata agtgcaacaa tgaatgtatg gagtctgtga agaacggcac ttacgactat  600
cccaaatatt ctgaagagag taagctgaat cgagagaaaa ttgac                  645

SEQ ID NO: 303         moltype = AA  length = 215
FEATURE                Location/Qualifiers
REGION                 1..215
                       note = Synthetic Construct
source                 1..215
                       mol_type = protein
                       organism = synthetic construct
SEQUENCE: 303
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNIV  120
NSVIEKMGSG GSGTDLAELL VLLINERTLD FHDSNVKNLY EKVKSQLKNN AKEIGNGCFE  180
FYHKCNNECM ESVKNGTYDY PKYSEESKLN REKID                             215

SEQ ID NO: 304         moltype = DNA  length = 645
FEATURE                Location/Qualifiers
misc_feature           1..645
                       note = Synthetic
source                 1..645
                       mol_type = other DNA
                       organism = synthetic construct
SEQUENCE: 304
gtcaatttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaaatcca gagtccgctc gttgatcagc agcaccagca gctcagccag  240
gtctgttccg gagcctccgc tgcccatttt ttcgatgaca gaattcacga tgttagtaat  300
gccattgatt gcgttctgtg tagacttctg atcagcggcg tagccgctgc cctgctcatt  360
ctgatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat                  645

SEQ ID NO: 305         moltype = DNA  length = 1155
FEATURE                Location/Qualifiers
misc_feature           1..1155
                       note = Synthetic
source                 1..1155
                       mol_type = other DNA
                       organism = synthetic construct
CDS                    1..1155
SEQUENCE: 305
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatcgtg  360
aattctgtca tcgaaaaaat gggcagcgga ggctccggaa cagacctggc tgagctgctg  420
gtgctgctga tcaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgacagtgg gggcgacatc  660
atcaagctgc tgaacgaaca ggtgaacaag gagatgcaga gctccaacct gtacatgagt  720
atgtctagtt ggtgttatac acactcactg gacggcgctg ggctgttcct gtttgatcac  780
gcagccgagg aatacgaaca tgcaaagaaa ctgatcattt tcctgaatga gaacaatgtg  840
cccgtccagc tgacttcaat cagcgcccct gaacataagt tcgagggcct gacccagatc  900
tttcagaaag cttacgaaca cgagcagcat atttccgaat ctatcaacaa tattgtggac  960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtcat gatga                                                   1155

SEQ ID NO: 306         moltype = AA  length = 383
FEATURE                Location/Qualifiers
REGION                 1..383
                       note = Synthetic Construct
source                 1..383
                       mol_type = protein
                       organism = synthetic construct
SEQUENCE: 306
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNIV  120
NSVIEKMGSG GSGTDLAELL VLLINERTLD FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
```

-continued

```
FQKAYEHEQH ISESINNIVD HAIKSKDHAT FNFLQWYVAE QHEEEVLFKD ILDKIELIGN  360
ENHGLYLADQ YVKGIAKSRK SGS                                          383

SEQ ID NO: 307          moltype = DNA  length = 1155
FEATURE                 Location/Qualifiers
misc_feature            1..1155
                        note = Synthetic
source                  1..1155
                        mol_type = other DNA
                        organism = synthetic construct
SEQUENCE: 307
tcatcatgac ccactttttc tggacttggc aatgcccttc acatactgat ctgccaggta  60
caggccatga ttctcgtttc caatcagttc gattttatcc aggatgtcct taaacaggac  120
ctcctcctcg tgctgctcgg ccacgtacca ctgcagaaag ttgaaggtag catgatcttt  180
gctcttaatg gcgtggtcca caatattgtt gatagattcg gaaatatgct gctcgtgttc  240
gtaagctttc tgaaagatct gggtcaggcc ctcgaactta tgttcagggg cgctgattga  300
agtcagctgg acgggcacat tgttctcatt caggaaaatg atcagtttct ttgcatgttc  360
gtattcctcg gctgcgtgat caaacaggaa cagcccagcg ccgtccagtg agtgtgtata  420
acaccaacta gacatactca tgtacaggtt ggagctctgc atctccttgt tcacctgttc  480
gttcagcagc ttgatgatgt cgccccccact gtcaattttc tctcgattca gcttactctc  540
ttcagaatat ttgggatagt cgtaagtgcc gttcttcaca gactccatac attcattgtt  600
gcacttatgg taaaactcga agcatccatt cccgatttct ttggcattgt tcttcagctg  660
ggatttgacc ttctcataca gattcttcac gttgctatcg tggaaatcca gagtccgctc  720
gttgatcagc agcaccagca gctcagccag gtctgttccg gagcctccgc tgcccatttt  780
ttcgatgaca gaattcacga tgttagtaat gccattgatt gcgttctgtg tagacttctg  840
atcagcggcg tagccgctgc cctgctcatt ctgatggtgg tagccgtacc acccgtccac  900
cattcctgtc cacccgccct caataaaccc tgcgatagcg ccgaacagtc ctcttgtttc  960
ccgctgtggg atgttgcgca gtccggtgac catcctcagt ccgctgccca gattcactga  1020
gtgggtgaca gtcacgttct tctccaggac ggtatccact gtgtcggtgg agttgtttgc  1080
gtgatagccg atgcagatag tgtcagcgta ggttgcggta aaagtacaca gcaggaccag  1140
cagtttggcc ttcat                                                   1155

SEQ ID NO: 308          moltype = DNA  length = 5579
FEATURE                 Location/Qualifiers
misc_feature            1..5579
                        note = Synthetic
source                  1..5579
                        mol_type = other DNA
                        organism = synthetic construct
SEQUENCE: 308
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcagattgg  240
ctattggcca ttgcatacgt tgtatccata tcataatatg tacatttata ttggctcatg  300
tccaacatta ccgccatgtt gacattgatt attgactagt tattaatagt aatcaattac  360
ggggtcatta gttcatagcc catatatgga gttccgcgtt acataactta cggtaaatgg  420
cccgcctggc tgaccgccca acgacccccg cccattgacg tcaataatga cgtatgttcc  480
catagtaacg ccaataggga ctttccattg acgtcaatgg gtggagtatt tacggtaaac  540
tgcccacttg gcagtacatc aagtgtatca tatgccaagt acgcccccta ttgacgtcaa  600
tgacggtaaa tggcccgcct ggcattatgc ccagtacatg accttatggg actttcctac  660
ttggcagtac atctacgtat tagtcatcgc tattaccatg gtgatgcggt tttggcagta  720
catcaatggg cgtggatagc ggtttgactc acggggattt ccaagtctcc accccattga  780
cgtcaatggg agtttgtttt ggcaccaaaa tcaacgggac tttccaaaat gtcgtaacaa  840
ctccgcccca ttgacgcaaa tgggcggtag gcgtgtacgg tgggaggtct atataagcag  900
agctcgttta gtgaaccgtc agatcgcctg gagacgccat ccacgctgtt ttgacctcca  960
tagaagacac cgggaccgat ccagcctcca tcggctcgca tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctcaggtc gagaccgggc  1140
ctttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgcggc cgctctagag  1380
atatcgccac catgaaggcc aaactgctgg tcctgctgtg tacttttacc gcaacctacg  1440
ctgacactat ctgcatcggc tatcacgcaa acaactccac cgacacagtg gataccgtcc  1500
tggagaagaa cgtgactgtc acccactcag tgaatctggg cagcggactg aggatggtca  1560
ccggactgcg caacatccca cagcgggaaa caagaggact gttcggcgct atcgcagggt  1620
ttattgaggg cgggtggaca ggaatggtgg acgggtggta cggctaccac catcagaatg  1680
agcagggcag cggctacgcc gctgatcaga agtctacaca gaacgcaatc aatggcatta  1740
ctaacatcgt gaattctgtc atcgaaaaaa tgggcagcgg aggctccgga acagacctgg  1800
ctgagctgct ggtgctgctg atcaacgagc ggactctgga tttccacgat agcaacgtga  1860
agaatctgta tgagaaggtc aaatcccagc tgaagaacaa tgccaaagaa atcgggaatg  1920
gatgcttcga gttttaccat aagtgcaaca atgaatgtat ggagtctgtg aagaacggca  1980
cttacgacta tcccaaatat tctgaagaga gtaagctgaa tcgagagaaa attgacagtg  2040
ggggcgacat catcaagctg ctgaacgaac aggtgaacaa ggagatgcag agctccaacc  2100
tgtacatgag tatgtctagt tggtgttata cacactcact ggacggcgct gggctgttcc  2160
tgtttgatca cgcagccgag gaatacgaac atgcaaagaa actgatcatt ttcctgaatg  2220
agaacaatgt gcccgtccag ctgacttcaa tcagcgcccc tgaacataag ttcgagggcc  2280
tgacccagat ctttcagaaa gcttacgaac acgagcagca tatttccgaa tctatcaaca  2340
```

-continued

```
atattgtgga ccacgccatt aagagcaaag atcatgctac cttcaacttt ctgcagtggt  2400
acgtggccga gcagcacgag gaggaggtcc tgtttaagga catcctggat aaaatcgaac  2460
tgattggaaa cgagaatcat ggcctgtacc tggcagatca gtatgtgaag ggcattgcca  2520
agtccagaaa aagtgggtca tgatgaacac gtgggatcca gatctgctgt gccttctagt  2580
tgccagccat ctgttgtttg cccctccccc gtgccttcct tgaccctgga aggtgccact  2640
cccactgtcc tttcctaata aaatgaggaa attgcatcgc attgtctgag taggtgtcat  2700
tctattctgg ggggtggggt ggggcaggac agcaaggggg aggattggga agacaatagc  2760
aggcatgctg gggatgcggt gggctctatg ggtacccagg tgctgaagaa ttgacccggt  2820
tcctcctggg ccagaaagaa gcaggcacat cccctcctct gtgacacacc ctgtccacgc  2880
ccctggttct tagttccagc cccactcata ggacactcat agctcaggag ggctccgcct  2940
tcaatcccac ccgctaaagt acttggagcg gtctctccct ccctcatcag cccaccaaac  3000
caaacctagc ctccaagagt gggaagaaat taaagcaaga taggctatta agtgcagagg  3060
gagagaaaat gcctccaaca tgtgaggaag taatgagaga aatcatagaa ttttaaggcc  3120
atgatttaag gccatcatgg ccttaatctt ccgcttcctc gctcactgac tcgctgcgct  3180
cggtcgttcg gctgcggcga gcggtatcag ctcactcaaa ggcggtaata cggttatcca  3240
cagaatcagg ggataacgca ggaaagaaca tgtgagcaaa aggccagcaa aaggccagga  3300
accgtaaaaa ggccgcgttg ctggcgtttt tccataggct ccgcccccct gacgagcatc  3360
acaaaaatcg acgctcaagt cagaggtggc gaaacccgac aggactataa agataccagg  3420
cgtttccccc tggaagctcc ctcgtgcgct ctcctgttcc gaccctgccg cttaccggat  3480
acctgtccgc ctttctccct tcgggaagcg tggcgctttc tcatagctca cgctgtaggt  3540
atctcagttc ggtgtaggtc gttcgctcca agctgggctg tgtgcacgaa ccccccgttc  3600
agcccgaccg ctgcgcctta tccggtaact atcgtcttga gtccaacccg gtaagacacg  3660
acttatcgcc actggcagca gccactggta acaggattag cagagcgagg tatgtaggcg  3720
gtgctacaga gttcttgaag tggtggccta actacggcta cactagaaga acagtatttg  3780
gtatctgcgc tctgctgaag ccagttacct tcggaaaaag agttggtagc tcttgatccg  3840
gcaaacaaac caccgctggt agcggtggtt tttttgtttg caagcagcag attacgcgca  3900
gaaaaaaagg atctcaagaa gatcctttga tcttttctac ggggtctgac gctcagtgga  3960
acgaaaactc acgttaaggg attttggtca tgagattatc aaaaaggatc ttcacctaga  4020
tccttttaaa ttaaaaatga agttttaaat caatctaaag tatatatgag taaacttggt  4080
ctgacagtta ccaatgctta atcagtgagg cacctatctc agcgatctgt ctatttcgtt  4140
catccatagt tgcctgactc ggggggggggg ggcgctgagg tctgcctcgt gaagaaggtg  4200
ttgctgactc ataccaggcc tgaatcgccc catcatccag ccagaaagtg agggagccac  4260
ggttgatgag agctttgttg taggtggacc agttggtgat tttgaacttt tgctttgcca  4320
cggaacggtc tgcgttgtcg ggaagatgcg tgatctgatc cttcaactca gcaaaagttc  4380
gatttattca acaaagccgc cgtcccgtca agtcagcgta atgctctgcc agtgttacaa  4440
ccaattaacc aattctgatt agaaaaactc atcgagcatc aaatgaaact gcaatttatt  4500
catatcagga ttatcaatac catatttttg aaaaagccgt ttctgtaatg aaggagaaaa  4560
ctcaccgagg cagttccata ggatggcaag atcctggtat cggtctgcga ttccgactcg  4620
tccaacatca atacaaccta ttaatttccc ctcgtcaaaa ataaggttat caagtgagaa  4680
atcaccatga gtgacgactg aatccggtga gaatggcaaa agcttatgca tttctttcca  4740
gacttgttca acaggccagc cattacgctc gtcatcaaaa tcactcgcat caaccaaacc  4800
gttattcatt cgtgattgcg cctgagcgag acgaaatacg cgatcgctgt taaaaggaca  4860
attacaaaca ggaatcgaat gcaaccggcg caggaacact gccagcgcat caacaatatt  4920
ttcacctgaa tcaggatatt cttctaatac ctggaatgct gttttcccgg ggatcgcagt  4980
ggtgagtaac catgcatcat caggagtacg gataaaatgc ttgatggtcg gaagaggcat  5040
aaattccgtc agccagttta gtctgaccat ctcatctgta acatcattgg caacgctacc  5100
tttgccatgt ttcagaaaca actctggcgc atcgggcttc ccatacaatc gatagattgt  5160
cgcacctgat tgcccgacat tatcgcgagc ccatttatac ccatataaat cagcatccat  5220
gttggaattt aatcgcggcc tcgagcaaga cgtttcccgt tgaatatggc tcataacacc  5280
ccttgtatta ctgtttatgt aagcagacag ttttattgtt catgatgata tattttttatc  5340
ttgtgcaatg taacatcaga gattttgaga cacaacgtgg ctttcccccc ccccccatta  5400
ttgaagcatt tatcagggtt attgtctcat gagcggatac atatttgaat gtatttagaa  5460
aaataaacaa ataggggttc cgcgcacatt tccccgaaaa gtgccacctg acgtctaaga  5520
aaccattatt atcatgacat taacctataa aaataggcgt atcacgaggc cctttcgtc   5579
```

```
SEQ ID NO: 309          moltype = DNA  length = 645
FEATURE                 Location/Qualifiers
misc_feature            1..645
                        note = Synthetic
source                  1..645
                        mol_type = other DNA
                        organism = synthetic construct
CDS                     1..645
SEQUENCE: 309
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacctggtg  360
aattctgtca tcgaaaaaat gggcagcgga ggctccggaa cagacctggc tgagctgctg  420
gtgctgctga tcaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                  645
```

```
SEQ ID NO: 310          moltype = AA  length = 215
FEATURE                 Location/Qualifiers
REGION                  1..215
```

```
                        note = Synthetic Construct
source                  1..215
                        mol_type = protein
                        organism = synthetic construct
SEQUENCE: 310
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNLV  120
NSVIEKMGSG GSGTDLAELL VLLINERTLD FHDSNVKNLY EKVKSQLKNN AKEIGNGCFE  180
FYHKCNNECM ESVKNGTYDY PKYSEESKLN REKID                            215

SEQ ID NO: 311          moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 311
gtcaatttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaaatcca gagtccgctc gttgatcagc agcaccagca gctcagccag  240
gtctgttccg gagcctccgc tgcccatttt ttcgatgaca gaattcacca ggttagtaat  300
gccattgatt gcgttctgtg tagacttctg atcagcggcg tagccgctgc cctgctcatt  360
ctgatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat                 645

SEQ ID NO: 312          moltype = DNA  length = 1155
FEATURE                 Location/Qualifiers
misc_feature            1..1155
                        note = Synthetic
source                  1..1155
                        mol_type = other DNA
                        organism = synthetic construct
CDS                     1..1155
SEQUENCE: 312
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacctggtg  360
aattctgtca tcgaaaaaat gggcagcgga ggctccggaa cagacctggc tgagctgctg  420
gtgctgctga tcaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgacagtgg gggcgacatc  660
atcaagctgc tgaacgaaca ggtgaacaag gagatgcaga gctccaacct gtacatgagt  720
atgtctagtt ggtgttatac acactcactg gacggcgctg ggctgttcct gtttgatcac  780
gcagccgagg aatacgaaca tgcaaagaaa ctgatcattt tcctgaatga gaacaatgtg  840
cccgtccagc tgacttcaat cagcgcccct gaacataagt tcgagggcct gacccagatc  900
tttcagaaag cttacgaaca cgagcagcat atttccgaat ctatcaacaa tattgtggac  960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtcat gatga                                                  1155

SEQ ID NO: 313          moltype = AA  length = 383
FEATURE                 Location/Qualifiers
REGION                  1..383
                        note = Synthetic Construct
source                  1..383
                        mol_type = protein
                        organism = synthetic construct
SEQUENCE: 313
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNLV  120
NSVIEKMGSG GSGTDLAELL VLLINERTLD FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                         383

SEQ ID NO: 314          moltype = DNA  length = 1155
FEATURE                 Location/Qualifiers
misc_feature            1..1155
```

```
                         note = Synthetic
source                   1..1155
                         mol_type = other DNA
                         organism = synthetic construct
SEQUENCE: 314
tcatcatgac ccactttttc tggacttggc aatgcccttc acatactgat ctgccaggta  60
caggccatga ttctcgtttc caatcagttc gattttatcc aggatgtcct taaacaggac  120
ctcctcctcg tgctgctcgg ccacgtacca ctgcagaaag ttgaaggtag catgatcttt  180
gctcttaatg gcgtggtcca caatattgtt gatagattcg gaaatatgct gctcgtgttc  240
gtaagctttc tgaaagatct gggtcaggcc ctcgaactta tgttcagggg cgctgattga  300
agtcagctgg acgggcacat tgttctcatt caggaaaatg atcagtttct ttgcatgttc  360
gtattcctcg gctgcgtgat caaacaggaa cagcccagcg ccgtccagtg agtgtgtata  420
acaccaacta gacatactca tgtacaggtt ggagctctgc atctccttgt tcacctgttc  480
gttcagcagc ttgatgatgt cgccccccact gtcaattttc tctcgattca gcttactctc  540
ttcagaatat ttgggatagt cgtaagtgcc gttcttcaca gactccatac attcattgtt  600
gcacttatgg taaaactcga agcatccatt cccgatttct ttggcattgt tcttcagctg  660
ggatttgacc ttctcataca gattcttcac gttgctatcg tggaaatcca gagtccgctc  720
gttgatcagc agcaccagca gctcagccag gtctgttccg gagcctccgc tgcccatttt  780
ttcgatgaca gaattcacca ggttagtaat gccattgatt gcgttctgtg tagacttctg  840
atcagcggcg tagccgctgc cctgctcatt ctgatggtgg tagccgtacc acccgtccac  900
cattcctgtc cacccgccct caataaaccc tgcgatagcg ccgaacagtc ctcttgtttc  960
ccgctgtggg atgttgcgca gtccggtgac catcctcagt ccgctgccca gattcactga  1020
gtgggtgaca gtcacgttct tctccaggac ggtatccact gtgtcggtgg agttgtttgc  1080
gtgatagccg atgcagatag tgtcagcgta ggttgcggta aaagtacaca gcaggaccag  1140
cagtttggcc ttcat                                                  1155

SEQ ID NO: 315           moltype = DNA  length = 5579
FEATURE                  Location/Qualifiers
misc_feature             1..5579
                         note = Synthetic
source                   1..5579
                         mol_type = other DNA
                         organism = synthetic construct
SEQUENCE: 315
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcagattgg  240
ctattggcca ttgcatacgt tgtatccata tcataatatg tacatttata ttggctcatg  300
tccaacatta ccgccatgtt gacattgatt attgactagt tattaatagt aatcaattac  360
ggggtcatta gttcatagcc catatatgga gttccgcgtt acataactta cggtaaatgg  420
cccgcctggc tgaccgccca acgacccccg cccattgacg tcaataatga cgtatgttcc  480
catagtaacg ccaataggga ctttccattg acgtcaatgg gtggagtatt tacggtaaac  540
tgcccacttg gcagtacatc aagtgtatca tatgccaagt acgcccccta ttgacgtcaa  600
tgacggtaaa tggcccgcct ggcattatgc ccagtacatg accttatggg actttcctac  660
ttggcagtac atctacgtat tagtcatcgc tattaccatg gtgatgcggt tttggcagta  720
catcaatggg cgtggatagc ggtttgactc acggggattt ccaagtctcc accccattga  780
cgtcaatggg agtttgtttt ggcaccaaaa tcaacgggac tttccaaaat gtcgtaacaa  840
ctccgcccca ttgacgcaaa tgggcggtag gcgtgtacgg tgggaggtct atataagcag  900
agctcgttta gtgaaccgtc agatcgcctg gagacgccat ccacgctgtt ttgacctcca  960
tagaagacac cgggaccgat ccagcctcca tcggctcgca tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctcaggtc gagaccgggc  1140
ctttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgcggc cgctctagag  1380
atatcgccac catgaaggcc aaactgctgg tcctgctgtg tacttttacc gcaacctacg  1440
ctgacactat ctgcatcggc tatcacgcaa acaactccac cgacacagtg gataccgtcc  1500
tggagaagaa cgtgactgtc acccactcag tgaatctggg cagcggactg aggatggtca  1560
ccggactgcg caacatccca cagcgggaaa caagaggact gttcggcgct atcgcagggt  1620
ttattgaggg cgggtggaca ggaatggtgg acgggtggta cggctaccac catcagaatg  1680
agcagggcag cggctacgcc gctgatcaga agtctacaca gaacgcaatc aatggcatta  1740
ctaacctggt gaattctgtc atcgaaaaaa tgggcagcgg aggctccgga acagacctgg  1800
ctgagctgct ggtgctgctg atcaacgagc ggactctgga tttccacgat agcaacgtga  1860
agaatctgta tgagaaggtc aaatcccagc tgaagaacaa tgccaaagaa atcgggaatg  1920
gatgcttcga gttttaccat aagtgcaaca atgaatgtat ggagtctgtg aagaacggca  1980
cttacgacta tcccaaatat tctgaagaga gtaagctgaa tcgagagaaa attgacagtg  2040
ggggcgacat catcaagctg ctgaacgaac aggtgaacaa ggagatgcag agctccaacc  2100
tgtacatgag tatgtctagt tggtgttata cacactcact ggacggcgct gggctgttcc  2160
tgtttgatca cgcagccgag gaatacgaac atgcaaagaa actgatcatt ttcctgaatg  2220
agaacaatgt gcccgtccag ctgacttcaa tcagcgcccc tgaacataag ttcgagggcc  2280
tgacccagat ctttcagaaa gcttacgaac acgagcagca tatttccgaa tctatcaaca  2340
atattgtgga ccacgccatt aagagcaaag atcatgctac cttcaacttt ctgcagtggt  2400
acgtggccga gcagcacgag gaggaggtcc tgtttaagga catcctggat aaaatcgaac  2460
tgattggaaa cgagaatcat ggcctgtacc tggcagatca gtatgtgaag ggcattgcca  2520
agtccagaaa aagtgggtca tgatgaacac gtgggatcca gatctgctgt gccttctagt  2580
tgccagccat ctgttgtttg cccctccccc gtgccttcct tgaccctgga aggtgccact  2640
cccactgtcc tttcctaata aaatgaggaa attgcatcgc attgtctgag taggtgtcat  2700
```

-continued

```
tctattctgg ggggtggggt ggggcaggac agcaaggggg aggattggga agacaatagc  2760
aggcatgctg gggatgcggt gggctctatg ggtacccagg tgctgaagaa ttgacccggt  2820
tcctcctggg ccagaaagaa gcaggcacat ccccttctct gtgacacacc ctgtccacgc  2880
ccctggttct tagttccagc cccactcata ggacactcat agctcaggag ggctccgcct  2940
tcaatcccac ccgctaaagt acttggagcg gtctctccct ccctcatcag cccaccaaac  3000
caaacctagc ctccaagagt gggaagaaat taaagcaaga taggctatta agtgcagagg  3060
gagagaaaat gcctccaaca tgtgaggaag taatgagaga aatcatagaa ttttaaggcc  3120
atgatttaag gccatcatgg ccttaatctt ccgcttcctc gctcactgac tcgctgcgct  3180
cggtcgttcg gctgcggcga gcggtatcag ctcactcaaa ggcggtaata cggttatcca  3240
cagaatcagg ggataacgca ggaaagaaca tgtgagcaaa aggccagcaa aaggccagga  3300
accgtaaaaa ggccgcgttg ctggcgtttt tccataggct ccgcccccct gacgagcatc  3360
acaaaaatcg acgctcaagt cagaggtggc gaaacccgac aggactataa agataccagg  3420
cgtttccccc tggaagctcc ctcgtgcgct ctcctgttcc gaccctgccg cttaccggat  3480
acctgtccgc ctttctccct tcgggaagcg tggcgctttc tcatagctca cgctgtaggt  3540
atctcagttc ggtgtaggtc gttcgctcca agctgggctg tgtgcacgaa ccccccgttc  3600
agcccgaccg ctgcgcctta tccggtaact atcgtcttga gtccaacccg gtaagacacg  3660
acttatcgcc actggcagca gccactggta acaggattag cagagcgagg tatgtaggcg  3720
gtgctacaga gttcttgaag tggtggccta actacggcta cactagaaga acagtatttg  3780
gtatctgcgc tctgctgaag ccagttacct tcggaaaaag agttggtagc tcttgatccg  3840
gcaaacaaac caccgctggt agcggtggtt tttttgtttg caagcagcag attacgcgca  3900
gaaaaaaagg atctcaagaa gatcctttga tcttttctac ggggtctgac gctcagtgga  3960
acgaaaactc acgttaaggg attttggtca tgagattatc aaaaaggatc ttcacctaga  4020
tccttttaaa ttaaaaatga agttttaaat caatctaaag tatatatgag taaacttggt  4080
ctgacagtta ccaatgctta atcagtgagg cacctatctc agcgatctgt ctatttcgtt  4140
catccatagt tgcctgactc gggggggggg ggcgctgagg tctgcctcgt gaagaaggtg  4200
ttgctgactc ataccaggcc tgaatcgccc catcatccag ccagaaagtg agggagccac  4260
ggttgatgag agctttgttg taggtggacc agttggtgat tttgaacttt tgctttgcca  4320
cggaacggtc tgcgttgtcg ggaagatgcg tgatctgatc cttcaactca gcaaaagttc  4380
gatttattca acaaagccgc cgtcccgtca agtcagcgta atgctctgcc agtgttacaa  4440
ccaattaacc aattctgatt agaaaaactc atcgagcatc aaatgaaact gcaatttatt  4500
catatcagga ttatcaatac catatttttg aaaaagccgt ttctgtaatg aaggagaaaa  4560
ctcaccgagg cagttccata ggatggcaag atcctggtat cggtctgcga ttccgactcg  4620
tccaacatca atacaaccta ttaatttccc ctcgtcaaaa ataaggttat caagtgagaa  4680
atcaccatga gtgacgactg aatccggtga gaatggcaaa agcttatgca tttctttcca  4740
gacttgttca acaggccagc cattacgctc gtcatcaaaa tcactcgcat caaccaaacc  4800
gttattcatt cgtgattgcg cctgagcgag acgaaatacg cgatcgctgt taaaaggaca  4860
attacaaaca ggaatcgaat gcaaccggcg caggaacact gccagcgcat caacaatatt  4920
ttcacctgaa tcaggatatt cttctaatac ctggaatgct gttttcccgg ggatcgcagt  4980
ggtgagtaac catgcatcat caggagtacg gataaaatgc ttgatggtcg gaagaggcat  5040
aaattccgtc agccagttta gtctgaccat ctcatctgta acatcattgg caacgctacc  5100
tttgccatgt ttcagaaaca actctggcgc atcgggcttc ccatacaatc gatagattgt  5160
cgcacctgat tgcccgacat tatcgcgagc ccatttatac ccatataaat cagcatccat  5220
gttggaattt aatcgcggcc tcgagcaaga cgtttcccgt tgaatatggc tcataacacc  5280
ccttgtatta ctgtttatgt aagcagacag ttttattgtt catgatgata tatttttatc  5340
ttgtgcaatg taacatcaga gattttgaga cacaacgtgg ctttcccccc ccccccatta  5400
ttgaagcatt tatcagggtt attgtctcat gagcggatac atatttgaat gtatttagaa  5460
aaataaacaa ataggggttc cgcgcacatt tccccgaaaa gtgccacctg acgtctaaga  5520
aaccattatt atcatgacat taacctataa aaataggcgt atcacgaggc cctttcgtc   5579
```

```
SEQ ID NO: 316          moltype = DNA  length = 645
FEATURE                 Location/Qualifiers
misc_feature            1..645
                        note = Synthetic
source                  1..645
                        mol_type = other DNA
                        organism = synthetic construct
CDS                     1..645
SEQUENCE: 316
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cggtggtac ggctaccacc atcagaatga gcagggcagc  300
ggctacgccg ctgatcagaa gtctacacag aacgcaatca atggcattac taacctggtg  360
aattctgtca tcgaaaaaat gggcagcgga ggctccggaa cagacctggc tgagctgctg  420
gtgctgctgc tgaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                 645
```

```
SEQ ID NO: 317          moltype = AA  length = 215
FEATURE                 Location/Qualifiers
REGION                  1..215
                        note = Synthetic Construct
source                  1..215
                        mol_type = protein
                        organism = synthetic construct
SEQUENCE: 317
MKAKLLVLLC TFTATYADTI CIGYHANNST DTVDTVLEKN VTVTHSVNLG SGLRMVTGLR  60
```

```
NIPQRETRGL FGAIAGFIEG GWTGMVDGWY GYHHQNEQGS GYAADQKSTQ NAINGITNLV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLN REKID                             215

SEQ ID NO: 318         moltype = DNA  length = 645
FEATURE                Location/Qualifiers
misc_feature           1..645
                       note = Synthetic
source                 1..645
                       mol_type = other DNA
                       organism = synthetic construct
SEQUENCE: 318
gtcaatttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaaatcca gagtccgctc gttcagcagc agcaccagca gctcagccag  240
gtctgttccg gagcctccgc tgcccatttt ttcgatgaca gaattcacca ggttagtaat  300
gccattgatt gcgttctgtg tagacttctg atcagcggcg tagccgctgc cctgctcatt  360
ctgatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat                  645

SEQ ID NO: 319         moltype = DNA  length = 1155
FEATURE                Location/Qualifiers
misc_feature           1..1155
                       note = Synthetic
source                 1..1155
                       mol_type = other DNA
                       organism = synthetic construct
CDS                    1..1155
SEQUENCE: 319
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cggtggtac ggctaccacc atcagaatga gcagggcagc  300
ggctacgccg ctgatcagaa gtctacacag aacgcaatca atggcattac taacctggtg  360
aattctgtca tcgaaaaaat gggcagcgga ggctccggaa cagacctggc tgagctgctg  420
gtgctgctgc tgaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgacagtgg gggcgacatc  660
atcaagctgc tgaacgaaca ggtgaacaag gagatgcaga gctccaacct gtacatgagt  720
atgtctagtt ggtgttatac acactcactg gacggcgctg ggctgttcct gtttgatcac  780
gcagccgagg aatacgaaca tgcaaagaaa ctgatcattt tcctgaatga gaacaatgtg  840
cccgtccagc tgacttcaat cagcgcccct gaacataagt tcgagggcct gacccagatc  900
tttcagaaag cttacgaaca cgagcagcat atttccgaat ctatcaacaa tattgtggac  960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtcat gatga                                                   1155

SEQ ID NO: 320         moltype = AA  length = 383
FEATURE                Location/Qualifiers
REGION                 1..383
                       note = Synthetic Construct
source                 1..383
                       mol_type = protein
                       organism = synthetic construct
SEQUENCE: 320
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNLV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                          383

SEQ ID NO: 321         moltype = DNA  length = 1155
FEATURE                Location/Qualifiers
misc_feature           1..1155
                       note = Synthetic
source                 1..1155
                       mol_type = other DNA
                       organism = synthetic construct
SEQUENCE: 321
tcatcatgac ccactttttc tggacttggc aatgcccttc acatactgat ctgccaggta  60
```

```
caggccatga ttctcgtttc caatcagttc gattttatcc aggatgtcct taaacaggac  120
ctcctcctcg tgctgctcgg ccacgtacca ctgcagaaag ttgaaggtag catgatcttt  180
gctcttaatg gcgtggtcca caatattgtt gatagattcg gaaatatgct gctcgtgttc  240
gtaagctttc tgaaagatct gggtcaggcc ctcgaactta tgttcagggg cgctgattga  300
agtcagctgg acgggcacat tgttctcatt caggaaaatg atcagtttct ttgcatgttc  360
gtattcctcg gctgcgtgat caaacaggaa cagcccagcg ccgtccagtg agtgtgtata  420
acaccaacta gacatactca tgtacaggtt ggagctctgc atctccttgt tcacctgttc  480
gttcagcagc ttgatgatgt cgcccccact gtcaattttc tctcgattca gcttactctc  540
ttcagaatat ttgggatagt cgtaagtgcc gttcttcaca gactccatac attcattgtt  600
gcacttatgg taaaactcga agcatccatt cccgatttct ttggcattgt tcttcagctg  660
ggatttgacc ttctcataca gattcttcac gttgctatcg tggaaatcca gagtccgctc  720
gttcagcagc agcaccagca gctcagccag gtctgttccg gagcctccgc tgcccatttt  780
ttcgatgaca gaattcacca ggttagtaat gccattgatt gcgttctgtg tagacttctg  840
atcagcggcg tagccgctgc cctgctcatt ctgatggtgg tagccgtacc acccgtccac  900
cattcctgtc cacccgccct caataaaccc tgcgatagcg ccgaacagtc ctcttgtttc  960
ccgctgtggg atgttgcgca gtccggtgac catcctcagt ccgctgccca gattcactga  1020
gtgggtgaca gtcacgttct tctccaggac ggtatccact gtgtcggtgg agttgtttgc  1080
gtgatagccg atgcagatag tgtcagcgta ggttgcggta aaagtacaca gcaggaccag  1140
cagtttggcc ttcat                                                    1155
```

```
SEQ ID NO: 322         moltype = DNA  length = 5579
FEATURE                Location/Qualifiers
misc_feature           1..5579
                       note = Synthetic
source                 1..5579
                       mol_type = other DNA
                       organism = synthetic construct
SEQUENCE: 322
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcagattgg  240
ctattggcca ttgcatacgt tgtatccata tcataatatg tacatttata ttggctcatg  300
tccaacatta ccgccatgtt gacattgatt attgactagt tattaatagt aatcaattac  360
ggggtcatta gttcatagcc catatatgga gttccgcgtt acataactta cggtaaatgg  420
cccgcctggc tgaccgccca acgacccccg cccattgacg tcaataatga cgtatgttcc  480
catagtaacg ccaataggga ctttccattg acgtcaatgg gtggagtatt tacggtaaac  540
tgcccacttg gcagtacatc aagtgtatca tatgccaagt acgcccccta ttgacgtcaa  600
tgacggtaaa tggcccgcct ggcattatgc ccagtacatg accttatggg actttcctac  660
ttggcagtac atctacgtat tagtcatcgc tattaccatg gtgatgcggt tttggcagta  720
catcaatggg cgtggatagc ggtttgactc acggggattt ccaagtctcc accccattga  780
cgtcaatggg agtttgtttt ggcaccaaaa tcaacgggac tttccaaaat gtcgtaacaa  840
ctccgcccca ttgacgcaaa tgggcggtag gcgtgtacgg tgggaggtct atataagcag  900
agctcgttta gtgaaccgtc agatcgcctg gagacgccat ccacgctgtt ttgacctcca  960
tagaagacac cgggaccgat ccagcctcca tcggctcgca tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctcaggtc gagaccgggc  1140
ctttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgcggc cgctctagag  1380
atatcgccac catgaaggcc aaactgctgg tcctgctgtg tacttttacc gcaacctacg  1440
ctgacactat ctgcatcggc tatcacgcaa acaactccac cgacacagtg gataccgtcc  1500
tggagaagaa cgtgactgtc acccactcag tgaatctggg cagcggactg aggatggtca  1560
ccggactgcg caacatccca cagcgggaaa caagaggact gttcggcgct atcgcagggt  1620
ttattgaggg cgggtggaca ggaatggtgg acgggtggta cggctaccac catcagaatg  1680
agcagggcag cggctacgcc gctgatcaga agtctacaca gaacgcaatc aatggcatta  1740
ctaacctggt gaattctgtc atcgaaaaaa tgggcagcgg aggctccgga acagacctgg  1800
ctgagctgct ggtgctgctg ctgaacgagc ggactctgga tttccacgat agcaacgtga  1860
agaatctgta tgagaaggtc aaatcccagc tgaagaacaa tgccaaagaa atcgggaatg  1920
gatgcttcga gttttaccat aagtgcaaca atgaatgtat ggagtctgtg aagaacggca  1980
cttacgacta tcccaaatat tctgaagaga gtaagctgaa tcgagagaaa attgacagtg  2040
ggggcgacat catcaagctg ctgaacgaac aggtgaacaa ggagatgcag agctccaacc  2100
tgtacatgag tatgtctagt tggtgttata cacactcact ggacggcgct gggctgttcc  2160
tgtttgatca cgcagccgag gaatacgaac atgcaaagaa actgatcatt ttcctgaatg  2220
agaacaatgt gcccgtccag ctgacttcaa tcagcgcccc tgaacataag ttcgagggcc  2280
tgacccagat ctttcagaaa gcttacgaac acgagcagca tatttccgaa tctatcaaca  2340
atattgtgga ccacgccatt aagagcaaag atcatgctac cttcaacttt ctgcagtggt  2400
acgtggccga gcagcacgag gaggaggtcc tgtttaagga catcctggat aaaatcgaac  2460
tgattggaaa cgagaatcat ggcctgtacc tggcagatca gtatgtgaag ggcattgcca  2520
agtccagaaa aagtgggtca tgatgaacac gtgggatcca gatctgctgt gccttctagt  2580
tgccagccat ctgttgtttg cccctccccc gtgccttcct tgaccctgga aggtgccact  2640
cccactgtcc tttcctaata aaatgaggaa attgcatcgc attgtctgag taggtgtcat  2700
tctattctgg ggggtggggt ggggcaggac agcaaggggg aggattggga agacaatagc  2760
aggcatgctg gggatgcggt gggctctatg ggtacccagg tgctgaagaa ttgacccggt  2820
tcctcctggg ccagaaagaa gcaggcacat ccccttctct gtgacacacc ctgtccacgc  2880
ccctggttct tagttccagc cccactcata ggacactcat agctcaggag ggctccgcct  2940
tcaatcccac ccgctaaagt acttggagcg gtctctccct ccctcatcag cccaccaaac  3000
caaacctagc ctccaagagt gggaagaaat taaagcaaga taggctatta agtgcagagg  3060
```

```
gagagaaaat gcctccaaca tgtgaggaag taatgagaga aatcatagaa ttttaaggcc  3120
atgatttaag gccatcatgg ccttaatctt ccgcttcctc gctcactgac tcgctgcgct  3180
cggtcgttcg gctgcggcga gcggtatcag ctcactcaaa ggcggtaata cggttatcca  3240
cagaatcagg ggataacgca ggaaagaaca tgtgagcaaa aggccagcaa aaggccagga  3300
accgtaaaaa ggccgcgttg ctggcgtttt tccataggct ccgcccccct gacgagcatc  3360
acaaaaatcg acgctcaagt cagaggtggc gaaacccgac aggactataa agataccagg  3420
cgtttccccc tggaagctcc ctcgtgcgct ctcctgttcc gaccctgccg cttaccggat  3480
acctgtccgc ctttctccct tcgggaagcg tggcgctttc tcatagctca cgctgtaggt  3540
atctcagttc ggtgtaggtc gttcgctcca agctgggctg tgtgcacgaa ccccccgttc  3600
agcccgaccg ctgcgcctta tccggtaact atcgtcttga gtccaacccg gtaagacacg  3660
acttatcgcc actggcagca gccactggta acaggattag cagagcgagg tatgtaggcg  3720
gtgctacaga gttcttgaag tggtggccta actacggcta cactagaaga acagtatttg  3780
gtatctgcgc tctgctgaag ccagttacct tcggaaaaag agttggtagc tcttgatccg  3840
gcaaacaaac caccgctggt agcggtggtt tttttgtttg caagcagcag attacgcgca  3900
gaaaaaaagg atctcaagaa gatcctttga tcttttctac ggggtctgac gctcagtgga  3960
acgaaaactc acgttaaggg attttggtca tgagattatc aaaaaggatc ttcacctaga  4020
tccttttaaa ttaaaaatga agttttaaat caatctaaag tatatatgag taaacttggt  4080
ctgacagtta ccaatgctta atcagtgagg cacctatctc agcgatctgt ctatttcgtt  4140
catccatagt tgcctgactc gggggggggg ggcgctgagg tctgcctcgt gaagaaggtg  4200
ttgctgactc ataccaggcc tgaatcgccc catcatccag ccagaaagtg agggagccac  4260
ggttgatgag agctttgttg taggtggacc agttggtgat tttgaacttt tgctttgcca  4320
cggaacggtc tgcgttgtcg ggaagatgcg tgatctgatc cttcaactca gcaaaagttc  4380
gatttattca acaaagccgc cgtcccgtca agtcagcgta atgctctgcc agtgttacaa  4440
ccaattaacc aattctgatt agaaaaactc atcgagcatc aaatgaaact gcaatttatt  4500
catatcagga ttatcaatac catatttttg aaaaagccgt ttctgtaatg aaggagaaaa  4560
ctcaccgagg cagttccata ggatggcaag atcctggtat cggtctgcga ttccgactcg  4620
tccaacatca atacaaccta ttaatttccc ctcgtcaaaa ataaggttat caagtgagaa  4680
atcaccatga gtgacgactg aatccggtga gaatggcaaa agcttatgca tttctttcca  4740
gacttgttca acaggccagc cattacgctc gtcatcaaaa tcactcgcat caaccaaacc  4800
gttattcatt cgtgattgcg cctgagcgag acgaaatacg cgatcgctgt taaaaggaca  4860
attacaaaca ggaatcgaat gcaaccggcg caggaacact gccagcgcat caacaatatt  4920
ttcacctgaa tcaggatatt cttctaatac ctggaatgct gttttcccgg ggatcgcagt  4980
ggtgagtaac catgcatcat caggagtacg gataaaatgc ttgatggtcg gaagaggcat  5040
aaattccgtc agccagttta gtctgaccat ctcatctgta acatcattgg caacgctacc  5100
tttgccatgt ttcagaaaca actctggcgc atcgggcttc ccatacaatc gatagattgt  5160
cgcacctgat tgcccgacat tatcgcgagc ccatttatac ccatataaat cagcatccat  5220
gttggaattt aatcgcggcc tcgagcaaga cgtttcccgt tgaatatggc tcataacacc  5280
ccttgtatta ctgtttatgt aagcagacag ttttattgtt catgatgata tatttttatc  5340
ttgtgcaatg taacatcaga gattttgaga cacaacgtgg ctttcccccc ccccccatta  5400
ttgaagcatt tatcagggtt attgtctcat gagcggatac atatttgaat gtatttagaa  5460
aaataaacaa ataggggttc cgcgcacatt tccccgaaaa gtgccacctg acgtctaaga  5520
aaccattatt atcatgacat taacctataa aaataggcgt atcacgaggc cctttcgtc   5579
```

```
SEQ ID NO: 323          moltype = DNA  length = 645
FEATURE                 Location/Qualifiers
misc_feature            1..645
                        note = Synthetic
source                  1..645
                        mol_type = other DNA
                        organism = synthetic construct
CDS                     1..645
SEQUENCE: 323
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cggtggtac ggctaccacc atcagaatga gcagggcagc  300
ggctacgccg ctgatcagaa gtctacacag aacgcaatca atggcattac taacatggtg  360
aattctgtca tcgaaaaaat gggcagcgga ggctccggaa cagacctggc tgagctgctg  420
gtgctgctga tgaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                 645
```

```
SEQ ID NO: 324          moltype = AA  length = 215
FEATURE                 Location/Qualifiers
REGION                  1..215
                        note = Synthetic Construct
source                  1..215
                        mol_type = protein
                        organism = synthetic construct
SEQUENCE: 324
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGSG GSGTDLAELL VLLMNERTLD FHDSNVKNLY EKVKSQLKNN AKEIGNGCFE  180
FYHKCNNECM ESVKNGTYDY PKYSEESKLN REKID                            215
```

```
SEQ ID NO: 325          moltype = DNA  length = 645
FEATURE                 Location/Qualifiers
```

-continued

```
misc_feature            1..645
                        note = Synthetic
source                  1..645
                        mol_type = other DNA
                        organism = synthetic construct
SEQUENCE: 325
gtcaattttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaaatcca gagtccgctc gttcatcagc agcaccagca gctcagccag  240
gtctgttccg gagcctccgc tgcccatttt ttcgatgaca gaattcacca tgttagtaat  300
gccattgatt gcgttctgtg tagacttctg atcagcggcg tagccgctgc cctgctcatt  360
ctgatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat                  645

SEQ ID NO: 326          moltype = DNA  length = 1155
FEATURE                 Location/Qualifiers
misc_feature            1..1155
                        note = Synthetic
source                  1..1155
                        mol_type = other DNA
                        organism = synthetic construct
CDS                     1..1155
SEQUENCE: 326
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcagcgga ggctccggaa cagacctggc tgagctgctg  420
gtgctgctga tgaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgacagtgg gggcgacatc  660
atcaagctgc tgaacgaaca ggtgaacaag gagatgcaga gctccaacct gtacatgagt  720
atgtctagtt ggtgttatac acactcactg gacggcgctg ggctgttcct gtttgatcac  780
gcagccgagg aatacgaaca tgcaaagaaa ctgatcattt tcctgaatga gaacaatgtg  840
cccgtccagc tgacttcaat cagcgcccct gaacataagt tcgagggcct gacccagatc  900
tttcagaaag cttacgaaca cgagcagcat atttccgaat ctatcaacaa tattgtggac  960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtcat gatga                                                   1155

SEQ ID NO: 327          moltype = AA  length = 383
FEATURE                 Location/Qualifiers
REGION                  1..383
                        note = Synthetic Construct
source                  1..383
                        mol_type = protein
                        organism = synthetic construct
SEQUENCE: 327
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGSG GSGTDLAELL VLLMNERTLD FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                          383

SEQ ID NO: 328          moltype = DNA  length = 1155
FEATURE                 Location/Qualifiers
misc_feature            1..1155
                        note = Synthetic
source                  1..1155
                        mol_type = other DNA
                        organism = synthetic construct
SEQUENCE: 328
tcatcatgac ccactttttc tggacttggc aatgcccttc acatactgat ctgccaggta  60
caggccatga ttctcgtttc caatcagttc gattttatcc aggatgtcct taaacaggac  120
ctcctcctcg tgctgctcgg ccacgtacca ctgcagaaag ttgaaggtag catgatcttt  180
gctcttaatg gcgtggtcca caatattgtt gatagattcg gaaatatgct gctcgtgttc  240
gtaagctttc tgaaagatct gggtcaggcc ctcgaactta tgttcagggg cgctgattga  300
agtcagctgg acgggcacat tgttctcatt caggaaaatg atcagtttct ttgcatgttc  360
gtattcctcg gctgcgtgat caaacaggaa cagcccagcg ccgtccagtg agtgtgtata  420
```

```
acaccaacta gacatactca tgtacaggtt ggagctctgc atctccttgt tcacctgttc  480
gttcagcagc ttgatgatgt cgccccccact gtcaattttc tctcgattca gcttactctc  540
ttcagaatat ttgggatagt cgtaagtgcc gttcttcaca gactccatac attcattgtt  600
gcacttatgg taaaactcga agcatccatt cccgatttct ttggcattgt tcttcagctg  660
ggatttgacc ttctcataca gattcttcac gttgctatcg tggaaatcca gagtccgctc  720
gttcatcagc agcaccagca gctcagccag gtctgttccg gagcctccgc tgcccatttt  780
ttcgatgaca gaattcacca tgttagtaat gccattgatt gcgttctgtg tagacttctg  840
atcagcggcg tagccgctgc cctgctcatt ctgatggtgg tagccgtacc acccgtccac  900
cattcctgtc cacccgccct caataaaccc tgcgatagcg ccgaacagtc ctcttgtttc  960
ccgctgtggg atgttgcgca gtccggtgac catcctcagt ccgctgccca gattcactga  1020
gtgggtgaca gtcacgttct tctccaggac ggtatccact gtgtcggtgg agttgtttgc  1080
gtgatagccg atgcagatag tgtcagcgta ggttgcggta aaagtacaca gcaggaccag  1140
cagtttggcc ttcat                                                    1155

SEQ ID NO: 329         moltype = DNA  length = 5579
FEATURE                Location/Qualifiers
misc_feature           1..5579
                       note = Synthetic
source                 1..5579
                       mol_type = other DNA
                       organism = synthetic construct
SEQUENCE: 329
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcagattgg  240
ctattggcca ttgcatacgt tgtatccata tcataatatg tacatttata ttggctcatg  300
tccaacatta ccgccatgtt gacattgatt attgactagt tattaatagt aatcaattac  360
ggggtcatta gttcatagcc catatatgga gttccgcgtt acataactta cggtaaatgg  420
cccgcctggc tgaccgccca acgacccccg cccattgacg tcaataatga cgtatgttcc  480
catagtaacg ccaataggga ctttccattg acgtcaatgg gtggagtatt tacggtaaac  540
tgcccacttg gcagtacatc aagtgtatca tatgccaagt acgcccccta ttgacgtcaa  600
tgacggtaaa tggcccgcct ggcattatgc ccagtacatg accttatggg actttcctac  660
ttggcagtac atctacgtat tagtcatcgc tattaccatg gtgatgcggt tttggcagta  720
catcaatggg cgtggatagc ggtttgactc acggggattt ccaagtctcc accccattga  780
cgtcaatggg agtttgtttt ggcaccaaaa tcaacgggac tttccaaaat gtcgtaacaa  840
ctccgcccca ttgacgcaaa tgggcggtag gcgtgtacgg tgggaggtct atataagcag  900
agctcgttta gtgaaccgtc agatcgcctg gagacgccat ccacgctgtt ttgacctcca  960
tagaagacac cgggaccgat ccagcctcca tcggctcgca tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctcaggtc gagaccgggc  1140
ctttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgcggc cgctctagag  1380
atatcgccac catgaaggcc aaactgctgg tcctgctgtg tactttttacc gcaacctacg  1440
ctgacactat ctgcatcggc tatcacgcaa acaactccac cgacacagtg gataccgtcc  1500
tggagaagaa cgtgactgtc acccactcag tgaatctggg cagcggactg aggatggtca  1560
ccggactgcg caacatccca cagcgggaaa caagaggact gttcggcgct atcgcagggt  1620
ttattgaggg cgggtggaca ggaatggtgg acgggtggta cggctaccac catcagaatg  1680
agcagggcag cggctacgcc gctgatcaga agtctacaca gaacgcaatc aatggcatta  1740
ctaacatggt gaattctgtc atcgaaaaaa tgggcagcgg aggctccgga acagacctgg  1800
ctgagctgct ggtgctgctg atgaacgagc ggactctgga tttccacgat agcaacgtga  1860
agaatctgta tgagaaggtc aaatcccagc tgaagaacaa tgccaaagaa atcgggaatg  1920
gatgcttcga gttttaccat aagtgcaaca atgaatgtat ggagtctgtg aagaacggca  1980
cttacgacta tcccaaatat tctgaagaga gtaagctgaa tcgagagaaa attgacagtg  2040
gggggcgacat catcaagctg ctgaacgaac aggtgaacaa ggagatgcag agctccaacc  2100
tgtacatgag tatgtctagt tggtgttata cacactcact ggacggcgct gggctgttcc  2160
tgtttgatca cgcagccgag gaatacagac atgcaaagaa actgatcatt ttcctgaatg  2220
agaacaatgt gcccgtccag ctgacttcaa tcagcgcccc tgaacataag ttcgagggcc  2280
tgacccagat ctttcagaaa gcttacgaac acgagcagca tatttccgaa tctatcaaca  2340
atattgtgga ccacgccatt aagagcaaag atcatgctac cttcaacttt ctgcagtggt  2400
acgtggccga gcagcacgag gaggaggtcc tgtttaagga catcctggat aaaatcgaac  2460
tgattggaaa cgagaatcat ggcctgtacc tggcagatca gtatgtgaag ggcattgcca  2520
agtccagaaa aagtgggtca tgatgaacac gtgggatcca gatctgctgt gccttctagt  2580
tgccagccat ctgttgtttg cccctccccc gtgccttcct tgaccctgga aggtgccact  2640
cccactgtcc tttcctaata aaatgaggaa attgcatcgc attgtctgag taggtgtcat  2700
tctattctgg ggggtggggt ggggcaggac agcaaggggg aggattggga agacaatagc  2760
aggcatgctg gggatgcggt gggctctatg ggtacccagg tgctgaagaa ttgacccggt  2820
tcctcctggg ccagaaagaa gcaggcacat ccccttctct gtgacacacc ctgtccacgc  2880
ccctggttct tagttccagc cccactcata ggacactcat agctcaggag ggctccgcct  2940
tcaatcccac ccgctaaagt acttggagcg gtctctccct ccctcatcag cccaccaaac  3000
caaacctagc ctccaagagt gggaagaaat taaagcaaga taggctatta agtgcagagg  3060
gagagaaaat gcctccaaca tgtgaggaag taatgagaga aatcatagaa ttttaaggcc  3120
atgatttaag gccatcatgg ccttaatctt ccgcttcctc gctcactgac tcgctgcgct  3180
cggtcgttcg gctgcggcga gcggtatcag ctcactcaaa ggcggtaata cggttatcca  3240
cagaatcagg ggataacgca ggaaagaaca tgtgagcaaa aggccagcaa aaggccagga  3300
accgtaaaaa ggccgcgttg ctggcgtttt tccataggct ccgcccccct gacgagcatc  3360
acaaaaatcg acgctcaagt cagaggtggc gaaacccgac aggactataa agataccagg  3420
```

```
cgtttccccc tggaagctcc ctcgtgcgct ctcctgttcc gaccctgccg cttaccggat  3480
acctgtccgc ctttctccct tcgggaagcg tggcgctttc tcatagctca cgctgtaggt  3540
atctcagttc ggtgtaggtc gttcgctcca agctgggctg tgtgcacgaa ccccccgttc  3600
agcccgaccg ctgcgcctta tccggtaact atcgtcttga gtccaacccg gtaagacacg  3660
acttatcgcc actggcagca gccactggta acaggattag cagagcgagg tatgtaggcg  3720
gtgctacaga gttcttgaag tggtggccta actacggcta cactagaaga acagtatttg  3780
gtatctgcgc tctgctgaag ccagttacct tcggaaaaag agttggtagc tcttgatccg  3840
gcaaacaaac caccgctggt agcggtggtt tttttgtttg caagcagcag attacgcgca  3900
gaaaaaaagg atctcaagaa gatcctttga tcttttctac ggggtctgac gctcagtgga  3960
acgaaaactc acgttaaggg attttggtca tgagattatc aaaaaggatc ttcacctaga  4020
tccttttaaa ttaaaaatga agttttaaat caatctaaag tatatatgag taaacttggt  4080
ctgacagtta ccaatgctta atcagtgagg cacctatctc agcgatctgt ctatttcgtt  4140
catccatagt tgcctgactc gggggggggg ggcgctgagg tctgcctcgt gaagaaggtg  4200
ttgctgactc ataccaggcc tgaatcgccc catcatccag ccagaaagtg agggagccac  4260
ggttgatgag agctttgttg taggtggacc agttggtgat tttgaacttt tgctttgcca  4320
cggaacggtc tgcgttgtcg ggaagatgcg tgatctgatc cttcaactca gcaaaagttc  4380
gatttattca acaaagccgc cgtcccgtca agtcagcgta atgctctgcc agtgttacaa  4440
ccaattaacc aattctgatt agaaaaactc atcgagcatc aaatgaaact gcaatttatt  4500
catatcagga ttatcaatac catatttttg aaaaagccgt ttctgtaatg aaggagaaaa  4560
ctcaccgagg cagttccata ggatggcaag atcctggtat cggtctgcga ttccgactcg  4620
tccaacatca atacaaccta ttaatttccc ctcgtcaaaa ataaggttat caagtgagaa  4680
atcaccatga gtgacgactg aatccggtga gaatggcaaa agcttatgca tttctttcca  4740
gacttgttca acaggccagc cattacgctc gtcatcaaaa tcactcgcat caaccaaacc  4800
gttattcatt cgtgattgcg cctgagcgag acgaaatacg cgatcgctgt taaaaggaca  4860
attacaaaca ggaatcgaat gcaaccggcg caggaacact gccagcgcat caacaatatt  4920
ttcacctgaa tcaggatatt cttctaatac ctggaatgct gttttcccgg ggatcgcagt  4980
ggtgagtaac catgcatcat caggagtacg gataaaatgc ttgatggtcg gaagaggcat  5040
aaattccgtc agccagttta gtctgaccat ctcatctgta acatcattgg caacgctacc  5100
tttgccatgt ttcagaaaca actctggcgc atcgggcttc ccatacaatc gatagattgt  5160
cgcacctgat tgcccgacat tatcgcgagc ccatttatac ccatataaat cagcatccat  5220
gttggaattt aatcgcggcc tcgagcaaga cgtttcccgt tgaatatggc tcataacacc  5280
ccttgtatta ctgtttatgt aagcagacag ttttattgtt catgatgata tatttttatc  5340
ttgtgcaatg taacatcaga gattttgaga cacaacgtgg ctttcccccc cccccccatta  5400
ttgaagcatt tatcagggtt attgtctcat gagcggatac atatttgaat gtatttagaa  5460
aaataaacaa ataggggttc cgcgcacatt tccccgaaaa gtgccacctg acgtctaaga  5520
aaccattatt atcatgacat taacctataa aaataggcgt atcacgaggc cctttcgtc   5579

SEQ ID NO: 330          moltype = DNA  length = 645
FEATURE                 Location/Qualifiers
misc_feature            1..645
                        note = Synthetic
source                  1..645
                        mol_type = other DNA
                        organism = synthetic construct
CDS                     1..645
SEQUENCE: 330
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taaccaggtg  360
aattctgtca tcgaaaaaat gggcagcgga ggctccggaa cagacctggc tgagctgctg  420
gtgctgctgc agaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                 645

SEQ ID NO: 331          moltype = AA  length = 215
FEATURE                 Location/Qualifiers
REGION                  1..215
                        note = Synthetic Construct
source                  1..215
                        mol_type = protein
                        organism = synthetic construct
SEQUENCE: 331
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNQV  120
NSVIEKMGSG GSGTDLAELL VLLQNERTLD FHDSNVKNLY EKVKSQLKNN AKEIGNGCFE  180
FYHKCNNECM ESVKNGTYDY PKYSEESKLN REKID                            215

SEQ ID NO: 332          moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 332
```

-continued

```
gtcaatttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaaatcca gagtccgctc gttctgcagc agcaccagca gctcagccag  240
gtctgttccg gagcctccgc tgcccatttt ttcgatgaca gaattcacct ggttagtaat  300
gccattgatt gcgttctgtg tagacttctg atcagcggcg tagccgctgc cctgctcatt  360
ctgatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat  645
```

```
SEQ ID NO: 333         moltype = DNA  length = 1155
FEATURE                Location/Qualifiers
misc_feature           1..1155
                       note = Synthetic
source                 1..1155
                       mol_type = other DNA
                       organism = synthetic construct
CDS                    1..1155
SEQUENCE: 333
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taaccaggtg  360
aattctgtca tcgaaaaaat gggcagcgga ggctccggaa cagacctggc tgagctgctg  420
gtgctgctgc agaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgacagtgg gggcgacatc  660
atcaagctgc tgaacgaaca ggtgaacaag gagatgcaga gctccaacct gtacatgagt  720
atgtctagtt ggtgttatac acactcactg gacggcgctg ggctgttcct gtttgatcac  780
gcagccgagg aatacgaaca tgcaaagaaa ctgatcattt tcctgaatga gaacaatgtg  840
cccgtccagc tgacttcaat cagcgcccct gaacataagt tcgagggcct gacccagatc  900
tttcagaaag cttacgaaca cgagcagcat atttccgaat ctatcaacaa tattgtggac  960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtcat gatga  1155
```

```
SEQ ID NO: 334         moltype = AA  length = 383
FEATURE                Location/Qualifiers
REGION                 1..383
                       note = Synthetic Construct
source                 1..383
                       mol_type = protein
                       organism = synthetic construct
SEQUENCE: 334
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNQV  120
NSVIEKMGSG GSGTDLAELL VLLQNERTLD FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS  383
```

```
SEQ ID NO: 335         moltype = DNA  length = 1155
FEATURE                Location/Qualifiers
misc_feature           1..1155
                       note = Synthetic
source                 1..1155
                       mol_type = other DNA
                       organism = synthetic construct
SEQUENCE: 335
tcatcatgac ccactttttc tggacttggc aatgcccttc acatactgat ctgccaggta  60
caggccatga ttctcgtttc caatcagttc gattttatcc aggatgtcct taaacaggac  120
ctcctcctcg tgctgctcgg ccacgtacca ctgcagaaag ttgaaggtag catgatcttt  180
gctcttaatg gcgtggtcca caatattgtt gatagattcg gaaatatgct gctcgtgttc  240
gtaagctttc tgaaagatct gggtcaggcc ctcgaactta tgttcagggg cgctgattga  300
agtcagctgg acgggcacat tgttctcatt caggaaaatg atcagtttct ttgcatgttc  360
gtattcctcg gctgcgtgat caaacaggaa cagcccagcg ccgtccagtg agtgtgtata  420
acaccaacta gacatactca tgtacaggtt ggagctctgc atctccttgt tcacctgttc  480
gttcagcagc ttgatgatgt cgcccccact gtcaattttc tctcgattca gcttactctc  540
ttcagaatat ttgggatagt cgtaagtgcc gttcttcaca gactccatac attcattgtt  600
gcacttatgg taaaactcga agcatccatt cccgatttct ttggcattgt tcttcagctg  660
ggatttgacc ttctcataca gattcttcac gttgctatcg tggaaatcca gagtccgctc  720
gttctgcagc agcaccagca gctcagccag gtctgttccg gagcctccgc tgcccatttt  780
```

```
ttcgatgaca gaattcacct ggttagtaat gccattgatt gcgttctgtg tagacttctg  840
atcagcggcg tagccgctgc cctgctcatt ctgatggtgg tagccgtacc acccgtccac  900
cattcctgtc cacccgccct caataaaccc tgcgatagcg ccgaacagtc ctcttgtttc  960
ccgctgtggg atgttgcgca gtccggtgac catcctcagt ccgctgccca gattcactga  1020
gtgggtgaca gtcacgttct tctccaggac ggtatccact gtgtcggtgg agttgtttgc  1080
gtgatagccg atgcagatag tgtcagcgta ggttgcggta aaagtacaca gcaggaccag  1140
cagtttggcc ttcat                                                  1155

SEQ ID NO: 336          moltype = DNA  length = 5579
FEATURE                 Location/Qualifiers
misc_feature            1..5579
                        note = Synthetic
source                  1..5579
                        mol_type = other DNA
                        organism = synthetic construct
SEQUENCE: 336
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcagattgg  240
ctattggcca ttgcatacgt tgtatccata tcataatatg tacatttata ttggctcatg  300
tccaacatta ccgccatgtt gacattgatt attgactagt tattaatagt aatcaattac  360
ggggtcatta gttcatagcc catatatgga gttccgcgtt acataactta cggtaaatgg  420
cccgcctggc tgaccgccca acgacccccg cccattgacg tcaataatga cgtatgttcc  480
catagtaacg ccaataggga ctttccattg acgtcaatgg gtggagtatt tacggtaaac  540
tgcccacttg gcagtacatc aagtgtatca tatgccaagt acgcccccta ttgacgtcaa  600
tgacggtaaa tggcccgcct ggcattatgc ccagtacatg accttatggg actttcctac  660
ttggcagtac atctacgtat tagtcatcgc tattaccatg gtgatgcggt tttggcagta  720
catcaatggg cgtggatagc ggtttgactc acggggattt ccaagtctcc accccattga  780
cgtcaatggg agtttgtttt ggcaccaaaa tcaacgggac tttccaaaat gtcgtaacaa  840
ctccgcccca ttgacgcaaa tgggcggtag gcgtgtacgg tgggaggtct atataagcag  900
agctcgttta gtgaaccgtc agatcgcctg gagacgccat ccacgctgtt ttgacctcca  960
tagaagacac cgggaccgat ccagcctcca tcggctcgca tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctcaggtc gagaccgggc  1140
ctttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgcggc cgctctagag  1380
atatcgccac catgaaggcc aaactgctgg tcctgctgtg tacttttacc gcaacctacg  1440
ctgacactat ctgcatcggc tatcacgcaa acaactccac cgacacagtg gataccgtcc  1500
tggagaagaa cgtgactgtc acccactcag tgaatctggg cagcggactg aggatggtca  1560
ccggactgcg caacatccca cagcgggaaa caagaggact gttcggcgct atcgcagggt  1620
ttattgaggg cgggtggaca ggaatggtgg acgggtggta cggctaccac catcagaatg  1680
agcagggcag cggctacgcc gctgatcaga agtctacaca gaacgcaatc aatggcatta  1740
ctaaccaggt gaattctgtc atcgaaaaaa tgggcagcgg aggctccgga acagacctgg  1800
ctgagctgct ggtgctgctg cagaacgagc ggactctgga tttccacgat agcaacgtga  1860
agaatctgta tgagaaggtc aaatcccagc tgaagaacaa tgccaaagaa atcgggaatg  1920
gatgcttcga gttttaccat aagtgcaaca atgaatgtat ggagtctgtg aagaacggca  1980
cttacgacta tcccaaatat tctgaagaga gtaagctgaa tcgagagaaa attgacagtg  2040
ggggcgacat catcaagctg ctgaacgaac aggtgaacaa ggagatgcag agctccaacc  2100
tgtacatgag tatgtctagt tggtgttata cacactcact ggacggcgct gggctgttcc  2160
tgtttgatca cgcagccgag gaatacgaac atgcaaagaa actgatcatt ttcctgaatg  2220
agaacaatgt gcccgtccag ctgacttcaa tcagcgcccc tgaacataag ttcgagggcc  2280
tgacccagat ctttcagaaa gcttacgaac acgagcagca tatttccgaa tctatcaaca  2340
atattgtgga ccacgccatt aagagcaaag atcatgctac cttcaacttt ctgcagtggt  2400
acgtggccga gcagcacgag gaggaggtcc tgtttaagga catcctggat aaaatcgaac  2460
tgattggaaa cgagaatcat ggcctgtacc tggcagatca gtatgtgaag ggcattgcca  2520
agtccagaaa aagtgggtca tgatgaacac gtgggatcca gatctgctgt gccttctagt  2580
tgccagccat ctgttgtttg cccctccccc gtgccttcct tgaccctgga aggtgccact  2640
cccactgtcc tttcctaata aaatgaggaa attgcatcgc attgtctgag taggtgtcat  2700
tctattctgg ggggtggggt ggggcaggac agcaaggggg aggattggga agacaatagc  2760
aggcatgctg gggatgcggt gggctctatg ggtacccagg tgctgaagaa ttgacccggt  2820
tcctcctggg ccagaaagaa gcaggcacat ccccttctct gtgacacacc ctgtccacgc  2880
ccctggttct tagttccagc cccactcata ggacactcat agctcaggag ggctccgcct  2940
tcaatcccac ccgctaaagt acttggagcg gtctctccct ccctcatcag cccaccaaac  3000
caaacctagc ctccaagagt gggaagaaat taaagcaaga taggctatta agtgcagagg  3060
gagagaaaat gcctccaaca tgtgaggaag taatgagaga aatcatagaa ttttaaggcc  3120
atgatttaag gccatcatgg ccttaatctt ccgcttcctc gctcactgac tcgctgcgct  3180
cggtcgttcg gctgcggcga gcggtatcag ctcactcaaa ggcggtaata cggttatcca  3240
cagaatcagg ggataacgca ggaaagaaca tgtgagcaaa aggccagcaa aaggccagga  3300
accgtaaaaa ggccgcgttg ctggcgtttt tccataggct ccgcccccct gacgagcatc  3360
acaaaaatcg acgctcaagt cagaggtggc gaaacccgac aggactataa agataccagg  3420
cgtttccccc tggaagctcc ctcgtgcgct ctcctgttcc gaccctgccg cttaccggat  3480
acctgtccgc ctttctccct tcgggaagcg tggcgctttc tcatagctca cgctgtaggt  3540
atctcagttc ggtgtaggtc gttcgctcca agctgggctg tgtgcacgaa ccccccgttc  3600
agcccgaccg ctgcgcctta tccggtaact atcgtcttga gtccaacccg gtaagacacg  3660
acttatcgcc actggcagca gccactggta acaggattag cagagcgagg tatgtaggcg  3720
gtgctacaga gttcttgaag tggtggccta actacggcta cactagaaga acagtatttg  3780
```

-continued

```
gtatctgcgc tctgctgaag ccagttacct tcggaaaaag agttggtagc tcttgatccg  3840
gcaaacaaac caccgctggt agcggtggtt tttttgtttg caagcagcag attacgcgca  3900
gaaaaaaagg atctcaagaa gatcctttga tcttttctac ggggtctgac gctcagtgga  3960
acgaaaactc acgttaaggg attttggtca tgagattatc aaaaaggatc ttcacctaga  4020
tccttttaaa ttaaaaatga agttttaaat caatctaaag tatatatgag taaacttggt  4080
ctgacagtta ccaatgctta atcagtgagg cacctatctc agcgatctgt ctatttcgtt  4140
catccatagt tgcctgactc gggggggggg ggcgctgagg tctgcctcgt gaagaaggtg  4200
ttgctgactc ataccaggcc tgaatcgccc catcatccag ccagaaagtg agggagccac  4260
ggttgatgag agctttgttg taggtggacc agttggtgat tttgaacttt tgctttgcca  4320
cggaacggtc tgcgttgtcg ggaagatgcg tgatctgatc cttcaactca gcaaaagttc  4380
gatttattca acaaagccgc cgtcccgtca agtcagcgta atgctctgcc agtgttacaa  4440
ccaattaacc aattctgatt agaaaaactc atcgagcatc aaatgaaact gcaatttatt  4500
catatcagga ttatcaatac catatttttg aaaaagccgt ttctgtaatg aaggagaaaa  4560
ctcaccgagg cagttccata ggatggcaag atcctggtat cggtctgcga ttccgactcg  4620
tccaacatca atacaaccta ttaatttccc ctcgtcaaaa ataaggttat caagtgagaa  4680
atcaccatga gtgacgactg aatccggtga gaatggcaaa agcttatgca tttctttcca  4740
gacttgttca acaggccagc cattacgctc gtcatcaaaa tcactcgcat caaccaaacc  4800
gttattcatt cgtgattgcg cctgagcgag acgaaatacg cgatcgctgt taaaaggaca  4860
attacaaaca ggaatcgaat gcaaccggcg caggaacact gccagcgcat caacaatatt  4920
ttcacctgaa tcaggatatt cttctaatac ctggaatgct gttttcccgg ggatcgcagt  4980
ggtgagtaac catgcatcat caggagtacg gataaaatgc ttgatggtcg gaagaggcat  5040
aaattccgtc agccagttta gtctgaccat ctcatctgta acatcattgg caacgctacc  5100
tttgccatgt ttcagaaaca actctggcgc atcgggcttc ccatacaatc gatagattgt  5160
cgcacctgat tgcccgacat tatcgcgagc ccatttatac ccatataaat cagcatccat  5220
gttggaattt aatcgcggcc tcgagcaaga cgtttcccgt tgaatatggc tcataacacc  5280
ccttgtatta ctgtttatgt aagcagacag ttttattgtt catgatgata tatttttatc  5340
ttgtgcaatg taacatcaga gattttgaga cacaacgtgg ctttcccccc ccccccatta  5400
ttgaagcatt tatcagggtt attgtctcat gagcggatac atatttgaat gtatttagaa  5460
aaataaacaa ataggggttc cgcgcacatt tccccgaaaa gtgccacctg acgtctaaga  5520
aaccattatt atcatgacat taacctataa aaataggcgt atcacgaggc cctttcgtc   5579

SEQ ID NO: 337          moltype = DNA  length = 645
FEATURE                 Location/Qualifiers
misc_feature            1..645
                        note = Synthetic
source                  1..645
                        mol_type = other DNA
                        organism = synthetic construct
CDS                     1..645
SEQUENCE: 337
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca ccaactcaac taatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcagcgga ggctccggaa cagacctggc tgagctgctg  420
gtgctgctgc tgaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                645

SEQ ID NO: 338          moltype = AA  length = 215
FEATURE                 Location/Qualifiers
REGION                  1..215
                        note = Synthetic Construct
source                  1..215
                        mol_type = protein
                        organism = synthetic construct
SEQUENCE: 338
MKAKLLVLLC TFTATYADTI CIGYHANNST DTVDTVLEKN VTVTNSTNLG SGLRMVTGLR  60
NIPQRETRGL FGAIAGFIEG GWTGMVDGWY GYHHQNEQGS GYAADQKSTQ NAINGITNMV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLN REKID                           215

SEQ ID NO: 339          moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 339
gtcaattttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaaatcca gagtccgctc gttcagcagc agcaccagca gctcagccag  240
gtctgttccg gagcctccgc tgcccatttt ttcgatgaca gaattcacca tgttagtaat  300
gccattgatt gcgttctgtg tagacttctg atcagcggcg tagccgctgc cctgctcatt  360
```

```
ctgatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattagttga gttggtgaca gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat                  645

SEQ ID NO: 340         moltype = DNA  length = 1155
FEATURE                Location/Qualifiers
misc_feature           1..1155
                       note = Synthetic
source                 1..1155
                       mol_type = other DNA
                       organism = synthetic construct
CDS                    1..1155
SEQUENCE: 340
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca ccaactcaac taatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcagcgga ggctccggaa cagacctggc tgagctgctg  420
gtgctgctgc tgaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgacagtgg gggcgacatc  660
atcaagctgc tgaacgaaca ggtgaacaag gagatgcaga gctccaacct gtacatgagt  720
atgtctagtt ggtgttatac acactcactg gacggcgctg ggctgttcct gtttgatcac  780
gcagccgagg aatacgaaca tgcaaagaaa ctgatcattt tcctgaatga gaacaatgtg  840
cccgtccagc tgacttcaat cagcgcccct gaacataagt tcgagggcct gacccagatc  900
tttcagaaag cttacgaaca cgagcagcat atttccgaat ctatcaacaa tattgtggac  960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtcat gatga                                                   1155

SEQ ID NO: 341         moltype = AA  length = 383
FEATURE                Location/Qualifiers
REGION                 1..383
                       note = Synthetic Construct
source                 1..383
                       mol_type = protein
                       organism = synthetic construct
SEQUENCE: 341
MKAKLLVLLC TFTATYADTI CIGYHANNST DTVDTVLEKN VTVTNSTNLG SGLRMVTGLR  60
NIPQRETRGL FGAIAGFIEG GWTGMVDGWY GYHHQNEQGS GYAADQKSTQ NAINGITNMV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                          383

SEQ ID NO: 342         moltype = DNA  length = 1155
FEATURE                Location/Qualifiers
misc_feature           1..1155
                       note = Synthetic
source                 1..1155
                       mol_type = other DNA
                       organism = synthetic construct
SEQUENCE: 342
tcatcatgac ccactttttc tggacttggc aatgcccttc acatactgat ctgccaggta  60
caggccatga ttctcgtttc caatcagttc gattttatcc aggatgtcct taaacaggac  120
ctcctcctcg tgctgctcgg ccacgtacca ctgcagaaag ttgaaggtag catgatcttt  180
gctcttaatg gcgtggtcca caatattgtt gatagattcg gaaatatgct gctcgtgttc  240
gtaagctttc tgaaagatct gggtcaggcc ctcgaactta tgttcagggg cgctgattga  300
agtcagctgg acgggcacat tgttctcatt caggaaaatg atcagtttct ttgcatgttc  360
gtattcctcg gctgcgtgat caaacaggaa cagcccagcg ccgtccagtg agtgtgtata  420
acaccaacta gacatactca tgtacaggtt ggagctctgc atctccttgt tcacctgttc  480
gttcagcagc ttgatgatgt cgcccccact gtcaattttc tctcgattca gcttactctc  540
ttcagaatat ttgggatagt cgtaagtgcc gttcttcaca gactccatac attcattgtt  600
gcacttatgg taaaactcga agcatccatt cccgatttct ttggcattgt tcttcagctg  660
ggatttgacc ttctcataca gattcttcac gttgctatcg tggaaatcca gagtccgctc  720
gttcagcagc agcaccagca gctcagccag gtctgttccg gagcctccgc tgcccatttt  780
ttcgatgaca gaattcacca tgttagtaat gccattgatt gcgttctgtg tagacttctg  840
atcagcggcg tagccgctgc cctgctcatt ctgatggtgg tagccgtacc acccgtccac  900
cattcctgtc cacccgccct caataaaccc tgcgatagcg ccgaacagtc ctcttgtttc  960
ccgctgtggg atgttgcgca gtccggtgac catcctcagt ccgctgccca gattagttga  1020
gttggtgaca gtcacgttct tctccaggac ggtatccact gtgtcggtgg agttgtttgc  1080
gtgatagccg atgcagatag tgtcagcgta ggttgcggta aaagtacaca gcaggaccag  1140
```

```
cagtttggcc ttcat                                                   1155

SEQ ID NO: 343          moltype = DNA  length = 5579
FEATURE                 Location/Qualifiers
misc_feature            1..5579
                        note = Synthetic
source                  1..5579
                        mol_type = other DNA
                        organism = synthetic construct
SEQUENCE: 343
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcagattgg  240
ctattggcca ttgcatacgt tgtatccata tcataatatg tacatttata ttggctcatg  300
tccaacatta ccgccatgtt gacattgatt attgactagt tattaatagt aatcaattac  360
ggggtcatta gttcatagcc catatatgga gttccgcgtt acataactta cggtaaatgg  420
cccgcctggc tgaccgccca acgacccccg cccattgacg tcaataatga cgtatgttcc  480
catagtaacg ccaataggga ctttccattg acgtcaatgg gtggagtatt tacggtaaac  540
tgcccacttg gcagtacatc aagtgtatca tatgccaagt acgcccccta ttgacgtcaa  600
tgacggtaaa tggcccgcct ggcattatgc ccagtacatg accttatggg actttcctac  660
ttggcagtac atctacgtat tagtcatcgc tattaccatg gtgatgcggt tttggcagta  720
catcaatggg cgtggatagc ggtttgactc acggggattt ccaagtctcc accccattga  780
cgtcaatggg agtttgtttt ggcaccaaaa tcaacgggac tttccaaaat gtcgtaacaa  840
ctccgcccca ttgacgcaaa tgggcggtag gcgtgtacgg tgggaggtct atataagcag  900
agctcgttta gtgaaccgtc agatcgcctg gagacgccat ccacgctgtt ttgacctcca  960
tagaagacac cgggaccgat ccagcctcca tcggctcgca tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctcaggtc gagaccgggc  1140
ctttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgcggc cgctctagag  1380
atatcgccac catgaaggcc aaactgctgg tcctgctgtg tactttttacc gcaacctacg  1440
ctgacactat ctgcatcggc tatcacgcaa acaactccac cgacacagtg gataccgtcc  1500
tggagaagaa cgtgactgtc accaactcaa ctaatctggg cagcggactg aggatggtca  1560
ccggactgcg caacatccca cagcgggaaa caagaggact gttcggcgct atcgcagggt  1620
ttattgaggg cgggtggaca ggaatggtgg acgggtggta cggctaccac catcagaatg  1680
agcagggcag cggctacgcc gctgatcaga agtctacaca gaacgcaatc aatggcatta  1740
ctaacatggt gaattctgtc atcgaaaaaa tgggcagcgg aggctccgga acagacctgg  1800
ctgagctgct ggtgctgctg ctgaacgagc ggactctgga tttccacgat agcaacgtga  1860
agaatctgta tgagaaggtc aaatcccagc tgaagaacaa tgccaaagaa atcgggaatg  1920
gatgcttcga gttttaccat aagtgcaaca atgaatgtat ggagtctgtg aagaacggca  1980
cttacgacta tcccaaatat tctgaagaga gtaagctgaa tcgagagaaa attgacagtg  2040
ggggcgacat catcaagctg ctgaacgaac aggtgaacaa ggagatgcag agctccaacc  2100
tgtacatgag tatgtctagt tggtgttata cacactcact ggacggcgct gggctgttcc  2160
tgtttgatca cgcagccgag gaatacgaac atgcaaagaa actgatcatt ttcctgaatg  2220
agaacaatgt gcccgtccag ctgacttcaa tcagcgcccc tgaacataag ttcgagggcc  2280
tgacccagat ctttcagaaa gcttacgaac acgagcagca tatttccgaa tctatcaaca  2340
atattgtgga ccacgccatt aagagcaaag atcatgctac cttcaacttt ctgcagtggt  2400
acgtggccga gcagcacgag gaggaggtcc tgtttaagga catcctggat aaaatcgaac  2460
tgattggaaa cgagaatcat ggcctgtacc tggcagatca gtatgtgaag ggcattgcca  2520
agtccagaaa aagtgggtca tgatgaacac gtgggatcca gatctgctgt gccttctagt  2580
tgccagccat ctgttgtttg cccctccccc gtgccttcct tgaccctgga aggtgccact  2640
cccactgtcc tttcctaata aaatgaggaa attgcatcgc attgtctgag taggtgtcat  2700
tctattctgg ggggtggggt ggggcaggac agcaaggggg aggattggga agacaatagc  2760
aggcatgctg gggatgcggt gggctctatg ggtacccagg tgctgaagaa ttgacccggt  2820
tcctcctggg ccagaaagaa gcaggcacat ccccttctct gtgacacacc ctgtccacgc  2880
ccctggttct tagttccagc cccactcata ggacactcat agctcaggag ggctccgcct  2940
tcaatcccac ccgctaaagt acttggagcg gtctctccct ccctcatcag cccaccaaac  3000
caaacctagc ctccaagagt gggaagaaat taaagcaaga taggctatta agtgcagagg  3060
gagagaaaat gcctccaaca tgtgaggaag taatgagaga aatcatagaa ttttaaggcc  3120
atgatttaag gccatcatgg ccttaatctt ccgcttcctc gctcactgac tcgctgcgct  3180
cggtcgttcg gctgcggcga gcggtatcag ctcactcaaa ggcggtaata cggttatcca  3240
cagaatcagg ggataacgca ggaaagaaca tgtgagcaaa aggccagcaa aaggccagga  3300
accgtaaaaa ggccgcgttg ctggcgtttt tccataggct ccgcccccct gacgagcatc  3360
acaaaaatcg acgctcaagt cagaggtggc gaaacccgac aggactataa agataccagg  3420
cgtttccccc tggaagctcc ctcgtgcgct ctcctgttcc gaccctgccg cttaccggat  3480
acctgtccgc ctttctccct tcgggaagcg tggcgctttc tcatagctca cgctgtaggt  3540
atctcagttc ggtgtaggtc gttcgctcca agctgggctg tgtgcacgaa ccccccgttc  3600
agcccgaccg ctgcgcctta tccggtaact atcgtcttga gtccaacccg gtaagacacg  3660
acttatcgcc actggcagca gccactggta acaggattag cagagcgagg tatgtaggcg  3720
gtgctacaga gttcttgaag tggtggccta actacggcta cactagaaga acagtatttg  3780
gtatctgcgc tctgctgaag ccagttacct tcggaaaaag agttggtagc tcttgatccg  3840
gcaaacaaac caccgctggt agcggtggtt tttttgtttg caagcagcag attacgcgca  3900
gaaaaaaagg atctcaagaa gatcctttga tcttttctac ggggtctgac gctcagtgga  3960
acgaaaactc acgttaaggg attttggtca tgagattatc aaaaaggatc ttcacctaga  4020
tccttttaaa ttaaaaatga agttttaaat caatctaaag tatatatgag taaacttggt  4080
ctgacagtta ccaatgctta atcagtgagg cacctatctc agcgatctgt ctatttcgtt  4140
```

```
catccatagt tgcctgactc gggggggggg ggcgctgagg tctgcctcgt gaagaaggtg  4200
ttgctgactc ataccaggcc tgaatcgccc catcatccag ccagaaagtg agggagccac  4260
ggttgatgag agctttgttg taggtggacc agttggtgat tttgaacttt tgctttgcca  4320
cggaacggtc tgcgttgtcg ggaagatgcg tgatctgatc cttcaactca gcaaaagttc  4380
gatttattca acaaagccgc cgtcccgtca agtcagcgta atgctctgcc agtgttacaa  4440
ccaattaacc aattctgatt agaaaaactc atcgagcatc aaatgaaact gcaatttatt  4500
catatcagga ttatcaatac catatttttg aaaaagccgt ttctgtaatg aaggagaaaa  4560
ctcaccgagg cagttccata ggatggcaag atcctggtat cggtctgcga ttccgactcg  4620
tccaacatca atacaaccta ttaatttccc ctcgtcaaaa ataaggttat caagtgagaa  4680
atcaccatga gtgacgactg aatccggtga gaatggcaaa agcttatgca tttctttcca  4740
gacttgttca acaggccagc cattacgctc gtcatcaaaa tcactcgcat caaccaaacc  4800
gttattcatt cgtgattgcg cctgagcgag acgaaatacg cgatcgctgt taaaaggaca  4860
attacaaaca ggaatcgaat gcaaccggcg caggaacact gccagcgcat caacaatatt  4920
ttcacctgaa tcaggatatt cttctaatac ctggaatgct gttttcccgg ggatcgcagt  4980
ggtgagtaac catgcatcat caggagtacg gataaaatgc ttgatggtcg gaagaggcat  5040
aaattccgtc agccagttta gtctgaccat ctcatctgta acatcattgg caacgctacc  5100
tttgccatgt ttcagaaaca actctggcgc atcgggcttc ccatacaatc gatagattgt  5160
cgcacctgat tgcccgacat tatcgcgagc ccatttatac ccatataaat cagcatccat  5220
gttggaattt aatcgcggcc tcgagcaaga cgtttcccgt tgaatatggc tcataacacc  5280
ccttgtatta ctgtttatgt aagcagacag ttttattgtt catgatgata tatttttatc  5340
ttgtgcaatg taacatcaga gattttgaga cacaacgtgg ctttcccccc ccccccatta  5400
ttgaagcatt tatcagggtt attgtctcat gagcggatac atatttgaat gtatttagaa  5460
aaataaacaa ataggggttc cgcgcacatt tccccgaaaa gtgccacctg acgtctaaga  5520
aaccattatt atcatgacat taacctataa aaataggcgt atcacgaggc cctttcgtc   5579

SEQ ID NO: 344         moltype = DNA  length = 645
FEATURE                Location/Qualifiers
misc_feature           1..645
                       note = Synthetic
source                 1..645
                       mol_type = other DNA
                       organism = synthetic construct
CDS                    1..645
SEQUENCE: 344
atgaaggcca aactgctggt cctgctgtgt acttttaccg caacctacgc tgacactatc  60
tgcatcggct atcacgcaaa caactccacc gacacagtgg ataccattct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cggtggtac ggctaccacc atcagaatga gcagggcagc  300
ggctacgccg ctgatcagaa gtctacacag aacgcaatca atggcattac taacatggtg  360
aattctgtca tcgaaaaaat gggcagcgga ggctccggaa cagacctggc tgagctgctg  420
gtgctgatgc tgaaccagtt cactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                645

SEQ ID NO: 345         moltype = AA  length = 215
FEATURE                Location/Qualifiers
REGION                 1..215
                       note = Synthetic Construct
source                 1..215
                       mol_type = protein
                       organism = synthetic construct
SEQUENCE: 345
MKAKLLVLLC TFTATYADTI CIGYHANNST DTVDTILEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGSG GSGTDLAELL VLMLNQFTLL FHDSNVKNLY EKVKSQLKNN AKEIGNGCFE  180
FYHKCNNECM ESVKNGTYDY PKYSEESKLN REKID                           215

SEQ ID NO: 346         moltype = DNA  length = 645
FEATURE                Location/Qualifiers
misc_feature           1..645
                       note = Synthetic
source                 1..645
                       mol_type = other DNA
                       organism = synthetic construct
SEQUENCE: 346
gtcaattttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaacagca gagtgaactg gttcagcatc agcaccagca gctcagccag  240
gtctgttccg gagcctccgc tgcccatttt ttcgatgaca gaattcacca tgttagtaat  300
gccattgatt gcgttctgtg tagacttctg atcagcggcg tagccgctgc cctgctcatt  360
ctgatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccagaat  540
ggtatccact gtgtcggtgg agttgtttgc gtgatagccg atgcagatag tgtcagcgta  600
ggttgcggta aaagtacaca gcaggaccag cagtttggcc ttcat                645
```

-continued

```
SEQ ID NO: 347         moltype = DNA  length = 1155
FEATURE                Location/Qualifiers
misc_feature           1..1155
                       note = Synthetic
source                 1..1155
                       mol_type = other DNA
                       organism = synthetic construct
CDS                    1..1155
SEQUENCE: 347
atgaaggcca aactgctggt cctgctgtgt acttttaccg caacctacgc tgacactatc  60
tgcatcggct atcacgcaaa caactccacc gacacagtgg ataccattct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cggtggtac ggctaccacc atcagaatga gcagggcagc  300
ggctacgccg ctgatcagaa gtctacacag aacgcaatca atggcattac taacatggtg  360
aattctgtca tcgaaaaaat gggcagcgga ggctccggaa cagacctggc tgagctgctg  420
gtgctgatgc tgaaccagtt cactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgacagtgg gggcgacatc  660
atcaagctgc tgaacgaaca ggtgaacaag gagatgcaga gctccaacct gtacatgagt  720
atgtctagtt ggtgttatac acactcactg gacggcgctg ggctgttcct gtttgatcac  780
gcagccgagg aatacgaaca tgcaaagaaa ctgatcattt tcctgaatga gaacaatgtg  840
cccgtccagc tgacttcaat cagcgcccct gaacataagt tcgagggcct gacccagatc  900
tttcagaaag cttacgaaca cgagcagcat atttccgaat ctatcaacaa tattgtggac  960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtcat gatga                                                   1155

SEQ ID NO: 348         moltype = AA  length = 383
FEATURE                Location/Qualifiers
REGION                 1..383
                       note = Synthetic Construct
source                 1..383
                       mol_type = protein
                       organism = synthetic construct
SEQUENCE: 348
MKAKLLVLLC TFTATYADTI CIGYHANNST DTVDTILEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGSG GSGTDLAELL VLMLNQFTLL FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                          383

SEQ ID NO: 349         moltype = DNA  length = 1155
FEATURE                Location/Qualifiers
misc_feature           1..1155
                       note = Synthetic
source                 1..1155
                       mol_type = other DNA
                       organism = synthetic construct
SEQUENCE: 349
tcatcatgac ccactttttc tggacttggc aatgcccttc acatactgat ctgccaggta  60
caggccatga ttctcgtttc caatcagttc gattttatcc aggatgtcct taaacaggac  120
ctcctcctcg tgctgctcgg ccacgtacca ctgcagaaag ttgaaggtag catgatcttt  180
gctcttaatg gcgtggtcca caatattgtt gatagattcg gaaatatgct gctcgtgttc  240
gtaagctttc tgaaagatct gggtcaggcc ctcgaactta tgttcagggg cgctgattga  300
agtcagctgg acgggcacat tgttctcatt caggaaaatg atcagtttct ttgcatgttc  360
gtattcctcg gctgcgtgat caaacaggaa cagcccagcg ccgtccagtg agtgtgtata  420
acaccaacta gacatactca tgtacaggtt ggagctctgc atctccttgt tcacctgttc  480
gttcagcagc ttgatgatgt cgcccccact gtcaattttc tctcgattca gcttactctc  540
ttcagaatat ttgggatagt cgtaagtgcc gttcttcaca gactccatac attcattgtt  600
gcacttatgg taaaactcga agcatccatt cccgatttct ttggcattgt tcttcagctg  660
ggatttgacc ttctcataca gattcttcac gttgctatcg tggaacagca gagtgaactg  720
gttcagcatc agcaccagca gctcagccag gtctgttccg gagcctccgc tgcccatttt  780
ttcgatgaca gaattcacca tgttagtaat gccattgatt gcgttctgtg tagacttctg  840
atcagcggcg tagccgctgc cctgctcatt ctgatggtgg tagccgtacc acccgtccac  900
cattcctgtc cacccgccct caataaaccc tgcgatagcg ccgaacagtc ctcttgtttc  960
ccgctgtggg atgttgcgca gtccggtgac catcctcagt ccgctgccca gattcactga  1020
gtgggtgaca gtcacgttct tctccagaat ggtatccact gtgtcggtgg agttgtttgc  1080
gtgatagccg atgcagatag tgtcagcgta ggttgcggta aaagtacaca gcaggaccag  1140
cagtttggcc ttcat                                                   1155

SEQ ID NO: 350         moltype = DNA  length = 5579
FEATURE                Location/Qualifiers
misc_feature           1..5579
                       note = Synthetic
```

```
source                  1..5579
                        mol_type = other DNA
                        organism = synthetic construct
SEQUENCE: 350
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcagattgg  240
ctattggcca ttgcatacgt tgtatccata tcataatatg tacatttata ttggctcatg  300
tccaacatta ccgccatgtt gacattgatt attgactagt tattaatagt aatcaattac  360
ggggtcatta gttcatagcc catatatgga gttccgcgtt acataactta cggtaaatgg  420
cccgcctggc tgaccgccca acgacccccg cccattgacg tcaataatga cgtatgttcc  480
catagtaacg ccaataggga ctttccattg acgtcaatgg gtggagtatt tacggtaaac  540
tgcccacttg gcagtacatc aagtgtatca tatgccaagt acgcccccta ttgacgtcaa  600
tgacggtaaa tggcccgcct ggcattatgc ccagtacatg accttatggg actttcctac  660
ttggcagtac atctacgtat tagtcatcgc tattaccatg gtgatgcggt tttggcagta  720
catcaatggg cgtggatagc ggtttgactc acggggattt ccaagtctcc accccattga  780
cgtcaatggg agtttgtttt ggcaccaaaa tcaacgggac tttccaaaat gtcgtaacaa  840
ctccgcccca ttgacgcaaa tgggcggtag gcgtgtacgg tgggaggtct atataagcag  900
agctcgttta gtgaaccgtc agatcgcctg gagacgccat ccacgctgtt ttgacctcca  960
tagaagacac cgggaccgat ccagcctcca tcggctcgca tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctcaggtc gagaccgggc  1140
ctttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgcggc cgctctagag  1380
atatcgccac catgaaggcc aaactgctgg tcctgctgtg tacttttacc gcaacctacg  1440
ctgacactat ctgcatcggc tatcacgcaa acaactccac cgacacagtg gataccattc  1500
tggagaagaa cgtgactgtc acccactcag tgaatctggg cagcggactg aggatggtca  1560
ccggactgcg caacatccca cagcgggaaa caagaggact gttcggcgct atcgcagggt  1620
ttattgaggg cgggtggaca ggaatggtgg acgggtggta cggctaccac catcagaatg  1680
agcagggcag cggctacgcc gctgatcaga agtctacaca gaacgcaatc aatggcatta  1740
ctaacatggt gaattctgtc atcgaaaaaa tgggcagcgg aggctccgga acagacctgg  1800
ctgagctgct ggtgctgatg ctgaaccagt tcactctgct gttccacgat agcaacgtga  1860
agaatctgta tgagaaggtc aaatcccagc tgaagaacaa tgccaaagaa atcgggaatg  1920
gatgcttcga gttttaccat aagtgcaaca atgaatgtat ggagtctgtg aagaacggca  1980
cttacgacta tcccaaatat tctgaagaga gtaagctgaa tcgagagaaa attgacagtg  2040
ggggcgacat catcaagctg ctgaacgaac aggtgaacaa ggagatgcag agctccaacc  2100
tgtacatgag tatgtctagt tggtgttata cacactcact ggacggcgct gggctgttcc  2160
tgtttgatca cgcagccgag gaatacgaac atgcaaagaa actgatcatt ttcctgaatg  2220
agaacaatgt gcccgtccag ctgacttcaa tcagcgcccc tgaacataag ttcgagggcc  2280
tgacccagat ctttcagaaa gcttacgaac acgagcagca tatttccgaa tctatcaaca  2340
atattgtgga ccacgccatt aagagcaaag atcatgctac cttcaacttt ctgcagtggt  2400
acgtggccga gcagcacgag gaggaggtcc tgtttaagga catcctggat aaaatcgaac  2460
tgattggaaa cgagaatcat ggcctgtacc tggcagatca gtatgtgaag ggcattgcca  2520
agtccagaaa aagtgggtca tgatgaacac gtgggatcca gatctgctgt gccttctagt  2580
tgccagccat ctgttgtttg cccctccccc gtgccttcct tgaccctgga aggtgccact  2640
cccactgtcc tttcctaata aaatgaggaa attgcatcgc attgtctgag taggtgtcat  2700
tctattctgg ggggtggggt ggggcaggac agcaaggggg aggattggga agacaatagc  2760
aggcatgctg gggatgcggt gggctctatg ggtacccagg tgctgaagaa ttgacccggt  2820
tcctcctggg ccagaaagaa gcaggcacat ccccttctct gtgacacacc ctgtccacgc  2880
ccctggttct tagttccagc cccactcata ggacactcat agctcaggag ggctccgcct  2940
tcaatcccac ccgctaaagt acttggagcg gtctctccct ccctcatcag cccaccaaac  3000
caaacctagc ctccaagagt gggaagaaat taaagcaaga taggctatta agtgcagagg  3060
gagagaaaat gcctccaaca tgtgaggaag taatgagaga aatcatagaa ttttaaggcc  3120
atgatttaag gccatcatgg ccttaatctt ccgcttcctc gctcactgac tcgctgcgct  3180
cggtcgttcg gctgcggcga gcggtatcag ctcactcaaa ggcggtaata cggttatcca  3240
cagaatcagg ggataacgca ggaaagaaca tgtgagcaaa aggccagcaa aaggccagga  3300
accgtaaaaa ggccgcgttg ctggcgtttt tccataggct ccgcccccct gacgagcatc  3360
acaaaaatcg acgctcaagt cagaggtggc gaaacccgac aggactataa agataccagg  3420
cgtttccccc tggaagctcc ctcgtgcgct ctcctgttcc gaccctgccg cttaccggat  3480
acctgtccgc ctttctccct tcgggaagcg tggcgctttc tcatagctca cgctgtaggt  3540
atctcagttc ggtgtaggtc gttcgctcca agctgggctg tgtgcacgaa ccccccgttc  3600
agcccgaccg ctgcgcctta tccggtaact atcgtcttga gtccaacccg gtaagacacg  3660
acttatcgcc actggcagca gccactggta acaggattag cagagcgagg tatgtaggcg  3720
gtgctacaga gttcttgaag tggtggccta actacggcta cactagaaga acagtatttg  3780
gtatctgcgc tctgctgaag ccagttacct tcggaaaaag agttggtagc tcttgatccg  3840
gcaaacaaac caccgctggt agcggtggtt tttttgtttg caagcagcag attacgcgca  3900
gaaaaaaagg atctcaagaa gatcctttga tcttttctac ggggtctgac gctcagtgga  3960
acgaaaactc acgttaaggg attttggtca tgagattatc aaaaaggatc ttcacctaga  4020
tccttttaaa ttaaaaatga agttttaaat caatctaaag tatatatgag taaacttggt  4080
ctgacagtta ccaatgctta atcagtgagg cacctatctc agcgatctgt ctatttcgtt  4140
catccatagt tgcctgactc gggggggggg ggcgctgagg tctgcctcgt gaagaaggtg  4200
ttgctgactc ataccaggcc tgaatcgccc catcatccag ccagaaagtg agggagccac  4260
ggttgatgag agctttgttg taggtggacc agttggtgat tttgaacttt tgctttgcca  4320
cggaacggtc tgcgttgtcg ggaagatgcg tgatctgatc cttcaactca gcaaaagttc  4380
gatttattca acaaagccgc cgtcccgtca agtcagcgta atgctctgcc agtgttacaa  4440
ccaattaacc aattctgatt agaaaaactc atcgagcatc aaatgaaact gcaatttatt  4500
```

```
catatcagga ttatcaatac catatttttg aaaaagccgt ttctgtaatg aaggagaaaa  4560
ctcaccgagg cagttccata ggatggcaag atcctggtat cggtctgcga ttccgactcg  4620
tccaacatca atacaaccta ttaatttccc ctcgtcaaaa ataaggttat caagtgagaa  4680
atcaccatga gtgacgactg aatccggtga gaatggcaaa agcttatgca tttctttcca  4740
gacttgttca acaggccagc cattacgctc gtcatcaaaa tcactcgcat caaccaaacc  4800
gttattcatt cgtgattgcg cctgagcgag acgaaatacg cgatcgctgt taaaaggaca  4860
attacaaaca ggaatcgaat gcaaccggcg caggaacact gccagcgcat caacaatatt  4920
ttcacctgaa tcaggatatt cttctaatac ctggaatgct gttttcccgg ggatcgcagt  4980
ggtgagtaac catgcatcat caggagtacg gataaaatgc ttgatggtcg gaagaggcat  5040
aaattccgtc agccagttta gtctgaccat ctcatctgta acatcattgg caacgctacc  5100
tttgccatgt ttcagaaaca actctggcgc atcgggcttc ccatacaatc gatagattgt  5160
cgcacctgat tgcccgacat tatcgcgagc ccatttatac ccatataaat cagcatccat  5220
gttggaattt aatcgcggcc tcgagcaaga cgtttcccgt tgaatatggc tcataacacc  5280
ccttgtatta ctgtttatgt aagcagacag ttttattgtt catgatgata tatttttatc  5340
ttgtgcaatg taacatcaga gattttgaga cacaacgtgg ctttcccccc ccccccatta  5400
ttgaagcatt tatcagggtt attgtctcat gagcggatac atatttgaat gtatttagaa  5460
aaataaacaa ataggggttc cgcgcacatt tccccgaaaa gtgccacctg acgtctaaga  5520
aaccattatt atcatgacat taacctataa aaataggcgt atcacgaggc cctttcgtc   5579

SEQ ID NO: 351          moltype = DNA  length = 645
FEATURE                 Location/Qualifiers
misc_feature            1..645
                        note = Synthetic
source                  1..645
                        mol_type = other DNA
                        organism = synthetic construct
CDS                     1..645
SEQUENCE: 351
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cggtggtac ggctaccacc atcagaatga gcagggcagc  300
ggctacgccg ctgatcagaa gtctacacag aacgcaatca atggcattac taacatggtg  360
aattctgtca tcgaaaaaat gggcaatgga acaggcggag ctgacctggc tgagctgctg  420
gtgctgctgc tgaaccagtg gactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                 645

SEQ ID NO: 352          moltype = AA  length = 215
FEATURE                 Location/Qualifiers
REGION                  1..215
                        note = Synthetic Construct
source                  1..215
                        mol_type = protein
                        organism = synthetic construct
SEQUENCE: 352
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGNG TGGADLAELL VLLLNQWTLL FHDSNVKNLY EKVKSQLKNN AKEIGNGCFE  180
FYHKCNNECM ESVKNGTYDY PKYSEESKLN REKID                             215

SEQ ID NO: 353          moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 353
gtcaattttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaacagca gagtccactg gttcagcagc agcaccagca gctcagccag  240
gtcagctccg cctgttccat tgcccatttt ttcgatgaca gaattcacca tgttagtaat  300
gccattgatt gcgttctgtg tagacttctg atcagcggcg tagccgctgc cctgctcatt  360
ctgatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat                 645

SEQ ID NO: 354          moltype = DNA  length = 1155
FEATURE                 Location/Qualifiers
misc_feature            1..1155
                        note = Synthetic
source                  1..1155
                        mol_type = other DNA
```

```
                        organism = synthetic construct
CDS                     1..1155
SEQUENCE: 354
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcaatgga acaggcggag ctgacctggc tgagctgctg  420
gtgctgctgc tgaaccagtg gactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgacagtgg gggcgacatc  660
atcaagctgc tgaacgaaca ggtgaacaag gagatgcaga gctccaacct gtacatgagt  720
atgtctagtt ggtgttatac acactcactg gacggcgctg ggctgttcct gtttgatcac  780
gcagccgagg aatacgaaca tgcaaagaaa ctgatcattt tcctgaatga gaacaatgtg  840
cccgtccagc tgacttcaat cagcgcccct gaacataagt tcgagggcct gacccagatc  900
tttcagaaag cttacgaaca cgagcagcat atttccgaat ctatcaacaa tattgtggac  960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtcat gatga                                                   1155

SEQ ID NO: 355          moltype = AA  length = 383
FEATURE                 Location/Qualifiers
REGION                  1..383
                        note = Synthetic Construct
source                  1..383
                        mol_type = protein
                        organism = synthetic construct
SEQUENCE: 355
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGNG TGGADLAELL VLLLNQWTLL FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                          383

SEQ ID NO: 356          moltype = DNA  length = 1155
FEATURE                 Location/Qualifiers
misc_feature            1..1155
                        note = Synthetic
source                  1..1155
                        mol_type = other DNA
                        organism = synthetic construct
SEQUENCE: 356
tcatcatgac ccactttttc tggacttggc aatgcccttc acatactgat ctgccaggta  60
caggccatga ttctcgtttc caatcagttc gattttatcc aggatgtcct taaacaggac  120
ctcctcctcg tgctgctcgg ccacgtacca ctgcagaaag ttgaaggtag catgatcttt  180
gctcttaatg gcgtggtcca caatattgtt gatagattcg gaaatatgct gctcgtgttc  240
gtaagctttc tgaaagatct gggtcaggcc ctcgaactta tgttcagggg cgctgattga  300
agtcagctgg acgggcacat tgttctcatt caggaaaatg atcagtttct ttgcatgttc  360
gtattcctcg gctgcgtgat caaacaggaa cagcccagcg ccgtccagtg agtgtgtata  420
acaccaacta gacatactca tgtacaggtt ggagctctgc atctccttgt tcacctgttc  480
gttcagcagc ttgatgatgt cgcccccact gtcaattttc tctcgattca gcttactctc  540
ttcagaatat ttgggatagt cgtaagtgcc gttcttcaca gactccatac attcattgtt  600
gcacttatgg taaaactcga agcatccatt cccgatttct ttggcattgt tcttcagctg  660
ggatttgacc ttctcataca gattcttcac gttgctatcg tggaacagca gagtccactg  720
gttcagcagc agcaccagca gctcagccag gtcagctccg cctgttccat tgcccatttt  780
ttcgatgaca gaattcacca tgttagtaat gccattgatt gcgttctgtg tagacttctg  840
atcagcggcg tagccgctgc cctgctcatt ctgatggtgg tagccgtacc acccgtccac  900
cattcctgtc cacccgccct caataaaccc tgcgatagcg ccgaacagtc ctcttgtttc  960
ccgctgtggg atgttgcgca gtccggtgac catcctcagt ccgctgccca gattcactga  1020
gtgggtgaca gtcacgttct tctccaggac ggtatccact gtgtcggtgg agttgtttgc  1080
gtgatagccg atgcagatag tgtcagcgta ggttgcggta aaagtacaca gcaggaccag  1140
cagtttggcc ttcat                                                   1155

SEQ ID NO: 357          moltype = DNA  length = 5579
FEATURE                 Location/Qualifiers
misc_feature            1..5579
                        note = Synthetic
source                  1..5579
                        mol_type = other DNA
                        organism = synthetic construct
SEQUENCE: 357
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
```

-continued

```
ttggcgggtg tcggggctgg cttaactatg cggcatcaga gcagattgta ctgagagtgc  180
accatatgcg gtgtgaaata ccgcacagat gcgtaaggag aaaataccgc atcagattgg  240
ctattggcca ttgcatacgt tgtatccata tcataatatg tacatttata ttggctcatg  300
tccaacatta ccgccatgtt gacattgatt attgactagt tattaatagt aatcaattac  360
ggggtcatta gttcatagcc catatatgga gttccgcgtt acataactta cggtaaatgg  420
cccgcctggc tgaccgccca acgacccccg cccattgacg tcaataatga cgtatgttcc  480
catagtaacg ccaataggga ctttccattg acgtcaatgg gtggagtatt tacggtaaac  540
tgcccacttg gcagtacatc aagtgtatca tatgccaagt acgcccccta ttgacgtcaa  600
tgacggtaaa tggcccgcct ggcattatgc ccagtacatg accttatggg actttcctac  660
ttggcagtac atctacgtat tagtcatcgc tattaccatg gtgatgcggt tttggcagta  720
catcaatggg cgtggatagc ggtttgactc acggggattt ccaagtctcc accccattga  780
cgtcaatggg agtttgtttt ggcaccaaaa tcaacgggac tttccaaaat gtcgtaacaa  840
ctccgcccca ttgacgcaaa tgggcggtag gcgtgtacgg tgggaggtct atataagcag  900
agctcgttta gtgaaccgtc agatcgcctg gagacgccat ccacgctgtt ttgacctcca  960
tagaagacac cgggaccgat ccagcctcca tcggctcgca tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctcaggtc gagaccgggc  1140
ctttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgcggc cgctctagag  1380
atatcgccac catgaaggcc aaactgctgg tcctgctgtg tactttttacc gcaacctacg  1440
ctgacactat ctgcatcggc tatcacgcaa acaactccac cgacacagtg gataccgtcc  1500
tggagaagaa cgtgactgtc acccactcag tgaatctggg cagcggactg aggatggtca  1560
ccggactgcg caacatccca cagcgggaaa caagaggact gttcggcgct atcgcagggt  1620
ttattgaggg cgggtggaca ggaatggtgg acgggtggta cggctaccac catcagaatg  1680
agcagggcag cggctacgcc gctgatcaga agtctacaca gaacgcaatc aatggcatta  1740
ctaacatggt gaattctgtc atcgaaaaaa tgggcaatgg aacaggcgga gctgacctgg  1800
ctgagctgct ggtgctgctg ctgaaccagt ggactctgct gttccacgat agcaacgtga  1860
agaatctgta tgagaaggtc aaatcccagc tgaagaacaa tgccaaagaa atcgggaatg  1920
gatgcttcga gttttaccat aagtgcaaca atgaatgtat ggagtctgtg aagaacggca  1980
cttacgacta tcccaaatat tctgaagaga gtaagctgaa tcgagagaaa attgacagtg  2040
gggcgacat catcaagctg ctgaacgaac aggtgaacaa ggagatgcag agctccaacc  2100
tgtacatgag tatgtctagt tggtgttata cacactcact ggacggcgct gggctgttcc  2160
tgtttgatca cgcagccgag gaatacgaac atgcaaagaa actgatcatt ttcctgaatg  2220
agaacaatgt gcccgtccag ctgacttcaa tcagcgcccc tgaacataag ttcgagggcc  2280
tgacccagat ctttcagaaa gcttacgaac acgagcagca tatttccgaa tctatcaaca  2340
atattgtgga ccacgccatt aagagcaaag atcatgctac cttcaacttt ctgcagtggt  2400
acgtggccga gcagcacgag gaggaggtcc tgtttaagga catcctggat aaaatcgaac  2460
tgattggaaa cgagaatcat ggcctgtacc tggcagatca gtatgtgaag ggcattgcca  2520
agtccagaaa aagtgggtca tgatgaacac gtgggatcca gatctgctgt gccttctagt  2580
tgccagccat ctgttgtttg cccctccccc gtgccttcct tgaccctgga aggtgccact  2640
cccactgtcc tttcctaata aaatgaggaa attgcatcgc attgtctgag taggtgtcat  2700
tctattctgg ggggtggggt ggggcaggac agcaaggggg aggattggga agacaatagc  2760
aggcatgctg gggatgcggt gggctctatg ggtacccagg tgctgaagaa ttgacccggt  2820
tcctcctggg ccagaaagaa gcaggcacat ccccttctct gtgacacacc ctgtccacgc  2880
ccctggttct tagttccagc cccactcata ggacactcat agctcaggag ggctccgcct  2940
tcaatcccac ccgctaaagt acttggagcg gtctctccct ccctcatcag cccaccaaac  3000
caaacctagc ctccaagagt gggaagaaat taaagcaaga taggctatta agtgcagagg  3060
gagagaaaat gcctccaaca tgtgaggaag taatgagaga aatcatagaa ttttaaggcc  3120
atgatttaag gccatcatgg ccttaatctt ccgcttcctc gctcactgac tcgctgcgct  3180
cggtcgttcg gctgcggcga gcggtatcag ctcactcaaa ggcggtaata cggttatcca  3240
cagaatcagg ggataacgca ggaaagaaca tgtgagcaaa aggccagcaa aaggccagga  3300
accgtaaaaa ggccgcgttg ctggcgtttt tccataggct ccgcccccct gacgagcatc  3360
acaaaaatcg acgctcaagt cagaggtggc gaaacccgac aggactataa agataccagg  3420
cgtttccccc tggaagctcc ctcgtgcgct ctcctgttcc gaccctgccg cttaccggat  3480
acctgtccgc ctttctccct tcgggaagcg tggcgctttc tcatagctca cgctgtaggt  3540
atctcagttc ggtgtaggtc gttcgctcca agctgggctg tgtgcacgaa ccccccgttc  3600
agcccgaccg ctgcgcctta tccggtaact atcgtcttga gtccaacccg gtaagacacg  3660
acttatcgcc actggcagca gccactggta acaggattag cagagcgagg tatgtaggcg  3720
gtgctacaga gttcttgaag tggtggccta actacggcta cactagaaga acagtatttg  3780
gtatctgcgc tctgctgaag ccagttacct tcggaaaaag agttggtagc tcttgatccg  3840
gcaaacaaac caccgctggt agcggtggtt tttttgtttg caagcagcag attacgcgca  3900
gaaaaaaagg atctcaagaa gatcctttga tcttttctac ggggtctgac gctcagtgga  3960
acgaaaactc acgttaaggg attttggtca tgagattatc aaaaaggatc ttcacctaga  4020
tccttttaaa ttaaaaatga agttttaaat caatctaaag tatatatgag taaacttggt  4080
ctgacagtta ccaatgctta atcagtgagg cacctatctc agcgatctgt ctatttcgtt  4140
catccatagt tgcctgactc gggggggggg ggcgctgagg tctgcctcgt gaagaaggtg  4200
ttgctgactc ataccaggcc tgaatcgccc catcatccag ccagaaagtg agggagccac  4260
ggttgatgag agctttgttg taggtggacc agttggtgat tttgaacttt tgctttgcca  4320
cggaacggtc tgcgttgtcg ggaagatgcg tgatctgatc cttcaactca gcaaaagttc  4380
gatttattca acaaagccgc cgtcccgtca agtcagcgta atgctctgcc agtgttacaa  4440
ccaattaacc aattctgatt agaaaaactc atcgagcatc aaatgaaact gcaatttatt  4500
catatcagga ttatcaatac catatttttg aaaaagccgt ttctgtaatg aaggagaaaa  4560
ctcaccgagg cagttccata ggatggcaag atcctggtat cggtctgcga ttccgactcg  4620
tccaacatca atacaaccta ttaatttccc ctcgtcaaaa ataaggttat caagtgagaa  4680
atcaccatga gtgacgactg aatccggtga gaatggcaaa agcttatgca tttctttcca  4740
gacttgttca acaggccagc cattacgctc gtcatcaaaa tcactcgcat caaccaaacc  4800
gttattcatt cgtgattgcg cctgagcgag acgaaatacg cgatcgctgt taaaaggaca  4860
```

```
attacaaaca ggaatcgaat gcaaccggcg caggaacact gccagcgcat caacaatatt  4920
ttcacctgaa tcaggatatt cttctaatac ctggaatgct gttttcccgg ggatcgcagt  4980
ggtgagtaac catgcatcat caggagtacg gataaaatgc ttgatggtcg gaagaggcat  5040
aaattccgtc agccagttta gtctgaccat ctcatctgta acatcattgg caacgctacc  5100
tttgccatgt ttcagaaaca actctggcgc atcgggcttc ccatacaatc gatagattgt  5160
cgcacctgat tgcccgacat tatcgcgagc ccatttatac ccatataaat cagcatccat  5220
gttggaattt aatcgcggcc tcgagcaaga cgtttcccgt tgaatatggc tcataacacc  5280
ccttgtatta ctgtttatgt aagcagacag ttttattgtt catgatgata tatttttatc  5340
ttgtgcaatg taacatcaga gattttgaga cacaacgtgg ctttcccccc ccccccatta  5400
ttgaagcatt tatcagggtt attgtctcat gagcggatac atatttgaat gtatttagaa  5460
aaataaacaa ataggggttc cgcgcacatt tccccgaaaa gtgccacctg acgtctaaga  5520
aaccattatt atcatgacat taacctataa aaataggcgt atcacgaggc cctttcgtc   5579

SEQ ID NO: 358         moltype = DNA  length = 645
FEATURE                Location/Qualifiers
misc_feature           1..645
                       note = Synthetic
source                 1..645
                       mol_type = other DNA
                       organism = synthetic construct
CDS                    1..645
SEQUENCE: 358
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcggaaat ggcactggag ctgacctggc tgagctgctg  420
gtgctgctgc tgaaccagtg gactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                 645

SEQ ID NO: 359         moltype = AA  length = 215
FEATURE                Location/Qualifiers
REGION                 1..215
                       note = Synthetic Construct
source                 1..215
                       mol_type = protein
                       organism = synthetic construct
SEQUENCE: 359
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGGN GTGADLAELL VLLLNQWTLL FHDSNVKNLY EKVKSQLKNN AKEIGNGCFE  180
FYHKCNNECM ESVKNGTYDY PKYSEESKLN REKID                            215

SEQ ID NO: 360         moltype = DNA  length = 645
FEATURE                Location/Qualifiers
misc_feature           1..645
                       note = Synthetic
source                 1..645
                       mol_type = other DNA
                       organism = synthetic construct
SEQUENCE: 360
gtcaattttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaacagca gagtccactg gttcagcagc agcaccagca gctcagccag  240
gtcagctcca gtgccatttc cgcccatttt ttcgatgaca gaattcacca tgttagtaat  300
gccattgatt gcgttctgtg tagacttctg atcagcggcg tagccgctgc cctgctcatt  360
ctgatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat                 645

SEQ ID NO: 361         moltype = DNA  length = 1155
FEATURE                Location/Qualifiers
misc_feature           1..1155
                       note = Synthetic
source                 1..1155
                       mol_type = other DNA
                       organism = synthetic construct
CDS                    1..1155
SEQUENCE: 361
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
```

-continued

```
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcggaaat ggcactggag ctgacctggc tgagctgctg  420
gtgctgctgc tgaaccagtg gactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgacagtgg gggcgacatc  660
atcaagctgc tgaacgaaca ggtgaacaag gagatgcaga gctccaacct gtacatgagt  720
atgtctagtt ggtgttatac acactcactg gacggcgctg ggctgttcct gtttgatcac  780
gcagccgagg aatacgaaca tgcaaagaaa ctgatcattt tcctgaatga gaacaatgtg  840
cccgtccagc tgacttcaat cagcgcccct gaacataagt tcgagggcct gacccagatc  900
tttcagaaag cttacgaaca cgagcagcat atttccgaat ctatcaacaa tattgtggac  960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtcat gatga                                                   1155

SEQ ID NO: 362          moltype = AA  length = 383
FEATURE                 Location/Qualifiers
REGION                  1..383
                        note = Synthetic Construct
source                  1..383
                        mol_type = protein
                        organism = synthetic construct
SEQUENCE: 362
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGGN GTGADLAELL VLLLNQWTLL FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                          383

SEQ ID NO: 363          moltype = DNA  length = 1155
FEATURE                 Location/Qualifiers
misc_feature            1..1155
                        note = Synthetic
source                  1..1155
                        mol_type = other DNA
                        organism = synthetic construct
SEQUENCE: 363
tcatcatgac ccactttttc tggacttggc aatgcccttc acatactgat ctgccaggta  60
caggccatga ttctcgtttc caatcagttc gattttatcc aggatgtcct taaacaggac  120
ctcctcctcg tgctgctcgg ccacgtacca ctgcagaaag ttgaaggtag catgatcttt  180
gctcttaatg gcgtggtcca caatattgtt gatagattcg gaaatatgct gctcgtgttc  240
gtaagctttc tgaaagatct gggtcaggcc ctcgaactta tgttcagggg cgctgattga  300
agtcagctgg acgggcacat tgttctcatt caggaaaatg atcagtttct ttgcatgttc  360
gtattcctcg gctgcgtgat caaacaggaa cagcccagcg ccgtccagtg agtgtgtata  420
acaccaacta gacatactca tgtacaggtt ggagctctgc atctccttgt tcacctgttc  480
gttcagcagc ttgatgatgt cgcccccact gtcaattttc tctcgattca gcttactctc  540
ttcagaatat ttgggatagt cgtaagtgcc gttcttcaca gactccatac attcattgtt  600
gcacttatgg taaaactcga agcatccatt cccgatttct ttggcattgt tcttcagctg  660
ggatttgacc ttctcataca gattcttcac gttgctatcg tggaacagca gagtccactg  720
gttcagcagc agcaccagca gctcagccag gtcagctcca gtgccatttc cgcccatttt  780
ttcgatgaca gaattcacca tgttagtaat gccattgatt gcgttctgtg tagacttctg  840
atcagcggcg tagccgctgc cctgctcatt ctgatggtgg tagccgtacc acccgtccac  900
cattcctgtc cacccgccct caataaaccc tgcgatagcg ccgaacagtc ctcttgtttc  960
ccgctgtggg atgttgcgca gtccggtgac catcctcagt ccgctgccca gattcactga  1020
gtgggtgaca gtcacgttct tctccaggac ggtatccact gtgtcggtgg agttgtttgc  1080
gtgatagccg atgcagatag tgtcagcgta ggttgcggta aaagtacaca gcaggaccag  1140
cagtttggcc ttcat                                                   1155

SEQ ID NO: 364          moltype = DNA  length = 5579
FEATURE                 Location/Qualifiers
misc_feature            1..5579
                        note = Synthetic
source                  1..5579
                        mol_type = other DNA
                        organism = synthetic construct
SEQUENCE: 364
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcagattgg  240
ctattggcca ttgcatacgt tgtatccata tcataatatg tacatttata ttggctcatg  300
tccaacatta ccgccatgtt gacattgatt attgactagt tattaatagt aatcaattac  360
ggggtcatta gttcatagcc catatatgga gttccgcgtt acataactta cggtaaatgg  420
cccgcctggc tgaccgccca acgacccccg cccattgacg tcaataatga cgtatgttcc  480
```

-continued

```
catagtaacg ccaataggga ctttccattg acgtcaatgg gtggagtatt tacggtaaac  540
tgcccacttg gcagtacatc aagtgtatca tatgccaagt acgcccccta ttgacgtcaa  600
tgacggtaaa tggcccgcct ggcattatgc ccagtacatg accttatggg actttcctac  660
ttggcagtac atctacgtat tagtcatcgc tattaccatg gtgatgcggt tttggcagta  720
catcaatggg cgtggatagc ggtttgactc acggggattt ccaagtctcc accccattga  780
cgtcaatggg agtttgtttt ggcaccaaaa tcaacgggac tttccaaaat gtcgtaacaa  840
ctccgcccca ttgacgcaaa tgggcggtag gcgtgtacgg tgggaggtct atataagcag  900
agctcgttta gtgaaccgtc agatcgcctg gagacgccat ccacgctgtt ttgacctcca  960
tagaagacac cgggaccgat ccagcctcca tcggctcgca tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctcaggtc gagaccgggc  1140
ctttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgcggc cgctctagag  1380
atatcgccac catgaaggcc aaactgctgg tcctgctgtg tacttttacc gcaacctacg  1440
ctgacactat ctgcatcggc tatcacgcaa acaactccac cgacacagtg gataccgtcc  1500
tggagaagaa cgtgactgtc acccactcag tgaatctggg cagcggactg aggatggtca  1560
ccggactgcg caacatccca cagcgggaaa caagaggact gttcggcgct atcgcagggt  1620
ttattgaggg cgggtggaca ggaatggtgg acgggtggta cggctaccac catcagaatg  1680
agcagggcag cggctacgcc gctgatcaga agtctacaca gaacgcaatc aatggcatta  1740
ctaacatggt gaattctgtc atcgaaaaaa tgggcggaaa tggcactgga gctgacctgg  1800
ctgagctgct ggtgctgctg ctgaaccagt ggactctgct gttccacgat agcaacgtga  1860
agaatctgta tgagaaggtc aaatcccagc tgaagaacaa tgccaaagaa atcgggaatg  1920
gatgcttcga gttttaccat aagtgcaaca atgaatgtat ggagtctgtg aagaacggca  1980
cttacgacta tcccaaatat tctgaagaga gtaagctgaa tcgagagaaa attgacagtg  2040
ggggcgacat catcaagctg ctgaacgaac aggtgaacaa ggagatgcag agctccaacc  2100
tgtacatgag tatgtctagt tggtgttata cacactcact ggacggcgct gggctgttcc  2160
tgtttgatca cgcagccgag gaatacgaac atgcaaagaa actgatcatt ttcctgaatg  2220
agaacaatgt gcccgtccag ctgacttcaa tcagcgcccc tgaacataag ttcgagggcc  2280
tgacccagat ctttcagaaa gcttacgaac acgagcagca tatttccgaa tctatcaaca  2340
atattgtgga ccacgccatt aagagcaaag atcatgctac cttcaacttt ctgcagtggt  2400
acgtggccga gcagcacgag gaggaggtcc tgtttaagga catcctggat aaaatcgaac  2460
tgattggaaa cgagaatcat ggcctgtacc tggcagatca gtatgtgaag ggcattgcca  2520
agtccagaaa aagtgggtca tgatgaacac gtgggatcca gatctgctgt gccttctagt  2580
tgccagccat ctgttgtttg cccctccccc gtgccttcct tgaccctgga aggtgccact  2640
cccactgtcc tttcctaata aaatgaggaa attgcatcgc attgtctgag taggtgtcat  2700
tctattctgg ggggtggggt ggggcaggac agcaaggggg aggattggga agacaatagc  2760
aggcatgctg gggatgcggt gggctctatg ggtacccagg tgctgaagaa ttgacccggt  2820
tcctcctggg ccagaaagaa gcaggcacat cccctctct gtgacacacc ctgtccacgc  2880
ccctggttct tagttccagc cccactcata ggacactcat agctcaggag ggctccgcct  2940
tcaatcccac ccgctaaagt acttggagcg gtctctccct ccctcatcag cccaccaaac  3000
caaacctagc ctccaagagt gggaagaaat taaagcaaga taggctatta agtgcagagg  3060
gagagaaaat gcctccaaca tgtgaggaag taatgagaga aatcatagaa ttttaaggcc  3120
atgatttaag gccatcatgg ccttaatctt ccgcttcctc gctcactgac tcgctgcgct  3180
cggtcgttcg gctgcggcga gcggtatcag ctcactcaaa ggcggtaata cggttatcca  3240
cagaatcagg ggataacgca ggaaagaaca tgtgagcaaa aggccagcaa aaggccagga  3300
accgtaaaaa ggccgcgttg ctggcgtttt tccataggct ccgcccccct gacgagcatc  3360
acaaaaatcg acgctcaagt cagaggtggc gaaacccgac aggactataa agataccagg  3420
cgtttccccc tggaagctcc ctcgtgcgct ctcctgttcc gaccctgccg cttaccggat  3480
acctgtccgc ctttctccct tcgggaagcg tggcgctttc tcatagctca cgctgtaggt  3540
atctcagttc ggtgtaggtc gttcgctcca agctgggctg tgtgcacgaa ccccccgttc  3600
agcccgaccg ctgcgcctta tccggtaact atcgtcttga gtccaacccg gtaagacacg  3660
acttatcgcc actggcagca gccactggta acaggattag cagagcgagg tatgtaggcg  3720
gtgctacaga gttcttgaag tggtggccta actacggcta cactagaaga acagtatttg  3780
gtatctgcgc tctgctgaag ccagttacct tcggaaaaag agttggtagc tcttgatccg  3840
gcaaacaaac caccgctggt agcggtggtt tttttgtttg caagcagcag attacgcgca  3900
gaaaaaaagg atctcaagaa gatcctttga tcttttctac ggggtctgac gctcagtgga  3960
acgaaaactc acgttaaggg attttggtca tgagattatc aaaaaggatc ttcacctaga  4020
tccttttaaa ttaaaaatga agttttaaat caatctaaag tatatatgag taaacttggt  4080
ctgacagtta ccaatgctta atcagtgagg cacctatctc agcgatctgt ctatttcgtt  4140
catccatagt tgcctgactc gggggggggg ggcgctgagg tctgcctcgt gaagaaggtg  4200
ttgctgactc ataccaggcc tgaatcgccc catcatccag ccagaaagtg agggagccac  4260
ggttgatgag agctttgttg taggtggacc agttggtgat tttgaacttt tgctttgcca  4320
cggaacggtc tgcgttgtcg ggaagatgcg tgatctgatc cttcaactca gcaaaagttc  4380
gatttattca acaaagccgc cgtcccgtca agtcagcgta atgctctgcc agtgttacaa  4440
ccaattaacc aattctgatt agaaaaactc atcgagcatc aaatgaaact gcaatttatt  4500
catatcagga ttatcaatac catatttttg aaaaagccgt ttctgtaatg aaggagaaaa  4560
ctcaccgagg cagttccata ggatggcaag atcctggtat cggtctgcga ttccgactcg  4620
tccaacatca atacaaccta ttaatttccc ctcgtcaaaa ataaggttat caagtgagaa  4680
atcaccatga gtgacgactg aatccggtga gaatggcaaa agcttatgca tttctttcca  4740
gacttgttca acaggccagc cattacgctc gtcatcaaaa tcactcgcat caaccaaacc  4800
gttattcatt cgtgattgcg cctgagcgag acgaaatacg cgatcgctgt taaaaggaca  4860
attacaaaca ggaatcgaat gcaaccggcg caggaacact gccagcgcat caacaatatt  4920
ttcacctgaa tcaggatatt cttctaatac ctggaatgct gttttcccgg ggatcgcagt  4980
ggtgagtaac catgcatcat caggagtacg gataaaatgc ttgatggtcg gaagaggcat  5040
aaattccgtc agccagttta gtctgaccat ctcatctgta acatcattgg caacgctacc  5100
tttgccatgt ttcagaaaca actctggcgc atcgggcttc ccatacaatc gatagattgt  5160
cgcacctgat tgcccgacat tatcgcgagc ccatttatac ccatataaat cagcatccat  5220
```

```
gttggaattt aatcgcggcc tcgagcaaga cgtttcccgt tgaatatggc tcataacacc  5280
ccttgtatta ctgtttatgt aagcagacag ttttattgtt catgatgata tatttttatc  5340
ttgtgcaatg taacatcaga gattttgaga cacaacgtgg ctttcccccc ccccccatta  5400
ttgaagcatt tatcagggtt attgtctcat gagcggatac atatttgaat gtatttagaa  5460
aaataaacaa ataggggttc cgcgcacatt tccccgaaaa gtgccacctg acgtctaaga  5520
aaccattatt atcatgacat taacctataa aaataggcgt atcacgaggc cctttcgtc   5579

SEQ ID NO: 365         moltype = DNA  length = 645
FEATURE                Location/Qualifiers
misc_feature           1..645
                       note = Synthetic
source                 1..645
                       mol_type = other DNA
                       organism = synthetic construct
CDS                    1..645
SEQUENCE: 365
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcagcgga ggcaacggaa cagacctggc tgagctgctg  420
gtgctgctgc tgaaccagtg gactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                 645

SEQ ID NO: 366         moltype = AA  length = 215
FEATURE                Location/Qualifiers
REGION                 1..215
                       note = Synthetic Construct
source                 1..215
                       mol_type = protein
                       organism = synthetic construct
SEQUENCE: 366
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGSG GNGTDLAELL VLLLNQWTLL FHDSNVKNLY EKVKSQLKNN AKEIGNGCFE  180
FYHKCNNECM ESVKNGTYDY PKYSEESKLN REKID                            215

SEQ ID NO: 367         moltype = DNA  length = 645
FEATURE                Location/Qualifiers
misc_feature           1..645
                       note = Synthetic
source                 1..645
                       mol_type = other DNA
                       organism = synthetic construct
SEQUENCE: 367
gtcaattttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaacagca gagtccactg gttcagcagc agcaccagca gctcagccag  240
gtctgttccg ttgcctccgc tgcccatttt ttcgatgaca gaattcacca tgttagtaat  300
gccattgatt gcgttctgtg tagacttctg atcagcggcg tagccgctgc cctgctcatt  360
ctgatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat                 645

SEQ ID NO: 368         moltype = DNA  length = 1155
FEATURE                Location/Qualifiers
misc_feature           1..1155
                       note = Synthetic
source                 1..1155
                       mol_type = other DNA
                       organism = synthetic construct
CDS                    1..1155
SEQUENCE: 368
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcagcgga ggcaacggaa cagacctggc tgagctgctg  420
gtgctgctgc tgaaccagtg gactctgctg ttccacgata gcaacgtgaa gaatctgtat  480
gagaaggtca aatcccagct gaagaacaat gccaaagaaa tcgggaatgg atgcttcgag  540
```

```
ttttaccata agtgcaacaa tgaatgtatg gagtctgtga agaacggcac ttacgactat  600
cccaaatatt ctgaagagag taagctgaat cgagagaaaa ttgacagtgg gggcgacatc  660
atcaagctgc tgaacgaaca ggtgaacaag gagatgcaga gctccaacct gtacatgagt  720
atgtctagtt ggtgttatac acactcactg gacggcgctg ggctgttcct gtttgatcac  780
gcagccgagg aatacgaaca tgcaaagaaa ctgatcattt tcctgaatga gaacaatgtg  840
cccgtccagc tgacttcaat cagcgcccct gaacataagt tcgagggcct gacccagatc  900
tttcagaaag cttacgaaca cgagcagcat atttccgaat ctatcaacaa tattgtggac  960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtcat gatga                                                   1155

SEQ ID NO: 369         moltype = AA  length = 383
FEATURE                Location/Qualifiers
REGION                 1..383
                       note = Synthetic Construct
source                 1..383
                       mol_type = protein
                       organism = synthetic construct
SEQUENCE: 369
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGSG GNGTDLAELL VLLLNQWTLL FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                          383

SEQ ID NO: 370         moltype = DNA  length = 1155
FEATURE                Location/Qualifiers
misc_feature           1..1155
                       note = Synthetic
source                 1..1155
                       mol_type = other DNA
                       organism = synthetic construct
SEQUENCE: 370
tcatcatgac ccactttttc tggacttggc aatgcccttc acatactgat ctgccaggta  60
caggccatga ttctcgtttc caatcagttc gattttatcc aggatgtcct taaacaggac  120
ctcctcctcg tgctgctcgg ccacgtacca ctgcagaaag ttgaaggtag catgatcttt  180
gctcttaatg gcgtggtcca caatattgtt gatagattcg gaaatatgct gctcgtgttc  240
gtaagctttc tgaaagatct gggtcaggcc ctcgaactta tgttcagggg cgctgattga  300
agtcagctgg acgggcacat tgttctcatt caggaaaatg atcagtttct ttgcatgttc  360
gtattcctcg gctgcgtgat caaacaggaa cagcccagcg ccgtccagtg agtgtgtata  420
acaccaacta gacatactca tgtacaggtt ggagctctgc atctccttgt tcacctgttc  480
gttcagcagc ttgatgatgt cgcccccact gtcaattttc tctcgattca gcttactctc  540
ttcagaatat ttgggatagt cgtaagtgcc gttcttcaca gactccatac attcattgtt  600
gcacttatgg taaaactcga agcatccatt cccgatttct ttggcattgt tcttcagctg  660
ggatttgacc ttctcataca gattcttcac gttgctatcg tggaacagca gagtccactg  720
gttcagcagc agcaccagca gctcagccag gtctgttccg ttgcctccgc tgcccatttt  780
ttcgatgaca gaattcacca tgttagtaat gccattgatt gcgttctgtg tagacttctg  840
atcagcggcg tagccgctgc cctgctcatt ctgatggtgg tagccgtacc acccgtccac  900
cattcctgtc cacccgccct caataaaccc tgcgatagcg ccgaacagtc ctcttgtttc  960
ccgctgtggg atgttgcgca gtccggtgac catcctcagt ccgctgccca gattcactga  1020
gtgggtgaca gtcacgttct tctccaggac ggtatccact gtgtcggtgg agttgtttgc  1080
gtgatagccg atgcagatag tgtcagcgta ggttgcggta aaagtacaca gcaggaccag  1140
cagtttggcc ttcat                                                   1155

SEQ ID NO: 371         moltype = DNA  length = 5579
FEATURE                Location/Qualifiers
misc_feature           1..5579
                       note = Synthetic
source                 1..5579
                       mol_type = other DNA
                       organism = synthetic construct
SEQUENCE: 371
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcagattgg  240
ctattggcca ttgcatacgt tgtatccata tcataatatg tacatttata ttggctcatg  300
tccaacatta ccgccatgtt gacattgatt attgactagt tattaatagt aatcaattac  360
ggggtcatta gttcatagcc catatatgga gttccgcgtt acataactta cggtaaatgg  420
cccgcctggc tgaccgccca acgacccccg cccattgacg tcaataatga cgtatgttcc  480
catagtaacg ccaataggga ctttccattg acgtcaatgg gtggagtatt tacggtaaac  540
tgcccacttg gcagtacatc aagtgtatca tatgccaagt acgcccccta ttgacgtcaa  600
tgacggtaaa tggcccgcct ggcattatgc ccagtacatg accttatggg actttcctac  660
ttggcagtac atctacgtat tagtcatcgc tattaccatg gtgatgcggt tttggcagta  720
catcaatggg cgtggatagc ggtttgactc acggggattt ccaagtctcc accccattga  780
cgtcaatggg agtttgtttt ggcaccaaaa tcaacgggac tttccaaaat gtcgtaacaa  840
```

-continued

```
ctccgcccca ttgacgcaaa tgggcggtag gcgtgtacgg tgggaggtct atataagcag  900
agctcgttta gtgaaccgtc agatcgcctg gagacgccat ccacgctgtt ttgacctcca  960
tagaagacac cgggaccgat ccagcctcca tcggctcgca tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctcaggtc gagaccgggc  1140
ctttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgcggc cgctctagag  1380
atatcgccac catgaaggcc aaactgctgg tcctgctgtg tacttttacc gcaacctacg  1440
ctgacactat ctgcatcggc tatcacgcaa acaactccac cgacacagtg gataccgtcc  1500
tggagaagaa cgtgactgtc acccactcag tgaatctggg cagcggactg aggatggtca  1560
ccggactgcg caacatccca cagcgggaaa caagaggact gttcggcgct atcgcagggt  1620
ttattgaggg cgggtggaca ggaatggtgg acgggtggta cggctaccac catcagaatg  1680
agcagggcag cggctacgcc gctgatcaga agtctacaca gaacgcaatc aatggcatta  1740
ctaacatggt gaattctgtc atcgaaaaaa tgggcagcgg aggcaacgga acagacctgg  1800
ctgagctgct ggtgctgctg ctgaaccagt ggactctgct gttccacgat agcaacgtga  1860
agaatctgta tgagaaggtc aaatcccagc tgaagaacaa tgccaaagaa atcgggaatg  1920
gatgcttcga gttttaccat aagtgcaaca atgaatgtat ggagtctgtg aagaacggca  1980
cttacgacta tcccaaatat tctgaagaga gtaagctgaa tcgagagaaa attgacagtg  2040
gggcgacat catcaagctg ctgaacgaac aggtgaacaa ggagatgcag agctccaacc  2100
tgtacatgag tatgtctagt tggtgttata cacactcact ggacggcgct gggctgttcc  2160
tgtttgatca cgcagccgag gaatacgaac atgcaaagaa actgatcatt ttcctgaatg  2220
agaacaatgt gcccgtccag ctgacttcaa tcagcgcccc tgaacataag ttcgagggcc  2280
tgacccagat ctttcagaaa gcttacgaac acgagcagca tatttccgaa tctatcaaca  2340
atattgtgga ccacgccatt aagagcaaag atcatgctac cttcaacttt ctgcagtggt  2400
acgtggccga gcagcacgag gaggaggtcc tgtttaagga catcctggat aaaatcgaac  2460
tgattggaaa cgagaatcat ggcctgtacc tggcagatca gtatgtgaag ggcattgcca  2520
agtccagaaa aagtgggtca tgatgaacac gtgggatcca gatctgctgt gccttctagt  2580
tgccagccat ctgttgtttg cccctccccc gtgccttcct tgaccctgga aggtgccact  2640
cccactgtcc tttcctaata aaatgaggaa attgcatcgc attgtctgag taggtgtcat  2700
tctattctgg ggggtggggt ggggcaggac agcaaggggg aggattggga agacaatagc  2760
aggcatgctg gggatgcggt gggctctatg ggtacccagg tgctgaagaa ttgacccggt  2820
tcctcctggg ccagaaagaa gcaggcacat ccccttctct gtgacacacc ctgtccacgc  2880
ccctggttct tagttccagc cccactcata ggacactcat agctcaggag ggctccgcct  2940
tcaatcccac ccgctaaagt acttggagcg gtctctccct ccctcatcag cccaccaaac  3000
caaacctagc ctccaagagt gggaagaaat taaagcaaga taggctatta agtgcagagg  3060
gagagaaaat gcctccaaca tgtgaggaag taatgagaga aatcatagaa ttttaaggcc  3120
atgatttaag gccatcatgg ccttaatctt ccgcttcctc gctcactgac tcgctgcgct  3180
cggtcgttcg gctgcggcga gcggtatcag ctcactcaaa ggcggtaata cggttatcca  3240
cagaatcagg ggataacgca ggaaagaaca tgtgagcaaa aggccagcaa aaggccagga  3300
accgtaaaaa ggccgcgttg ctggcgtttt tccataggct ccgcccccct gacgagcatc  3360
acaaaaatcg acgctcaagt cagaggtggc gaaacccgac aggactataa agataccagg  3420
cgtttccccc tggaagctcc ctcgtgcgct ctcctgttcc gaccctgccg cttaccggat  3480
acctgtccgc ctttctccct tcgggaagcg tggcgctttc tcatagctca cgctgtaggt  3540
atctcagttc ggtgtaggtc gttcgctcca agctgggctg tgtgcacgaa ccccccgttc  3600
agcccgaccg ctgcgcctta tccggtaact atcgtcttga gtccaacccg gtaagacacg  3660
acttatcgcc actggcagca gccactggta acaggattag cagagcgagg tatgtaggcg  3720
gtgctacaga gttcttgaag tggtggccta actacggcta cactagaaga acagtatttg  3780
gtatctgcgc tctgctgaag ccagttacct tcggaaaaag agttggtagc tcttgatccg  3840
gcaaacaaac caccgctggt agcggtggtt tttttgtttg caagcagcag attacgcgca  3900
gaaaaaaagg atctcaagaa gatcctttga tcttttctac ggggtctgac gctcagtgga  3960
acgaaaactc acgttaaggg attttggtca tgagattatc aaaaaggatc ttcacctaga  4020
tccttttaaa ttaaaaatga agttttaaat caatctaaag tatatatgag taaacttggt  4080
ctgacagtta ccaatgctta atcagtgagg cacctatctc agcgatctgt ctatttcgtt  4140
catccatagt tgcctgactc gggggggggg ggcgctgagg tctgcctcgt gaagaaggtg  4200
ttgctgactc ataccaggcc tgaatcgccc catcatccag ccagaaagtg agggagccac  4260
ggttgatgag agctttgttg taggtggacc agttggtgat tttgaacttt tgctttgcca  4320
cggaacggtc tgcgttgtcg ggaagatgcg tgatctgatc cttcaactca gcaaaagttc  4380
gatttattca acaaagccgc cgtcccgtca agtcagcgta atgctctgcc agtgttacaa  4440
ccaattaacc aattctgatt agaaaaactc atcgagcatc aaatgaaact gcaatttatt  4500
catatcagga ttatcaatac catatttttg aaaaagccgt ttctgtaatg aaggagaaaa  4560
ctcaccgagg cagttccata ggatggcaag atcctggtat cggtctgcga ttccgactcg  4620
tccaacatca atacaaccta ttaatttccc ctcgtcaaaa ataaggttat caagtgagaa  4680
atcaccatga gtgacgactg aatccggtga gaatggcaaa agcttatgca tttctttcca  4740
gacttgttca acaggccagc cattacgctc gtcatcaaaa tcactcgcat caaccaaacc  4800
gttattcatt cgtgattgcg cctgagcgag acgaaatacg cgatcgctgt taaaaggaca  4860
attacaaaca ggaatcgaat gcaaccggcg caggaacact gccagcgcat caacaatatt  4920
ttcacctgaa tcaggatatt cttctaatac ctggaatgct gttttcccgg ggatcgcagt  4980
ggtgagtaac catgcatcat caggagtacg gataaaatgc ttgatggtcg gaagaggcat  5040
aaattccgtc agccagttta gtctgaccat ctcatctgta acatcattgg caacgctacc  5100
tttgccatgt ttcagaaaca actctggcgc atcgggcttc ccatacaatc gatagattgt  5160
cgcacctgat tgcccgacat tatcgcgagc ccatttatac ccatataaat cagcatccat  5220
gttggaattt aatcgcggcc tcgagcaaga cgtttcccgt tgaatatggc tcataacacc  5280
ccttgtatta ctgtttatgt aagcagacag ttttattgtt catgatgata tatttttatc  5340
ttgtgcaatg taacatcaga gattttgaga cacaacgtgg ctttcccccc ccccccatta  5400
ttgaagcatt tatcagggtt attgtctcat gagcggatac atatttgaat gtatttagaa  5460
aaataaacaa ataggggttc cgcgcacatt tccccgaaaa gtgccacctg acgtctaaga  5520
aaccattatt atcatgacat taacctataa aaataggcgt atcacgaggc cctttcgtc   5579
```

```
SEQ ID NO: 372          moltype = DNA  length = 645
FEATURE                 Location/Qualifiers
misc_feature            1..645
                        note = Synthetic
source                  1..645
                        mol_type = other DNA
                        organism = synthetic construct
CDS                     1..645
SEQUENCE: 372
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc ataacaatac ccagggcagc  300
ggctacgccg ctgatcagaa gtctacacag aacgcaatca atggcattac taacatggtg  360
aattctgtca tcgaaaaaat gggcggaaat ggcactggag ctgacctggc tgagctgctg  420
gtgctgctgc tgaaccagtg gactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                  645

SEQ ID NO: 373          moltype = AA  length = 215
FEATURE                 Location/Qualifiers
REGION                  1..215
                        note = Synthetic Construct
source                  1..215
                        mol_type = protein
                        organism = synthetic construct
SEQUENCE: 373
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHNNTQGS GYAADQKSTQ NAINGITNMV  120
NSVIEKMGGN GTGADLAELL VLLLNQWTLL FHDSNVKNLY EKVKSQLKNN AKEIGNGCFE  180
FYHKCNNECM ESVKNGTYDY PKYSEESKLN REKID                              215

SEQ ID NO: 374          moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 374
gtcaatttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaacagca gagtccactg gttcagcagc agcaccagca gctcagccag  240
gtcagctcca gtgccatttc cgcccatttt ttcgatgaca gaattcacca tgttagtaat  300
gccattgatt gcgttctgtg tagacttctg atcagcggcg tagccgctgc cctgggtatt  360
gttatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat                  645

SEQ ID NO: 375          moltype = DNA  length = 1155
FEATURE                 Location/Qualifiers
misc_feature            1..1155
                        note = Synthetic
source                  1..1155
                        mol_type = other DNA
                        organism = synthetic construct
CDS                     1..1155
SEQUENCE: 375
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc ataacaatac ccagggcagc  300
ggctacgccg ctgatcagaa gtctacacag aacgcaatca atggcattac taacatggtg  360
aattctgtca tcgaaaaaat gggcggaaat ggcactggag ctgacctggc tgagctgctg  420
gtgctgctgc tgaaccagtg gactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgacagtgg gggcgacatc  660
atcaagctgc tgaacgaaca ggtgaacaag gagatgaaca gcaccaacct gtacatgagt  720
atgtctagtt ggtgttatac acactcactg gacggcgctg ggctgttcct gtttgatcac  780
gcagccgagg aatacgaaca tgcaaagaaa ctgatcattt tcctgaatga gaacaatgtg  840
cccgtccagc tgacttcaat cagcgcccct gaacataagt tcgagggcct gacccagatc  900
```

```
tttcagaaag cttacgaaca cgagcagcat atttccgaat ctatcaacaa tattgtggac  960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtcat gatga                                                   1155

SEQ ID NO: 376          moltype = AA  length = 383
FEATURE                 Location/Qualifiers
REGION                  1..383
                        note = Synthetic Construct
source                  1..383
                        mol_type = protein
                        organism = synthetic construct
SEQUENCE: 376
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHNNTQGS GYAADQKSTQ NAINGITNMV  120
NSVIEKMGGN GTGADLAELL VLLLNQWTLL FHDSNVKNLY EKVKSQLKNN AKEIGNGCFE  180
FYHKCNNECM ESVKNGTYDY PKYSEESKLN REKIDSGGDI IKLLNEQVNK EMNSTNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                          383

SEQ ID NO: 377          moltype = DNA  length = 1155
FEATURE                 Location/Qualifiers
misc_feature            1..1155
                        note = Synthetic
source                  1..1155
                        mol_type = other DNA
                        organism = synthetic construct
SEQUENCE: 377
tcatcatgac ccactttttc tggacttggc aatgcccttc acatactgat ctgccaggta  60
caggccatga ttctcgtttc caatcagttc gattttatcc aggatgtcct taaacaggac  120
ctcctcctcg tgctgctcgg ccacgtacca ctgcagaaag ttgaaggtag catgatcttt  180
gctcttaatg gcgtggtcca caatattgtt gatagattcg gaaatatgct gctcgtgttc  240
gtaagctttc tgaaagatct gggtcaggcc ctcgaactta tgttcagggg cgctgattga  300
agtcagctgg acgggcacat tgttctcatt caggaaaatg atcagtttct ttgcatgttc  360
gtattcctcg gctgcgtgat caaacaggaa cagcccagcg ccgtccagtg agtgtgtata  420
acaccaacta gacatactca tgtacaggtt ggtgctgttc atctccttgt tcacctgttc  480
gttcagcagc ttgatgatgt cgccccccact gtcaattttc tctcgattca gcttactctc  540
ttcagaatat ttgggatagt cgtaagtgcc gttcttcaca gactccatac attcattgtt  600
gcacttatgg taaaactcga agcatccatt cccgatttct ttggcattgt tcttcagctg  660
ggatttgacc ttctcataca gattcttcac gttgctatcg tggaacagca gagtccactg  720
gttcagcagc agcaccagca gctcagccag gtcagctcca gtgccatttc cgcccatttt  780
ttcgatgaca gaattcacca tgttagtaat gccattgatt gcgttctgtg tagacttctg  840
atcagcggcg tagccgctgc cctgggtatt gttatggtgg tagccgtacc acccgtccac  900
cattcctgtc cacccgccct caataaaccc tgcgatagcg ccgaacagtc ctcttgtttc  960
ccgctgtggg atgttgcgca gtccggtgac catcctcagt ccgctgccca gattcactga  1020
gtgggtgaca gtcacgttct tctccaggac ggtatccact gtgtcggtgg agttgtttgc  1080
gtgatagccg atgcagatag tgtcagcgta ggttgcggta aaagtacaca gcaggaccag  1140
cagtttggcc ttcat                                                   1155

SEQ ID NO: 378          moltype = DNA  length = 5579
FEATURE                 Location/Qualifiers
misc_feature            1..5579
                        note = Synthetic
source                  1..5579
                        mol_type = other DNA
                        organism = synthetic construct
SEQUENCE: 378
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcagattgg  240
ctattggcca ttgcatacgt tgtatccata tcataatatg tacatttata ttggctcatg  300
tccaacatta ccgccatgtt gacattgatt attgactagt tattaatagt aatcaattac  360
ggggtcatta gttcatagcc catatatgga gttccgcgtt acataactta cggtaaatgg  420
cccgcctggc tgaccgccca acgacccccg cccattgacg tcaataatga cgtatgttcc  480
catagtaacg ccaataggga ctttccattg acgtcaatgg gtggagtatt tacggtaaac  540
tgcccacttg gcagtacatc aagtgtatca tatgccaagt acgcccccta ttgacgtcaa  600
tgacggtaaa tggcccgcct ggcattatgc ccagtacatg accttatggg actttcctac  660
ttggcagtac atctacgtat tagtcatcgc tattaccatg gtgatgcggt tttggcagta  720
catcaatggg cgtggatagc ggtttgactc acggggattt ccaagtctcc accccattga  780
cgtcaatggg agtttgtttt ggcaccaaaa tcaacgggac tttccaaaat gtcgtaacaa  840
ctccgcccca ttgacgcaaa tgggcggtag gcgtgtacgg tgggaggtct atataagcag  900
agctcgttta gtgaaccgtc agatcgcctg gagacgccat ccacgctgtt ttgacctcca  960
tagaagacac cgggaccgat ccagcctcca tcggctcgca tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctcaggtc gagaccgggc  1140
ctttgtccgg cgctcccttg gagcctacct agactcagcc ggctctccac gctttgcctg  1200
```

```
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgcggc cgctctagag  1380
atatcgccac catgaaggcc aaactgctgg tcctgctgtg tacttttacc gcaacctacg  1440
ctgacactat ctgcatcggc tatcacgcaa acaactccac cgacacagtg gataccgtcc  1500
tggagaagaa cgtgactgtc acccactcag tgaatctggg cagcggactg aggatggtca  1560
ccggactgcg caacatccca cagcgggaaa caagaggact gttcggcgct atcgcagggt  1620
ttattgaggg cgggtggaca ggaatggtgg acgggtggta cggctaccac cataacaata  1680
cccagggcag cggctacgcc gctgatcaga agtctacaca gaacgcaatc aatggcatta  1740
ctaacatggt gaattctgtc atcgaaaaaa tgggcggaaa tggcactgga gctgacctgg  1800
ctgagctgct ggtgctgctg ctgaaccagt ggactctgct gttccacgat agcaacgtga  1860
agaatctgta tgagaaggtc aaatcccagc tgaagaacaa tgccaaagaa atcgggaatg  1920
gatgcttcga gttttaccat aagtgcaaca atgaatgtat ggagtctgtg aagaacggca  1980
cttacgacta tcccaaatat tctgaagaga gtaagctgaa tcgagagaaa attgacagtg  2040
ggggcgacat catcaagctg ctgaacgaac aggtgaacaa ggagatgaac agcaccaacc  2100
tgtacatgag tatgtctagt tggtgttata cacactcact ggacggcgct gggctgttcc  2160
tgtttgatca cgcagccgag gaatacgaac atgcaaagaa actgatcatt ttcctgaatg  2220
agaacaatgt gcccgtccag ctgacttcaa tcagcgcccc tgaacataag ttcgagggcc  2280
tgacccagat ctttcagaaa gcttacgaac acgagcagca tatttccgaa tctatcaaca  2340
atattgtgga ccacgccatt aagagcaaag atcatgctac cttcaacttt ctgcagtggt  2400
acgtggccga gcagcacgag gaggaggtcc tgtttaagga catcctggat aaaatcgaac  2460
tgattggaaa cgagaatcat ggcctgtacc tggcagatca gtatgtgaag ggcattgcca  2520
agtccagaaa aagtgggtca tgatgaacac gtgggatcca gatctgctgt gccttctagt  2580
tgccagccat ctgttgtttg cccctccccc gtgccttcct tgaccctgga aggtgccact  2640
cccactgtcc tttcctaata aaatgaggaa attgcatcgc attgtctgag taggtgtcat  2700
tctattctgg ggggtggggt ggggcaggac agcaaggggg aggattggga agacaatagc  2760
aggcatgctg gggatgcggt gggctctatg ggtacccagg tgctgaagaa ttgacccggt  2820
tcctcctggg ccagaaagaa gcaggcacat ccccttctct gtgacacacc ctgtccacgc  2880
ccctggttct tagttccagc cccactcata ggacactcat agctcaggag ggctccgcct  2940
tcaatcccac ccgctaaagt acttggagcg gtctctccct ccctcatcag cccaccaaac  3000
caaacctagc ctccaagagt gggaagaaat taaagcaaga taggctatta agtgcagagg  3060
gagagaaaat gcctccaaca tgtgaggaag taatgagaga aatcatagaa ttttaaggcc  3120
atgatttaag gccatcatgg ccttaatctt ccgcttcctc gctcactgac tcgctgcgct  3180
cggtcgttcg gctgcggcga gcggtatcag ctcactcaaa ggcggtaata cggttatcca  3240
cagaatcagg ggataacgca ggaaagaaca tgtgagcaaa aggccagcaa aaggccagga  3300
accgtaaaaa ggccgcgttg ctggcgtttt tccataggct ccgcccccct gacgagcatc  3360
acaaaaatcg acgctcaagt cagaggtggc gaaacccgac aggactataa agataccagg  3420
cgtttccccc tggaagctcc ctcgtgcgct ctcctgttcc gaccctgccg cttaccggat  3480
acctgtccgc ctttctccct tcgggaagcg tggcgctttc tcatagctca cgctgtaggt  3540
atctcagttc ggtgtaggtc gttcgctcca agctgggctg tgtgcacgaa ccccccgttc  3600
agcccgaccg ctgcgcctta tccggtaact atcgtcttga gtccaacccg gtaagacacg  3660
acttatcgcc actggcagca gccactggta acaggattag cagagcgagg tatgtaggcg  3720
gtgctacaga gttcttgaag tggtggccta actacggcta cactagaaga acagtatttg  3780
gtatctgcgc tctgctgaag ccagttacct tcggaaaaag agttggtagc tcttgatccg  3840
gcaaacaaac caccgctggt agcggtggtt tttttgtttg caagcagcag attacgcgca  3900
gaaaaaaagg atctcaagaa gatcctttga tcttttctac ggggtctgac gctcagtgga  3960
acgaaaactc acgttaaggg attttggtca tgagattatc aaaaaggatc ttcacctaga  4020
tccttttaaa ttaaaaatga agttttaaat caatctaaag tatatatgag taaacttggt  4080
ctgacagtta ccaatgctta atcagtgagg cacctatctc agcgatctgt ctatttcgtt  4140
catccatagt tgcctgactc gggggggggg ggcgctgagg tctgcctcgt gaagaaggtg  4200
ttgctgactc ataccaggcc tgaatcgccc catcatccag ccagaaagtg agggagccac  4260
ggttgatgag agctttgttg taggtggacc agttggtgat tttgaacttt tgctttgcca  4320
cggaacggtc tgcgttgtcg ggaagatgcg tgatctgatc cttcaactca gcaaaagttc  4380
gatttattca acaaagccgc cgtcccgtca agtcagcgta atgctctgcc agtgttacaa  4440
ccaattaacc aattctgatt agaaaaactc atcgagcatc aaatgaaact gcaatttatt  4500
catatcagga ttatcaatac catatttttg aaaaagccgt ttctgtaatg aaggagaaaa  4560
ctcaccgagg cagttccata ggatggcaag atcctggtat cggtctgcga ttccgactcg  4620
tccaacatca atacaaccta ttaatttccc ctcgtcaaaa ataaggttat caagtgagaa  4680
atcaccatga gtgacgactg aatccggtga gaatggcaaa agcttatgca tttctttcca  4740
gacttgttca acaggccagc cattacgctc gtcatcaaaa tcactcgcat caaccaaacc  4800
gttattcatt cgtgattgcg cctgagcgag acgaaatacg cgatcgctgt taaaaggaca  4860
attacaaaca ggaatcgaat gcaaccggcg caggaacact gccagcgcat caacaatatt  4920
ttcacctgaa tcaggatatt cttctaatac ctggaatgct gttttcccgg ggatcgcagt  4980
ggtgagtaac catgcatcat caggagtacg gataaaatgc ttgatggtcg gaagaggcat  5040
aaattccgtc agccagttta gtctgaccat ctcatctgta acatcattgg caacgctacc  5100
tttgccatgt ttcagaaaca actctggcgc atcgggcttc ccatacaatc gatagattgt  5160
cgcacctgat tgcccgacat tatcgcgagc ccatttatac ccatataaat cagcatccat  5220
gttggaattt aatcgcggcc tcgagcaaga cgtttcccgt tgaatatggc tcataacacc  5280
ccttgtatta ctgtttatgt aagcagacag ttttattgtt catgatgata tatttttatc  5340
ttgtgcaatg taacatcaga gattttgaga cacaacgtgg ctttcccccc ccccccatta  5400
ttgaagcatt tatcagggtt attgtctcat gagcggatac atatttgaat gtatttagaa  5460
aaataaacaa ataggggttc cgcgcacatt tccccgaaaa gtgccacctg acgtctaaga  5520
aaccattatt atcatgacat taacctataa aaataggcgt atcacgaggc cctttcgtc   5579
```

```
SEQ ID NO: 379          moltype = DNA  length = 645
FEATURE                 Location/Qualifiers
misc_feature            1..645
                        note = Synthetic
source                  1..645
```

```
                         mol_type = other DNA
                         organism = synthetic construct
CDS                      1..645
SEQUENCE: 379
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cggtggtac ggctaccacc ataacaatac ccagggcagc  300
ggctacgccg ctgatcagaa gtctacacag aacgcaatca atggcattac taacatggtg  360
aattctgtca tcgaaaaaat gggcggaaat ggcactggag ctgacctggc tgagctgctg  420
gtgctgctgc tgaaccagtg gactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                  645

SEQ ID NO: 380           moltype = AA  length = 215
FEATURE                  Location/Qualifiers
REGION                   1..215
                         note = Synthetic Construct
source                   1..215
                         mol_type = protein
                         organism = synthetic construct
SEQUENCE: 380
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHNNTQGS GYAADQKSTQ NAINGITNMV  120
NSVIEKMGGN GTGADLAELL VLLLNQWTLL FHDSNVKNLY EKVKSQLKNN AKEIGNGCFE  180
FYHKCNNECM ESVKNGTYDY PKYSEESKLN REKID                             215

SEQ ID NO: 381           moltype = DNA  length = 645
FEATURE                  Location/Qualifiers
misc_feature             1..645
                         note = Synthetic
source                   1..645
                         mol_type = other DNA
                         organism = synthetic construct
SEQUENCE: 381
gtcaatttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaacagca gagtccactg gttcagcagc agcaccagca gctcagccag  240
gtcagctcca gtgccatttc cgcccatttt ttcgatgaca gaattcacca tgttagtaat  300
gccattgatt gcgttctgtg tagacttctg atcagcggcg tagccgctgc cctgggtatt  360
gttatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat                  645

SEQ ID NO: 382           moltype = DNA  length = 1155
FEATURE                  Location/Qualifiers
misc_feature             1..1155
                         note = Synthetic
source                   1..1155
                         mol_type = other DNA
                         organism = synthetic construct
CDS                      1..1155
SEQUENCE: 382
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cggtggtac ggctaccacc ataacaatac ccagggcagc  300
ggctacgccg ctgatcagaa gtctacacag aacgcaatca atggcattac taacatggtg  360
aattctgtca tcgaaaaaat gggcggaaat ggcactggag ctgacctggc tgagctgctg  420
gtgctgctgc tgaaccagtg gactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgacagtgg gggcgacatc  660
atcaagctgc tgaacgaaca ggtgaacaag gagatgaaca gcaccaacct gtacatgagt  720
atgtctagtt ggtgttatac acactcactg gacggcgctg ggctgttcct gtttgatcac  780
gcagccgagg aatacgaaca tgcaaagaaa ctgatcattt tcctgaatga gaacaatgtg  840
cccgtcaacc tgacttcaat cagcgcccct gaacataagt tcgagggcct gacccagatc  900
tttcagaaag cttacgaaca cgagcagcat atttccgaat ctatcaacaa tattgtggac  960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtcat gatga                                                   1155
```

-continued

```
SEQ ID NO: 383         moltype = AA  length = 383
FEATURE                Location/Qualifiers
REGION                 1..383
                       note = Synthetic Construct
source                 1..383
                       mol_type = protein
                       organism = synthetic construct
SEQUENCE: 383
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHNNTQGS GYAADQKSTQ NAINGITNMV  120
NSVIEKMGGN GTGADLAELL VLLLNQWTLL FHDSNVKNLY EKVKSQLKNN AKEIGNGCFE  180
FYHKCNNECM ESVKNGTYDY PKYSEESKLN REKIDSGGDI IKLLNEQVNK EMNSTNLYMS  240
MSSWCYTHSL DGAGLFLFDH AAEEYEHAKK LIIFLNENNV PVNLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                          383

SEQ ID NO: 384         moltype = DNA  length = 1155
FEATURE                Location/Qualifiers
misc_feature           1..1155
                       note = Synthetic
source                 1..1155
                       mol_type = other DNA
                       organism = synthetic construct
SEQUENCE: 384
tcatcatgac ccactttttc tggacttggc aatgcccttc acatactgat ctgccaggta  60
caggccatga ttctcgtttc caatcagttc gattttatcc aggatgtcct taaacaggac  120
ctcctcctcg tgctgctcgg ccacgtacca ctgcagaaag ttgaaggtag catgatcttt  180
gctcttaatg gcgtggtcca caatattgtt gatagattcg gaaatatgct gctcgtgttc  240
gtaagcttc tgaaagatct gggtcaggcc ctcgaactta tgttcagggg cgctgattga  300
agtcaggttg acgggcacat tgttctcatt caggaaaatg atcagtttct ttgcatgttc  360
gtattcctcg gctgcgtgat caaacaggaa cagcccagcg ccgtccagtg agtgtgtata  420
acaccaacta gacatactca tgtacaggtt ggtgctgttc atctccttgt tcacctgttc  480
gttcagcagc ttgatgatgt cgccccccact gtcaattttc tctcgattca gcttactctc  540
ttcagaatat ttgggatagt cgtaagtgcc gttcttcaca gactccatac attcattgtt  600
gcacttatgg taaaactcga agcatccatt cccgatttct ttggcattgt tcttcagctg  660
ggatttgacc ttctcataca gattcttcac gttgctatcg tggaacagca gagtccactg  720
gttcagcagc agcaccagca gctcagccag gtcagctcca gtgccatttc cgcccatttt  780
ttcgatgaca gaattcacca tgttagtaat gccattgatt gcgttctgtg tagacttctg  840
atcagcggcg tagccgctgc cctgggtatt gttatggtgg tagccgtacc acccgtccac  900
cattcctgtc cacccgccct caataaaccc tgcgatagcg ccgaacagtc ctcttgtttc  960
ccgctgtggg atgttgcgca gtccggtgac catcctcagt ccgctgccca gattcactga  1020
gtgggtgaca gtcacgttct tctccaggac ggtatccact gtgtcggtgg agttgtttgc  1080
gtgatagccg atgcagatag tgtcagcgta ggttgcggta aaagtacaca gcaggaccag  1140
cagtttggcc ttcat                                                   1155

SEQ ID NO: 385         moltype = DNA  length = 5579
FEATURE                Location/Qualifiers
misc_feature           1..5579
                       note = Synthetic
source                 1..5579
                       mol_type = other DNA
                       organism = synthetic construct
SEQUENCE: 385
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcagattgg  240
ctattggcca ttgcatacgt tgtatccata tcataatatg tacatttata ttggctcatg  300
tccaacatta ccgccatgtt gacattgatt attgactagt tattaatagt aatcaattac  360
ggggtcatta gttcatagcc catatatgga gttccgcgtt acataactta cggtaaatgg  420
cccgcctggc tgaccgccca acgacccccg cccattgacg tcaataatga cgtatgttcc  480
catagtaacg ccaataggga ctttccattg acgtcaatgg gtggagtatt tacggtaaac  540
tgcccacttg gcagtacatc aagtgtatca tatgccaagt acgcccccta ttgacgtcaa  600
tgacggtaaa tggcccgcct ggcattatgc ccagtacatg accttatggg actttcctac  660
ttggcagtac atctacgtat tagtcatcgc tattaccatg gtgatgcggt tttggcagta  720
catcaatggg cgtggatagc ggtttgactc acggggattt ccaagtctcc accccattga  780
cgtcaatggg agtttgtttt ggcaccaaaa tcaacgggac tttccaaaat gtcgtaacaa  840
ctccgcccca ttgacgcaaa tgggcggtag gcgtgtacgg tgggaggtct atataagcag  900
agctcgttta gtgaaccgtc agatcgcctg gagacgccat ccacgctgtt ttgacctcca  960
tagaagacac cgggaccgat ccagcctcca tcggctcgca tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctcaggtc gagaccgggc  1140
ctttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgcggc cgctctagag  1380
atatcgccac catgaaggcc aaactgctgg tcctgctgtg tacttttacc gcaacctacg  1440
ctgacactat ctgcatcggc tatcacgcaa acaactccac cgacacagtg gataccgtcc  1500
tggagaagaa cgtgactgtc acccactcag tgaatctggg cagcggactg aggatggtca  1560
```

```
ccggactgcg caacatccca cagcgggaaa caagaggact gttcggcgct atcgcagggt  1620
ttattgaggg cgggtggaca ggaatggtgg acgggtggta cggctaccac cataacaata  1680
cccagggcag cggctacgcc gctgatcaga agtctacaca gaacgcaatc aatggcatta  1740
ctaacatggt gaattctgtc atcgaaaaaa tgggcggaaa tggcactgga gctgacctgg  1800
ctgagctgct ggtgctgctg ctgaaccagt ggactctgct gttccacgat agcaacgtga  1860
agaatctgta tgagaaggtc aaatcccagc tgaagaacaa tgccaaagaa atcgggaatg  1920
gatgcttcga gttttaccat aagtgcaaca atgaatgtat ggagtctgtg aagaacggca  1980
cttacgacta tcccaaatat tctgaagaga gtaagctgaa tcgagagaaa attgacagtg  2040
ggggcgacat catcaagctg ctgaacgaac aggtgaacaa ggagatgaac agcaccaacc  2100
tgtacatgag tatgtctagt tggtgttata cacactcact ggacggcgct gggctgttcc  2160
tgtttgatca cgcagccgag gaatacgaac atgcaaagaa actgatcatt ttcctgaatg  2220
agaacaatgt gcccgtcaac ctgacttcaa tcagcgcccc tgaacataag ttcgagggcc  2280
tgacccagat ctttcagaaa gcttacgaac acgagcagca tatttccgaa tctatcaaca  2340
atattgtgga ccacgccatt aagagcaaag atcatgctac cttcaacttt ctgcagtggt  2400
acgtggccga gcagcacgag gaggaggtcc tgtttaagga catcctggat aaaatcgaac  2460
tgattggaaa cgagaatcat ggcctgtacc tggcagatca gtatgtgaag ggcattgcca  2520
agtccagaaa aagtgggtca tgatgaacac gtgggatcca gatctgctgt gccttctagt  2580
tgccagccat ctgttgtttg cccctccccc gtgccttcct tgaccctgga aggtgccact  2640
cccactgtcc tttcctaata aaatgaggaa attgcatcgc attgtctgag taggtgtcat  2700
tctattctgg ggggtggggt ggggcaggac agcaaggggg aggattggga agacaatagc  2760
aggcatgctg gggatgcggt gggctctatg ggtacccagg tgctgaagaa ttgacccggt  2820
tcctcctggg ccagaaagaa gcaggcacat ccccttctct gtgacacacc ctgtccacgc  2880
ccctggttct tagttccagc cccactcata ggacactcat agctcaggag ggctccgcct  2940
tcaatcccac ccgctaaagt acttggagcg gtctctccct ccctcatcag cccaccaaac  3000
caaacctagc ctccaagagt gggaagaaat taaagcaaga taggctatta agtgcagagg  3060
gagagaaaat gcctccaaca tgtgaggaag taatgagaga aatcatagaa ttttaaggcc  3120
atgatttaag gccatcatgg ccttaatctt ccgcttcctc gctcactgac tcgctgcgct  3180
cggtcgttcg gctgcggcga gcggtatcag ctcactcaaa ggcggtaata cggttatcca  3240
cagaatcagg ggataacgca ggaaagaaca tgtgagcaaa aggccagcaa aaggccagga  3300
accgtaaaaa ggccgcgttg ctggcgtttt tccataggct ccgcccccct gacgagcatc  3360
acaaaaatcg acgctcaagt cagaggtggc gaaacccgac aggactataa agataccagg  3420
cgtttccccc tggaagctcc ctcgtgcgct ctcctgttcc gaccctgccg cttaccggat  3480
acctgtccgc ctttctccct tcgggaagcg tggcgctttc tcatagctca cgctgtaggt  3540
atctcagttc ggtgtaggtc gttcgctcca agctgggctg tgtgcacgaa ccccccgttc  3600
agcccgaccg ctgcgcctta tccggtaact atcgtcttga gtccaacccg gtaagacacg  3660
acttatcgcc actggcagca gccactggta acaggattag cagagcgagg tatgtaggcg  3720
gtgctacaga gttcttgaag tggtggccta actacggcta cactagaaga acagtatttg  3780
gtatctgcgc tctgctgaag ccagttacct tcggaaaaag agttggtagc tcttgatccg  3840
gcaaacaaac caccgctggt agcggtggtt tttttgtttg caagcagcag attacgcgca  3900
gaaaaaaagg atctcaagaa gatcctttga tcttttctac ggggtctgac gctcagtgga  3960
acgaaaactc acgttaaggg attttggtca tgagattatc aaaaaggatc ttcacctaga  4020
tccttttaaa ttaaaaatga agttttaaat caatctaaag tatatatgag taaacttggt  4080
ctgacagtta ccaatgctta atcagtgagg cacctatctc agcgatctgt ctatttcgtt  4140
catccatagt tgcctgactc gggggggggg ggcgctgagg tctgcctcgt gaagaaggtg  4200
ttgctgactc ataccaggcc tgaatcgccc catcatccag ccagaaagtg agggagccac  4260
ggttgatgag agctttgttg taggtggacc agttggtgat tttgaacttt tgctttgcca  4320
cggaacggtc tgcgttgtcg ggaagatgcg tgatctgatc cttcaactca gcaaaagttc  4380
gatttattca acaaagccgc cgtcccgtca agtcagcgta atgctctgcc agtgttacaa  4440
ccaattaacc aattctgatt agaaaaactc atcgagcatc aaatgaaact gcaatttatt  4500
catatcagga ttatcaatac catatttttg aaaaagccgt ttctgtaatg aaggagaaaa  4560
ctcaccgagg cagttccata ggatggcaag atcctggtat cggtctgcga ttccgactcg  4620
tccaacatca atacaaccta ttaatttccc ctcgtcaaaa ataaggttat caagtgagaa  4680
atcaccatga gtgacgactg aatccggtga gaatggcaaa agcttatgca tttctttcca  4740
gacttgttca acaggccagc cattacgctc gtcatcaaaa tcactcgcat caaccaaacc  4800
gttattcatt cgtgattgcg cctgagcgag acgaaatacg cgatcgctgt taaaaggaca  4860
attacaaaca ggaatcgaat gcaaccggcg caggaacact gccagcgcat caacaatatt  4920
ttcacctgaa tcaggatatt cttctaatac ctggaatgct gttttcccgg ggatcgcagt  4980
ggtgagtaac catgcatcat caggagtacg gataaaatgc ttgatggtcg gaagaggcat  5040
aaattccgtc agccagttta gtctgaccat ctcatctgta acatcattgg caacgctacc  5100
tttgccatgt ttcagaaaca actctggcgc atcgggcttc ccatacaatc gatagattgt  5160
cgcacctgat tgcccgacat tatcgcgagc ccatttatac ccatataaat cagcatccat  5220
gttggaattt aatcgcggcc tcgagcaaga cgtttcccgt tgaatatggc tcataacacc  5280
ccttgtatta ctgtttatgt aagcagacag ttttattgtt catgatgata tatttttatc  5340
ttgtgcaatg taacatcaga gattttgaga cacaacgtgg ctttcccccc ccccccatta  5400
ttgaagcatt tatcagggtt attgtctcat gagcggatac atatttgaat gtatttagaa  5460
aaataaacaa ataggggttc cgcgcacatt tccccgaaaa gtgccacctg acgtctaaga  5520
aaccattatt atcatgacat taacctataa aaataggcgt atcacgaggc cctttcgtc   5579
```

```
SEQ ID NO: 386          moltype = DNA  length = 384
FEATURE                 Location/Qualifiers
misc_feature            1..384
                        note = Synthetic
source                  1..384
                        mol_type = other DNA
                        organism = synthetic construct
CDS                     1..384
SEQUENCE: 386
atgaaggcca agctgctggt gctcctgtgc accttcaccg ccacctacgc cgacaccatc  60
tgcatcggct accacgccaa caacagcacc gacaccgtgg ataccgtgct ggaaaagaac  120
```

-continued

```
gtgaccgtga cccacagcgt gaacctgggc agcggcctgc ggatggtgac aggcctgcgg  180
aacatccccc agagagagac acggggcctg ttcggcgcca ttgccggctt tatcgagggc  240
ggctggaccg gcatggtgga cgggtggtac ggctaccacc accagaacga gcagggcagc  300
ggctacgccg ccgaccagaa gtccacccag aacgccatca acggcatcac caacatggtg  360
aacagcgtga tcgagaagat gggc                                        384

SEQ ID NO: 387         moltype = AA  length = 128
FEATURE                Location/Qualifiers
REGION                 1..128
                       note = Synthetic Construct
source                 1..128
                       mol_type = protein
                       organism = synthetic construct
SEQUENCE: 387
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMG                                                          128

SEQ ID NO: 388         moltype = DNA  length = 384
FEATURE                Location/Qualifiers
misc_feature           1..384
                       note = Synthetic
source                 1..384
                       mol_type = other DNA
                       organism = synthetic construct
SEQUENCE: 388
gcccatcttc tcgatcacgc tgttcaccat gttggtgatg ccgttgatgg cgttctgggt  60
ggacttctgg tcggcggcgt agccgctgcc ctgctcgttc tggtggtggt agccgtacca  120
cccgtccacc atgccggtcc agccgccctc gataaagccg gcaatggcgc cgaacaggcc  180
ccgtgtctct ctctggggga tgttccgcag gcctgtcacc atccgcaggc cgctgcccag  240
gttcacgctg tgggtcacgg tcacgttctt ttccagcacg gtatccacgg tgtcggtgct  300
gttgttggcg tggtagccga tgcagatggt gtcggcgtag gtggcggtga aggtgcacag  360
gagcaccagc agcttggcct tcat                                        384

SEQ ID NO: 389         moltype = DNA  length = 1110
FEATURE                Location/Qualifiers
misc_feature           1..1110
                       note = Synthetic
source                 1..1110
                       mol_type = other DNA
                       organism = synthetic construct
CDS                    1..1110
SEQUENCE: 389
atgaaggcca agctgctggt gctcctgtgc accttcaccg ccacctacgc cgacaccatc  60
tgcatcggct accacgccaa caacagcacc gacaccgtgg ataccgtgct ggaaaagaac  120
gtgaccgtga cccacagcgt gaacctgggc agcggcctgc ggatggtgac aggcctgcgg  180
aacatccccc agagagagac acggggcctg ttcggcgcca ttgccggctt tatcgagggc  240
ggctggaccg gcatggtgga cgggtggtac ggctaccacc accagaacga gcagggcagc  300
ggctacgccg ccgaccagaa gtccacccag aacgccatca acggcatcac caacatggtg  360
aacagcgtga tcgagaagat gggctccggc ggcagcggca ccgatctggc tgaactgctg  420
gtcctgctgc tgaacgagcg gaccctggac ttccacgaca gcaacgtgaa gaacctgtac  480
gagaaagtga agtcccagct gaagaacaac gccaaagaga tcggcaacgg ctgcttcgag  540
ttctaccaca agtgcaacaa cgagtgcatg gaaagcgtga agaacggcac ctacgactac  600
cccaagtaca gcgaggaaag caagctgaac cgcgagggag gcatgcaaat ctacgagggc  660
aagctgacag ccgagggcct gagattcggc atcgtggcca gccggttcaa ccacgccctg  720
gtggacagac tggtggaagg cgccatcgac tgcatcgtgc ggcacggcgg cagagaagag  780
gacatcaccc tggtccgcgt gcccggcagc tgggaaattc ctgtggctgc cggcgagctg  840
gcccggaaag aggatatcga cgccgtcatc gccatcggcg tgctgatcag aggcgccacc  900
ccccacttcg actatatcgc cagcgaggtg tccaagggcc tggccaacct gagcctggaa  960
ctgcggaagc ccatcacctt cggagtgatc accgccgaca ccctggaaca ggccatcgag  1020
agagccggca ccaagcacgg caacaaggga tgggaagccg ccctgagcgc catcgagatg  1080
gccaatctgt tcaagagcct gcgctgatga                                  1110

SEQ ID NO: 390         moltype = AA  length = 368
FEATURE                Location/Qualifiers
REGION                 1..368
                       note = Synthetic Construct
source                 1..368
                       mol_type = protein
                       organism = synthetic construct
SEQUENCE: 390
MKAKLLVLLC TFTATYADTI CIGYHANNST DTVDTVLEKN VTVTHSVNLG SGLRMVTGLR  60
NIPQRETRGL FGAIAGFIEG GWTGMVDGWY GYHHQNEQGS GYAADQKSTQ NAINGITNMV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLN REGGMQIYEG KLTAEGLRFG IVASRFNHAL  240
VDRLVEGAID CIVRHGGREE DITLVRVPGS WEIPVAAGEL ARKEDIDAVI AIGVLIRGAT  300
PHFDYIASEV SKGLANLSLE LRKPITFGVI TADTLEQAIE RAGTKHGNKG WEAALSAIEM  360
ANLFKSLR                                                          368
```

```
SEQ ID NO: 391         moltype = DNA  length = 1110
FEATURE                Location/Qualifiers
misc_feature           1..1110
                       note = Synthetic
source                 1..1110
                       mol_type = other DNA
                       organism = synthetic construct
SEQUENCE: 391
tcatcagcgc aggctcttga acagattggc catctcgatg gcgctcaggg cggcttccca  60
tcccttgttg ccgtgcttgg tgccggctct ctcgatggcc tgttccaggg tgtcggcggt  120
gatcactccg aaggtgatgg gcttccgcag ttccaggctc aggttggcca ggcccttgga  180
cacctcgctg gcgatatagt cgaagtgggg ggtggcgcct ctgatcagca cgccgatggc  240
gatgacggcg tcgatatcct ctttccgggc cagctcgccg gcagccacag gaatttccca  300
gctgccgggc acgcggacca gggtgatgtc ctcttctctg ccgccgtgcc gcacgatgca  360
gtcgatggcg ccttccacca gtctgtccac cagggcgtgg ttgaaccggc tggccacgat  420
gccgaatctc aggccctcgg ctgtcagctt gccctcgtag atttgcatgc ctccctcgcg  480
gttcagcttg ctttcctcgc tgtacttggg gtagtcgtag gtgccgttct tcacgctttc  540
catgcactcg ttgttgcact tgtggtagaa ctcgaagcag ccgttgccga tctctttggc  600
gttgttcttc agctgggact tcactttctc gtacaggttc ttcacgttgc tgtcgtggaa  660
gtccagggtc cgctcgttca gcagcaggac cagcagttca gccagatcgg tgccgctgcc  720
gccggagccc atcttctcga tcacgctgtt caccatgttg gtgatgccgt tgatggcgtt  780
ctgggtggac ttctggtcgg cggcgtagcc gctgccctgc tcgttctggt ggtggtagcc  840
gtaccacccg tccaccatgc cggtccagcc gccctcgata aagccggcaa tggcgccgaa  900
caggccccgt gtctctctct gggggatgtt ccgcaggcct gtcaccatcc gcaggccgct  960
gcccaggttc acgctgtggg tcacggtcac gttcttttcc agcacggtat ccacggtgtc  1020
ggtgctgttg ttggcgtggt agccgatgca gatggtgtcg gcgtaggtgg cggtgaaggt  1080
gcacaggagc accagcagct tggccttcat                                   1110

SEQ ID NO: 392         moltype = DNA  length = 5528
FEATURE                Location/Qualifiers
misc_feature           1..5528
                       note = Synthetic
source                 1..5528
                       mol_type = other DNA
                       organism = synthetic construct
SEQUENCE: 392
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcagattgg  240
ctattggcca ttgcatacgt tgtatccata tcataatatg tacatttata ttggctcatg  300
tccaacatta ccgccatgtt gacattgatt attgactagt tattaatagt aatcaattac  360
ggggtcatta gttcatagcc catatatgga gttccgcgtt acataactta cggtaaatgg  420
cccgcctggc tgaccgccca acgacccccg cccattgacg tcaataatga cgtatgttcc  480
catagtaacg ccaataggga ctttccattg acgtcaatgg gtggagtatt tacggtaaac  540
tgcccacttg gcagtacatc aagtgtatca tatgccaagt acgcccccta ttgacgtcaa  600
tgacggtaaa tggcccgcct ggcattatgc ccagtacatg accttatggg actttcctac  660
ttggcagtac atctacgtat tagtcatcgc tattaccatg gtgatgcggt tttggcagta  720
catcaatggg cgtggatagc ggtttgactc acggggattt ccaagtctcc accccattga  780
cgtcaatggg agtttgtttt ggcaccaaaa tcaacgggac tttccaaaat gtcgtaacaa  840
ctccgcccca ttgacgcaaa tgggcggtag gcgtgtacgg tgggaggtct atataagcag  900
agctcgttta gtgaaccgtc agatcgcctg gagacgccat ccacgctgtt ttgacctcca  960
tagaagacac cgggaccgat ccagcctcca tcggctcgca tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctcaggtc gagaccgggc  1140
ctttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgcggc cgctctagag  1380
ccaccatgaa ggccaagctg ctggtgctcc tgtgcacctt caccgccacc tacgccgaca  1440
ccatctgcat cggctaccac gccaacaaca gcaccgacac cgtggatacc gtgctggaaa  1500
agaacgtgac cgtgacccac agcgtgaacc tgggcagcgg cctgcggatg gtgacaggcc  1560
tgcggaacat cccccagaga gagacacggg gcctgttcgg cgccattgcc ggctttatcg  1620
agggcggctg gaccggcatg gtggacgggt ggtacggcta ccaccaccag aacgagcagg  1680
gcagcggcta cgccgccgac cagaagtcca cccagaacgc catcaacggc atcaccaaca  1740
tggtgaacag cgtgatcgag aagatgggct ccggcggcag cggcaccgat ctggctgaac  1800
tgctggtcct gctgctgaac gagcggaccc tggacttcca cgacagcaac gtgaagaacc  1860
tgtacgagaa agtgaagtcc cagctgaaga acaacgccaa agagatcggc aacggctgct  1920
tcgagttcta ccacaagtgc aacaacgagt gcatggaaag cgtgaagaac ggcacctacg  1980
actaccccaa gtacagcgag gaaagcaagc tgaaccgcga gggaggcatg caaatctacg  2040
agggcaagct gacagccgag ggcctgagat tcggcatcgt ggccagccgg ttcaaccacg  2100
ccctggtgga cagactggtg gaaggcgcca tcgactgcat cgtgcggcac ggcggcagag  2160
aagaggacat caccctggtc cgcgtgcccg gcagctggga aattcctgtg gctgccggcg  2220
agctggcccg gaaagaggat atcgacgccg tcatcgccat cggcgtgctg atcagaggcg  2280
ccaccccccca cttcgactat atcgccagcg aggtgtccaa gggcctggcc aacctgagcc  2340
tggaactgcg gaagcccatc accttcggag tgatcaccgc cgacaccctg gaacaggcca  2400
tcgagagagc cggcaccaag cacggcaaca agggatggga agccgccctg agcgccatcg  2460
agatggccaa tctgttcaag agcctgcgct gatgaacacg tgggatccag atctgctgtg  2520
ccttctagtt gccagccatc tgttgtttgc ccctcccccg tgccttcctt gaccctggaa  2580
```

-continued

```
ggtgccactc ccactgtcct ttcctaataa aatgaggaaa ttgcatcgca ttgtctgagt  2640
aggtgtcatt ctattctggg gggtggggtg gggcaggaca gcaaggggga ggattgggaa  2700
gacaatagca ggcatgctgg ggatgcggtg ggctctatgg gtacccaggt gctgaagaat  2760
tgacccggtt cctcctgggc cagaaagaag caggcacatc cccttctctg tgacacaccc  2820
tgtccacgcc cctggttctt agttccagcc ccactcatag gacactcata gctcaggagg  2880
gctccgcctt caatcccacc cgctaaagta cttggagcgg tctctccctc cctcatcagc  2940
ccaccaaacc aaacctagcc tccaagagtg ggaagaaatt aaagcaagat aggctattaa  3000
gtgcagaggg agagaaaatg cctccaacat gtgaggaagt aatgagagaa atcatagaat  3060
tttaaggcca tgatttaagg ccatcatggc cttaatcttc cgcttcctcg ctcactgact  3120
cgctgcgctc ggtcgttcgg ctgcggcgag cggtatcagc tcactcaaag gcggtaatac  3180
ggttatccac agaatcaggg gataacgcag gaaagaacat gtgagcaaaa ggccagcaaa  3240
aggccaggaa ccgtaaaaag gccgcgttgc tggcgttttt ccataggctc cgcccccctg  3300
acgagcatca caaaaatcga cgctcaagtc agaggtggcg aaacccgaca ggactataaa  3360
gataccaggc gtttccccct ggaagctccc tcgtgcgctc tcctgttccg accctgccgc  3420
ttaccggata cctgtccgcc tttctccctt cgggaagcgt ggcgctttct catagctcac  3480
gctgtaggta tctcagttcg gtgtaggtcg ttcgctccaa gctgggctgt gtgcacgaac  3540
cccccgttca gcccgaccgc tgcgccttat ccggtaacta tcgtcttgag tccaacccgg  3600
taagacacga cttatcgcca ctggcagcag ccactggtaa caggattagc agagcgaggt  3660
atgtaggcgg tgctacagag ttcttgaagt ggtggcctaa ctacggctac actagaagaa  3720
cagtatttgg tatctgcgct ctgctgaagc cagttacctt cggaaaaaga gttggtagct  3780
cttgatccgg caaacaaacc accgctggta gcggtggttt ttttgtttgc aagcagcaga  3840
ttacgcgcag aaaaaaagga tctcaagaag atcctttgat cttttctacg gggtctgacg  3900
ctcagtggaa cgaaaactca cgttaaggga ttttggtcat gagattatca aaaaggatct  3960
tcacctagat ccttttaaat taaaaatgaa gttttaaatc aatctaaagt atatatgagt  4020
aaacttggtc tgacagttac caatgcttaa tcagtgaggc acctatctca gcgatctgtc  4080
tatttcgttc atccatagtt gcctgactcg gggggggggg gcgctgaggt ctgcctcgtg  4140
aagaaggtgt tgctgactca taccaggcct gaatcgcccc atcatccagc cagaaagtga  4200
gggagccacg gttgatgaga gctttgttgt aggtggacca gttggtgatt ttgaactttt  4260
gctttgccac ggaacggtct gcgttgtcgg gaagatgcgt gatctgatcc ttcaactcag  4320
caaaagttcg atttattcaa caaagccgcc gtcccgtcaa gtcagcgtaa tgctctgcca  4380
gtgttacaac caattaacca attctgatta gaaaaactca tcgagcatca aatgaaactg  4440
caatttattc atatcaggat tatcaatacc atatttttga aaaagccgtt tctgtaatga  4500
aggagaaaac tcaccgaggc agttccatag gatggcaaga tcctggtatc ggtctgcgat  4560
tccgactcgt ccaacatcaa tacaacctat taatttcccc tcgtcaaaaa taaggttatc  4620
aagtgagaaa tcaccatgag tgacgactga atccggtgag aatggcaaaa gcttatgcat  4680
ttctttccag acttgttcaa caggccagcc attacgctcg tcatcaaaat cactcgcatc  4740
aaccaaaccg ttattcattc gtgattgcgc ctgagcgaga cgaaatacgc gatcgctgtt  4800
aaaaggacaa ttacaaacag gaatcgaatg caaccggcgc aggaacactg ccagcgcatc  4860
aacaatattt tcacctgaat caggatattc ttctaatacc tggaatgctg ttttcccggg  4920
gatcgcagtg gtgagtaacc atgcatcatc aggagtacgg ataaaatgct tgatggtcgg  4980
aagaggcata aattccgtca gccagtttag tctgaccatc tcatctgtaa catcattggc  5040
aacgctacct ttgccatgtt tcagaaacaa ctctggcgca tcgggcttcc catacaatcg  5100
atagattgtc gcacctgatt gcccgacatt atcgcgagcc catttatacc catataaatc  5160
agcatccatg ttggaattta atcgcggcct cgagcaagac gtttcccgtt gaatatggct  5220
cataacaccc cttgtattac tgtttatgta agcagacagt tttattgttc atgatgatat  5280
atttttatct tgtgcaatgt aacatcagag attttgagac acaacgtggc tttccccccc  5340
cccccattat tgaagcattt atcagggtta ttgtctcatg agcggataca tatttgaatg  5400
tatttagaaa aataaacaaa taggggttcc gcgcacattt ccccgaaaag tgccacctga  5460
cgtctaagaa accattatta tcatgacatt aacctataaa aataggcgta tcacgaggcc  5520
ctttcgtc                                                            5528

SEQ ID NO: 393          moltype = DNA  length = 594
FEATURE                 Location/Qualifiers
misc_feature            1..594
                        note = Synthetic
source                  1..594
                        mol_type = other DNA
                        organism = synthetic construct
CDS                     1..594
SEQUENCE: 393
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacgggtcag gctggacagg aatggtggac gggtggtacg gctaccacca tcagaatgag  240
cagggcagcg gctacgccgc tgatcagaag tctacacaga acgcaatcaa tggcattact  300
aacatggtga attctgtcat cgaaaaaatg ggcagcggag gctccggaac agacctggct  360
gagctgctgg tgctgctgct gaaccagtgg actctgctgt tccacgatag caacgtgaag  420
aatctgtatg agaaggtcaa atcccagctg aagaacaatg ccaaagaaat cgggaatgga  480
tgcttcgagt tttaccataa gtgcaacaat gaatgtatgg agtctgtgaa gaacggcact  540
tacgactatc ccaaatattc tgaagagagt aagctgaatc gagagaaaat tgac        594

SEQ ID NO: 394          moltype = AA  length = 198
FEATURE                 Location/Qualifiers
REGION                  1..198
                        note = Synthetic Construct
source                  1..198
                        mol_type = protein
                        organism = synthetic construct
SEQUENCE: 394
```

-continued

```
MKAKLLVLLC TFTATYADTI CIGYHANNST DTVDTVLEKN VTVTHSVNLG SGLRMVTGLR  60
NGSGWTGMVD GWYGYHHQNE QGSGYAADQK STQNAINGIT NMVNSVIEKM GSGGSGTDLA  120
ELLVLLLNQW TLLFHDSNVK NLYEKVKSQL KNNAKEIGNG CFEFYHKCNN ECMESVKNGT  180
YDYPKYSEES KLNREKID                                              198

SEQ ID NO: 395         moltype = DNA  length = 594
FEATURE                Location/Qualifiers
misc_feature           1..594
                       note = Synthetic
source                 1..594
                       mol_type = other DNA
                       organism = synthetic construct
SEQUENCE: 395
gtcaatttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaacagca gagtccactg gttcagcagc agcaccagca gctcagccag  240
gtctgttccg gagcctccgc tgcccatttt ttcgatgaca gaattcacca tgttagtaat  300
gccattgatt gcgttctgtg tagacttctg atcagcggcg tagccgctgc cctgctcatt  360
ctgatggtgg tagccgtacc acccgtccac cattcctgtc cagcctgacc cgttgcgcag  420
tccggtgacc atcctcagtc cgctgcccag attcactgag tgggtgacag tcacgttctt  480
ctccaggacg gtatccactg tgtcggtgga gttgtttgcg tgatagccga tgcagatagt  540
gtcagcgtag gttgcggtaa aagtacacag caggaccagc agtttggcct tcat        594

SEQ ID NO: 396         moltype = DNA  length = 1104
FEATURE                Location/Qualifiers
misc_feature           1..1104
                       note = Synthetic
source                 1..1104
                       mol_type = other DNA
                       organism = synthetic construct
CDS                    1..1104
SEQUENCE: 396
atgaaggcca aactgctggt cctgctgtgt actttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacgggtcag gctggacagg aatggtggac gggtggtacg gctaccacca tcagaatgag  240
cagggcagcg gctacgccgc tgatcagaag tctacacaga acgcaatcaa tggcattact  300
aacatggtga attctgtcat cgaaaaaatg ggcagcggag gctccggaac agacctggct  360
gagctgctgg tgctgctgct gaaccagtgg actctgctgt tccacgatag caacgtgaag  420
aatctgtatg agaaggtcaa atcccagctg aagaacaatg ccaaagaaat cgggaatgga  480
tgcttcgagt tttaccataa gtgcaacaat gaatgtatgg agtctgtgaa gaacggcact  540
tacgactatc ccaaatattc tgaagagagt aagctgaatc gagagaaaat tgacagtggg  600
ggcgacatca tcaagctgct gaacgaacag gtgaacaagg agatgcagag ctccaacctg  660
tacatgagta tgtctagttg gtgttataca cactcactgg acggcgctgg gctgttcctg  720
tttgatcacg cagccgagga atacgaacat gcaaagaaac tgatcatttt cctgaatgag  780
aacaatgtgc ccgtccagct gacttcaatc agcgcccctg aacataagtt cgagggcctg  840
acccagatct ttcagaaagc ttacgaacac gagcagcata tttccgaatc tatcaacaat  900
attgtggacc acgccattaa gagcaaagat catgctacct tcaactttct gcagtggtac  960
gtggccgagc agcacgagga ggaggtcctg tttaaggaca tcctggataa aatcgaactg  1020
attggaaacg agaatcatgg cctgtacctg gcagatcagt atgtgaaggg cattgccaag  1080
tccagaaaaa gtgggtcatg atga                                        1104

SEQ ID NO: 397         moltype = AA  length = 366
FEATURE                Location/Qualifiers
REGION                 1..366
                       note = Synthetic Construct
source                 1..366
                       mol_type = protein
                       organism = synthetic construct
SEQUENCE: 397
MKAKLLVLLC TFTATYADTI CIGYHANNST DTVDTVLEKN VTVTHSVNLG SGLRMVTGLR  60
NGSGWTGMVD GWYGYHHQNE QGSGYAADQK STQNAINGIT NMVNSVIEKM GSGGSGTDLA  120
ELLVLLLNQW TLLFHDSNVK NLYEKVKSQL KNNAKEIGNG CFEFYHKCNN ECMESVKNGT  180
YDYPKYSEES KLNREKIDSG GDIIKLLNEQ VNKEMQSSNL YMSMSSWCYT HSLDGAGLFL  240
FDHAAEEYEH AKKLIIFLNE NNVPVQLTSI SAPEHKFEGL TQIFQKAYEH EQHISESINN  300
IVDHAIKSKD HATFNFLQWY VAEQHEEEVL FKDILDKIEL IGNENHGLYL ADQYVKGIAK  360
SRKSGS                                                            366

SEQ ID NO: 398         moltype = DNA  length = 1104
FEATURE                Location/Qualifiers
misc_feature           1..1104
                       note = Synthetic
source                 1..1104
                       mol_type = other DNA
                       organism = synthetic construct
SEQUENCE: 398
tcatcatgac ccactttttc tggacttggc aatgcccttc acatactgat ctgccaggta  60
caggccatga ttctcgtttc caatcagttc gattttatcc aggatgtcct taaacaggac  120
```

```
ctcctcctcg tgctgctcgg ccacgtacca ctgcagaaag ttgaaggtag catgatcttt  180
gctcttaatg gcgtggtcca caatattgtt gatagattcg gaaatatgct gctcgtgttc  240
gtaagctttc tgaaagatct gggtcaggcc ctcgaactta tgttcagggg cgctgattga  300
agtcagctgg acgggcacat tgttctcatt caggaaaatg atcagtttct ttgcatgttc  360
gtattcctcg gctgcgtgat caaacaggaa cagcccagcg ccgtccagtg agtgtgtata  420
acaccaacta gacatactca tgtacaggtt ggagctctgc atctccttgt tcacctgttc  480
gttcagcagc ttgatgatgt cgccccccact gtcaattttc tctcgattca gcttactctc  540
ttcagaatat ttgggatagt cgtaagtgcc gttcttcaca gactccatac attcattgtt  600
gcacttatgg taaaactcga agcatccatt cccgatttct ttggcattgt tcttcagctg  660
ggatttgacc ttctcataca gattcttcac gttgctatcg tggaacagca gagtccactg  720
gttcagcagc agcaccagca gctcagccag gtctgttccg gagcctccgc tgcccatttt  780
ttcgatgaca gaattcacca tgttagtaat gccattgatt gcgttctgtg tagacttctg  840
atcagcggcg tagccgctgc cctgctcatt ctgatggtgg tagccgtacc acccgtccac  900
cattcctgtc cagcctgacc cgttgcgcag tccggtgacc atcctcagtc cgctgcccag  960
attcactgag tgggtgacag tcacgttctt ctccaggacg gtatccactg tgtcggtgga  1020
gttgtttgcg tgatagccga tgcagatagt gtcagcgtag gttgcggtaa aagtacacag  1080
caggaccagc agtttggcct tcat                                        1104

SEQ ID NO: 399         moltype = DNA  length = 5528
FEATURE                Location/Qualifiers
misc_feature           1..5528
                       note = Synthetic
source                 1..5528
                       mol_type = other DNA
                       organism = synthetic construct
SEQUENCE: 399
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcagattgg  240
ctattggcca ttgcatacgt tgtatccata tcataatatg tacatttata ttggctcatg  300
tccaacatta ccgccatgtt gacattgatt attgactagt tattaatagt aatcaattac  360
ggggtcatta gttcatagcc catatatgga gttccgcgtt acataactta cggtaaatgg  420
cccgcctggc tgaccgccca acgacccccg cccattgacg tcaataatga cgtatgttcc  480
catagtaacg ccaataggga ctttccattg acgtcaatgg gtggagtatt tacggtaaac  540
tgcccacttg gcagtacatc aagtgtatca tatgccaagt acgcccccta ttgacgtcaa  600
tgacggtaaa tggcccgcct ggcattatgc ccagtacatg accttatggg actttcctac  660
ttggcagtac atctacgtat tagtcatcgc tattaccatg gtgatgcggt tttggcagta  720
catcaatggg cgtggatagc ggtttgactc acggggattt ccaagtctcc accccattga  780
cgtcaatggg agtttgtttt ggcaccaaaa tcaacgggac tttccaaaat gtcgtaacaa  840
ctccgcccca ttgacgcaaa tgggcggtag gcgtgtacgg tgggaggtct atataagcag  900
agctcgttta gtgaaccgtc agatcgcctg gagacgccat ccacgctgtt ttgacctcca  960
tagaagacac cgggaccgat ccagcctcca tcggctcgca tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctcaggtc gagaccgggc  1140
ctttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgcggc cgctctagag  1380
atatcgccac catgaaggcc aaactgctgg tcctgctgtg tacttttacc gcaacctacg  1440
ctgacactat ctgcatcggc tatcacgcaa acaactccac cgacacagtg gataccgtcc  1500
tggagaagaa cgtgactgtc acccactcag tgaatctggg cagcggactg aggatggtca  1560
ccggactgcg caacgggtca ggctggacag gaatggtgga cgggtggtac ggctaccacc  1620
atcagaatga gcagggcagc ggctacgccg ctgatcagaa gtctacacag aacgcaatca  1680
atggcattac taacatggtg aattctgtca tcgaaaaaat gggcagcgga ggctccggaa  1740
cagacctggc tgagctgctg gtgctgctgc tgaaccagtg gactctgctg ttccacgata  1800
gcaacgtgaa gaatctgtat gagaaggtca aatcccagct gaagaacaat gccaaagaaa  1860
tcgggaatgg atgcttcgag ttttaccata agtgcaacaa tgaatgtatg gagtctgtga  1920
agaacggcac ttacgactat cccaaatatt ctgaagagag taagctgaat cgagagaaaa  1980
ttgacagtgg gggcgacatc atcaagctgc tgaacgaaca ggtgaacaag gagatgcaga  2040
gctccaacct gtacatgagt atgtctagtt ggtgttatac acactcactg gacggcgctg  2100
ggctgttcct gtttgatcac gcagccgagg aatacgaaca tgcaaagaaa ctgatcattt  2160
tcctgaatga gaacaatgtg cccgtccagc tgacttcaat cagcgcccct gaacataagt  2220
tcgagggcct gacccagatc tttcagaaag cttacgaaca cgagcagcat atttccgaat  2280
ctatcaacaa tattgtggac cacgccatta agagcaaaga tcatgctacc ttcaactttc  2340
tgcagtggta cgtggccgag cagcacgagg aggaggtcct gtttaaggac atcctggata  2400
aaatcgaact gattggaaac gagaatcatg gcctgtacct ggcagatcag tatgtgaagg  2460
gcattgccaa gtccagaaaa agtgggtcat gatgaacacg tgggatccag atctgctgtg  2520
ccttctagtt gccagccatc tgttgtttgc ccctcccccg tgccttcctt gaccctggaa  2580
ggtgccactc ccactgtcct ttcctaataa aatgaggaaa ttgcatcgca ttgtctgagt  2640
aggtgtcatt ctattctggg gggtggggtg gggcaggaca gcaaggggga ggattgggaa  2700
gacaatagca ggcatgctgg ggatgcggtg ggctctatgg gtacccaggt gctgaagaat  2760
tgacccggtt cctcctgggc cagaaagaag caggcacatc cccttctctg tgacacaccc  2820
tgtccacgcc cctggttctt agttccagcc ccactcatag gacactcata gctcaggagg  2880
gctccgcctt caatcccacc cgctaaagta cttggagcgg tctctccctc cctcatcagc  2940
ccaccaaacc aaacctagcc tccaagagtg ggaagaaatt aaagcaagat aggctattaa  3000
gtgcagaggg agagaaaatg cctccaacat gtgaggaagt aatgagagaa atcatagaat  3060
tttaaggcca tgatttaagg ccatcatggc cttaatcttc cgcttcctcg ctcactgact  3120
cgctgcgctc ggtcgttcgg ctgcggcgag cggtatcagc tcactcaaag gcggtaatac  3180
```

-continued

```
ggttatccac agaatcaggg gataacgcag gaaagaacat gtgagcaaaa ggccagcaaa  3240
aggccaggaa ccgtaaaaag gccgcgttgc tggcgttttt ccataggctc cgcccccctg  3300
acgagcatca caaaaatcga cgctcaagtc agaggtggcg aaacccgaca ggactataaa  3360
gataccaggc gtttccccct ggaagctccc tcgtgcgctc tcctgttccg accctgccgc  3420
ttaccggata cctgtccgcc tttctccctt cgggaagcgt ggcgctttct catagctcac  3480
gctgtaggta tctcagttcg gtgtaggtcg ttcgctccaa gctgggctgt gtgcacgaac  3540
cccccgttca gcccgaccgc tgcgccttat ccggtaacta tcgtcttgag tccaacccgg  3600
taagacacga cttatcgcca ctggcagcag ccactggtaa caggattagc agagcgaggt  3660
atgtaggcgg tgctacagag ttcttgaagt ggtggcctaa ctacggctac actagaagaa  3720
cagtatttgg tatctgcgct ctgctgaagc cagttacctt cggaaaaaga gttggtagct  3780
cttgatccgg caaacaaacc accgctggta gcggtggttt ttttgtttgc aagcagcaga  3840
ttacgcgcag aaaaaaagga tctcaagaag atcctttgat cttttctacg gggtctgacg  3900
ctcagtggaa cgaaaactca cgttaaggga ttttggtcat gagattatca aaaaggatct  3960
tcacctagat ccttttaaat taaaaatgaa gttttaaatc aatctaaagt atatatgagt  4020
aaacttggtc tgacagttac caatgcttaa tcagtgaggc acctatctca gcgatctgtc  4080
tatttcgttc atccatagtt gcctgactcg gggggggggg gcgctgaggt ctgcctcgtg  4140
aagaaggtgt tgctgactca taccaggcct gaatcgcccc atcatccagc cagaaagtga  4200
gggagccacg gttgatgaga gctttgttgt aggtggacca gttggtgatt ttgaactttt  4260
gctttgccac ggaacggtct gcgttgtcgg gaagatgcgt gatctgatcc ttcaactcag  4320
caaaagttcg atttattcaa caaagccgcc gtcccgtcaa gtcagcgtaa tgctctgcca  4380
gtgttacaac caattaacca attctgatta gaaaaactca tcgagcatca aatgaaactg  4440
caatttattc atatcaggat tatcaatacc atatttttga aaaagccgtt tctgtaatga  4500
aggagaaaac tcaccgaggc agttccatag gatggcaaga tcctggtatc ggtctgcgat  4560
tccgactcgt ccaacatcaa tacaacctat taatttcccc tcgtcaaaaa taaggttatc  4620
aagtgagaaa tcaccatgag tgacgactga atccggtgag aatggcaaaa gcttatgcat  4680
ttctttccag acttgttcaa caggccagcc attacgctcg tcatcaaaat cactcgcatc  4740
aaccaaaccg ttattcattc gtgattgcgc ctgagcgaga cgaaatacgc gatcgctgtt  4800
aaaaggacaa ttacaaacag gaatcgaatg caaccggcgc aggaacactg ccagcgcatc  4860
aacaatattt tcacctgaat caggatattc ttctaatacc tggaatgctg ttttcccggg  4920
gatcgcagtg gtgagtaacc atgcatcatc aggagtacgg ataaaatgct tgatggtcgg  4980
aagaggcata aattccgtca gccagtttag tctgaccatc tcatctgtaa catcattggc  5040
aacgctacct ttgccatgtt tcagaaacaa ctctggcgca tcgggcttcc catacaatcg  5100
atagattgtc gcacctgatt gcccgacatt atcgcgagcc catttatacc catataaatc  5160
agcatccatg ttggaattta atcgcggcct cgagcaagac gtttcccgtt gaatatggct  5220
cataacaccc cttgtattac tgtttatgta agcagacagt tttattgttc atgatgatat  5280
atttttatct tgtgcaatgt aacatcagag attttgagac acaacgtggc tttccccccc  5340
cccccattat tgaagcattt atcagggtta ttgtctcatg agcggataca tatttgaatg  5400
tatttagaaa aataaacaaa taggggttcc gcgcacattt ccccgaaaag tgccacctga  5460
cgtctaagaa accattatta tcatgacatt aacctataaa aataggcgta tcacgaggcc  5520
ctttcgtc                                                            5528

SEQ ID NO: 400         moltype = AA  length = 198
FEATURE                Location/Qualifiers
REGION                 1..198
                       note = Synthetic
source                 1..198
                       mol_type = protein
                       organism = synthetic construct
SEQUENCE: 400
MKAKLLVLLC TFTATYADTI CIGYHANNST DTVDTVLEKN VTVTHSVNLG SGLRMVTGLR  60
NGSGWTGMVD GWYGYHHQNE QGSGYAADQK STQNAINGIT NMVNSVIEKM GSGGSGTDLA  120
ELLVLLLNQW TLLFHDSNVK NLYEKVKSQL KNNAKEIGNG CFEFYHKCNN ECMESVKNGT  180
YDYPKYSEES KLNREKID                                                 198

SEQ ID NO: 401         moltype = AA  length = 366
FEATURE                Location/Qualifiers
REGION                 1..366
                       note = Synthetic
source                 1..366
                       mol_type = protein
                       organism = synthetic construct
SEQUENCE: 401
MKAKLLVLLC TFTATYADTI CIGYHANNST DTVDTVLEKN VTVTHSVNLG SGLRMVTGLR  60
NGSGWTGMVD GWYGYHHQNE QGSGYAADQK STQNAINGIT NMVNSVIEKM GSGGSGTDLA  120
ELLVLLLNQW TLLFHDSNVK NLYEKVKSQL KNNAKEIGNG CFEFYHKCNN ECMESVKNGT  180
YDYPKYSEES KLNREKIDSG GDIIKLLNEQ VNKEMQSSNL YMSMSSWCYT HSLDGAGLFL  240
FDHAAEEYEH AKKLIIFLNE NNVPVQLTSI SAPEHKFEGL TQIFQKAYEH EQHISESINN  300
IVDHAIKSKD HATFNFLQWY VAEQHEEEVL FKDILDKIEL IGNENHGLYL ADQYVKGIAK  360
SRKSGS                                                              366
```

It is claimed:

1. A method to vaccinate an individual against influenza virus, comprising administering to the individual a nanoparticle comprising a protein construct, the protein construct comprising:

an HA protein domain and a linker sequence, wherein the HA protein domain comprises the sequence of an influenza hemagglutinin (HA) protein that lacks at least 95% of the head region amino acid sequence, and in place of the missing sequence comprises a first linker sequence, wherein the first linker sequence is less than 10 amino acids in length; and wherein the HA protein domain comprises at least one alteration selected from the group consisting of:

a. deletion of the amino acid region corresponding to amino acids N403-W435 of the internal loop region of the influenza HA protein set forth as SEQ ID NO: 8, wherein the resulting ends of the HA protein are joined directly together;

b. replacement of the amino acid sequence corresponding to the internal loop region with a second linker sequence; and, c. substitution of at least one amino acid residue in a pair of amino acid residues in the HA protein domain, wherein the pair of amino acid residues form a noncovalent bond in the folded HA protein; and, wherein the strength of the noncovalent bond between the amino acid pair in the folded protein construct is greater than the strength of the non-covalent bond between the amino acid pair in a folded wild-type HA protein.

2. The method of claim 1, wherein substitutions are made to both amino acid residues in the amino acid pair.

3. The method of claim 1, wherein one amino acid of the amino acid pair corresponds to K1 of SEQ ID NO:149, and the other amino acid of the amino acid pair corresponds to E53 of SEQ ID NO:149.

4. The method of claim 3, wherein a substitution is made at the position corresponding to K1, and a second substitution is made at the position corresponding to position E53.

5. The method of claim 1, wherein the first linker sequence comprises less than 5 contiguous amino acids from the head region of an influenza HA protein.

6. The method of claim 1, wherein the HA protein domain is joined to a monomeric subunit protein that allows the protein construct to form a nanoparticle.

7. The method of claim 1, wherein the HA protein domain comprises a first amino acid sequence from the stem region of an HA protein and a second amino acid sequence from the stem region of an HA protein, the first and second amino acid sequences being covalently linked by the first linker sequence, wherein the first amino acid sequence comprises at least 20 contiguous amino acid residues from the amino acid sequence upstream of the amino-terminal end of the head region sequence, and wherein the second amino acid sequence comprises at least 20 contiguous amino acid residues from the amino acid sequence downstream of the carboxyl-terminal end of the head region sequence.

8. The method of claim 7, wherein the first amino acid sequence and the second amino acid sequence are from the stem region of an HA protein from a virus selected from the group consisting of A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), B/Brisbane/60/2008 (2008 Bris, B).

9. The method of claim 7, wherein the first amino acid sequence comprises a sequence at least 80% identical to at least 40 contiguous amino acid residues from a sequence selected from the group consisting of SEQ ID NO: 20, SEQ ID NO:35, SEQ ID NO:50 and SEQ ID NO:65.

10. The method of claim 7, wherein the second amino acid sequence comprises a sequence at least 80% identical to at least 40 contiguous amino acid residues from a sequence selected from the group consisting of SEQ ID NO:26, SEQ ID NO:32, SEQ ID NO:41, SEQ ID NO:44, SEQ ID NO:47, SEQ ID NO:56, SEQ ID NO:62, SEQ ID NO:71 and SEQ ID NO:77.

11. The method of claim 7, wherein the second amino acid sequence comprises at least 60 contiguous amino acids from the amino acid sequence downstream of the carboxyl-terminal end of the head region sequence;

wherein the 60 contiguous amino acids comprise a polypeptide sequence corresponding to the sequence of SEQ ID NO:149 or SEQ ID NO:150 from influenza virus H1N1 NC.

12. The method of claim 7, wherein the first amino acid sequence comprises a sequence selected from the group consisting of SEQ ID NO: 20, SEQ ID NO:35, SEQ ID NO:50 and SEQ ID NO:65; and, wherein the second amino acid sequence comprises a sequence selected from the group consisting of SEQ ID NO:29, SEQ ID NO:32, SEQ ID NO:47, SEQ ID NO:59, SEQ ID NO:62, SEQ ID NO:74 and SEQ ID NO:77.

13. The method of claim 1, wherein the HA protein domain comprises at least one other mutation at an amino acid position corresponding to an amino acid position in SEQ ID NO:8 selected from the group consisting of amino acid position 36, amino acid position 45, amino acid position 47, amino acid position 49, amino acid position 339, amino acid position 340, amino acid position 341, amino acid position 342, amino acid position 361, amino acid position 372, amino acid position 394, amino acid position 402, amino acid position 437, amino acid position 438, amino acid position 445, amino acid position 446, amino acid position 448, amino acid 449, amino acid position 450 and amino acid position 452.

14. The method of claim 1, wherein the protein construct comprises an amino acid sequence at least 85% identical to a sequence selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400.

15. The method of claim 1, wherein the second linker sequence is between 2 and 20 amino acid residues in length.

16. The method of claim 1, wherein the influenza HA protein is from a virus selected from the group consisting of A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), and B/Brisbane/60/2008 (2008 Bris, B).

17. The method of claim 1, wherein the protein construct comprises an amino acid sequence at least 95% identical to a sequence selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400.

18. The method of claim 1, wherein the protein construct comprises an amino acid sequence set forth as any one of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400.

19. The method of claim 1, wherein the protein construct comprises an amino acid sequence at least 90% identical to SEQ ID NO: 92.

20. The method of claim 1, wherein the protein construct comprises the amino acid sequence set forth as SEQ ID NO: 92.

* * * * *